(12) United States Patent
Jakobovits et al.

(10) Patent No.: US 7,494,646 B2
(45) Date of Patent: Feb. 24, 2009

(54) ANTIBODIES AND MOLECULES DERIVED THEREFROM THAT BIND TO STEAP-1 PROTEINS

(75) Inventors: Aya Jakobovits, Beverly Hills, CA (US); Soudabeh Etessami, Tarzana, CA (US); Pia M. Challita-Eid, Encino, CA (US); Juan J. Perez-Villar, Los Angeles, CA (US); Karen J. Morrison, Santa Monica, CA (US); Xiao-Chi Jia, Los Angeles, CA (US); Mary Faris, Los Angeles, CA (US); Jean Gudas, Pacific Palisades, CA (US); Arthur B. Raitano, Los Angeles, CA (US)

(73) Assignee: Agensys, Inc., Santa Monica, CA (US)

( * ) Notice: Subject to any disclaimer, the term of this patent is extended or adjusted under 35 U.S.C. 154(b) by 509 days.

(21) Appl. No.: 10/830,899

(22) Filed: Apr. 23, 2004

(65) Prior Publication Data
US 2004/0253232 A1 Dec. 16, 2004

Related U.S. Application Data

(63) Continuation-in-part of application No. 10/236,878, filed on Sep. 6, 2002, now abandoned.

(60) Provisional application No. 60/370,387, filed on Apr. 5, 2002, provisional application No. 60/317,840, filed on Sep. 6, 2001.

(51) Int. Cl.
*A61K 48/00* (2006.01)
(52) U.S. Cl. .................... 424/130.1; 424/178.1; 435/7.1
(58) Field of Classification Search ........................ None
See application file for complete search history.

(56) References Cited

U.S. PATENT DOCUMENTS

| 5,869,045 | A | * | 2/1999 | Hellstrom et al. ......... 424/130.1 |
| 6,048,970 | A | | 4/2000 | Lal et al. |
| 6,329,503 | B1 | | 12/2001 | Afar et al. .................... 530/350 |
| 6,342,219 | B1 | * | 1/2002 | Thorpe et al. ............ 424/145.1 |
| 2002/0022248 | A1 | | 2/2002 | Xu et al. ..................... 435/69.1 |
| 2003/0045682 | A1 | | 3/2003 | Afar et al. |
| 2003/0060612 | A1 | | 3/2003 | Goddard et al. ............ 536/23.1 |
| 2003/0064397 | A1 | | 4/2003 | Spancake et al. ................ 435/6 |

FOREIGN PATENT DOCUMENTS

| EP | 0 834 563 | 4/1998 |
| EP | 0834563 | 4/1998 |
| EP | 1308459 | 5/2003 |
| JP | 11164691 | 6/1999 |
| JP | 11164691 A | 6/1999 |
| WO | WO 94/09150 | 4/1994 |
| WO | WO 95/14772 | 6/1995 |
| WO | WO9514772 | 6/1995 |
| WO | WO9514772 A1 | 6/1995 |
| WO | WO 98/18489 | 5/1998 |
| WO | WO 98/37093 | 8/1998 |
| WO | WO 98/37418 | 8/1998 |
| WO | WO 98/53071 | 11/1998 |
| WO | WO9853071 A1 | 11/1998 |
| WO | WO 99/06548 | 2/1999 |
| WO | WO 99/06550 | 2/1999 |
| WO | WO 99/61469 | 2/1999 |
| WO | WO9906548 A2 | 2/1999 |
| WO | WO9906550 A2 | 2/1999 |
| WO | WO 99/62941 | 12/1999 |
| WO | WO9962941 | 12/1999 |
| WO | WO9962941 A2 | 12/1999 |
| WO | WO 00/04149 | 1/2000 |
| WO | WO0004149 A2 | 1/2000 |
| WO | WO 00/35937 | 2/2000 |
| WO | WO 00/35937 | 6/2000 |
| WO | WO0035937 | 6/2000 |
| WO | WO 00/77021 | 12/2000 |
| WO | WO0077021 A1 | 12/2000 |
| WO | WO 01/12662 | 2/2001 |
| WO | WO0112662 | 2/2001 |
| WO | WO 01/25272 | 4/2001 |
| WO | WO0125272 A2 | 4/2001 |
| WO | WO 01/34802 | 5/2001 |
| WO | WO0134802 A2 | 5/2001 |
| WO | WO 01/40276 | 6/2001 |
| WO | WO0140276 | 6/2001 |
| WO | WO0140276 A2 | 6/2001 |
| WO | WO 01/51633 | 7/2001 |
| WO | WO0151633 A2 | 7/2001 |
| WO | WO 01/57190 | 8/2001 |
| WO | WO 01/57276 | 8/2001 |

(Continued)

OTHER PUBLICATIONS

Paul, Fundamental Immunology, 3rd Edition, 1993, pp. 292-295.*

(Continued)

*Primary Examiner*—Misook Yu
*Assistant Examiner*—Mark Halvorson
(74) *Attorney, Agent, or Firm*—Atulya Agarwal; Ginger R. Dreger, Esq.; Goodwin Procter LLP

(57) ABSTRACT

Antibodies and molecules derived therefrom that bind to novel STEAP-1 protein, and variants thereof, are described wherein STEAP-1 exhibits tissue specific expression in normal adult tissue, and is aberrantly expressed in the cancers listed in Table I. Consequently, STEAP-1 provides a diagnostic, prognostic, prophylactic and/or therapeutic target for cancer. The STEAP-1 gene or fragment thereof, or its encoded protein, or variants thereof, or a fragment thereof, can be used to elicit a humoral or cellular immune response; antibodies or T cells reactive with STEAP-1 can be used in active or passive immunization.

21 Claims, 87 Drawing Sheets
(7 of 87 Drawing Sheet(s) Filed in Color)

FOREIGN PATENT DOCUMENTS

| WO | WO 01/57277 | 8/2001 |
|---|---|---|
| WO | WO 01/60860 | 8/2001 |
| WO | WO0157190 A2 | 8/2001 |
| WO | WO0157276 A2 | 8/2001 |
| WO | WO0157277 A2 | 8/2001 |
| WO | WO0160860 A2 | 8/2001 |
| WO | WO 01/72962 | 10/2001 |
| WO | WO 01/73032 | 10/2001 |
| WO | WO 01/75067 | 10/2001 |
| WO | WO0172962 | 10/2001 |
| WO | WO0173032 A2 | 10/2001 |
| WO | WO0175067 A2 | 10/2001 |
| WO | WO 01/86003 | 11/2001 |
| WO | WO0186003 A2 | 11/2001 |
| WO | WO 01/94629 | 12/2001 |
| WO | WO 01/96388 | 12/2001 |
| WO | WO0194629 A2 | 12/2001 |
| WO | WO0196388 A2 | 12/2001 |
| WO | WO 02/10449 | 2/2002 |
| WO | WO 02/16429 | 2/2002 |
| WO | WO0210449 A2 | 2/2002 |
| WO | WO 02/26822 | 4/2002 |
| WO | WO 02/30268 | 4/2002 |
| WO | WO0230268 A2 | 4/2002 |
| WO | WO 02/057303 | 7/2002 |
| WO | WO02057303 | 7/2002 |
| WO | WO 02/059260 | 8/2002 |
| WO | WO02059260 | 8/2002 |
| WO | WO 02/095010 | 11/2002 |
| WO | WO02095010 | 11/2002 |
| WO | WO 02/102993 | 12/2002 |
| WO | WO 02/102994 | 12/2002 |
| WO | WO02102993 | 12/2002 |
| WO | WO02102994 | 12/2002 |
| WO | WO 03/004622 | 1/2003 |
| WO | WO03004622 | 1/2003 |
| WO | WO 03/009814 | 2/2003 |
| WO | WO03009814 | 2/2003 |
| WO | WO 03/022995 | 3/2006 |

OTHER PUBLICATIONS

Rudikoff et al, Proc. Natl. Acad. Sci. USA 1982 vol. 79: p. 1979.*
Abu-Threideh et al., Jun. 1998, EMBL/Genbank/DDBJ Databases.
Abu-Threideh et al., Genbank, (Accession No. 095034), National Library of Medicine, Bethesda MD, May 1, 1999.
Bowie et al. (1990) Science 247:1306-1310.
Burgess et al. (1990) Jnl. Cell Biol. 111:2129-2138.
Cate et al., Genbank, (Accession No. W86309), National Library of Medicine, Bethesda MD, Nov. 1998.
Database EMBL Nucleotide and Protein Sequences, Aug. 25, 1996, XP002128081, AA032221, Hinxton, GB.
Database EMBL Nucleotide and Protein Sequences, May 13, 1997, XP002128082, AC002064, Hinxton, GB.
Database EMBL Nucleotide and Protein Sequences, Jun. 15, 1998, XP002128084, AC004969 (clone DJ1121E10), Hinxton, GB.
Database EMBL Nucleotide and Protein Sequences, May 1, 1999, XP002128083, O95034 (clone RG041D11), Hinxton, GB.
Diss et al. (1998) "Expression of skeletal muscle-type voltage-gated Na+ channel in rat and human prostate cancer cell lines," FEBS Letters 427:5-10.
Dulcert et al., Genbank, (Accession No. Y11840), National Library of Medicine, Bethesda MD, Feb. 11, 1999.
Greenspan et al., (Nature Biotechnology 7:936-937 (1999)).
Grimes et al. (1998) "Electrophysiological characterization of voltage-gated Na+ current expressed in the highly metastatic Mat-LyLu cell line of rat prostate cancer," Journal of Cellular Physiology 175:50-58.
Gutierrez et al. (1999) "Activation of a $Ca^{2+}$-permeable cation channel by two different inducers of appoptosis in a human prostatic cancer cell line," Journal of Physiology 517.1:95-107.
Haverstick et al. (2000) "Inhibition of human prostate cancer proliferation in vitro and in a mouse model by a compound synthesized to block $Ca^{2+}$ Entry[1]," Cancer Research pp. 1002-1008.
Herbert et al. (The Dictionary of Immunology, Academic Press, 4th edition, 1995).
International Search Report mailed on Apr. 28, 2003, for PCT patent appliction No. PCT/US02/28371 filed on Sep. 6, 2002, 1 page.
Lazar et al. (1988) Mol. Cell. Biol. 8(3):1247-1252.
Lepple-Wienhues et al. (1996) "K + Channels and the intracellular calcium signal in human melanoma cell proliferation," J. Membrane Biol. 151:149-157.
Marino et al. (1994) "Association between cell membrane potential and breast cancer," Tumor Biol. 15:82-89.
Nie et al. (1997) "Inhibition of proliferation of MCF-7 breast cancer cells by a blocker of $Ca^{2+}$-permeable channel," Cell Calcium 22(2):75-82.
Pancrazio et al. (1989) "Voltage-dependent ion channels in small-cell lung cancer cells[1]," Cancer Research 49:5901-5906.
Rieger et al., Glossary of Genetics and Cytogenetics, Springer-Verlag (1976) p. 17.
Skryma et al. (1997) "Potassium conductance in the androgen-sensitive prostate cancer cell line, LNCaP: involvement in cell proliferation," The Prostate 33:112-122.
International Search Report mailed on Apr. 28, 2003, for PCT patent application No. PCT/US02/28371 filed on Sep. 6, 2002, 1 page.
Haverstick et al., Cancer Research (2000) pp. 1002-1008.
Diss et al., FEBS Letters (1998) 427:5-10.
Grimes and Djamgoz, Journal of Cellular Physiology (1998) 175:50-58.
Skryma et al., The Prostate (1997) 33:112-122.
Gutierrez et al., Journal of Physiology (1999) 517.1:95-107.
Lepple-Wienhues et al., J. Membrane Biol. (1996) 151:149-157.
Marino et al., Tumor Biol. (1994) 15:82-89.
Pancrazio et al., Cancer Research (1989) 49:5901-5906.
Nie et al., Cell Calcium (1997) 22(2):75-82.
Abu-Threideh et al., EMBL/Genbank/DDBJ Databases, Jun. 1998.
Abu-Threidah et al., Genbank, (Accession No. 095034), National Library of Medicine, Bethesda MD, May 1, 1999.
Herbert et al., The Dictionary of Immunology, Academic Press, 4th edition, 1995.
Greenspan et al., Nature Biotechnology (1999) 7:936-937.
Duclert et al., Genbank, (Accession No. Y11840), National Library of Medicine, Bethesda MD, Feb. 11, 1999.
Gura, Science (1997) 278:1041-1042.
Spitler, Cancer Biotherapy (1995) 10:1-3.
Bellone et al., Immunology Today (1999) 20(10):457-462.
Alberts et al., Molecular Biology of the Cell, 3rd edition, 1994, p. 465.
Shantz and Pegg, Int. J. of Biochem. and Cell Biol. (1999) 31:107-122.
McClean and Hill, Eur. J. of Cancer (1993) 29:2243-2248.
Fu et al., EMBO Journal (1996) 15:4392-4401.
Database EMBL "Human BAC clone CTB-167B5 from 7q21, complete sequence," Jun. 17, 1998, XP002173859 (Accession AC 003991 Waterstone, R.).
Hubert et al., PNAS USA (1999) 96(25):14523-14528.
Burgess et al., Jnl. Cell Bio. (1990) 111:2129-2138.
Lazar et al., Mol. Cell Bio. (1988) 8(3):1247-1252.
Bowie et al., Science (1990) 247:1306-1310.
Rieger et al., Glossary of Genetics and Cytogenetics, Springer-Verlag 1976, p. 17.
International Search Report mailed on May 11, 2004, for PCT patent application No. PCT/US03/18661 filed on Jun. 11, 2003, 3 pages.
Challita-Eid Pia M., et al., "Monoclonal antibodies to six-transmembrane epithelial antigen of the prostate-1 inhibit intercellular communication in vitro and growth of human tumor xenografts in vivo", vol. 67, No. 12, pp. 5798-5805, (2007).
Faris M., et al., "Validation of STEAP-1 as a cell surface cancer therapeutic target", Proceedings of the annual meeting of the American Association for Cancer Research, vol. 43. p. 947, (2002).

* cited by examiner

STEAP-1 SSH sequence of 436 nucleotides. (SEQ ID NO: 1)

```
  1 GTACAGCAAA AAAGAAACTG AGAAGCCCAA ACTGCTTTCT TGTTAACATC CACTTATCCA
 61 ACCAATGTGG AAACTTCTTA TACTTGGTTC CATTATGAAG TTGGACAATT GCTGCTATCA
121 CACCTGGCAG GTAAACCAAT GCCAAGAGAG TGATGGAAAC CATTGGCAAG ACTTTGTTGA
181 TGACCAGGAT TGGAATTTTA TAAAAATATT GTTGATGGGA AGTTGCTAAA GGGTGAATTA
241 CTTCCCTCAG AAGAGTGTAA AGAAAAGTCA GAGATGCTAT AATAGCAGCT ATTTTAATTG
301 GCAAGTGCCA CTGTGGAAAG AGTTCCTGTG TGTGCTGAAG TTCTGAAGGG CAGTCAAATT
361 CATCAGCATG GGCTATTTGG TGCAAATGCA AAAGCACAGG TCTTTTTAGC ATGCTGGTCT
421 CTCCCGTGTC CTTATG
```

Figure 1

The cDNA (SEQ ID NO: 2) and amino acid sequence (SEQ ID NO: 3) of STEAP-1 v.1
The start methionine is underlined. The open reading frame extends from nucleic acid
66-1085 including the stop codon

```
   1 ccgagactcacggtcaagctaaggcgaagagtgggtggctgaagccatactattttatag
   1      M  E  S  R  K  D  I  T  N  Q  E  E  L  W  K  M  K  P  R
  61 aattaATGGAAAGCAGAAAAGACATCACAAACCAAGAAGAACTTTGGAAAATGAAGCCTA
  20   R  N  L  E  E  D  D  Y  L  H  K  D  T  G  E  T  S  M  L  K
 121 GGAGAAATTTAGAAGAAGACGATTATTTGCATAAGGACACGGGAGAGACCAGCATGCTAA
  40   R  P  V  L  L  H  L  H  Q  T  A  H  A  D  E  F  D  C  P  S
 181 AAAGACCTGTGCTTTTGCATTTGCACCAAACAGCCCATGCTGATGAATTTGACTGCCCTT
  60   E  L  Q  H  T  Q  E  L  F  P  Q  W  H  L  P  I  K  I  A  A
 241 CAGAACTTCAGCACACACAGGAACTCTTTCCACAGTGGCACTTGCCAATTAAAATAGCTG
  80   I  I  A  S  L  T  F  L  Y  T  L  L  R  E  V  I  H  P  L  A
 301 CTATTATAGCATCTCTGACTTTTCTTTACACTCTTCTGAGGGAAGTAATTCACCCTTTAG
 100   T  S  H  Q  Q  Y  F  Y  K  I  P  I  L  V  I  N  K  V  L  P
 361 CAACTTCCCATCAACAATATTTTTATAAAATTCCAATCCTGGTCATCAACAAAGTCTTGC
 120   M  V  S  I  T  L  L  A  L  V  Y  L  P  G  V  I  A  A  I  V
 421 CAATGGTTTCCATCACTCTCTTGGCATTGGTTTACCTGCCAGGTGTGATAGCAGCAATTG
 140   Q  L  H  N  G  T  K  Y  K  K  F  P  H  W  L  D  K  W  M  L
 481 TCCAACTTCATAATGGAACCAAGTATAAGAAGTTTCCACATTGGTTGGATAAGTGGATGT
 160   T  R  K  Q  F  G  L  L  S  F  F  F  A  V  L  H  A  I  Y  S
 541 TAACAAGAAAGCAGTTTGGGCTTCTCAGTTTCTTTTTTGCTGTACTGCATGCAATTTATA
 180   L  S  Y  P  M  R  R  S  Y  R  Y  K  L  L  N  W  A  Y  Q  Q
 601 GTCTGTCTTACCCAATGAGGCGATCCTACAGATACAAGTTGCTAAACTGGGCATATCAAC
 200   V  Q  Q  N  K  E  D  A  W  I  E  H  D  V  W  R  M  E  I  Y
 661 AGGTCCAACAAAATAAAGAAGATGCCTGGATTGAGCATGATGTTTGGAGAATGGAGATTT
 220   V  S  L  G  I  V  G  L  A  I  L  A  L  L  A  V  T  S  I  P
 721 ATGTGTCTCTGGGAATTGTGGGATTGGCAATACTGGCTCTGTTGGCTGTGACATCTATTC
 240   S  V  S  D  S  L  T  W  R  E  F  H  Y  I  Q  S  K  L  G  I
 781 CATCTGTGAGTGACTCTTTGACATGGAGAGAATTTCACTATATTCAGAGCAAGCTAGGAA
 260   V  S  L  L  G  T  I  H  A  L  I  F  A  W  N  K  W  I  D
 841 TTGTTTCCCTTCTACTGGGCACAATACACGCATTGATTTTTGCCTGGAATAAGTGGATAG
 280   I  K  Q  F  V  W  Y  T  P  P  T  F  M  I  A  V  F  L  P  I
 901 ATATAAAACAATTTGTATGGTATACACCTCCAACTTTTATGATAGCTGTTTTCCTTCCAA
 300   V  V  L  I  F  K  S  I  L  F  L  P  C  L  R  K  K  I  L  K
 961 TTGTTGTCCTGATATTTAAAAGCATACTATTCCTGCCATGCTTGAGGAAGAAGATACTGA
 320   I  R  H  G  W  E  D  V  T  K  I  N  K  T  E  I  C  S  Q  L
1021 AGATTAGACATGGTTGGGAAGACGTCACCAAAATTAACAAAACTGAGATATGTTCCCAGT
 340   *
1081 TGTAGaattactgtttacacacattttgttcaatattgatatattttatcaccaacatt
1141 tcaagtttgtatttgttaataaatgattacaaggaaaaaaaaaaaaaaaaa
```

Figure 2A

The cDNA (SEQ ID NO: 4) and amino acid sequence (SEQ ID NO: 5) of STEAP-1 v.2
The start methionine is underlined. The open reading frame extends from nucleic acid
96-872 including the stop codon

```
   1 ggggcccgcacctctgggcagcagcggcagccgagactcacggtcaagctaaggcgaaga
   1                                             M  E  S  R  K  D  I  T  N
  61 gtgggtggctgaagccatactatttatagaattaATGGAAAGCAGAAAAGACATCACAA
  10  Q  E  E  L  W  K  M  K  P  R  R  N  L  E  E  D  D  Y  L  H
 121 ACCAAGAAGAACTTTGGAAAATGAAGCCTAGGAGAAATTTAGAAGAAGACGATTATTTGC
  30  K  D  T  G  E  T  S  M  L  K  R  P  V  L  L  H  L  H  Q  T
 181 ATAAGGACACGGGAGAGACCAGCATGCTAAAAAGACCTGTGCTTTTGCATTTGCACCAAA
  50  A  H  A  D  E  F  D  C  P  S  E  L  Q  H  T  E  L  F  P
 241 CAGCCCATGCTGATGAATTTGACTGCCCTTCAGAACTTCAGCACACACAGGAACTCTTTC
  70  Q  W  H  L  P  I  K  I  A  A  I  I  A  S  L  T  F  L  Y  T
 301 CACAGTGGCACTTGCCAATTAAAATAGCTGCTATTATAGCATCTCTGACTTTTCTTTACA
  90  L  L  R  E  V  I  H  P  L  A  T  S  H  Q  Q  Y  F  Y  K  I
 361 CTCTTCTGAGGGAAGTAATTCACCCCTTAGCAACTTCCCATCAACAATATTTTTATAAAA
 110  P  I  L  V  I  N  K  V  L  P  M  V  S  I  T  L  L  A  L  V
 421 TTCCAATCCTGGTCATCAACAAAGTCTTGCCAATGGTTTCCATCACTCTCTTGGCATTGG
 130  Y  L  P  G  V  I  A  A  I  V  Q  L  H  N  G  T  K  Y  K  K
 481 TTTACCTGCCAGGTGTGATAGCAGCAATTGTCCAACTTCATAATGGAACCAAGTATAAGA
 150  F  P  H  W  L  D  K  W  M  L  T  R  K  Q  F  G  L  L  S  F
 541 AGTTTCCACATTGGTTGGATAAGTGGATGTTAACAAGAAAGCAGTTTGGGCTTCTCAGTT
 170  F  F  A  V  L  H  A  I  Y  S  L  S  Y  P  M  R  R  S  Y  R
 601 TCTTTTTTGCTGTACTGCATGCAATTTATAGTCTGTCTTACCCAATGAGGCGATCCTACA
 190  Y  K  L  L  N  W  A  Y  Q  Q  V  Q  Q  N  K  E  D  A  W  I
 661 GATACAAGTTGCTAAACTGGGCATATCAACAGGTCCAACAAAATAAAGAAGATGCCTGGA
 210  E  H  D  V  W  R  M  E  I  Y  V  S  L  G  I  V  G  L  A  I
 721 TTGAGCATGATGTTTGGAGAATGGAGATTTATGTGTCTCTGGGAATTGTGGGATTGGCAA
 230  L  A  L  L  A  V  T  S  I  P  S  V  S  D  S  L  T  W  R  E
 781 TACTGGCTCTGTTGGCTGTGACATCTATTCCATCTGTGAGTGACTCTTTGACATGGAGAG
 250  F  H  Y  I  Q  V  N  N  I  *
 841 AATTTCACTATATTCAGGTAAATAATATATAAaataaccctaagaggtaaatcttctttt
 901 tgtgtttatgatatagaatatgttgactttaccccataaaaataacaaatgtttttcaa
 961 cagcaaagatcttatacttgttccaattaataatgtgctctcctgttgttttccctattg
1021 cttctaattaggacaagtgtttcctagacataaataaaaggcattaaaatattctttgtt
1081 ttttttttttgtttgtttgttttttgtttgtttgttttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaatttttgtattttagtagagacagggttttcccatgttggccagg
1321 ctggtctcgatctcctgacctcaaatgatccgcccacctcggcctcccaaagtgctggga
1381 tgacagttgtgagccaccacactcagcctgctctttctaatatttgaaacttgttagaca
1441 atttgctacccatctaatgtgatattttaggaatccaatatgcatggtttattatttctt
```

Figure 2B (Part 1)

```
1501 aaaaaaaatattcttttacctgtcacctgaatttagtaatgccttttatgttacacaact
1561 tagcactttccagaaacaaaaactctctccttgaaataatagagttttatctaccaaag
1621 atatgctagtgtctcatttcaaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctgggatccttg
1801 tctgacaagattcaaggactaaattaattcagtcatgaacactgccaattaccgttta
1861 tgggtagacatctttggaaatttccacaaggtcagacattcgcaactatcccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgcttttagacttcattaggaatt
2161 taggactgcatcttgacaactgagcctattctactatatgtacaatacctagcccataat
2221 aggtatacaatacacatttggtaaaactaattttcaaccaatgacatgtattttcaact
2281 agtaacctagaaatgtttcacttaaaatctgagaactggttacactacaagttaccttgg
2341 agattcatatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaaagaggtgttgtcagaacaccgttgagattacata
2521 ggtgaacaactattttaagcaactttatttgtgtagtgacaaagcatcccaatgcaggc
2581 tgaaatgtttcatcacatctctggatctctattttgtgcagacattgaaaaaattgtt
2641 catattatttccatgttatcagaatatttgattttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtccctgatttaggtatcctgtgaaaagcagaattaagacaaatacacaagagacaa
2941 agcacaaaaataaatatcataaggggatgaacaaaatggtggagaaagagtagacaaag
3001 ttttgatcacctgccttcaaagaaaggctgtgaattttgttcacttagacagcttggag
3061 acaagaaattacccaaaagtaaggtgaggaggataggcaaaaagagcagaaagatgtgaa
3121 tggacattgttgagaaatgtgataggaaaacaatcatagataaaggatttccaagcaaca
3181 gagcatatccagatgaggtaggatgggataaactcttattgaaccaatcttcaccaattt
3241 tgttttcttttgcagagcaagctaggaattgtttcccttctactgggcacaatacacgc
3301 attgattttgcctggaataagtggatagatataaaacaatttgtatggtatacacctcc
3361 aacttttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacatttttgtt
3541 caatattgatatatttttatcaccaacatttcaagtttgtatttgttaataaaatgattat
3601 tcaaggaaaaaaaaaaaaaaaaaaaaa
```

Figure 2B (Part 2)

The cDNA (SEQ ID NO: 6) and amino acid sequence (SEQ ID NO: 7) of STEAP-1 v.3
The start methionine is underlined. The open reading frame extends from nucleic acid
96-944 including the stop codon

```
   1 ggggcccgcacctctgggcagcagcggcagccgagactcacggtcaagctaaggcgaaga
   1                                              M  E  S  R  K  D  I  T  N
  61 gtgggtggctgaagccatactattttatagaattaATGGAAAGCAGAAAAGACATCACAA
  10  Q  E  E  L  W  M  K  P  R  R  N  L  E  E  D  D  Y  L  H
 121 ACCAAGAAGAACTTTGGAAAATGAAGCCTAGGAGAAATTTAGAAGAAGACGATTATTTGC
  30  K  D  T  G  E  T  S  M  L  K  R  P  V  L  L  H  L  H  Q  T
 181 ATAAGGACACGGGAGAGACCAGCATGCTAAAAAGACCTGTGCTTTTGCATTTGCACCAAA
  50  A  H  A  D  E  F  D  C  P  S  E  L  Q  H  T  Q  E  L  F  P
 241 CAGCCCATGCTGATGAATTTGACTGCCCTTCAGAACTTCAGCACACACAGGAACTCTTTC
  70  Q  W  H  L  P  I  K  I  A  A  I  I  A  S  L  T  F  L  Y  T
 301 CACAGTGGCACTTGCCAATTAAAATAGCTGCTATTATAGCATCTCTGACTTTTCTTTACA
  90  L  L  R  E  V  I  H  P  L  A  T  S  H  Q  Q  Y  F  Y  K  I
 361 CTCTTCTGAGGGAAGTAATTCACCCTTTAGCAACTTCCCATCAACAATATTTTTATAAAA
 110  P  I  L  V  I  N  K  V  L  P  M  V  S  I  T  L  L  A  L  V
 421 TTCCAATCCTGGTCATCAACAAAGTCTTGCCAATGGTTTCCATCACTCTCTTGGCATTGG
 130  Y  L  P  G  V  I  A  A  I  V  Q  L  H  N  G  T  K  Y  K  K
 481 TTTACCTGCCAGGTGTGATAGCAGCAATTGTCCAACTTCATAATGGAACCAAGTATAAGA
 150  F  P  H  W  L  D  K  W  M  L  T  R  K  Q  F  G  L  L  S  F
 541 AGTTTCCACATTGGTTGGATAAGTGGATGTTAACAAGAAAGCAGTTTGGGCTTCTCAGTT
 170  F  F  A  V  L  H  A  I  Y  S  L  S  Y  P  M  R  R  S  Y  R
 601 TCTTTTTTGCTGTACTGCATGCAATTTATAGTCTGTCTTACCCAATGAGGCGATCCTACA
 190  Y  K  L  L  N  W  A  Y  Q  Q  V  Q  Q  N  K  E  D  A  W  I
 661 GATACAAGTTGCTAAACTGGGCATATCAACAGGTCCAACAAAATAAAGAAGATGCCTGGA
 210  E  H  D  V  W  R  M  E  I  Y  V  S  L  G  I  V  G  L  A  I
 721 TTGAGCATGATGTTTGGAGAATGGAGATTTATGTGTCTCTGGGAATTGTGGGATTGGCAA
 230  L  A  L  L  A  V  T  S  I  P  S  V  S  D  S  L  T  W  R  E
 781 TACTGGCTCTGTTGGCTGTGACATCTATTCCATCTGTGAGTGACTCTTTGACATGGAGAG
 250  F  H  Y  I  Q  I  I  H  K  K  S  D  V  P  E  S  L  W  D  P
 841 AATTTCACTATATTCAGATTATCCATAAGAAGAGTGATGTGCCAGAATCACTCTGGGATC
 270  C  L  T  R  F  K  G  L  N  L  I  Q  S  *
 901 CTTGTCTGACAAGATTCAAAGGACTAAATTTAATTCAGTCATGAacactgccaattaccg
 961 tttatgggtagacatctttggaaatttccacaagagcaagctaggaattgtttcccttct
1021 actggcacaatacacgcattgattttgcctggaataagtggatagatataaaacaatt
1081 tgtatggtatacacctccaacttttatgatagctgttttccttccaattgttgtcctgat
1141 atttaaaagcatactattcctgccatgcttgaggaagaagatactgaagattagacatgg
1201 ttgggaagacgtcaccaaaattaacaaaactgagatatgttcccagttgtagaattactg
1261 tttacacacattttgttcaatattgatatatttcatccaacatttcaagtttgtatt
1321 tgttaataaaatgattattcaaggaaaaaaaaaaaaaaaaaaaa
```

Figure 2C

The cDNA (SEQ ID NO: 8) and amino acid sequence (SEQ ID NO: 9) of STEAP-1 v.4
The start methionine is underlined. The open reading frame extends from nucleic acid
96-872 including the stop codon

```
   1 ggggcccgcacctctgggcagcagcggcagccgagactcacggtcaagctaaggcgaaga
   1                                                 M  E  S  R  K  D  I  T  N
  61 gtgggtggctgaagccatactatttatagaattaATGGAAAGCAGAAAAGACATCACAA
  10  Q  E  E  L  W  K  M  K  P  R  R  N  L  E  E  D  D  Y  L  H
 121 ACCAAGAAGAACTTTGGAAAATGAAGCCTAGGAGAAATTTAGAAGAAGACGATTATTTGC
  30  K  D  T  G  E  T  S  M  L  K  R  P  V  L  L  H  L  H  Q  T
 181 ATAAGGACACGGGAGAGACCAGCATGCTAAAAAGACCTGTGCTTTTGCATTTGCACCAAA
  50  A  H  A  D  E  F  D  C  P  S  E  L  Q  H  T  Q  E  L  F  P
 241 CAGCCCATGCTGATGAATTTGACTGCCCTTCAGAACTTCAGCACACACAGGAACTCTTTC
  70  Q  W  H  L  P  I  K  I  A  A  I  I  A  S  L  T  F  L  Y  T
 301 CACAGTGGCACTTGCCAATTAAAATAGCTGCTATTATAGCATCTCTGACTTTTCTTTACA
  90  L  L  R  E  V  I  H  P  L  A  T  S  H  Q  Q  Y  F  Y  K  I
 361 CTCTTCTGAGGGAAGTAATTCACCCCTTAGCAACTTCCCATCAACAATATTTTTATAAAA
 110  P  I  L  V  I  N  K  V  L  P  M  V  S  I  T  L  L  A  L  V
 421 TTCCAATCCTGGTCATCAACAAAGTCTTGCCAATGGTTTCCATCACTCTCTTGGCATTGG
 130  Y  L  P  G  V  I  A  A  I  V  Q  L  H  N  G  T  K  Y  K  K
 481 TTTACCTGCCAGGTGTGATAGCAGCAATTGTCCAACTTCATAATGGAACCAAGTATAAGA
 150  F  P  H  W  L  D  K  W  M  L  T  R  K  Q  F  G  L  L  S  L
 541 AGTTTCCACATTGGTTGGATAAGTGGATGTTAACAAGAAAGCAGTTTGGGCTTCTCAGTT
 170  F  F  A  V  L  H  A  I  Y  S  L  S  Y  P  M  R  R  S  Y  R
 601 TGTTTTTTGCTGTACTGCATGCAATTTATAGTCTGTCTTACCCAATGAGGCGATCCTACA
 190  Y  K  L  L  N  W  A  Y  Q  Q  V  Q  Q  N  K  E  D  A  W  I
 661 GATACAAGTTGCTAAACTGGGCATATCAACAGGTCCAACAAAATAAAGAAGATGCCTGGA
 210  E  H  D  V  W  R  M  E  I  Y  V  S  L  G  I  V  G  L  A  I
 721 TTGAGCATGATGTTTGGAGAATGGAGATTTATGTGTCTCTGGGAATTGTGGGATTGGCAA
 230  L  A  L  L  A  V  T  S  I  P  S  V  S  D  S  L  T  W  R  E
 781 TACTGGCTCTGTTGGCTGTGACATCTATTCCATCTGTGAGTGACTCTTTGACATGGAGAG
 250  F  H  Y  I  Q  V  N  N  I  *
 841 AATTTCACTATATTCAGGTAAATAATATATAAaataaccctaagaggtaaatcttcttt
 901 tgtgtttatgatatagaatatgttgactttaccccataaaaataacaaatgtttttcaa
 961 cagcaaagatcttatacttgttccaattaataatgtgctctcctgttgttttccctattg
1021 cttctaattaggacaagtgtttcctagacataaataaaaggcattaaaatattctttgtt
1081 ttttttttttgtttgtttgtttttgtttgtttgtttttttgagatgaagtctcg
1141 ctctgttgccatgctggagtacagtggcacgatctcggctcactgcaacctgcgcctcc
1201 tgggttcaggcgattctcttgcctcagcctcctgagtagctgggattacaggcacccatc
1261 accatgtccagctaattttgtattttagtagagacagggttttcccatgttggccagg
1321 ctggtctcgatctcctgacctcaaatgatccgcccacctcggcctcccaaagtgctggga
1381 tgacagttgtgagccaccacactcagcctgctctttctaatatttgaacttgttagaca
1441 atttgctacccatctaatgtgatattttaggaatccaatatgcatggtttattatttctt
```

Figure 2D (Part 1)

```
1501 aaaaaaaatattcttttacctgtcacctgaatttagtaatgccttttatgttacacaact
1561 tagcactttccagaaacaaaaactctctccttgaaataatagagttttatctaccaaag
1621 atatgctagtgtctcatttcaaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctgggatccttg
1801 tctgacaagattcaaaggactaaatttaattcagtcatgaacactgccaattaccgttta
1861 tgggtagacatctttggaaatttccacaaggtcagacattcgcaactatcccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgcttttagacttcattaggaatt
2161 taggactgcatcttgacaactgagcctattctactatatgtacaatacctagcccataat
2221 aggtatacaatacacatttggtaaaactaattttcaaccaatgacatgtatttttcaact
2281 agtaacctagaaatgtttcacttaaaatctgagaactggttacactacaagttaccttgg
2341 agattcatatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaagaggtgttgtcagaacaccgttgagattacata
2521 ggtgaacaactattttaagcaactttatttgtgtagtgacaaagcatcccaatgcaggc
2581 tgaaatgtttcatcacatctctggatctctctattttgtgcagacattgaaaaattgtt
2641 catattatttccatgttatcagaatatttgatttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtccctgattttaggtatcctgtgaaaagcagaattaagacaaatacacaagagacaa
2941 agcacaaaaataaatatcataaggggatgaacaaaatggtggagaaagagtagacaaag
3001 tttttgatcacctgccttcaaagaaaggctgtgaattttgttcacttagacagcttggag
3061 acaagaaattacccaaaagtaaggtgaggaggataggcaaaaagagcagaaagatgtgaa
3121 tggacattgttgagaaatgtgataggaaaacaatcatagataaaggatttccaagcaaca
3181 gagcatatccagatgaggtaggatgggataaactcttattgaaccaatcttcaccaattt
3241 tgttttcttttgcagagcaagctaggaattgtttccttctactgggcacaatacacgc
3301 attgattttgcctggaataagtggatagatataaaacaatttgtatggtatacacctcc
3361 aacttttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacattttgtt
3541 caatattgatatatttatcaccaacatttcaagtttgtatttgttaataaaatgattat
3601 tcaaggaaaaaaaaaaaaaaaaaaaaaa
```

Figure 2D (Part 2)

The cDNA (SEQ ID NO: 10) and amino acid sequence (SEQ ID NO: 11) of STEAP-1 v.5
The start methionine is underlined. The open reading frame extends from nucleic acid
96-872 including the stop codon

```
   1 ggggcccgcacctctgggcagcagcggcagccgagactcacggtcaagctaaggcgaaga
   1                                            M  E  S  R  K  D  I  T  N
  61 gtgggtggctgaagccatactatttaatagaattaATGGAAAGCAGAAAAGACATCACAA
  10  Q  E  E  L  W  K  M  P  R  R  N  L  E  E  D  D  Y  L  H
 121 ACCAAGAAGAACTTTGGAAAATGAAGCCTAGGAGAAATTTAGAAGAAGACGATTATTTGC
  30  K  D  T  G  E  T  S  M  L  K  R  P  V  L  L  H  L  Q  T
 181 ATAAGGACACGGGAGAGACCAGCATGCTAAAAAGACCTGTGCTTTTGCATTTGCACCAAA
  50  A  H  A  D  E  F  D  C  P  S  E  L  Q  H  T  Q  E  L  F  P
 241 CAGCCCATGCTGATGAATTTGACTGCCCTTCAGAACTTCAGCACACACAGGAACTCTTTC
  70  Q  W  H  L  P  I  K  I  A  A  I  I  A  S  L  T  F  L  Y  T
 301 CACAGTGGCACTTGCCAATTAAAATAGCTGCTATTATAGCATCTCTGACTTTTCTTTACA
  90  L  L  R  E  V  I  H  P  L  A  T  S  H  Q  Q  Y  F  Y  K  I
 361 CTCTTCTGAGGGAAGTAATTCACCCTTTAGCAACTTCCCATCAACAATATTTTTATAAAA
 110  P  I  L  V  I  N  K  V  L  P  M  V  S  I  T  L  L  A  L  V
 421 TTCCAATCCTGGTCATCAACAAAGTCTTGCCAATGGTTTCCATCACTCTCTTGGCATTGG
 130  Y  L  P  G  V  I  A  A  I  V  Q  L  H  N  G  T  K  Y  K  K
 481 TTTACCTGCCAGGTGTGATAGCAGCAATTGTCCAACTTCATAATGGAACCAAGTATAAGA
 150  F  P  H  W  L  D  K  W  M  L  T  R  K  Q  F  G  L  L  S  F
 541 AGTTTCCACATTGGTTGGATAAGTGGATGTTAACAAGAAAGCAGTTTGGGCTTCTCAGTT
 170  F  F  A  V  L  H  A  I  Y  S  L  S  Y  P  M  R  R  S  Y  R
 601 TCTTTTTTGCTGTACTGCATGCAATTTATAGTCTGTCTTACCCAATGAGGCGATCCTACA
 190  Y  K  L  L  N  W  A  Y  Q  Q  V  Q  Q  N  K  E  D  A  W  I
 661 GATACAAGTTGCTAAACTGGGCATATCAACAGGTCCAACAAAATAAAGAAGATGCCTGGA
 210  E  H  D  V  W  R  M  E  I  Y  V  S  L  G  I  V  G  L  A  I
 721 TTGAGCATGATGTTTGGAGAATGGAGATTTATGTGTCTCTGGGAATTGTGGGATTGGCAA
 230  L  A  L  L  A  V  T  S  I  P  S  V  S  D  S  L  T  W  R  E
 781 TACTGGCTCTGTTGGCTGTGACATCTATTCCATCTGTGAGTGACTCTTTGACATGGAGAG
 250  F  H  Y  I  Q  V  N  N  I  *
 841 AATTTCACTATATTCAGGTAAATAATATATAAaataaccctaagaggtaaatcttctttt
 901 tgtgtttatgatatagaatatgttgactttaccccataaaaaataacaaatgtttttcaa
 961 cagcaaagatcttatacttgttccaattaataatgtgctctcctgttgttttcctattg
1021 cttctaattaggacaagtgtttcctagacataaataaaaggcattaaaatattctttgtt
1081 tttttttttttgtttgtttgttttttgtttgtttgtttgtttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaattttgtatttttagtagagacagggttttccatgttggccagg
1321 ctggtctcgatctcctgacctcaaatgatccgcccacctcggcctcccaaagtgctggga
1381 tgacagttgtgagccaccacactcagcctgctctttctaatatttgaaacttgttagaca
1441 atttgctacccatctaatgtgatattttaggaatccaatatgcatggtttattatttctt
```

Figure 2E (Part 1)

```
1501 aaaaaaaatattcttttacctgtcacctgaatttagtaatgccttttatgttacacaact
1561 tagcactttccagaaacaaaaactctctccttgaaataatagagttttatctaccaaag
1621 atatgctagtgtctcatttcaaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctgggatccttg
1801 tctgacaagattcaaaggactaaatttaattcagtcatgaacactgccaattaccgttta
1861 tgggtagacatctttggaaatttccacaaggtcagacattcgcaactatcccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgcttttagacttcattaggaatt
2161 taggactgcatcttgacaactgagcctattctactatatgtacaatacctagcccataat
2221 aggtatacaatacacatttggtaaaactaattttcaaccaatgacatgtattttcaact
2281 agtaacctagaaatgtttcacttaaaatctgagaactggttacactacaagttaccttgg
2341 agattcatatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaagaggtgttgtcagaacaccgttgagattacata
2521 ggtgaacaactattttaagcaactttatttgtgtagtgacaaagcatcccaatgcaggc
2581 tgaaatgtttcatcacatctctggatctctctattttgtgcagacattgaaaaaattgtt
2641 catattatttccatgttatcagaatatttgatttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtcctgattttaggtatcctgtgaaaagcagaattaagacaaatacacaagagacaa
2941 agcacaaaaataaatatcataagggatgaacaaaatggtggagaaagagtagacaaag
3001 ttttgatcacctgccttcaaagaaaggctgtgaattttgttcacttagacagcttggag
3061 acaagaaattacccaaaagtaaggtgaggaggataggcaaaagagcagaaagatgtgaa
3121 tggacattgttgagaaatgtgataggaaaacaatcatagataaggatttccaagcaaca
3181 gagcatatccagatgaggtaggatgggataaactcttattgaaccaatcttcaccaattt
3241 tgttttcttttgcagagcaagctaggaattgtttccttctactgggcacaatacacgc
3301 attgattttgcctggaataagtggatagatataaaacaatttgtatggtatacacctcc
3361 aactttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacattttgtt
3541 caatattgatatattttatcaccaacatttcaagtttgtatttgttaataaaatgattat
3601 tcaaggaaaaaaaaaaaaaaaaaaaaaa
```

Figure 2E (Part 2)

The cDNA (SEQ ID. NO.: 12) and amino acid sequence (SEQ ID NO: 13) of STEAP-1 v.6
The start methionine is underlined. The open reading frame extends from nucleic acid
96-872 including the stop codon

```
   1 ggggcccgcacctctgggcagcagcggcagccgagactcacggtcaagctaaggcgaaga
   1                                                  M  E  S  R  K  D  I  T  N
  61 gtgggtggctgaagccatactatttatagaattaATGGAAAGCAGAAAAGACATCACAA
  10  Q  E  E  L  W  K  M  K  P  R  R  N  L  E  E  D  D  Y  L  H
 121 ACCAAGAAGAACTTTGGAAAATGAAGCCTAGGAGAAATTTAGAAGAAGACGATTATTTGC
  30  K  D  T  G  E  T  S  M  L  K  R  P  V  L  L  H  L  H  Q  T
 181 ATAAGGACACGGGAGAGACCAGCATGCTAAAAAGACCTGTGCTTTTGCATTTGCACCAAA
  50  A  H  A  D  E  F  D  C  P  S  E  L  Q  H  T  Q  E  L  F  P
 241 CAGCCCATGCTGATGAATTTGACTGCCCTTCAGAACTTCAGCACACACAGGAACTCTTTC
  70  Q  W  H  L  P  I  K  I  A  A  I  I  A  S  L  T  F  L  Y  T
 301 CACAGTGGCACTTGCCAATTAAAATAGCTGCTATTATAGCATCTCTGACTTTTCTTTACA
  90  L  L  R  E  V  I  H  P  L  A  T  S  H  Q  Q  Y  F  Y  K  I
 361 CTCTTCTGAGGGAAGTAATTCACCCCTTAGCAACTTCCCATCAACAATATTTTTATAAAA
 110  P  I  L  V  I  N  K  V  L  P  M  V  S  I  T  L  L  A  L  V
 421 TTCCAATCCTGGTCATCAACAAAGTCTTGCCAATGGTTTCCATCACTCTCTTGGCATTGG
 130  Y  L  P  G  V  I  A  A  I  V  Q  L  H  N  G  T  K  Y  K  K
 481 TTTACCTGCCAGGTGTGATAGCAGCAATTGTCCAACTTCATAATGGAACCAAGTATAAGA
 150  F  P  H  W  L  D  K  W  M  L  T  R  K  Q  F  G  L  L  S  F
 541 AGTTTCCACATTGGTTGGATAAGTGGATGTTAACAAGAAAGCAGTTTGGGCTTCTCAGTT
 170  F  F  A  V  L  H  A  I  Y  S  L  S  Y  P  M  R  R  S  Y  R
 601 TCTTTTTTGCTGTACTGCATGCAATTTATAGTCTGTCTTACCCAATGAGGCGATCCTACA
 190  Y  K  L  L  N  W  A  Y  Q  Q  V  Q  Q  N  K  E  D  A  W  I
 661 GATACAAGTTGCTAAACTGGGCATATCAACAGGTCCAACAAAATAAAGAAGATGCCTGGA
 210  E  H  D  V  W  R  M  E  I  Y  V  S  L  G  I  V  G  L  A  I
 721 TTGAGCATGATGTTTGGAGAATGGAGATTTATGTGTCTCTGGGAATTGTGGGATTGGCAA
 230  L  A  L  L  A  V  T  S  I  P  S  V  S  D  S  L  T  W  R  E
 781 TACTGGCTCTGTTGGCTGTGACATCTATTCCATCTGTGAGTGACTCTTTGACATGGAGAG
 250  F  H  Y  I  Q  V  N  N  I  *
 841 AATTTCACTATATTCAGGTAAATAATATATAAataaccctaagaggtaaatcttcttt
 901 tgtgtttatgatatagaatatgttgactttaccccataaaaaataacaaatgttttcaa
 961 cagcaaagatcttatacttgttccaattaataatgtgctctcctgttgttttccctattg
1021 cttctaattaggacaagtgtttcctagacataaataaaggcattaaaatattctttgtt
1081 ttttttgttttgtttgtttgtttttgtttgtttgttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaattttgtattttagtagagacagggttttcccatgttggccagg
1321 ctggtctcgatctcctgacctcaaatgatccgcccacctcggcctcccaaagtgctggga
1381 tgacagttgtgagccaccacactcagcctgctctttctaatatttgaacttgttagaca
1441 atttgctacccatctaatgtgatattttaggaatccaatatgcatggtttattatttctt
```

```
1501 aaaaaaaatattcttttacctgtcacctgaatttagtaatgccttttatgttacacaact
1561 tagcactttccagaaacaaaaactctctccttgaaataatagagttttatctaccaaag
1621 atatgctagtgtctcatttcaaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctgggatccttg
1801 tctgacaagattcaaaggactaaatttaattcagtcatgaacactgccaattaccgttta
1861 tgggtagacatctttggaaatttccacaaggtcagacattcgcaactatcccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgcttttagacttcattaggaatt
2161 taggactgcatcttgacaactgagcctattctactatatgtacaatacctagcccataat
2221 aggtatacaatacacatttggtaaaactaattttcaaccaatgacatgtattttcaact
2281 agtaacctagaaatgtttcacttaaaatctgagaactggttacactacaagttaccttgg
2341 agattcatatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaagaggtgttgtcagaacaccgttgagattacata
2521 ggtgaacaactattttaagcaactttatttgtgtagtgacaaagcatcccaatgcaggc
2581 tgaaatgtttcatcacatctctggatctctctatttgtgcagacattgaaaaaattgtt
2641 catattatttccatgttatcagaatatttgattttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtcctgattttaggtatcctgtgaaaagcagaattaagacaaatacacaagagacaa
2941 agcacaaaaataaatatcataaggggatgaacaaaatggtggagaaagagtagacaaag
3001 ttttgatcacctgccttcaaagaaaggctgtgaattttgttcacttagacagcttggag
3061 acaagaaattacccaaaagtaaggtgaggaggataggcaaaaagagcagaaagatgtgaa
3121 tggacattgttgagaaatgtgataggaaaacaatcatagataaaggatttccaagcaaca
3181 gagcatatccagatgaggtaggatgggataaactcttattgaaccaatcttcaccaattt
3241 tgttttcttttgcagagcaagctaggaattgtttcccttctactgggcacaatacacgc
3301 attgattttgcctggaataagtggatagatataaaacaatttgtatggtatacacctcc
3361 aacttttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacattttgtt
3541 caatattgatatatttatcaccaacatttcaagtttgtatttgttaataaaatgattat
3601 tcaaggaaaaaaaaaaaaaaaaaaaaa
```

Figure 2F (Part 2)

The cDNA (SEQ ID NO: 14) and amino acid sequence (SEQ ID NO: 15) of STEAP-1 v.7
The start methionine is underlined. The open reading frame extends from nucleic acid
96-872 including the stop codon

```
   1 ggggcccgcacctctgggcagcagcggcagccgagactcacggtcaagctaaggcgaaga
   1                                    M  E  S  R  K  D  I  T  N
  61 gtgggtggctgaagccatactatttatagaattaATGGAAAGCAGAAAAGACATCACAA
  10  Q  E  E  L  W  K  M  K  P  R  R  N  L  E  E  D  D  Y  L  H
 121 ACCAAGAAGAACTTTGGAAAATGAAGCCTAGGAGAAATTTAGAAGAAGACGATTATTTGC
  30  K  D  T  G  E  T  S  M  L  K  R  P  V  L  L  H  L  H  Q  T
 181 ATAAGGACACGGGAGAGACCAGCATGCTAAAAAGACCTGTGCTTTTGCATTTGCACCAAA
  50  A  H  A  D  E  F  D  C  P  S  E  L  Q  H  T  Q  E  L  F  P
 241 CAGCCCATGCTGATGAATTTGACTGCCCTTCAGAACTTCAGCACACACAGGAACTCTTTC
  70  Q  W  H  L  P  I  K  I  A  A  I  I  A  S  L  T  F  L  Y  T
 301 CACAGTGGCACTTGCCAATTAAAATAGCTGCTATTATAGCATCTCTGACTTTTCTTTACA
  90  L  L  R  E  V  I  H  P  L  A  T  S  H  Q  Q  Y  F  Y  K  I
 361 CTCTTCTGAGGGAAGTAATTCACCCCTTAGCAACTTCCCATCAACAATATTTTTATAAAA
 110  P  I  L  V  I  N  K  V  L  P  M  V  S  I  T  L  L  A  L  V
 421 TTCCAATCCTGGTCATCAACAAAGTCTTGCCAATGGTTTCCATCACTCTCTTGGCATTGG
 130  Y  L  P  G  V  I  A  A  I  V  Q  L  H  N  G  T  K  Y  K  K
 481 TTTACCTGCCAGGTGTGATAGCAGCAATTGTCCAACTTCATAATGGAACCAAGTATAAGA
 150  F  P  H  W  L  D  K  W  M  L  T  R  K  Q  F  G  L  L  S  F
 541 AGTTTCCACATTGGTTGGATAAGTGGATGTTAACAAGAAAGCAGTTTGGGCTTCTCAGTT
 170  F  F  A  V  L  H  A  I  Y  S  L  S  Y  P  M  R  R  S  Y  R
 601 TCTTTTTTGCTGTACTGCATGCAATTTATAGTCTGTCTTACCCAATGAGGCGATCCTACA
 190  Y  K  L  L  N  W  A  Y  Q  Q  V  Q  Q  N  K  E  D  A  W  I
 661 GATACAAGTTGCTAAACTGGGCATATCAACAGGTCCAACAAAATAAAGAAGATGCCTGGA
 210  E  H  D  V  W  R  M  E  I  Y  V  S  L  G  I  V  G  L  A  I
 721 TTGAGCATGATGTTTGGAGAATGGAGATTTATGTGTCTCTGGGAATTGTGGGATTGGCAA
 230  L  A  L  L  A  V  T  S  I  P  S  V  S  D  S  L  T  W  R  E
 781 TACTGGCTCTGTTGGCTGTGACATCTATTCCATCTGTGAGTGACTCTTTGACATGGAGAG
 250  F  H  Y  I  Q  V  N  N  I  *
 841 AATTTCACTATATTCAGGTAAATAATATATAAaataaccctaagaggtaaatcttcttt
 901 tgtgtttatgatatagaatatgttgactttaccccataaaaataacaaatgttttcaa
 961 cagcaaagatcttatacttgttccaattaataatgtgctctcctgttgttttccctattg
1021 cttctaattaggacaagtgtttcctagacataaataaaggcattaaaatattctttgtt
1081 tttttttttttgtttgtttgttttttgtttgtttgtttgttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaatttttgtattttagtagagacagggttttccatgttggccagg
1321 ctggtctcgatctcctgacctcaaatgatccgcccacctcggcctcccaaagtgctggga
1381 tgacagttgtgagccaccacactcagcctgctctttctaatatttgaacttgttagaca
1441 atttgccacccatctaatgtgatattttaggaatccaatatgcatggtttattatttctt
```

```
1501 aaaaaaaatattcttttacctgtcacctgaatttagtaatgccttttatgttacacaact
1561 tagcactttccagaaacaaaaactctctccttgaaataatagagttttatctaccaaag
1621 atatgctagtgtctcatttcaaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctggatccttg
1801 tctgacaagattcaaaggactaaatttaattcagtcatgaacactgccaattaccgttta
1861 tgggtagacatctttggaaatttccacaaggtcagacattcgcaactatcccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgcttttttagacttcattaggaatt
2161 taggactgcatcttgacaactgagcctattctactatatgtacaatacctagcccataat
2221 aggtatacaatacacatttggtaaaactaattttcaaccaatgacatgtattttttcaact
2281 agtaacctagaaatgtttcacttaaaatctgagaactggttacactacaagttaccttgg
2341 agattcatatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaaagaggtgttgtcagaacaccgttgagattacata
2521 ggtgaacaactattttttaagcaactttatttgtgtagtgacaaagcatcccaatgcaggc
2581 tgaaatgtttcatcacatctctggatctctctattttgtgcagacattgaaaaaattgtt
2641 catattatttccatgttatcagaatatttgatttttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtccctgattttaggtatcctgtgaaaagcagaattaagacaaatacacaagagacaa
2941 agcacaaaaataaatatcataaggggatgaacaaaatggtggagaaagagtagacaaag
3001 ttttgatcacctgccttcaaagaaaggctgtgaattttgttcacttagacagcttggag
3061 acaagaaattacccaaaagtaaggtgaggaggataggcaaaagagcagaagatgtgaa
3121 tggacattgttgagaaatgtgataggaaaacaatcatagataaggatttccaagcaaca
3181 gagcatatccagatgaggtaggatgggataaactcttattgaaccaatcttcaccaattt
3241 tgttttcttttgcagagcaagctaggaattgtttcccttctactgggcacaatacacgc
3301 attgattttgcctggaataagtggatagatataaaacaatttgtatggtatacacctcc
3361 aactttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacattttgtt
3541 caatattgatatattttatcaccaacatttcaagtttgtatttgttaataaaatgattat
3601 tcaaggaaaaaaaaaaaaaaaaaaaaaa
```

Figure 2G (Part 2)

The cDNA (SEQ ID NO: 16) and amino acid sequence (SEQ ID NO: 17) of STEAP-1 v.8
The start methionine is underlined. The open reading frame extends from nucleic acid
96-872 including the stop codon

```
   1 ggggcccgcacctctgggcagcagcggcagccgagactcacggtcaagctaaggcgaaga
   1                                              M  E  S  R  K  D  I  T  N
  61 gtgggtggctgaagccatactatttatagaattaATGGAAAGCAGAAAAGACATCACAA
  10  Q  E  E  L  W  K  M  P  R  R  N  L  E  E  D  D  Y  L  H
 121 ACCAAGAAGAACTTTGGAAAATGAAGCCTAGGAGAAATTTAGAAGAAGACGATTATTTGC
  30  K  D  T  G  E  T  S  M  L  K  R  P  V  L  L  H  L  H  Q  T
 181 ATAAGGACACGGGAGAGACCAGCATGCTAAAAAGACCTGTGCTTTTGCATTTGCACCAAA
  50  A  H  A  D  E  F  D  C  P  S  E  L  Q  H  T  Q  E  L  F  P
 241 CAGCCCATGCTGATGAATTTGACTGCCCTTCAGAACTTCAGCACACACAGGAACTCTTTC
  70  Q  W  H  L  P  I  K  I  A  A  I  I  A  S  L  T  F  L  Y  T
 301 CACAGTGGCACTTGCCAATTAAAATAGCTGCTATTATAGCATCTCTGACTTTTCTTTACA
  90  L  L  R  E  V  I  H  P  L  A  T  S  H  Q  Q  Y  F  Y  K  I
 361 CTCTTCTGAGGGAAGTAATTCACCCCTTAGCAACTTCCCATCAACAATATTTTTATAAAA
 110  P  I  L  V  I  N  K  V  L  P  M  V  S  I  T  L  L  A  L  V
 421 TTCCAATCCTGGTCATCAACAAAGTCTTGCCAATGGTTTCCATCACTCTCTTGGCATTGG
 130  Y  L  P  G  V  I  A  A  I  V  Q  L  H  N  G  T  K  Y  K  K
 481 TTTACCTGCCAGGTGTGATAGCAGCAATTGTCCAACTTCATAATGGAACCAAGTATAAGA
 150  F  P  H  W  L  D  K  W  M  L  T  R  K  Q  F  G  L  L  S  F
 541 AGTTTCCACATTGGTTGGATAAGTGGATGTTAACAAGAAAGCAGTTTGGGCTTCTCAGTT
 170  F  F  A  V  L  H  A  I  Y  S  L  S  Y  P  M  R  R  S  Y  R
 601 TCTTTTTTGCTGTACTGCATGCAATTTATAGTCTGTCTTACCCAATGAGGCGATCCTACA
 190  Y  K  L  L  N  W  A  Y  Q  Q  V  Q  Q  N  K  E  D  A  W  I
 661 GATACAAGTTGCTAAACTGGGCATATCAACAGGTCCAACAAAATAAAGAAGATGCCTGGA
 210  E  H  D  V  W  R  M  E  I  Y  V  S  L  G  I  V  G  L  A  I
 721 TTGAGCATGATGTTTGGAGAATGGAGATTTATGTGTCTCTGGGAATTGTGGGATTGGCAA
 230  L  A  L  L  A  V  T  S  I  P  S  V  S  D  S  L  T  W  R  E
 781 TACTGGCTCTGTTGGCTGTGACATCTATTCCATCTGTGAGTGACTCTTTGACATGGAGAG
 250  F  H  Y  I  Q  V  N  N  I  *
 841 AATTTCACTATATTCAGGTAAATAATATATAAaataaccctaagaggtaaatcttcttt
 901 tgtgtttatgatatagaatatgttgactttaccccataaaaaataacaaatgttttttcaa
 961 cagcaaagatcttatacttgttccaattaataatgtgctctcctgttgttttccctattg
1021 cttctaattaggacaagtgtttcctagacataaataaaaggcattaaaatattctttgtt
1081 ttttttttttgtttgtttgtttttgtttgtttgttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaattttgtattttagtagagacagggttttcccatgttggccagg
1321 ctggtctcgatctcctgacctcaaatgatccgcccacctcggcctcccaaagtgctggga
1381 tgacagttgtgagccaccacactcagcctgctctttctaatatttgaaacttgttagaca
1441 atttgctacccatctaatgtgatattttaggaatccaatatgcatggtttattatttctt
```

```
1501 aaaaaaaatattcttttacctgtcacctgaatttagtaatgccttttatgttacacaact
1561 tagcactttccagaaacaaaaactctctccttgaaataatagagttttatctaccaaag
1621 ttatgctagtgtctcatttcaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctgggatccttg
1801 tctgacaagattcaaggactaaatttaattcagtcatgaacactgccaattaccgttta
1861 tgggtagacatctttggaaatttccacaaggtcagacattcgcaactatcccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgcttttagacttcattaggaatt
2161 taggactgcatcttgacaactgagcctattctactatatgtacaatacctagcccataat
2221 aggtatacaatacacatttggtaaaactaattttcaaccaatgacatgtattttcaact
2281 agtaacctagaaatgtttcacttaaatctgagaactggttacactacaagttaccttgg
2341 agattcatatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaagaggtgttgtcagaacaccgttgagattacata
2521 ggtgaacaactattttaagcaactttatttgtgtagtgacaaagcatcccaatgcaggc
2581 tgaaatgtttcatcacatctctggatctctctatttgtgcagacattgaaaaaattgtt
2641 catattatttccatgttatcagaatatttgattttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtccctgattttaggtatcctgtgaaaagcagaattaagacaaatacacaagagacaa
2941 agcacaaaaaataaatatcataaggggatgaacaaaatggtggagaaagagtagacaaag
3001 ttttgatcacctgccttcaaagaaaggctgtgaattttgttcacttagacagcttggag
3061 acaagaaattacccaaaagtaaggtgaggaggataggcaaaagagcagaagatgtgaa
3121 tggacattgttgagaaatgtgataggaaaacaatcatagataaggatttccaagcaaca
3181 gagcatatccagatgaggtaggatgggataaactcttattgaaccaatcttcaccaattt
3241 tgttttcttttgcagagcaagctaggaattgtttccttctactgggcacaatacacgc
3301 attgattttgcctggaataagtggatagatataaaacaatttgtatggtatacacctcc
3361 aacttttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacattttgtt
3541 caatattgatatatttatcaccaacatttcaagtttgtatttgttaataaaatgattat
3601 tcaaggaaaaaaaaaaaaaaaaaaaaa
```

Figure 2H (Part 2)

The cDNA (SEQ ID NO: 18) and amino acid sequence (SEQ ID NO: 19) of STEAP-1 v.9
The start methionine is underlined. The open reading frame extends from nucleic acid
96-872 including the stop codon

```
   1 ggggcccgcacctctgggcagcagcggcagccgagactcacggtcaagctaaggcgaaga
   1                                       M  E  S  R  K  D  I  T  N
  61 gtgggtggctgaagccatactatttatagaattaATGGAAAGCAGAAAAGACATCACAA
  10  Q  E  E  L  W  K  M  K  P  R  R  N  L  E  E  D  D  Y  L  H
 121 ACCAAGAAGAACTTTGGAAAATGAAGCCTAGGAGAAATTTAGAAGAAGACGATTATTTGC
  30  K  D  T  G  E  T  S  M  L  K  R  P  V  L  L  H  L  H  Q  T
 181 ATAAGGACACGGGAGAGACCAGCATGCTAAAAAGACCTGTGCTTTTGCATTTGCACCAAA
  50  A  H  A  D  E  F  D  C  P  S  E  L  Q  H  T  Q  E  L  F  P
 241 CAGCCCATGCTGATGAATTTGACTGCCCTTCAGAACTTCAGCACACACAGGAACTCTTTC
  70  Q  W  H  L  P  I  K  I  A  A  I  I  A  S  L  T  F  L  Y  T
 301 CACAGTGGCACTTGCCAATTAAAATAGCTGCTATTATAGCATCTCTGACTTTTCTTTACA
  90  L  L  R  E  V  I  H  P  L  A  T  S  H  Q  Q  Y  F  Y  K  I
 361 CTCTTCTGAGGGAAGTAATTCACCCCTTAGCAACTTCCCATCAACAATATTTTTATAAAA
 110  P  I  L  V  I  N  K  V  L  P  M  V  S  I  T  L  A  L  V
 421 TTCCAATCCTGGTCATCAACAAAGTCTTGCCAATGGTTTCCATCACTCTCTTGGCATTGG
 130  Y  L  P  G  V  I  A  A  I  V  Q  L  H  N  G  T  K  Y  K  K
 481 TTTACCTGCCAGGTGTGATAGCAGCAATTGTCCAACTTCATAATGGAACCAAGTATAAGA
 150  F  P  H  W  L  D  K  W  M  L  T  R  Q  F  G  L  L  S  F
 541 AGTTTCCACATTGGTTGGATAAGTGGATGTTAACAAGAAAGCAGTTTGGGCTTCTCAGTT
 170  F  F  A  V  L  H  A  I  Y  S  L  S  Y  P  M  R  R  S  Y  R
 601 TCTTTTTTGCTGTACTGCATGCAATTTATAGTCTGTCTTACCCAATGAGGCGATCCTACA
 190  Y  K  L  L  N  W  A  Y  Q  Q  V  Q  Q  N  K  E  D  A  W  I
 661 GATACAAGTTGCTAAACTGGGCATATCAACAGGTCCAACAAAATAAAGAAGATGCCTGGA
 210  E  H  D  V  W  R  M  E  I  Y  V  S  L  G  I  V  G  L  A  I
 721 TTGAGCATGATGTTTGGAGAATGGAGATTTATGTGTCTCTGGGAATTGTGGGATTGGCAA
 230  L  A  L  L  A  V  T  S  I  P  S  V  S  D  S  L  T  W  R  E
 781 TACTGGCTCTGTTGGCTGTGACATCTATTCCATCTGTGAGTGACTCTTTGACATGGAGAG
 250  F  H  Y  I  Q  V  N  N  I  *
 841 AATTTCACTATATTCAGGTAAATAATATATAAaataaccctaagaggtaaatcttctttt
 901 tgtgtttatgatatagaatatgttgactttaccccataaaaaataacaaatgttttcaa
 961 cagcaaagatcttatacttgttccaattaataatgtgctctcctgttgttttccctattg
1021 cttctaattaggacaagtgtttcctagacataaataaaaggcattaaaatattctttgtt
1081 ttttttttttgtttgtttgtttttgtttgtttgtttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaattttgtattttagtagagacagggttttcccatgttggccagg
1321 ctggtctcgatctcctgacctcaaatgatccgcccacctcggcctcccaaagtgctggga
1381 tgacagttgtgagccaccacactcagcctgctctttctaatatttgaaacttgttagaca
1441 atttgctacccatctaatgtgatattttaggaatccaatatgcatggtttattatttctt
```

Figure 2I (Part 1)

```
1501 aaaaaaaatattcttttacctgtcacctgaatttagtaatgccttttatgttacacaact
1561 tagcactttccagaaacaaaaactctctccttgaaataatagagttttttatctaccaaag
1621 atattctagtgtctcatttcaaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctgggatccttg
1801 tctgacaagattcaaaggactaaatttaattcagtcatgaacactgccaattaccgttta
1861 tgggtagacatctttggaaatttccacaaggtcagacattcgcaactatcccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgcttttagacttcattaggaatt
2161 taggactgcatcttgacaactgagcctattctactatatgtacaataccctagcccataat
2221 aggtatacaatacacatttggtaaaactaattttcaaccaatgacatgtattttcaact
2281 agtaacctagaaatgtttcacttaaaatctgagaactggttacactacaagttaccttgg
2341 agattcatatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaaagaggtgttgtcagaacaccgttgagattacata
2521 ggtgaacaactattttaagcaactttatttgtgtagtgacaaagcatcccaatgcaggc
2581 tgaaatgtttcatcacatctctggatctctctattttgtgcagacattgaaaaaattgtt
2641 catattatttccatgttatcagaatatttgatttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtccctgattttaggtatcctgtgaaaagcagaattaagacaaatacacaagagacaa
2941 agcacaaaaataaatatcataaggggatgaacaaaatggtggagaaagagtagacaaag
3001 ttttgatcacctgccttcaaagaaaggctgtgaattttgttcacttagacagcttggag
3061 acaagaaattacccaaaagtaaggtgaggaggataggcaaaaagagcagaaagatgtgaa
3121 tggacattgttgagaaatgtgataggaaaacaatcatagataaaggatttccaagcaaca
3181 gagcatatccagatgaggtaggatgggataaactcttattgaaccaatcttcaccaattt
3241 tgttttctttttgcagagcaagctaggaattgtttcccttctactgggcacaatacacgc
3301 attgattttgcctggaataagtggatagatataaaacaatttgtatggtatacacctcc
3361 aacttttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacattttttgtt
3541 caatattgatatatttttatcaccaacatttcaagtttgtatttgttaataaaatgattat
3601 tcaaggaaaaaaaaaaaaaaaaaaaaa
```

Figure 2I (Part 2)

The cDNA (SEQ ID NO: 20) and amino acid sequence (SEQ ID NO.: 21) of STEAP-1 v.10
The start methionine is underlined. The open reading frame extends from nucleic acid
96-872 including the stop codon

```
   1 ggggcccgcacctctgggcagcagcggcagccgagactcacggtcaagctaaggcgaaga
   1                                        M   E   S   R   K   D   I   T   N
  61 gtgggtggctgaagccatactattttatagaattaATGGAAAGCAGAAAAGACATCACAA
  10  Q   E   E   L   W   K   M   K   P   R   R   N   L   E   E   D   D   Y   L   H
 121 ACCAAGAAGAACTTTGGAAAATGAAGCCTAGGAGAAATTTAGAAGAAGACGATTATTTGC
  30  K   D   T   G   E   T   S   M   L   K   R   P   V   L   L   H   L   H   Q   T
 181 ATAAGGACACGGGAGAGACCAGCATGCTAAAAGACCTGTGCTTTTGCATTTGCACCAAA
  50  A   H   A   D   E   F   D   C   P   S   E   L   Q   H   T   Q   E   L   F   P
 241 CAGCCCATGCTGATGAATTTGACTGCCCTTCAGAACTTCAGCACACACAGGAACTCTTTC
  70  Q   W   H   L   P   I   K   I   A   A   I   I   A   S   L   T   F   L   Y   T
 301 CACAGTGGCACTTGCCAATTAAAATAGCTGCTATTATAGCATCTCTGACTTTTCTTTACA
  90  L   L   R   E   V   I   H   P   L   A   T   S   H   Q   Q   Y   F   Y   K   I
 361 CTCTTCTGAGGGAAGTAATTCACCCCTTAGCAACTTCCCATCAACAATATTTTTATAAAA
 110  P   I   L   V   I   N   K   V   L   P   M   V   S   I   T   L   L   A   L   V
 421 TTCCAATCCTGGTCATCAACAAAGTCTTGCCAATGGTTTCCATCACTCTCTTGGCATTGG
 130  Y   L   P   G   V   I   A   A   I   V   Q   L   H   N   G   T   K   Y   K   K
 481 TTTACCTGCCAGGTGTGATAGCAGCAATTGTCCAACTTCATAATGGAACCAAGTATAAGA
 150  F   P   H   W   L   D   K   W   M   L   T   R   K   Q   F   G   L   L   S   F
 541 AGTTTCCACATTGGTTGGATAAGTGGATGTTAACAAGAAAGCAGTTTGGGCTTCTCAGTT
 170  F   F   A   V   L   H   A   I   Y   S   L   S   Y   P   M   R   R   S   Y   R
 601 TCTTTTTTGCTGTACTGCATGCAATTTATAGTCTGTCTTACCCAATGAGGCGATCCTACA
 190  Y   K   L   L   N   W   A   Y   Q   Q   V   Q   Q   N   K   E   D   A   W   I
 661 GATACAAGTTGCTAAACTGGGCATATCAACAGGTCCAACAAAATAAAGAAGATGCCTGGA
 210  E   H   D   V   W   R   M   E   I   Y   V   S   L   G   I   V   G   L   A   I
 721 TTGAGCATGATGTTTGGAGAATGGAGATTTATGTGTCTCTGGGAATTGTGGGATTGGCAA
 230  L   A   L   L   A   V   T   S   I   P   S   V   S   D   S   L   T   W   R   E
 781 TACTGGCTCTGTTGGCTGTGACATCTATTCCATCTGTGAGTGACTCTTTGACATGGAGAG
 250  F   H   Y   I   Q   V   N   N   I   *
 841 AATTTCACTATATTCAGGTAAATAATATATAAaataaccctaagaggtaaatcttctttt
 901 tgtgtttatgatatagaatatgttgactttaccccataaaaaataacaaatgttttcaa
 961 cagcaaagatcttatacttgttccaattaataatgtgctctcctgttgttttccctattg
1021 cttctaattaggacaagtgtttcctagacataaataaaaggcattaaaatattctttgtt
1081 ttttttttttgtttgtttgtttttgtttgtttgtttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaattttgtattttagtagagacagggtttcccatgttggccagg
1321 ctggtctcgatctcctgacctcaaatgatccgcccacctcggcctcccaaagtgctggga
1381 tgacagttgtgagccaccacactcagcctgctctttctaatatttgaacttgttagaca
1441 atttgctaccatctaatgtgatatttaggaatccaatatgcatggtttattatttctt
```

Figure 2J (Part 1)

```
1501 aaaaaaaatattcttttacctgtcacctgaatttagtaatgccttttatgttacacaact
1561 tagcactttccagaaacaaaaactctctccttgaaataatagagttttatctaccaaag
1621 atatgctagtgtctcatttcaaaggctgcttttccagcttacattttatatacttactc
1681 acttgaagtttctaaatattcttgtaattttaaaaatatctcagatttactgaggtttat
1741 cttctggtggtagattatccataagaagagtgatgtgccagaatcactctgggatccttg
1801 tctgacaagattcaaaggactaaatttaattcagtcatgaacactgccaattaccgttta
1861 tgggtagacatctttggaaatttccacaaggtcagacattcgcaactatcccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgcttttagacttcattaggaatt
2161 taggactgcatcttgacaactgagcctattctactatatgtacaatacctagcccataat
2221 aggtatacaatacacatttggtaaaactaattttcaaccaatgacatgtattttcaact
2281 agtaacctagaaatgtttcacttaaaatctgagaactggttacactacaagttaccttgg
2341 agattcatatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaagaggtgttgtcagaacaccgttgagattacata
2521 ggtgaacaactattttaagcaactttatttgtgtagtgacaaagcatcccaatgcaggc
2581 tgaaatgtttcatcacatctctggatctctctattttgtgcagacattgaaaaaattgtt
2641 catattatttccatgttatcagaatatttgatttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtccctgatttaggtatcctgtgaaaagcagaattaagacaaatacacaagagacaa
2941 agcacaaaaaataaatatcataagggatgaacaaaatggtggagaaagagtagacaaag
3001 ttttgatcacctgccttcaaagaaaggctgtgaattttgttcacttagacagcttggag
3061 acaagaaattacccaaaagtaaggtgaggaggataggcaaaagagcagaaagatgtgaa
3121 tggacattgttgagaaatgtgataggaaaacaatcatagataaaggatttccaagcaaca
3181 gagcatatccagatgaggtaggatgggataaactcttattgaaccaatcttcaccaatt
3241 tgttttcttttgcagagcaagctaggaattgtttcccttctactgggcacaatacacgc
3301 attgattttgcctggaataagtggatagatataaaacaatttgtatggtatacacctcc
3361 aactttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacatttttgtt
3541 caatattgatatattttatcaccaacatttcaagtttgtatttgttaataaaatgattat
3601 tcaaggaaaaaaaaaaaaaaaaaaaaa
```

Figure 2J (Part 2)

The cDNA (SEQ ID NO: 22) and amino acid sequence (SEQ ID NO: 23) of STEAP-1 v.11
The start methionine is underlined. The open reading frame extends from nucleic acid
96-872 including the stop codon

```
   1 ggggcccgcacctctgggcagcagcggcagccgagactcacggtcaagctaaggcgaaga
   1                                              M  E  S  R  K  D  I  T  N
  61 gtgggtggctgaagccatactatttatagaattaATGGAAAGCAGAAAAGACATCACAA
  10  Q  E  E  L  W  K  M  K  P  R  R  N  L  E  E  D  D  Y  L  H
 121 ACCAAGAAGAACTTTGGAAAATGAAGCCTAGGAGAAATTTAGAAGAAGACGATTATTTGC
  30  K  D  T  G  E  T  S  M  L  K  R  P  V  L  L  H  L  H  Q  T
 181 ATAAGGACACGGGAGAGACCAGCATGCTAAAAAGACCTGTGCTTTTGCATTTGCACCAAA
  50  A  H  A  D  E  F  D  C  P  S  E  L  Q  H  T  Q  E  L  F  P
 241 CAGCCCATGCTGATGAATTTGACTGCCCTTCAGAACTTCAGCACACACAGGAACTCTTTC
  70  Q  W  H  L  P  I  K  I  A  A  I  I  A  S  L  T  F  L  Y  T
 301 CACAGTGGCACTTGCCAATTAAAATAGCTGCTATTATAGCATCTCTGACTTTTCTTTACA
  90  L  L  R  E  V  I  H  P  L  A  T  S  H  Q  Q  Y  F  Y  K  I
 361 CTCTTCTGAGGGAAGTAATTCACCCCTTAGCAACTTCCCATCAACAATATTTTTATAAAA
 110  P  I  L  V  I  N  K  V  L  P  M  V  S  I  T  L  L  A  L  V
 421 TTCCAATCCTGGTCATCAACAAAGTCTTGCCAATGGTTTCCATCACTCTCTTGGCATTGG
 130  Y  L  P  G  V  I  A  A  I  V  Q  L  H  N  G  T  K  Y  K  K
 481 TTTACCTGCCAGGTGTGATAGCAGCAATTGTCCAACTTCATAATGGAACCAAGTATAAGA
 150  F  P  H  W  L  D  K  W  M  L  T  R  K  Q  F  G  L  L  S  F
 541 AGTTTCCACATTGGTTGGATAAGTGGATGTTAACAAGAAAGCAGTTTGGGCTTCTCAGTT
 170  F  F  A  V  L  H  A  I  Y  S  L  S  Y  P  M  R  R  S  Y  R
 601 TCTTTTTTGCTGTACTGCATGCAATTTATAGTCTGTCTTACCCAATGAGGCGATCCTACA
 190  Y  K  L  L  N  W  A  Y  Q  Q  V  Q  Q  N  K  E  D  A  W  I
 661 GATACAAGTTGCTAAACTGGGCATATCAACAGGTCCAACAAAATAAAGAAGATGCCTGGA
 210  E  H  D  V  W  R  M  E  I  Y  V  S  L  G  I  V  G  L  A  I
 721 TTGAGCATGATGTTTGGAGAATGGAGATTTATGTGTCTCTGGGAATTGTGGGATTGGCAA
 230  L  A  L  L  A  V  T  S  I  P  S  V  S  D  S  L  T  W  R  E
 781 TACTGGCTCTGTTGGCTGTGACATCTATTCCATCTGTGAGTGACTCTTTGACATGGAGAG
 250  F  H  Y  I  Q  V  N  N  I  *
 841 AATTTCACTATATTCAGGTAAATAATATATAAaataaccctaagaggtaaatcttctttt
 901 tgtgtttatgatatagaatatgttgactttaccccataaaaataacaaatgttttttcaa
 961 cagcaaagatcttatacttgttccaattaataatgtgctctcctgttgttttccctattg
1021 cttctaattaggacaagtgtttcctagacataaataaaaggcattaaaatattctttgtt
1081 tttttttttgtttgtttgtttttgtttgtttgtttgttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaattttgtatttttagtagagacagggttttcccatgttggccagg
1321 ctggtctcgatctcctgacctcaaatgatccgcccacctcggcctcccaaagtgctggga
1381 tgacagttgtgagccaccacactcagcctgctctttctaatatttgaaacttgttagaca
1441 atttgctacccatctaatgtgatattttaggaatccaatatgcatggtttattatttctt
```

Figure 2K (Part 1)

```
1501 aaaaaaaatattcttttacctgtcacctgaatttagtaatgccttttatgttacacaact
1561 tagcactttccagaaacaaaaactctctccttgaaataatagagttttttatctaccaaag
1621 atatgctagtgtctcatttcaaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctggatccttg
1801 tctgacaagattcaaaggactaaatttaattcagtcatgaacactgccaattaccgttta
1861 tgggtagacatctttggaaatttccacaaggtcagacattcgcaactatccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgctttttagacttcattaggaatt
2161 taggactgcatcttgacaactgagcctattctactatatgtacaatacctagcccataat
2221 aggtatacaatacacatttggtaaaactaattttcaaccaatgacatgtattttcaact
2281 agtaacctagaaatgtttcacttaaaatctgagaactggttacactacaagttaccttgg
2341 agattcatatatgaaaatgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaagaggtgttgtcagaacaccgttgagattacata
2521 ggtgaacaactattttaagcaactttatttgtgtagtgacaaagcatcccaatgcaggc
2581 tgaaatgtttcatcacatctctggatctctctattttgtgcagacattgaaaaaattgtt
2641 catattatttccatgttatcagaatatttgatttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtccctgattttaggtatcctgtgaaaagcagaattaagacaaatacacaagagacaa
2941 agcacaaaaataaatatcataaggggatgaacaaaatggtggagaaagagtagacaaag
3001 ttttgatcacctgccttcaaagaaaggctgtgaattttgttcacttagacagcttggag
3061 acaagaaattacccaaaagtaaggtgaggaggataggcaaaaagagcagaaagatgtgaa
3121 tggacattgttgagaaatgtgataggaaacaatcatagataaaggatttccaagcaaca
3181 gagcatatccagatgaggtaggatgggataaactcttattgaaccaatcttcaccaattt
3241 tgtttttcttttgcagagcaagctaggaattgtttccttctactgggcacaatacacgc
3301 attgattttgcctggaataagtggatagatataaaacaatttgtatggtatacacctcc
3361 aacttttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacattttgtt
3541 caatattgatatattttatcaccaacatttcaagtttgtatttgttaataaaatgattat
3601 tcaaggaaaaaaaaaaaaaaaaaaaaa
```

The cDNA (SEQ ID NO: 24) and amino acid sequence (SEQ ID NO: 25) of STEAP-1 v.12
The start methionine is underlined. The open reading frame extends from nucleic acid
96-872 including the stop codon

```
   1 ggggcccgcacctctgggcagcagcggcagccgagactcacggtcaagctaaggcgaaga
   1                                                              
  61 gtgggtggctgaagccatactattttatagaattaATGGAAAGCAGAAAAGACATCACAA
  10                                     M  E  S  R  K  D  I  T  N
 121 ACCAAGAAGAACTTTGGAAAATGAAGCCTAGGAGAAATTTAGAAGAAGACGATTATTTGC
  30  Q  E  E  L  W  K  M  K  P  R  R  N  L  E  E  D  D  Y  L  H
 181 ATAAGGACACGGGAGAGACCAGCATGCTAAAAAGACCTGTGCTTTTGCATTTGCACCAAA
  50  K  D  T  G  E  T  S  M  L  K  R  P  V  L  L  H  L  H  Q  T
 241 CAGCCCATGCTGATGAATTTGACTGCCCTTCAGAACTTCAGCACACACAGGAACTCTTTC
  70  A  H  A  D  E  F  D  C  P  S  E  L  Q  H  T  Q  E  L  F  P
 301 CACAGTGGCACTTGCCAATTAAAATAGCTGCTATTATAGCATCTCTGACTTTTCTTTACA
  90  Q  W  H  L  P  I  K  I  A  A  I  I  A  S  L  T  F  L  Y  T
 361 CTCTTCTGAGGGAAGTAATTCACCCCTTAGCAACTTCCCATCAACAATATTTTTATAAAA
 110  L  L  R  E  V  I  H  P  L  A  T  S  H  Q  Q  Y  F  Y  K  I
 421 TTCCAATCCTGGTCATCAACAAAGTCTTGCCAATGGTTTCCATCACTCTCTTGGCATTGG
 130  P  I  L  V  I  N  K  V  L  P  M  V  S  I  T  L  L  A  L  V
 481 TTTACCTGCCAGGTGTGATAGCAGCAATTGTCCAACTTCATAATGGAACCAAGTATAAGA
 150  Y  L  P  G  V  I  A  A  I  V  Q  L  H  N  G  T  K  Y  K  K
 541 AGTTTCCACATTGGTTGGATAAGTGGATGTTAACAAGAAAGCAGTTTGGGCTTCTCAGTT
 170  F  P  H  W  L  D  K  W  M  L  T  R  K  Q  F  G  L  L  S  F
 601 TCTTTTTTGCTGTACTGCATGCAATTTATAGTCTGTCTTACCCAATGAGGCGATCCTACA
 190  F  F  A  V  L  H  A  I  Y  S  L  S  Y  P  M  R  R  S  Y  R
 661 GATACAAGTTGCTAAACTGGGCATATCAACAGGTCCAACAAAATAAAGAAGATGCCTGGA
 210  Y  K  L  L  N  W  A  Y  Q  Q  V  Q  Q  N  K  E  D  A  W  I
 721 TTGAGCATGATGTTTGGAGAATGGAGATTTATGTGTCTCTGGGAATTGTGGGATTGGCAA
 230  E  H  D  V  W  R  M  E  I  Y  V  S  L  G  I  V  G  L  A  I
 781 TACTGGCTCTGTTGGCTGTGACATCTATTCCATCTGTGAGTGACTCTTTGACATGGAGAG
 250  L  A  L  L  A  V  T  S  I  P  S  V  S  D  S  L  T  W  R  E
     F  H  Y  I  Q  V  N  N  I  *
 841 AATTTCACTATATTCAGGTAAATAATATATAAaataaccctaagaggtaaatcttctttt
 901 tgtgtttatgatatagaatatgttgactttaccccataaaaaataacaaatgttttttcaa
 961 cagcaaagatcttatacttgttccaattaataatgtgctctcctgttgttttccctattg
1021 cttctaattaggacaagtgtttcctagacataaataaaggcattaaaatattctttgtt
1081 ttttttttttgtttgtttgttttttgtttgtttgtttgttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaattttgtattttagtagagacagggttttccatgttggccagg
1321 ctggtctcgatctcctgacctcaaatgatccgcccacctcggcctcccaaagtgctggga
1381 tgacagttgtgagccaccacactcagcctgctcttctaatatttgaaacttgttagaca
1441 atttgctacccatctaatgtgatattttaggaatccaatatgcatggtttattattctt
```

Figure 2L (Part 1)

```
1501 aaaaaaaatattcttttacctgtcacctgaatttagtaatgccttttatgttacacaact
1561 tagcacttttccagaaacaaaaactctctccttgaaataatagagttttatctaccaaag
1621 atatgctagtgtctcatttcaaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctgggatccttg
1801 tctgacaagattcaaaggactaaatttaattcagtcatgaacactgccaattaccgttta
1861 tgggtagacatctttggaaatttccacaaggtcagacattcgcaactatcccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgcttttagacttcattaggaatt
2161 taggactgcatcttgacaactgagcctattctactatatgtacaatacctagcccataat
2221 aggtatacaatacacatttggtaaaactaattttcaaccaatgacatgtattttcaact
2281 agtaacctagaaatgtttcacttaaaatctgagaactggttacactacaagttaccttgg
2341 agattcatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaagaggtgttgtcagaacaccgttgagattacata
2521 ggtgaacaactattttaagcaactttatttgtgtagtgacaaagcatcccaatgcaggc
2581 tgaaatgtttcatcacatctctggatctctctattttgtgcagacattgaaaaaattgtt
2641 catatgatttccatgttatcagaatatttgattttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtccctgatttaggtatcctgtgaaaagcagaattaagacaaatacacaagagacaa
2941 agcacaaaaataaatatcataaggggatgaacaaaatggtggagaaagagtagacaaag
3001 tttttgatcacctgccttcaaagaaaggctgtgaattttgttcacttagacagcttggag
3061 acaagaaattacccaaagtaaggtgaggaggataggcaaaaagagcagaaagatgtgaa
3121 tggacattgttgagaaatgtgataggaaaacaatcatagataaaggatttccaagcaaca
3181 gagcatatccagatgaggtaggatgggataaactcttattgaaccaatcttcaccaattt
3241 tgttttcttttgcagagcaagctaggaattgtttccttctactgggcacaatacacgc
3301 attgattttgcctggaataagtggatagatataaaacaatttgtatggtatacacctcc
3361 aacttttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacattttttgtt
3541 caatattgatatattttatcaccaacatttcaagtttgtatttgttaataaaatgattat
3601 tcaaggaaaaaaaaaaaaaaaaaaaaaaa
```

Figure 2L (Part 2)

The cDNA (SEQ ID NO: 26) and amino acid sequence (SEQ ID NO: 27) of STEAP-1 v.13
The start methionine is underlined. The open reading frame extends from nucleic acid
96-872 including the stop codon

```
   1 gggccccgcacctctgggcagcagcggcagccgagactcacggtcaagctaaggcgaaga
   1                                                            M   E   S   R   K   D   I   T   N
  61 gtgggtggctgaagccatactatttttatagaattaATGGAAAGCAGAAAAGACATCACAA
  10   Q   E   E   L   W   K   M   K   P   R   R   N   L   E   E   D   D   Y   L   H
 121 ACCAAGAAGAACTTTGGAAAATGAAGCCTAGGAGAAATTTAGAAGAAGACGATTATTTGC
  30   K   D   T   G   E   T   S   M   L   K   R   P   V   L   L   H   L   H   Q   T
 181 ATAAGGACACGGGAGAGACCAGCATGCTAAAAAGACCTGTGCTTTTGCATTTGCACCAAA
  50   A   H   A   D   E   F   D   C   P   S   E   L   Q   H   T   Q   E   L   F   P
 241 CAGCCCATGCTGATGAATTTGACTGCCCTTCAGAACTTCAGCACACACAGGAACTCTTTC
  70   Q   W   H   L   P   I   K   I   A   A   I   I   A   S   L   T   F   L   Y   T
 301 CACAGTGGCACTTGCCAATTAAAATAGCTGCTATTATAGCATCTCTGACTTTTCTTTACA
  90   L   L   R   E   V   I   H   P   L   A   T   S   H   Q   Q   Y   F   Y   K   I
 361 CTCTTCTGAGGGAAGTAATTCACCCCTTAGCAACTTCCCATCAACAATATTTTTATAAAA
 110   P   I   L   V   I   N   K   V   L   P   M   V   S   I   T   L   L   A   L   V
 421 TTCCAATCCTGGTCATCAACAAAGTCTTGCCAATGGTTTCCATCACTCTCTTGGCATTGG
 130   Y   L   P   G   V   I   A   A   I   V   Q   L   H   N   G   T   K   Y   K   K
 481 TTTACCTGCCAGGTGTGATAGCAGCAATTGTCCAACTTCATAATGGAACCAAGTATAAGA
 150   F   P   H   W   L   D   K   W   M   L   T   R   K   Q   F   G   L   L   S   F
 541 AGTTTCCACATTGGTTGGATAAGTGGATGTTAACAAGAAAGCAGTTTGGGCTTCTCAGTT
 170   F   F   A   V   L   H   A   I   Y   S   L   S   Y   P   M   R   R   S   Y   R
 601 TCTTTTTTGCTGTACTGCATGCAATTTATAGTCTGTCTTACCCAATGAGGCGATCCTACA
 190   Y   K   L   L   N   W   A   Y   Q   Q   V   Q   Q   N   K   E   D   A   W   I
 661 GATACAAGTTGCTAAACTGGGCATATCAACAGGTCCAACAAAATAAAGAAGATGCCTGGA
 210   E   H   D   V   W   R   M   E   I   Y   V   S   L   G   I   V   G   L   A   I
 721 TTGAGCATGATGTTTGGAGAATGGAGATTTATGTGTCTCTGGGAATTGTGGGATTGGCAA
 230   L   A   L   L   A   V   T   S   I   P   S   V   S   D   S   L   T   W   R   E
 781 TACTGGCTCTGTTGGCTGTGACATCTATTCCATCTGTGAGTGACTCTTTGACATGGAGAG
 250   F   H   Y   I   Q   V   N   N   I   *
 841 AATTTCACTATATTCAGGTAAATAATATATAAaataaccctaagaggtaaatcttcttt
 901 tgtgtttatgatatagaatatgttgactttaccccataaaaataacaaatgttttttcaa
 961 cagcaaagatcttatacttgttccaattaataatgtgctctcctgttgttttccctattg
1021 cttctaattaggacaagtgtttcctagacataaataaaaggcattaaaatattctttgtt
1081 ttttttttttgtttgtttgttttttgtttgtttgtttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaatttttgtatttttagtagagacagggttttcccatgttggccagg
1321 ctggtctcgatctcctgacctcaaatgatccgcccacctcggcctcccaaagtgctggga
1381 tgacagttgtgagccaccacactcagcctgctctttctaatatttgaaacttgttagaca
1441 atttgctacccatctaatgtgatatttttaggaatccaatatgcatggtttattatttctt
```

Figure 2M (Part 1)

```
1501 aaaaaaaatattcttttacctgtcacctgaatttagtaatgccttttatgttacacaact
1561 tagcactttccagaaacaaaaactctctccttgaaataatagagttttatctaccaaag
1621 atatgctagtgtctcatttcaaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctggatccttg
1801 tctgacaagattcaaaggactaaatttaattcagtcatgaacactgccaattaccgttta
1861 tgggtagacatctttggaaatttccacaaggtcagacattcgcaactatcccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgcttttagacttcattaggaatt
2161 taggactgcatcttgacaactgagcctattctactatatgtacaatacctagcccataat
2221 aggtatacaatacacatttggtaaaactaattttcaaccaatgacatgtattttcaact
2281 agtaacctagaaatgtttcacttaaaatctgagaactggttacactacaagttaccttgg
2341 agattcatatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaagaggtgttgtcagaacaccgttgagattacata
2521 ggtgaacaactattttaagcaactttatttgtgtagtgacaaagcatcccaatgcaggc
2581 tgaaatgtttcatcacatctctggatctctctatttgtgcagacattgaaaaaattgtt
2641 catattatttccatgttatcagaatatttgattttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagggatcctgctataagtaagact
2881 cagtccctgatttaggtatcctgtgaaaagcagaattaagacaaatacacaagagacaa
2941 agcacaaaaaataaatatcataaggggatgaacaaaatggtggagaaagagtagacaaag
3001 ttttgatcacctgccttcaaagaaaggctgtgaattttgttcacttagacagcttggag
3061 acaagaaattacccaaagtaaggtgaggaggataggcaaaagagcagaaagatgtgaa
3121 tggacattgttgagaaatgtgataggaaaacaatcatagataaaggatttccaagcaaca
3181 gagcatatccagatgaggtaggatgggataaactcttattgaaccaatcttccaatttt
3241 tgttttcttttgcagagcaagctaggaattgtttcccttctactgggcacaatacacgc
3301 attgattttgcctggaataagtggatagatataaaacaatttgtatggtatacacctcc
3361 aacttttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacatttttgtt
3541 caatattgatatatttatcaccaacatttcaagtttgtatttgttaataaaatgattat
3601 tcaaggaaaaaaaaaaaaaaaaaaaaaa
```

Figure 2M (Part 2)

The cDNA (SEQ ID NO: 28) and amino acid sequence (SEQ ID NO: 29) of STEAP-1 v.14
The start methionine is underlined. The open reading frame extends from nucleic acid
96-872 including the stop codon

```
   1 ggggcccgcacctctgggcagcagcggcagccgagactcacggtcaagctaaggcgaaga
   1                                                M  E  S  R  K  D  I  T  N
  61 gtgggtggctgaagccatactatttatagaattaATGGAAAGCAGAAAAGACATCACAA
  10  Q  E  E  L  W  K  M  K  P  R  R  N  L  E  E  D  D  Y  L  H
 121 ACCAAGAAGAACTTTGGAAAATGAAGCCTAGGAGAAATTTAGAAGAAGACGATTATTTGC
  30  K  D  T  G  E  T  S  M  L  K  R  P  V  L  L  H  L  H  Q  T
 181 ATAAGGACACGGGAGAGACCAGCATGCTAAAAAGACCTGTGCTTTTGCATTTGCACCAAA
  50  A  H  A  D  E  F  D  C  P  S  E  L  Q  H  T  Q  E  L  F  P
 241 CAGCCCATGCTGATGAATTTGACTGCCCTTCAGAACTTCAGCACACACAGGAACTCTTTC
  70  Q  W  H  L  P  I  K  I  A  A  I  I  A  S  L  T  F  L  Y  T
 301 CACAGTGGCACTTGCCAATTAAAATAGCTGCTATTATAGCATCTCTGACTTTTCTTTACA
  90  L  L  R  E  V  I  H  P  L  A  T  S  H  Q  Q  Y  F  Y  K  I
 361 CTCTTCTGAGGGAAGTAATTCACCCCTTAGCAACTTCCCATCAACAATATTTTTATAAAA
 110  P  I  L  V  I  N  K  V  L  P  M  V  S  I  T  L  L  A  L  V
 421 TTCCAATCCTGGTCATCAACAAAGTCTTGCCAATGGTTTCCATCACTCTCTTGGCATTGG
 130  Y  L  P  G  V  I  A  A  I  V  Q  L  H  N  G  T  K  Y  K  K
 481 TTTACCTGCCAGGTGTGATAGCAGCAATTGTCCAACTTCATAATGGAACCAAGTATAAGA
 150  F  P  H  W  L  D  K  W  M  L  T  R  K  Q  F  G  L  L  S  F
 541 AGTTTCCACATTGGTTGGATAAGTGGATGTTAACAAGAAAGCAGTTTGGGCTTCTCAGTT
 170  F  F  A  V  L  H  A  I  Y  S  L  S  Y  P  M  R  R  S  Y  R
 601 TCTTTTTTGCTGTACTGCATGCAATTTATAGTCTGTCTTACCCAATGAGGCGATCCTACA
 190  Y  K  L  L  N  W  A  Y  Q  Q  V  Q  Q  N  K  E  D  A  W  I
 661 GATACAAGTTGCTAAACTGGGCATATCAACAGGTCCAACAAAATAAAGAAGATGCCTGGA
 210  E  H  D  V  W  R  M  E  I  Y  V  S  L  G  I  V  G  L  A  I
 721 TTGAGCATGATGTTTGGAGAATGGAGATTTATGTGTCTCTGGGAATTGTGGGATTGGCAA
 230  L  A  L  L  A  V  T  S  I  P  S  V  S  D  S  L  T  W  R  E
 781 TACTGGCTCTGTTGGCTGTGACATCTATTCCATCTGTGAGTGACTCTTTGACATGGAGAG
 250  F  H  Y  I  Q  V  N  N  I  *
 841 AATTTCACTATATTCAGGTAAATAATATATAAaataaccctaagaggtaaatcttctttt
 901 tgtgtttatgatatagaatatgttgactttaccccataaaaataacaaatgttttcaa
 961 cagcaaagatcttatacttgttccaattaataatgtgctctcctgttgttttccctattg
1021 cttctaattaggacaagtgtttcctagacataaataaaaggcattaaaatattctttgtt
1081 ttttttttttgtttgtttgtttttgtttgtttgtttgtttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaattttgtatttagtagagacagggttttcccatgttggccagg
1321 ctggtctcgatctcctgacctcaaatgatccgcccacctcggcctcccaaagtgctggga
1381 tgacagttgtgagccaccacactcagcctgctctttctaatatttgaacttgttagaca
1441 atttgctacccatctaatgtgatattttaggaatccaatatgcatggtttattatttctt
```

Figure 2N (Part 1)

```
1501 aaaaaaaatattcttttacctgtcacctgaatttagtaatgccttttatgttacacaact
1561 tagcactttccagaaacaaaaactctctccttgaaataatagagttttatctaccaaag
1621 atatgctagtgtctcatttcaaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctgggatccttg
1801 tctgacaagattcaaaggactaaatttaattcagtcatgaacactgccaattaccgttta
1861 tgggtagacatctttggaaatttccacaaggtcagacattcgcaactatccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttcttttggtcctcattaaatagctttcttca
2101 cacattgctctgcctgttacacatatgatgaacactgcttttagacttcattaggaatt
2161 taggactgcatcttgacaactgagcctattctactatatgtacaatacctagcccataat
2221 aggtatacaatacacatttggtaaaactaattttcaaccaatgacatgtattttcaact
2281 agtaacctagaaatgtttcacttaaaatctgagaactggttacactacaagttaccttgg
2341 agattcatatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaagaggtgttgtcagaacaccgttgagattacata
2521 ggtgaacaactattttaagcaactttatttgtgtagtgacaaagcatcccaatgcaggc
2581 tgaaatgtttcatcacatctctggatctctctattttgtgcagacattgaaaaaattgtt
2641 catattatttccatgttatcagaatatttgatttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtccctgattttaggtatcctgtgataagcagaattaagacaaatacacaagagacaa
2941 agcacaaaaataaatatcataaggggatgaacaaaatggtggagaaagagtagacaaag
3001 ttttgatcacctgccttcaaagaaaggctgtgaattttgttcacttagacagcttggag
3061 acaagaaattacccaaaagtaaggtgaggaggataggcaaaagagcagaaagatgtgaa
3121 tggacattgttgagaaatgtgataggaaaacaatcatagataaaggatttccaagcaaca
3181 gagcatatccagatgaggtaggatgggataaactcttattgaaccaatcttcaccaattt
3241 tgttttcttttgcagagcaagctaggaattgtttccttctactgggcacaatacacgc
3301 attgattttgcctggaataagtggatagatataaaacaatttgtatggtatacacctcc
3361 aacttttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacattttgtt
3541 caatattgatatatttatcaccaacatttcaagtttgtatttgttaataaaatgattat
3601 tcaaggaaaaaaaaaaaaaaaaaaaaa
```

Figure 2N (Part 2)

The cDNA (SEQ ID NO: 30) and amino acid sequence (SEQ ID NO: 31) of STEAP-1 v.15
The start methionine is underlined. The open reading frame extends from nucleic acid
96-872 including the stop codon

```
   1 ggggcccgcacctctgggcagcagcggcagccgagactcacggtcaagctaaggcgaaga
   1                                              M  E  S  R  K  D  I  T  N
  61 gtgggtggctgaagccatactattttatagaattaATGGAAAGCAGAAAAGACATCACAA
  10  Q  E  E  L  W  K  M  K  P  R  R  N  L  E  E  D  D  Y  L  H
 121 ACCAAGAAGAACTTTGGAAAATGAAGCCTAGGAGAAATTTAGAAGAAGACGATTATTTGC
  30  K  D  T  G  E  T  S  M  L  K  R  P  V  L  L  H  L  H  Q  T
 181 ATAAGGACACGGGAGAGACCAGCATGCTAAAAAGACCTGTGCTTTTGCATTTGCACCAAA
  50  A  H  A  D  E  F  D  C  P  S  E  L  Q  H  T  Q  E  L  F  P
 241 CAGCCCATGCTGATGAATTTGACTGCCCTTCAGAACTTCAGCACACACAGGAACTCTTTC
  70  Q  W  H  L  P  I  K  I  A  A  I  I  A  S  L  T  F  L  Y  T
 301 CACAGTGGCACTTGCCAATTAAAATAGCTGCTATTATAGCATCTCTGACTTTTCTTTACA
  90  L  L  R  E  V  I  H  P  L  A  T  S  H  Q  Q  Y  F  Y  K  I
 361 CTCTTCTGAGGGAAGTAATTCACCCCTTAGCAACTTCCCATCAACAATATTTTTATAAAA
 110  P  I  L  V  I  N  K  V  L  P  M  V  S  I  T  L  L  A  L  V
 421 TTCCAATCCTGGTCATCAACAAAGTCTTGCCAATGGTTTCCATCACTCTCTTGGCATTGG
 130  Y  L  P  G  V  I  A  A  I  V  Q  L  H  N  G  T  K  Y  K  K
 481 TTTACCTGCCAGGTGTGATAGCAGCAATTGTCCAACTTCATAATGGAACCAAGTATAAGA
 150  F  P  H  W  L  D  K  W  M  L  T  R  K  Q  F  G  L  L  S  F
 541 AGTTTCCACATTGGTTGGATAAGTGGATGTTAACAAGAAAGCAGTTTGGGCTTCTCAGTT
 170  F  F  A  V  L  H  A  I  Y  S  L  S  Y  P  M  R  R  S  Y  R
 601 TCTTTTTTGCTGTACTGCATGCAATTTATAGTCTGTCTTACCCAATGAGGCGATCCTACA
 190  Y  K  L  L  N  W  A  Y  Q  Q  V  Q  Q  N  K  E  D  A  W  I
 661 GATACAAGTTGCTAAACTGGGCATATCAACAGGTCCAACAAAATAAAGAAGATGCCTGGA
 210  E  H  D  V  W  R  M  E  I  Y  V  S  L  G  I  V  G  L  A  I
 721 TTGAGCATGATGTTTGGAGAATGGAGATTTATGTGTCTCTGGGAATTGTGGGATTGGCAA
 230  L  A  L  L  A  V  T  S  I  P  S  V  S  D  S  L  T  W  R  E
 781 TACTGGCTCTGTTGGCTGTGACATCTATTCCATCTGTGAGTGACTCTTTGACATGGAGAG
 250  F  H  Y  I  Q  V  N  N  I  *
 841 AATTTCACTATATTCAGGTAAATAATATATAAaataaccctaagaggtaaatcttctttt
 901 tgtgtttatgatatagaatatgttgactttaccccataaaaataacaaatgtttttcaa
 961 cagcaaagatcttatacttgttccaattaataatgtgctctcctgttgttttccctattg
1021 cttctaattaggacaagtgtttcctagacataaataaaaggcattaaaatattctttgtt
1081 tttttttttttgtttgtttgtttttgtttgtttgttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaattttgtattttagtagagacagggttttcccatgttggccagg
1321 ctggtctcgatctcctgacctcaaatgatccgcccacctcggcctcccaaagtgctggga
1381 tgacagttgtgagccaccacactcagcctgctcttctaatatttgaaacttgttagaca
1441 atttgctacccatctaatgtgatatttaggaatccaatatgcatggtttattattctt
```

Figure 2O (Part 1)

```
1501 aaaaaaaatattcttttacctgtcacctgaatttagtaatgccttttatgttacacaact
1561 tagcactttccagaaacaaaaactctctccttgaaataatagagttttttatctaccaaag
1621 atatgctagtgtctcatttcaaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctgggatccttg
1801 tctgacaagattcaaaggactaaatttaattcagtcatgaacactgccaattaccgttta
1861 tgggtagacatctttggaaatttccacaaggtcagacattcgcaactatcccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgcttttagacttcattaggaatt
2161 taggactgcatcttgacaactgagcctattctactatatgtacaatacctagcccataat
2221 aggtatacaatacacatttggtaaaactaattttcaaccaatgacatgtatttttcaact
2281 agtaacctagaaatgtttcacttaaaatctgagaactggttacactacaagttaccttgg
2341 agattcatatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaaagaggtgttgtcagaacaccgttgagattacata
2521 ggtgaacaactattttaagcaactttatttgtgtagtgacaaagcatcccaatgcaggc
2581 tgaaatgtttcatcacatctctggatctctctattttgtgcagacattgaaaaaattgtt
2641 catattatttccatgttatcagaatatttgattttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtccctgattttaggtatcctgtgaaaagcagaattaagacaaatacacaagagacaa
2941 agcacaaaaataaatatcataaggggatgaacaaaatggtggagaaagagtagacaaag
3001 tttttcatcacctgccttcaaagaaaggctgtgaattttgttcacttagacagcttggag
3061 acaagaaattacccaaaagtaaggtgaggaggataggcaaaaagagcagaaagatgtgaa
3121 tggacattgttgagaaatgtgataggaaaacaatcatagataaaggatttccaagcaaca
3181 gagcatatccagatgaggtaggatgggataaactcttattgaaccaatcttcaccaattt
3241 tgttttcttttgcagagcaagctaggaattgtttcccttctactgggcacaatacacgc
3301 attgattttgcctggaataagtggatagatataaaacaatttgtatggtatacacctcc
3361 aactttttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttccagttgtagaattactgtttacacacatttttgtt
3541 caatattgatatatttatcaccaacatttcaagtttgtatttgttaataaaatgattat
3601 tcaaggaaaaaaaaaaaaaaaaaaaaa
```

Figure 2O (Part 2)

The cDNA (SEQ ID NO: 32) and amino acid sequence (SEQ ID NO: 33) of STEAP-1 v.16
The start methionine is underlined. The open reading frame extends from nucleic acid
96-872 including the stop codon

```
   1 ggggcccgcacctctgggcagcagcggcagccgagactcacggtcaagctaaggcgaaga
   1                                                M  E  S  R  K  D  I  T  N
  61 gtgggtggctgaagccatactattttatagaattaATGGAAAGCAGAAAAGACATCACAA
  10  Q  E  E  L  W  M  K  P  R  R  N  L  E  E  D  D  Y  L  H
 121 ACCAAGAAGAACTTTGGAAAATGAAGCCTAGGAGAAATTTAGAAGAAGACGATTATTTGC
  30  K  D  T  G  E  T  S  M  L  K  R  P  V  L  L  H  L  H  Q  T
 181 ATAAGGACACGGGAGAGACCAGCATGCTAAAAAGACCTGTGCTTTTGCATTTGCACCAAA
  50  A  H  A  D  E  F  D  C  P  S  E  L  Q  H  T  Q  E  L  F  P
 241 CAGCCCATGCTGATGAATTTGACTGCCCTTCAGAACTTCAGCACACACAGGAACTCTTTC
  70  Q  W  H  L  P  I  K  I  A  A  I  I  A  S  L  T  F  L  Y  T
 301 CACAGTGGCACTTGCCAATTAAAATAGCTGCTATTATAGCATCTCTGACTTTTCTTTACA
  90  L  L  R  E  V  I  H  P  L  A  T  S  H  Q  Q  Y  F  Y  K  I
 361 CTCTTCTGAGGGAAGTAATTCACCCCTTAGCAACTTCCCATCAACAATATTTTTATAAAA
 110  P  I  L  V  I  N  K  V  L  P  M  V  S  T  L  L  A  L  V
 421 TTCCAATCCTGGTCATCAACAAAGTCTTGCCAATGGTTTCCATCACTCTCTTGGCATTGG
 130  Y  L  P  G  V  I  A  A  I  V  Q  L  H  N  G  T  K  Y  K  K
 481 TTTACCTGCCAGGTGTGATAGCAGCAATTGTCCAACTTCATAATGGAACCAAGTATAAGA
 150  F  P  H  W  L  D  K  W  M  L  T  R  Q  F  G  L  L  S  F
 541 AGTTTCCACATTGGTTGGATAAGTGGATGTTAACAAGAAAGCAGTTTGGGCTTCTCAGTT
 170  F  F  A  V  L  H  A  I  Y  S  L  S  Y  P  M  R  R  S  Y  R
 601 TCTTTTTTGCTGTACTGCATGCAATTTATAGTCTGTCTTACCCAATGAGGCGATCCTACA
 190  Y  K  L  L  N  W  A  Y  Q  Q  V  Q  Q  N  K  E  D  A  W  I
 661 GATACAAGTTGCTAAACTGGGCATATCAACAGGTCCAACAAAATAAAGAAGATGCCTGGA
 210  E  H  D  V  W  R  M  E  I  Y  V  S  L  G  I  V  G  L  A  I
 721 TTGAGCATGATGTTTGGAGAATGGAGATTTATGTGTCTCTGGGAATTGTGGGATTGGCAA
 230  L  A  L  L  A  V  T  S  I  P  S  V  S  D  S  L  T  W  R  E
 781 TACTGGCTCTGTTGGCTGTGACATCTATTCCATCTGTGAGTGACTCTTTGACATGGAGAG
 250  F  H  Y  I  Q  V  N  N  I  *
 841 AATTTCACTATATTCAGGTAAATAATATATAAaataaccctaagaggtaaatcttctttt
 901 tgtgtttatgatatagaatatgttgactttaccccataaaaaataacaaatgttttcaa
 961 cagcaaagatcttatacttgttccaattaataatgtgctctcctgttgttttccctattg
1021 cttctaattaggacaagtgtttcctagacataaataaaaggcattaaaatattctttgtt
1081 ttttttttttgtttgtttgtttttgtttgtttgtttgtttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaattttgtattttagtagagacagggttttccatgttggccagg
1321 ctggtctcgatctcctgacctcaaatgatccgcccacctcggcctcccaaagtgctggga
1381 tgacagttgtgagccaccacactcagcctgctctttctaatatttgaacttgttagaca
1441 atttgctacccatctaatgtgatattttaggaatccaatatgcatggtttattatttctt
```

Figure 2P (Part 1)

```
1501 aaaaaaaatattcttttacctgtcacctgaatttagtaatgccttttatgttacacaact
1561 tagcactttccagaaacaaaaactctctccttgaaataatagagttttttatctaccaaag
1621 atatgctagtgtctcatttcaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctgggatccttg
1801 tctgacaagattcaaaggactaaatttaattcagtcatgaacactgccaattaccgttta
1861 tgggtagacatctttggaaatttccacaaggtcagacattcgcaactatcccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgcttttagacttcattaggaatt
2161 taggactgcatcttgacaactgagcctattctactatatgtacaatacctagcccataat
2221 aggtatacaatacacatttggtaaaactaattttcaaccaatgacatgtattttcaact
2281 agtaacctagaaatgtttcacttaaaatctgagaactggttacactacaagttaccttgg
2341 agattcatatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaagaggtgttgtcagaacaccgttgagattacata
2521 ggtgaacaactattttaagcaactttatttgtgtagtgacaaagcatcccaatgcaggc
2581 tgaaatgtttcatcacatctctggatctctctattttgtgcagacattgaaaaaattgtt
2641 catattatttccatgttatcagaatatttgatttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtccctgattttaggtatcctgtgaaaagcagaattaagacaaatacacaagagacaa
2941 agcacaaaaataaatatcataaggggatgaacaaaatggtggagaaagagtagacaaag
3001 ttttgatcacctgccttcaaagaaaggctgtgaattttgttcacttagacagcttggag
3061 acaagaaattacccaaaagtaaggtgaggaggataggcaaaaagagtagaaagatgtgaa
3121 tggacattgttgagaaatgtgataggaaaacaatcatagataaaggatttccaagcaaca
3181 gagcatatccagatgaggtaggatgggataaactcttattgaaccaatcttcaccaattt
3241 tgttttcttttgcagagcaagctaggaattgtttccttctactgggcacaatacacgc
3301 attgattttgcctggaataagtggatagatataaaacaatttgtatggtatacacctcc
3361 aacttttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacattttgtt
3541 caatattgatatatttttcaccaacatttcaagtttgtatttgttaataaaatgattat
3601 tcaaggaaaaaaaaaaaaaaaaaaaaa
```

The cDNA (SEQ ID NO: 34) and amino acid sequence (SEQ ID NO: 35) of STEAP-1 v.17
The start methionine is underlined. The open reading frame extends from nucleic acid
96-872 including the stop codon

```
   1 ggggcccgcacctctgggcagcagcggcagccgagactcacggtcaagctaaggcgaaga
   1                                             M  E  S  R  K  D  I  T  N
  61 gtgggtggctgaagccatactattttatagaattaATGGAAAGCAGAAAAGACATCACAA
  10  Q  E  E  L  W  K  M  K  P  R  R  N  L  E  E  D  D  Y  L  H
 121 ACCAAGAAGAACTTTGGAAAATGAAGCCTAGGAGAAATTTAGAAGAAGACGATTATTTGC
  30  K  D  T  G  E  T  S  M  L  K  R  P  V  L  L  H  L  H  Q  T
 181 ATAAGGACACGGGAGAGACCAGCATGCTAAAAAGACCTGTGCTTTTGCATTTGCACCAAA
  50  A  H  A  D  E  F  D  C  P  S  E  L  Q  H  T  Q  E  L  F  P
 241 CAGCCCATGCTGATGAATTTGACTGCCCTTCAGAACTTCAGCACACACAGGAACTCTTTC
  70  Q  W  H  L  P  I  K  I  A  A  I  I  A  S  L  T  F  L  Y  T
 301 CACAGTGGCACTTGCCAATTAAAATAGCTGCTATTATAGCATCTCTGACTTTTCTTTACA
  90  L  L  R  E  V  I  H  P  L  A  T  S  H  Q  Q  Y  F  Y  K  I
 361 CTCTTCTGAGGGAAGTAATTCACCCCTTAGCAACTTCCCATCAACAATATTTTTATAAAA
 110  P  I  L  V  I  N  K  V  L  P  M  V  S  I  T  L  L  A  L  V
 421 TTCCAATCCTGGTCATCAACAAAGTCTTGCCAATGGTTTCCATCACTCTCTTGGCATTGG
 130  Y  L  P  G  V  I  A  A  I  V  Q  L  H  N  G  T  K  Y  K  K
 481 TTTACCTGCCAGGTGTGATAGCAGCAATTGTCCAACTTCATAATGGAACCAAGTATAAGA
 150  F  P  H  W  L  D  K  W  M  L  T  R  K  Q  F  G  L  L  S  F
 541 AGTTTCCACATTGGTTGGATAAGTGGATGTTAACAAGAAAGCAGTTTGGGCTTCTCAGTT
 170  F  F  A  V  L  H  A  I  Y  S  L  S  Y  P  M  R  R  S  Y  R
 601 TCTTTTTTGCTGTACTGCATGCAATTTATAGTCTGTCTTACCCAATGAGGCGATCCTACA
 190  Y  K  L  L  N  W  A  Y  Q  Q  V  Q  Q  N  K  E  D  A  W  I
 661 GATACAAGTTGCTAAACTGGGCATATCAACAGGTCCAACAAAATAAAGAAGATGCCTGGA
 210  E  H  D  V  W  R  M  E  I  Y  V  S  L  G  I  V  G  L  A  I
 721 TTGAGCATGATGTTTGGAGAATGGAGATTTATGTGTCTCTGGGAATTGTGGGATTGGCAA
 230  L  A  L  L  A  V  T  S  I  P  S  V  S  D  S  L  T  W  R  E
 781 TACTGGCTCTGTTGGCTGTGACATCTATTCCATCTGTGAGTGACTCTTTGACATGGAGAG
 250  F  H  Y  I  Q  V  N  N  I  *
 841 AATTTCACTATATTCAGGTAAATAATATATAAaataaccctaagaggtaaatcttcttt
 901 tgtgtttatgatatagaatatgttgactttaccccataaaaaataacaaatgtttttcaa
 961 cagcaaagatcttatacttgttccaattaataatgtgctctcctgttgttttccctattg
1021 cttctaattaggacaagtgtttcctagacataaataaaaggcattaaaatattctttgtt
1081 ttttttttttgtttgtttgtttttgtttgtttgtttgttttttgagatgaagtctcg
1141 ctctgttgcccatgctggagtacagtggcacgatctcggctcactgcaacctgcgcctcc
1201 tgggttcaggcgattctcttgcctcagcctcctgagtagctgggattacaggcacccatc
1261 accatgtccagctaattttgtattttagtagagacagggttttccatgttggccagg
1321 ctggtctcgatctcctgacctcaaatgatccgcccacctcggcctcccaaagtgctggga
1381 tgacagttgtgagccaccacactcagcctgctcttctaatatttgaaacttgttagaca
1441 atttgctacccatctaatgtgatattttaggaatccaatatgcatggtttattattctt
```

Figure 2Q (Part 1)

```
1501 aaaaaaaatattcttttacctgtcacctgaatttagtaatgccttttatgttacacaact
1561 tagcactttccagaaacaaaaactctctccttgaaataatagagttttatctaccaaag
1621 atatgctagtgtctcatttcaaaggctgcttttccagcttacattttatatacttactc
1681 acttgaagtttctaaatattcttgtaattttaaaactatctcagatttactgaggtttat
1741 cttctggtggtagattatccataagaagagtgatgtgccagaatcactctgggatccttg
1801 tctgacaagattcaaaggactaaatttaattcagtcatgaacactgccaattaccgttta
1861 tgggtagacatctttggaaatttccacaaggtcagacattcgcaactatccttctacat
1921 gtccacacgtatactccaacactttattaggcatctgattagtttggaaagtatgcctcc
1981 atctgaattagtccagtgtggcttagagttggtacaacattctcacagaatttcctaatt
2041 ttgtaggttcagcctgataaccactggagttctttggtcctcattaaatagctttcttca
2101 cacattgctctgcctgttacacatatgatgaacactgcttttagacttcattaggaatt
2161 taggactgcatcttgacaactgagcctattctactatatgtacaatacctagcccataat
2221 aggtatacaatacacatttggtaaaactaattttcaaccaatgacatgtattttcaact
2281 agtaacctagaaatgtttcacttaaaatctgagaactggttacactacaagttaccttgg
2341 agattcatatatgaaaacgcaaacttagctatttgattgtattcactgggacttaagaat
2401 gcgcctgaataattgtgagttcgatttgttctggcaggctaatgaccatttccagtaaag
2461 tgaatagaggtcagaagtcgtataaagaggtgttgtcagaacaccgttgagattacata
2521 ggtgaacaactattttaagcaactttatttgtgtagtgacaaagcatcccaatgcaggc
2581 tgaaatgtttcatcacatctctggatctctctattttgtgcagacattgaaaaaattgtt
2641 catattatttccatgttatcagaatatttgattttttaaaaacataggccaagttcattc
2701 acttcattattcatttatcaaaatcagagtgaatcacattagtcgccttcacaactgata
2761 aagatcactgaagtcaaattgattttgctataatcttcaatctacctatatttaattga
2821 gaatctaaaatgtacaaatcattgtgttgattctgcagtgatcctgctataagtaagact
2881 cagtccctgattttaggtatcctgtgaaaagcagaattaagacaaatacacaagagacaa
2941 agcacaaaaataaatatcataaggggatgaacaaaatggtggagaaagagtagacaaag
3001 tttttgatcacctgccttcaaagaaaggctgtgaattttgttcacttagacagcttggag
3061 acaagaaattacccaaaagtaaggtgaggaggataggcaaaaagagcagaaagatgtgaa
3121 tggacattgttgagaaatgtgataggaaaacaatcatagataaaggatttccaagcaact
3181 gagcatatccagatgaggtaggatgggataaactcttattgaaccaatcttcaccaattt
3241 tgttttctttgcagagcaagctaggaattgtttcccttctactgggcacaatacacgc
3301 attgattttgcctggaataagtggatagatataaaacaatttgtatggtatacacctcc
3361 aacttttatgatagctgttttccttccaattgttgtcctgatatttaaaagcatactatt
3421 cctgccatgcttgaggaagaagatactgaagattagacatggttgggaagacgtcaccaa
3481 aattaacaaaactgagatatgttcccagttgtagaattactgtttacacacattttgtt
3541 caatattgatatatttatcaccaacatttcaagtttgtatttgttaataaaatgattat
3601 tcaaggaaaaaaaaaaaaaaaaaaaaa
```

Figure 2Q (Part 2)

Amino acid sequence of STEAP-1 v.1 (SEQ ID NO: 36)
The STEAP-1 v.1 protein has 339 amino acids

```
  1 MESRKDITNQ EELWKMKPRR NLEEDDYLHK DTGETSMLKR PVLLHLHQTA HADEFDCPSE
 61 LQHTQELFPQ WHLPIKIAAI IASLTFLYTL LREVIHPLAT SHQQYFYKIP ILVINKVLPM
121 VSITLLAIVY LPGVIAAIVQ LHNGTKYKKF PHWLDKWMLT RKQFGLLSFF FAVLHAIYSL
181 SYPMRRSYRY KLLNWAYQQV QQNKEDAWIE HDVWRMEIYV SLGIVGLAIL ALLAVTSIPS
241 VSDSLTWREF HYIQSKLGIV SLLLGTIHAL IFAWNKWIDI IFAWNKWIDI KQFVWYTPPT FMIAVFLPIV
301 VLIFKSILFL PCLRKKILKI RHGWEDVTKI NKTEICSQL
```

Figure 3A

Amino acid sequence of STEAP-1 v.2 (SEQ ID NO: 37)
The STEAP-1 v.2 protein has 258 amino acids

```
  1 MESRKDITNQ EELWKMKPRR NLEEDDYLHK DTGETSMLKR PVLLHLHQTA HADEFDCPSE
 61 LQHTQELFPQ WHLPIKIAAI IASLTFLYTL LREVIHPLAT SHQQYFYKIP ILVINKVLPM
121 VSITLLAIVY LPGVIAAIVQ LHNGTKYKKF PHWLDKWMLT RKQFGLLSFF FAVLHAIYSL
181 SYPMRRSYRY KLLNWAYQQV QQNKEDAWIE HDVWRMEIYV SLGIVGLAIL ALLAVTSIPS
241 VSDSLTWREF HYIQVNNI
```

Figure 3B

Amino acid sequence of STEAP-1 v.3 (SEQ ID NO: 38)
The STEAP-1 v.3 protein has 282 amino acids

```
  1 MESRKDITNQ EELWKMKPRR NLEEDYLHK DTGETSMLKR PVLLHLHQTA HADEFDCPSE
 61 LQHTQELFPQ WHLPIKIAAI IASLTFLYTL LREVIHPLAT SHQQYFYKIP ILVINKVLPM
121 VSITLLALVY LPGVIAAIVQ LHNGTKYKKF PHWLDKWMLT RKQFGLLSFF FAVLHAIYSL
181 SYPMRRSYRY KLLNWAYQQV QQNKEDAWIE HDVWRMEIYV SLGIVGLAIL ALLAVTSIPS
241 VSDSLTWREF HYIQIIHKKS DVPESLWDPC LTRFKGLNLI QS
```

Figure 3C

Amino acid sequence of STEAP-1 v.4 (SEQ ID NO: 39)
The STEAP-1 v.4 protein has 258 amino acids

```
  1 MESRKDITNQ EELWKMKPRR NLEEDYLHK DTGETSMLKR PVLLHLHQTA HADEFDCPSE
 61 LQHTQELFPQ WHLPIKIAAI IASLTFLYTL LREVIHPLAT SHQQYFYKIP ILVINKVLPM
121 VSITLLALVY LPGVIAAIVQ LHNGTKYKKF PHWLDKWMLT RKQFGLLSLF FAVLHAIYSL
181 SYPMRRSYRY KLLNWAYQQV QQNKEDAWIE HDVWRMEIYV SLGIVGLAIL ALLAVTSIPS
241 VSDSLTWREF HYIQVNNI
```

Figure 3D

Homology of STEAP-1 (SEQ ID NO: 40) to mouse TNF -induced adipose-related protein (gi|1690513|))
(SEQ ID NO: 41)

```
Score = 224 bits (570), Expect = 2e-57
Identities = 110/270 (40%), Positives = 174/270 (63%)

Query:  66  ELFPQWHLPIKIAAIIASLTFLYTLLREVIHPLATSHQQYFYKIPILVINKVLPMVSITL 125
            +LFP W P +++++     F+Y +REVI+P          Y++ I + N+V P+ ++ L
Sbjct: 195  QLFPMWRFPFYLSSVLCIFFFVCAIREVIPYVNGKTDATYRLAISIPNRVFPITALIL 254

Query: 126  LALVYLPGVIAAIVQLHNGTKYKKFPHWLDKWMLTRKQFGLLSFFFAVLHAIYSLSYPMR 185
            LALVYLPG++AAI+QL+   GTKY++FP+WLD WML RKQ  FA LH IY+L P+R
Sbjct: 255  LALVYLPGILAAILQLYRGTKYRFPNWLDHWMLCRKQLGLVALGFAFLHVIYTLVIPIR 314

Query: 186  RSYRYKLLNWAYQQVQQNKEDAWIEHDVWRMEIYVSLGIVGLAIALLAVTSIPSVSDSL 245
            R++L N    Q    NK+     +I    W   + Y++LGI+G  +  LL +TS+PSVS+ +
Sbjct: 315  YYVRWRLRNATITQALTNKDSPFITSYAWINDSYLALGILGFFLFLLLGITSLPSVSNMV 374

Query: 246  TWREFHYIQSKLGIVSLLLGTIHALIFAWNKWIDIKQFVWYTPPTFMIAVFLPIVVLIFK 305
            WREF ++QSKLG ++L+L T H L++       +++       W P +++A+ +P  VL+ K
Sbjct: 375  NWREFRFVQSKLGYLTLVLCTAHTLVYGGKRFLSPSIIRWSLPSAYILALLIPCAVLVLK 434

Query: 306  SILFLPCLRKKILKIRHGWEDVTKINKTEI 335
            +L +PC+ K + +IR GWE +K ++ +
Sbjct: 435  CILIMPCIDKTLTRIRQGWERNSKYTQSAL 464
```

Figure 4A

Homology of STEAP-1 (SEQ ID NO: 42) to rat pHyde protein (gi|21717655|) (SEQ ID NO: 43)

```
Score = 283 bits (724), Expect = 2e-75
Identities = 127/259 (49%), Positives = 184/259 (71%)

Query:  67  LFPQWHLPIKIAAIIASLTFLYTLLREVIHPLATSHQQYFYKIPILVINKVLPMVSITLL  126
            L P W +P  +A  ++ ++ Y  +R+V+ P    + FYK+P+ V+N  +P V+    LL
Sbjct: 208  LLPSWKVPTLLALGLSTQSYAYNFIRDVLQPYIRKDENKFYKMPLSVVNTTIPCVAYVLL  267

Query: 127  ALVYLPGVIAA+VQLHNGTKYKKFPHWLDKWMLTRKQFGLLSFFFAVLHAIYSLSYPMRR  186
            +LVYLPGV+AA +QL  GTKY++FP WLD W+ RKQ GLLSFFFA+LHA+YS   P+RR
Sbjct: 268  SLVYLPGVLAAALQLRRGTKYQRFPDWLDHWLQHRKQIGLLSFFFAMLHALYSFCLPLRR  327

Query: 187  SYRYKLLNWAYQQVQQNKEDAWIEHDVWRMEIYVSLGIVGLAILALLAVTSIPSVSDSLT  246
            S+RY L+N A +QV  NK    W+E +VWRMEIY+SLG++   L  +L+LLAVTSIPS+++SL
Sbjct: 328  SHRYDLVNLAVKQVLANKSRLWEEEVWRMEIYLSLGVLALGMLSLLAVTSIPSIANSLN  387

Query: 247  WREFHYIQSKLGIVSLLLGTIHALIFAWNKWIDIKQFVWYTPPTEMIAVFLPIVVLIFKS  306
            W+EF  ++QS LG V+L+L T+H L + W +    +  +Y PPTF + + LP V+++ K
Sbjct: 388  WKEFSFVQSTLGFVALMLSTMHTLTYGWTRAFEENHYKFYLPPTFTLTLLLPCVIILAKG  447

Query: 307  ILFLPCLRKKILKIRHGWE  325
            + LPCL  ++ KIR GWE
Sbjct: 448  LFLIPCLSHRLTKIRRGWE  466
```

Figure 4B

Homology of STEAP-1 (SEQ ID NO: 44) to mouse six transmembrane epithelial antigen of the prostate (gi|20820492|) (SEQ ID NO:45)

Score = 488 bits (1256), Expect = e-137
Identities = 255/303 (84%), Positives = 277/303 (91%)

```
Query:   1  MLKRPVLLHLHQTAHADEFDCPSELQHTQELFPQWHLPIKIAATIASLTFLYTLLREVIH   60
            MLKRP L HL    H D FDCPSELQHTQE   FP W  LP+K+AAII+SLTFLYTLLRE+I+
Sbjct:  37  MLKRPGLSHLQHAVHVDAFDCPSELQHTQEFFPNWRLPVKVAAIISSLTFLYTLLREIIY   96

Query:  61  PLATSHQQYFYKIPILVINKVLPMVSITLLALVYLPGVIAAIVQLHNGTKYKKFPHWLDK  120
            PL TS +QYFYKIPILVINKVLPMV+ITLLALVYLPG +AA+VQL NGTKYKKFP WLD+
Sbjct:  97  PLVTSREQYFYKIPILVINKVLPMVAITLLALVYLPGELAAVVQLRNGTKYKKFPPWLDR  156

Query: 121  WMLTRKQFGLLSFFFAVLHAIYSLSYPMRRSYRYKLLNWAYQQVQQNKEDAWIEHDVWRM  180
            WML RKQFGLLSFFFAVLHA+YSLSYPMRRSYRYKLLNWAY+QVQQNKEDAW+EHDVWRM
Sbjct: 157  WMLARKQFGLLSFFFAVLHAVYSLSYPMRRSYRYKLLNWAYKQVQQNKEDAWEHDVWRM  216

Query: 181  EIYVSLGIVGLAILALLAVTSIPSVSDSLTWREFHYIQSKLGIVSLLLGTIHALIFAWNK  240
            EIYVSLGIVGLAILALLAVTSIPSVSDSLTWREFHYIQSKLGIVSLLLGT+HAL+FAWNK
Sbjct: 217  EIYVSLGIVGLAILALLAVTSIPSVSDSLTWREFHYIQSKLGIVSLLLGTVHALVFAWNK  276

Query: 241  WIDIKQFVWYTPPTFMIAVFLPIVVLIFKSILFLPCLRKKILKIRHGWEDVTKINKTEIC  300
            W+D+ QFVWY PPTFMIAVFLP +VLI K   L LPCLRKKILKIR GWEDV+KIN+TE+
Sbjct: 277  WVDVSQFVWYMPPTFMIAVFLPTIVLICKIALCLPCLRKKILKIRCGWEDVSKINRTEMA  336

Query: 301  SQL  303
            S+L
Sbjct: 337  SRL  339
```

Figure 4C

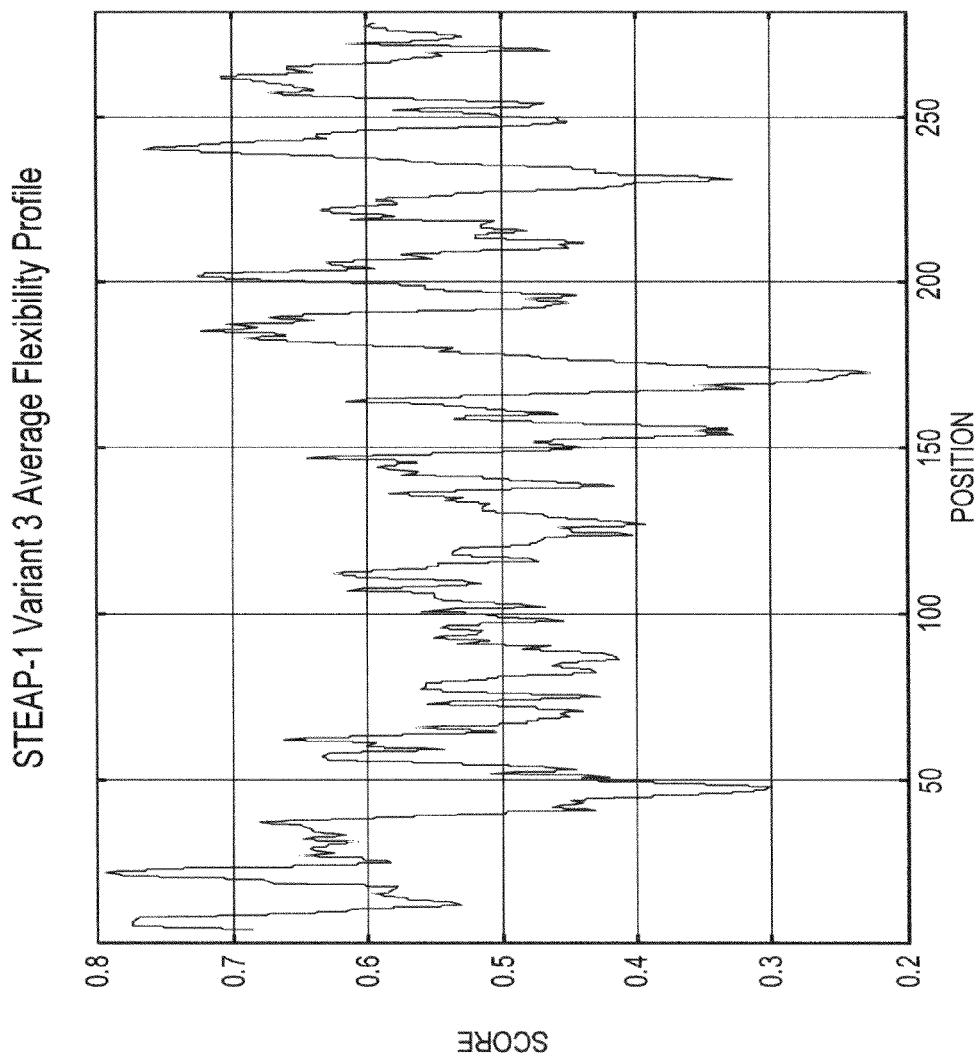

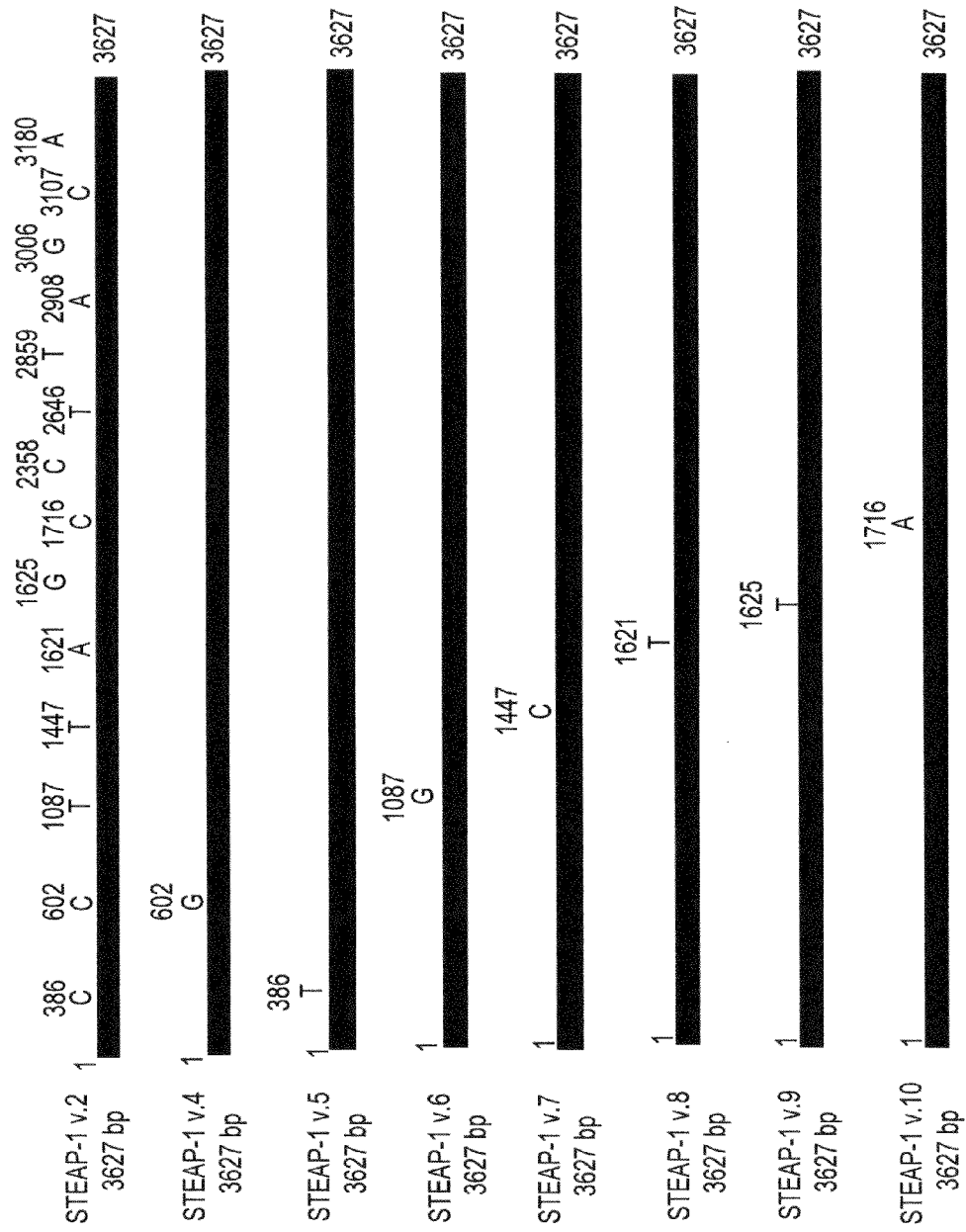
Figure 10 (Part 1)

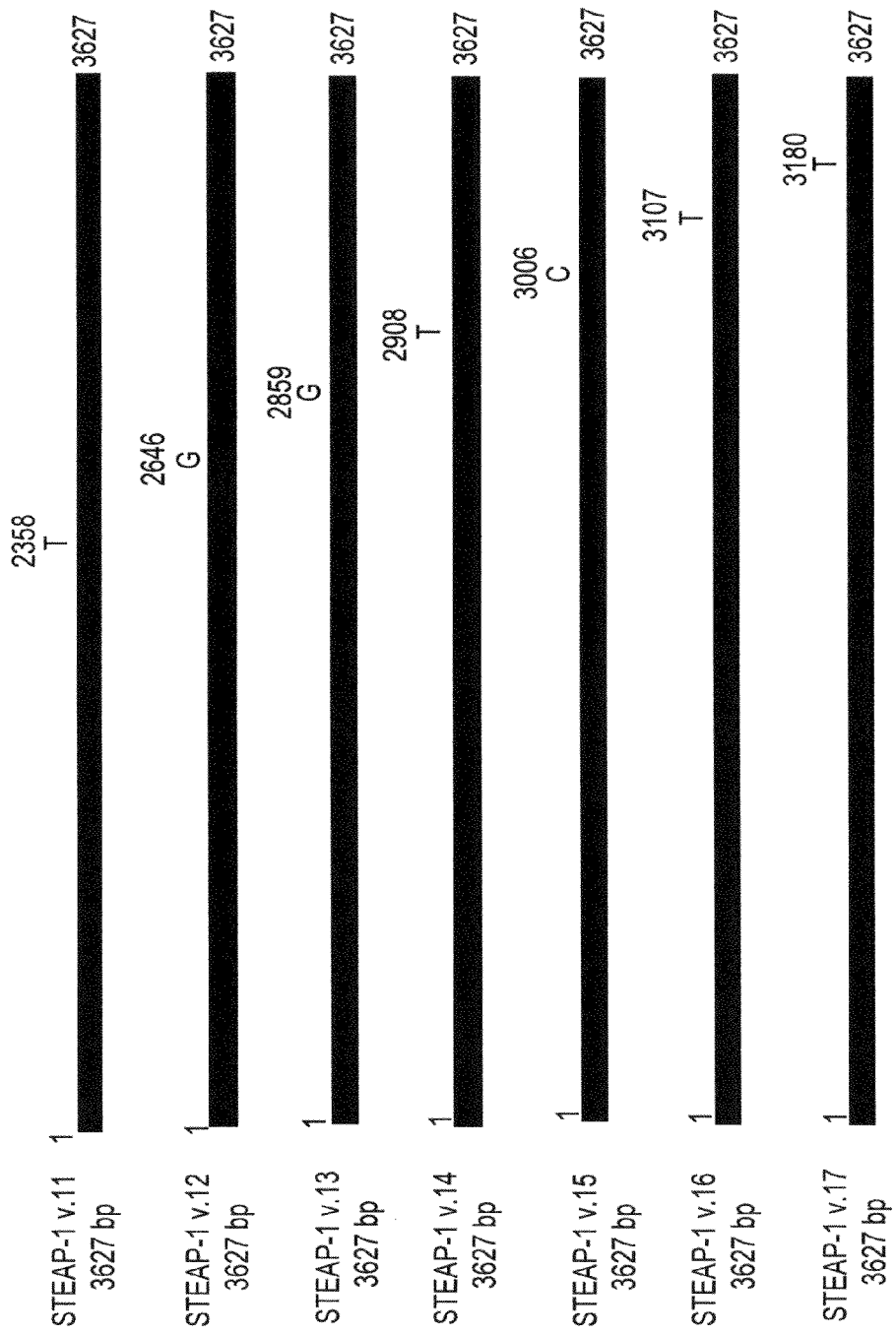
Figure 10 (Part 2)

Secondary Structure Prediction of STEAP-1 Variant 1

```
         10        20        30        40        50        60        70
         |         |         |         |         |         |         |
MESRKDITNQEELWKMKPRRNLEEDYLHKDTGETSMLKRPVLLHLHQTAHADEFDCPSELQHTQELFPQ
ccccccccchhhhhhhccccccccccccccccccchhhhhhhhhheccccccccccccccccchhccc WHLPIKIAAIIASLTFLYTLLREVIHPLATSHQQYFYKIPILVINKVLPMVSITLLALVLPGVIAAIVQ
chcchhhhhhhhhhhhhhhhhhhhcchhhhhhhhhheccceeehcchhchhhhhhhhhhhhhhhhhh LHNGTKYKKFPHWLDKWMLTRKQFGLLSFFFAVLHAIYSLSYPMRRSYRYKLLNWAYQQVQQNKEDAWIE
hccccccccchhhhhhhhhhhhhhhhhhhhhhhhhccchhahhhhhhhhhhhhhhhhcccchheh HDVWRMEIYVSLGIVGLAILALLAVTSIPSVSDSLTWREFHYIQSKLGIVSLLLGTIHALIFAWNKWIDI
hhhhhhhhhhhhhhhhhhhhhhhhhhhccccccchhhhhhhhchhhhhhhhhhhhhhhhhhhhhhheee KQFVWYTPPTFMIAVFLPIVLIFKSILFLPCLRKKILKIRHGWEDVTKINKTEICSQL
eeeeccccchhhhhhhhhhhhhhhhhhhhhhhhhhheccccccchhcccchcehhcc Alpha helix     (h) :  64.60%
Extended strand (e) :   4.72%
Random coil     (c) :  30.68%
```

Figure 13A

Secondary Structure Prediction of STEAP-1 Variant 2

```
         10        20        30        40        50        60        70
          |         |         |         |         |         |         |
MESRKDITNQEELWKMKPRRNLEEDDYLHKDTGETSMLKRPVLLHLHQTAHADEFDCPSELQHTQELFPQ
ccccccccchhhhhhhhhhcccccccccccccccchhhhhhhhhhheccccccccccccccchhhccc
WHLPIKIAAIIASLTFLYTLLREVIHPLATSHQQYFYKIPILVINKVLPMVSITLLALVYLPGVIAAIVQ
chcchhhhhhhhhhhhhhhhhhhhhhcchhhhhhhhheccceeehcchhhhhhhhhhhhhhhhhhhhh
LHNGTKYKKFPHWLDKWMLTRKQFGLLSFFFAVLHAIYSLSYPMRRSYRYKLLNWAYQQVQQNKEDAWIE
hcccccccccchhhhhhhhhhhhhhhhhhhhhhhhhhhhhhhhhhhhhhhcchhhhhhhhhhcccchheh
EDVWRMEIYVSLGIVGLAIALLAVTSIPSVSDSLTWREFHYIQVNNI
hhhhhhhhhhhhhhhhhhhhhhhhhhhcccccccchhhhhheehccc Alpha helix      (h)  :  62.79%
Extended strand  (e)  :   3.10%
Random coil      (c)  :  34.11%
```

Figure 13B

Secondary Structure Prediction of STEAP-1 Variant 3

```
         10        20        30        40        50        60        70
          |         |         |         |         |         |         |
MESRKDITNQEELWMKPRRNLEEDDYLHKDTGETSMLKRPVLLHLHQTAHADEFDCPSELQHTQELFPQ
cccccccchhhhhhcccccccccccccccccchhhhhhhheccccccccccccccccchhccc
WHLPIKIAAIIASLTFLYTLLREVIHPLATSHQQYFYKIPILVINKVLPMVSITLLALVYLPGVIAAIVQ
chcchhhhhhhhhhhhhhhhhhhhhcchhhhhhhheccceeehcchhchhhhhchhhhhhhh
LHNGTKYKKFPHWLDKWMLTRKQFGLLSFFFAVLHATYSLSYPMRRSYRYKLLNWAYQQVQQNKEDAWIE
hccccccccccchhhhhhhhhhhhhhhhhhhhhhhhcchhhhhhhhhhhhhhhccchheh
HDVWRMEIYVSLGIVGLAIALLALLAVTSIPSVSDSLTWREFHYIQIIHKKSDVPESLWDPCLTRFKGLNLI
hhhhhhhhhhhhhhhhhhhhhhhcccccccccchhhhhheeeeeecccccccchhhchhccccceee Alpha helix       (h) :  58.87%
Extended strand   (e) :   5.32%
Random coil       (c) :  35.82%
```

Figure 13C

STEAP-1 Expression in Lymphoma Patient Specimens

| Patient # | Diagnosis | STEAP1 expression |
|---|---|---|
| 1 | Spleen follicular lymphoma Atypical B-cell type | Strong expression |
| 2 | LCA+,CD20+,Ki+,CD3-,keratin- | Medium expression |
| 3 | Diffuse large B-cell type | Medium expression |
| 4 | Hodgkin's, mixed cellularity | No expression |
| 5 | Mantle-cell Lymphoma | Medium expression |
| 6 | Large cell B-cell type | No expression |
| 7 | Diffuse mixed large & small cell lymphoma-Stage II | No expression |
| 8 | Diffuse large cell lymphoma-Stage I | No expression |
| 9 | CD20+,CD10+,CD22+, CD14-,CD38-,CD5-,CD3- | Medium expression |
| 10 | B-Cell lymphoma (CD5-&CD10-) | Medium expression |
| 11 | Small B lymphocytic type (CLL) | Medium expression |
| Percentage | | 72.7% |

Legend: Strong expressin / Medium expression / No expresssion

Figure 14F

Cell Surface STEAP-1 - Specific MAbs

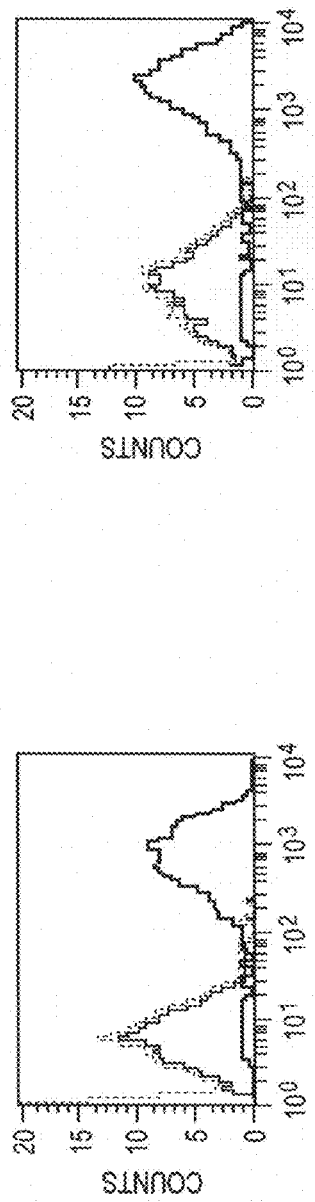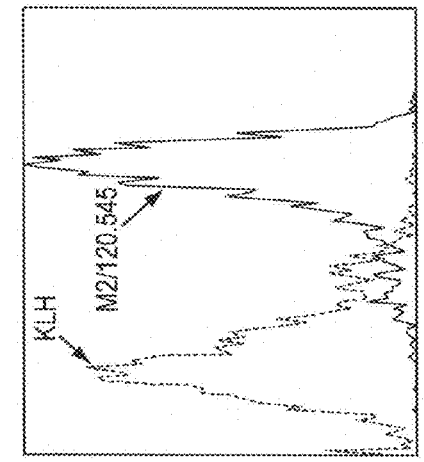
STEAP1/120.545 MAb Recognizes Cell Surface STEAP-1
Figure 18A — 3T3-STEAP1 cells
Figure 18B — RAT1-STEAP1 cells
Figure 18C — LNCaP cells
Figure 18D — FLUORESCENCE MICROSCOPY The cDNA and amino acid sequence of M2/X92.30 VH clone #2

```
  1 V  K  L  Q  E  S  G  P  E  L  K  K  P  G  E  T  V  K  I  S
  1 gtcaagctgcaggagtctggacctgagctgaagaagcctggagagacagtcaagatctcc
 21 C  K  A  S  G  Y  T  F  T  N  Y  G  M  N  W  V  K  Q  A  P
 61 tgcaaggcttctgggtataccttcacaaactatggaatgaactgggtgaagcaggctcca
 41 G  K  G  L  K  W  M  G  W  I  N  T  Y  T  G  E  P  T  Y  A
121 ggaaagggtttaaagtggatgggctggataaacacctacactggagagccaacatatgct
 61 D  D  F  K  G  R  F  A  F  S  L  E  T  S  A  S  T  A  Y  L
181 gatgacttcaaggacggttgccttctctttggaaacctctgccagcactgcctatttg
 81 Q  I  N  N  L  K  N  E  D  T  A  T  Y  F  C  A  R  P  W  F
241 cagatcaacaacctcaaaaatgaggacacggctacatatttctgtgcaagaccctggttt
101 A  Y  W  G  Q  G  T  T  V  T  V  S  S
301 gcttactggggccaagggaccacggtcaccgtctcctca
```

Figure 19A

The cDNA and amino acid sequence of M2/X92.30 VL clone #2

```
  1 G  L  F  E  A  A  T  M  K  L  P  V  R  L  L  V  L  W  I  R
  1 ggactgttcgaagccgccaccatgaagttgcctgttaggctgttggtgctctggattcgg
 21 E  T  N  G  D  V  V  M  T  Q  T  P  L  T  L  S  V  T  I  G
 61 gaaaccaacggtgatgttgtgatgacccagactccactcactttgtcggttaccattgga
 41 Q  P  A  S  I  S  C  K  S  S  Q  S  L  L  D  S  D  G  K  T
121 caaccagcctccatctcttgcaagtcaagtcagagcctcttagatagtgatggaaagaca
 61 Y  L  N  W  L  L  Q  R  P  G  Q  S  P  K  R  L  I  Y  L  V
181 tatttgaattggttgttacagaggccaggccagtctccaaagcgcctaatctatctggtg
 81 S  K  L  D  S  G  V  P  D  R  F  T  G  S  G  S  G  T  D  F
241 tctaaactggactctggagtccctgacaggttcactggcagtggatcagggacagatttc
101 T  L  K  I  S  R  V  E  A  E  D  L  G  V  Y  Y  C  W  Q  G
301 acactgaaaatcagcagagtggaggctgaggatttggagtttattattgctggcaaggt
121 T  H  F  P  F  T  F  G  S  G  T  K  L  E  I  K  R  T  D  A
361 acacatttccattcacgttcggctcggggacaaagttggaaataaaacgtacggatgct
141 A  P  T  V  S
421 gcaccaactgtatcc
```

Figure 19B

The cDNA and amino acid sequence of M2/X92.30 VL clone #6

```
  1 G  L  F  E  A  A  T  M  E  A  P  A  Q  L  T  L  S  V  T  I
  1 ggactgttcgaagccgccaccatggaagcccagctcagctcactttgtcggttaccatt
 21 G  Q  P  A  S  I  S  C  K  S  S  Q  S  L  L  D  S  D  G  K
 61 ggacaaccagcctccatctcttgcaagtcaagtcagagcctcttagatagtgatggaaag
 41 T  Y  L  N  W  L  L  Q  R  P  G  Q  S  P  K  R  L  I  Y  L
121 acatatttgaattggttgttacagaggccaggccagtctccaaagcgcctaatctatctg
 61 V  S  K  L  D  S  G  V  P  D  R  F  T  G  S  G  S  G  T  D
181 gtgtctaaactggactctggagtccctgacaggttcactggcagtggatcagggacagat
 81 F  T  L  K  I  S  R  V  E  A  E  D  L  G  V  Y  Y  C  W  Q
241 ttcacactgaaaatcagcagagtggaggctgaggatttgggagtttattattgctggcaa
101 G  T  H  F  P  F  T  F  G  S  G  T  K  L  E  I  K  R  T  D
301 ggtacacattttccattcacgttcggctcggggacaaagttggaaataaaacgtacggat
121 A  A  P  T  V  S
361 gctgcaccaactgtatcc
```

Figure 19C

The cDNA and amino acid sequence of M2/X120.545 VL clone #8

```
  1 M  G  F  K  M  E  S  Q  A  Q  V  L  M  L  L  L  L  W  V  S
  1 atgggcttcaagatggagtcacaggcccaggttcttatgttactgctgctatgggtatct
 21 G  T  C  G  D  I  V  M  S  Q  S  P  S  S  L  A  V  S  V  G
 61 ggtacctgtggggacattgtgatgtcacagtctccatcctccctagctgtgtcagttgga
 41 E  K  V  T  M  S  C  K  S  S  Q  S  L  L  Y  R  S  N  Q  K
121 gagaaggttaccatgagctgcaagtccagtcagagccttttatataggagcaatcaaaag
 61 N  Y  L  A  W  Y  Q  Q  K  P  G  Q  S  P  K  L  L  I  Y  W
181 aactacttggcctggtaccagcagaaaccagggcagtctcctaaactgctgatttattgg
 81 A  S  T  R  E  S  G  V  P  D  R  F  T  G  S  G  S  G  T  D
241 gcctccactagggaatctggggtccctgatcgcttcacaggcagtggatctgggacagat
101 F  T  L  T  I  S  S  V  K  A  E  D  L  A  V  Y  Y  C  Q  Q
301 ttcactctcaccatcagcagtgtgaaggctgaagacctggcagtttattactgtcagcaa
121 Y  Y  N  Y  P  R  T  F  G  G  G  T  K  L  E  I  K  R  T  D
361 tattataactatcctcggacgttcggtggaggcaccaagctggaaatcaaacgtacggat
141 A  A  P  T  V  S
421 gctgcaccaactgtatcc
```

Figure 19D

The amino acid sequence of M2/X92.30 VH clone #2

```
  1 VKLQESGPEL KKPGETVKIS CKASGYTFTN YGMNWVKQAP GKGLKWMGWI NTYTGEPTYA
 61 DDFKGRFAFS LETSASTAYL QINNLKNEDT ATYFCARPWF AYWGQGTTVT VSS
```

Figure 20A

The amino acid sequence of M2/X92.30 VL clone #2

```
  1 GLFEAATMKL PVRLLVLWIR ETNGDVVMTQ TPLTLSVTIG QPASISCKSS QSLLDSDGKT
 61 YLNWLLQRPG QSPKRLIYLV SKLDSGVPDR FTGSGSGTDF TLKISRVEAE DLGVYYCWQG
121 THFPFTFGSG TKLEIKRTDA APTVS
```

Figure 20B

The cDNA and amino acid sequence of M2/X92.30 VL clone #6

```
  1 G   L   F   E   A   A   T   M   E   A   P   A   Q   L   T   L   S   V   T   I
  1 ggactgttcgaagccgccaccatggaagcccagctcagctcactttgtcggttaccatt
 21 G   Q   P   A   S   I   S   C   K   S   S   Q   S   L   L   D   S   D   G   K
 61 ggacaaccagcctccatctcttgcaagtcaagtcagagcctcttagatagtgatggaaag
 41 T   Y   L   N   W   L   L   Q   R   P   G   Q   S   P   K   R   L   I   Y   L
121 acatatttgaattggttacagaggccaggccagtctccaaagcgcctaatctctg
 61 V   S   K   L   D   S   G   V   P   D   R   F   T   G   S   G   S   G   T   D
181 gtgtctaaactggactctggagtccctgacaggttcactggcagtggatcagggacagat
 81 F   T   L   K   I   S   R   V   E   A   E   D   L   G   V   Y   Y   C   W   Q
241 ttcacactgaaaatcagcagagtggaggctgaggattgggagtttattattgctggcaa
101 G   T   H   F   P   F   T   F   G   S   G   T   K   L   E   I   K   R   T   D
301 ggtacacatttccattcacgttcggctcggggacaaagttgaaataaaacgtacggat
121 A   A   P   T   V   S
361 gctgcaccaactgtatcc
```

Figure 20C

Amino acid alignment of M2/X92.30 VL clone #2 and M2/M92.30 VL clone #6

```
Clone 2:   1  GLFEAATMKLPVRLLVLWIRETNGDVVMTQTPLTLSVTIGQPASISCKSSQSLLDSDGKT   60
              GLFEAATM+    P   +L                TLSVTIGQPASISCKSSQSLLDSDGKT
Clone 6:   1  GLFEAATMEAPAQL---------------------TLSVTIGQPASISCKSSQSLLDSDGKT   41

Clone 2:  61  YLNWLLQRPGQSPKRLIYLVSKLDSGVPDRFTGSGSGTDFTLKISRVEAEDLGVYYCWQG  120
              YLNWLLQRPGQSPKRLIYLVSKLDSGVPDRFTGSGSGTDFTLKISRVEAEDLGVYYCWQG
Clone 6:  42  YLNWLLQRPGQSPKRLIYLVSKLDSGVPDRFTGSGSGTDFTLKISRVEAEDLGVYYCWQG  101

Clone 2: 121  THFPFTFGSGTKLEIKRTDAAPTVS  145
              THFPFTFGSGTKLEIKRTDAAPTVS
Clone 6: 102  THFPFTFGSGTKLEIKRTDAAPTVS  126
```

Figure 20D

The amino acid sequence of M2/X120.545 VL clone #8
The sequence of the signal peptide is underlined

```
  1  MGFKMESQAQ VLMLLLLWVS GTCGDIVMSQ SPSSLAVSVG EKVTMSCKSS QSLLYRSNQK
 61  NYLAWYQQKP GQSPKLLIYW ASTRESGVPD RFTGSGSGTD FTLTISSVKA EDLAVYYCQQ
121  YNYNPRTFGG GTKLEIKRTD AAPTVS
```

Figure 20E

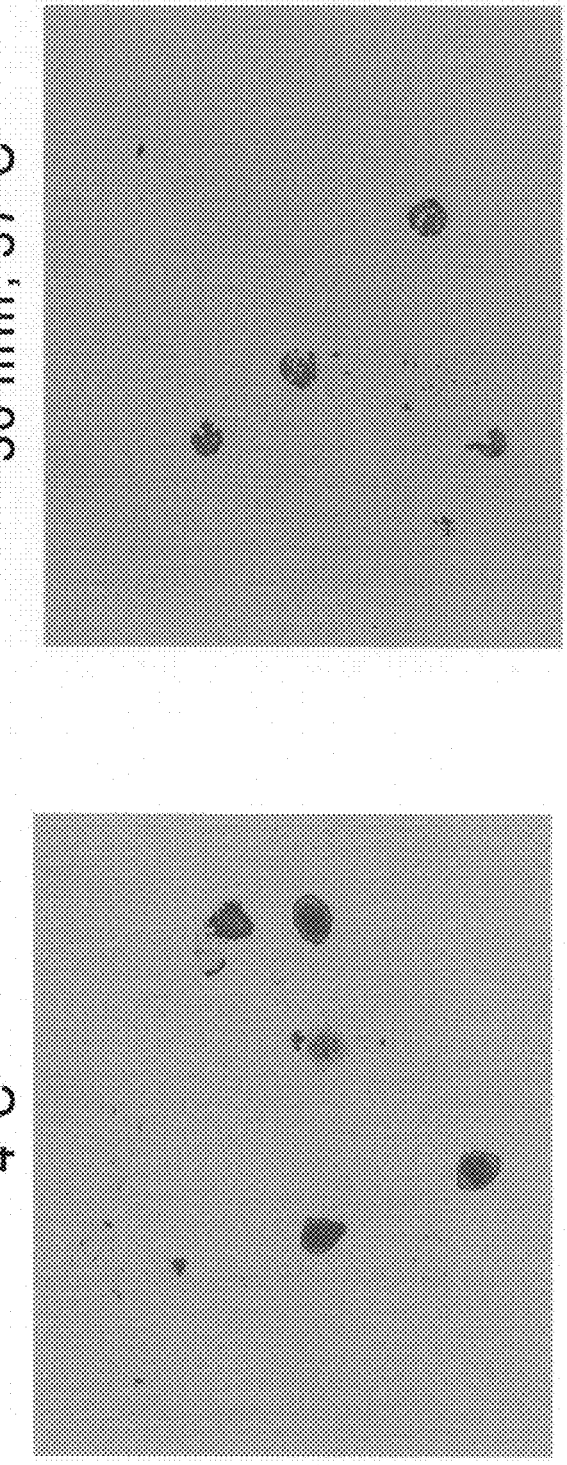
Figure 22A / Figure 22B

STEAP-1 Internalization by STEAP1 M2/120.545 MAb 30 min, 37°C

4°C

ANTIBODIES AND MOLECULES DERIVED THEREFROM THAT BIND TO STEAP-1 PROTEINS

CROSS-REFERENCE TO RELATED APPLICATIONS

This patent application is a continuation-in-part of U.S. patent application Ser. No. 10/236,878, filed 6 Sep. 2002, now abandoned, which claims priority to U.S. Provisional patent application No. 60/370,387, filed 5 Apr. 2002, now lapsed; and to U.S. Provisional patent application No. 60/317,840, filed 6 Sep. 2001, now lapsed. This patent application is also related to pending U.S. patent application Ser. No. 09/455,486, filed 6 Dec. 1999; which is a continuation-in-part of U.S. patent application Ser. No. 09/323,873, filed 1 Jun. 1999, now issued as U.S. Pat. No. 6,329,503; and to pending U.S. patent application Ser. No. 10/750,262, filed 31 Dec. 2003; and to pending U.S. patent application Ser. No. 10/011,095, filed 6 Dec. 2001; and to pending U.S. patent application Ser. No. 10/010,667, filed 6 Dec. 2001; and to U.S. Provisional patent application No. 60/091,183, filed 30 Jun. 1998, now lapsed; and to U.S. Provisional patent application No. 60/087,520, filed 1 Jun. 1998, now lapsed. The contents of each application listed in this paragraph are fully incorporated by reference herein.

STATEMENT OF RIGHTS TO INVENTIONS MADE UNDER FEDERALLY SPONSORED RESEARCH

Not applicable.

FIELD OF THE INVENTION

The invention described herein relates to antibodies, as well as binding fragments thereof and molecules engineered therefrom, that bind proteins, termed STEAP-1. The invention further relates to diagnostic, prognostic, prophylactic and therapeutic methods and compositions useful in the treatment of cancers that express STEAP-1.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, ovary, and bladder represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res 1996 Sep. 2 (9): 1445-51),STEAP (Hubert, et al., Proc Natl Acad Sci U S A. 1999 Dec. 7; 96(25): 14523-8) and prostate stem cell antigen (PSCA) (Reiter et al., 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and eight per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992-1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for cancers. These include the use of antibodies, vaccines, and small molecules as treatment modalities. Additionally, there is also a need to use these modalities as research tools to diagnose, detect, monitor, and further the state of the art in all areas of cancer treatment and studies.

SUMMARY OF THE INVENTION

The invention provides antibodies as well as binding fragments thereof and molecules engineered therefrom, that bind to STEAP-1 proteins and polypeptide fragments of STEAP-1 proteins. As used herein, the term STEAP-1 is synonamous with 8P1D4. The invention comprises polyclonal and monoclonal antibodies, murine and other mammalian antibodies, chimeric antibodies, humanized and fully human antibodies, and antibodies labeled with a detectable marker or therapeutic agent. In certain embodiments, there is a proviso that the entire nucleic acid sequence of FIG. 2 is not encoded and/or the entire amino acid sequence of FIG. 2 is not prepared. In certain embodiments, the entire nucleic acid sequence of FIG. 2 is encoded and/or the entire amino acid sequence of FIG. 2 is prepared, either of which are in respective human unit dose forms.

The invention further provides methods for detecting the presence and status of STEAP-1 polynudeotides and proteins in various biological samples, as well as methods for identifying cells that express STEAP-1. An embodiment of this invention provides methods for monitoring STEAP-1 gene products in a tissue or hematology sample having or suspected of having some form of growth dysregulation such as cancer.

The invention further provides various immunogenic or therapeutic compositions and strategies for treating cancers that express STEAP-1 such as cancers of tissues listed in Table I, including therapies aimed at inhibiting the transcription, translation, processing or function of STEAP-1 as well as cancer vaccines. In one aspect, the invention provides compositions, and methods comprising them, for treating a cancer that expresses STEAP-1 in a human subject wherein the composition comprises a carrier suitable for human use and a human unit dose of one or more than one agent that inhibits the production or function of STEAP-1. Preferably, the carrier is a uniquely human carrier. In another aspect of the invention, the agent is a moiety that is immunoreactive with STEAP-1 protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

In another aspect, the agent comprises one or more than one peptide which comprises a cytotoxic T lymphocyte (CTL) epitope that binds an HLA class I molecule in a human to elicit a CTL response to STEAP-1 and/or one or more than one peptide which comprises a helper T lymphocyte (HTL) epitope which binds an HLA class II molecule in a human to elicit an HTL response. The peptides of the invention may be on the same or on one or more separate polypeptide molecules. In a further aspect of the invention, the agent comprises one or more than one nucleic acid molecule that expresses one or more than one of the CTL or HTL response stimulating peptides as described above. In yet another aspect of the invention, the one or more than one nucleic acid molecule may express a moiety that is immunologically reactive with STEAP-1 as described above. The one or more than one nucleic acid molecule may also be, or encodes, a molecule that inhibits production of STEAP-1. Non-limiting examples of such molecules include, but are not limited to, those complementary to a nucleotide sequence essential for production of STEAP-1 (e.g. antisense sequences or molecules that form a triple helix with a nucleotide double helix essential for STEAP-1 production) or a ribozyme effective to lyse STEAP-1 mRNA.

Another embodiment of the invention is antibody epitopes, which comprise a peptide regions, or an oligonucleotide encoding the peptide region, that has one two, three, four, or five of the following characteristics:

i) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a peptide region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or v) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9.

The present invention also relates to a gene, designated STEAP-1, that has been found to be over-expressed in the cancer(s) listed in Table I. Northern blot expression analysis of STEAP-1 gene expression in normal tissues shows a restricted expression pattern in adult tissues. The nucleotide (FIG. 2) and amino acid (FIG. 2, and FIG. 3) sequences of STEAP-1 are provided. The tissue-related profile of STEAP-1 in normal adult tissues, combined with the over-expression observed in the tissues listed in Table I, shows that STEAP-1 is aberrantly over-expressed in at least some cancers, and thus serves as a useful diagnostic, prophylactic, prognostic, and/or therapeutic target for cancers of the tissue(s) such as those listed in Table I.

The invention provides polynucleotides corresponding or complementary to all or part of the STEAP-1 genes, mRNAs, and/or coding sequences, preferably in isolated form, including polynucleotides encoding STEAP-1-related proteins and fragments of 4, 5, 6, 7, 8, 9, 10, 11, 12, 13, 14, 15, 16, 17, 18, 19, 20, 21, 22, 23, 24, 25, or more than 25 contiguous amino acids; at least 30, 35, 40, 45, 50, 55, 60, 65, 70, 80, 85, 90, 95, 100 or more than 100 contiguous amino acids of a STEAP-1-related protein, as well as the peptides/proteins themselves; DNA, RNA, DNA/RNA hybrids, and related molecules; polynucleotides or oligonucleotides complementary or having at least a 90% homology to the STEAP-1 genes or mRNA sequences or parts thereof, and polynucleotides or oligonucleotides that hybridize to the STEAP-1 genes, mRNAs, or to STEAP-1-encoding polynucleotides. Also provided are means for isolating cDNAs and the genes encoding STEAP-1. Recombinant DNA molecules containing STEAP-1 polynucleotides, cells transformed or transduced with such molecules, and host-vector systems for the expression of STEAP-1 gene products are also provided.

BRIEF DESCRIPTION OF THE FIGURES

The file of this patent contains at least one drawing executed in color. Copies of this patent with color drawing(s) will be provided by the Patent and Trademark Office upon request and payment of the necessary fees.

FIG. 1. The STEAP-1 SSH sequence of 436 nucleotides.

FIG. 2. The cDNA and amino acid sequence of STEAP-1 variant 1 (also called "STEAP-1 v.1" or "STEAP-1 variant 1") is shown in FIG. 2A. The start methionine is underlined. The open reading frame extends from nucleic acid 66-1085 including the stop codon.

Figure 5A:
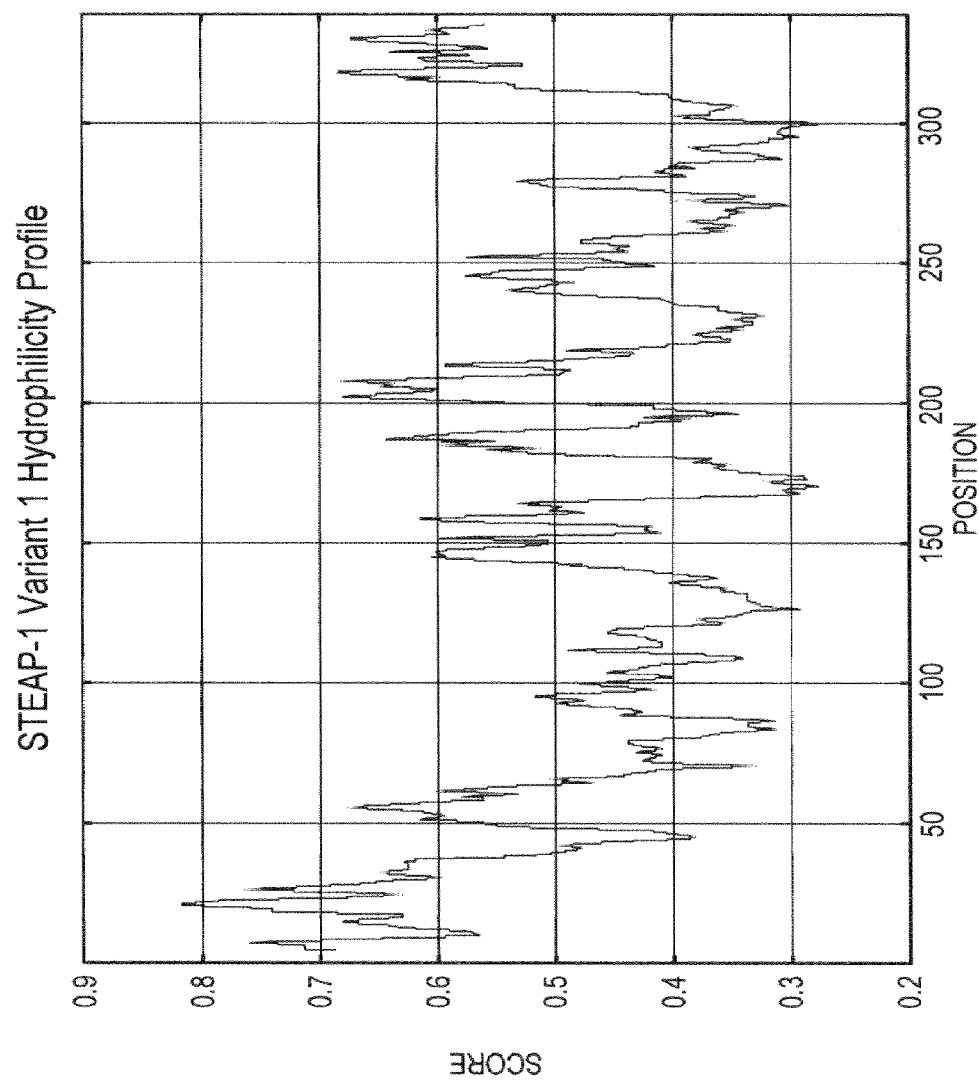

The cDNA and amino acid sequence of STEAP-1 variant 2 (also called "STEAP-1 v.2") is shown in FIG. 2B. The codon for the start methionine is underlined. The open reading frame extends from nucleic acid 96-872 including the stop codon.

The cDNA and amino acid sequence of STEAP-1 variant 3 (also called "STEAP-1 v.3") is shown in FIG. 2C. The codon for the start methionine is underlined. The open reading frame extends from nucleic acid 96-944 including the stop codon.

The cDNA and amino acid sequence of STEAP-1 variant 4 (also called "STEAP-1 v.4") is shown in FIG. 2D. The codon for the start methionine is underlined. The open reading frame extends from nucleic acid 96-872 including the stop codon.

The cDNA and amino acid sequence of STEAP-1 variant 5 (also called "STEAP-1 v.5") is shown in FIG. 2E. The codon for the start methionine is underlined. The open reading frame extends from nucleic acid 96-872 including the stop codon.

The cDNA and amino acid sequence of STEAP-1 variant 6 (also called "STEAP-1 v.6") is shown in FIG. 2F. The codon for the start methionine is underlined. The open reading frame extends from nucleic acid 96-872 including the stop codon.

The cDNA and amino acid sequence of STEAP-1 variant 7 (also called "STEAP-1 v.7") is shown in FIG. 2G. The codon for the start methionine is underlined. The open reading frame extends from nucleic acid 96-872 including the stop codon.

The cDNA and amino acid sequence of STEAP-1 variant 8 (also called "STEAP-1 v.8") is shown in FIG. 2H. The codon for the start methionine is underlined. The open reading frame extends from nucleic acid 96-872 including the stop codon.

The cDNA and amino acid sequence of STEAP-1 variant 9 (also called "STEAP-1 v.9") is shown in FIG. 2I. The codon for the start methionine is underlined. The open reading frame extends from nucleic acid 96-872 including the stop codon.

The cDNA and amino acid sequence of STEAP-1 variant 10 (also called "STEAP-1 v.10") is shown in FIG. 2J. The codon for the start methionine is underlined. The open reading frame extends from nucleic acid 96-872 including the stop codon.

The cDNA and amino acid sequence of STEAP-1 variant 11 (also called "STEAP-1 v.11") is shown in FIG. 2K. The codon for the start methionine is underlined. The open reading frame extends from nucleic acid 96-872 including the stop codon.

The cDNA and amino acid sequence of STEAP-1 variant 12 (also called "STEAP-1 v.12") is shown in FIG. 2L. The codon for the start methionine is underlined. The open reading frame extends from nucleic acid 96-872 including the stop codon.

The cDNA and amino acid sequence of STEAP-1 variant 13 (also called "STEAP-1 v.13") is shown in FIG. 2M. The codon for the start methionine is underlined. The open reading frame extends from nucleic acid 96-872 including the stop codon.

The cDNA and amino acid sequence of STEAP-1 variant 14 (also called "STEAP-1 v.14") is shown in FIG. 2N. The codon for the start methionine is underlined. The open reading frame extends from nucleic acid 96-872 including the stop codon.

The cDNA and amino acid sequence of STEAP-1 variant 15 (also called "STEAP-1 v.15") is shown in FIG. 2O. The codon for the start methionine is underlined. The open reading frame extends from nucleic acid 96-872 including the stop codon.

The cDNA and amino acid sequence of STEAP-1 variant 16 (also called "STEAP-1 v.16") is shown in FIG. 2P. The codon for the start methionine is underlined. The open reading frame extends from nucleic acid 96-872 including the stop codon.

The cDNA and amino acid sequence of STEAP-1 variant 17 (also called "STEAP-1 v.17") is shown in FIG. 2Q. The codon for the start methionine is underlined. The open reading frame extends from nucleic acid 96-872 including the stop codon. As used herein, a reference to STEAP-1 includes all variants thereof, including those shown in FIGS. 10, 11 and/or 12 unless the context clearly indicates otherwise.

FIG. 3. Amino acid sequence of STEAP-1 v.1 is shown in FIG. 3A; it has 339 amino acids.

The amino acid sequence of STEAP-1 v.2 is shown in FIG. 3B; it has 258 amino acids.

The amino acid sequence of STEAP-1 v.3 is shown in FIG. 3C; it has 282 amino acids.

The amino acid sequence of STEAP-1 v.4 is shown in FIG. 3D; it has 258 amino acids. As used herein, a reference to STEAP-1 includes all variants thereof, including those shown in FIGS. 10, 11 and/or 12 unless the context clearly indicates otherwise.

FIG. 4. FIG. 4A. The amino acid sequence alignment of STEAP-1 v.1 with mouse TNFa-induced adipose-related protein (gi/16905133). FIG. 4B. The amino acid sequence alignment of STEAP-1 v.1 with rat pHyde protein (gi/21717655/). FIG. 4C. Shows Homology of STEAP-1 to mouse six transmembrane epithelial antigen of the prostate (gi|20820492|1).

Figure 5B:
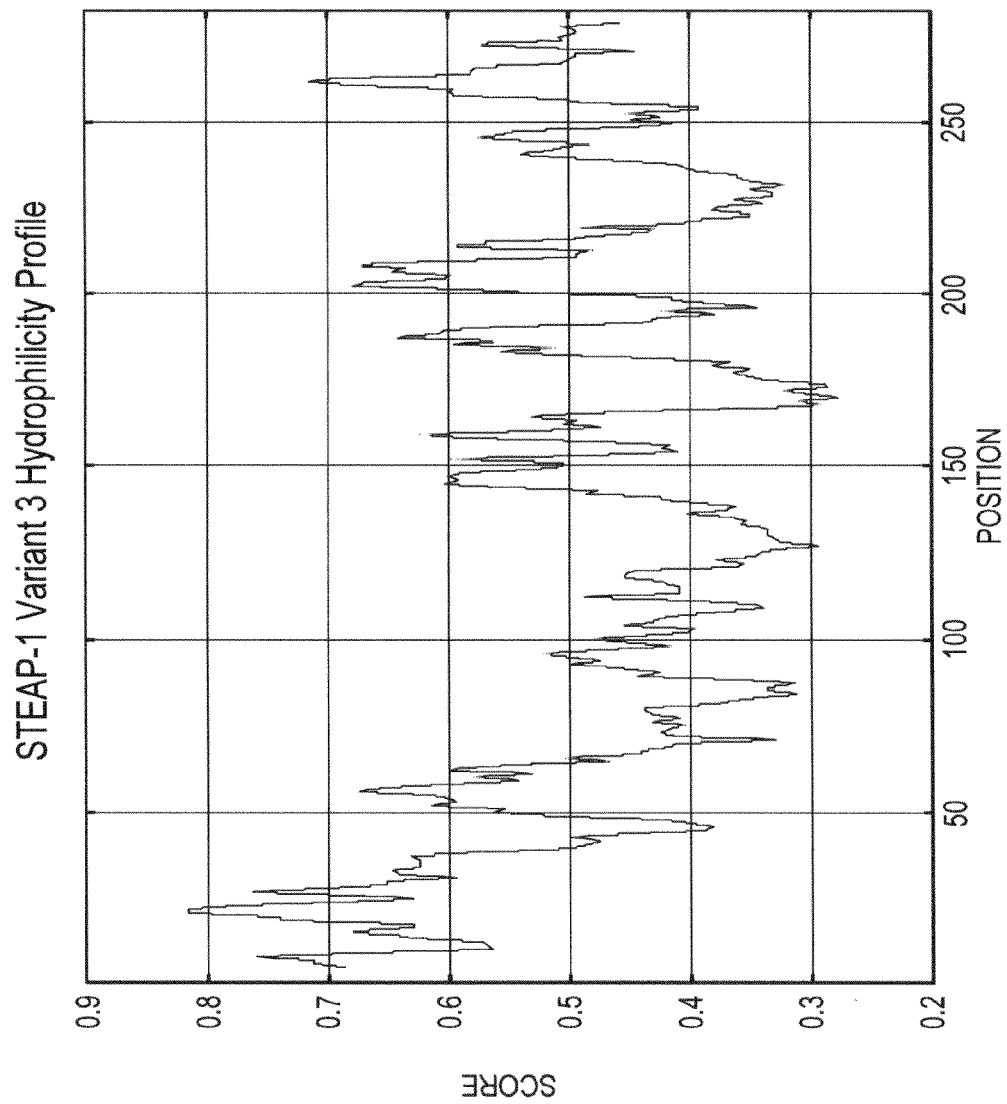

FIG. 5. Hydrophilicity amino acid profile of STEAP-1 variant 1 (FIG. 5(a)). Hydrophilicity amino acid profile of STEAP-1 variant 3 (FIG. 5(b)), determined by computer algorithm sequence analysis using the method of Hopp and Woods (Hopp T. P., Woods K. R., 1981. Proc. Natl. Acad. Sci. U.S.A. 78:3824-3828) accessed on the ProtScale website located on the world wide web URL ch/cgi-bin/protscale.pl) through the ExPasy molecular biology server.

Figure 6A:
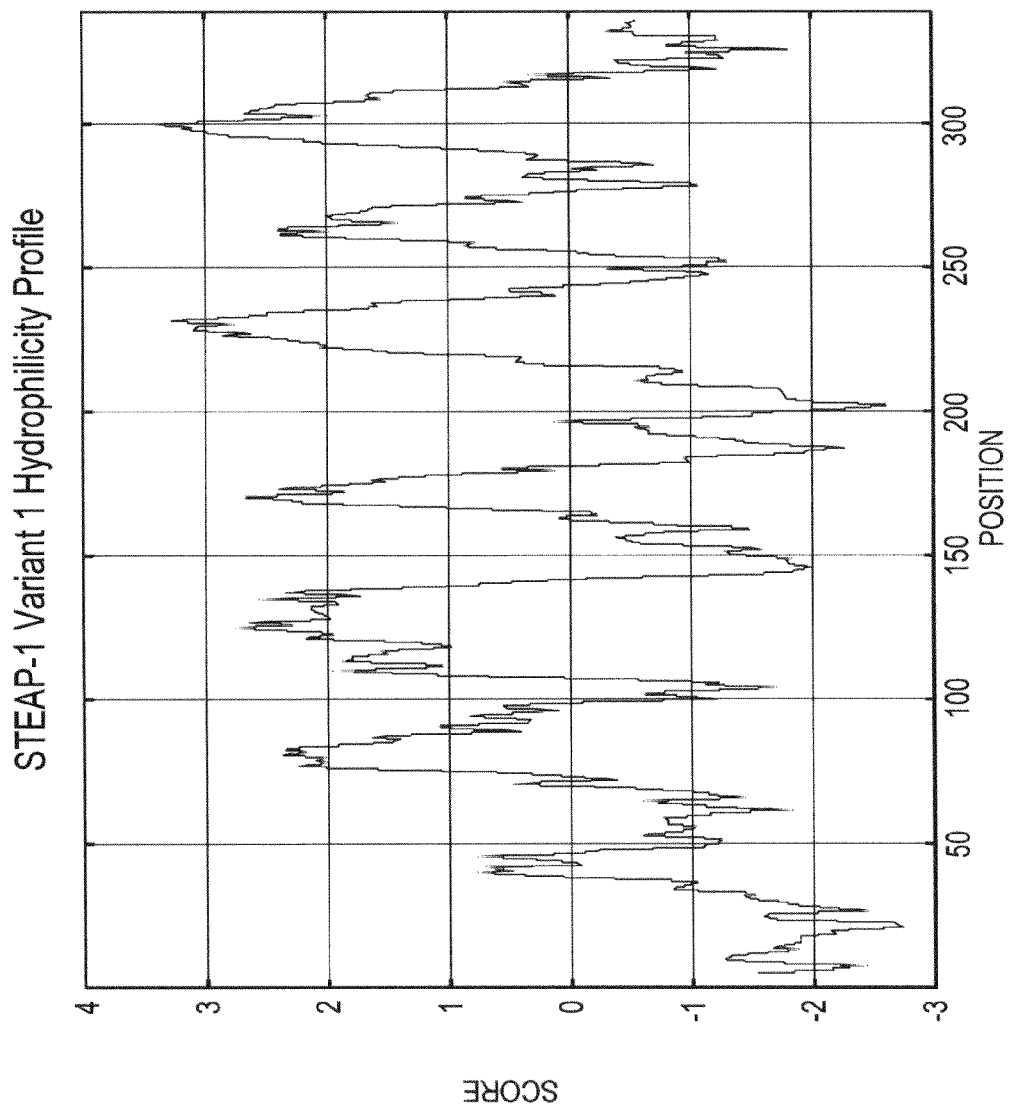
Figure 6B:
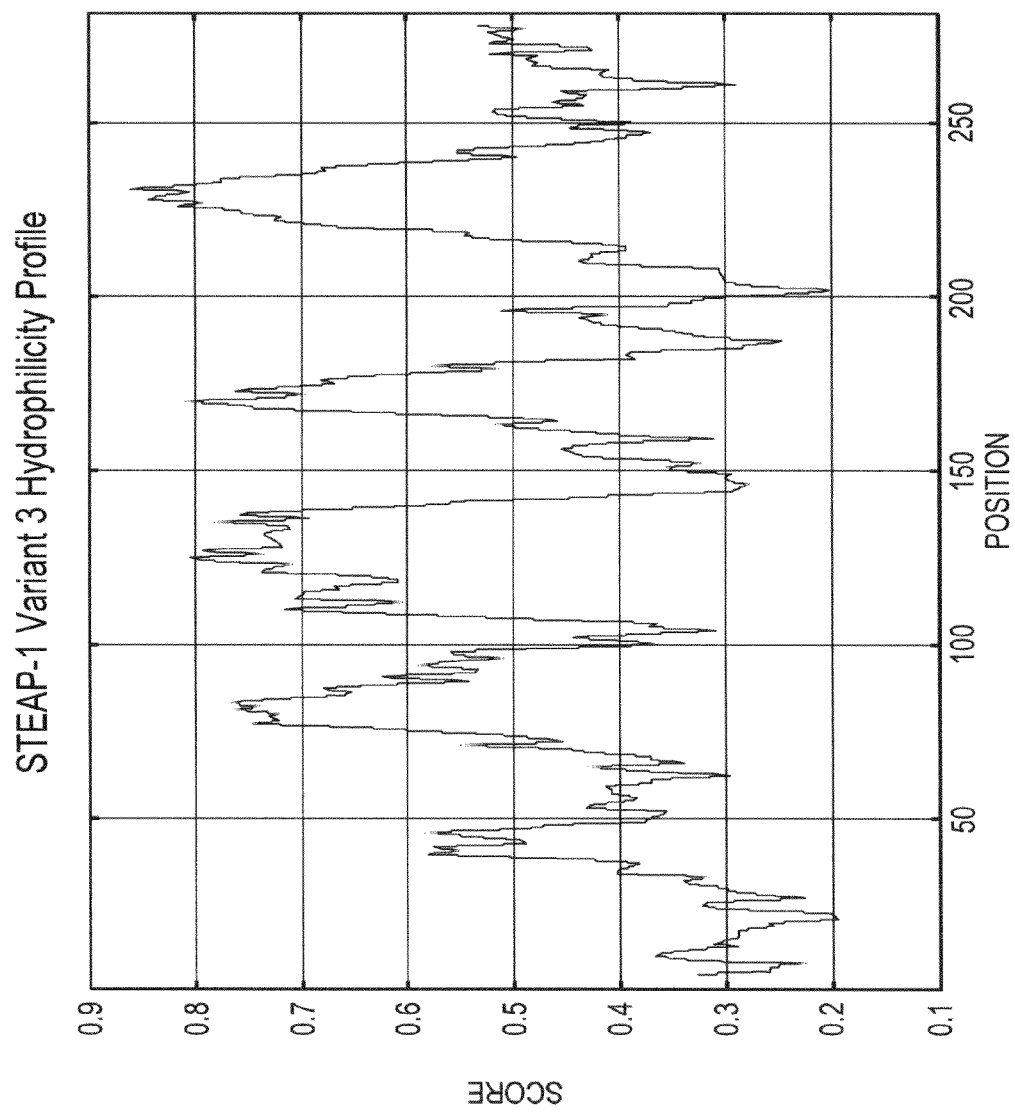

FIG. 6. (FIG. 6(a)). Hydropathicity amino acid profile of STEAP-1 variant 1. (FIG. 6(b)). Hydropathicity amino acid profile of STEAP-1 variant 3, determined by computer algorithm sequence analysis using the method of Kyte and Doolittle (Kyte J., Doolittle R. F., 1982. J. Mol. Biol. 157: 105-132) accessed on the ProtScale website located on the world wide web URL expasy.ch/cgi-bin/protscale.pl) through the ExPasy molecular biology server.

Figure 7A:
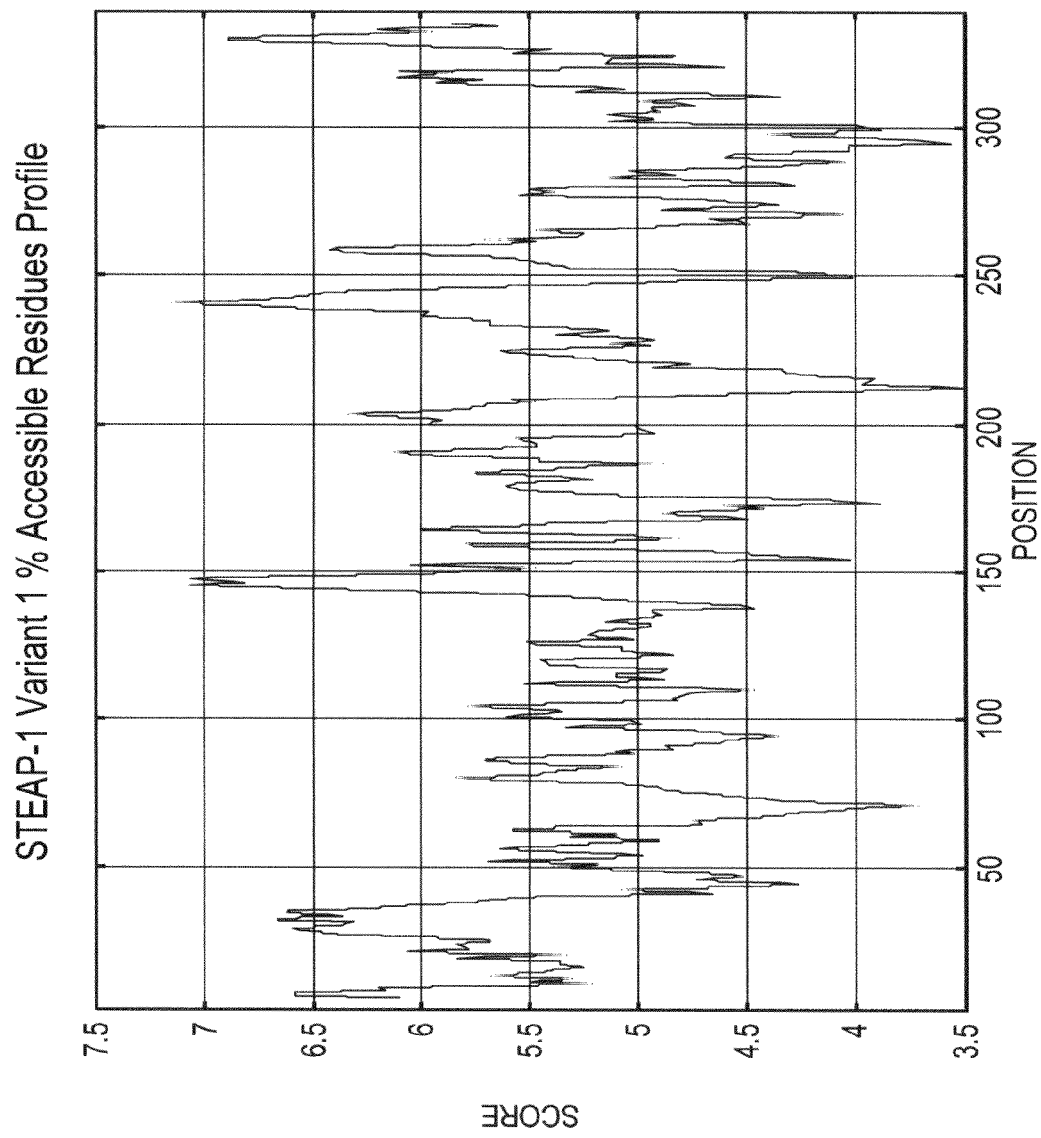
Figure 7B:
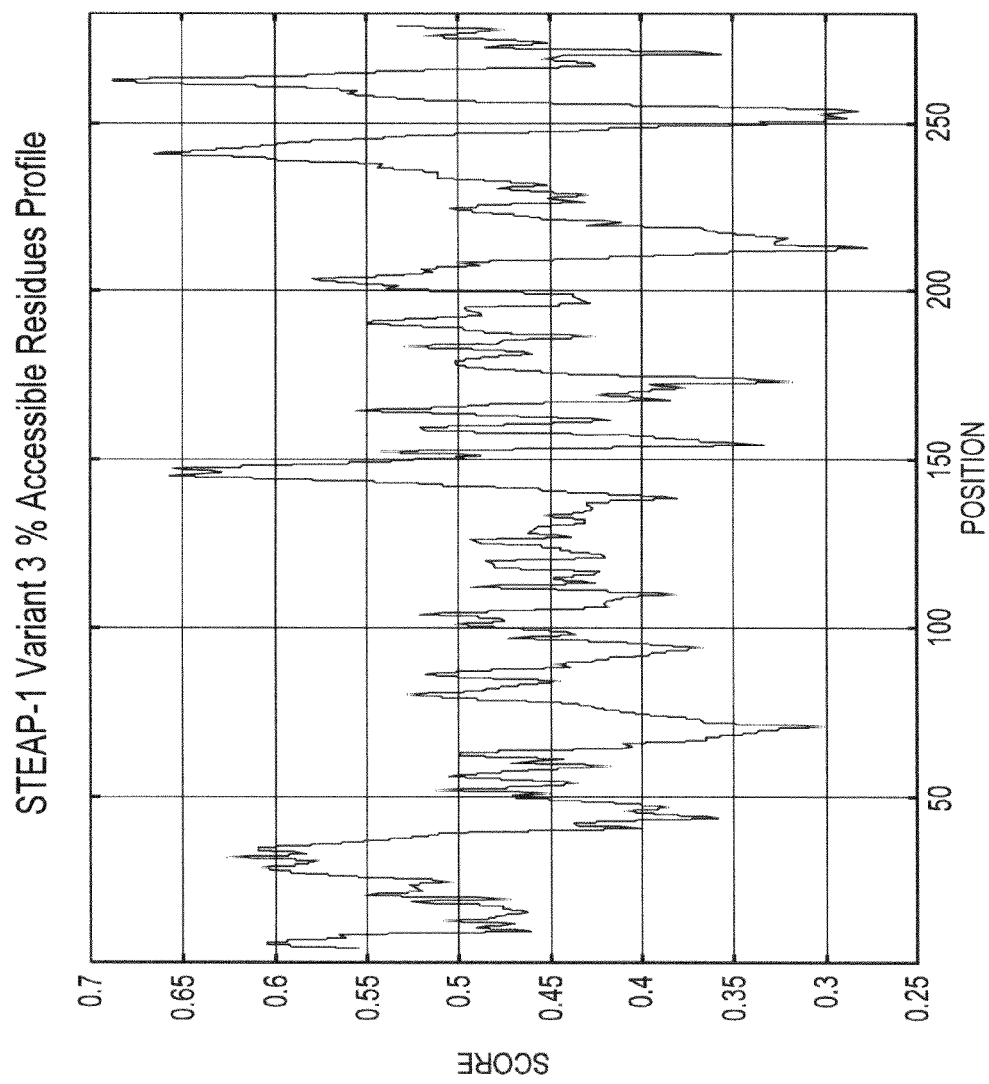

FIG. 7. (FIG. 7(a)). Percent accessible residues amino acid profile of STEAP-1 variant 1. (FIG. 7(b)). Percent accessible residues amino acid profile of STEAP-1 variant 3, determined by computer algorithm sequence analysis using the method of Janin (Janin J., 1979 Nature 277:491-492) accessed on the ProtScale website located on the world wide web URL expasy.ch/cgi-bin/protscale.pl) through the ExPasy molecular biology server.

Figure 8A:
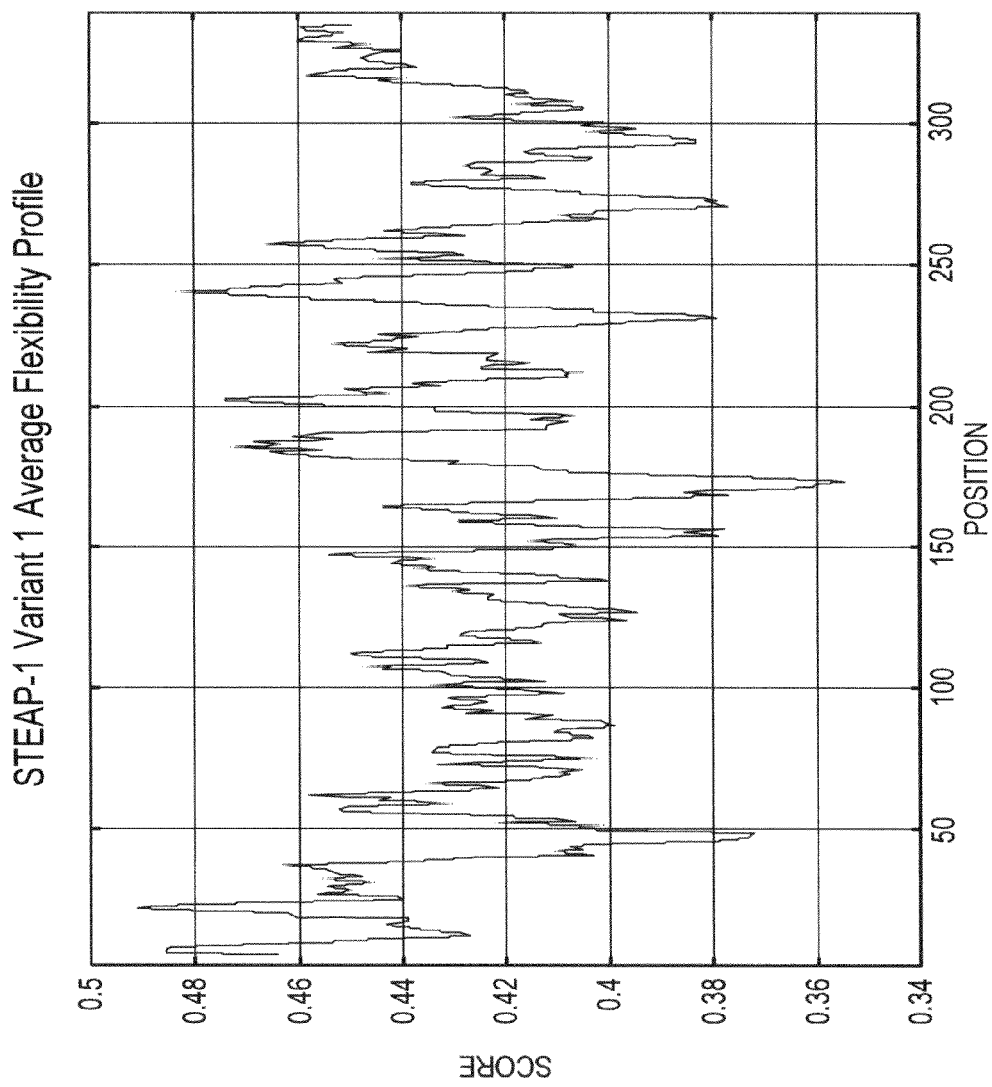

FIG. 8. (FIG. 8(a)). Average flexibility amino acid profile of STEAP-1 variant 1. (FIG. 8(b)). Average flexibility amino acid profile of STEAP-1 variant 3, determined by computer algorithm sequence analysis using the method of Bhaskaran and Ponnuswamy (Bhaskaran R., and Ponnuswamy P. K., 1988. Int. J. Pept. Protein Res. 32:242-255) accessed on the ProtScale website located on the world wide web URL expasy.ch/cgi-bin/protscale.pl) through the ExPasy molecular biology server.

Figure 9A:
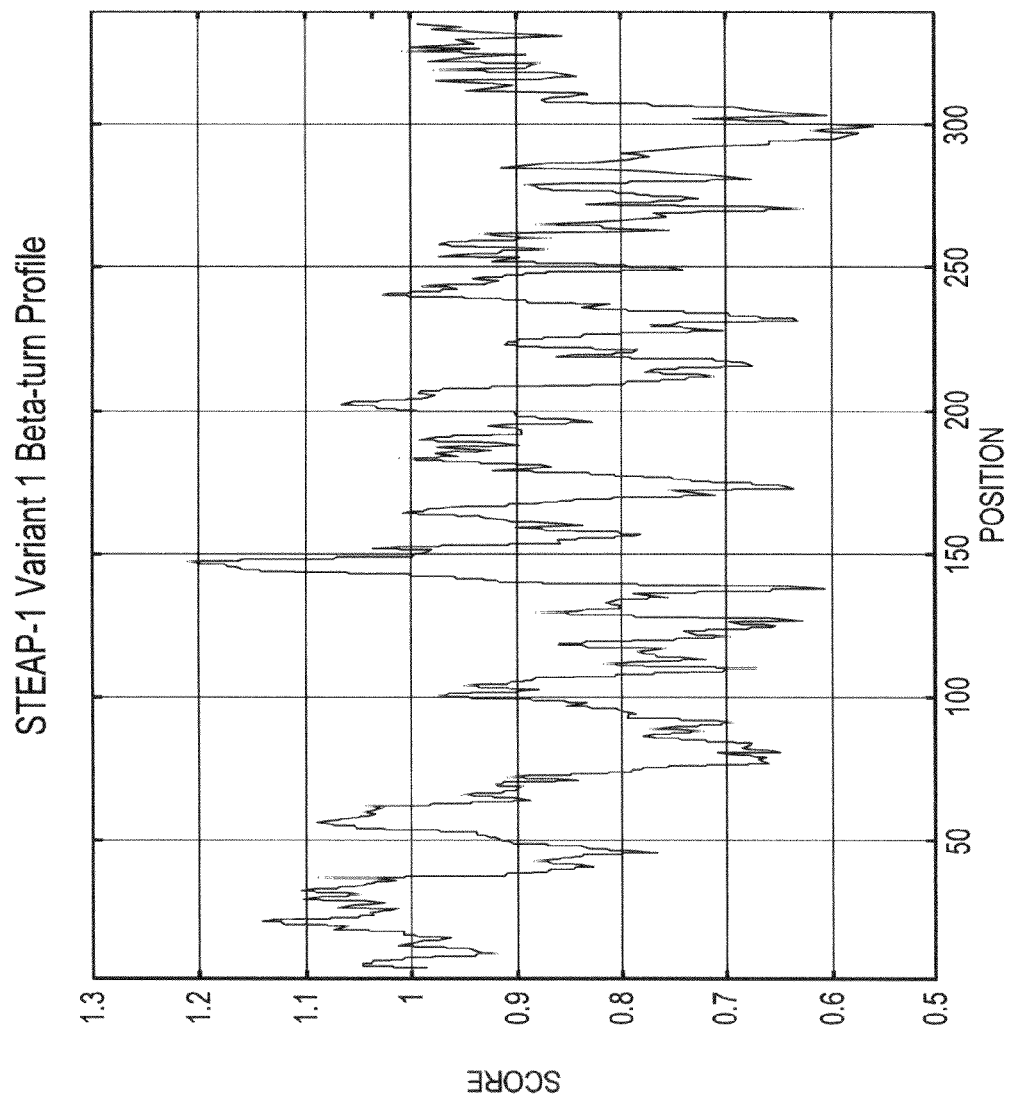
Figure 9B:
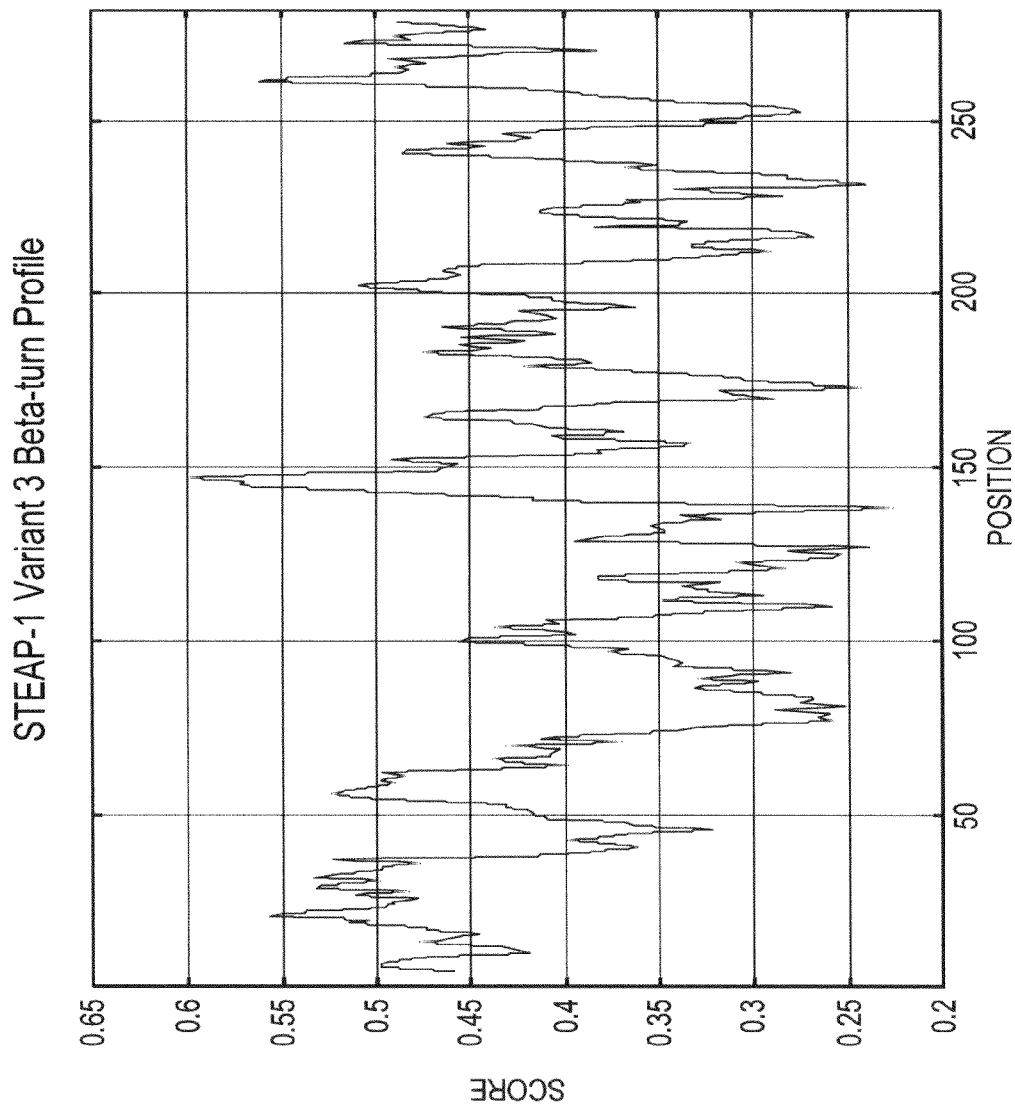

FIG. 9. (FIG. 9(a)). Beta-turn amino acid profile of STEAP-1 variant 1. (FIG. 9(b)). Beta-turn amino acid profile of STEAP-1 variant 3, determined by computer algorithm sequence analysis using the method of Deleage and Roux (Deleage, G., Roux B. 1987 Protein Engineering 1:289-294) accessed on the ProtScale website located on the world wide web URL expasy.ch/cgi-bin/protscale.pl) through the ExPasy molecular biology server.

FIG. 10. Schematic alignment of SNP variants of STEAP-1. Variants STEAP-1 v.4 through v.17 are variants with single nucleotide differences as compared to STEAP-1 v.2. Though these SNP variants are shown separately, they could also occur in any combinations and in any transcript variants that contains the base pairs, e.g., STEAP-1 v.1 and v.3. Numbers correspond to those of STEAP-1 v.2. Black box shows the same sequence as STEAP-1 v.2. SNPs are indicated above the box.

Figure 11:
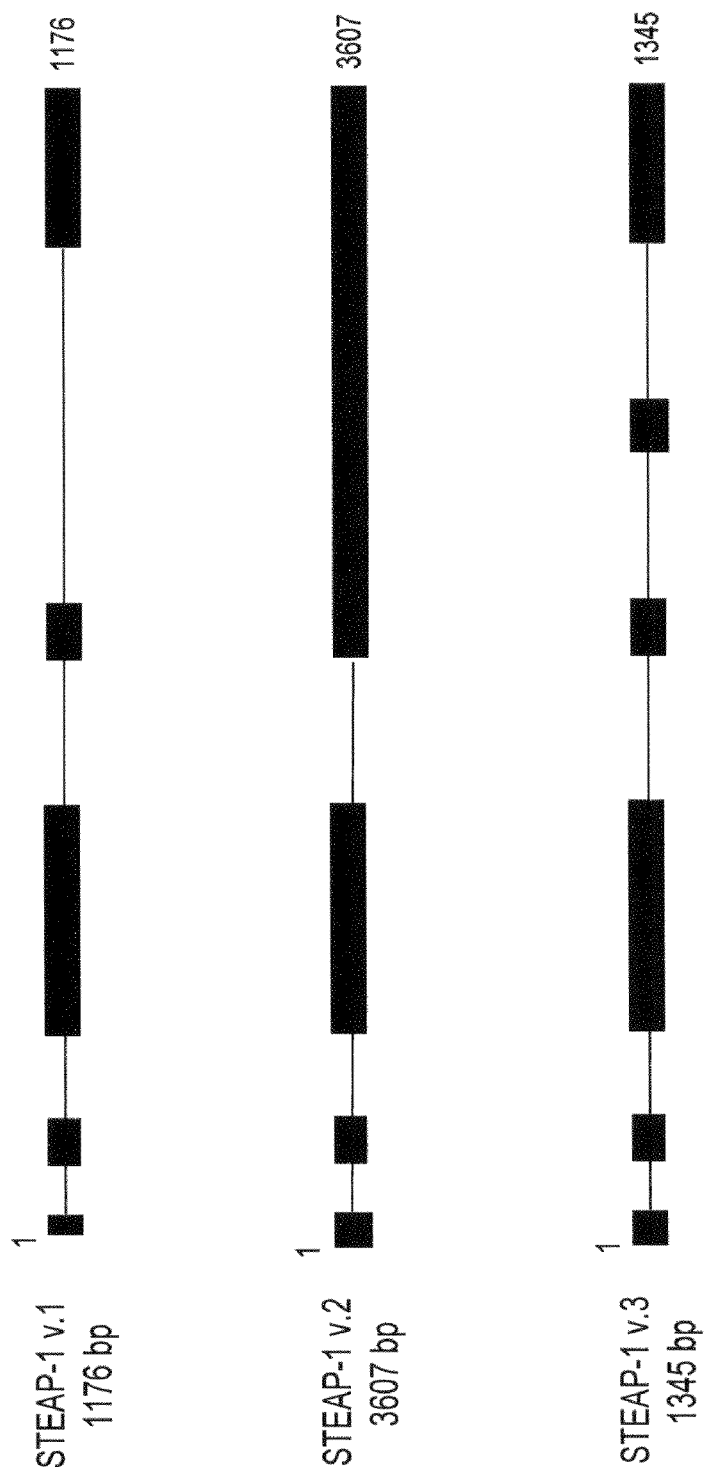

FIG. 11. Exon compositions of transcript variants of STEAP-1. This figure shows the structure of the transcript variants without poly A tail. Variants STEAP-1 v.1, v.2 and v.3 are transcript variants that share the same exons 2 and 3. The first exon of STEAP-1 v.1 is 30 bases shorter at 5' end than the first exons of the other two transcript variants. The fourth exon of STEAP-1 v.2 is the same as the combined exon 4, intron 4 and exon 5 of STEAP-1 v.1. Compared with STEAP-1 v.1, variant STEAP-1 v.3 has an additional exon spliced out from intron 4 of STEAP-1 v.1. Lengths of introns and exons are not proportional.

Figure 12:
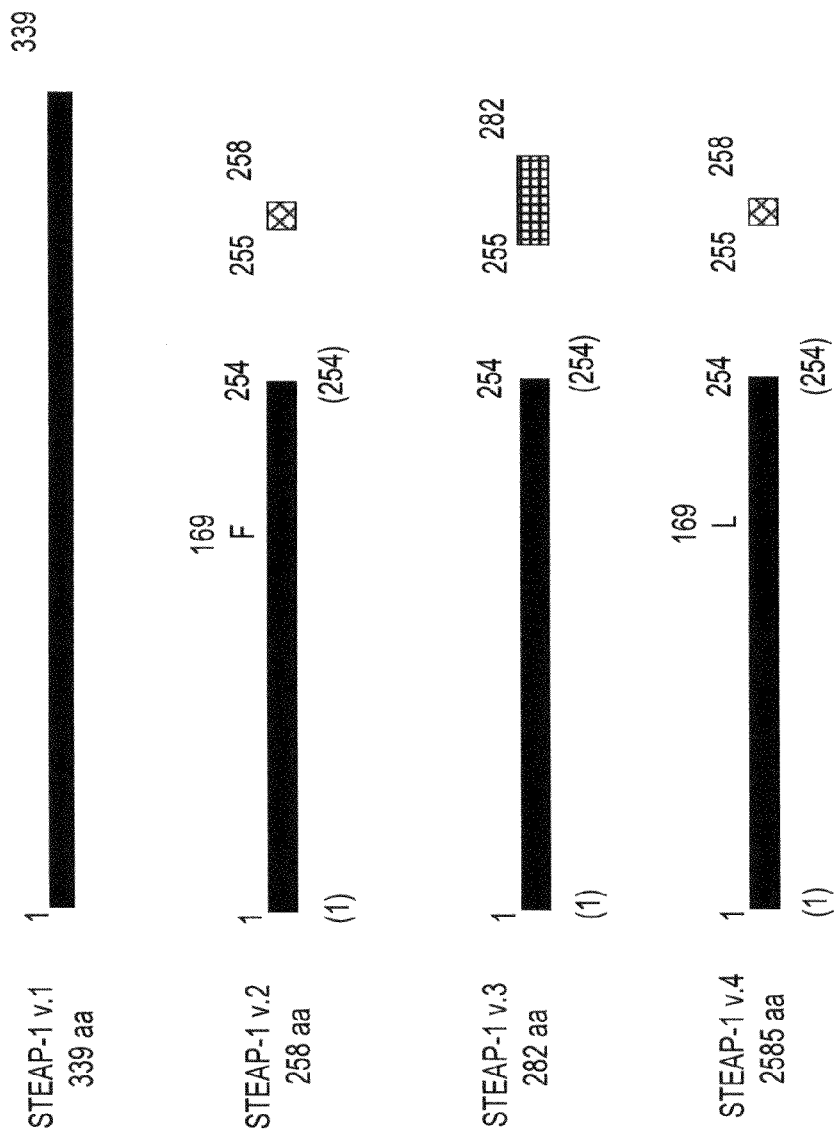

FIG. 12. Schematic alignment of protein variants of STEAP-1. Protein variants correspond to nucleotide variants. Nucleotide variants STEAP-1 v.5 through v.17 in FIG. 10 code for the same protein as STEAP-1 v.2. Proteins translated from transcript variants STEAP-1 v.1 and v.3 as shown in FIG. 11 may contain amino acid F (Phe) or L (Leu) at position 169. Single amino acid differences were indicated above the boxes. Black boxes represent the same sequence as STEAP-1 v. 1. Boxes with different patterns of filling show different sequences. Numbers underneath the box correspond to STEAP-1 v.1.

FIG. 13. FIGS. 13(a)-(c). Secondary structure and transmembrane domains prediction for STEAP-1 protein variants. The secondary structure of STEAP-1 protein variants 1 (SEQ ID NO: 46), 2 (SEQ ID NO: 47), and 3 (SEQ ID NO: 48); (FIGS. 13a-13c, respectively) were predicted using the HNN—Hierarchical Neural Network method (Guermeur, 1997, http://pbil.ibcp.fr/cgi-bin/npsa_automat.pl?page=npsa_nn.html), accessed from the ExPasy molecular biology server located on the World Wide Web at (.expasy.ch/tools/). This method predicts the presence and location of alpha helices, extended strands, and random coils from the primary protein sequence. The percent of the protein in a given secondary structure is also listed. FIGS. 13(d), 13(f) and 13(h): Schematic representations of the probability of existence of transmembrane regions and orientation of STEAP-1 variant 1-3, (FIGS. 13(d), 13(f) and 13(h) respectively, based on the TMpred algorithm of Hofmann and Stoffel which utilizes TMBASE (K. Hofmann, W. Stoffel. TMBASE—A database of membrane spanning protein segments Biol. Chem. Hoppe-Seyler 374:166, 1993). FIGS. 13(e), 13(g), and 13(i): Schematic representations of the probability of the existence of transmembrane regions and the extracellular and intracellular orientation of STEAP-1 variants 1-3, FIGS. 13(e), 13(g), and 13(i) respectively, based on the TMHMM algorithm of Sonnhammer, von Heijne, and Krogh (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998). The TMpred and TMHMM algorithms are accessed from the ExPasy molecular biology server located on the World Wide Web at (.expasy.ch/tools/).

FIG. 14. FIG. 14a. Expression of STEAP-1 in stomach cancer patient specimen. RNA was extracted from normal stomach (N) and from 10 different stomach cancer patient specimens (T). Northern blot with 10 μg of total RNA/lane was probed with STEAP-1 sequence. Results show strong expression of an approximately 1.6 kb STEAP-1 in the stomach tumor tissues. The lower panel represents ethidium bromide staining of the blot showing quality of the RNA samples. FIG. 14b. STEAP-1 expression in rectum cancer patient tissues. RNA was extracted from normal rectum (N), rectum cancer patient tumors (T), and rectum cancer metastasis (M). Northern blots with 10 μg of total RNA were probed with the STEAP-1 sequence. Results show strong expression of STEAP-1 in the rectum cancer patient tissues. The lower panel represents ethidium bromide staining of the blot showing quality of the RNA samples. FIG. 14c. Expression of STEAP-1 in human umbilical vein endothelial cells (HUVEC). First strand cDNA was prepared from HUVEC cells, LAPC-4AD and LAPC-9AD prostate cancer xenografts, as well as from human brain tissues. Normalization was performed by PCR using primers to actin and GAPDH. Semiquantitative PCR, using primers to STEAP-1, was performed at 27 and 30 cycles of amplification (A). As a control, PCR using primers to actin is shown in (B). Results show strong expression of STEAP-1 in HUVEC cells similar to the expression detected in prostate cancer xenograft tissues. Expression of STEAP-1 in HUVEC cells indicates that targeting STEAP-1 may also target endothelial cells of the neovasculature of the tumors. FIG. 14(d) and FIG. 14(e). STEAP-1 Expression in Normal and Cancer Tissues. First strand cDNA was prepared from normal tissues (bladder, brain, heart, kidney, liver, lung, prostate, spleen, skeletal muscle, testis, pancreas, colon and stomach), and from pools of patient cancer specimens (prostate cancer pool, bladder cancer pool, kidney cancer pool, colon cancer pool, lung cancer pool, ovary cancer pool, breast cancer pool, cancer metastasis pool, pancreas cancer pool, prostate cancer xenograft pool, and prostate metastasis to lymph node pool. Normalization was performed by PCR using primers to actin. Semi-quantitative PCR, using primers to STEAP-1, was performed at 26 and 30 cycles of amplification. In (FIG. 14d) picture of the RT-PCR agarose gel is shown. In (FIG. 14e)

PCR products were quantitated using the AlphaImager software. Results show strong of expression of STEAP-1 in normal prostate amongst all the normal tissues tested. Upregulation of STEAP-1 expression was detected in prostate cancer pool, bladder cancer pool, kidney cancer pool, colon cancer pool, lung cancer pool, ovary cancer pool, breast cancer pool, and pancreatic cancer pool. Strong expression of STEAP-1 was detected in cancer metastasis pool, prostate cancer xenograft pool, and prostate metastasis to lymph node. FIG. 14(f): STEAP-1 Expression in lymphoma patient specimens. First strand cDNA was prepared from a panel of lymphoma patient specimens. Normalization was performed by PCR using primers to actin. Semi-quantitative PCR, using primers to STEAP-1, was performed at 26 and 30 cycles of amplification. Samples were run on an agarose gel, and PCR products were quantitated using the AlphaImager software. Expression was recorded as strong or medium, if signal is detected as 26 or 30 cycles of amplification respectively, and absent if no signal is detected even at 30 cycles of amplification. Results show expression of STEAP-1 in 8 of 11 (72.7%) tumor specimens tested.

Figure 15C:
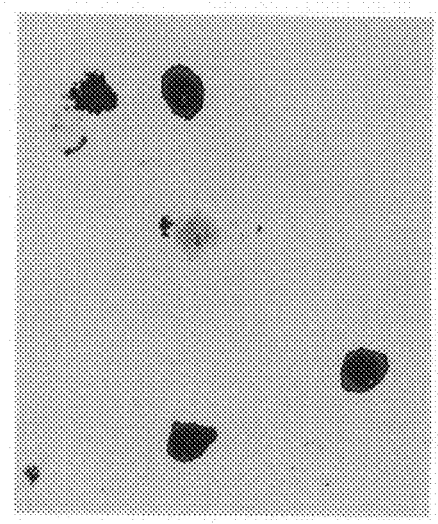
Figure 15A:
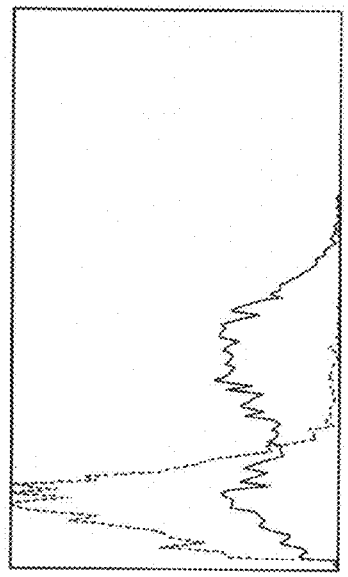
Figure 15B:
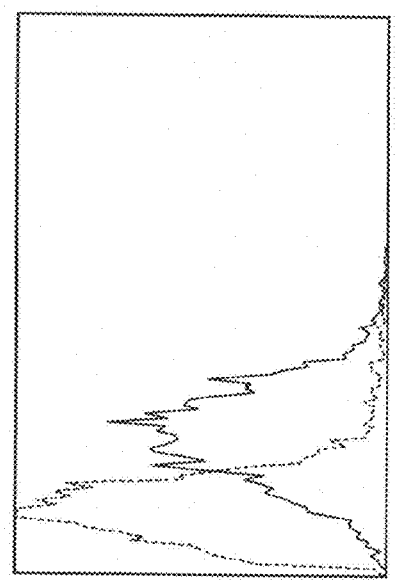

FIG. 15. Specific cell Surface staining of STEAP-1 by MAb M2/92.30. Left panels: FACS analysis of recombinant 3T3 and Rat1 cells stably expressing either STEAP1 (dark lines) or a control neomycin resistance gene (light lines) stained with anti-STEAP MAb M2/92.30 (10 µg/ml) and cell surface bound MAb was detected with a goat anti-mouse IgG-PE conjugate secondary reagent. The stained cells were then subjected to FACS analysis. As indicated by the fluorescent shift of the Rat1-STEAP1 and 3T3-STEAP1 cells compared to the respective control cells, MAb M2/92.30 specifically binds to cell surface STEAP1. Right panel: Fluorescent microscopy of 3T3-STEAP1 cells stained with MAb M2/92.30 showing bright cell surface fluorescence.

Figure 16:
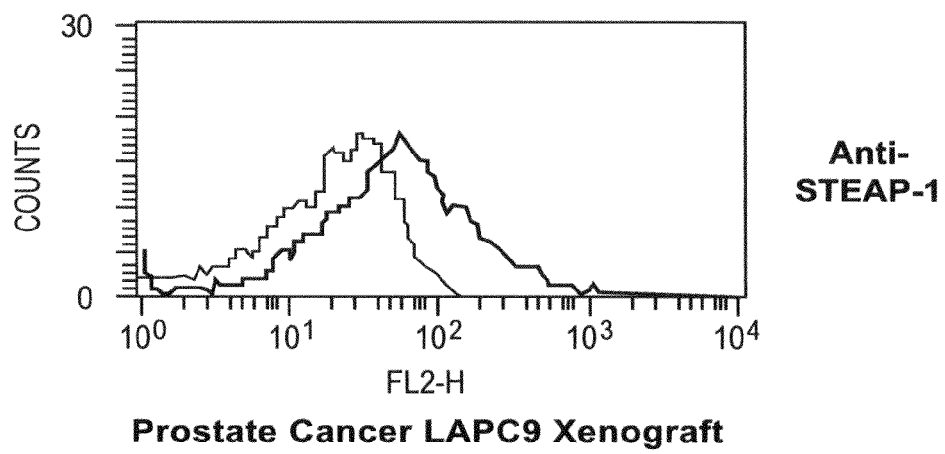

FIG. 16. STEAP1 M2/92.30 MAb Recognizes Cell-Surface STEAP-1 on Human Prostate Cancer Xenografts. LAPC9 prostate cancer cells were stained with 10 ug/ml of either MAb M2/92.30 or with a control anti-KLH MAb. Surface bound MAb was detected with goat-anti-mouse IgG-PE conjugated secondary Ab. Stained cells were then subjected to FACS analysis. These results demonstrate that the anti-STEAP1 MAb M2/120.545 specifically binds endogenous cell surface STEAP1 expressed in prostate cancer xenograft cells.

Figure 17:
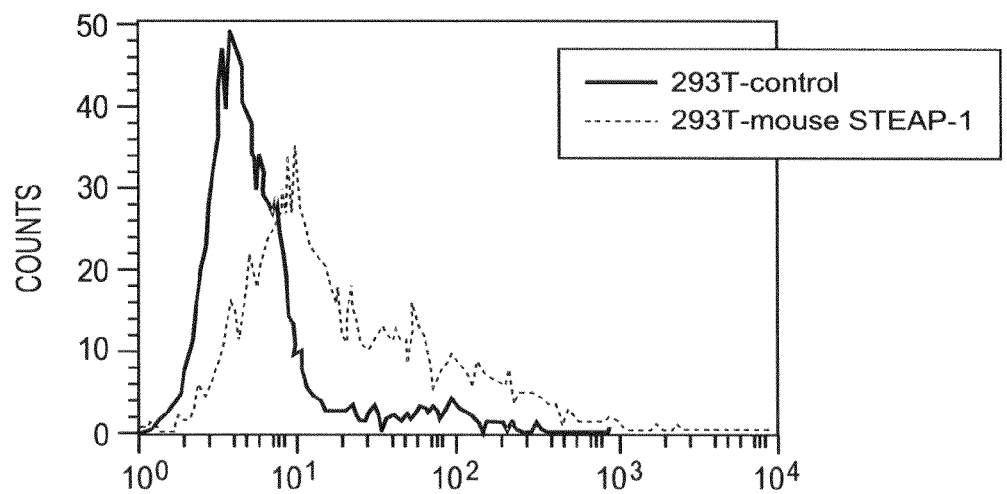

FIG. 17. STEAP1 M2/92.30 MAb Recognizes Mouse STEAP-1. 293T cells were transiently transfected with either pCDNA3.1 encoding the murine STEAP1 cDNA or with an empty vector. 2 days later, the cells were harvested and stained with anti-STEAP1 MAb M2/92.30 (10 ug/ml) and cell surface bound MAb was detected with a goat anti-mouse IgG-PE conjugate secondary reagent. Cells were then subjected to FACS analysis. As indicated by the fluorescent shift of the 293T cells transfected with murine STEAP1 compared to the cells transfected with the empty vector, MAb M2/92.30 specifically binds to murine STEAP1 protein.

FIG. 18. STEAP1/120.545 MAb recognizes cell surface STEAP-1. Panel A and Panel B. 3T3-neo (A, filled histograms) and 3T3-STEAP1 cells (A, no fill histograms) and Rat1-neo (B, filled histograms) and Rat1-STEAP cells (B, no fill histograms) were stained with MAb M2/120.545 (10 ug/ml) and surface bound MAb was detected with goat anti-mouse IgG-PE conjugated secondary Ab. Cells were then subjected to FACS analysis. As indicated by the fluorescence shift of the 3T3-STEAP1 and Rat1-STEAP1 cells compared to their respective neo controls, MAb M2/120.545 specifically binds cell surface STEAP1. Panel C. LNCaP cells were stained with either MAb M2/120.545 or a control anti-KLH MAb and subjected to FACS analysis as above. Panel D. Fluorescence microscopy of the M2/120.545 stained LNCaP cells showing bright cell surface fluorescence. These results demonstrate that the M2/120.545 MAb specifically binds endogenous cell surface STEAP1 in LNCaP cells.

FIG. 19. FIG. 19(a) The cDNA (SEQ ID NO: 49) and amino acid sequence (SEQ ID NO: 50) of M2/X92.30 VH clone #2. FIG. 19(b) The cDNA (SEQ ID NO: 51) and amino acid sequence (SEQ ID NO: 52) of M2/X9 2.30 VL clone #2. FIG. 19(c) The cDNA (SEQ ID NO: 53) and amino acid sequence (SEQ ID NO: 54) of M2/X92.30 VL clone #6. FIG. 19(d) The cDNA (SEQ ID NO: 55) and amino acid sequence (SEQ ID NO: 56) of M2/X120.545 VL clone #8.

FIG. 20. FIG. 20a. The amino acid sequence (SEQ ID NO: 57) of M2/X92.30 VH clone #2. FIG. 20b. The amino acid sequence (SEQ ID NO: 58) of M2/X92.30 VL clone #2. FIG. 20c. The cDNA (SEQ ID NO: 59) and amino acid sequence (SEQ ID NO: 60) of M2/X92.30 VL clone #6. FIG. 20d. Amino acid alignment of M2/X92.30 VL clone #2 (SEQ ID NO: 61) and M2/M92.30 VL clone #6 (SEQ ID NO: 62). FIG. 20e. The amino acid sequence (SEQ ID NO: 63) of M2/X120.545 VL clone #8. The sequence of the signal peptide is underlined.

Figures 21A, 21B:
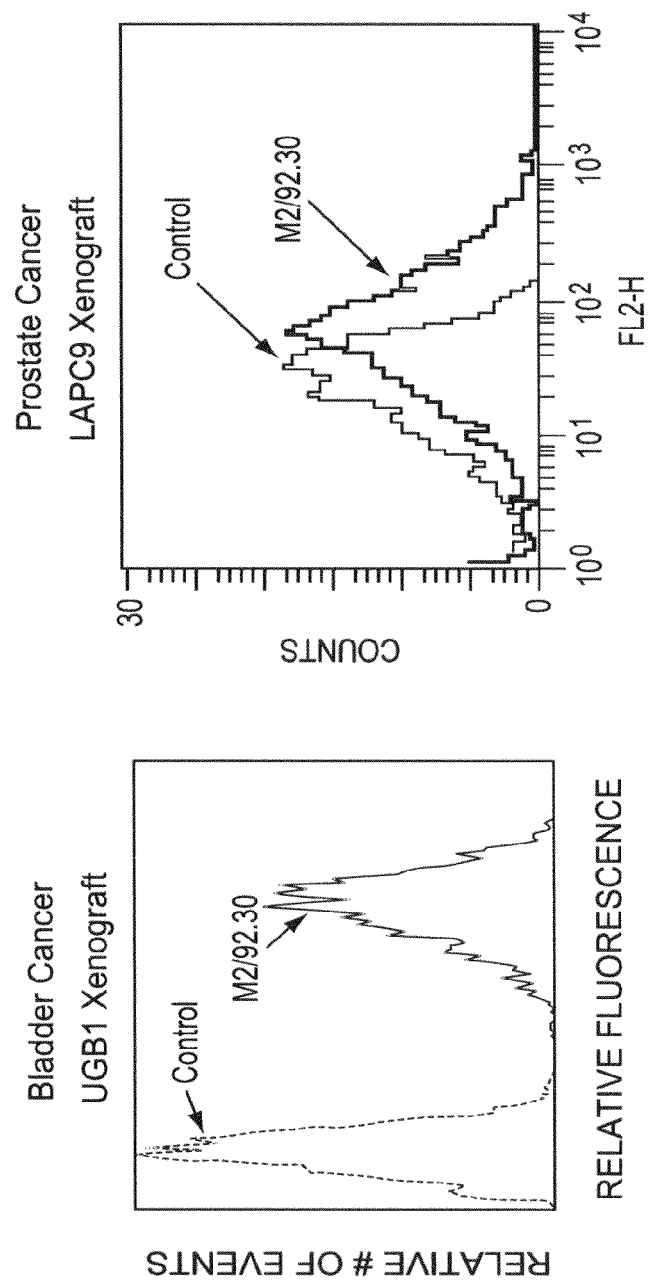

FIG. 21. STEAP1 M2/92.30 MAb Recognizes Cell-Surface STEAP-1 on Human Prostate and Bladder Cancer Xenografts. UGB1 bladder cancer cells (left panel) and LAPC9 prostate cancer cells (right panel) were stained with 10 ug/ml of either MAb M2/92.30 or with a control anti-KLH MAb. Surface bound MAb was detected with goat-ant-mouse IgG-PE conjugated secondary Ab. Stained cells were then subjected to FACS analysis. These results demonstrate that the anti-STEAP1 MAb M2/92.30 specifically binds endogenous cell surface STEAP1 expressed in bladder and prostate cancer xenograft cells.

FIG. 22. STEAP-1 internalization by STEAP1/92.30 MAb. 3T3-STEAP1 cells were stained at 4C with M2/92.30 MAb (10 ug/ml), washed, then incubated with goat anti-mouse IgG-PE conjugate secondary Ab at 4C. One-half of the cells were moved to 37C for 30 minutes and the other half remained at 4C. Cells from each treatment were then subjected to fluorescent microscopy. Cells that remained at 4C showed bright "ring-like" cell surface fluorescence. Cells that were moved to 37C showed loss of the "ring-like" cell surface fluorescence and the appearance of punctate and aggregated fluorescence indicative of capping and internalization.

Figure 23B:
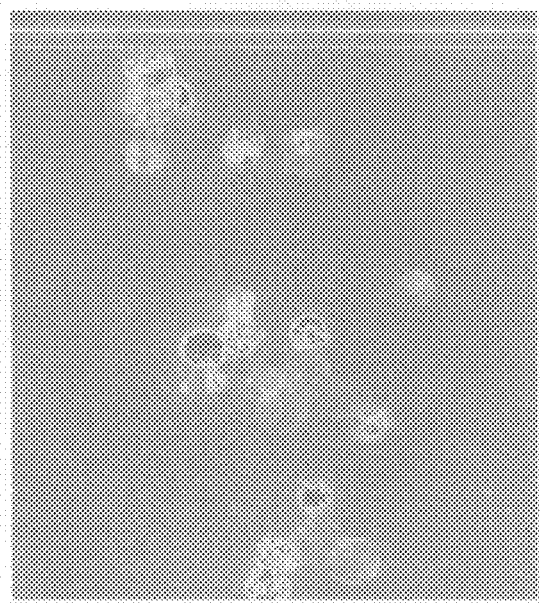
Figure 23A:
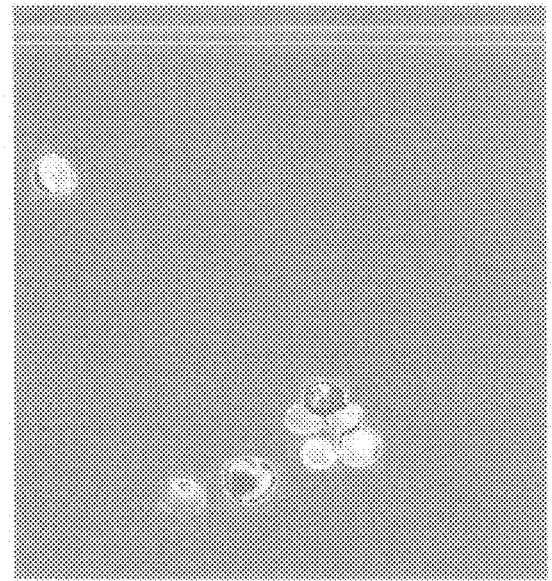

FIG. 23. STEAP-1 internalization by STEAP1 M21120.545 MAb. PC3-STEAP1 cells were stained at 4C with M2/120.545 MAb (10 ug/ml), washed, then incubated with goat anti-mouse IgG-PE conjugate secondary Ab. One-half of the cells were moved to 37C for 30 minutes and the other half remained at 4C. Cells from each treatment were then subjected to fluorescent microscopy. Cells that remained at 4C showed bright "ring-like" cell surface fluorescence. Cells that were moved to 37C showed loss of the "ring-like" cell surface fluorescence and the appearance of punctate and aggregated fluorescence indicative of capping and internalization.

Figure 24:
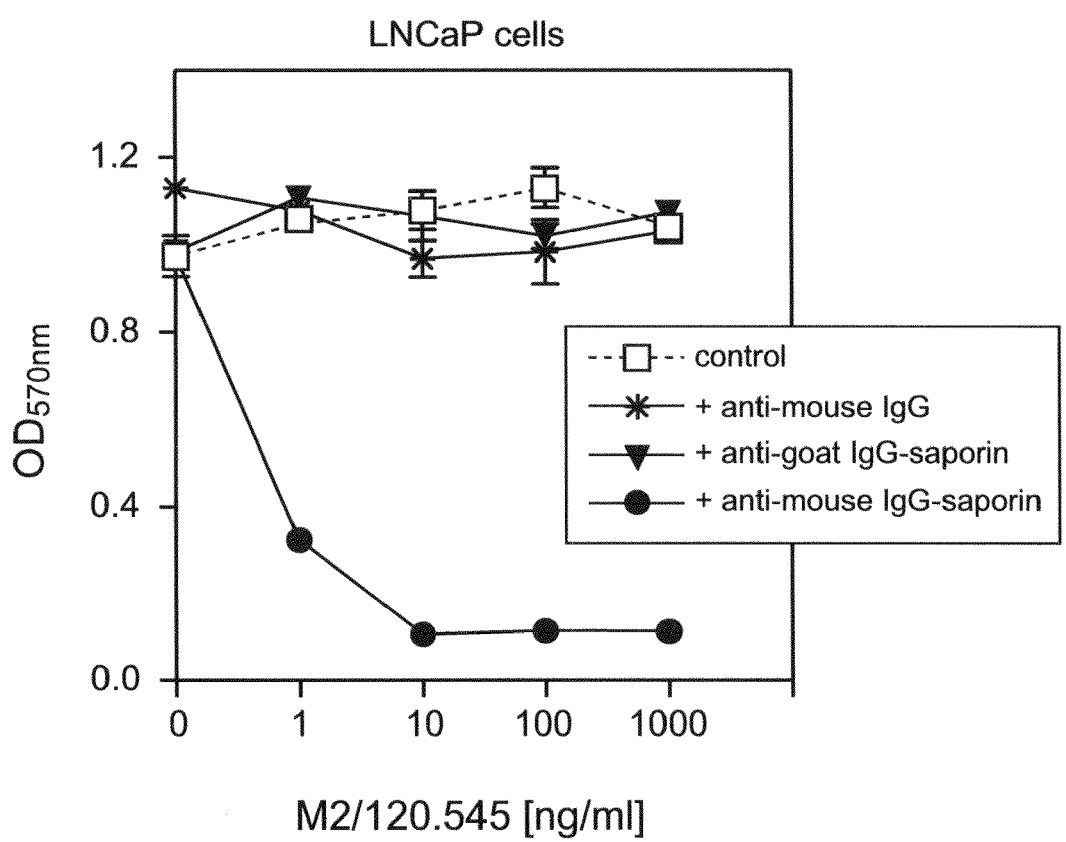

FIG. 24. STEAP-1 Internalization. Anti-mouse IgG—saporin conjugates (Advanced Targeting Systems, San Diego, Calif.) was used to demonstrate that murine Steap-1 M2/120.545 enters target cells via expression of Steap-1 on the surface of LNCaP cells. The following protocols were used. LNCaP cells were plated at 5000 cells/90 µl/well in 96-well plate and incubated overnight. Secondary immunotoxin conjugates (anti-mouse IgG-saporin and anti-goat IgG-saporin) or anti-mouse IgG were made in cell culture medium to yield a final concentration of 100 ng/ml. The primary antibody was added at concentrations ranging from 1-1000 ng/ml. The plates were incubated for 72 hours and the viability was determined by MTT assay. The results show that LNCaP cells were killed in the presence of M2/120.545 and anti-mouse IgG-saporin. No effects were detected with either the secondary antibody alone (anti-mouse IgG) or nonspecific secondary antibody conjugates (anti-goat IgG saporin). No toxicity was observed with the primary antibody (M2/120.545) alone tested up to 1 μg/ml.

Figure 25:
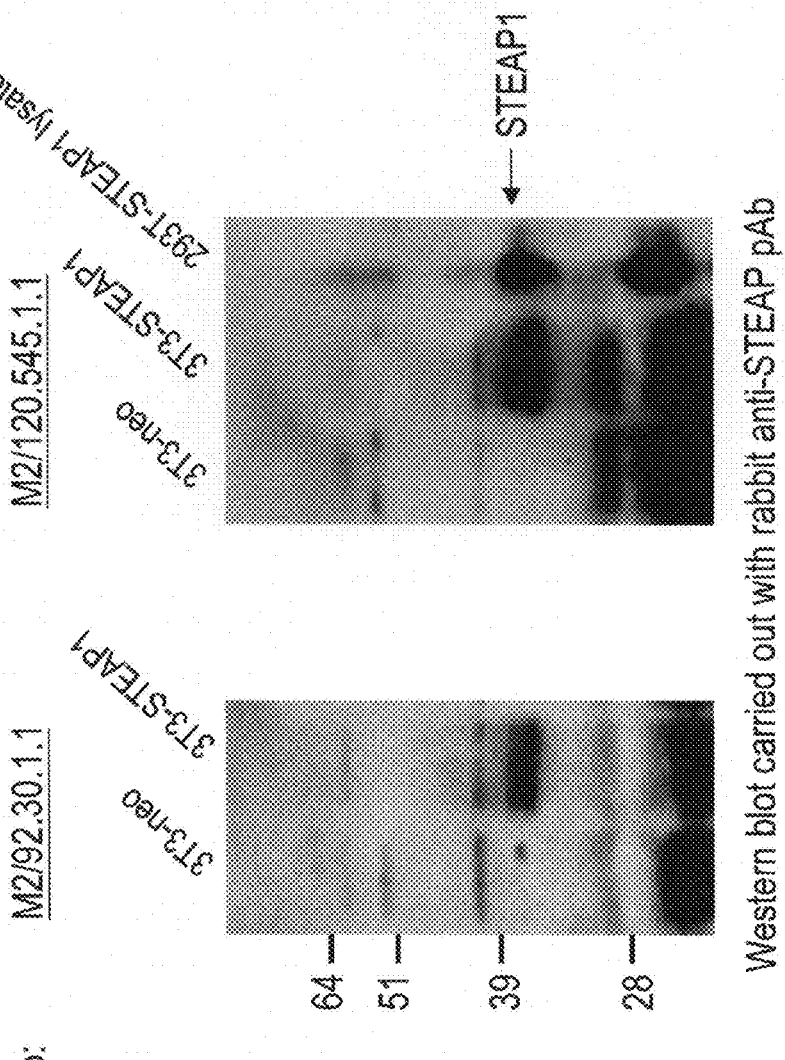

FIG. 25. Immunoprecipitation of STEAP1 by anti-STEAP-1 MAbs M2/92.30 and M2/120.545. 3T3-STEAP1 and 3T3-neo cells were lysed in RIPA buffer (25 mM Tris-Cl pH7.4; 150 mM NaCl, 0.5 mM EDTA, 1% Triton X-100, 0.5% deoxycholic acid, 0.1% SDS, and protease inhibitor cocktail). The cell lysates were precleared with protein G sepharose beads and then incubated with 5 ug of either MAb M2/92.30 or M2/120.545 for 2 hours at room temperature. Protein G beads were added and the mixture was further incubated for 1 hour. The immune complexes were washed and solubilized in SDS-PAGE sample buffer. The solubilized samples were then subjected to SDS-PAGE and Western blot analysis using a rabbit anti-STEAP pAb. Whole cell lysates of 293T cells transfected with STEAP1 was also run as a positive control. An immunoreactive band of ~37 kD was seen only in samples derived from 3T3-STEAP1 cells indicative of specific immunoprecipitation of STEAP1 by both M2/92.30 and M2/120.545 MAbs.

Figure 26:
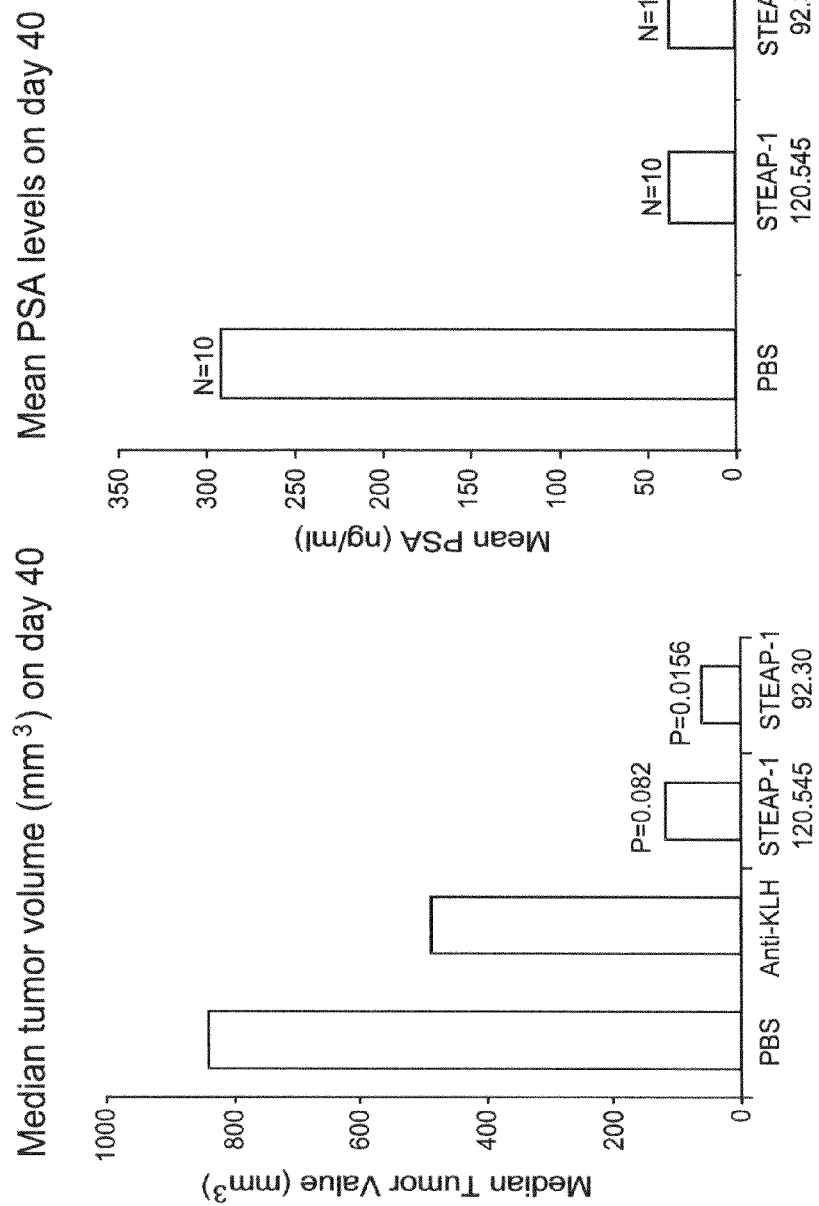

FIG. 26. Effect of STEAP-1 MAbs on the Growth of LAPC9 Human Prostate Cancer Xenografts in Mice. STEAP-1 M2/92.30 and M2/120.545 were tested at two different doses of 100 μg and 500 μg. PBS and anti-KLH MAb were used as controls. The study cohort consisted of 6 groups with 10 mice in each group. MAbs were dosed IP twice a week for a total of 12 doses, starting the same day as tumor cell injection. Tumor size was monitored through caliper measurements twice a week. The longest dimension (L) and the dimension perpendicular to it (W) were taken to calculate tumor volume using the formula: $W^2 \times L/2$. Serum PSA concentration at treatment day 40 for each animal was measured using commercial ELISA kit. The Kruskal-Wallis test and the Mann-Whitney U test were used to evaluate differences of tumor growth and PSA level among groups. All tests were two-sided with á=0.05. The data show that STEAP-1 M2/92.30 and M2/120.545 significantly retard the growth of human prostate xenograft in a dose-dependent tumor.

Figure 27:
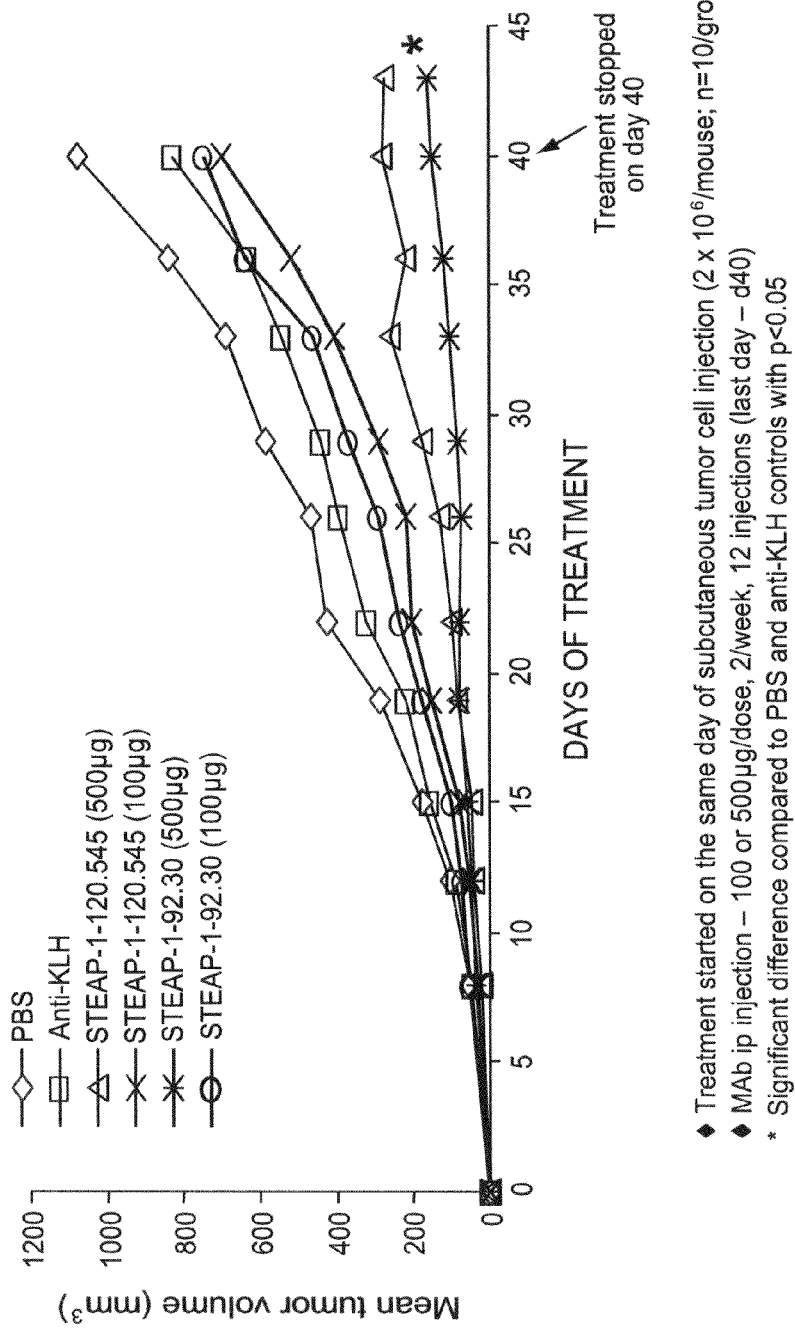

FIG. 27. Effect of STEAP-1 MAbs on the Growth of LAPC9 Human Prostate Cancer Xenograft in Mice. STEAP-1 M2/92.30 and M2/120.545 were tested at two different doses of 100 μg and 500 μg. PBS and anti-KLH MAb were used as controls. The study cohort consisted of 6 groups with 10 mice in each group. MAbs were dosed IP twice a week for a total of 12 doses, starting the same day as tumor cell injection. Tumor size was monitored through caliper measurements twice a week. The longest dimension (L) and the dimension perpendicular to it (W) were taken to calculate tumor volume using the formula: $W^2 \times L/2$. Serum PSA concentration at treatment day 40 for each animal was measured using commercial ELISA kit. The Kruskal-Wallis test and the Mann-Whitney U test were used to evaluate differences of tumor growth and PSA level among groups. All tests were two-sided with á=0.05. The results show that STEAP-1 M2/92.30 and M2/120.545 significantly retard the growth of human prostate xenograft in a dose-dependent tumor.

Figure 28:
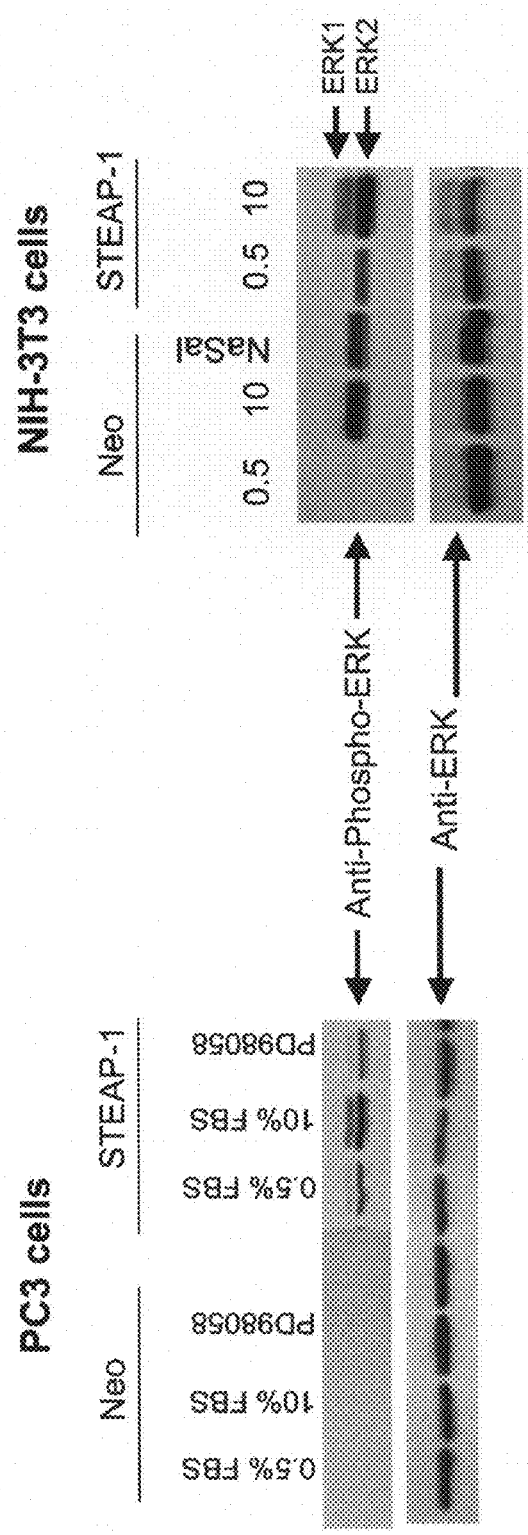

FIG. 28. STEAP-1 induced ERK-1 and ERK-2 phosphorylation. Left panels: PC3 cells were transfected with neomycin resistance gene alone or with STEAP-1 in pSRa vector. Cells were grown overnight in 0.5% FBS, then stimulated with 10% FBS for 5 minutes with or without 10 μg/ml MEK inhibitor PD98058. Cell lysates were resolved by 12.5% SDS-PAGE and Western blotted with anti-phospho-ERK (Cell Signaling) and anti-ERK(Zymed). Right panels: NIH-3T3 cells were transfected with neomycin resistance gene alone or with STEAP-1 in pSRa vector. Cells were treated as above but without the MEK inhibitor. In addition, NIH-3T3-Neo cells were treated with 10 mg/ml Na salycilate. Expression of STEAP-1 induces the phosphorylation of ERK-1 and ERK-2 in serum and was inhibited by the upstream MEK kinase inhibitor PD98058.

Figure 29:
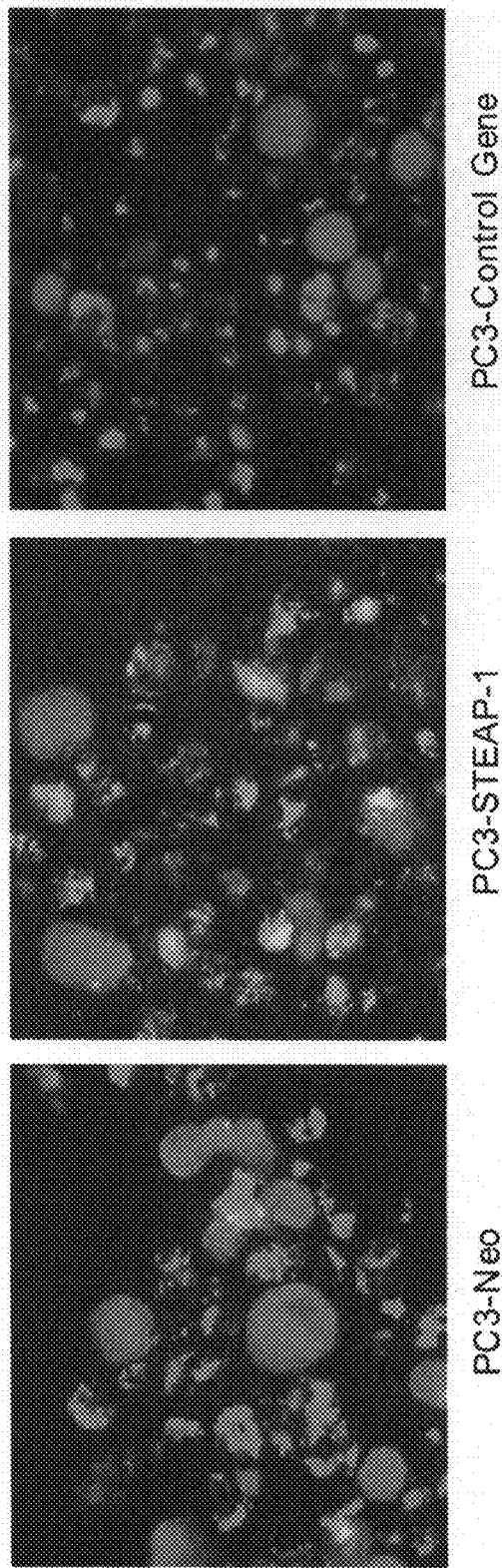

FIG. 29. STEAP-1 Mediates Cell-Cell Communication. PC3 cells were transfected with neomycin resistance gene alone or with STEAP-1 or a control gene in pSRa vector. Recipient cells were labeled with 1 mg/ml dextran-Texas Red and donor cells were labeled with 2.5 μg/ml calcein AM. The donor (green) and recipient (red) cells were co-cultured at 37° C. for 18-24 hours and analyzed by microscopy for the co-localization of fluorescent dyes. Left panel: PC3-Neo cells were used as both donor and recipient. Center panel: PC3-STEAP-1 cells were used as both donor and recipient. Right panel: PC3-control cells were used as both donor and recipient. STEAP-1 induced the transfer of calcein to cells containing dextran-Texas Red, indicating that STEAP-1 facilitates cell-cell communication.

Figure 30:
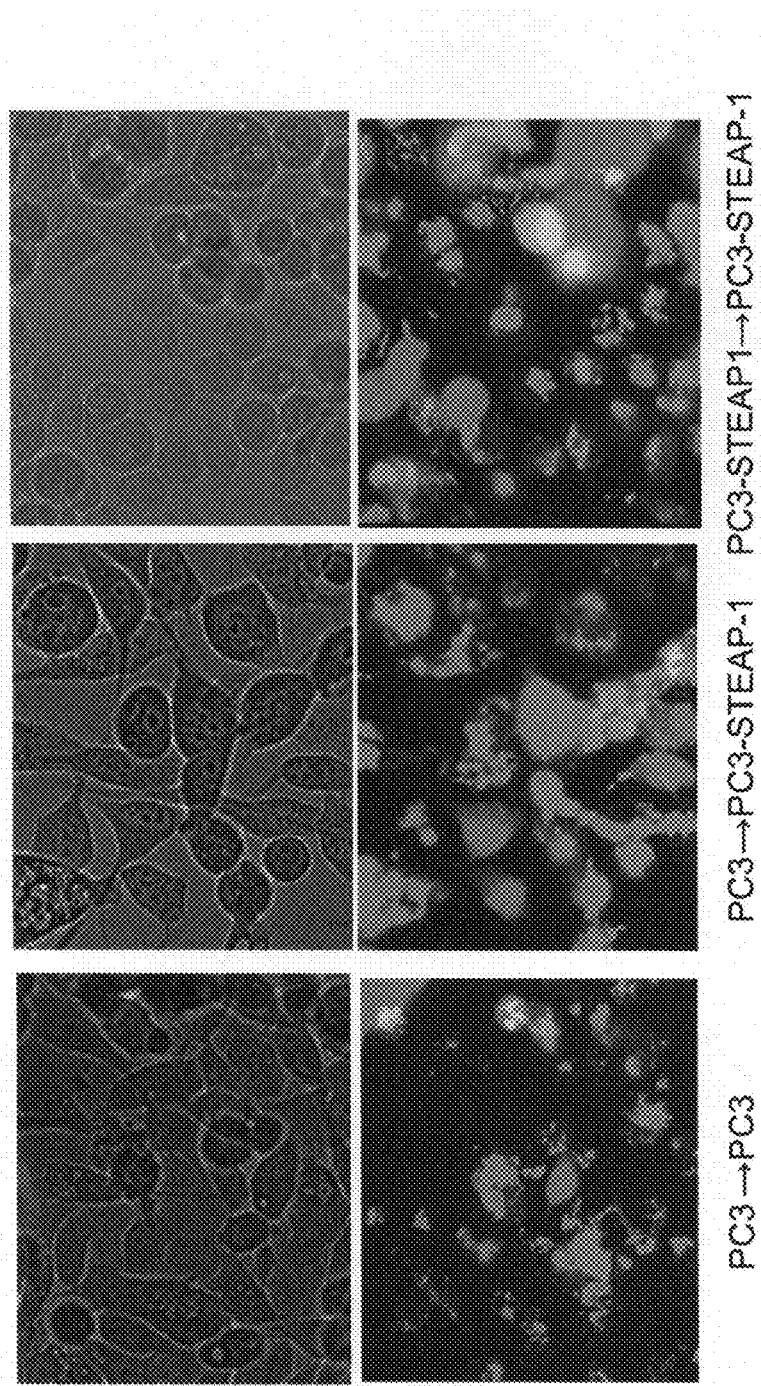

FIG. 30. Cell Communication Requires STEAP-1 Expression on Donor and Recipient Cells. PC3 cells were transfected with neomycin resistance gene alone or with STEAP-1 in pSRa vector. Recipient cells were labeled with 1 mg/ml dextran-Texas Red and donor cells were labled with 2.5 μg/ml calcein AM. The donor (green) and recipient (red) cells were co-cultured at 37° C. for 18-24 hours and analyzed by microscopy for the co-localization of fluorescent dyes. Upper panels: light microscopy; lower panels: UV fluorescence. Left panels: PC3-Neo cells were both donor and recipient. Center panels: PC3-Neo were donor cells and PC3-STEAP-1 were recipient. Right panels: PC3-STEAP-1 cells were both donor and recipient. Only when STEAP-1 was expressed on both donor and recipient was cell-cell communication detected.

Figure 31:
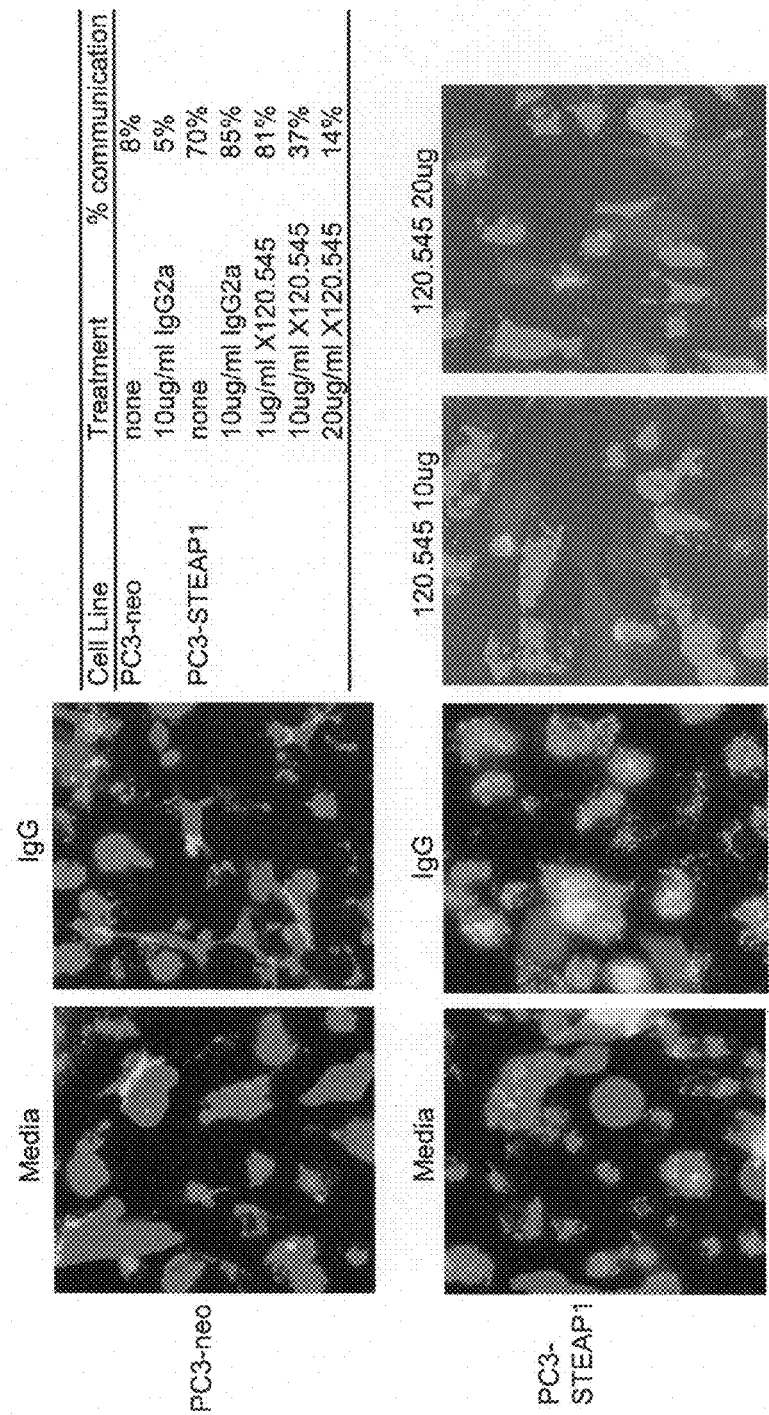

FIG. 31. STEAP-1/120.545 MAb Effect on Gap Junction. PC3 cells were transfected with neomycin resistance gene alone or with STEAP-1 in pSRa vector. Recipient cells were labeled with 1 mg/ml dextran-Texas Red and donor cells were labeled with 2.5 μg/ml calcein AM. The donor (green) and recipient (red) cells were co-cultured at 37° C. for 18-24 hours and analyzed by microscopy for the co-localization of fluorescent dyes. In all experiments, the same cells were used as donor and acceptor. Cells were incubated with the indicated amounts of STEAP-1/120.545 MAb for 10 minutes prior to plating and MAb was maintained in the culture for 24 hours prior to analysis. STEAP1/120.545 reduces STEAP-1 mediated gap junction in a dose-dependent manner.

Figure 32:
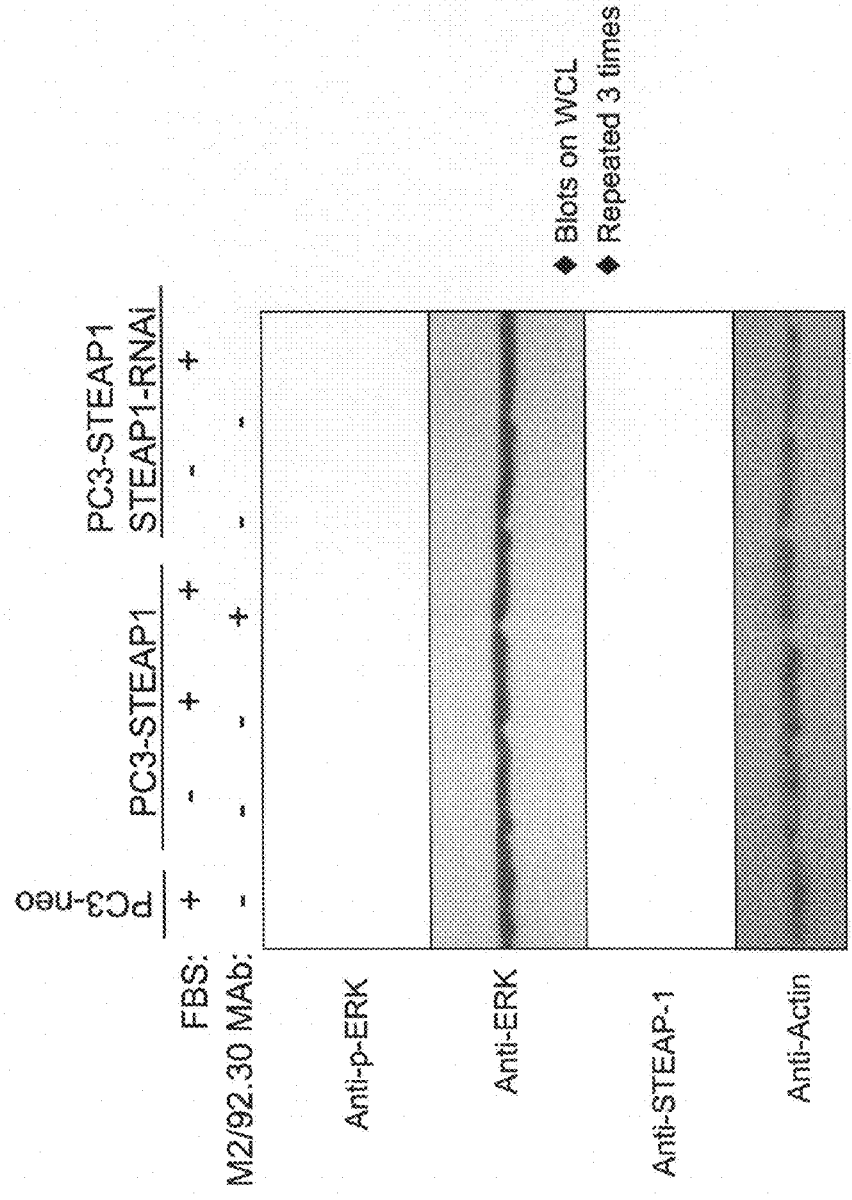

FIG. 32. Inhibition of ERK-1 and ERK-2 phosphorylation by STEAP-1 MAb and RNAi. PC3 cells were transfected with neomycin resistance gene alone or with STEAP-1 and MAb in pSRa vector. For RNAi knockdown, PC3-STEAP-1 cells were stably transfected with a pPUR-U6-27-STEAP-1 vector containing siRNA to STEAP-1. Cells were starved in 0.1% FBS for 18 hours at 37° C., placed on ice for 10 minutes without or with 10 μg/ml M2/92.30 Mab brought to RT for 3 minutes then stimulated with 10% FBS for 5 minutes. Cells were lysed in RIPA buffer, whole cell lysates resolved by 12.5% SDS-PAGE and proteins detected by Western blotting. Phospho-ERK was detected with rabbit antiserum (Cell Signaling) and ERK was detected with rabbit anti-ERK (Zymed). STEAP-1 was detected with sheep anti-STEAP-1 and actin was detected with anti-actin MAb (Santa Cruz).

ERK-1 and ERK-2 phosphorylation were both induced by 10% serum, and were inhibited by M2/92.30 MAb and siRNA to STEAP-1.

Figure 33:
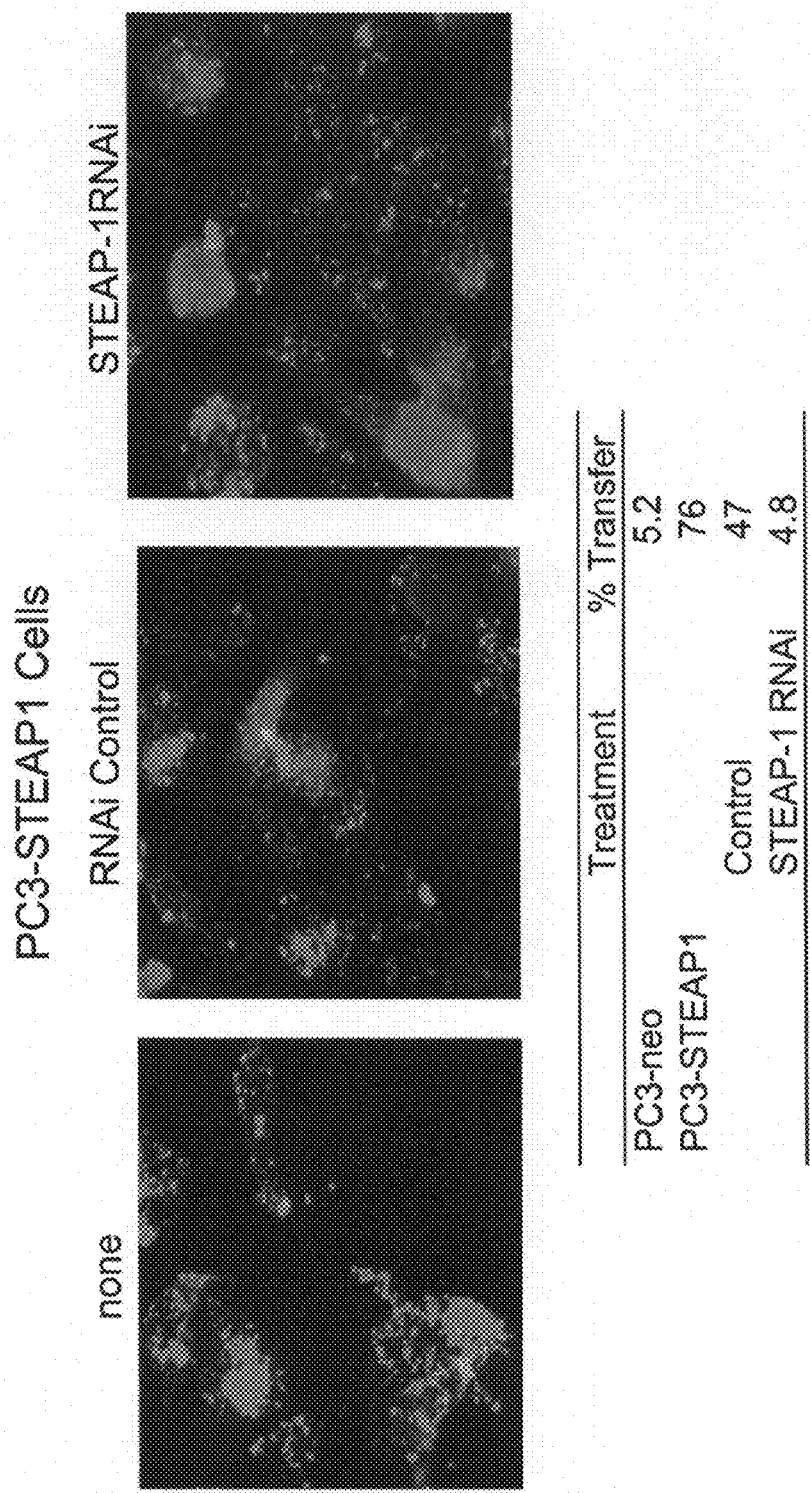

FIG. 33. Effect of STEAP-1 RNAi on Cell-Cell Communication. PC3 cells were transfected with neomycin resistance gene alone or with STEAP-1 in pSRa vector. For RNAi knockdown, PC3-STEAP-1 cells were stably transfected with a pPUR-U6-27-STEAP-1 vector containing siRNA to STEAP-1 or an empty vector. Recipient cells were labeled with 1 mg/ml dextran-Texas Red and donor cells were labeled with 2.5 µg/ml calcein AM. The donor (green) and recipient (red) cells were co-cultured at 37° C. for 18-24 hours and analyzed by microscopy for the co-localization of fluorescent dyes. In all experiments, the same cells were used as donor and acceptor. Specific STEAP-1 RNAi stably expressed in PC3-STEAP-1 cells reduces the STEAP-1 induced cell-cell communication.

DETAILED DESCRIPTION OF THE INVENTION

Outline of Sections
I.) Definitions
II.) STEAP-1 Polynucleotides
II.A.) Uses of STEAP-1 Polynucleotides
II.A.1.) Monitoring of Genetic Abnormalities
II.A.2.) Antisense Embodiments
II.A.3.) Primers and Primer Pairs
II.A.4.) Isolation of STEAP-1-Encoding Nucleic Acid Molecules
II.A.5.) Recombinant Nucleic Acid Molecules and Host-Vector Systems
III.) STEAP-1-related Proteins
III.A.) Motif-bearing Protein Embodiments
III.B.) Expression of STEAP-1-related Proteins
III.C.) Modifications of STEAP-1-related Proteins
III.D.) Uses of STEAP-1-related Proteins
IV.) STEAP-1 Antibodies
V.) STEAP-1 Cellular Immune Responses
VI.) STEAP-1 Transgenic Animals
VII.) Methods for the Detection of STEAP-1
VII.) Methods for Monitoring the Status of STEAP-1-related Genes and Their Products
IX.) Identification of Molecules That Interact With STEAP-1
X.) Therapeutic Methods and Compositions
X.A.) Anti-Cancer Vaccines
X.B.) STEAP-1 as a Target for Antibody-Based Therapy
X.C.) STEAP-1 as a Target for Cellular Immune Responses
X.C.1. Minigene Vaccines
X.C.2. Combinations of CTL Peptides with Helper Peptides
X.C.3. Combinations of CTL Peptides with T Cell Priming Agents
X.C.4. Vaccine Compositions Comprising DC Pulsed with CTL and/or HTL Peptides
X.D.) Adoptive Immunotherapy
X.E.) Administration of Vaccines for Therapeutic or Prophylactic Purposes
XI.) Diagnostic and Prognostic Embodiments of STEAP-1.
XII.) Inhibition of STEAP-1 Protein Function
XII.A.) Inhibition of STEAP-1 With Intracellular Antibodies
XII.B.) Inhibition of STEAP-1 with Recombinant Proteins
XII.C.) Inhibition of STEAP-1 Transcription or Translation
XII.D.) General Considerations for Therapeutic Strategies
XIII.) Identification, Characterization and Use of Modulators of STEAP-1
XIV.) RNAi and Therapeutic use of small interfering RNA (siRNAs)
XV.) KITS/Articles of Manufacture
I.) Definitions:

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence STEAP-1 (either by removing the underlying glycosylation site or by deleting the glycosylation by chemical and/or enzymatic means), and/or adding one or more glycosylation sites that are not present in the native sequence STEAP-1. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a STEAP-1-related protein). For example, an analog of a STEAP-1 protein can be specifically bound by an antibody or T cell that specifically binds to STEAP-1.

The term "antibody" is used in the broadest sense unless clearly indicated otherwise. Therefore, an "antibody" can be naturally occurring or man-made such as monoclonal antibodies produced by conventional hybridoma technology. Anti-STEAP-1 antibodies comprise monoclonal and polyclonal antibodies as well as fragments containing the antigen-binding domain and/or one or more complementarity determining regions of these antibodies. As used herein, the term "antibody" refers to any form of antibody or fragment thereof that specifically binds STEAP-1 and/or exhibits the desired biological activity and specifically covers monoclonal antibodies (including full length monoclonal antibodies), polyclonal antibodies, multispecific antibodies (e.g., bispecific antibodies), and antibody fragments so long as they specifically bind STEAP-1 and/or exhibit the desired biological activity. Any specific antibody can be used in the methods and compositions provided herein. Thus, in one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is a $IgG_1$, $IgG_2$, IgG3, or IgG4 antibody. The antibodies useful in the present methods and compositions can be generated in cell culture, in phage, or in various animals, including but not limited to cows, rabbits, goats, mice, rats, hamsters, guinea pigs, sheep, dogs, cats, monkeys, chimpanzees, apes. Therefore, in one embodiment, an antibody of the present invention is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, ANTIBODY PRODUCTION: ESSENTIAL TECHNIQUES (Wiley, 1997); Shephard, et al., MONOCLONAL ANTIBODIES (Oxford University Press, 2000); Goding, MONOCLONAL ANTIBODIES: PRINCIPLES AND PRACTICE (Academic Press, 1993); CURRENT PROTOCOLS IN IMMUNOLOGY (John Wiley & Sons, most recent edition). An antibody of the present invention can be modified by recombinant means to increase greater efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. No. 5,624,821, U.S. Pat. No. 6,194,551, application Ser. No. WO 9958572; and Angal, et al., *Mol. Immunol.* 30: 105-08 (1993). The modification in amino acids includes deletions, additions, substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to normal or defective STEAP-1. See e.g., ANTIBODY ENGINEERING: A PRACTICAL APPROACH (Oxford University Press, 1996). Suitable antibodies with the desired biologic activities can be identified the following in vitro assays including but not limited to: proliferation, migration, adhesion, soft agar growth, angiogenesis, cell-cell communication, apoptosis, transport, signal transduction, and the following in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays. They can also be used to quantify the STEAP-1 or its receptor.

An "antibody fragment" is defined as at least a portion of the variable region of the immunoglobulin molecule that binds to its target, i.e., the antigen-binding region. In one embodiment it specifically covers single anti-STEAP-1 antibodies and clones thereof (including agonist, antagonist and neutralizing antibodies) and anti-STEAP-1 antibody compositions with polyepitopic specificity. The antibody of the present methods and compositions can be monoclonal or polyclonal. An antibody can be in the form of an antigen binding antibody fragment including a Fab fragment, $F(ab')_2$ fragment, a single chain variable region, and the like. Fragments of intact molecules can be generated using methods well known in the art and include enzymatic digestion and recombinant means.

As used herein, any form of the "antigen" can be used to generate an antibody that is specific for STEAP-1. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids. In one embodiment, the antibody of the methods and compositions herein specifically bind at least a portion of the extracellular domain of the STEAP-1 of interest.

The antibodies or antigen binding fragments thereof provided herein may be conjugated to a "bioactive agent." As used herein, the term "bioactive agent" refers to any synthetic or naturally occurring compound that binds the antigen and/or enhances or mediates a desired biological effect to enhance cell-killing toxins.

In one embodiment, the binding fragments useful in the present invention are biologically active fragments. As used herein, the term "biologically active" refers to an antibody or antibody fragment that is capable of binding the desired the antigenic epitope and directly or indirectly exerting a biologic effect. Direct effects include, but are not limited to the modulation, stimulation, and/or inhibition of a growth signal, the modulation, stimulation, and/or inhibition of an anti-apoptotic signal, the modulation, stimulation, and/or inhibition of an apoptotic or necrotic signal, modulation, stimulation, and/or inhibition the ADCC cascade, and modulation, stimulation, and/or inhibition the CDC cascade.

"Bispecific" antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., *Nature* 305:537-39 (1983). Alternatively, bispecific antibodies can be prepared using chemical linkage. See, e.g., Brennan, et al., *Science* 229:81 (1985). Bispecific antibodies include bispecific antibody fragments. See, e.g., Hollinger, et al., *Proc. Natl. Acad. Sci. U.S.A.* 90:6444-48 (1993), Gruber, et al., *J. Immunol.* 152:5368 (1994).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison et al., *Proc. Natl. Acad. Sci. USA* 81: 6851-6855 (1984)).

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

A "combinatorial library" is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Numerous chemical compounds are synthesized through such combinatorial mixing of chemical building blocks (Gallop et al., J. Med. Chem. 37(9): 1233-1251 (1994)).

Preparation and screening of combinatorial libraries is well known to those of skill in the art. Such combinatorial chemical libraries include, but are not limited to, peptide libraries (see, e.g., U.S. Pat. No. 5,010,175, Furka, Pept. Prot. Res. 37:487-493 (1991), Houghton et al., Nature, 354:84-88 (1991)), peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with a Beta-D-Glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbarnates (Cho, et al., Science 261: 1303 (1993)), and/or peptidyl phosphonates (Campbell et al., J. Org. Chem. 59:658 (1994)). See, generally, Gordon et al., J. Med. Chem. 37:1385 (1994), nucleic acid libraries (see, e.g., Stratagene Corp.), peptide nucleic acid libraries (see, e.g., U.S. Pat. No. 5,539,083), antibody libraries (see, e.g., Vaughn et al., Nature Biotechnology 14(3): 309-314 (1996), and PCT/US96/10287), carbohydrate libraries (see, e.g., Liang et al., Science 274:1520-1522 (1996), and U.S. Pat. No. 5,593,853), and small organic molecule libraries (see, e.g., benzodiazepines, Baum, C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514; and the like).

Devices for the preparation of combinatorial libraries are commercially available (see, e.g., 357 NIPS, 390 NIPS, Advanced Chem Tech, Louisville Ky.; Symphony, Rainin, Woburn, Mass.; 433A, Applied Biosystems, Foster City, Calif.; 9050, Plus, Millipore, Bedford, NIA). A number of well-known robotic systems have also been developed for solution phase chemistries. These systems include automated workstations such as the automated synthesis apparatus developed by Takeda Chemical Industries, LTD. (Osaka, Japan) and many robotic systems utilizing robotic arms (Zymate H, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J.; Asinex, Moscow, RU; Tripos, Inc., St. Louis, Mo.; ChemStar, Ltd, Moscow, RU; 3D Pharmaceuticals, Exton, Pa.; Martek Biosciences, Columbia, Md.; etc.).

As used herein, the term "conservative substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., MOLECULAR BIOLOGY OF THE GENE, The Benjamin/Cummings Pub. Co., p. 224 (4th Edition 1987)). Such exemplary substitutions are preferably made in accordance with those set forth in Table(s) III(a-b). For example, such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III(a) herein; pages 13-15 "Biochemistry" $2^{nd}$ ED. Lubert Stryer ed (Stanford University); Henikoff et al., PNAS 1992 Vol 89 10915-10919; Lei et al., J Biol Chem 1995 May 19; 270(20):11882-6). Other substitutions are also permissible and may be determined empirically or in accord with known conservative substitutions.

The term "cytotoxic agent" refers to a substance that inhibits or prevents the expression activity of cells, function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to auristatins, auristatin e, auromycins, maytansinoids, yttrium, bismuth, ricin, ricin A-chain, combrestatin, duocarmycins, dolostatins, doxorubicin, daunorubicin, taxol, cisplatin, cc1065, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, *Sapaonaria officinalis* inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212 \, or \, 213}$, $P^{32}$ and radioactive isotopes of Lu including $Lu^{177}$. Antibodies may also be conjugated to an anticancer pro-drug activating enzyme capable of converting the pro-drug to its active form.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Hollinger et al., *Proc. Natl. Acad. Sci. USA* 90:6444-48 (1993).

The "gene product" is used herein to indicate a peptide/protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc. In one embodiment, the cancer protein is encoded by a nucleic acid of FIG. 2. The cancer protein can be a fragment, or alternatively, be the full-length protein encoded by nucleic acids of FIG. 2. In one embodiment, a cancer amino acid sequence is used to determine sequence identity or similarity. In another embodiment, the sequences are naturally occurring allelic variants of a protein encoded by a nucleic acid of FIG. 2. In another embodiment, the sequences are sequence variants as further described herein. "Heteroconjugate" antibodies are useful in the present methods and compositions. As used herein, the term "heteroconjugate antibody" refers to two covalently joined antibodies. Such antibodies can be prepared using known methods in synthetic protein chemistry, including using crosslinking agents. See, e.g., U.S. Pat. No. 4,676,980.

"High throughput screening" assays for the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins; U.S. Pat. No. 5,585,639 discloses high throughput screening methods for nucleic acid binding (i.e., in arrays); while U.S. Pat. Nos. 5,576,220 and 5,541,061 disclose high throughput methods of screening for ligand/antibody binding.

In addition, high throughput screening systems are commercially available (see, e.g., Amersham Biosciences, Piscataway, N.J.; Zymark Corp., Hopkinton, Mass.; Air Technical Industries, Mentor, Ohio; Beckman Instruments, Inc. Fullerton, Calif.; Precision Systems, Inc., Natick, Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

The term "homolog" refers to a molecule which exhibits homology to another molecule, by for example, having sequences of chemical residues that are the same or similar at corresponding positions.

In one embodiment, the antibody provided herein is a "human antibody." As used herein, the term "human antibody" refers to an antibody in which essentially the entire sequences of the light chain and heavy chain sequences, including the complementary determining regions (CDRs), are from human genes. In one embodiment, human monoclonal antibodies are prepared by the trioma technique, the human B-cell technique (see, e.g., Kozbor, et al., *Immunol. Today* 4: 72 (1983), EBV transformation technique (see, e.g., Cole et al. MONOCLONAL ANTIBODIES AND CANCER THERAPY 77-96 (1985)), or using phage display (see, e.g., Marks et al., *J. Mol Biol*. 222:581 (1991)). In a specific embodiment, the human antibody is generated in a transgenic mouse. Techniques for making such partially to fully human antibodies are known in the art and any such techniques can be used. According to one particularly preferred embodiment, fully human antibody sequences are made in a transgenic mouse engineered to express human heavy and light chain antibody genes. An exemplary description of preparing transgenic mice that produce human antibodies found in Application No. WO 02/43478 and U.S. Pat. No. 6,657,103 (Abgenix) and its progeny. B cells from transgenic mice that produce the desired antibody can then be fused to make hybridoma cell lines for continuous production of the antibody. See, e.g., U.S. Pat. Nos. 5,569,825; 5,625,126; 5,633,425; 5,661,016; and 5,545,806; and Jakobovits, *Adv. Drug Del. Rev*. 31:33-42 (1998); Green, et al., *J. Exp. Med*. 188:483-95 (1998).

"Human Leukocyte Antigen" or "HLA" is a human class I or class II Major Histocompatibility Complex (MHC) protein (see, e.g., Stites, et al., IMMUNOLOGY, $8^{TH}$ ED., Lange Publishing, Los Altos, Calif. (1994).

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially the six complementary determining regions (CDRs) was inserted after "comprises". all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. See e.g., Cabilly U.S. Pat. No. 4,816,567; Queen et al. (1989) *Proc. Nat'l Acad. Sci. USA* 86:10029-10033; and ANTIBODY ENGINEERING: A PRACTICAL APPROACH (Oxford University Press 1996).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/100 µg/ml ssDNA, in which temperatures for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynudeotide is said to be "isolated" when it is substantially separated from contaminant polynudeotides that correspond or are complementary to genes other than the STEAP-1 genes or that encode polypeptides other than STEAP-1 gene product or fragments thereof. A skilled artisan can readily employ nucleic acid isolation procedures to obtain an isolated STEAP-1 polynudeotide. A protein is said to be "isolated," for example, when physical, mechanical or chemical methods are employed to remove the STEAP-1 proteins from cellular constituents that are normally associated with the protein. A skilled artisan can readily employ standard purification methods to obtain an isolated STEAP-1 protein. Alternatively, an isolated protein can be prepared by chemical means.

Suitable "labels" include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. In addition, the antibodies provided herein can be useful as the antigen-binding component of fluorobodies. See e.g., Zeytun et al., *Nat. Biotechnol.* 21:1473-79 (2003).

The term "mammal" refers to any organism classified as a mammal, induding mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage T×N×M+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g. to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

Modulators of cancer can also be nucleic acids. Nucleic acid modulating agents can be naturally occurring nucleic acids, random nucleic acids, or "biased" random nucleic acids. For example, digests of prokaryotic or eukaryotic genomes can be used in an approach analogous to that outlined above for proteins.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. In one embodiment, the polyclonal antibody contains a plurality of monoclonal antibodies with different epitope specificities, affinities, or avidities within a single antigen that contains multiple antigenic epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352: 624-628 (1991) and Marks et al., J. Mol. Biol. 222: 581-597 (1991), for example. These monoclonal antibodies will usually bind with at least a $K_d$ of about 1 ☐M, more usually at least about 300 nM, typically at least about 30 nM, preferably at least about 10 nM, more preferably at least about 3 nM or better, usually determined by ELISA.

A "motif", as in biological motif of a STEAP-1-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonudeotide". A polynucleotide can comprise a nucleotide sequence disclosed herein wherein thymidine (T), as shown for example in FIG. 2, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. Alternatively, in another embodiment, the primary anchor residues of a peptide binds an HLA class II molecule are spaced relative to each other, rather than to the termini of a peptide, where the peptide is generally of at least 9 amino acids in length. The primary anchor positions for each motif and supermotif are set forth in Table IV(a). For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

"Radioisotopes" include, but are not limited to the following (non-limiting exemplary uses are also set forth in Table IV(I)).

By "randomized" or grammatical equivalents as herein applied to nucleic acids and proteins is meant that each nucleic acid and peptide consists of essentially random nucleotides and amino acids, respectively. These random peptides (or nucleic acids, discussed herein) can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, a library is "fully randomized," with no sequence preferences or constants at any position. In another embodiment, the library is a "biased random" library. That is, some positions within the sequence either are held constant, or are selected from a limited number of possibilities. For example, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

A "recombinant" DNA or RNA molecule is a DNA or RNA molecule that has been subjected to molecular manipulation in vitro.

As used herein, the term "single-chain Fv" or "scFv" or "single chain" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun, THE PHARMACOLOGY OF MONOCLONAL ANTIBODIES, vol. 113, Rosenburg and Moore eds. Springer-Verlag, New York, pp. 269-315 (1994).

Non-limiting examples of "small molecules" include compounds that bind or interact with STEAP-1, ligands including hormones, neuropeptides, chemokines, odorants, phospholipids, and functional equivalents thereof that bind and preferably inhibit STEAP-1 protein function. Such non-limiting small molecules preferably have a molecular weight of less than about 10 kDa, more preferably below about 9, about 8, about 7, about 6, about 5 or about 4 kDa. In certain embodiments, small molecules physically associate with, or bind, STEAP-1 protein; are not found in naturally occurring metabolic pathways; and/or are more soluble in aqueous than non-aqueous solutions.

As used herein, the term "specific" refers to the selective binding of the antibody to the target antigen epitope. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific. In one embodiment, a specific antibody is one that only binds the STEAP-1 antigen, but does not bind to the irrelevent antigen. In another embodiment, a specific antibody is one that binds human STEAP-1 antigen but does not bind a non-human STEAP-1 antigen with 70%, 75%, 80%, 85%, 90%, 91%, 92%, 93%, 94%, 95%, 96%, 97%, 98%, 99% or greater amino acid homology with the STEAP-1 antigen. In another embodiment, a specific antibody is one that binds human STEAP-1 antigen and binds murine STEAP-1 antigen, but with a higher degree of binding the human antigen. In another embodiment, a specific antibody is one that binds human STEAP-1 antigen and binds primate STEAP-1 antigen, but with a higher degree of binding the human antigen. In another embodiment, the specific antibody binds to human STEAP-1 antigen and any non-human STEAP-1 antigen, but with a higher degree of binding the human antigen or any combination thereof.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 65° C. in a solution comprising: 1% bovine serum albumin, 0.5M sodium phosphate pH7.5, 1.25 mM EDTA, and 7% SDS 5×SSC (150 mM NaCl, 15 mM trisodium citrate), followed by washing the filters in 2×SSC/1% SDS at 50° C. and 0.2×SSC/0.1% SDS at 50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles. Overall phenotypic frequencies of HLA-supertypes in different ethnic populations are set forth in Table IV (f). The non-limiting constituents of various supertypes are as follows:

A2: A*0201, A*0202, A*0203, A*0204, A* 0205, A*0206, A*6802, A*6901, A*0207

A3: A3, A11, A31, A*3301, A*6801, A*0301, A*1101, A*3101

B7: B7, B*3501-03, B*51, B*5301, B*5401, B*5501, B*5502, B*5601, B*6701, B*7801, B*0702, B*5101, B*5602

B44: B*3701, B*4402, B*4403, B*60 (B*4001), B61 (B*4006)

A1: A*0102, A*2604, A*3601, A*4301, A*8001

A24: A*24, A*30, A*2403, A*2404, A*3002, A*3003

B27: B*1401-02, B*1503, B*1509, B*1510, B*1518, B*3801-02, B*3901, B*3902, B*3903-04, B*7301, B*2701-08

B58: B*1516, B*1517, B*5701, B*5702, B58

B62: B*4601, B52, B*1501 (B62), B*1502 (B75), B*1513 (B77) Calculated population coverage afforded by different HLA-supertype combinations are set forth in Table IV(g).

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred out albeit not a requirement for a treatment act.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes.

HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding positon(s) of a specifically described protein (e.g. the STEAP-1 protein shown in FIG. 2 or FIG. 3. An analog is an example of a variant protein. Splice isoforms and single nucleotides polymorphisms (SNPs) are further examples of variants.

The "STEAP-1-related proteins" of the invention include those specifically identified herein, as well as allelic variants, conservative substitution variants, analogs and homologs that can be isolated/generated and characterized without undue experimentabon following the methods outlined herein or readily available in the art. Fusion proteins that combine parts of different STEAP-1 proteins or fragments thereof, as well as fusion proteins of a STEAP-1 protein and a heterologous polypeptide are also included. Such STEAP-1 proteins are collectively referred to as the STEAP-1-related proteins, the proteins of the invention, or STEAP-1. The term "STEAP-1-related protein" refers to a polypeptide fragment or a STEAP-1 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 330, 335, 339 or more amino acids.

II.) STEAP-1 Polynucleotides

One aspect of the invention provides polynucleotides corresponding or complementary to all or part of a STEAP-1 gene, mRNA, and/or coding sequence, preferably in isolated form, including polynucleotides encoding a STEAP-1-related protein and fragments thereof, DNA, RNA, DNA/RNA hybrid, and related molecules, polynucleotides or oligonucleotides complementary to a STEAP-1 gene or mRNA sequence or a part thereof, and polynucleotides or oligonucleotides that hybridize to a STEAP-1 gene, mRNA, or to a STEAP-1 encoding polynucleotide (collectively, "STEAP-1 polynucleotides"). In all instances when referred to in this section, T can also be U in FIG. 2.

Embodiments of a STEAP-1 polynucleotide include: a STEAP-1 polynucleotide having the sequence shown in FIG. 2, the nucleotide sequence of STEAP-1 as shown in FIG. 2 wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. For example, embodiments of STEAP-1 nucleotides comprise, without limitation:

(I) a polynucleotide comprising, consisting essentially of, or consisting of a sequence as shown in FIG. 2, wherein T can also be U;

(II) a polynucleotide comprising, consisting essentially of, or consisting of the sequence as shown in FIG. 2A, from nucleotide residue number 66 through nucleotide residue number 1085, including the stop codon, wherein T can also be U;

(III) a polynucleotide comprising, consisting essentially of, or consisting of the sequence as shown in FIG. 2B, from nucleotide residue number 96 through nucleotide residue number 872, including the stop codon, wherein T can also be U;

(IV) a polynucleotide comprising, consisting essentially of, or consisting of the sequence as shown in FIG. 2C, from nucleotide residue number 96 through nucleotide residue number 944, including the a stop codon, wherein T can also be U;

(V) a polynucleotide comprising, consisting essentially of, or consisting of the sequence as shown in FIG. 2D, from nucleotide residue number 96 through nucleotide residue number 872, including the stop codon, wherein T can also be U;

(VI) a polynucleotide comprising, consisting essentially of, or consisting of the sequence as shown in FIG. 2E, from nucleotide residue number 96 through nucleotide residue number 872, including the stop codon, wherein T can also be U;

(VII) a polynucleotide comprising, consisting essentially of, or consisting of the sequence as shown in FIG. 2F, from nucleotide residue number 96 through nucleotide residue number 872, including the stop codon, wherein T can also be U;

(VIII) a polynucleotide comprising, consisting essentially of, or consisting of the sequence as shown in FIG. 2G, from nucleotide residue number 96 through nucleotide residue number 872, including the stop codon, wherein T can also be U;

(IX) a polynucleotide comprising, consisting essentially of, or consisting of the sequence as shown in FIG. 2H, from nucleotide residue number 96 through nucleotide residue number 872, including the stop codon, wherein T can also be U;

(X) a polynucleotide comprising, consisting essentially of, or consisting of the sequence as shown in FIG. 2I, from nucleotide residue number 96 through nucleotide residue number 872, including the stop codon, wherein T can also be U;

(XI) a polynucleotide comprising, consisting essentially of, or consisting of the sequence as shown in FIG. 2J, from nucleotide residue number 96 through nucleotide residue number 872, including the stop codon, wherein T can also be U;

(XII) a polynucleotide comprising, consisting essentially of, or consisting of the sequence as shown in FIG. 2K, from nucleotide residue number 96 through nucleotide residue number 872, including the stop codon, wherein T can also be U;

(XIII) a polynucleotide comprising, consisting essentially of, or consisting of the sequence as shown in FIG. 2L, from nucleotide residue number 96 through nucleotide residue number 872, including the stop codon, wherein T can also be U;

(XIV) a polynucleotide comprising, consisting essentially of, or consisting of the sequence as shown in FIG. 2M, from nucleotide residue number 96 through nucleotide residue number 872, including the stop codon, wherein T can also be U;

(XV) a polynucleotide comprising, consisting essentially of, or consisting of the sequence as shown in FIG. 2N, from nucleotide residue number 96 through nucleotide residue number 872, including the stop codon, wherein T can also be U;

(XVI) a polynucleotide comprising, consisting essentially of, or consisting of the sequence as shown in FIG. 2O, from nucleotide residue number 96 through nucleotide residue number 872, including the stop codon, wherein T can also be U;

(XVII) a polynucleotide comprising, consisting essentially of, or consisting of the sequence as shown in FIG. 2P, from nucleotide residue number 96 through nucleotide residue number 872, including the stop codon, wherein T can also be U;

(XVIII) a polynucleotide comprising, consisting essentially of, or consisting of the sequence as shown in FIG. 2Q, from nucleotide residue number 96 through nucleotide residue number 872, including the stop codon, wherein T can also be U;

(XIX) a polynucleotide that encodes a STEAP-1-related protein that is at least 90, 91, 92, 93, 94, 95, 96, 97, 98, 99 or 100% homologous to an entire amino acid sequence shown in FIG. 2A-Q;

(XX) a polynucleotide that encodes a STEAP-1-related protein that is at least 90, 91, 92, 93, 94, 95, 96, 97, 98, 99 or 100% identical to an entire amino acid sequence shown in FIG. 2A-Q;

(XXI) a polynucleotide that encodes at least one peptide set forth in Tables V-XVIII and XXII-LI as set forth in U.S. patent application Ser. No. 10/236,878 filed 06-Sep.-2002, the specific contents of which are fully incorporated by reference herein.;

(XXII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A in any whole number increment up to 339 that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XXIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A in any whole number increment up to 339 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XXIV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A in any whole number increment up to 339 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XXV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A in any whole number increment up to 399 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XXVI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A in any whole number increment up to 339 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XXVII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3B and 3D in any whole number increment up to 258 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XXVIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3B and 3D in any whole number increment up to 258 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XXIX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3B and 3D in any whole number increment up to 258 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XXX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3B and 3D in any whole number increment up to 258 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XXXI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3B and 3D in any whole number increment up to 258 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XXXII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3C in any whole number increment up to 282 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XXXIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3C in any whole number increment up to 282 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XXXIV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3C in any whole number increment up to 282 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XXXV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3C in any whole number increment up to 282 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XXXVI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3C in any whole number increment up to 282 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XXXVII) a polynucleotide that is fully complementary to a polynucleotide of any one of (I)-(XXXVI);

(XXXVIII) a polynucleotide that is fully complementary to a polynucleotide of any one of (I)-(XXXVII);

(XXXIX) a peptide that is encoded by any of (I) to (XXXVIII); and;

(XL) a composition comprising a polynucleotide of any of (I)-(XXXVIII) or peptide of (XXXIX) together with a pharmaceutical excipient and/or in a human unit dose form;

(XLI) a method of using a polynucleotide of any (I)-(XXXVIII) or peptide of (XXXIX) or a composition of (XL) in a method to modulate a cell expressing STEAP-1;

(XLII) a method of using a polynucleotide of any (I)-(XXXVIII) or peptide of (XXXIX) or a composition of (XL) in a method to diagnose, prophylax, prognose, or treat an individual who bears a cell expressing STEAP-1;

(XLIII) a method of using a polynucleotide of any (I)-(XXXVIII) or peptide of (XXXIX) or a composition of (XL) in a method to diagnose, prophylax, prognose, or treat an individual who bears a cell expressing STEAP-1, said cell from a cancer of a tissue listed in Table I;

(XLIV) a method of using a polynucleotide of any (I)-(XXXVIII) or peptide of (XXXIX) or a composition of (XL) in a method to diagnose, prophylax, prognose, or treat a cancer;

(XLV) a method of using a polynucleotide of any (I)-(XXXVIII) or peptide of (XXXIX) or a composition of (XL) in a method to diagnose, prophylax, prognose, or treat a cancer of a tissue listed in Table I; and;

(XLVI) a method of using a polynucleotide of any (I)-(XXXVIII) or peptide of (XXXIX) or a composition of (XL) in a method to identify or characterize a modulator of a cell expressing STEAP-1.

As used herein, a range is understood to disclose specifically all whole unit positions thereof.

Typical embodiments of the invention disclosed herein include STEAP-1 polynucleotides that encode specific portions of STEAP-1 mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 330, 335, 339 or more contiguous amino acids of STEAP-1 variant 1; the maximal lengths relevant for other variants are: variant 2, 258 amino acids; variant 3, 282 amino acids, and variant 4, 258 amino acids.

For example, representative embodiments of the invention disclosed herein include: polynucleotides and their encoded peptides themselves encoding about amino acid 1 to about amino acid 10 of the STEAP-1 protein shown in FIG. 2 or FIG. 3, polynucleotides encoding about amino acid 10 to about amino acid 20 of the STEAP-1 protein shown in FIG. 2 or FIG. 3, polynucleotides encoding about amino acid 20 to about amino acid 30 of the STEAP-1 protein shown in FIG. 2 or FIG. 3, polynucleotides encoding about amino acid 30 to about amino acid 40 of the STEAP-1 protein shown in FIG. 2 or FIG. 3, polynucleotides encoding about amino acid 40 to about amino acid 50 of the STEAP-1 protein shown in FIG. 2 or FIG. 3, polynucleotides encoding about amino acid 50 to about amino acid 60 of the STEAP-1 protein shown in FIG. 2 or FIG. 3, polynucleotides encoding about amino acid 60 to about amino acid 70 of the STEAP-1 protein shown in FIG. 2 or FIG. 3, polynucleotides encoding about amino acid 70 to about amino acid 80 of the STEAP-1 protein shown in FIG. 2 or FIG. 3, polynucleotides encoding about amino acid 80 to about amino acid 90 of the STEAP-1 protein shown in FIG. 2 or FIG. 3, polynucleotides encoding about amino acid 90 to about amino acid 100 of the STEAP-1 protein shown in FIG. 2 or FIG. 3, in increments of about 10 amino acids, ending at the carboxyl terminal amino acid set forth in FIG. 2 or FIG. 3. Accordingly, polynucleotides encoding portions of the amino acid sequence (of about 10 amino acids), of amino acids, 100 through the carboxyl terminal amino acid of the STEAP-1 protein are embodiments of the invention. Wherein it is understood that each particular amino acid position discloses that position plus or minus five amino acid residues.

Polynucleotides encoding relatively long portions of a STEAP-1 protein are also within the scope of the invention. For example, polynucleotides encoding from about amino acid 1 (or 20 or 30 or 40 etc.) to about amino acid 20, (or 30, or 40 or 50 etc.) of the STEAP-1 protein "or variant" shown in FIG. 2 or FIG. 3 can be generated by a variety of techniques well known in the art. These polynucleotide fragments can include any portion of the STEAP-1 sequence as shown in FIG. 2.

Additional illustrative embodiments of the invention disclosed herein include STEAP-1 polynucleotide fragments encoding one or more of the biological motifs contained within a STEAP-1 protein "or variant" sequence, including one or more of the motif-bearing subsequences of a STEAP-1 protein "or variant" set forth in Tables V-XVIII and XXII-LI. In another embodiment, typical polynucleotide fragments of the invention encode one or more of the regions of STEAP-1 protein or variant that exhibit homology to a known molecule. In another embodiment of the invention, typical polynucleotide fragments can encode one or more of the STEAP-1 protein or variant N-glycosylation sites, cAMP and cGMP-dependent protein kinase phosphorylation sites, casein kinase II phosphorylation sites or N-myristoylation site and amidation sites.

Note that to determine the starting position of any peptide set forth in Tables V-XVIII and Tables XXII to LI (collectively HLA Peptide Tables) respective to its parental protein, e.g., variant 1, variant 2, etc., reference is made to three factors: the particular variant, the length of the peptide in an HLA Peptide Table, and the Search Peptides listed in Table LII. Generally, a unique Search Peptide is used to obtain HLA peptides for a particular variant. The position of each Search Peptide relative to its respective parent molecule is listed in Table LII. Accordingly, if a Search Peptide begins at position "X", one must add the value "X minus 1" to each position in Tables V-XVIII and Tables XXII-LI to obtain the actual position of the HLA peptides in their parental molecule. For example if a particular Search Peptide begins at position 150 of its parental molecule, one must add 150-1, i.e., 149 to each HLA peptide amino acid position to calculate the position of that amino acid in the parent molecule.

II.A.) Uses of STEAP-1 Polynucleotides

II.A.1.) Monitoring of Genetic Abnormalities

The polynucleotides of the preceding paragraphs have a number of different specific uses. The human STEAP-1 gene maps to the chromosomal location set forth in the Example entitled "Chromosomal Mapping of STEAP-1." For example, because the STEAP-1 gene maps to this chromosome, polynucleotides that encode different regions of the STEAP-1 proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(34): 81-83 (1998); Johansson et al., Blood 86(10): 3905-3914 (1995) and Finger et al., P.N.A.S. 85(23): 9158-9162 (1988)). Thus, polynucleotides encoding specific regions of the STEAP-1 proteins provide new tools that can be used to delineate, with greater precision than previously possible, cytogenetic abnormalities in the chromosomal region that encodes STEAP-1 that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055-1057 (1994)).

Furthermore, as STEAP-1 was shown to be highly expressed in prostate and other cancers, STEAP-1 polynucleotides are used in methods assessing the status of STEAP-1 gene products in normal versus cancerous tissues. Typically, polynucleotides that encode specific regions of the STEAP-1 proteins are used to assess the presence of perturbations (such as deletions, insertions, point mutations, or alterations resulting in a loss of an antigen etc.) in specific regions of the STEAP-1 gene, such as regions containing one or more motifs. Exemplary assays include both RT-PCR assays as well as single-strand conformation polymorphism (SSCP) analysis (see, e.g., Marrogi et al., J. Cutan. Pathol. 26(8): 369-378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of STEAP-1. For example, antisense molecules can be RNAs or other molecules, including peptide nucleic acids (PNAs) or non-nucleic acid molecules such as phosphorothioate derivatives that specifically bind DNA or RNA in a base pair-dependent manner. A skilled artisan can readily obtain these classes of nucleic acid molecules using the STEAP-1 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., STEAP-1. See for example, Jack Cohen, Oligodeoxynucleotides, Antisense Inhibitors of Gene Expression, CRC Press, 1989; and Synthesis 1:1-5 (1988). The STEAP-1 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleotide phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P. et al., J. Org. Chem. 55:4693-4698 (1990); and Iyer, R. P. et al., J. Am. Chem. Soc. 112:1253-1254 (1990). Additional STEAP-1 antisense oligonucleotides of the present invention include morpholino antisense oligonucleotides known in the art (see, e.g., Partridge et al., 1996, Antisense & Nucleic Acid Drug Development 6: 169-175).

The STEAP-1 antisense oligonucleotides of the present invention typically can be RNA or DNA that is complementary to and stably hybridizes with the first 100 5' codons or last 100 3' codons of a STEAP-1 genomic sequence or the corresponding mRNA. Absolute complementarity is not required, although high degrees of complementarity are preferred. Use of an oligonucleotide complementary to this region allows for the selective hybridization to STEAP-1 mRNA and not to mRNA specifying other regulatory subunits of protein kinase. In one embodiment, STEAP-1 antisense oligonucleotides of the present invention are 15 to 30-mer fragments of the antisense DNA molecule that have a sequence that hybridizes to STEAP-1 mRNA. Optionally, STEAP-1 antisense oligonucleotide is a 30-mer oligonucleotide that is complementary to a region in the first 10 5' codons or last 10 3' codons of STEAP-1. Alternatively, the antisense molecules are modified to employ ribozymes in the inhibition of STEAP-1 expression, see, e.g., L. A. Couture & D. T. Stinchcomb; *Trends Genet* 12: 510-515 (1996).

II.A.3.) Primers and Primer Pairs

Further specific embodiments of these nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a STEAP-1 polynucleotide in a sample and as a means for detecting a cell expressing a STEAP-1 protein.

Examples of such probes include polypeptides comprising all or part of the human STEAP-1 cDNA sequence shown in FIG. 2. Examples of primer pairs capable of specifically amplifying STEAP-1 mRNAs are also described in the Examples. As will be understood by the skilled artisan, a great many different primers and probes can be prepared based on the sequences provided herein and used effectively to amplify and/or detect a STEAP-1 mRNA.

The STEAP-1 polynucleotides of the invention are useful for a variety of purposes, including but not limited to their use as probes and primers for the amplification and/or detection of the STEAP-1 gene(s), mRNA(s), or fragments thereof; as reagents for the diagnosis and/or prognosis of prostate cancer and other cancers; as coding sequences capable of directing the expression of STEAP-1 polypeptides; as tools for modulating or inhibiting the expression of the STEAP-1 gene(s) and/or translation of the STEAP-1 transcript(s); and as therapeutic agents.

The present invention includes the use of any probe as described herein to identify and isolate a STEAP-1 or STEAP-1 related nucleic acid sequence from a naturally occurring source, such as humans or other mammals, as well as the isolated nucleic acid sequence per se, which would comprise all or most of the sequences found in the probe used.

II.A.4.) Isolation of STEAP-1-Encoding Nucleic Acid Molecules

The STEAP-1 cDNA sequences described herein enable the isolation of other polynucleotides encoding STEAP-1 gene product(s), as well as the isolation of polynucleotides encoding STEAP-1 gene product homologs, alternatively spliced isoforms, allelic variants, and mutant forms of a STEAP-1 gene product as well as polynucleotides that encode analogs of STEAP-1-related proteins. Various molecular cloning methods that can be employed to isolate full length cDNAs encoding a STEAP-1 gene are well known (see, for example, Sambrook, J. et al., Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing STEAP-1 gene cDNAs can be identified by probing with a labeled STEAP-1 cDNA or a fragment thereof. For example, in one embodiment, a STEAP-1 cDNA (e.g., FIG. 2) or a portion thereof can be synthesized and used as a probe to retrieve overlapping and full-length cDNAs corresponding to a STEAP-1 gene. A STEAP-1 gene itself can be isolated by screening genomic DNA libraries, bacterial artificial chromosome libraries (BACs), yeast artificial chromosome libraries (YACs), and the like, with STEAP-1 DNA probes or primers.

II.A.5.) Recombinant Nucleic Acid Molecules and Host-Vector Systems

The invention also provides recombinant DNA or RNA molecules containing a STEAP-1 polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a STEAP-1 polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of STEAP-1 or a fragment, analog or homolog thereof can be used to generate STEAP-1 proteins or fragments thereof using any number of host-vector systems routinely used and widely known in the art.

A wide range of host-vector systems suitable for the expression of STEAP-1 proteins or fragments thereof are available, see for example, Sambrook et al, 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, STEAP-1 can be expressed in several prostate cancer and non-prostate cell lines, including for example 293, 293T, rat-1, NIH 3T3 and TsuPr1. The host-vector systems of the invention are useful for the production of a STEAP-1 protein or fragment thereof. Such host-vector systems can be employed to study the functional properties of STEAP-1 and STEAP-1 mutations or analogs.

Recombinant human STEAP-1 protein or an analog or homolog or fragment thereof can be produced by mammalian cells transfected with a construct encoding a STEAP-1-related nucleotide. For example, 293T cells can be transfected with an expression plasmid encoding STEAP-1 or fragment, analog or homolog thereof, a STEAP-1-related protein is expressed in the 293T cells, and the recombinant STEAP-1 protein is isolated using standard purification methods (e.g., affinity purification using anti-STEAP-1 antibodies). In another embodiment, a STEAP-1 coding sequence is subcloned into the retroviral vector pSRαMSVtkneo and used to infect various mammalian cell lines, such as NIH 3T3, TsuPr1, 293 and rat-1 in order to establish STEAP-1 expressing cell lines. Various other expression systems well known in the art can also be employed. Expression constructs encoding a leader peptide joined in frame to a STEAP-1 coding sequence can be used for the generation of a secreted form of recombinant STEAP-1 protein.

As discussed herein, redundancy in the genetic code permits variation in STEAP-1 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as at URL dna.affrc.go.jp/~nakamura/codon.html.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell Biol.*, 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

III.) STEAP-1-related Proteins

Another aspect of the present invention provides STEAP-1-related proteins. Specific embodiments of STEAP-1 proteins comprise a polypeptide having all or part of the amino acid sequence of human STEAP-1 as shown in FIG. 2 or FIG. 3, preferably FIG. 2A. Alternatively, embodiments of STEAP-1 proteins comprise variant, homolog or analog polypeptides that have alterations in the amino acid sequence of STEAP-1 shown in FIG. 2 or FIG. 3.

Embodiments of a STEAP-1 polypeptide include: a STEAP-1 polypeptide having a sequence shown in FIG. 2, a peptide sequence of a STEAP-1 as shown in FIG. 2 wherein T is U; at least 10 contiguous nucleotides of a polypeptide having the sequence as shown in FIG. 2; or, at least 10 contiguous peptides of a polypeptide having the sequence as shown in FIG. 2 where T is U. For example, embodiments of STEAP-1 peptides comprise, without limitation:

(I) a protein comprising, consisting essentially of, or consisting of an amino acid sequence as shown in FIG. 2A-Q or FIG. 3A-D;

(II) a STEAP-1-related protein that is at least 90, 91, 92, 93, 94, 95, 96, 97, 98, 99 or 100% homologous to an entire amino acid sequence shown in FIG. 2A-Q or 3A-D;

(III) a STEAP-1-related protein that is at least 90, 91, 92, 93, 94, 95, 96, 97, 98, 99 or 100% identical to an entire amino acid sequence shown in FIG. 2A-Q or 3A-D;

(IV) a protein that comprises at least one peptide set forth in Tables V to LI as set forth in U.S. patent application Ser. No. 10/236,878 filed 06-Sep.-2002 the specific contents of which are fully incorporated by reference herein, optionally with a proviso that it is not an entire protein of FIG. 2;

(V) a protein that comprises at least one peptide set forth in Tables V-XVIII, collectively, which peptide is also set forth in Tables XXII to LI, collectively, optionally with a proviso that it is not an entire protein of FIG. 2;

(VI) a protein that comprises at least two peptides selected from the peptides set forth in Tables V-LI, optionally with a proviso that it is not an entire protein of FIG. 2;

(VII) a protein that comprises at least two peptides selected from the peptides set forth in Tables V to LI collectively, with a proviso that the protein is not a contiguous sequence from an amino acid sequence of FIG. 2;

(VIII) a protein that comprises at least one peptide selected from the peptides set forth in Tables V-XVIII; and at least one peptide selected from the peptides set forth in Tables XXII to LI, with a proviso that the protein is not a contiguous sequence from an amino acid sequence of FIG. 2;

(IX) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A in any whole number increment up to 339 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(X) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A in any whole number increment up to 339 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XI) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A in any whole number increment up to 339 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A in any whole number increment up to 339 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XIII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, amino acids of a protein of FIG. 3A in any whole number increment up to 339 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XIV) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3B or 3D, in any whole number increment up to 258 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XV) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3B or 3D, in any whole number increment up to 258 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XVI) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3B or 3D, in any whole number increment up to 258 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XVII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3B or 3D, in any whole number increment up to 258 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XVIII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, amino acids of a protein of FIG. 3B or 3D in any whole number increment up to 258 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XIX) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3C, in any whole number increment up to 282 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XX) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3C, in any whole number increment up to 282 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XXI) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3C, in any whole number increment up to 282 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XXII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3C, in any whole number increment up to 282 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XXIII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, amino acids of a protein of FIG. 3C in any whole number increment up to 282 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XXIV) a peptide that occurs at least twice in Tables V-XVIII and XXII to LI, collectively;

(XXV) a peptide that occurs at least three times in Tables VI-XVIII and XXII to LI, collectively;

(XXVI) a peptide that occurs at least four times in Tables V-XXVIII and XXII to LI, collectively;

(XXVII) a peptide that occurs at least five times in Tables V-XVIII and XXII to LI, collectively;

(XXVIII) a peptide that occurs at least once in Tables V-XVIII, and at least once in tables XXII to LI;

(XXIX) a peptide that occurs at least once in Tables V-XVIII, and at least twice in tables XXII to LI;

(XXX) a peptide that occurs at least twice in Tables V-XVIII, and at least once in tables XXII to LI;

(XXXI) a peptide that occurs at least twice in Tables V-XVIII, and at least twice in tables XXII to LI;

(XXXII) a peptide which comprises one two, three, four, or five of the following characteristics, or an oligonucleotide encoding such peptide:

i) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or, v) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9;

(XXXIII) a composition comprising a peptide of (I)-(XXXII) or an antibody or binding region thereof together with a pharmaceutical excipient and/or in a human unit dose form.

(XXXIV) a method of using a peptide of (I)-(XXXII), or an antibody or binding region thereof or a composition of (XXXIII) in a method to modulate a cell expressing STEAP-1,;

(XXXV) a method of using a peptide of (I)-(XXXII) or an antibody or binding region thereof or a composition of (XXXIII) in a method to diagnose, prophylax, prognose, or treat an individual who bears a cell expressing STEAP-1;

(XXXVI) a method of using a peptide of (I)-(XXXII) or an antibody or binding region thereof or a composition of (XXXIII) in a method to diagnose, prophylax, prognose, or treat an individual who bears a cell expressing STEAP-1, said cell from a cancer of a tissue listed in Table I;

(XXXVII) a method of using a peptide of (I)-(XXXII) or an antibody or binding region thereof or a composition of (XXXIII) in a method to diagnose, prophylax, prognose, or treat a cancer;

(XXXVIII) a method of using a peptide of (I)-(XXXII) or an antibody or binding region thereof or a composition of (XXXIII) in a method to diagnose, prophylax, prognose, or treat a cancer of a tissue listed in Table I; and;

(XXXIX) a method of using a peptide of (I)-(XXXII) or an antibody or binding region thereof or a composition (XXXIII) in a method to identify or characterize a modulator of a cell expressing STEAP-1;

As used herein, a range is understood to specifically disclose all whole unit positions thereof.

Typical embodiments of the invention disclosed herein include STEAP-1 polynucleotides that encode specific portions of STEAP-1 mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 330, 335, 339 or more contiguous amino acids of STEAP-1 variant 1; the maximal lengths relevant for other variants are: variant 2, 258 amino acids; variant 3, 282 amino acids, variant 4, 258 amino acids.

In general, naturally occurring allelic variants of human STEAP-1 share a high degree of structural identity and homology (e.g., 90% or more homology). Typically, allelic variants of a STEAP-1 protein contain conservative amino acid substitutions within the STEAP-1 sequences described herein or contain a substitution of an amino acid from a corresponding position in a homologue of STEAP-1. One class of STEAP-1 allelic variants are proteins that share a high degree of homology with at least a small region of a particular STEAP-1 amino acid sequence, but further contain a radical departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions.

Embodiments of the invention disclosed herein include a wide variety of art-accepted variants or analogs of STEAP-1 proteins such as polypeptides having amino acid insertions, deletions and substitutions. STEAP-1 variants can be made using methods known in the art such as site-directed mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10.6487 (1987)), cassette mutagenesis (Wells et al., Gene, 34:315 (1985)), restriction selection mutagenesis (Wells et al., *Philos. Trans. R. Soc. London SerA*, 317:415 (1986)) or other known techniques can be performed on the cloned DNA to produce the STEAP-1 variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isosteric amino acid can be used.

As defined herein, STEAP-1 variants, analogs or homologs, have the distinguishing attribute of having at least one epitope that is "cross reactive" with a STEAP-1 protein having an amino acid sequence of FIG. 3. As used in this sentence, "cross reactive" means that an antibody or T cell that specifically binds to a STEAP-1 variant also specifically binds to a STEAP-1 protein having an amino acid sequence set forth in FIG. 3. A polypeptide ceases to be a variant of a protein shown in FIG. 3, when it no longer contains any epitope capable of being recognized by an antibody or T cell that specifically binds to the starting STEAP-1 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol 2000 165(12): 6949-6955; Hebbes et al., Mol Immunol (1989) 26(9):865-73; Schwartz et al., J Immunol (1985) 135(4):2598-608.

Other classes of STEAP-1-related protein variants share 70%, 75%, 80%, 85% or 90% or more similarity with an amino acid sequence of FIG. 3, or a fragment thereof. Another specific class of STEAP-1 protein variants or analogs comprises one or more of the STEAP-1 biological motifs described herein or presently known in the art. Thus, encompassed by the present invention are analogs of STEAP-1 fragments (nucleic or amino acid) that have altered functional (e.g. immunogenic) properties relative to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of a STEAP-1 protein shown in FIG. 2 or FIG. 3. For example, representative embodiments of the invention comprise peptides/proteins having any 4, 5, 6, 7, 8, 9, 10, 11, 12, 13, 14, 15 or more contiguous amino acids of a STEAP-1 protein shown in FIG. 2 or FIG. 3.

Moreover, representative embodiments of the invention disclosed herein include polypeptides consisting of about amino acid 1 to about amino acid 10 of a STEAP-1 protein shown in FIG. 2 or FIG. 3, polypeptides consisting of about amino acid 10 to about amino acid 20 of a STEAP-1 protein shown in FIG. 2 or FIG. 3, polypeptides consisting of about amino acid 20 to about amino acid 30 of a STEAP-1 protein shown in FIG. 2 or FIG. 3, polypeptides consisting of about amino acid 30 to about amino acid 40 of a STEAP-1 protein shown in FIG. 2 or FIG. 3, polypeptides consisting of about amino acid 40 to about amino acid 50 of a STEAP-1 protein shown in FIG. 2 or FIG. 3, polypeptides consisting of about amino acid 50 to about amino acid 60 of a STEAP-1 protein shown in FIG. 2 or FIG. 3, polypeptides consisting of about amino acid 60 to about amino acid 70 of a STEAP-1 protein shown in FIG. 2 or FIG. 3, polypeptides consisting of about amino acid 70 to about amino acid 80 of a STEAP-1 protein shown in FIG. 2 or FIG. 3, polypeptides consisting of about amino acid 80 to about amino acid 90 of a STEAP-1 protein shown in FIG. 2 or FIG. 3, polypeptides consisting of about amino acid 90 to about amino acid 100 of a STEAP-1 protein shown in FIG. 2 or FIG. 3, etc. throughout the entirety of a STEAP-1 amino acid sequence. Moreover, polypeptides consisting of about amino acid 1 (or 20 or 30 or 40 etc.) to about amino acid 20, (or 130, or 140 or 150 etc.) of a STEAP-1 protein shown in FIG. 2 or FIG. 3 are embodiments of the invention. It is to be appreciated that the starting and stopping positions in this paragraph refer to the specified position as well as that position plus or minus 5 residues.

STEAP-1-related proteins are generated using standard peptide synthesis technology or using chemical cleavage methods well known in the art. Alternatively, recombinant methods can be used to generate nucleic acid molecules that encode a STEAP-1-related protein. In one embodiment, nucleic acid molecules provide a means to generate defined fragments of a STEAP-1 protein (or variants, homologs or analogs thereof).

III.A.) Motif-bearing Protein Embodiments

Additional illustrative embodiments of the invention disclosed herein include STEAP-1 polypeptides comprising the amino acid residues of one or more of the biological motifs contained within a STEAP-1 polypeptide sequence set forth in FIG. 2 or FIG. 3. Various motifs are known in the art, and a protein can be evaluated for the presence of such motifs by a number of publicly available Internet sites (see, e.g., URL addresses: pfam.wustl.edu/; searchlauncher.bcm.tmc.edu/seq-search/struc-predict.html; psort.ims.u-tokyo.ac.jp/; cbs-.dtu.dk/; ebi.ac.uk/interpro/scan.html; expasy.ch/tools/scnpsit1.html; Epimatrix™ and Epimer™, Brown University, brown.edu/Research/TB-HIV_Lab/epimatrix/epimatrix.html; and BIMAS, bimas.dcrt.nih.gov/.).

Motif bearing subsequences of all STEAP-1 variant proteins are set forth and identified in Tables V-XVIII and XXII-LI.

Table IV(h) sets forth several frequently occurring motifs based on pfam searches (see URL address pfam.wustl.edu/). The columns of Table IV(h) list (1) motif name abbreviation, (2) percent identity found amongst the different member of the motif family, (3) motif name or description and (4) most common function; location information is included if the motif is relevant for location.

Polypeptides comprising one or more of the STEAP-1 motifs discussed above are useful in elucidating the specific characteristics of a malignant phenotype in view of the observation that the STEAP-1 motifs discussed above are associated with growth dysregulation and because STEAP-1 is overexpressed in certain cancers (See, e.g., Table I). Casein kinase II, cAMP and camp-dependent protein kinase, and Protein Kinase C, for example, are enzymes known to be associated with the development of the malignant phenotype (see e.g. Chen et al., Lab Invest., 78(2): 165-174 (1998); Gaiddon et al., Endocrinology 136(10): 4331-4338 (1995); Hall et al., Nucleic Acids Research 24(6): 1119-1126 (1996); Perterziel et al., Oncogene 18(46): 6322-6329 (1999) and O'Brian, Oncol. Rep. 5(2): 305-309 (1998)). Moreover, both glycosylation and myristoylation are protein modifications also associated with cancer and cancer progression (see e.g. Dennis et al., Biochem. Biophys. Acta 1473(1):21-34 (1999); Raju et al., Exp. Cell Res. 235(1): 145-154 (1997). Amidation is another protein modification also associated with cancer and cancer progression (see e.g. Treston et al., J. Natl. Cancer Inst. Monogr. (13): 169-175 (1992)).

In another embodiment, proteins of the invention comprise one or more of the immunoreactive epitopes identified in accordance with art-accepted methods, such as the peptides set forth in Tables V-XVIII and XXII-LI. CTL epitopes can be determined using specific algorithms to identify peptides within a STEAP-1 protein that are capable of optimally binding to specified HLA alleles (e.g., Table IV; Epimatrixm and Epimer™, Brown University, URL brown.edu/Research/TB-HIV_Lab/epimatrix/epimatrix.html; and BIMAS, URL bimas.dcrt.nih.gov/.) Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/supermofifs of Table IV). The epitope is analoged by substituting out an amino acid at one of the specified positions, and replacing it with another amino acid specified for that position. For example, on the basis of residues defined in Table IV, one can substitute out a deleterious residue in favor of any other residue, such as a preferred residue; substitute a less-preferred residue with a preferred residue; or substitute an originally-occurring preferred residue with another preferred residue. Substitutions can occur at primary anchor positions or at other positions in a peptide; see, e.g., Table IV.

A variety of references reflect the art regarding the identification and generation of epitopes in a protein of interest as well as analogs thereof. See, for example, WO 97/33602 to Chesnut et al.; Sette, Immunogenetics 1999 50(3-4): 201-212; Sette et al., J. Immunol. 2001 166(2): 1389-1397; Sidney et al., Hum. Immunol. 1997 58(1): 12-20; Kondo et al., Immunogenetics 1997 45(4): 249-258; Sidney et al., J. Immunol. 1996 157(8): 3480-90; and Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)); Kast et al, 1994 152(8): 3904-12; Borras-Cuesta et al., Hum. Immunol. 2000 61(3): 266-278; Alexander et al., J. Immunol. 2000 164(3); 164(3): 1625-1633; Alexander et al., PMID: 7895164, UI: 95202582; O'Sullivan et al., J. Immunol. 1991 147(8): 2663-2669; Alexander et al., Immunity 1994 1(9): 751-761 and Alexander et al., Immunol. Res. 1998 18(2): 79-92.

Related embodiments of the invention include polypeptides comprising combinations of the different motifs set forth in Table(s) IV(a), IV(b), IV(c), IV(d), and IV(h), and/or, one or more of the predicted CTL epitopes of Tables V-XVIII and XXII-LI, and/or, one or more of the predicted HTL epitopes of Tables XLVIII-LI, and/or, one or more of the T cell binding motifs known in the art. Preferred embodiments contain no insertions, deletions or substitutions either within the motifs or within the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically, the number of N-terminal and/or C-terminal amino acid residues on either side of a motif is between about 1 to about 100 amino acid residues, preferably 5 to about 5 to about 50 amino acid residues.

STEAP-1-related proteins are embodied in many forms, preferably in isolated form. A purified STEAP-1 protein molecule will be substantially free of other proteins or molecules that impair the binding of STEAP-1 to antibody, T cell or other ligand. The nature and degree of isolation and purification will depend on the intended use. Embodiments of a STEAP-1-related proteins include purified STEAP-1-related proteins and functional, soluble STEAP-1-related proteins. In one embodiment, a functional, soluble STEAP-1 protein or fragment thereof retains the ability to be bound by antibody, T cell or other ligand.

The invention also provides STEAP-1 proteins comprising biologically active fragments of a STEAP-1 amino acid sequence shown in FIG. 2 or FIG. 3. Such proteins exhibit properties of the starting STEAP-1 protein, such as the ability to elicit the generation of antibodies that specifically bind an epitope associated with the starting STEAP-1 protein; to be bound by such antibodies; to elicit the activation of HTL or CTL; and/or, to be recognized by HTL or CTL that also specifically bind to the starting protein.

STEAP-1-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or based on immunogenicity. Fragments that contain such structures are particularly useful in generating subunit-specific anti-STEAP-1 antibodies or T cells or in identifying cellular factors that bind to STEAP-1. For example, hydrophilicity profiles can be generated, and immunogenic peptide fragments identified, using the method of Hopp, T. P. and Woods, K. R., 1981, Proc. Natl. Acad. Sci. U.S.A. 78:3824-3828. Hydropathicity profiles can be generated, and immunogenic peptide fragments identified, using the method of Kyte, J. and Doolittle, R. F., 1982, J. Mol. Biol. 157:105-132. Percent (%) Accessible Residues profiles can be generated, and immunogenic peptide fragments identified, using the method of Janin J., 1979, Nature 277:491-492. Average Flexibility profiles can be generated, and immunogenic peptide fragments identified, using the method of Bhaskaran R., Ponnuswamy P. K., 1988, Int. J. Pept. Protein Res. 32:242-255. Beta-turn profiles can be generated, and immunogenic peptide fragments identified, using the method of Deleage, G., Roux B., 1987, Protein Engineering 1:289-294.

CTL epitopes can be determined using specific algorithms to identify peptides within a STEAP-1 protein that are capable of optimally binding to specified HLA alleles (e.g., by using the SYFPEITHI site at World Wide Web URL syfpeithi.bmi-heidelberg.com/; the listings in Table IV(A)-(E); Epimatrixm and Epimer™, Brown University, URL (brown.edu/Research/TB-HIV_Lab/epimatrix/epimatrix.html); and BIMAS, URL bimas.dcrt.nih.gov/). Illustrating this, peptide epitopes from STEAP-1 that are presented in the context of human MHC Class I molecules, e.g., HLA-A1, A2, A3, Al1, A24, B7 and B35 were predicted (see, e.g., Tables V-XVIII, XXII-LI). Specifically, the complete amino acid sequence of the STEAP-1 protein and relevant portions of other variants, i.e., for HLA Class I predictions 9 flanking residues on either side of a point mutation or exon juction, and for HLA Class II predictions 14 flanking residues on either side of a point mutation or exon junction corresponding to that variant, were entered into the HLA Peptide Motif Search algorithm found in the Bioinformatics and Molecular Analysis Section (BIMAS) web site listed above; in addition to the site SYFPEITHI, at URL syfpeithi.bmi-heidelberg.com/.

The HLA peptide motif search algorithm was developed by Dr. Ken Parker based on binding of specific peptide sequences in the groove of HLA Class I molecules, in particular HLA-A2 (see, e.g., Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for Class I HLA-A2, the epitopes preferably contain a leucine (L) or methionine (M) at position 2 and a valine (V) or leucine (L) at the C-terminus (see, e.g., Parker et al., J. Immunol. 149: 3580-7 (1992)). Selected results of STEAP-1 predicted binding peptides are shown in Tables V-XVIII and XXII-LI herein. In Tables V-XVIII and XXII-XLVIII, selected candidates, 9-mers and 10-mers, for each family member are shown along with their location, the amino acid sequence of each specific peptide, and an estimated binding score. In Tables XLVIII-LI, selected candidates, 15-mers, for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73-8(1997) and Peshwa et al., Prostate 36:129-38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV (or determined using World Wide Web site URL syfpeithi.bmi-heidelberg.com/, or BIMAS, bimas.dcrt.nih.govI) are to be "applied" to a STEAP-1 protein in accordance with the invention. As used in this context "applied" means that a STEAP-1 protein is evaluated, e.g., visually or by computer-based patterns finding methods, as appreciated by those of skill in the relevant art. Every subsequence of a STEAP-1 protein of 8, 9, 10, or 11 amino acid residues that bears an HLA Class I motif, or a subsequence of 9 or more amino acid residues that bear an HLA Class II motif are within the scope of the invention.

III.B.) Expression of STEAP-1-related Proteins

In an embodiment described in the examples that follow, STEAP-1 can be conveniently expressed in cells (such as 293T cells) transfected with a commercially available expression vector such as a CMV-driven expression vector encoding STEAP-1 with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted STEAP-1 protein in transfected cells. The secreted HIS-tagged STEAP-1 in the culture media can be purified, e.g., using a nickel column using standard techniques.

III.C.) Modifications of STEAP-1-related Proteins

Modifications of STEAP-1-related proteins such as covalent modifications are included within the scope of this invention. One type of covalent modification includes reacting targeted amino acid residues of a STEAP-1 polypeptide with an organic derivatizing agent that is capable of reacting with selected side chains or the N- or C-terminal residues of a STEAP-1 protein. Another type of covalent modification of a STEAP-1 polypeptide included within the scope of this invention comprises altering the native glycosylation pattern of a protein of the invention. Another type of covalent modification of STEAP-1 comprises linking a STEAP-1 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The STEAP-1-related proteins of the present invention can also be modified to form a chimeric molecule comprising STEAP-1 fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a STEAP-1 sequence (amino or nucleic acid) such that a molecule is created that is not, through its length, directly homologous to the amino or nucleic acid sequences shown in FIG. 2 or FIG. 3. Such a chimeric molecule can comprise multiples of the same subsequence of STEAP-1. A chimeric molecule can comprise a fusion of a STEAP-1-related protein with a polyhistidine epitope tag, which provides an epitope to which immobilized nickel can selectively bind, with cytokines or with growth factors. The epitope tag is generally placed at the amino- or carboxyl-terminus of a STEAP-1 protein. In an alternative embodiment, the chimeric molecule can comprise a fusion of a STEAP-1-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a STEAP-1 polypeptide in place of at least one variable region within an Ig molecule. In a preferred embodiment, the immunoglobulin fusion includes the hinge, CH2 and CH3, or the hinge, CH1, CH2 and CH3 regions of an IgGl molecule. For the production of immunoglobulin fusions see, e.g., U.S. Pat. No. 5,428, 130 issued Jun. 27, 1995.

III.D.) Uses of STEAP-1-related Proteins

The proteins of the invention have a number of different specific uses. As STEAP-1 is highly expressed in prostate and other cancers, STEAP-1-related proteins are used in methods that assess the status of STEAP-1 gene products in normal versus cancerous tissues, thereby elucidating the malignant phenotype. Typically, polypeptides from specific regions of a STEAP-1 protein are used to assess the presence of perturbations (such as deletions, insertions, point mutations etc.) in those regions (such as regions containing one or more motifs). Exemplary assays utilize antibodies or T cells targeting STEAP-1-related proteins comprising the amino acid residues of one or more of the biological motifs contained within a STEAP-1 polypeptide sequence in order to evaluate the characteristics of this region in normal versus cancerous tissues or to elicit an immune response to the epitope. Alternatively, STEAP-1-related proteins that contain the amino acid residues of one or more of the biological motifs in a STEAP-1 protein are used to screen for factors that interact with that region of STEAP-1.

STEAP-1 protein fragments/subsequences are particularly useful in generating and characterizing domain-specific antibodies (e.g., antibodies recognizing an extracellular or intracellular epitope of a STEAP-1 protein), for identifying agents or cellular factors that bind to STEAP-1 or a particular structural domain thereof, and in various therapeutic and diagnostic contexts, including but not limited to diagnostic assays, cancer vaccines and methods of preparing such vaccines.

Proteins encoded by the STEAP-1 genes, or by analogs, homologs or fragments thereof, have a variety of uses, including but not limited to generating antibodies and in methods for identifying ligands and other agents and cellular constituents that bind to a STEAP-1 gene product. Antibodies raised against a STEAP-1 protein or fragment thereof are useful in diagnostic and prognostic assays, and imaging methodologies in the management of human cancers characterized by expression of STEAP-1 protein, such as those listed in Table I. Such antibodies can be expressed intracellularly and used in methods of treating patients with such cancers. STEAP-1-related nucleic acids or proteins are also used in generating HTL or CTL responses.

Various immunological assays useful for the detection of STEAP-1 proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting STEAP-1-expressing cells (e.g., in radioscintigraphic imaging methods). STEAP-1 proteins are also particularly useful in generating cancer vaccines, as further described herein.

IV.) STEAP-1 Antibodies

Another aspect of the invention provides antibodies that bind to STEAP-1-related proteins. Preferred antibodies specifically bind to a STEAP-1-related protein and do not bind (or bind weakly) to peptides or proteins that are not STEAP-1-related proteins under physiological conditions. In this context, examples of physiological conditions include: 1) phosphate buffered saline; 2) Tris-buffered saline containing 25 mM Tris and 150 mM NaCl; or normal saline (0.9% NaCl); 4) animal serum such as human serum; or, 5) a combination of any of 1) through 4); these reactions preferably taking place at pH 7.5, alternatively in a range of pH 7.0 to 8.0, or alternatively in a range of pH 6.5 to 8.5; also, these reactions taking place at a temperature between 4° C. to 37° C. For example, antibodies that bind STEAP-1 can bind STEAP-1-related proteins such as the homologs or analogs thereof.

STEAP-1 antibodies of the invention are particularly useful in cancer (see, e.g., Table I) diagnostic and prognostic assays, and imaging methodologies. Similarly, such antibodies are useful in the treatment, diagnosis, and/or prognosis of prostate and other cancers, to the extent STEAP-1 is also expressed or overexpressed in these other cancers. Moreover, intracellularly expressed antibodies (e.g., single chain antibodies) are therapeutically useful in treating cancers in which the expression of STEAP-1 is involved, such as advanced or metastatic prostate cancers or other advanced or metastatic cancers.

The invention also provides various immunological assays useful for the detection and quantification of STEAP-1 and mutant STEAP-1-related proteins. Such assays can comprise one or more STEAP-1 antibodies capable of recognizing and binding a STEAP-1-related protein, as appropriate. These assays are performed within various immunological assay formats well known in the art, including but not limited to various types of radioimmunoassays, enzyme-linked immunosorbent assays (ELISA), enzymelinked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate cancer and other cancers expressing STEAP-1 are also provided by the invention, including but not limited to radioscintigraphic imaging methods using labeled STEAP-1 antibodies. Such assays are clinically useful in the detection, monitoring, and prognosis of STEAP-1 expressing cancers such as prostate cancer.

STEAP-1 antibodies are also used in methods for purifying a STEAP-1-related protein and for isolating STEAP-1 homologues and related molecules. For example, a method of purifying a STEAP-1-related protein comprises incubating a STEAP-1 antibody, which has been coupled to a solid matrix, with a lysate or other solution containing a STEAP-1-related protein under conditions that permit the STEAP-1 antibody to bind to the STEAP-1-related protein; washing the solid matrix to eliminate impurities; and eluting the STEAP-1-related protein from the coupled antibody. Other uses of STEAP-1 antibodies in accordance with the invention include generating anti-idiotypic antibodies that mimic a STEAP-1 protein.

Various methods for the preparation of antibodies are well known in the art. For example, antibodies can be prepared by immunizing a suitable mammalian host using a STEAP-1-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of STEAP-1 can also be used, such as a STEAP-1 GST-fusion protein. In a particular embodiment, a GST fusion protein comprising all or most of the amino acid sequence of FIG. 2 or FIG. 3 is produced, then used as an immunogen to generate appropriate antibodies. In another embodiment, a STEAP-1-related protein is synthesized and used as an immunogen.

In addition, naked DNA immunization techniques known in the art are used (with or without purified STEAP-1-related protein or STEAP-1 expressing cells) to generate an immune response to the encoded immunogen (for review, see Donnelly et al., 1997, Ann. Rev. Immunol. 15:617-648).

The amino acid sequence of a STEAP-1 protein as shown in FIG. 2 or FIG. 3 can be analyzed to select specific regions of the STEAP-1 protein for generating antibodies. For example, hydrophobicity and hydrophilicity analyses of a STEAP-1 amino acid sequence are used to identify hydrophilic regions in the STEAP-1 structure. Regions of a STEAP-1 protein that show immunogenic structure, as well as other regions and domains, can readily be identified using various other methods known in the art, such as Chou-Fasman, Gamier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Preferred methods for the generation of STEAP-1 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a STEAP-1 immunogen is often conducted by injection over a suitable time period and with use of a suitable adjuvant, as is understood in the art. During the immunization schedule, titiers of antibodies can be taken to determine adequacy of antibody formation.

STEAP-1 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a STEAP-1-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a STEAP-1 protein can also be produced in the context of chimeric or complementarity-determining region (CDR) grafted antibodies of multiple species origin. Humanized or human STEAP-1 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al, 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

Methods for producing fully human monoclonal antibodies include phage display and transgenic methods (for review, see Vaughan et al., 1998, Nature Biotechnology 16: 535-539). Fully human STEAP-1 monoclonal antibodies can be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries. Id., pp 65-82). Fully human STEAP-1 monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614; U.S. Pat. No. 6,162,963 issued 19 Dec. 2000; U.S. Pat. No. 6,150,584 issued 12 Nov. 2000; and, U.S. Pat. No. 6,114,598 issued 5 Sep. 2000). This method avoids the in vitro manipulation required with phage display technology and efficiently produces high affinity authentic human antibodies.

Reactivity of STEAP-1 antibodies with a STEAP-1-related protein can be established by a number of well known means, including Western blot, immunoprecipitation, ELISA, and FACS analyses using, as appropriate, STEAP-1-related proteins, STEAP-1-expressing cells or extracts thereof. A STEAP-1 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more STEAP-1 epitopes are generated using methods generally known in the art. Homodimeric antibodies can also be generated by cross-linking techniques known in the art (e.g., Wolff et al., Cancer Res. 53: 2560-2565).

In one embodiment, the invention provides for monoclonal antibodies identified as mouse hybridoma X92.1.30.1.1(1) and mouse hybridoma XI 20.545.1.1 deposited with the American Type Culture Collection, located at 10801 University Blvd. Manassas, Va. 20110-2209 on 06 Feb. 2004 and assigned ATCC Accession numbers PTA-5802 and PTA-5803 respectively.

V.) STEAP-1 Cellular Immune Responses

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al., *Cell* 47:1071, 1986; Babbitt, B. P. et al., Nature 317: 359, 1985; Townsend, A. and Bodmer, H., *Annu. Rev. Immunol.* 7:601, 1989; Germain, R. N., *Annu. Rev. Immuno.* 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., *J. Immunol.* 160: 3363, 1998; Rammensee, et al., *Immunogenetics* 41:178, 1995; Rammensee et al., SYFPEITHI, access via World Wide Web at URL (134.2.96.221/scripts.hlaserver.dll/home.htm); Sette, A. and Sidney, *J. Curr. Opin. Immunol.* 10:478, 1998; Engelhard, V. H., *Curr. Opin. Immunol.* 6:13, 1994; Sette, A. and Grey, H. M., *Curr. Opin. Immunol.* 4:79, 1992; Sinigaglia, F. and Hammer, *J. Curr. Biol.* 6:52,1994; Ruppert et al., *Cell* 74:929-937, 1993; Kondo et al., *J. Immunol.* 155: 4307-4312, 1995; Sidney et al., *J. Immunol.* 157:3480-3490, 1996; Sidney et al., *Human Immunol.* 45:79-93,1996; Sette, A. and Sidney, *J. Immunogenetics* 1999 November; 50(3-4): 201-12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. *Annu. Rev. Immunol.* 13:587, 1995; Smith, et al., *Immunity* 4:203, 1996; Fremont et al., *Immunity* 8:305, 1998; Stern et al., *Structure* 2:245, 1994; Jones, E. Y. *Curr. Opin. Immunol.* 9:75, 1997; Brown, J. H. et al., *Nature* 364:33, 1993; Guo, H. C. et al., *Proc. Natl. Acad. Sci. USA* 90:8053, 1993; Guo, H. C. et al., Nature 360:364, 1992; Silver, M. L. et al., *Nature* 360:367, 1992; Matsumura, M. et al., *Science* 257:927, 1992; Madden et al., *Cell* 70:1035, 1992; Fremont, D. H. et al., *Science* 257:919, 1992; Saper, M. A., Bjorkman, P. J. and Wiley, D. C., *J. Mol. Biol.* 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., *J. Immunol.* 26:97, 1996; Wentworth, P. A. et al., *Int. Immunol.* 8:651, 1996; Alexander, J. et al., *J. Immunol.* 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B. et al., *J. Exp. Med.* 181:1047, 1995; Doolan, D. L. et al., *Immunity* 7:97, 1997; Bertoni, R. et al., *J. Clin. Invest.* 100:503,1997; Threlkeld, S. C. et al., *J. Immunol.* 159:1648, 1997; Diepolder, H. M. et al., *J. Virol.* 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide-sensitized targets, T cell proliferation, or lymphokine release.

VI.) STEAP-1 Transgenic Animals

Nucleic acids that encode a STEAP-1-related protein can also be used to generate either transgenic animals or "knock out" animals that, in turn, are useful in the development and screening of therapeutically useful reagents. In accordance with established techniques, cDNA encoding STEAP-1 can be used to clone genomic DNA that encodes STEAP-1. The cloned genomic sequences can then be used to generate transgenic animals containing cells that express DNA that encode STEAP-1. Methods for generating transgenic animals, particularly animals such as mice or rats, have become conventional in the art and are described, for example, in U.S. Pat. No. 4,736,866 issued 12 Apr. 1988, and U.S. Pat. No. 4,870, 009 issued 26 Sep. 1989. Typically, particular cells would be targeted for STEAP-1 transgene incorporation with tissue-specific enhancers.

Transgenic animals that include a copy of a transgene encoding STEAP-1 can be used to examine the effect of increased expression of DNA that encodes STEAP-1. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of STEAP-1 can be used to construct a STEAP-1 "knock out" animal that has a defective or altered gene encoding STEAP-1 as a result of homologous recombination between the endogenous gene encoding STEAP-1 and altered genomic DNA encoding STEAP-1 introduced into an embryonic cell of the animal. For example, cDNA that encodes STEAP-1 can be used to clone genomic DNA encoding STEAP-1 in accordance with established techniques. A portion of the genomic DNA encoding STEAP-1 can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, *Cell*, 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell*, 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a STEAP-1 polypeptide.

VII.) Methods for the Detection of STEAP-1

Another aspect of the present invention relates to methods for detecting STEAP-1 polynucleotides and STEAP-1-related proteins, as well as methods for identifying a cell that expresses STEAP-1. The expression profile of STEAP-1 makes it a diagnostic marker for metastasized disease. Accordingly, the status of STEAP-1 gene products provides information useful for predicting a variety of factors including susceptibility to advanced stage disease, rate of progression, and/or tumor aggressiveness. As discussed in detail herein, the status of STEAP-1 gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of STEAP-1 polynucleotides in a biological sample, such as serum, bone, prostate, and other tissues, urine, semen, cell preparations, and the like. Detectable STEAP-1 polynucleotides include, for example, a STEAP-1 gene or fragment thereof, STEAP-1 mRNA, alternative splice variant STEAP-1 mRNAs, and recombinant DNA or RNA molecules that contain a STEAP-1 polynucleotide. A number of methods for amplifying and/or detecting the presence of STEAP-1 polynucleotides are well known in the art and can be employed in the practice of this aspect of the invention.

In one embodiment, a method for detecting a STEAP-1 mRNA in a biological sample comprises producing cDNA from the sample by reverse transcription using at least one primer; amplifying the cDNA so produced using a STEAP-1 polynucleotides as sense and antisense primers to amplify STEAP-1 cDNAs therein; and detecting the presence of the amplified STEAP-1 cDNA. Optionally, the sequence of the amplified STEAP-1 cDNA can be determined.

In another embodiment, a method of detecting a STEAP-1 gene in a biological sample comprises first isolating genomic DNA from the sample; amplifying the isolated genomic DNA using STEAP-1 polynucleotides as sense and antisense primers; and detecting the presence of the amplified STEAP-1 gene. Any number of appropriate sense and antisense probe combinations can be designed from a STEAP-1 nucleotide sequence (see, e.g., FIG. 2) and used for this purpose.

The invention also provides assays for detecting the presence of a STEAP-1 protein in a issue or other biological sample such as serum, semen, bone, prostate, urine, cell preparations, and the like. Methods for detecting a STEAP-1-related protein are also well known and include, for example, immunoprecipitation, immunohistochemical analysis, Western blot analysis, molecular binding assays, ELISA, ELIFA and the like. For example, a method of detecting the presence of a STEAP-1-related protein in a biological sample comprises first contacting the sample with a STEAP-1 antibody, a STEAP-1-reactive fragment thereof, or a recombinant protein containing an antigen-binding region of a STEAP-1 antibody; and then detecting the binding of STEAP-1-related protein in the sample.

Methods for identifying a cell that expresses STEAP-1 are also within the scope of the invention. In one embodiment, an assay for identifying a cell that expresses a STEAP-1 gene comprises detecting the presence of STEAP-1 mRNA in the cell. Methods for the detection of particular mRNAs in cells are well known and include, for example, hybridization assays using complementary DNA probes (such as in situ hybridization using labeled STEAP-1 riboprobes, Northern blot and related techniques) and various nucleic acid amplification assays (such as RT-PCR using complementary primers specific for STEAP-1, and other amplification type detection methods, such as, for example, branched DNA, SISBA, TMA and the like). Alternatively, an assay for identifying a cell that expresses a STEAP-1 gene comprises detecting the presence of STEAP-1-related protein in the cell or secreted by the cell. Various methods for the detection of proteins are well known in the art and are employed for the detection of STEAP-1-related proteins and cells that express STEAP-1-related proteins.

STEAP-1 expression analysis is also useful as a tool for identifying and evaluating agents that modulate STEAP-1 gene expression. For example, STEAP-1 expression is significantly upregulated in prostate cancer, and is expressed in cancers of the tissues listed in Table I. Identification of a molecule or biological agent that inhibits STEAP-1 expression or over-expression in cancer cells is of therapeutic value. For example, such an agent can be identified by using a screen that quantifies STEAP-1 expression by RT-PCR, nucleic acid hybridization or antibody binding.

VII.) Methods for Monitoring the Status of STEAP-1-related Genes and Their Products Oncogenesis is known to be a multistep process where cellular growth becomes progressively dysregulated and cells progress from a normal physiological state to precancerous and then cancerous states (see, e.g., Alers et al., Lab Invest. 77(5): 437-438 (1997) and Isaacs et al., Cancer Surv. 23: 19-32 (1995)). In this context, examining a biological sample for evidence of dysregulated cell growth (such as aberrant STEAP-1 expression in cancers) allows for early detection of such aberrant physiology, before a pathologic state such as cancer has progressed to a stage that therapeutic options are more limited and or the prognosis is worse. In such examinations, the status of STEAP-1 in a biological sample of interest can be compared, for example, to the status of STEAP-1 in a corresponding normal sample (e.g. a sample from that individual or alternatively another individual that is not affected by a pathology). An alteration in the status of STEAP-1 in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9; 376(2): 306-14 and U.S. Pat. No. 5,837,501) to compare STEAP-1 status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of STEAP-1 expressing cells) as well as the level, and biological activity of expressed gene products (such as STEAP-1 mRNA, polynucleotides and polypeptides). Typically, an alteration in the status of STEAP-1 comprises a change in the location of STEAP-1 and/or STEAP-1 expressing cells and/or an increase in STEAP-1 mRNA and/or protein expression.

STEAP-1 status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of a STEAP-1 gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of STEAP-1 in a biological sample is evaluated by various methods utilized by skilled artisans including, but not limited to genomic Southern analysis (to examine, for example perturbations in a STEAP-1 gene), Northern analysis and/or PCR analysis of STEAP-1 mRNA (to examine, for example alterations in the polynucleotide sequences or expression levels of STEAP-1 mRNAs), and, Western and/or immunohistochemical analysis (to examine, for example alterations in polypeptide sequences, alterations in polypeptide localization within a sample, alterations in expression levels of STEAP-1 proteins and/or associations of STEAP-1 proteins with polypeptide binding partners). Detectable STEAP-1 polynucleotides include, for example, a STEAP-1 gene or fragment thereof, STEAP-1 mRNA, alternative splice variants, STEAP-1 mRNAs, and recombinant DNA or RNA molecules containing a STEAP-1 polynucleotide.

The expression profile of STEAP-1 makes it a diagnostic marker for local and/or metastasized disease, and provides information on the growth or oncogenic potential of a biological sample. In particular, the status of STEAP-1 provides information useful for predicting susceptibility to particular disease stages, progression, and/or tumor aggressiveness. The invention provides methods and assays for determining STEAP-1 status and diagnosing cancers that express STEAP-1, such as cancers of the tissues listed in Table I. For example, because STEAP-1 mRNA is so highly expressed in prostate and other cancers relative to normal prostate tissue, assays that evaluate the levels of STEAP-1 mRNA transcripts or proteins in a biological sample can be used to diagnose a disease associated with STEAP-1 dysregulation, and can provide prognostic information useful in defining appropriate therapeutic options.

The expression status of STEAP-1 provides information including the presence, stage and location of dysplastic, pre-cancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of STEAP-1 in biological samples such as those from individuals suffering from, or suspected of suffering from a pathology characterized by dysregulated cellular growth, such as cancer.

As described above, the status of STEAP-1 in a biological sample can be examined by a number of well-known procedures in the art. For example, the status of STEAP-1 in a biological sample taken from a specific location in the body can be examined by evaluating the sample for the presence or absence of STEAP-1 expressing cells (e.g. those that express STEAP-1 mRNAs or proteins). This examination can provide evidence of dysregulated cellular growth, for example, when STEAP-1-expressing cells are found in a biological sample that does not normally contain such cells (such as a lymph node), because such alterations in the status of STEAP-1 in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000);Su et al., Semin. Surg. Oncol. 18(1): 17-28 (2000) and Freeman et al., J Urol 1995 August 154(2 Pt 1):474-8).

In one aspect, the invention provides methods for monitoring STEAP-1 gene products by determining the status of STEAP-1 gene products expressed by cells from an individual suspected of having a disease associated with dysregulated cell growth (such as hyperplasia or cancer) and then comparing the status so determined to the status of STEAP-1 gene products in a corresponding normal sample. The presence of aberrant STEAP-1 gene products in the test sample relative to the normal sample provides an indication of the presence of dysregulated cell growth within the cells of the individual.

In another aspect, the invention provides assays useful in determining the presence of cancer in an individual, comprising detecting a significant increase in STEAP-1 mRNA or protein expression in a test cell or tissue sample relative to expression levels in the corresponding normal cell or tissue. The presence of STEAP-1 mRNA can, for example, be evaluated in tissues including but not limited to those listed in Table I. The presence of significant STEAP-1 expression in any of these tissues is useful to indicate the emergence, presence and/or severity of a cancer, since the corresponding normal tissues do not express STEAP-1 mRNA or express it at lower levels.

In a related embodiment, STEAP-1 status is determined at the protein level rather than at the nucleic acid level. For example, such a method comprises determining the level of STEAP-1 protein expressed by cells in a test tissue sample and comparing the level so determined to the level of STEAP-1 expressed in a corresponding normal sample. In one embodiment, the presence of STEAP-1 protein is evaluated, for example, using immunohistochemical methods. STEAP-1 antibodies or binding partners capable of detecting STEAP-1 protein expression are used in a variety of assay formats well known in the art for this purpose.

In a further embodiment, one can evaluate the status of STEAP-1 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of STEAP-1 may be indicative of the presence or promotion of a tumor. Such assays therefore have diagnostic and predictive value where a mutation in STEAP-1 indicates a potential loss of function or increase in tumor growth.

A wide variety of assays for observing perturbations in nucleotide and amino acid sequences are well known in the art. For example, the size and structure of nucleic acid or amino acid sequences of STEAP-1 gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. No. 5,382,510 issued 7 Sep. 1999, and U.S. Pat. No. 5,952, 170 issued 17 Jan. 1995).

Additionally, one can examine the methylation status of a STEAP-1 gene in a biological sample. Aberrant demethylation and/or hypennethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al., Cancer Epidemiol. Biomarkers Prev., 1998, 7:531-536). In another example, expression of the LAGE-1 tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). A variety of assays for examining methylation status of a gene are well known in the art. For example, one can utilize, in Southern hybridization approaches, methylation-sensitive restriction enzymes that cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995.

Gene amplification is an additional method for assessing the status of STEAP-1. Gene amplification is measured in a sample directly, for example, by conventional Southern blotting or Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect STEAP-1 expression. The presence of RT-PCR amplifiable STEAP-1 mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373-384; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting STEAP-1 mRNA or STEAP-1 protein in a tissue sample, its presence indicating susceptibility to cancer, wherein the degree of STEAP-1 mRNA expression correlates to the degree of susceptibility. In a specific embodiment, the presence of STEAP-1 in prostate or other tissue is examined, with the presence of STEAP-1 in the sample providing an indication of prostate cancer susceptibility (or the emergence or existence of a prostate tumor). Similarly, one can evaluate the integrity STEAP-1 nucleotide and amino acid sequences in a biological sample, in order to identify perturbations in the structure of these molecules such as insertions, deletions, substitutions and the like. The presence of one or more perturbations in STEAP-1 gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of STEAP-1 mRNA or STEAP-1 protein expressed by tumor cells, comparing the level so determined to the level of STEAP-1 mRNA or STEAP-1 protein expressed in a corresponding normal tissue taken from the same individual or a normal tissue reference sample, wherein the degree of STEAP-1 mRNA or STEAP-1 protein expression in the tumor sample relative to the normal sample indicates the degree of aggressiveness. In a specific embodiment, aggressiveness of a tumor is evaluated by determining the extent to which STEAP-1 is expressed in the tumor cells, with higher expression levels indicating more aggressive tumors. Another embodiment is the evaluation of the integrity of STEAP-1 nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of STEAP-1 mRNA or STEAP-1 protein expressed by cells in a sample of the tumor, comparing the level so determined to the level of STEAP-1 mRNA or STEAP-1 protein expressed in an equivalent tissue sample taken from the same individual at a different time, wherein the degree of STEAP-1 mRNA or STEAP-1 protein expression in the tumor sample over time provides information on the progression of the cancer. In a specific embodiment, the progression of a cancer is evaluated by determining STEAP-1 expression in the tumor cells over time, where increased expression over time indicates a progression of the cancer. Also, one can evaluate the integrity STEAP-1 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of STEAP-1 gene and STEAP-1 gene products (or perturbations in STEAP-1 gene and STEAP-1 gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, Anal. Quant. Cytol. 6(2):74-88; Epstein, 1995, Hum. Pathol. 26(2):223-9; Thorson et al., 1998, Mod. Pathol. 11(6):543-51; Baisden et al., 1999, Am. J. Surg. Pathol. 23(8):918-24). Methods for observing a coincidence between the expression of STEAP-1 gene and STEAP-1 gene products (or perturbations in STEAP-1 gene and STEAP-1 gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of STEAP-1 gene and STEAP-1 gene products (or perturbations in STEAP-1 gene and STEAP-1 gene products) and another factor associated with malignancy entails detecting the overexpression of STEAP-1 mRNA or protein in a tissue sample, detecting the overexpression of PSA mRNA or protein in a tissue sample (or PSCA or PSM expression), and observing a coincidence of STEAP-1 mRNA or protein and PSA mRNA or protein overexpression (or PSCA or PSM expression). In a specific embodiment, the expression of STEAP-1 and PSA mRNA in prostate tissue is examined, where the coincidence of STEAP-1 and PSA mRNA overexpression in the sample indicates the existence of prostate cancer, prostate cancer susceptibility or the emergence or status of a prostate tumor.

Methods for detecting and quantifying the expression of STEAP-1 mRNA or protein are described herein, and standard nucleic acid and protein detection and quantification technologies are well known in the art Standard methods for the detection and quantification of STEAP-1 mRNA include in situ hybridization using labeled STEAP-1 riboprobes, Northern blot and related techniques using STEAP-1 polynucleotide probes, RT-PCR analysis using primers specific for STEAP-1, and other amplification type detection methods, such as, for example, branched DNA, SISBA, TMA and the like. In a specific embodiment, semi-quantitative RT-PCR is used to detect and quantify STEAP-1 mRNA expression. Any number of primers capable of amplifying STEAP-1 can be used for this purpose, including but not limited to the various primer sets specifically described herein. In a specific embodiment, polyclonal or monoclonal antibodies specifically reactive with the wild-type STEAP-1 protein can be used in an immunohistochemical assay of biopsied tissue.

IX.) Identification of Molecules That Interact With STEAP-1

The STEAP-1 protein and nucleic acid sequences disclosed herein allow a skilled artisan to identify proteins, small molecules and other agents that interact with STEAP-1, as well as pathways activated by STEAP-1 via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. No. 5,955,280 issued 21 Sep. 1999, U.S. Pat. No. 5,925,523 issued 20 Jul. 1999, U.S. Pat. No. 5,846,722 issued 8 Dec. 1998 and 6,004,746 issued 21 Dec. 1999. Algorithms are also available in the art for genome-based predictions of protein function (see, e.g., Marcotte, et al., Nature 402: 4 Nov. 1999, 83-86).

Alternatively one can screen peptide libraries to identify molecules that interact with STEAP-1 protein sequences. In such methods, peptides that bind to STEAP-1 are identified by screening libraries that encode a random or controlled collection of amino acids. Peptides encoded by the libraries are expressed as fusion proteins of bacteriophage coat proteins, the bacteriophage particles are then screened against the STEAP-1 protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with STEAP-1 protein sequences are disclosed for example in U.S. Pat. Nos. 5,723,286 issued 3 March 1998 and 5,733,731 issued 31 Mar. 1998.

Alternatively, cell lines that express STEAP-1 are used to identify protein-protein interactions mediated by STEAP-1. Such interactions can be examined using immunoprecipitation techniques (see, e.g., Hamilton B. J., et al. Biochem. Biophys. Res. Commun. 1999, 261:646-51). STEAP-1 protein can be immunoprecipitated from STEAP-1-expressing cell lines using anti-STEAP-1 antibodies. Alternatively, antibodies against His-tag can be used in a cell line engineered to express fusions of STEAP-1 and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with STEAP-1 can be identified through related embodiments of such screening assays. For example, small molecules can be identified that interfere with protein function, including molecules that interfere with STEAP-1's ability to mediate phosphorylation and de-phosphorylation, interaction with DNA or RNA molecules as an indication of regulation of cell cycles, second messenger signaling or tumorigenesis. Similarly, small molecules that modulate STEAP-1-related ion channel, protein pump, or cell communication functions are identified and used to treat patients that have a cancer that expresses STEAP-1 (see, e.g., Hille, B., Ionic Channels of Excitable Membranes 2$^{nd}$ Ed., Sinauer Assoc., Sunderland, Mass., 1992). Moreover, ligands that regulate STEAP-1 function can be identified based on their ability to bind STEAP-1 and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of STEAP-1 and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators, which activate or inhibit STEAP-1.

An embodiment of this invention comprises a method of screening for a molecule that interacts with a STEAP-1 amino acid sequence shown in FIG. 2 or FIG. 3, comprising the steps of contacting a population of molecules with a STEAP-1 amino acid sequence, allowing the population of molecules and the STEAP-1 amino acid sequence to interact under conditions that facilitate an interaction, determining the presence of a molecule that interacts with the STEAP-1 amino acid sequence, and then separating molecules that do not interact with the STEAP-1 amino acid sequence from molecules that do. In a specific embodiment, the method further comprises purifying, characterizing and identifying a molecule that interacts with the STEAP-1 amino acid sequence. The identified molecule can be used to modulate a function performed by STEAP-1. In a preferred embodiment, the STEAP-1 amino acid sequence is contacted with a library of peptides.

X.) Therapeutic Methods and Compositions

The identification of STEAP-1 as a protein that is normally expressed in a restricted set of tissues, but which is also expressed in cancers such as those listed in Table I, opens a number of therapeutic approaches to the treatment of such cancers.

Of note, targeted antitumor therapies have been useful even when the targeted protein is expressed on normal tissues, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

For example, Herceptin® is an FDA approved pharmaceutical that consists of an antibody which is immunoreactive with the protein variously known as HER2, HER2/neu, and erb-b-2. It is marketed by Genentech and has been a commercially successful antitumor agent. Herceptin® sales reached almost $400 million in 2002. Herceptin® is a treatment for HER2 positive metastatic breast cancer. However, the expression of HER2 is not limited to such tumors. The same protein is expressed in a number of normal tissues. In particular, it is known that HER2/neu is present in normal kidney and heart, thus these tissues are present in all human recipients of Herceptin. The presence of HER2/neu in normal kidney is also confirmed by Latif, Z., et al., *B.J.U. International* (2002) 89:5-9. As shown in this article (which evaluated whether renal cell carcinoma should be a preferred indication for anti-HER2 antibodies such as Herceptin) both protein and mRNA are produced in benign renal tissues. Notably, HER2/neu protein was strongly overexpressed in benign renal tissue. Despite the fact that HER2/neu is expressed in such vital tissues as heart and kidney, Herceptin is a very useful, FDA approved, and commercially successful drug. The effect of Herceptin on cardiac tissue, i.e., "cardiotoxicity," has merely been a side effect to treatment. When patients were treated with Herceptin alone, significant cardiotoxicity occurred in a very low percentage of patients. To minimize cariotoxicity there is a more stringent entry requirement for the treatment with HER2/neu. Factors such as predisposition to heart condition are evaluated before treatment can occur.

Of particular note, although kidney tissue is indicated to exhibit normal expression, possibly even higher expression than cardiac tissue, kidney has no appreciable Herceptin side effect whatsoever. Moreover, of the diverse array of normal tissues in which HER2 is expressed, there is very little occurrence of any side effect. Only cardiac tissue has manifested any appreciable side effect at all. A tissue such as kidney, where HER2/neu expression is especially notable, has not been the basis for any side effect.

Furthermore, favorable therapeutic effects have been found for antitumor therapies that target epidermal growth factor receptor (EGFR); Erbitux (ImClone). EGFR is also expressed in numerous normal tissues. There have been very limited side effects in normal tissues following use of anti-EGFR therapeutics. A general side effect that occurs with the EGFR treatment is a severe skin rash observed in 100% of the patients undergoing treatment.

Thus, expression of a target protein in normal tissue, even vital normal tissue, does not defeat the utility of a targeting agent for the protein as a therapeutic for certain tumors in which the protein is also overexpressed. For example, expression in vital organs is not in and of itself detrimental. In addition, organs regarded as dispensible, such as the prostate and ovary, can be removed without affecting mortality. Finally, some vital organs are not affected by normal organ expression because of an immunoprivilage. Immunoprivilaged organs are organs that are protected from blood by a blood-organ barrier and thus are not accessible to immunotherapy. Examples of immunoprivilaged organs are the brain and testis.

Accordingly, therapeutic approaches that inhibit the activity of a STEAP-1 protein are useful for patients suffering from a cancer that expresses STEAP-1. These therapeutic approaches generally fall into three classes. The first class modulates STEAP-1 function as it relates to tumor cell growth leading to inhibition or retardation of tumor cell growth or inducing its killing. The second class comprises various methods for inhibiting the binding or association of a STEAP-1 protein with its binding partner or with other proteins. The third class comprises a variety of methods for inhibiting the transcription of a STEAP-1 gene or translation of STEAP-1 mRNA.

X.A.) Anti-Cancer Vaccines

The invention provides cancer vaccines comprising a STEAP-1-related protein or STEAP-1-related nucleic acid. In view of the expression of STEAP-1, cancer vaccines prevent and/or treat STEAP-1-expressing cancers with minimal or no effects on non-target tissues. The use of a tumor antigen in a vaccine that generates cell-mediated humoral immune responses as anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159:3113-3117).

Such methods can be readily practiced by employing a STEAP-1-related protein, or a STEAP-1-encoding nucleic acid molecule and recombinant vectors capable of expressing and presenting the STEAP-1 immunogen (which typically comprises a number of T-cell epitopes or antibody). Skilled artisans understand that a wide variety of vaccine systems for delivery of immunoreactive epitopes are known in the art (see, e.g., Heryln et al., Ann Med 1999 February 31(1):66-78; Maruyama et al., Cancer Immunol Immunother 2000 June 49(3):123-32) Briefly, such methods of generating an immune response (e.g. cell-mediated and/or humoral) in a mammal, comprise the steps of: exposing the mammal's immune system to an immunoreactive epitope (e.g. an epitope present in a STEAP-1 protein shown in FIG. 3 or analog or homolog thereof) so that the mammal generates an immune response that is specific for that epitope (e.g. generates antibodies that specifically recognize that epitope). In a preferred method, a STEAP-1 immunogen contains a biological motif, see e.g., Tables V-XVIII and XXII-LI, or a peptide of a size range from STEAP-1 indicated in FIG. 5, FIG. 6, FIG. 7, FIG. 8, and FIG. 9.

The entire STEAP-1 protein, immunogenic regions or epitopes thereof can be combined and delivered by various means. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287-294,1991: Alonso et al., *Vaccine* 12:299-306, 1994; Jones et al., *Vaccine* 13:675-681, 1995), peptide compositions contained in immune stimulating complexes (ISCOMS) (see, e.g., Takahashi et al., *Nature* 344:873-875, 1990; Hu et al., *Clin Exp Immunol.* 113:235-243,1998), multiple antigen peptide systems (MAPs) (see e.g., Tam, J. P., *Proc. Natl. Acad. Sci. U.S.A.* 85:5409-5413, 1988; Tam, J. P., *J. Immunol. Methods* 196:17-32, 1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537,1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods*. 192:25, 1996; Eldridge, J. H. et al., *Sem. Hematol.* 30:16, 1993; Falo, L. D., Jr. et al., *Nature Med.* 7:649,1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148: 1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

In patients with STEAP-1-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within STEAP-1 protein that bind corresponding HLA alleles (see e.g., Table IV; Epimer™ and Epimatrix™, Brown University (URL brown.edu/Research/TB-HIV_Lab/epimatrix/epimatrix.html); and, BIMAS, (URL bimas.dcrt.nih.gov/; SYFPEITHI at URL syfpeithi.bmi-heidelberg.com/). In a preferred embodiment, a STEAP-1 immunogen contains one or more amino acid sequences identified using techniques well known in the art, such as the sequences shown in Tables V-XVIII and XXII-LI or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. a STEAP-1 protein) so that an immune response is generated. A typical embodiment consists of a method for generating an immune response to STEAP-1 in a host, by contacting the host with a sufficient amount of at least one STEAP-1 B cell or cytotoxic T-cell epitope or analog thereof; and at least one periodic interval thereafter re-contacting the host with the STEAP-1 B cell or cytotoxic T-cell epitope or analog thereof. A specific embodiment consists of a method of generating an immune response against a STEAP-1-related protein or a man-made multiepitopic peptide comprising: administering STEAP-1 immunogen (e.g. a STEAP-1 protein or a peptide fragment thereof, a STEAP-1 fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3); 164(3): 1625-1633; Alexander et al., Immunity 1994 1(9): 751-761 and Alexander et al., Immunol. Res. 1998 18(2): 79-92). An alternative method comprises generating an immune response in an individual against a STEAP-1 immunogen by: administering in vivo to muscle or skin of the individual's body a DNA molecule that comprises a DNA sequence that encodes a STEAP-1 immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antiidiotypic antibody can be administered that mimics STEAP-1, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing STEAP-1. Constructs comprising DNA encoding a STEAP-1-related protein/immunogen and appropriate regulatory sequences can be injected directly into muscle or skin of an individual, such that the cells of the muscle or skin take-up the construct and express the encoded STEAP-1 protein/immunogen. Alternatively, a vaccine comprises a STEAP-1-related protein. Expression of the STEAP-1-related protein immunogen results in the generation of prophylactic or therapeutic humoral and cellular immunity against cells that bear a STEAP-1 protein. Various prophylactic and therapeutic genetic immunization techniques known in the art can be used (for review, see information and references published at Internet address genweb.com). Nucleic acid-based delivery is described, for instance, in Wolff et. al., Science 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol. 8:658-663; Tsang et al. J. Natl. Cancer Inst. 87:982-990 (1995)). Non-viral delivery systems can also be employed by introducing naked DNA encoding a STEAP-1-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 351:456-460 (1991). A wide variety of other vectors useful for therapeutic administration or immunization of the peptides of the invention, e.g. adeno and adeno-associated virus vectors, retroviral vectors, Salmonella typhi vectors, detoxified anthrax toxin vectors, and the like, will be apparent to those skilled in the art from the description herein.

Thus, gene delivery systems are used to deliver a STEAP-1-related nucleic acid molecule. In one embodiment, the full-length human STEAP-1 cDNA is employed. In another embodiment, STEAP-1 nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present STEAP-1 antigen to a patent's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Thus, dendritic cells can be used to present STEAP-1 peptides to T cells in the context of MHC class I or II molecules. In one embodiment, autologous dendritic cells are pulsed with STEAP-1 peptides capable of binding to MHC class I and/or class II molecules. In another embodiment, dendritic cells are pulsed with the complete STEAP-1 protein. Yet another embodiment involves engineering the overexpression of a STEAP-1 gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), or tumor-derived RNA transfection (Ashley et al., 1997, J. Exp. Med 186:1177-1182). Cells that express STEAP-1 can also be engineered to express immune modulators, such as GM-CSF, and used as immunizing agents.

X.B.) STEAP-1 as a Target for Antibody-based Therapy

STEAP-1 is an attractive target for antibody-based therapeutic strategies. A number of antibody strategies are known in the art for targeting both extracellular and intracellular molecules (see, e.g., complement and ADCC mediated killing as well as the use of intrabodies). Because STEAP-1 is expressed by cancer cells of various lineages relative to corresponding normal cells, systemic administration of STEAP-1-immunoreactive compositions are prepared that exhibit excellent sensitivity without toxic, non-specific and/or non-target effects caused by binding of the immunoreactive composition to non-target organs and tissues. Antibodies specifically reactive with domains of STEAP-1 are useful to treat STEAP-1-expressing cancers systemically, either as conjugates with a toxin or therapeutic agent, or as naked antibodies capable of inhibiting cell proliferation or function.

STEAP-1 antibodies can be introduced into a patient such that the antibody binds to STEAP-1 and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of STEAP-1, inhibition of ligand binding or signal transduction pathways, modulation of tumor cell differentiation, alteration of tumor angiogenesis factor profiles, and/or apoptosis. Examples include Rituxan® for Non-Hodgkins Lymphoma, Herceptin® for metastatic breast cancer, and Erbitux® for colorectal cancer.

Those skilled in the art understand that antibodies can be used to specifically target and bind immunogenic molecules such as an immunogenic region of a STEAP-1 sequence shown in FIG. 2 or FIG. 3. In addition, skilled artisans understand that it is routine to conjugate antibodies to cytotoxic agents (see, e.g., Slevers et al. Blood 93:11 3678-3684 (Jun. 1, 1999)). When cytotoxic and/or therapeutic agents are delivered directly to cells, such as by conjugating them to antibodies specific for a molecule expressed by that cell (e.g. STEAP-1), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-STEAP-1 antibody) that binds to a marker (e.g. STEAP-1) expressed, accessible to binding or localized on the cell surfaces. A typical embodiment is a method of delivering a cytotoxic and/or therapeutic agent to a cell expressing STEAP-1, comprising conjugating the cytotoxic agent to an antibody that immunospecifically binds to a STEAP-1 epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-STEAP-1 antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin or radioisotope, such as the conjugation of $Y^{91}$ or $I^{131}$ to anti-CD20 antibodies (e.g., Zevalin ™, IDEC Pharmaceuticals Corp. or Bexxar™, Coulter Pharmaceuticals) respectively, while others involve co-administration of antibodies and other therapeutic agents, such as Herceptin™ (trastuzuMAb) with paclitaxel (Genentech, Inc.). The antibodies can be conjugated to a therapeutic agent. To treat prostate cancer, for example, STEAP-1 antibodies can be administered in conjunction with radiation, chemotherapy or hormone ablation. Also, antibodies can be conjugated to a toxin such as calicheamicin (e.g., Mylotarg™, Wyeth-Ayerst, Madison, N.J., a recombinant humanized $IgG_4$ kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064) or Auristatin E (Seattle Genetics).

Although STEAP-1 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

Although STEAP-1 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of STEAP-1 expression, preferably using immunohistochemical assessments of tumor tissue, quantitative STEAP-1 imaging, or other techniques that reliably indicate the presence and degree of STEAP-1 expression. Immunohistochemical analysis of tumor biopsies or surgical specimens is preferred for this purpose. Methods for immunohistochemical analysis of tumor tissues are well known in the art.

Anti-STEAP-1 monoclonal antibodies that treat prostate and other cancers include those that initiate a potent immune response against the tumor or those that are directly cytotoxic. In this regard, anti-STEAP-1 monoclonal antibodies (MAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-STEAP-1 MAbs that exert a direct biological effect on tumor growth are useful to treat cancers that express STEAP-1. Mechanisms by which directly cytotoxic MAbs act include: inhibition of cell growth, modulation of cellular differentiation, modulation of tumor angiogenesis factor profiles, and the induction of apoptosis. The mechanism(s) by which a particular anti-STEAP-1 MAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric MAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target STEAP-1 antigen with high affinity but exhibit low or no antigenicity in the patient.

Therapeutic methods of the invention contemplate the administration of single anti-STEAP-1 MAbs as well as combinations, or cocktails, of different MAbs. Such MAb cocktails can have certain advantages inasmuch as they contain MAbs that target different epitopes, exploit different effector mechanisms or combine directly cytotoxic MAbs with MAbs that rely on immune effector functionality. Such MAbs in combination can exhibit synergistic therapeutic effects. In addition, anti-STEAP-1 MAbs can be administered concomitantly with other therapeutic modalities, including but not limited to various chemotherapeutic agents, androgen-blockers, immune modulators (e.g., IL-2, GM-CSF), surgery or radiation. The anti-STEAP-1 MAbs are administered in their "naked" or unconjugated form, or can have a therapeutic agent(s) conjugated to them.

Anti-STEAP-1 antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-STEAP-1 antibody preparation, via an acceptable route of administration such as intravenous injection (IV), typically at a dose in the range of about 0.1, 0.2, 0.3, 0.4, 0.5, 0.6, 0.7, 0.8, 0.9., 1, 2, 3, 4, 5, 6, 7, 8, 9, 10, 15, 20, or 25 mg/kg body weight. In general, doses in the range of 10-1000 mg MAb per week are effective and well tolerated.

Based on clinical experience with the Herceptin™ MAb in the treatment of metastatic breast cancer, an initial loading dose of approximately 4 mg/kg patient body weight IV, followed by weekly doses of about 2 mg/kg IV of the anti-STEAP-1 MAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or MAbs used, the degree of STEAP-1 expression in the patient, the extent of circulating shed STEAP-1 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of STEAP-1 in a given sample (e.g. the levels of circulating STEAP-1 antigen and/or STEAP-1 expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-STEAP-1 antibodies can also be used in anti-cancer therapy as a vaccine for inducing an immune response to cells expressing a STEAP-1-related protein. In particular, the generation of anti-idiotypic antibodies is well known in the art; this methodology can readily be adapted to generate anti-idiotypic anti-STEAP-1 antibodies that mimic an epitope on a STEAP-1-related protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

X.C.) STEAP-1 as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$). Moreover, an adjuvant such as a synthetic cytosine-phosphorothiolated-guanine-containing (CpG) oligonucleotides has been found to increase CTL responses 10- to 100-fold. (see, e.g. Davila and Celis, J. Immunol. 165:539-547 (2000))

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress STEAP-1 antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 34 epitopes that come from at least one tumor associated antigen (TM). For HLA Class II a similar rationale is employed; again 3-4 epitopes are selected from at least one™ (see, e.g., Rosenberg et al., *Science* 278:1447-1450).

Epitopes from one ™ may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an IC50 of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.I. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., J. Immunol. 162:3915-3925, 1999; An, L. and Whitton, J. L., J. Virol. 71:2292, 1997; Thomson, S. A. et al., J. Immunol. 157:822, 1996; Whitton, J. L. et al., J. Virol. 67:348, 1993; Hanke, R. et al., Vaccine 16:426, 1998. For example, a multi-epitope DNA plasmid encoding supermotif- and/or motif-bearing epitopes derived STEAP-1, the PADRE® universal helper T cell epitope or multiple HTL epitopes from STEAP-1 (see e.g., Tables V-XVIII and XXII to LI), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an E. coli origin of replication; and an E. coli selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, *Bio Techniques* 6(7): 682 (1988); U.S. Pat. No. 5,279,833; WO 91/06309; and Felgner, et al., Proc. Nat'l Acad. Sci. USA 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class II molecules. Examples of such amino acid bind many HLA Class II molecules include sequences from antigens such as tetanus toxoid at positions 830-843 QYIKANSKFIGITE; (SEQ ID NO: 64), *Plasmodium falciparum* circumsporozoite (CS) protein at positions 378-398 DIEKKIAKMEKASS-VFNWNS; (SEQ ID NO: 65), and *Streptococcus* 18 kD protein at positions 116-131 GAVDSILGGVATYGAA; (SEQ ID NO: 66). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed, most preferably, to bind most HLA-DR (human HLA class II) molecules. For instance, a pan-DR-binding epitope peptide having the formula: XKXVAAWTLKAAX (SEQ ID NO: 67), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the $\epsilon$- and $\alpha$-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to $\epsilon$- and $\alpha$-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinyl-seryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to prime specifically an immune response to the target antigen. Moreover, because the induction of neutralizing antibodies can also be primed with $P_3CSS$-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to STEAP-1. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses STEAP-1.

X.D. Adoptive Immunotherapy

Antigenic STEAP-1-related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administration of Vaccines for Therapeutic or Prophylactic Purposes

Pharmaceutical and vaccine compositions of the invention are typically used to treat and/or prevent a cancer that expresses or overexpresses STEAP-1. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses STEAP-1. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of STEAP-1-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses STEAP-1, a vaccine comprising STEAP-1-specific CTL may be more efficacious in killing tumor cells in patient with advanced disease than alternative embodiments.

It is generally important to provide an amount of the peptide epitope delivered by a mode of administration sufficient to stimulate effectively a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 μg and the higher value is about 10,000; 20,000; 30,000; or 50,000 μg. Dosage values for human typically range from about 500 μg to about 50,000 μg per 70 kilogram patient. Boosting dosages of between about 1.0 μg to about 50,000 μg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 μg and the higher value is about 10,000; 20,000; 30,000; or 50,000 μg. Dosage values for a human typically range from about 500 μg to about 50,000 μg per 70 kilogram patient. This is followed by boosting dosages of between about 1.0 μg to about 50,000 μg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., Remington's Pharmaceutical Sciences, $17^{th}$ Edition, A. Gennaro, Editor, Mack Publishing Co., Easton, Pa., 1985). For example a peptide dose for initial immunization can be from about 1 to about 50,000 μg, generally 100-5,000 μg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 μg) can also be administered using a gene gun. Following an incubation period of 3-4 weeks, a booster dose is then administered. The booster can be recombinant fowlpox virus administered at a dose of $5-10^7$ to $5 \times 10^9$ pfu.

For antibodies, a treatment generally involves repeated administration of the anti-STEAP-1 antibody preparation, via an acceptable route of administration such as intravenous injection (IV), typically at a dose in the range of about 0.1 to about 10 mg/kg body weight. In general, doses in the range of 10-500 mg MAb per week are effective and well tolerated. Moreover, an initial loading dose of approximately 4 mg/kg patient body weight IV, followed by weekly doses of about 2 mg/kg IV of the anti-STEAP-1 MAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of STEAP-1 expression in the patient, the extent of circulating shed STEAP-1 antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 μg-1 mg, 1 mg-50 mg, 50 mg-100 mg, 100 mg-200 mg, 200 mg-300 mg, 400 mg-500 mg, 500 mg-600 mg, 600 mg-700 mg, 700 mg-800 mg, 800 mg-900 mg, 900 mg-1 g, or 1 mg-700 mg. In certain embodiments, the dose is in a range of 2-5 mg/kg body weight, e.g., with follow on weekly doses of 1-3 mg/kg; 0.5mg, 1, 2, 3, 4, 5, 6, 7, 8, 9, 10 mg/kg body weight followed e.g., in two, three or four weeks by weekly doses; 0.5-10 mg/kg body weight, e.g., followed in two, three or four weeks by weekly doses; 225, 250, 275, 300, 325, 350, 375, 400 mg $m^2$ of body area weekly; 1-600 mg $m^2$ of body area weekly; 225-400 mg $m^2$ of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $10^8$ to $5 \times 10^{10}$ cells. A dose may also about $10^6$ cells/m$^2$ to about $10^{10}$ cells/m$^2$, or about $10^6$ cells/m$^2$ to about $10^8$ cells/m$^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, immunogenic peptides are preferably supplied in finely divided form along with a surfactant and propellant. Typical percentages of peptides are about 0.01%-20% by weight, preferably about 1%-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

XI.) Diagnostic and Prognostic Embodiments of STEAP-1.

As disclosed herein, STEAP-1 polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in the Example entitled "Expression analysis of STEAP-1 in normal tissues, and patient specimens").

STEAP-1 can be analogized to a prostate associated antigen PSA, the archetypal marker that has been used by medical practitioners for years to identify and monitor the presence of prostate cancer (see, e.g., Merrill et al., J. Urol. 163(2): 503-5120 (2000); Polascik et al., J. Urol. August; 162(2):293-306 (1999) and Fortier et al., J. Nat. Cancer Inst. 91(91): 1635-1640(1999)). A variety of other diagnostic markers are also used in similar contexts including p53 and K-ras (see, e.g., Tulchinsky et al., Int J Mol Med 1999 Jul. 4(1):99-102 and Minimoto et al., Cancer Detect Prev 2000;24(1-12). Therefore, this disclosure of STEAP-1 polynucleotides and polypeptides (as well as STEAP-1 polynucleotide probes and anti-STEAP-1 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the STEAP-1 polynucleotides, polypeptides, reactive T cells and antibodies are analogous to those methods from well-established diagnostic assays, which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567-74(1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the STEAP-1 polynucleotides described herein can be utilized in the same way to detect STEAP-1 overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192(3):233-7 (1996)), the STEAP-1 polypepbdes described herein can be utilized to generate antibodies for use in detecting STEAP-1 overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing STEAP-1 polynucleotides and/or polypeptides can be used to provide evidence of metastasis. For example, when a biological sample from tissue that does not normally contain STEAP-1-expressing cells (lymph node) is found to contain STEAP-1-expressing cells such as the STEAP-1 expression seen in LAPC4 and LAPC9, xenografts isolated from lymph node and bone metastasis, respectively, this finding is indicative of metastasis.

Alternatively STEAP-1 polynucleotides and/or polypeptides can be used to provide evidence of cancer, for example, when cells in a biological sample that do not normally express STEAP-1 or express STEAP-1 at a different level are found to express STEAP-1 or have an increased expression of STEAP-1 (see, e.g., the STEAP-1 expression in the cancers listed in Table I and in patient samples etc. shown in the accompanying Figures). In such assays, artisans may further wish to generate supplementary evidence of metastasis by testing the biological sample for the presence of a second tissue restricted marker (in addition to STEAP-1) such as PSA, PSCA etc. (see, e.g., Alanen et al., Pathol. Res. Pract. 192(3): 233-237 (1996)).

The use of immunohistochemistry to identify the presence of a STEAP-1 polypeptide within a tissue section can indicate an altered state of certain cells within that tissue. It is well understood in the art that the ability of an antibody to localize to a polypeptide that is expressed in cancer cells is a way of diagnosing presence of disease, disease stage, progression and/or tumor aggressiveness. Such an antibody can also detect an altered distribution of the polypeptide within the cancer cells, as compared to corresponding non-malignant tissue.

The STEAP-1 polypeptide and immunogenic compositions are also useful in view of the phenomena of altered subcellular protein localization in disease states. Alteration of cells from normal to diseased state causes changes in cellular morphology and is often associated with changes in subcellular protein localization/distribution. For example, cell membrane proteins that are expressed in a polarized manner in normal cells can be altered in disease, resulting in distribution of the protein in a non-polar manner over the whole cell surface.

The phenomenon of altered subcellular protein localization in a disease state has been demonstrated with MUC1 and Her2 protein expression by use of immunohistochemical means. Normal epithelial cells have a typical apical distribution of MUC1, in addition to some supranuclear localization of the glycoprotein, whereas malignant lesions often demonstrate an apolar staining pattern (Diaz et al, The Breast Journal, 7; 40-45 (2001); Zhang et al, Clinical Cancer Research, 4; 2669-2676 (1998): Cao, et al, The Journal of Histochemistry and Cytochemistry, 45: 1547-1557 (1997)). In addition, normal breast epithelium is either negative for Her2 protein or exhibits only a basolateral distribution whereas malignant cells can express the protein over the whole cell surface (De Potter, et al, International Journal of Cancer, 44; 969-974 (1989): McCormick, et al, 117; 935-943 (2002)). Alternatively, distribution of the protein may be altered from a surface only localization to include diffuse cytoplasmic expression in the diseased state. Such an example can be seen with MUC1 (Diaz, et al, The Breast Journal, 7: 40-45 (2001)).

Alteration in the localization/distribution of a protein in the cell, as detected by immunohistochemical methods, can also provide valuable information concerning the favorability of certain treatment modalities. This last point is illustrated by a situation where a protein may be intracellular in normal tissue, but cell surface in malignant cells; the cell surface location makes the cells favorably amenable to antibody-based diagnostic and treatment regimens. When such an alteration of protein localization occurs for STEAP-1, the STEAP-1 protein and immune responses related thereto are very useful. Accordingly, the ability to determine whether alteration of subcellular protein localization occurred for 24P4C12 make the STEAP-1 protein and immune responses related thereto very useful. Use of the STEAP-1 compositions allows those skilled in the art to make important diagnostic and therapeutic decisions. Immunohistochemical reagents specific to STEAP-1 are also useful to detect metastases of tumors expressing STEAP-1 when the polypeptide appears in tissues where STEAP-1 is not normally produced.

Thus, STEAP-1 polypeptides and antibodies resulting from immune responses thereto are useful in a variety of important contexts such as diagnostic, prognostic, preventative and/or therapeutic purposes known to those skilled in the art.

Just as PSA polynucleotide fragments and polynucleotide variants are employed by skilled artisans for use in methods of monitoring PSA, STEAP-1 polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472-476, 478-480 (1998); Robertson et al., Methods Mol. Biol. 98:121-154 (1998)). An additional illustration of the use of such fragments is provided in the Example entitled "Expression analysis of STEAP-1 in normal tissues, and patient specimens," where a STEAP-1 polynucleotide fragment is used as a probe to show the expression of STEAP-1 RNAs in cancer cells. In addition, variant polynucleotide sequences are typically used as primers and probes for the corresponding mRNAs in PCR and Northern analyses (see, e.g., Sawai et al., Fetal Diagn. Ther. 1996 November-December 11(6):407-13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g., a STEAP-1 polynucleotide shown in FIG. 2 or variant thereof) under conditions of high stringency.

Furthermore, PSA polypeptides which contain an epitope that can be recognized by an antibody or T cell that specifically binds to that epitope are used in methods of monitoring PSA. STEAP-1 polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. No. 5,840,501 and U.S. Pat. No. 5,939,533). For example it may be preferable to utilize a polypeptide comprising one of the STEAP-1 biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g. a STEAP-1 polypeptide shown in FIG. 3).

As shown herein, the STEAP-1 polynucleotides and polypeptides (as well as the STEAP-1 polynucleotide probes and anti-STEAP-1 antibodies or T cells used to identify the presence of these molecules) exhibit specific properties that make them useful in diagnosing cancers such as those listed in Table I. Diagnostic assays that measure the presence of STEAP-1 gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233-237 (1996)), and materials such as STEAP-1 polynucleotides and polypeptides (as well as the STEAP-1 polynucleotide probes and anti-STEAP-1 antibodies used to identify the presence of these molecules) need to be employed to confirm a metastases of prostatic origin.

Finally, in addition to their use in diagnostic assays, the STEAP-1 polynucleotides disclosed herein have a number of other utilities such as their use in the identification of oncogenetic associated chromosomal abnormalities in the chromosomal region to which the STEAP-1 gene maps (see the Example entitled "Chromosomal Mapping of STEAP-1" below). Moreover, in addition to their use in diagnostic assays, the STEAP-1-related proteins and polynucleotides disclosed herein have other utilities such as their use in the forensic analysis of tissues of unknown origin (see, e.g., Takahama K Forensic Sci Int 1996 Jun. 28;80(1-2): 63-9).

Additionally, STEAP-1-related proteins or polynucleotides of the invention can be used to treat a pathologic condition characterized by the over-expression of STEAP-1. For example, the amino acid or nucleic acid sequence of FIG. 2 or FIG. 3, or fragments of either, can be used to generate an immune response to a STEAP-1 antigen. Antibodies or other molecules that react with STEAP-1 can be used to modulate the function of this molecule, and thereby provide a therapeutic benefit.

XII.) Inhibition of STEAP-1 Protein Function

The invention includes various methods and compositions for inhibiting the binding of STEAP-1 to its binding partner or its association with other protein(s) as well as methods for inhibiting STEAP-1 function.

XII.A.) Inhibition of STEAP-1 With Intracellular Antibodies

In one approach, a recombinant vector that encodes single chain antibodies that specifically bind to STEAP-1 are introduced into STEAP-1 expressing cells via gene transfer technologies. Accordingly, the encoded single chain anti-STEAP-1 antibody is expressed intracellularly, binds to STEAP-1 protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to target precisely the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture STEAP-1 in the nucleus, thereby preventing its activity within the nucleus. Nuclear targeting signals are engineered into such STEAP-1 intrabodies in order to achieve the desired targeting. Such STEAP-1 intrabodies are designed to bind specifically to a particular STEAP-1 domain. In another embodiment, cytosolic intrabodies that specifically bind to a STEAP-1 protein are used to prevent STEAP-1 from gaining access to the nucleus, thereby preventing it from exerting any biological activity within the nucleus (e.g., preventing STEAP-1 from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XII.B.) Inhibition of STEAP-1 with Recombinant Proteins

In another approach, recombinant molecules bind to STEAP-1 and thereby inhibit STEAP-1 function. For example, these recombinant molecules prevent or inhibit STEAP-1 from accessing/binding to its binding partner(s) or associating with other protein(s). Such recombinant molecules can, for example, contain the reactive part(s) of a STEAP-1 specific antibody molecule. In a particular embodiment, the STEAP-1 binding domain of a STEAP-1 binding partner is engineered into a dimeric fusion protein, whereby the fusion protein comprises two STEAP-1 ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of STEAP-1, whereby the dimeric fusion protein specifically binds to STEAP-1 and blocks STEAP-1 interaction with a binding partner. Such dimeric fusion proteins are further combined into multimeric proteins using known antibody linking technologies.

XII.C.) Inhibition of STEAP-1 Transcription or Translation

The present invention also comprises various methods and compositions for inhibiting the transcription of the STEAP-1 gene. Similarly, the invention also provides methods and compositions for inhibiting the translation of STEAP-1 mRNA into protein.

In one approach, a method of inhibiting the transcription of the STEAP-1 gene comprises contacting the STEAP-1 gene with a STEAP-1 antisense polynucleotide. In another approach, a method of inhibiting STEAP-1 mRNA translation comprises contacting a STEAP-1 mRNA with an antisense polynucleotide. In another approach, a STEAP-1 specific ribozyme is used to cleave a STEAP-1 message, thereby inhibiting translation. Such antisense and ribozyme based methods can also be directed to the regulatory regions of the STEAP-1 gene, such as STEAP-1 promoter and/or enhancer elements. Similarly, proteins capable of inhibiting a STEAP-1 gene transcription factor are used to inhibit STEAP-1 mRNA transcription. The various polynucleotides and compositions useful in the aforementioned methods have been described above. The use of antisense and ribozyme molecules to inhibit transcription and translation is well known in the art.

Other factors that inhibit the transcription of STEAP-1 by interfering with STEAP-1 transcriptional activation are also useful to treat cancers expressing STEAP-1. Similarly, factors that interfere with STEAP-1 processing are useful to treat cancers that express STEAP-1. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing STEAP-1 (i.e., antisense, ribozyme, polynucleotides encoding intrabodies and other STEAP-1 inhibitory molecules). A number of gene therapy approaches are known in the art. Recombinant vectors encoding STEAP-1 antisense polynucleotides, ribozymes, factors capable of interfering with STEAP-1 transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of STEAP-1 to a binding partner, etc.

In vivo, the effect of a STEAP-1 therapeutic composition can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences $16^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) Identification, Characterization and Use of Modulators of STEAP-1

Methods to Identify and Use Modulators

In one embodiment, screening is performed to identify modulators that induce or suppress a particular expression profile, suppress or induce specific pathways, preferably generating the associated phenotype thereby. In another embodiment, having identified differentially expressed genes important in a particular state; screens are performed to identify modulators that alter expression of individual genes, either increase or decrease. In another embodiment, screening is performed to identify modulators that alter a biological function of the expression product of a differentially expressed gene. Again, having identified the importance of a gene in a particular state, screens are performed to identify agents that bind and/or modulate the biological activity of the gene product.

In addition, screens are done for genes that are induced in response to a candidate agent. After identifying a modulator (one that suppresses a cancer expression pattern leading to a normal expression pattern, or a modulator of a cancer gene that leads to expression of the gene as in normal tissue) a screen is performed to identify genes that are specifically modulated in response to the agent. Comparing expression profiles between normal tissue and agent-treated cancer tissue reveals genes that are not expressed in normal tissue or cancer tissue, but are expressed in agent treated tissue, and vice versa. These agent-specific sequences are identified and used by methods described herein for cancer genes or proteins. In particular these sequences and the proteins they encode are used in marking or identifying agent-treated cells. In addition, antibodies are raised against the agent-induced proteins and used to target novel therapeutics to the treated cancer tissue sample.

Modulator-related Identification and Screening Assays:

Gene Expression-related Assays

Proteins, nucleic acids, and antibodies of the invention are used in screening assays. The cancer-associated proteins, antibodies, nucleic acids, modified proteins and cells containing these sequences are used in screening assays, such as evaluating the effect of drug candidates on a "gene expression profile," expression profile of polypeptides or alteration of biological function. In one embodiment, the expression profiles are used, preferably in conjunction with high throughput screening techniques to allow monitoring for expression profile genes after treatment with a candidate agent (e.g., Davis, G F, et al, J Biol Screen 7:69 (2002); Zlokarnik, et al., Science 279:84-8 (1998); Heid, Genome Res 6:986-94, 1996).

The cancer proteins, antibodies, nucleic acids, modified proteins and cells containing the native or modified cancer proteins or genes are used in screening assays. That is, the present invention comprises methods for screening for compositions which modulate the cancer phenotype or a physiological function of a cancer protein of the invention. This is done on a gene itself or by evaluating the effect of drug candidates on a "gene expression profile" or biological function. In one embodiment, expression profiles are used, preferably in conjunction with high throughput screening techniques to allow monitoring after treatment with a candidate agent, see Zlokamik, supra.

A variety of assays are executed directed to the genes and proteins of the invention. Assays are run on an individual nucleic acid or protein level. That is, having identified a particular gene as up regulated in cancer, test compounds are screened for the ability to modulate gene expression or for binding to the cancer protein of the invention. "Modulation" in this context includes an increase or a decrease in gene expression. The preferred amount of modulation will depend on the original change of the gene expression in normal versus tissue undergoing cancer, with changes of at least 10%, preferably 50%, more preferably 100-300%, and in some embodiments 300-1000% or greater. Thus, if a gene exhibits a 4-fold increase in cancer tissue compared to normal tissue, a decrease of about four-fold is often desired; similarly, a 10-fold decrease in cancer tissue compared to normal tissue a target value of a 10-fold increase in expression by the test compound is often desired. Modulators that exacerbate the type of gene expression seen in cancer are also useful, e.g., as an upregulated target in further analyses.

The amount of gene expression is monitored using nucleic acid probes and the quantification of gene expression levels, or, alternatively, a gene product itself is monitored, e.g., through the use of antibodies to the cancer protein and standard immunoassays. Proteomics and separation techniques also allow for quantification of expression.

Expression Monitoring to Identify Compounds that Modify Gene Expression

In one embodiment, gene expression monitoring, i.e., an expression profile, is monitored simultaneously for a number of entities. Such profiles will typically involve one or more of the genes of FIG. 2. In this embodiment, e.g., cancer nucleic acid probes are attached to biochips to detect and quantify cancer sequences in a particular cell. Alternatively, PCR can be used. Thus, a series, e.g., wells of a microtiter plate, can be used with dispensed primers in desired wells. A PCR reaction can then be performed and analyzed for each well.

Expression monitoring is performed to identify compounds that modify the expression of one or more cancer-associated sequences, e.g., a polynucleotide sequence set out in FIG. 2. Generally, a test modulator is added to the cells prior to analysis. Moreover, screens are also provided to identify agents that modulate cancer, modulate cancer proteins of the invention, bind to a cancer protein of the invention, or interfere with the binding of a cancer protein of the invention and an antibody or other binding partner.

In one embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds," as compounds for screening, or as therapeutics.

In certain embodiments, combinatorial libraries of potential modulators are screened for an ability to bind to a cancer polypeptide or to modulate activity. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

As noted above, gene expression monitoring is conveniently used to test candidate modulators (e.g., protein, nucleic acid or small molecule). After the candidate agent has been added and the cells allowed to incubate for a period, the sample containing a target sequence to be analyzed is, e.g., added to a biochip.

If required, the target sequence is prepared using known techniques. For example, a sample is treated to lyse the cells, using known lysis buffers, electroporation, etc., with purification and/or amplification such as PCR performed as appropriate. For example, an in vitro transcription with labels covalently attached to the nucleotides is performed. Generally, the nucleic acids are labeled with biotin-FITC or PE, or with cy3 or cy5.

The target sequence can be labeled with, e.g., a fluorescent, a chemiluminescent, a chemical, or a radioactive signal, to provide a means of detecting the target sequence's specific binding to a probe. The label also can be an enzyme, such as alkaline phosphatase or horseradish peroxidase, which when provided with an appropriate substrate produces a product that is detected. Alternatively, the label is a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. Unbound labeled streptavidin is typically removed prior to analysis.

As will be appreciated by those in the art, these assays can be direct hybridization assays or can comprise "sandwich assays", which include the use of multiple probes, as is generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124, 246; and 5,681,697. In this embodiment, in general, the target nucleic acid is prepared as outlined above, and then added to the biochip comprising a plurality of nucleic acid probes, under conditions that allow the formation of a hybridization complex.

A variety of hybridization conditions are used in the present invention, including high, moderate and low stringency conditions as outlined above. The assays are generally run under stringency conditions which allow formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc. These parameters may also be used to control non-specific binding, as is generally outlined in U.S. Pat. No. 5,681,697. Thus, it can be desirable to perform certain steps at higher stringency conditions to reduce non-specific binding.

The reactions outlined herein can be accomplished in a variety of ways. Components of the reaction can be added simultaneously, or sequentially, in different orders, with preferred embodiments outlined below. In addition, the reaction may include a variety of other reagents. These include salts, buffers, neutral proteins, e.g. albumin, detergents, etc. which can be used to facilitate optimal hybridization and detection, and/or reduce nonspecific or background interactions. Reagents that otherwise improve the efficiency of the assay, such as protease inhibitors, nuclease inhibitors, anti-microbial agents, etc., may also be used as appropriate, depending on the sample preparation methods and purity of the target. The assay data are analyzed to determine the expression levels of individual genes, and changes in expression levels as between states, forming a gene expression profile.

Biological Activity-related Assays

The invention provides methods identify or screen for a compound that modulates the activity of a cancer-related gene or protein of the invention. The methods comprise adding a test compound, as defined above, to a cell comprising a cancer protein of the invention. The cells contain a recombinant nucleic acid that encodes a cancer protein of the invention. In another embodiment, a library of candidate agents is tested on a plurality of cells.

In one aspect, the assays are evaluated in the presence or absence or previous or subsequent exposure of physiological signals, e.g. hormones, antibodies, peptides, antigens, cytokines, growth factors, action potentials, pharmacological agents including chemotherapeutics, radiation, carcinogenics, or other cells (i.e., cell-cell contacts). In another example, the determinations are made at different stages of the cell cycle process. In this way, compounds that modulate genes or proteins of the invention are identified. Compounds with pharmacological activity are able to enhance or interfere with the activity of the cancer protein of the invention. Once identified, similar structures are evaluated to identify critical structural features of the compound.

In one embodiment, a method of modulating (e.g., inhibiting) cancer cell division is provided; the method comprises administration of a cancer modulator. In another embodiment, a method of modulating (e.g., inhibiting) cancer is provided; the method comprises administration of a cancer modulator. In a further embodiment, methods of treating cells or individuals with cancer are provided; the method comprises administration of a cancer modulator.

In one embodiment, a method for modulating the status of a cell that expresses a gene of the invention is provided. As used herein status comprises such art-accepted parameters such as growth, proliferation, survival, function, apoptosis, senescence, location, enzymatic activity, signal transduction, etc. of a cell. In one embodiment, a cancer inhibitor is an antibody as discussed above. In another embodiment, the cancer inhibitor is an antisense molecule. A variety of cell growth, proliferation, and metastasis assays are known to those of skill in the art, as described herein.

High Throughput Screening to Identify Modulators

The assays to identify suitable modulators are amenable to high throughput screening. Preferred assays thus detect enhancement or inhibition of cancer gene transcription, inhibition or enhancement of polypeptide expression, and inhibition or enhancement of polypeptide activity.

In one embodiment, modulators evaluated in high throughput screening methods are proteins, often naturally occurring proteins or fragments of naturally occurring proteins. Thus, e.g., cellular extracts containing proteins, or random or directed digests of proteinaceous cellular extracts, are used. In this way, libraries of proteins are made for screening in the methods of the invention. Particularly preferred in this embodiment are libraries of bacterial, fungal, viral, and mammalian proteins, with the latter being preferred, and human proteins being especially preferred. Particularly useful test compound will be directed to the class of proteins to which the target belongs, e.g., substrates for enzymes, or ligands and receptors.

Use of Soft Agar Growth and Colony Formation to Identify and Characterize Modulators Normal cells require a solid substrate to attach and grow. When cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, can regenerate normal phenotype and once again require a solid substrate to attach to and grow. Soft agar growth or colony formation in assays are used to identify modulators of cancer sequences, which when expressed in host cells, inhibit abnormal cellular proliferation and transformation. A modulator reduces or eliminates the host cells' ability to grow suspended in solid or semisolid media, such as agar.

Techniques for soft agar growth or colony formation in suspension assays are described in Freshney, Culture of Animal Cells a Manual of Basic Technique (3rd ed., 1994). See also, the methods section of Garkavtsev et al. (1996), supra.

Evaluation of Contact Inhibition and Growth Density Limitation to Identify and Characterize Modulators Normal cells typically grow in a flat and organized pattern in cell culture until they touch other cells. When the cells touch one another, they are contact inhibited and stop growing. Transformed cells, however, are not contact inhibited and continue to grow to high densities in disorganized foci. Thus, transformed cells grow to a higher saturation density than corresponding normal cells. This is detected morphologically by the formation of a disoriented monolayer of cells or cells in foci. Alternatively, labeling index with ($^3$H)-thymidine at saturation density is used to measure density limitation of growth, similarly an MTT or Alamar blue assay will reveal proliferation capacity of cells and the ability of modulators to affect same. See Freshney (1994), supra. Transformed cells, when transfected with tumor suppressor genes, can regenerate a normal phenotype and become contact inhibited and would grow to a lower density.

In this assay, labeling index with $^3$H)-thymidine at saturation density is a preferred method of measuring density limitation of growth. Transformed host cells are transfected with a cancer-associated sequence and are grown for 24 hours at saturation density in non-limiting medium conditions. The percentage of cells labeling with ($^3$H)-thymidine is determined by incorporated cpm.

Contact independent growth is used to identify modulators of cancer sequences, which had led to abnormal cellular proliferation and transformation. A modulator reduces or eliminates contact independent growth, and returns the cells to a normal phenotype.

Evaluation of Growth Factor or Serum Dependence to Identify and Characterize Modulators Transformed cells have lower serum dependence than their normal counterparts (see, e.g., Temin, J. Natl. Cancer Inst. 37:167-175 (1966); Eagle et al., J. Exp. Med 131:836-879 (1970)); Freshney, supra. This is in part due to release of various growth factors by the transformed cells. The degree of growth factor or serum dependence of transformed host cells can be compared with that of control. For example, growth factor or serum dependence of a cell is monitored in methods to identify and characterize compounds that modulate cancer-associated sequences of the invention.

Use of Tumor-specific Marker Levels to Identify and Characterize Modulators

Tumor cells release an increased amount of certain factors (hereinafter "tumor specific markers") than their normal counterparts. For example, plasminogen activator (PA) is released from human glioma at a higher level than from normal brain cells (see, e.g., Gullino, Angiogenesis, Tumor Vascularization, and Potential Interference with Tumor Growth, in Biological Responses in Cancer, pp. 178-184 (Mihich (ed.) 1985)). Similarly, Tumor Angiogenesis Factor (TAF) is released at a higher level in tumor cells than their normal counterparts. See, e.g., Folkman, Angiogenesis and Cancer, Sem Cancer Biol. (1992)), while bFGF is released from endothelial tumors (Ensoli, B et al).

Various techniques which measure the release of these factors are described in Freshney (1994), supra. Also, see, Unkless et al., J. Biol. Chem. 249:4295-4305 (1974); Strickland & Beers, J. Biol. Chem. 251:5694-5702 (1976); Whur et al., Br. J. Cancer 42:305 312 (1980); Gullino, Angiogenesis, Tumor Vascularization, and Potential Interference with Tumor Growth, in Biological Responses in Cancer, pp. 178-184 (Mihich (ed.) 1985); Freshney, Anticancer Res. 5:111-130 (1985). For example, tumor specific marker levels are monitored in methods to identify and characterize compounds that modulate cancer-associated sequences of the invention.

Invasiveness into Matrigel to Identify and Characterize Modulators

The degree of invasiveness into Matrigel or an extracellular matrix constituent can be used as an assay to identify and characterize compounds that modulate cancer associated sequences. Tumor cells exhibit a positive correlation between malignancy and invasiveness of cells into Matrigel or some other extracellular matrix constituent. In this assay, tumorigenic cells are typically used as host cells. Expression of a tumor suppressor gene in these host cells would decrease invasiveness of the host cells. Techniques described in Cancer Res. 1999; 59:6010; Freshney (1994), supra, can be used. Briefly, the level of invasion of host cells is measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$1 and counting the radioactivity on the distal side of the filter or bottom of the dish. See, e.g., Freshney (1984), supra.

Evaluation of Tumor Growth In Vivo to Identify and Characterize Modulators

Effects of cancer-associated sequences on cell growth are tested in transgenic or immune-suppressed organisms. Transgenic organisms are prepared in a variety of art-accepted ways. For example, knock-out transgenic organisms, e.g., mammals such as mice, are made, in which a cancer gene is disrupted or in which a cancer gene is inserted. Knock-out transgenic mice are made by insertion of a marker gene or other heterologous gene into the endogenous cancer gene site in the mouse genome via homologous recombination. Such mice can also be made by substituting the endogenous cancer gene with a mutated version of the cancer gene, or by mutating the endogenous cancer gene, e.g., by exposure to carcinogens.

To prepare transgenic chimeric animals, e.g., mice, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells some of which are derived from the mutant cell line. Therefore, by breeding the chimeric mice it is possible to obtain a new line of mice containing the introduced genetic lesion (see, e.g., Capecchi et al., Science 244:1288 (1989)). Chimeric mice can be derived according to U.S. Pat. No. 6,365,797, issued 2 Apr. 2002; U.S. Pat. No. 6,107,540 issued 22 Aug. 2000; Hogan et al., Manipulating the Mouse Embryo: A laboratory Manual, Cold Spring Harbor Laboratory (1988) and Teratocarcinomas and Embryonic Stem Cells: A Practical Approach, Robertson, ed., IRL Press, Washington, D.C., (1987).

Alternatively, various immune-suppressed or immune-deficient host animals can be used. For example, a genetically athymic "nude" mouse (see, e.g., Giovanella et al., J. Natl. Cancer Inst. 52:921 (1974)), a SCID mouse, a thymectornized mouse, or an irradiated mouse (see, e.g., Bradley et al., Br. J. Cancer 38:263 (1978); Selby et al., Br. J. Cancer 41:52 (1980)) can be used as a host. Transplantable tumor cells (typically about $10^6$ cells) injected into isogenic hosts produce invasive tumors in a high proportion of cases, while normal cells of similar origin will not. In hosts which developed invasive tumors, cells expressing cancer-associated sequences are injected subcutaneously or orthotopically. Mice are then separated into groups, including control groups and treated experimental groups) e.g. treated with a modulator). After a suitable length of time, preferably 4-8 weeks, tumor growth is measured (e.g., by volume or by its two largest dimensions, or weight) and compared to the control. Tumors that have statistically significant reduction (using, e.g., Student's T test) are said to have inhibited growth.

In Vitro Assays to Identify and Characterize Modulators

Assays to identify compounds with modulating activity can be performed in vitro. For example, a cancer polypeptide is first contacted with a potential modulator and incubated for a suitable amount of time, e.g., from 0.5 to 48 hours. In one embodiment, the cancer polypeptide levels are determined in vitro by measuring the level of protein or mRNA. The level of protein is measured using immunoassays such as Western blotting, ELISA and the like with an antibody that selectively binds to the cancer polypeptide or a fragment thereof. For measurement of mRNA, amplification, e.g., using PCR, LCR, or hybridization assays, e.g., Northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using a cancer protein promoter operably linked to a reporter gene such as luciferase, green fluorescent protein, CAT, or β-gal. The reporter construct is typically transfected into a cell. After treatment with a potential modulator, the amount of reporter gene transcription, translation, or activity is measured according to standard techniques known to those of skill in the art (Davis GF, supra; Gonzalez, J. & Negulescu, P. Curr. Opin. Biotechnol. 1998: 9:624).

As outlined above, in vitro screens are done on individual genes and gene products. That is, having identified a particular differentially expressed gene as important in a particular state, screening of modulators of the expression of the gene or the gene product itself is performed.

In one embodiment, screening for modulators of expression of specific gene(s) is performed. Typically, the expression of only one or a few genes is evaluated. In another embodiment, screens are designed to first find compounds that bind to differentially expressed proteins. These compounds are then evaluated for the ability to modulate differentially expressed activity. Moreover, once initial candidate compounds are identified, variants can be further screened to better evaluate structure activity relationships.

Binding Assays to Identify and Characterize Modulators

In binding assays in accordance with the invention, a purified or isolated gene product of the invention is generally used. For example, antibodies are generated to a protein of the invention, and immunoassays are run to determine the amount and/or location of protein. Alternatively, cells comprising the cancer proteins are used in the assays.

Thus, the methods comprise combining a cancer protein of the invention and a candidate compound such as a ligand, and determining the binding of the compound to the cancer protein of the invention. Preferred embodiments utilize the human cancer protein; animal models of human disease of can also be developed and used. Also, other analogous mammalian proteins also can be used as appreciated by those of skill in the art. Moreover, in some embodiments variant or derivative cancer proteins are used.

Generally, the cancer protein of the invention, or the ligand, is non-diffusibly bound to an insoluble support. The support can, e.g., be one having isolated sample receiving areas (a microtiter plate, an array, etc.). The insoluble supports can be made of any composition to which the compositions can be bound, is readily separated from soluble material, and is otherwise compatible with the overall method of screening. The surface of such supports can be solid or porous and of any convenient shape.

Examples of suitable insoluble supports include microtiter plates, arrays, membranes and beads. These are typically made of glass, plastic (e.g., polystyrene), polysaccharide, nylon, nitrocellulose, or Teflon™, etc. Microtiter plates and arrays are especially convenient because a large number of assays can be carried out simultaneously, using small amounts of reagents and samples. The particular manner of binding of the composition to the support is not crucial so long as it is compatible with the reagents and overall methods of the invention, maintains the activity of the composition and is nondiffusable. Preferred methods of binding include the use of antibodies which do not sterically block either the ligand binding site or activation sequence when attaching the protein to the support, direct binding to "sticky" or ionic supports, chemical crosslinking, the synthesis of the protein or agent on the surface, etc. Following binding of the protein or ligand/binding agent to the support, excess unbound material is removed by washing. The sample receiving areas may then be blocked through incubation with bovine serum albumin (BSA), casein or other innocuous protein or other moiety.

Once a cancer protein of the invention is bound to the support, and a test compound is added to the assay. Alternatively, the candidate binding agent is bound to the support and the cancer protein of the invention is then added. Binding agents include specific antibodies, non-natural binding agents identified in screens of chemical libraries, peptide analogs, etc.

Of particular interest are assays to identify agents that have a low toxicity for human cells. A wide variety of assays can be used for this purpose, including proliferation assays, cAMP assays, labeled in vitro protein-protein binding assays, electrophoretic mobility shift assays, immunoassays for protein binding, functional assays (phosphorylation assays, etc.) and the like.

A determination of binding of the test compound (ligand, binding agent, modulator, etc.) to a cancer protein of the invention can be done in a number of ways. The test compound can be labeled, and binding determined directly, e.g., by attaching all or a portion of the cancer protein of the invention to a solid support, adding a labeled candidate compound (e.g., a fluorescent label), washing off excess reagent, and determining whether the label is present on the solid support. Various blocking and washing steps can be utilized as appropriate.

In certain embodiments, only one of the components is labeled, e.g., a protein of the invention or ligands labeled. Alternatively, more than one component is labeled with different labels, e.g., $I^{125}$, for the proteins and a fluorophor for the compound. Proximity reagents, e.g., quenching or energy transfer reagents are also useful.

Competitive Binding to Identify and Characterize Modulators

In one embodiment, the binding of the "test compound" is determined by competitive binding assay with a "competitor." The competitor is a binding moiety that binds to the target molecule (e.g., a cancer protein of the invention). Competitors include compounds such as antibodies, peptides, binding partners, ligands, etc. Under certain circumstances, the competitive binding between the test compound and the competitor displaces the test compound. In one embodiment, the test compound is labeled. Either the test compound, the competitor, or both, is added to the protein for a time sufficient to allow binding. Incubations are performed at a temperature that facilitates optimal activity, typically between four and 40° C. Incubation periods are typically optimized, e.g., to facilitate rapid high throughput screening; typically between zero and one hour will be sufficient. Excess reagent is generally removed or washed away. The second component is then added, and the presence or absence of the labeled component is followed, to indicate binding.

In one embodiment, the competitor is added first, followed by the test compound. Displacement of the competitor is an indication that the test compound is binding to the cancer protein and thus is capable of binding to, and potentially modulating, the activity of the cancer protein. In this embodiment, either component can be labeled. Thus, e.g., if the competitor is labeled, the presence of label in the post-test compound wash solution indicates displacement by the test compound. Alternatively, if the test compound is labeled, the presence of the label on the support indicates displacement.

In an alternative embodiment, the test compound is added first, with incubation and washing, followed by the competitor. The absence of binding by the competitor indicates that the test compound binds to the cancer protein with higher affinity than the competitor. Thus, if the test compound is labeled, the presence of the label on the support, coupled with a lack of competitor binding, indicates that the test compound binds to and thus potentially modulates the cancer protein of the invention.

Accordingly, the competitive binding methods comprise differential screening to identity agents that are capable of modulating the activity of the cancer proteins of the invention. In this embodiment, the methods comprise combining a cancer protein and a competitor in a first sample. A second sample comprises a test compound, the cancer protein, and a competitor. The binding of the competitor is determined for both samples, and a change, or difference in binding between the two samples indicates the presence of an agent capable of binding to the cancer protein and potentially modulating its activity. That is, if the binding of the competitor is different in the second sample relative to the first sample, the agent is capable of binding to the cancer protein.

Alternatively, differential screening is used to identify drug candidates that bind to the native cancer protein, but cannot bind to modified cancer proteins. For example the structure of the cancer protein is modeled and used in rational drug design to synthesize agents that interact with that site, agents which generally do not bind to site-modified proteins. Moreover, such drug candidates that affect the activity of a native cancer protein are also identified by screening drugs for the ability to either enhance or reduce the activity of such proteins.

Positive controls and negative controls can be used in the assays. Preferably control and test samples are performed in at least triplicate to obtain statistically significant results. Incubation of all samples occurs for a time sufficient to allow for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g. albumin, detergents, etc. which are used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components is added in an order that provides for the requisite binding.

Use of Polynucleotides to Down-regulate or Inhibit a Protein of the Invention.

Polynucleotide modulators of cancer can be introduced into a cell containing the target nucleotide sequence by formation of a conjugate with a ligand-binding molecule, as described in WO 91/04753. Suitable ligand-binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a polynucleotide modulator of cancer can be introduced into a cell containing the target nucleic acid sequence, e.g., by formation of a polynucleotide-lipid complex, as described in WO 90/10448. It is understood that the use of antisense molecules or knock out and knock in models may also be used in screening assays as discussed above, in addition to methods of treatment.

Inhibitory and Antisense Nucleotides

In certain embodiments, the activity of a cancer-associated protein is down-regulated, or entirely inhibited, by the use of antisense polynucleotide or inhibitory small nuclear RNA (snRNA), i.e., a nucleic acid complementary to, and which can preferably hybridize specifically to, a coding mRNA nucleic acid sequence, e.g., a cancer protein of the invention, mRNA, or a subsequence thereof. Binding of the antisense polynucleotide to the mRNA reduces the translation and/or stability of the mRNA.

In the context of this invention, antisense polynucleotides can comprise naturally occurring nucleotides, or synthetic species formed from naturally occurring subunits or their close homologs. Antisense polynucleotides may also have altered sugar moieties or inter-sugar linkages. Exemplary among these are the phosphorothioate and other sulfur containing species which are known for use in the art. Analogs are comprised by this invention so long as they function effectively to hybridize with nucleotides of the invention. See, e.g., Isis Pharmaceuticals, Carlsbad, Calif.; Sequitor, Inc., Natick, Mass.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Antisense molecules as used herein include antisense or sense oligonucleotides. Sense oligonucleotides can, e.g., be employed to block transcription by binding to the anti-sense strand. The antisense and sense oligonucleotide comprise a single stranded nucleic acid sequence (either RNA or DNA) capable of binding to target mRNA (sense) or DNA (antisense) sequences for cancer molecules. Antisense or sense oligonucleotides, according to the present invention, comprise a fragment generally at least about 12 nucleotides, preferably from about 12 to 30 nucleotides. The ability to derive an antisense or a sense oligonucleotide, based upon a cDNA sequence encoding a given protein is described in, e.g., Stein & Cohen (Cancer Res. 48:2659 (1988 and van der Krol et al. (Bio Techniques 6:958 (1988)).

Ribozymes

In addition to antisense polynucleotides, ribozymes can be used to target and inhibit transcription of cancer-associated nucleotide sequences. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto et al., Adv. in Pharmacology 25: 289-317 (1994) for a general review of the properties of different ribozymes).

The general features of hairpin ribozymes are described, e.g., in Hampel et al., Nucl. Acids Res. 18:299-304 (1990); European Patent Publication No. 0360257; U.S. Pat. No. 5,254,678. Methods of preparing are well known to those of skill in the art (see, e.g., WO 94/26877; Ojwang et al., Proc. Natl. Acad. Sci. USA 90:6340-6344 (1993); Yamada et al., Human Gene Therapy 1:39-45 (1994); Leavitt et al., Proc. Natl. Acad Sci. USA 92:699-703 (1995); Leavitt et al., Human Gene Therapy 5: 1151-120 (1994); and Yamada et al., Virology 205: 121-126 (1994)).

Use of Modulators in Phenotypic Screening

In one embodiment, a test compound is administered to a population of cancer cells, which have an associated cancer expression profile. By "administration" or "contacting" herein is meant that the modulator is added to the cells in such a manner as to allow the modulator to act upon the cell, whether by uptake and intracellular action, or by action at the cell surface. In some embodiments, a nucleic acid encoding a proteinaceous agent (i.e., a peptide) is put into a viral construct such as an adenoviral or retroviral construct, and added to the cell, such that expression of the peptide agent is accomplished, e.g., PCT US97/01019. Regulatable gene therapy systems can also be used. Once the modulator has been administered to the cells, the cells are washed if desired and are allowed to incubate under preferably physiological conditions for some period. The cells are then harvested and a new gene expression profile is generated. Thus, e.g., cancer tissue is screened for agents that modulate, e.g., induce or suppress, the cancer phenotype. A change in at least one gene, preferably many, of the expression profile indicates that the agent has an effect on cancer activity. Similarly, altering a biological function or a signaling pathway is indicative of modulator activity. By defining such a signature for the cancer phenotype, screens for new drugs that alter the phenotype are devised. With this approach, the drug target need not be known and need not be represented in the original gene/protein expression screening platform, nor does the level of transcript for the target protein need to change. The modulator inhibiting function will serve as a surrogate marker As outlined above, screens are done to assess genes or gene products. That is, having identified a particular differentially expressed gene as important in a particular state, screening of modulators of either the expression of the gene or the gene product itself is performed.

Use of Modulators to Affect Peptides of the Invention

Measurements of cancer polypeptide activity, or of the cancer phenotype are performed using a variety of assays. For example, the effects of modulators upon the function of a cancer polypeptide(s) are measured by examining parameters described above. A physiological change that affects activity is used to assess the influence of a test compound on the polypeptides of this invention. When the functional outcomes are determined using intact cells or animals, a variety of effects can be assesses such as, in the case of a cancer associated with solid tumors, tumor growth, tumor metastasis, neovascularization, hormone release, transcriptional changes to both known and uncharacterized genetic markers (e.g., by Northern blots), changes in cell metabolism such as cell growth or pH changes, and changes in intracellular second messengers such as cGNIP.

Methods of Identifying Characterizing Cancer-associated Sequences

Expression of various gene sequences is correlated with cancer. Accordingly, disorders based on mutant or variant cancer genes are determined. In one embodiment, the invention provides methods for identifying cells containing variant cancer genes, e.g., determining the presence of, all or part, the sequence of at least one endogenous cancer gene in a cell. This is accomplished using any number of sequencing techniques. The invention comprises methods of identifying the cancer genotype of an individual, e.g., determining all or part of the sequence of at least one gene of the invention in the individual. This is generally done in at least one tissue of the individual, e.g., a tissue set forth in Table I, and may include the evaluation of a number of tissues or different samples of the same tissue. The method may include comparing the sequence of the sequenced gene to a known cancer gene, i.e., a wild-type gene to determine the presence of family members, homologies, mutations or variants. The sequence of all or part of the gene can then be compared to the sequence of a known cancer gene to determine if any differences exist. This is done using any number of known homology programs, such as BLAST, Bestfit, etc. The presence of a difference in the sequence between the cancer gene of the patient and the known cancer gene correlates with a disease state or a propensity for a disease state, as outlined herein.

In a preferred embodiment, the cancer genes are used as probes to determine the number of copies of the cancer gene in the genome. The cancer genes are used as probes to determine the chromosomal localization of the cancer genes. Information such as chromosomal localization finds use in providing a diagnosis or prognosis in particular when chromosomal abnormalities such as translocations, and the like are identified in the cancer gene locus.

XIV.) RNAi and Therapeutic Use of Small Interfering RNA (siRNAs)

The present invention is also directed towards siRNA oligonucleotides, particularly double stranded RNAs encompassing at least a fragment of the STEAP-1 coding region or 5" UTR regions, or complement, or any antisense oligonucleotide specific to the STEAP-1 sequence. In one embodiment such oligonucleotides are used to elucidate a function of STEAP-1, or are used to screen for or evaluate modulators of STEAP-1 function or expression. In another embodiment, gene expression of STEAP-1 is reduced by using siRNA transfection and results in significantly diminished proliferative capacity of transformed cancer cells that endogenously express the antigen; cells treated with specific STEAP-1 siRNAs show reduced survival as measured, e.g., by a metabolic readout of cell viability, correlating to the reduced proliferative capacity. Thus, STEAP-1 siRNA compositions comprise siRNA (double stranded RNA) that correspond to the nucleic acid ORF sequence of the STEAP-1 protein or subsequences thereof; these subsequences are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more than 35 contiguous RNA nucleotides in length and contain sequences that are complementary and non-complementary to at least a portion of the mRNA coding sequence In a preferred embodiment, the subsequences are 19-25 nucleotides in length, most preferably 21-23 nucleotides in length.

RNA interference is a novel approach to silencing genes in vitro and in vivo, thus small double stranded RNAs (siRNAs) are valuable therapeutic agents. The power of siRNAs to silence specific gene activities has now been brought to animal models of disease and is used in humans as well. For example, hydrodynamic infusion of a solution of siRNA into a mouse with a siRNA against a particular target has been proven to be therapeutically effective.

The pioneering work by Song et al. indicates that one type of entirely natural nucleic acid, small interfering RNAs (siRNAs), served as therapeutic agents even without further chemical modification (Song, E., et al. "RNA interference targeting Fas protects mice from fulminant hepatitis" *Nat. Med.* 9(3): 347-51(2003)). This work provided the first in vivo evidence that infusion of siRNAs into an animal could alleviate disease. In that case, the authors gave mice injections of siRNA designed to silence the FAS protein (a cell death receptor that when over-activated during inflammatory response induces hepatocytes and other cells to die). The next day, the animals were given an antibody specific to Fas. Control mice died of acute liver failure within a few days, while over 80% of the siRNA-treated mice remained free from serious disease and survived. About 80% to 90% of their liver cells incorporated the naked siRNA oligonucleotides. Furthermore, the RNA molecules functioned for 10 days before losing effect after 3 weeks.

For use in human therapy, siRNA is delivered by efficient systems that induce long-lasting RNAi activity. A major caveat for clinical use is delivering siRNAs to the appropriate cells. Hepatocytes seem to be particularly receptive to exogenous RNA. Today, targets located in the liver are attractive because liver is an organ that can be readily targeted by nucleic acid molecules and viral vectors. However, other tissue and organs targets are preferred as well.

Formulations of siRNAs with compounds that promote transit across cell membranes are used to improve administration of siRNAs in therapy. Chemically modified synthetic siRNA, that are resistant to nucleases and have serum stability have concomitant enhanced duration of RNAi effects, are an additional embodiment.

Thus, siRNA technology is a therapeutic for human malignancy by delivery of siRNA molecules directed to STEAP-1 to individuals with the cancers, such as those listed in Table 1. Such administration of siRNAs leads to reduced growth of cancer cells expressing STEAP-1, and provides an anti-tumor therapy, lessening the morbidity and/or mortality associated with malignancy.

The effectiveness of this modality of gene product knockdown is significant when measured in vitro or in vivo. Effectiveness in vitro is readily demonstrable through application of siRNAs to cells in culture (as described above) or to aliquots of cancer patient biopsies when in vitro methods are used to detect the reduced expression of STEAP-1 protein.

XV.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a probe that is or can be detectably labeled. Such probe can be an antibody or polynucleotide specific for a protein or a gene or message of the invention, respectively. Where the method utilizes nucleic acid hybridization to detect the target nucleic acid, the kit can also have containers containing nucleotide(s) for amplification of the target nucleic acid sequence. Kits can comprise a container comprising a reporter, such as a biotin-binding protein, such as avidin or streptavidin, bound to a reporter molecule, such as an enzymatic, fluorescent, or radioisotope label; such a reporter can be used with, e.g., a nucleic acid or antibody. The kit can include all or part of the amino acid sequences in FIG. 2 or FIG. 3 or analogs thereof, or a nucleic acid molecule that encodes such amino acid sequences.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vftro use, such as those described herein. Directions and or other information can also be included on an insert(s) or label(s) which is included with or on the kit. The label can be on or associated with the container. A label can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a neoplasia of a tissue set forth in Table I.

The terms "kit" and "article of manufacture" can be used as synonyms.

In another embodiment of the invention, an article(s) of manufacture containing compositions, such as amino acid sequence(s), small molecule(s), nucleic acid sequence(s), and/or antibody(s), e.g., materials useful for the diagnosis, prognosis, prophylaxis and/or treatment of neoplasias of tissues such as those set forth in Table I is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s). In one embodiment, the container holds a polynucleotide for use in examining the mRNA expression profile of a cell, together with reagents used for this purpose. In another embodiment a container comprises an antibody, binding fragment thereof or specific binding protein for use in evaluating protein expression of STEAP-1 in cells and tissues, or for relevant laboratory, prognostic, diagnostic, prophylactic and therapeutic purposes; indications and/or directions for such uses can be included on or with such container, as can reagents and other compositions or tools used for these purposes. In another embodiment, a container comprises materials for eliciting a cellular or humoral immune response, together with associated indications and/or directions. In another embodiment, a container comprises materials for adoptive immunotherapy, such as cytotoxic T cells (CTL) or helper T cells (HTL), together with associated indications and/or directions; reagents and other compositions or tools used for such purpose can also be included.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding STEAP-1 and modulating the function of STEAP-1.

The article of manufacture can further comprise a second container comprising a pharmaceutically-acceptable buffer, such as phosphate-buffered saline, Ringers solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which is intended to limit the scope of the invention.

Example 1

SSH-Generated Isolation of cDNA Fragment of the STEAP-1 Gene

Materials and Methods

LAPC Xenografts

LAPC xenografts were obtained from Dr. Charles Sawyers (UCLA) and generated as described (Klein et al, 1997, Nature Med. 3: 402-408; Craft et al., 1999, Cancer Res. 59: 5030-5036). Androgen dependent and independent LAPC-4 xenografts (LAPC-4 AD and AI, respectively) and LAPC-9 xenografts (LAPC-9 AD and AI, respectively) were grown in intact male SCID mice or in castrated males, respectively, and were passaged as small tissue chunks in recipient males. LAPC-4 AI xenografts were derived from LAPC-4 AD tumors and LAPC-9 AI xenografts were derived from LAPC-9 AD tumors. To generate the AI xenografts, male mice bearing LAPC AD tumors were castrated and maintained for 2-3 months. After the LAPC tumors re-grew, the tumors were harvested and passaged in castrated males or in female SCID mice.

LAPC-4 AD xenografts were grown intratibially as follows. LAPC-4 AD xenograft tumor tissue grown subcutaneously was minced into 1-2 mm$^3$ sections while the tissue was bathed in 1×Iscoves medium, minced tissue was then centrifuged at 1.3K rpm for 4 minutes, the supernatant was resuspended in 10 ml ice cold 1× Iscoves medium and centrifuged at 1.3K rpm for 4 minutes. The pellet was then resuspended in 1× Iscoves with 1% pronase E and incubated for 20 minutes at room temperature with mild rocking agitation followed by incubation on ice for 2-4 minutes. Filtrate was centrifuged at 1.3K rpm for 4 minutes, and the pronase was removed from the aspirated pellet by resuspending in 10 ml Iscoves and re-centrifuging. Clumps of cells were then plated in PrEGM medium and grown overnight. The cells were then harvested, filtered, washed 2×RPMI, and counted. Approximately 50,000 cells were mixed with and equal volume of ice-cold Matrigel on ice, and surgically injected into the proximal tibial metaphyses of SCID mice via a 27 gauge needle. After 10-12 weeks, LAPC-4 tumors growing in bone marrow were recovered.

Cell Lines and Tissues

Human cell lines (e.g., HeLa) were obtained from the ATCC and were maintained in DMEM with 5% fet al calf serum. Human tissues for RNA and protein analyses were obtained from the Human Tissue Resource Center (HTRC) at the UCLA (Los Angeles, Calif.) and from QualTek, Inc. (Santa Barbara, Calif.).

RNA Isolation

Tumor tissue and cell lines were homogenized in Trizol reagent (Life Technologies, Gibco BRL) using 10 ml/g tissue or 10 ml/10$^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides

The following HPLC purified oligonucleotides were used.

DPNCDN (cDNA synthesis primer):

5'TTTTGATCAAGCTT$_{30}$3'
(SEQ ID NO: 68)

Adaptor 1:

5'CTAATACGACTCACTATAGGGCTCGAGCGGCCGCCCGGGCAG3'
(SEQ ID NO: 69)

3'GGCCCGTCCTAG5'
(SEQ ID NO: 70)

Adaptor 2:

5'GTAATACGACTCACTATAGGGCAGCGTGGTCGCGGCCGAG3'
(SEQ ID NO: 71)

3'CGGCTCCTAG5'
(SEQ ID NO: 72)

PCR primer 1:

5'CTAATACGACTCACTATAGGGC3'
(SEQ ID NO: 73)

Nested primer (NP)1:

5'TCGAGCGGCCGCCCGGGCAGGA3'
(SEQ ID NO: 74)

Nested primer (NP)2:

5'AGCGTGGTCGCGGCCGAGGA3'
(SEQ ID NO: 75)

Suppression Subtractive Hybridization

Suppression Subtractive Hybridization (SSH) was used to identify cDNAs corresponding to genes, which may be up-regulated in androgen dependent prostate cancer compared to benign prostatic hyperplasia (BPH).

Double stranded cDNAs corresponding to the LAPC-4 AD xenograft (tester) and the BPH tissue (driver) were synthesized from 2 µg of poly(A)+ RNA isolated from xenograft and BPH tissue, as described above, using CLONTECH's PCR-Select cDNA Subtraction Kit and 1 ng of oligonucleotide RSACDN as primer. First- and second-strand synthesis were carried out as described in the Kit's user manual protocol (CLONTECH Protocol No. PT1117-1, Catalog No. K1804-1). The resulting cDNA was digested with Rsa I for 3 hrs. at 37° C. Digested cDNA was extracted with phenol/chloroform (1:1) and ethanol precipitated.

Driver cDNA (BPH) was generated by combining in a 4 to 1 ratio Rsa I digested BPH cDNA with digested cDNA from mouse liver, in order to ensure that murine genes were subtracted from the tester cDNA (LAPC-4 AD).

Tester cDNA (LAPC-4 AD) was generated by diluting 1 µl of Rsa I digested LAPC-4 AD cDNA (400 ng) in 5 µl of water. The diluted cDNA (2 µl, 160 ng) was then ligated to 2 µl of adaptor 1 and adaptor 2 (10 µM), in separate ligation reactions, in a total volume of 10 µl at 16° C. overnight, using 400 u of T4 DNA ligase (CLONTECH). Ligation was terminated with 1 µl of 0.2 M EDTA and heating at 72° C. for 5 min.

The first hybridization was performed by adding 1.5 µl (600 ng) of driver cDNA to each of two tubes containing 1.5 µl (20 ng) adaptor 1- and adaptor 2-ligated tester cDNA. In a final volume of 4 µl, the samples were overlayed with mineral oil, denatured in an MJ Research thermal cycler at 98° C. for 1.5 minutes, and then were allowed to hybridize for 8 hrs at 68° C. The two hybridizations were then mixed together with an additional 1 µl of fresh denatured driver cDNA and were allowed to hybridize overnight at 68° C. The second hybridization was then diluted in 200 µof 20 mM Hepes, pH 8.3, 50 mM NaCl, 0.2 mM EDTA, heated at 70° C. for 7 min. and stored at −20° C.

PCR Amplification. Cloning and Sequencing of Gene Fragments Generated from SSH

To amplify gene fragments resulting from SSH reactions, two PCR amplifications were performed. In the primary PCR reaction 1 µl of the diluted final hybridization mix was added to 1 µl of PCR primer 1 (10 µM), 0.5 µl dNTP mix (10 µM), 2.5 µl 10× reaction buffer (CLONTECH) and 0.5 µl 50×Advantage cDNA polymerase Mix (CLONTECH) in a final volume of 25 µl. PCR 1 was conducted using the following conditions: 75° C. for 5 min., 94° C. for 25 sec., the 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 µl from the pooled and diluted primary PCR reaction was added to the same reaction mix as used for PCR 1, except that primers NP1 and NP2 (10 µM) were used instead of PCR primer 1. PCR 2 was performed using 10-12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed *E. coli* were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dbEST, and NCI-CGAP databases.

RT-PCR Expression Analysis

First strand cDNAs were generated from 1 µg of mRNA with oligo (dT)12-18 priming using the Gibco-BRL Superscript Preamplification system. The manufacturer's protocol was used and included an incubation for 50 min at 42° C. with reverse transcriptase followed by RNase H treatment at 37° C. for 20 min. After completing the reaction, the volume was increased to 200 µl with water prior to normalization. First strand cDNAs from 16 different normal human tissues were obtained from Clontech.

Normalization of the first strand cDNAs from multiple tissues was performed by using the primers 5'atatcgc-cgcgctcgtcgtcgacaa3' (SEQ ID NO: 76) and 5'agccacacg-cagctcattgtagaagg 3' (SEQ ID NO: 77) to amplify β-actin. First strand cDNA (5 µl) was amplified in a total volume of 50 µl containing 0.4 µM primers, 0.2 µM each dNTPs, 1×PCR buffer (Clontech, 10 mM Tris-HCL, 1.5 mM MgCl₂, 50 mM KCl, pH8.3) and 1×Klentaq DNA polymerase (Clontech). Five µl of the PCR reaction was removed at 18, 20, and 22 cycles and used for agarose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the STEAP-1 gene, 5 µl of normalized first strand cDNA was analyzed by PCR using 25, 30, and 35 cycles of amplification using the following primer pairs:

```
                                        (SEQ ID NO: 78)
    5'ACT TTG TTG ATG ACC AGG ATT GGA 3'

(SEQ ID NO: 78)
    5'CAG AAC TTC AGC ACA CAC AGG AAC 3'
```

Semi quantitative expression analysis was achieved by comparing the PCR products at cycle numbers that give light band intensities.

Results

Several SSH experiments were conduced as described in the Materials and Methods, supra, and led to the isolation of numerous candidate gene fragment clones. All candidate clones were sequenced and subjected to homology analysis against all sequences in the major public gene and EST databases in order to provide information on the identity of the corresponding gene and to help guide the decision to analyze a particular gene for differential expression. In general, gene fragments which had no homology to any known sequence in any of the searched databases, and thus considered to represent novel genes, as well as gene fragments showing homology to previously sequenced expressed sequence tags (ESTs), were subjected to differential expression analysis by RT-PCR and/or Northern analysis.

One of the cDNA clones, designated STEAP-1, was 436 bp in length and showed homology to an EST sequence in the NCI-CGAP tumor gene database. The full length cDNA encoding the STEAP-1 gene was subsequently isolated using this cDNA and re-named STEAP-1. The STEAP-1 cDNA nucleotide sequence corresponds to nucleotide residues 150 through 585 in the STEAP-1 cDNA sequence as shown in FIG. 1. Another clone, designated 28P3E1, 561 bp in length showed homology to a number of EST sequences in the NCI-CGAP tumor gene database or in other databases. Part of the 28P3E1 sequence (356 bp) is identical to an EST derived from human fet al tissue. After the full-length STEAP-1 cDNA was obtained and sequenced, it became apparent that this clone also corresponds to STEAP-1 (more specifically, to residues 622 through the 3' end of the STEAP-1 nucleotide sequence as shown in FIG. 1).

Example 2

Isolation of Full Length STEAP-1 Encoding cDNA

The 436 bp STEAP-1 gene fragment (See Example Entitled, "SSH-Generated Isolation of cDNA Fragment of the STEAP-1 Gene") was used to isolate additional cDNAs encoding the 8P1D4/STEAP-1 gene. Briefly, a normal human prostate cDNA library (Clontech) was screened with a labeled probe generated from the 436 bp STEAP-1 cDNA. One of the positive clones, clone 10, is 1195 bp in length and encodes a 339 amino acid protein having nucleotide and encoded amino acid sequences bearing no significant homology to any known human genes or proteins (homology to a rat Kidney Injury Protein described in International Application WO98/53071). The encoded protein contains at least 6 predicted transmembrane motifs implying a cell surface orientation These structural features led to the designation "STEAP", for "Six Transmembrane Epithelial Antigen of the Prostate".

Subsequent identification of additional "STEAP" proteins led to the re-designation of the STEAP-1 gene product as "STEAP-1". The STEAP-1 cDNA and encoded amino acid sequences are shown in FIG. 2A-Q. STEAP-1 cDNA clone 10 was deposited with the American Type Culture Collection ("ATCC") (10801 University Blvd., Manassas, Va. 20110-2209 USA) as plasmid STEAP-1 clone 10.1 on Aug. 26, 1998 as ATCC Accession Number 98849. The STEAP-1 cDNA clone can be excised therefrom using EcoRI/Xbal double digest (EcoRI at the 5'end, Xbal at the 3'end).

Example 3

Chromosomal Mapping of STEAP-1

Chromosomal localization can implicate genes in disease pathogenesis. Several chromosome mapping approaches are available including fluorescent in situ hybridization (FISH), human/hamster radiation hybrid (RH) panels (Walter et al., 1994; Nature Genetics 7:22; Research Genetics, Huntsville Ala.), human-rodent somatic cell hybrid panels such as is available from the Coriell Institute (Camden, N.J.), and genomic viewers utilizing BLAST homologies to sequenced and mapped genomic clones (NCBI, Bethesda, Md.).

STEAP-1 maps to chromosome 7q21 using STEAP-1 sequence and the NCBI BLAST tool: (located on the World Wide Web at (.ncbi.nlm.nih.gov/genome/seq/page.cgi?F=HsBlast.html&&ORG=Hs)).

Example 4

Expression Analysis of STEAP-1

Figure 14A:
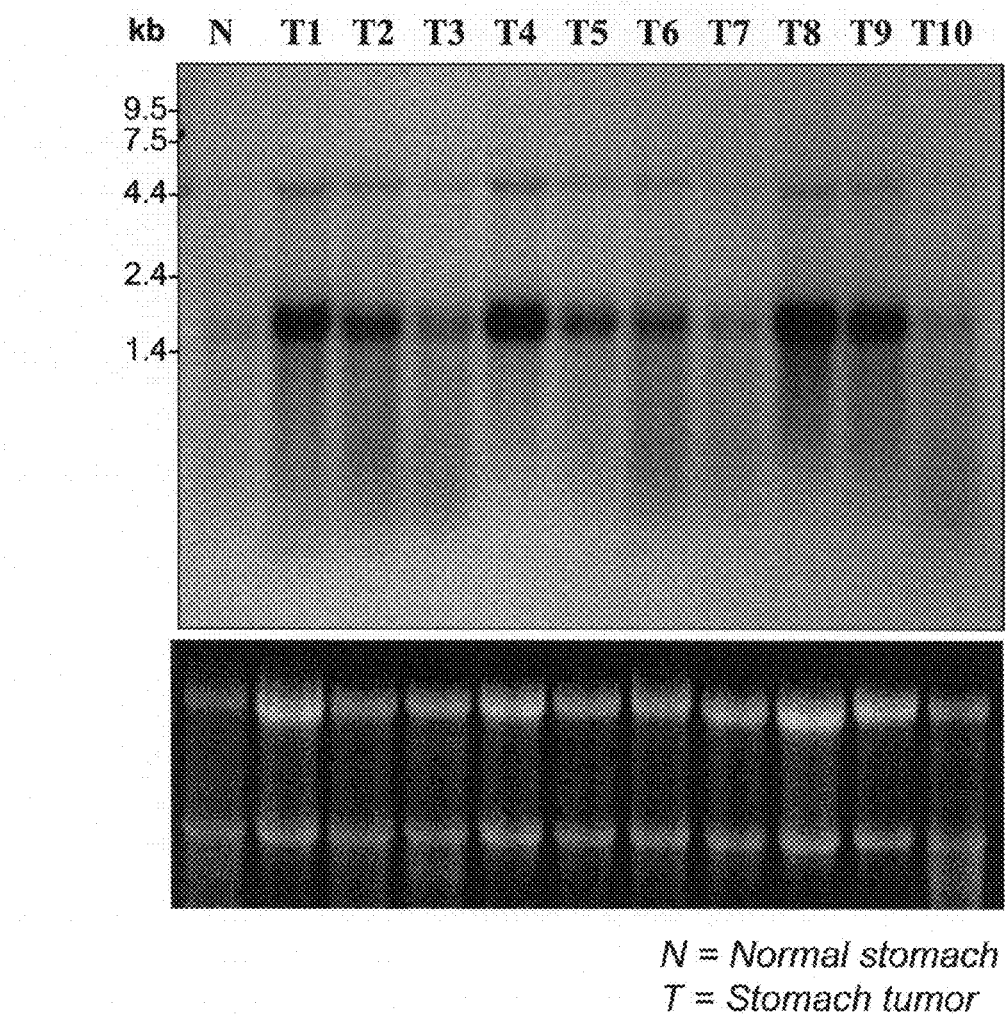

Expression of STEAP-1 in stomach cancer patient specimens is shown in FIG. 14(a)-(e). FIG. 14(a) RNA was extracted from normal stomach (N) and from 10 different stomach cancer patient specimens (T). Northern blot with 10 µg of total RNA/lane was probed with STEAP-1 sequence. Results show strong expression of an approximately 1.6 kb STEAP-1 in the stomach tumor tissues. The lower panel represents ethidium bromide staining of the blot showing quality of the RNA samples.

Figure 14B:
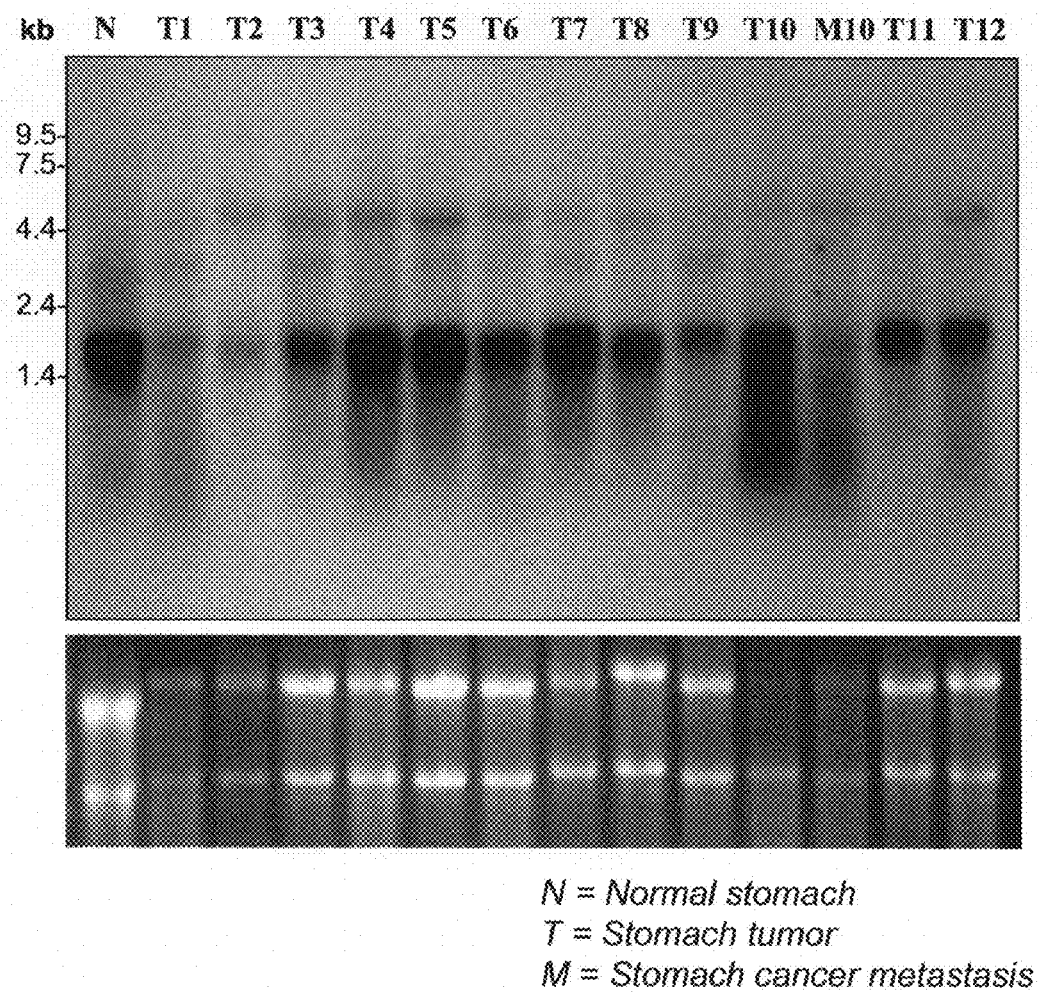

FIG. 14(b) shows that STEAP-1 was expressed in rectum cancer patient tissues. RNA was extracted from normal rectum (N), rectum cancer patient tumors (T), and rectum cancer metastasis (M). Northern blots with 10 µg of total RNA were probed with the STEAP-1 sequence. Results show strong expression of STEAP-1 in the rectum cancer patient tissues. The lower panel represents ethidium bromide staining of the blot showing quality of the RNA samples.

Figure 14C:
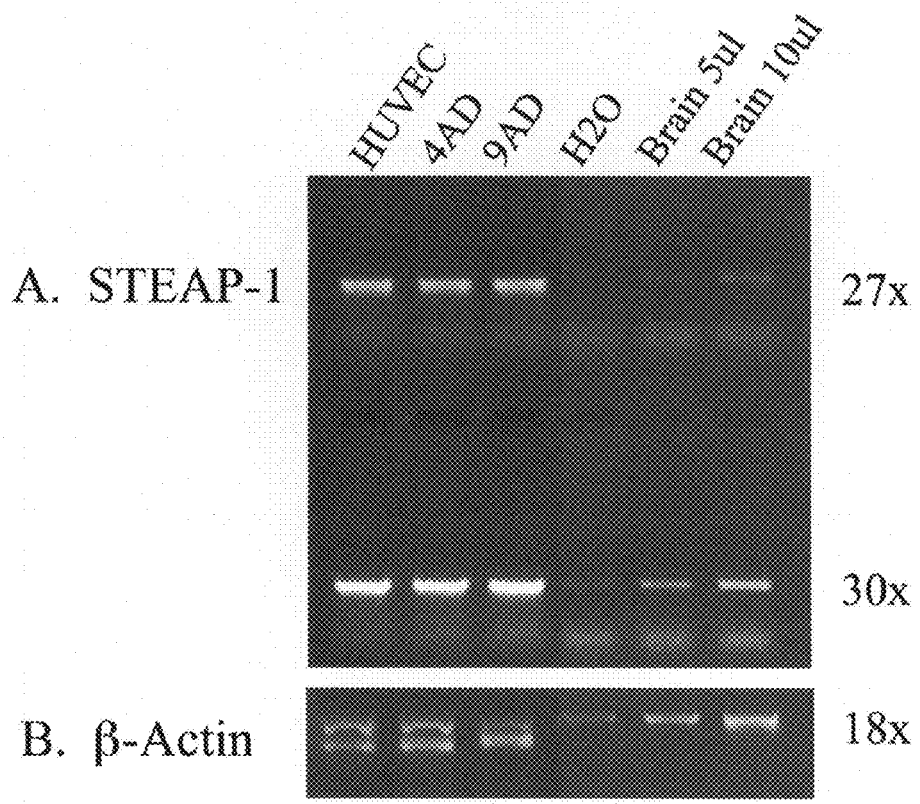
Figure 14D:
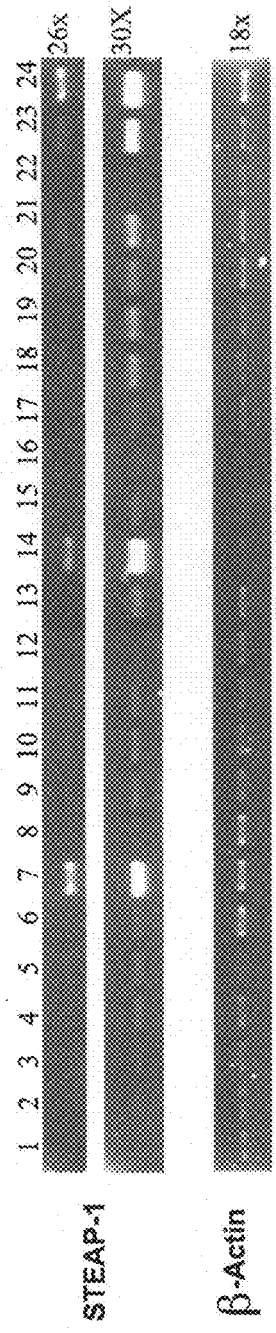
Figure 14E:
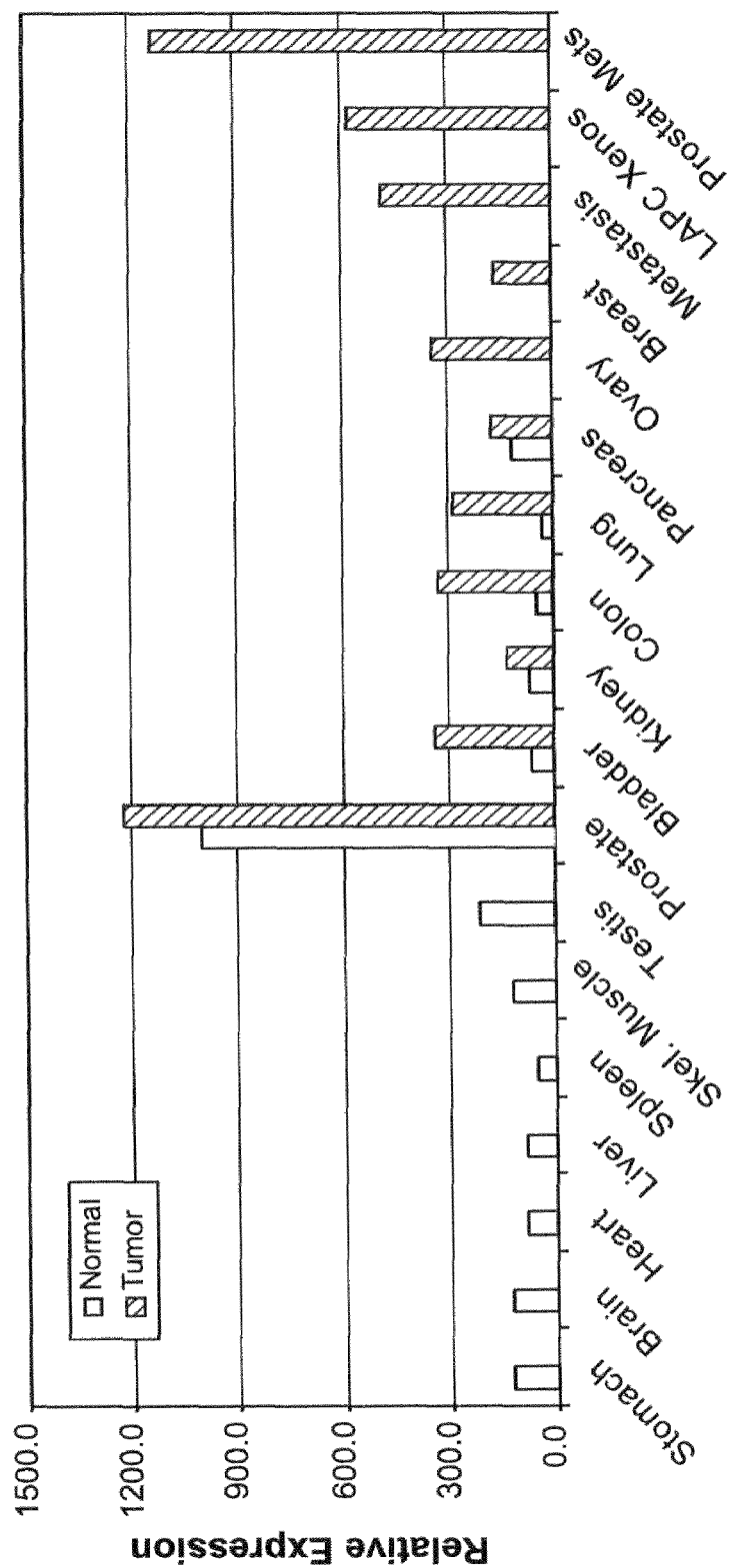

Expression of STEAP-1 by RT-PCR demonstrated that STEAP-1 is strongly expressed in human umbilical vein endothelial cells (HUVEC) (FIG. 14(c)). First strand cDNA was prepared from HUVEC cells, LAPC-4AD and LAPC-9AD prostate cancer xenografts, as well as from human brain tissues. Normalization was performed by PCR using primers to actin and GAPDH. Semi-quantitative PCR, using primers to STEAP-1, was performed at 27 and 30 cycles of amplification. As a control, PCR using primers to actin is shown. Results show strong expression of STEAP-1 in HUVEC cells similar to the expression detected in prostate cancer xenograft tissues. Expression of STEAP-1 in HUVEC cells indicates that targeting STEAP-1 may also target endothelial cells of the neovasculature of the tumors. In FIG. 14(d) picture of the RT-PCR agarose gel is shown. In FIG. 14(e) PCR products were quantitated using the Alphalmager software. Results show strong of expression of STEAP-1 in normal prostate amongst all the normal tissues tested. Upregulation of STEAP-1 expression was detected in prostate cancer pool, bladder cancer pool, kidney cancer pool, colon cancer pool, lung cancer pool, ovary cancer pool, and breast cancer pool. Strong expression of STEAP-1 was detected in cancer metastasis pool, prostate cancer xenograft pool, and prostate metastasis to lymph node.

STEAP-1 Expression in lymphoma patient specimens (FIG. 14(f)). First strand cDNA was prepared from a panel of lymphoma patient specimens. Normalization was performed by PCR using primers to actin. Semi-quantitative PCR, using primers to STEAP-1, was performed at 26 and 30 cycles of amplification. Samples were run on an agarose gel, and PCR products were quantitated using the Alphalmager software. Expression was recorded as strong or medium, if signal is detected as 26 or 30 cycles of amplification respectively, and absent if no signal is detected even at 30 cycles of amplification. Results show expression of STEAP-1 in 8 of 11 (72.7%) tumor specimens tested.

Example 5

Splice Variants of STEAP-1

Transcript variants are variants of mature mRNA from the same gene which arise by alternative transcription or alternative splicing. Alternative transcripts are transcripts from the same gene but start transcription at different points. Splice variants are mRNA variants spliced differently from the same transcript. In eukaryotes, when a multi-exon gene is transcribed from genomic DNA, the initial RNA is spliced to produce functional mRNA, which has only exons and is used for translation into an amino acid sequence. Accordingly, a given gene can have zero to many alternative transcripts and each transcript can have zero to many splice variants. Each transcript variant has a unique exon makeup, and can have different coding and/or non-coding (5' or 3' end) portions, from the original transcript. Transcript variants can code for similar or different proteins with the same or a similar function or can encode proteins with different functions, and can be expressed in the same tissue at the same time, or in different tissues at the same time, or in the same tissue at different times, or in different tissues at different times. Proteins encoded by transcript variants can have similar or different cellular or extracellular localizations, e.g., secreted versus intracellular.

Transcript variants are identified by a variety of art-accepted methods. For example, alternative transcripts and splice variants are identified by full-length cloning experiment, or by use of full-length transcript and EST sequences. First, all human ESTs were grouped into clusters which show direct or indirect identity with each other. Second, ESTs in the same cluster were further grouped into sub-clusters and assembled into a consensus sequence. The original gene sequence is compared to the consensus sequence(s) or other full-length sequences. Each consensus sequence is a potential splice variant for that gene (see, e.g., Kan, Z., et al., Gene structure prediction and alternative splicing analysis using genomically aligned ESTs, Genome Research, 2001 May, 11(5):889-900.) Even when a variant is identified that is not a full-length clone, that portion of the variant is very useful for antigen generation and for further cloning of the full-length splice variant, using techniques known in the art.

Moreover, computer programs are available in the art that identify transcript variants based on genomic sequences. Genomic-based transcript variant identification programs include FgenesH (A. Salamov and V. Solovyev, "Ab initio gene finding in Drosophila genomic DNA," Genome Research. 2000 April;10(4):516-22); Grail (URL compbio.oml.gov/Grail-bin/EmptyGrailForm) and GenScan (URL genes.mit.edu/GENSCAN.html). For a general discussion of splice variant identification protocols see., e.g., Southan, C., A genomic perspective on human proteases, FEBS Lett. 2001 Jun 8; 498(2-3):214-8; de Souza, S.J., et al., Identification of human chromosome 22 transcribed sequences with ORF expressed sequence tags, Proc. Natl Acad Sci U S A. 2000 Nov. 7; 97(23):12690-3.

To further confirm the parameters of a transcript variant, a variety of techniques are available in the art, such as full-length cloning, proteomic validation, PCR-based validation, and 5' RACE validation, etc. (see e.g., Proteomic Validation: Brennan, S. O., et al., Albumin banks peninsula: a new termination variant characterized by electrospray mass spectrometry, Biochem Biophys Acta. 1999 Aug. 17;1433(1-2): 321-6; Ferranti P, et al., Differential splicing of premessenger RNA produces multiple forms of mature caprine alpha(sl)-casein, Eur J Biochem. 1997 Oct 1;249(1):1-7. For PCR-based Validation: Wellmann S, et al., Specific reverse transcription-PCR quantification of vascular endothelial growth factor (VEGF) splice variants by LightCycler technology, Clin Chem. 2001 April;47(4):654-60; Jia, H. P., et al., Discovery of new human beta-defensins using a genomics-based approach, Gene. 2001 Jan. 24; 263(1-2):211-8. For PCR-based and 5' RACE Validation: Brigle, K. E., et al., Organization of the murine reduced folate carrier gene and identification of variant splice forms, Biochem Biophys Acta. 1997 Aug. 7; 1353(2): 191-8).

It is known in the art that genomic regions are modulated in cancers. When the genomic region to which a gene maps is modulated in a particular cancer, the alternative transcripts or splice variants of the gene are modulated as well. Disclosed herein is that STEAP-1 has a particular expression profile related to cancer. Alternative transcripts and splice variants of STEAP-1 may also be involved in cancers in the same or different tissues, thus serving as tumor-associated markers/antigens.

The exon composition of the original transcript, designated as STEAP-1 v.1, is shown in Table LIII. Using the full-length gene and EST sequences, two transcript variants were identified, designated as STEAP-1 v.2 and v.3. Compared with STEAP-1 v.1, transcript variant STEAP-1 v.2 did not splice out intron 4 of STEAP-1 v.1 and variant STEAP-1 v.3 spliced out one additional exon from intron 4 of STEAP-1 v.1, as shown in FIG. 11. Theoretically, each different combination of exons in spatial order, e.g. exons 2 and 3, is a potential splice variant. FIG. 11 shows the schematic alignment of exons of the transcript variants.

Example 6

Single Nucleotide Polymorphisms of STEAP-1

A Single Nucleotide Polymorphism (SNP) is a single base pair variation in a nucleotide sequence at a specific location. At any given point of the genome, there are four possible nucleotide base pairs: A/T, C/G, G/C and T/A. Genotype refers to the specific base pair sequence of one or more locations in the genome of an individual. Haplotype refers to the base pair sequence of more than one location on the same DNA molecule (or the same chromosome in higher organisms), often in the context of one gene or in the context of several lightly linked genes. SNPs that occur on a cDNA are called cSNPs. These cSNPs may change amino acids of the protein encoded by the gene and thus change the functions of the protein. Some SNPs cause inherited diseases; others contribute to quantitative variations in phenotype and reactions to environmental factors including diet and drugs among individuals. Therefore, SNPs and/or combinations of alleles (called haplotypes) have many applications, including diagnosis of inherited diseases, determination of drug reactions and dosage, identification of genes responsible for diseases, and analysis of the genetic relationship between individuals (P. Nowotny, J. M. Kwon and A. M. Goate, "SNP analysis to dissect human traits," Curr. Opin. Neurobiol. 2001 October; 11(5):637-641; M. Pirmohamed and B. K. Park, "Genetic susceptibility to adverse drug reactions," Trends Pharmacol. Sci. 2001 June; 22(6):298-305; J. H. Riley, C. J. Allan, E. Lai and A. Roses, "The use of single nucleotide polymorphisms in the isolation of common disease genes," Pharmacogenomics. 2000 February; 1(1):39-47; R. Judson, J. C. Stephens and A. Windemuth, "The predictive power of haplotypes in clinical response," Pharmacogenomics. 2000 Feburary; 1(1):15-26).

SNPs are identified by a variety of art-accepted methods (P. Bean, "The promising voyage of SNP target discovery," Am. Clin. Lab. 2001 October-November; 20(9):18-20; K. M. Weiss, "In search of human variation, " Genome Res. 1998July; 8(7):691-697; M. M. She, "Enabling large-scale pharmacogenetic studies by high-throughput mutation detection and genotyping technologies," Clin. Chem. 2001 Feburary; 47(2):164-172). For example, SNPs are identified by sequencing DNA fragments that show polymorphism by gel-based methods such as restriction fragment length polymorphism (RFLP) and denaturing gradient gel electrophoresis (DGGE). They can also be discovered by direct sequencing of DNA samples pooled from different individuals or by comparing sequences from different DNA samples. With the rapid accumulation of sequence data in public and private databases, one can discover SNPs by comparing sequences using computer programs (Z. Gu, L. Hillier and P. Y. Kwok, "Single nucleotide polymorphism hunting in cyberspace," Hum. Mutat. 1998; 12(4):221-225). SNPs can be verified and genotype or haplotype of an individual can be determined by a variety of methods including direct sequencing and high throughput microarrays (P. Y. Kwok, "Methods for genotyping single nucleotide polymorphisms," Annu. Rev. Genomics Hum. Genet. 2001; 2:235-258; M. Kokoris, K. Dix, K. Moynihan, J. Mathis, B. Erwin, P. Grass, B. Hines and A. Duesterhoeft, "High-throughput SNP genotyping with the Masscode system," Mol. Diagn. 2000 December; 5(4):329-340).

Using the methods described above, fourteen SNPs were identified in the transcript from clone GTH9, designated as STEAP-1 v.2, at positions 602 (C/G), 386 (C/T), 1087 (T/G), 1447 (T/C), 1621 (A/T), 1625 (G/T), 1716 (C/A), 2358 (C/T), 2646 (T/G), 2859 (T/G), 2908 (A/T), 3006 (G/C), 3107 (C/T), and 3180 (A/T). The transcripts or proteins with alternative alleles were designated as variants STEAP-1 v.4, v.5, v.6, v.7, v.8, v.9, v.10, v.11, v.12, v.13, v.14, v.15, v.16 and v.17, respectively. FIG. 10 shows the schematic alignment of the SNP variants. FIG. 12 shows the schematic alignment of protein variants, corresponding to nucleotide variants. These alleles of the SNPs, though shown separately here, can occur in different combinations (haplotypes) and in any one of the transcript variants (such as STEAP-1 v.1 and v.3) that contains the sequence context of the SNPs. E.g., the first two SNP were also on STEAP-1 v.3 at the same positions, but at 572 and 356, respectively, on STEAP-1 v.1.

Example 7

Production of Recombinant STEAP-1 in Prokaryotic Systems

To express recombinant STEAP-1 and STEAP-1 variants in prokaryotic cells, the full or partial length STEAP-1 and STEAP-1 variant cDNA sequences are cloned into any one of a variety of expression vectors known in the art. The full length cDNA, or any 8, 9, 10, 11, 12, 13, 14, 15, 16, 17, 18, 19, 20, 21, 22, 23, 24, 25, 26, 27, 28, 29, 30 or more contiguous amino acids from STEAP-1, variants, or analogs thereof are used.

A. In vitro Transcription and Translation Constructs:

pCRII: To generate STEAP-1 sense and anti-sense RNA probes for RNA in situ investigations, pCRII constructs (Invitrogen, Carlsbad Calif.) are generated encoding either all or fragments of the STEAP-1 cDNA. The pCRII vector has Sp6 and T7 promoters flanking the insert to drive the transcription of STEAP-1 RNA for use as probes in RNA in situ hybridization experiments. These probes are used to analyze the cell and tissue expression of STEAP-1 at the RNA level. Transcribed STEAP-1 RNA represenUng the cDNA amino acid coding region of the STEAP-1 gene is used in in vitro translation systems such as the TnT™ Coupled Reticulolysate System (Promega, Corp., Madison, Wis.) to synthesize STEAP-1 protein.

B. Bacterial Constructs:

pGEX Constructs: To generate recombinant STEAP-1 proteins in bacteria that are fused to the Glutathione S-transferase (GST) protein, all or parts of the STEAP-1 cDNA or variants are cloned into the GST-fusion vector of the pGEX family (Amersham Pharmacia Biotech, Piscataway, N.J.). These constructs allow controlled expression of recombinant STEAP-1 protein sequences with GST fused at the amino-terminus and a six histidine epitope (6×His) at the carboxyl-terminus. The GST and 6×His tags permit purification of the recombinant fusion protein from induced bacteria with the appropriate affinity matrix and allow recognition of the fusion protein with anti-GST and anti-His antibodies. The 6×His tag is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from STEAP-1-related protein. The ampicillin resistance gene and pBR322 origin permits selection and maintenance of the pGEX plasmids in E. coli.

pMAL Constructs: To generate, in bacteria, recombinant STEAP-1 proteins that are fused to maltose-binding protein (MBP), all or parts of the STEAP-1 cDNA protein coding sequence are fused to the MBP gene by cloning into the pMAL-c2X and pMAL-p2X vectors (New England Biolabs, Beverly, Mass.). These constructs allow controlled expression of recombinant STEAP-1 protein sequences with MBP fused at the amino-terminus and a 6×His epitope tag at the carboxyl-terminus. The MBP and 6×His tags permit purification of the recombinant protein from induced bacteria with the appropriate affinity matrix and allow recognition of the fusion protein with anti-MBP and anti-His antibodies. The 6×His epitope tag is generated by adding 6 histidine codons to the 3' cloning primer. A Factor Xa recognition site permits cleavage of the pMAL tag from STEAP-1. The pMAL-c2X and pMAL-p2X vectors are optimized to express the recombinant protein in the cytoplasm or periplasm respectively. Periplasm expression enhances folding of proteins with disulfide bonds.

pET Constructs: To express STEAP-1 in bacterial cells, all or parts of the STEAP-1 cDNA protein coding sequence are cloned into the pET family of vectors (Novagen, Madison, Wis.). These vectors allow tightly controlled expression of recombinant STEAP-1 protein in bacteria with and without fusion to proteins that enhance solubility, such as NusA and thioredoxin (Trx), and epitope tags, such as 6×His and S-Tag™ that aid purification and detection of the recombinant protein. For example, constructs are made utilizing pET NusA fusion system 43.1 such that regions of the STEAP-1 protein are expressed as amino-terminal fusions to NusA.

C. Yeast Constructs:

pESC Constructs: To express STEAP-1 in the yeast species *Saccharomyces cerevisiae* for generation of recombinant protein and functional studies, all or parts of the STEAP-1 cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein-protein interactions of STEAP-1. In addition, expression in yeast yields similar post-translational modifications, such as glycosylations and phosphorylations, that are found when expressed in eukaryotic cells.

pESP Constructs: To express STEAP-1 in the yeast species *Saccharomyces pombe*, all or parts of the STEAP-1 cDNA protein coding sequence are cloned into the pESP family of vectors. These vectors allow controlled high level of expression of a STEAP-1 protein sequence that is fused at either the amino terminus or at the carboxyl terminus to GST which aids purification of the recombinant protein. A Flag™epitope tag allows detection of the recombinant protein with anti-Flag™ antibody.

Example 8

Production of Recombinant STEAP-1 in Higher Eukaryotic Systems

A. Mammalian Constructs:

To express recombinant STEAP-1 in eukaryotic cells, the full or partial length STEAP-1 cDNA sequences can be cloned into any one of a variety of expression vectors known in the art. One or more of the following regions of STEAP-1 are expressed in these constructs, amino acids 1 to 339 of STEAP-1 v.1, v.4, amino acids 1 to 258 of v. 2, amino acids 1 to 282 of v.3, or any 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more contiguous amino acids from STEAP-1, variants, or analogs thereof. In certain embodiments a region of a specific variant of STEAP-1 is expressed that encodes an amino acid at a specific position which differs from the amino acid of any other variant found at that position. In other embodiments, a region of a variant of STEAP-1 is expressed that lies partly or entirely within a sequence that is unique to that variant.

The constructs can be transfected into any one of a wide variety of mammalian cells such as 293T cells. Transfected 293T cell lysates can be probed with the anti-STEAP-1 polyclonal serum, described herein.

pcDNA4/HisMax Constructs: To express STEAP-1 in mammalian cells, a STEAP-1 ORF, or portions thereof, of STEAP-1 are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6×His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in E. coli.

pcDNA3.1/MycHis Constructs: To express STEAP-1 in mammalian cells, a STEAP-1 ORF, or portions thereof, of STEAP-1 with a consensus Kozak translation initiation site was cloned into pcDNA3.1/MycHis Version A (Invitrogen, Carlsbad, Calif.). Protein expression is driven from the cytomegalovirus (CMV) promoter. The recombinant proteins have the myc epitope and 6×His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene was used, as it allows for selection of mammalian cells expressing the protein and the ampicillin resistance gene and ColE1 origin permits selection and maintenance of the plasmid in E coli.

pcDNA3.1/CT-GFP-TOPO Construct: To express STEAP-1 in mammalian cells and to allow detection of the recombinant proteins using fluorescence, a STEAP-1 ORF, or portions thereof, with a consensus Kozak translation initiation site are cloned into pcDNA3.1/CT-GFP-TOPO (Invitrogen, Calif.). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in E. coli. Additional constructs with an amino-terminal GFP fusion are made in pcDNA3.1/NT-GFP-TOPO spanning the entire length of a STEAP-1 protein.

PAPtag: A STEAP-1 ORF, or portions thereof, is cloned into pAPtag-5 (GenHunter Corp. Nashville, Tenn.). This construct generates an alkaline phosphatase fusion at the carboxyl-terminus of a STEAP-1 protein while fusing the IgGK signal sequence to the amino-terminus. Constructs are also generated in which alkaline phosphatase with an amino-terminal IgGK signal sequence is fused to the amino-terminus of a STEAP-1 protein. The resulting recombinant STEAP-1 proteins are optimized for secretion into the media of transfected mammalian cells and can be used to identify proteins such as ligands or receptors that interact with STEAP-1 proteins. Protein expression is driven from the CMV promoter and the recombinant proteins also contain myc and 6×His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in E. coli.

ptag5: A STEAP-1 ORF, or portions thereof, was cloned into pTag-5. This vector is similar to pAPtag but without the alkaline phosphatase fusion. This construct generated STEAP-1 protein with an amino-terminal IgGK signal sequence and myc and 6×His epitope tags at the carboxyl-terminus that facilitate detection and affinity purification. The resulting recombinant STEAP-1 protein was optimized for secretion into the media of transfected mammalian cells, and is used as immunogen or ligand to identify proteins such as ligands or receptors that interact with the STEAP-1 proteins. Protein expression was driven from the CMV promoter. The Zeocin resistance gene present in the vector allowed for selection of mammalian cells expressing the protein, and the ampicillin resistance gene permits selection of the plasmid in E. coli.

PsecFc: A STEAP-1 ORF, or portions thereof, was also cloned into psecFc. The psecFc vector was assembled by cloning the human immunoglobulin G1 (IgG) Fc (hinge, CH2, CH3 regions) into pSecTag2 (Invitrogen, Calif.). This construct generated an IgG1 Fc fusion at the carboxyl-terminus of the STEAP-1 proteins, while fusing the IgGK signal sequence to N-terminus. STEAP-1 fusions utilizing the murine IgG1 Fc region are also used. The resulting recombinant STEAP-1 proteins were optimized for secretion into the media of transfected mammalian cells, and can were used as immunogens or to identify proteins such as ligands or receptors that interact with STEAP-1 protein. Protein expression is driven from the CMV promoter. The hygromycin resistance gene present in the vector allowed for selection of mammalian cells that express the recombinant protein, and the ampicillin resistance gene permits selection of the plasmid in E. coli.

pSRα Constructs: To generate mammalian cell lines that express STEAP-1 constitutively, STEAP-1 ORF, or portions thereof, of STEAP-1 were cloned into pSRα constructs. Amphotropic and ecotropic retroviruses were generated by transfection of pSRα constructs into the 293T-10 A1 packaging line or co-transfection of pSRα and a helper plasmid (containing deleted packaging sequences) into the 293 cells, respectively. The retrovirus was used to infect a variety of mammalian cell lines, resulting in the integration of the cloned gene, STEAP-1, into the host cell-lines. Protein expression was driven from a long terminal repeat (LTR). The Neomycin resistance gene present in the vector allowed for selection of mammalian cells that express the protein, and the ampicillin resistance gene and ColE1 origin permit selection and maintenance of the plasmid in E. coli. The retroviral vectors were thereafter be used for infection and generation of various cell lines using, for example, PC3, NIH 3T3, TsuPr1, 293 or rat-1 cells.

Additional pSRα constructs are made that fuse an epitope tag such as the FLAG™ tag to the carboxyl-terminus of STEAP-1 sequences to allow detection using anti-Flag antibodies. For example, the FLAG™ sequence 5' gat tac aag gat gac gac gat aag 3' (SEQ ID NO: 80) is added to cloning primer at the 3' end of the ORF. Additional pSRα constructs were made to produce both amino-terminal and carboxyl-terminal GFP and myc/6×His fusion proteins of the full-length STEAP-1 proteins.

Additional Viral Vectors: Additional constructs are made for viral-mediated delivery and expression of STEAP-1. High virus titer leading to high level expression of STEAP-1 is achieved in viral delivery systems such as adenoviral vectors and herpes amplicon vectors. A STEAP-1 coding sequences or fragments thereof are amplified by PCR and subcloned into the AdEasy shuttle vector (Stratagene). Recombination and virus packaging are performed according to the manufacturer's instructions to generate adenoviral vectors. Alternatively, STEAP-1 coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems: To control expression of STEAP-1 in mammalian cells, coding sequences of STEAP-1, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant STEAP-1. These vectors are thereafter used to control expression of STEAP-1 in various cell lines such as PC3, NIH 3T3, 293 or rat-1 cells.

B. Baculovirus Expression Systems

To generate recombinant STEAP-1 proteins in a baculovirus expression system, STEAP-1 ORF, or portions thereof, are cloned into the baculovirus transfer vector pBlueBac 4.5 (Invitrogen), which provides a His-tag at the N-terminus. Specifically, pBlueBac-STEAP-1 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay. Recombinant STEAP-1 protein is then generated by infection of HighFive insect cells (Invitrogen) with purified baculovirus. Recombinant STEAP-1 protein can be detected using anti-STEAP-1 or anti-His-tag antibody. STEAP-1 protein can be purified and used in various cell-based assays or as immunogen to generate polyclonal and monoclonal antibodies specific for STEAP-1.

Example 9

Antigenicity Profiles and Secondary Structure

FIGS. 5(a)-9(a) and 5(b)-9(b) depict graphically five amino acid profiles of the STEAP-1 variants 1 and 3 respectively, each assessment available by accessing the ProtScale website located on the World Wide Web at (URL.expasy.ch/cgi-bin/protscale.pl) on the ExPasy molecular biology server.

These profiles: FIGS. 5(a) and (b), Hydrophilicity, (Hopp T. P., Woods K. R., 1981. Proc. Natl. Acad. Sci. U.S.A. 78:3824-3828); FIGS. 6(a) and (b), Hydropathicity, (Kyte J., Doolittle R. F., 1982. J. Mol. Biol. 157:1 05-132); FIGS. 7(a) and (b), Percentage Accessible Residues (Janin J., 1979 Nature 277:491-492); FIGS. 8(a) and (b), Average Flexibility, (Bhaskaran R., and Ponnuswamy P. K., 1988. Int. J. Pept. Protein Res. 32:242-255); FIGS. 9(a) and (b), Beta-turn (Deleage, G., Roux B. 1987 Protein Engineering 1:289-294); and optionally others available in the art, such as on the ProtScale website, were used to identify antigenic regions of the STEAP-1 protein. Each of the above amino acid profiles of STEAP-1 were generated using the following ProtScale parameters for analysis: 1) A window size of 9; 2) 100% weight of the window edges compared to the window center; and, 3) amino acid profile values normalized to lie between 0 and 1.

Hydrophilicity (FIGS. 5(a) and (b)), Hydropathicity (FIGS. 6(a) and (b)) and Percentage Accessible Residues (FIGS. 7(a) and (b)) profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus available for immune recognition, such as by antibodies.

Average Flexibility (FIGS. 8(a) and (b)) and Beta-turn (FIGS. 9(a) and (b)) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the STEAP-1 protein and of the variant proteins indicated, e.g., by the profiles set forth in FIGS. 5(a) and (b), FIGS. 6(a) and (b), FIGS. 7(a) and (b), FIGS. 8(a) and (b), and/or FIGS. 9(a) and (b) are used to prepare immunogens, either peptides or nucleic acids that encode them, to generate therapeutic and diagnostic anti-STEAP-1 antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the STEAP-1 protein variants listed in FIGS. 2 and 3. In particular, peptide immunogens of the invention can comprise, a peptide region of at least 5 amino acids of FIGS. 2 and 3 in any whole number increment that includes an amino acid position having a value greater than 0.5 in the Hydrophilicity profile of FIGS. 5(a) and (b); a peptide region of at least 5 amino acids of FIGS. 2 and 3 in any whole number increment that includes an amino acid position having a value less than 0.5 in the Hydropathicity profile of FIGS. 6(a) and (b); a peptide region of at least 5 amino acids of FIGS. 2 and 3 in any whole number increment that includes an amino acid position having a value greater than 0.5 in the Percent Accessible Residues profile of FIGS. 7(a) and (b); a peptide region of at least 5 amino acids of FIGS. 2 and 3 in any whole number increment that includes an amino acid position having a value greater than 0.5 in the Average Flexibility profile on FIGS. 8(a) and (b); and, a peptide region of at least 5 amino acids of FIGS. 2 and 3 in any whole number increment that includes an amino acid position having a value greater than 0.5 in the Beta-turn profile of FIGS. 9(a) and (b). Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structures of STEAP-1 variant 1 and variant 3, namely the predicted presence and location of alpha helices, extended strands, and random coils, are predicted from the respective primary amino acid sequences using the HNN—Hierarchical Neural Network method (Guermeur, 1997, http://pbil.ibcp.fr/cgi-bin/npsa_automat.pl?page= npsa_nn.html), accessed from the ExPasy molecular biology server located on the World Wide Web at (.expasy.ch/tools/). The analysis indicates that STEAP-1 variant 1 is composed of 64.60% alpha helix, 4.72% extended strand, and 30.68% random coil (FIG. 13a). STEAP-1 variant 2 is composed of 62.79% alpha helix, 3.10% extended strand, and 34.11% random coil (FIG. 13b). STEAP-1 variant 3 is composed of 58.87% alpha helix, 5.32% extended strand, and 35.82% random coil (FIG. 13c).

Figure 13D:
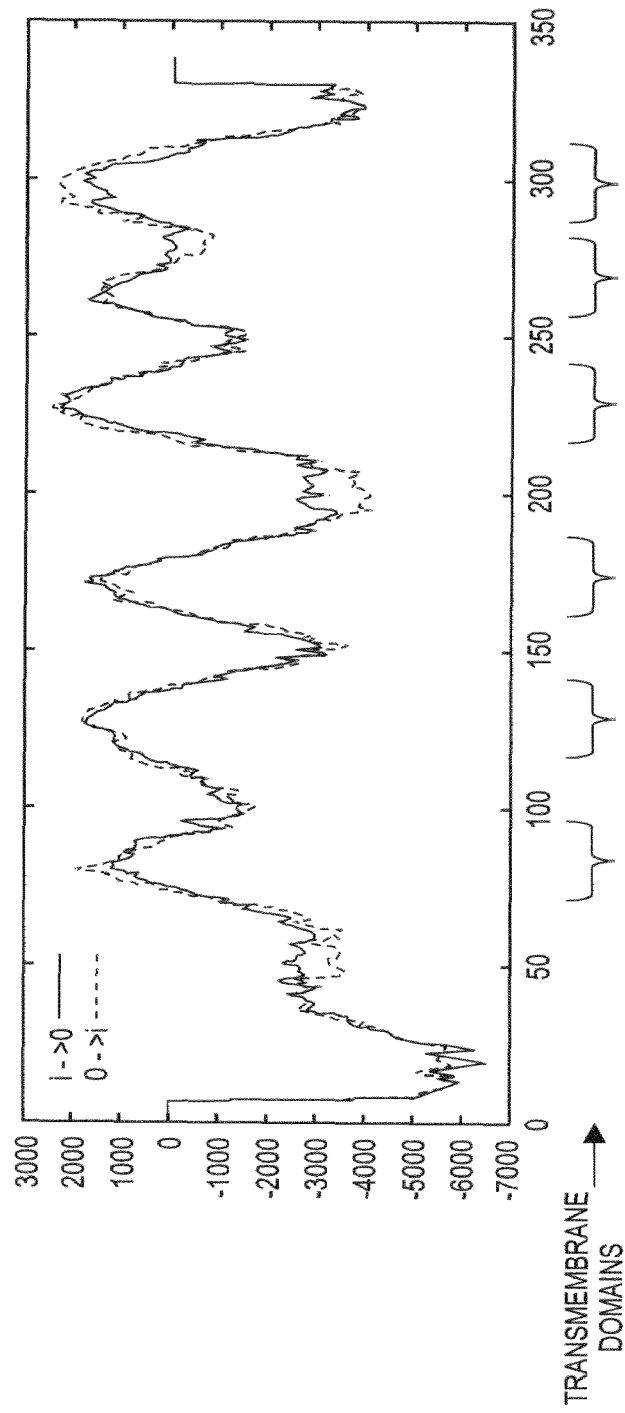
Figure 13E:
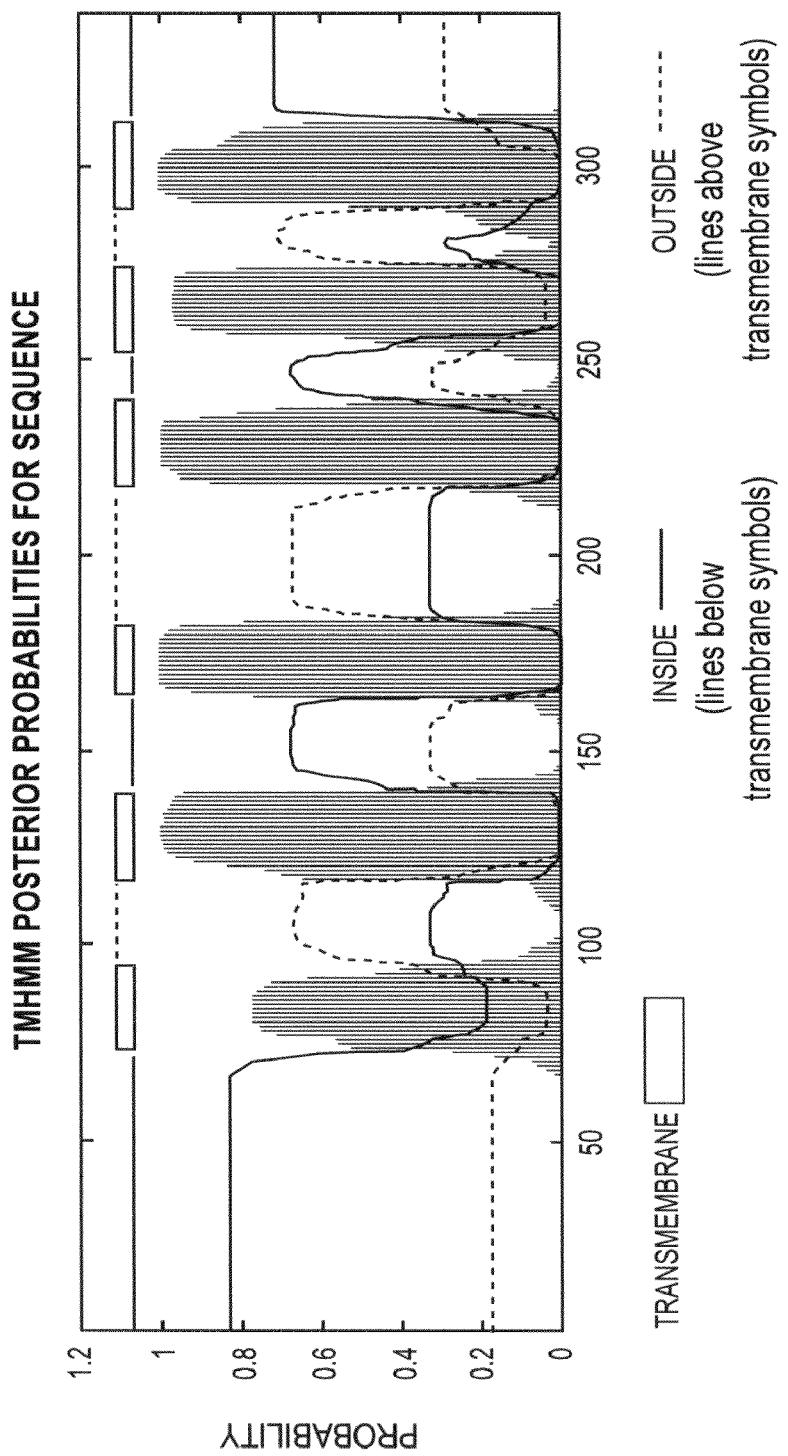
Figure 13F:
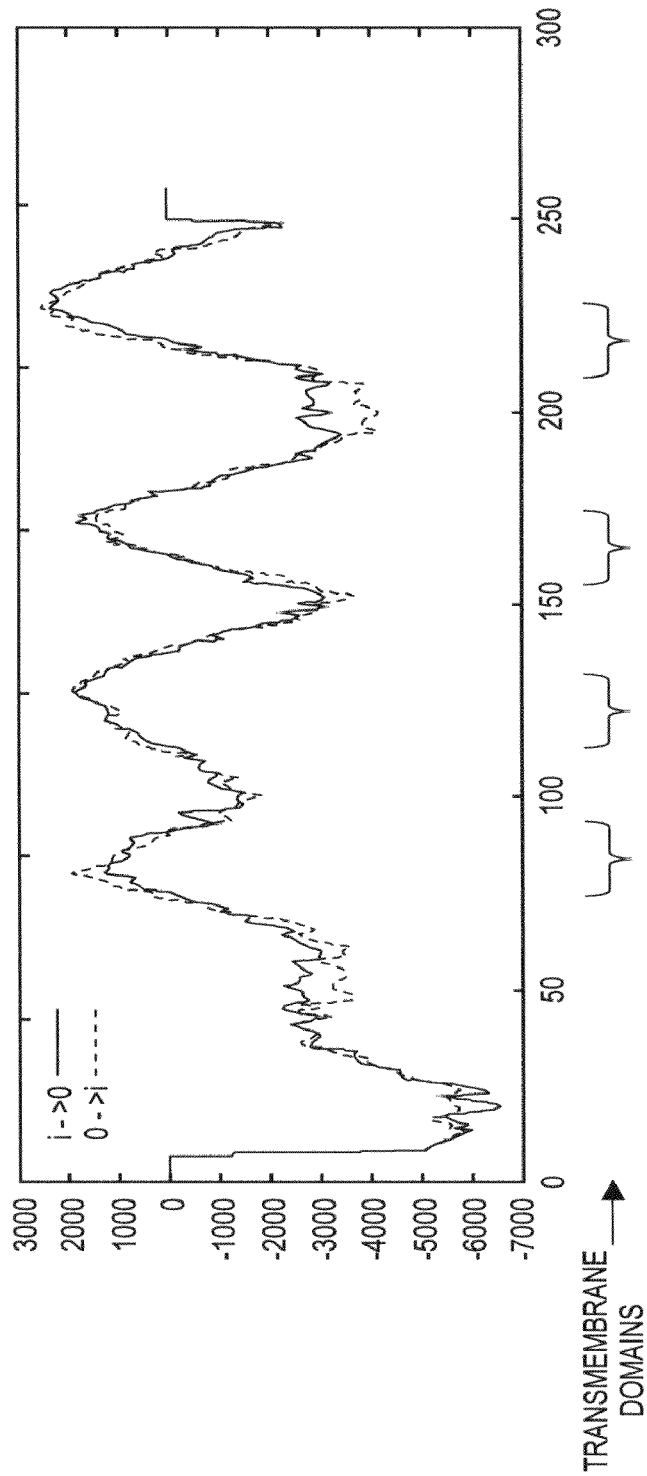
Figure 13G:
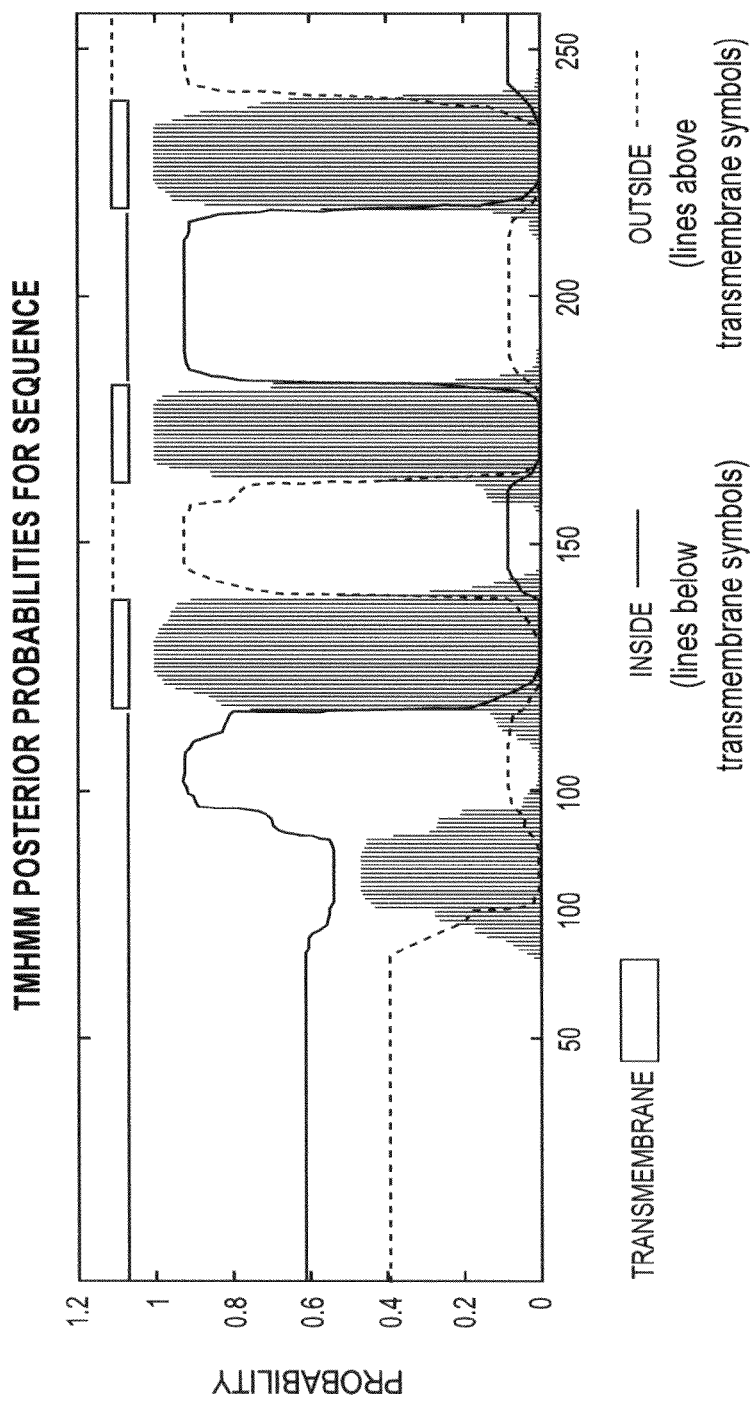
Figure 13H:
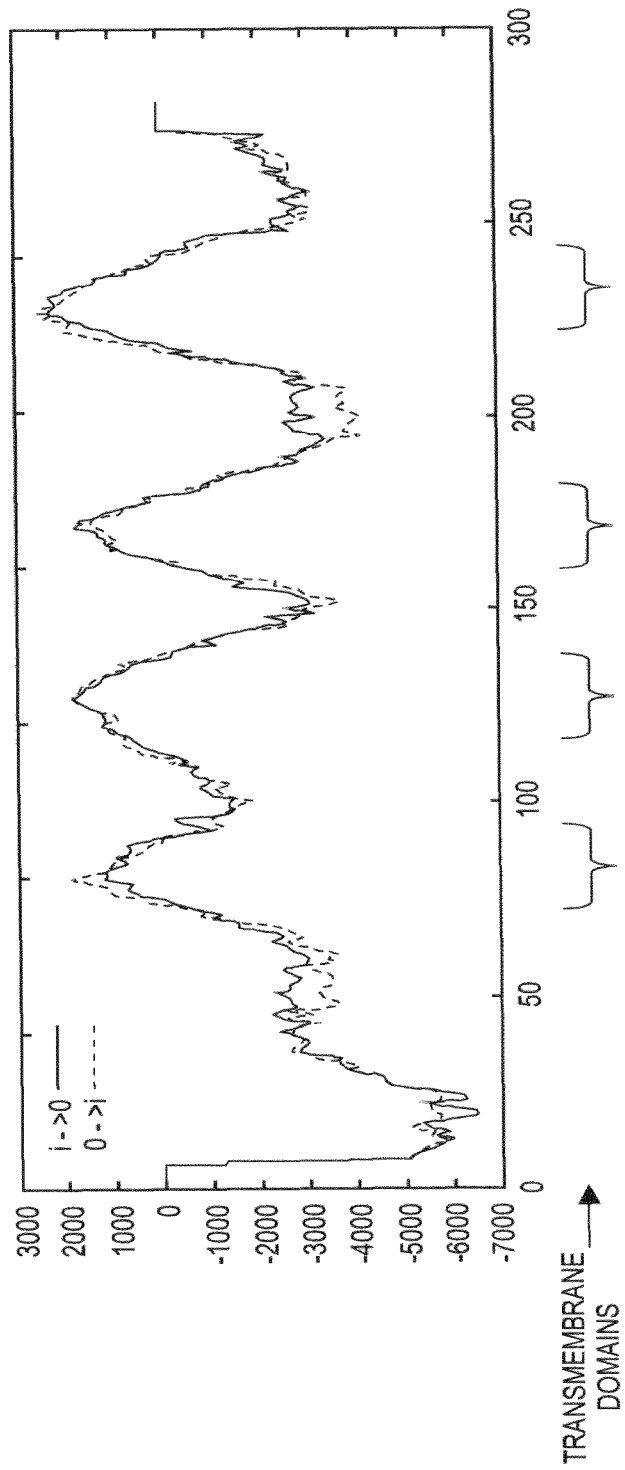
Figure 13I:
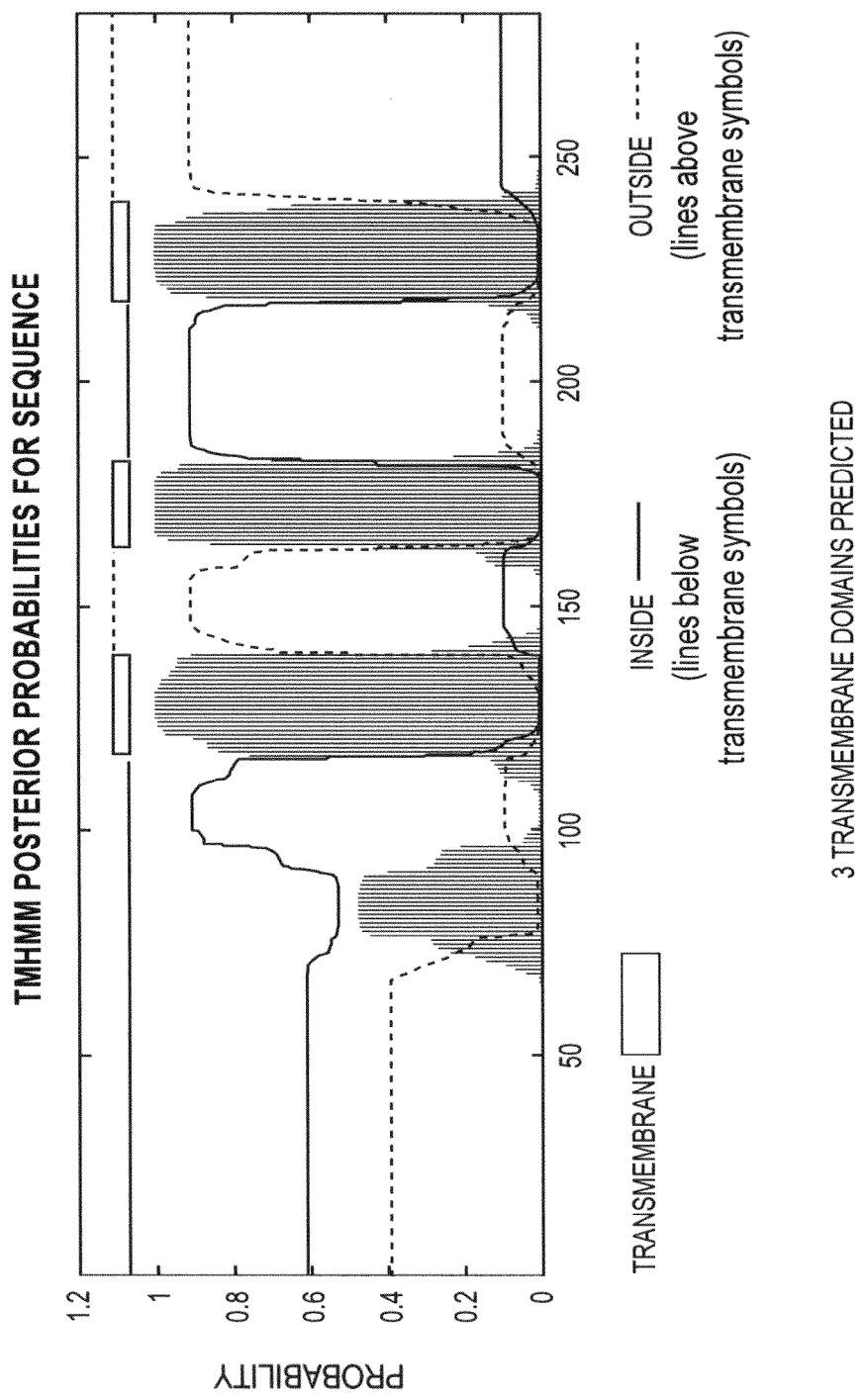

Analysis for the potential presence of transmembrane domains in STEAP-1 variants were carried out using a variety of transmembrane prediction algorithms accessed from the ExPasy molecular biology server located on the World Wide Web at (.expasy.ch/tools/). Shown graphically are the results of analysis of variant 1 depicting the presence and location of 6 transmembrane domains using the TMpred program (FIG. 13d) and TMHMM program (FIG. 13e). Also shown are the results of analysis of variant 2 depicting the presence and location of 4 transmembrane domains using TMpred (FIG. 13f) and 3 transmembrane domains using TMHMM (FIG. 13g). Analysis of variant 3 predicts the presence of 4 transmembrane domains using the TMpred (FIG. 13h) and 3 transmembrane domains with TMHMM (FIG. 13i). The results of each program, namely the amino acids encoding the transmembrane domains are summarized in Table XX.

Example 10

Generation of STEAP-1 Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with a full length STEAP-1 protein variant, computer algorithms are employed in design of immunogens that, based on amino acid sequence analysis contain characteristics of being antigenic and available for recognition by the immune system of the immunized host (see the Example entitled "Antigenicity Profiles and Secondary Structure"). Such regions would be predicted to be hydrophilic, flexible, in beta-turn conformations, and be exposed on the surface of the protein (see, e.g., FIGS. 5(a) and (b), FIGS. 6(a) and (b), FIGS. 7(a) and (b), FIGS. 8(a) and (b), and/or FIGS. 9(a) and (b) for amino acid profiles that indicate such regions of STEAP-1 protein variants 1 and 3).

For example, recombinant bacterial fusion proteins or peptides containing hydrophilic, flexible, beta-turn regions of STEAP-1 protein variants are used as antigens to generate polyclonal antibodies in New Zealand White rabbits or monoclonal antibodies as described in example entitled ("Generation of STEAP-1 Monoclonal Antibodies (MAbs). For example, such regions include, but are not limited to, amino acids 1-40, amino acids 143-165, amino acids 180-220, of STEAP-1 variants 1, 2, and 3, amino acids 312-339 of STEAP-1 variant 1, and amino acids 250-282 of STEAP-1 variant 3. It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 250-282 of STEAP-1 variant 3 is conjugated to KLH. This peptide is then used as immunogen. Alternatively the immunizing agent may include all or portions of the STEAP-1 variant proteins, analogs or fusion proteins thereof.

For example, the STEAP-1 variant 1 amino acid sequence can be fused using recombinant DNA techniques to any one of a variety of fusion protein partners that are well known in the art, such as glutathione-S-transferase (GST) and HIS tagged fusion proteins. In another embodiment, amino acids 250-282 of STEAP-1 variant 1 is fused to GST using recombinant techniques and the pGEX expression vector, expressed, purified and used to immunize a rabbit. Such fusion proteins are purified from induced bacteria using the appropriate affinity matrix.

Other recombinant bacterial fusion proteins that may be employed include maltose binding protein, LacZ, thioredoxin, NusA, or an immunoglobulin constant region (see the section entitled "Production of STEAP-1 in Prokaryotic Systems" and Current Protocols In Molecular Biology, Volume 2, Unit 16, Frederick M. Ausubul et al. eds., 1995; Linsley, P. S., Brady, W., Urnes, M., Grosmaire, L., Damle, N., and Ledbetter, L.(1991) J.Exp. Med. 174, 561-566).

In addition to bacterial derived fusion proteins, mammalian expressed protein antigens are also used. These antigens are expressed from mammalian expression vectors such as the Tag5 and Fc-fusion vectors (see the section entitled "Production of Recombinant STEAP-1 in Eukaryotic Systems"), and retain post-translational modifications such as glycosylations found in native protein. In one embodiment, amino acids 185-218 of STEAP-1 variant 1 were cloned into the Tag5 mammalian secretion vector, and expressed in 293T cells. The recombinant protein was purified by metal chelate chromatography from tissue culture supernatants of 293T cells stably expressing the recombinant vector. The purified Tag5 STEAP-1 variant 1 protein is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 μg, typically 100-200 μg, of fusion protein or peptide conjugated to KLH mixed in complete Freund's adjuvant (CFA). Rabbits are then injected subcutaneously every two weeks with up to 200 μg, typically 100-200 μg, of the immunogen in incomplete Freund's adjuvant (IFA). Test bleeds are taken approximately 7-10 days following each immunization and used to monitor the titer of the antiserum by ELISA.

To test reactivity and specificity of immune serum, such as the rabbit serum derived from immunization with the GST-fusion of STEAP-1 variant 1 protein, the full-length STEAP-1 variant 1 cDNA is cloned into pCDNA 3.1 myc-his expression vector (Invitrogen, see the Example entitled "Production of Recombinant STEAP-1 in Eukaryotic Systems"). After transfection of the constructs into 293T cells, cell lysates are probed with the anti-STEAP-1 serum and with anti-His antibody (Santa Cruz Biotechnologies, Santa Cruz, Calif.) to determine specific reactivity to denatured STEAP-1 protein using the Western blot technique. In addition, the immune serum is tested by fluorescence microscopy, flow cytometry and immunoprecipitation against 293T and other recombinant STEAP-1-expressing cells to determine specific recognition of native protein. Western blot, immunoprecipitation, fluorescent microscopy, and flow cytometric techniques using cells that endogenously express STEAP-1 are also carried out to test reactivity and specificity.

Anti-serum from rabbits immunized with STEAP-1 variant fusion proteins, such as GST and MBP fusion proteins, are purified by depletion of antibodies reactive to the fusion partner sequence by passage over an affinity column containing the fusion partner either alone or in the context of an irrelevant fusion protein. For example, antiserum derived from a GST-STEAP-1 variant 1 fusion protein is first purified by passage over a column of GST protein covalently coupled to AffiGel matrix (BioRad, Hercules, Calif.). The antiserum is then affinity purified by passage over a column composed of a MBP-STEAP-1 fusion protein covalently coupled to Affigel matrix. The serum is then further purified by protein G affinity chromatography to isolate the IgG fraction. Sera from other His-tagged antigens and peptide immunized rabbits as well as fusion partner depleted sera are affinity purified by passage over a column matrix composed of the original protein immunogen or free peptide.

Example 11

Generation of STEAP-1 Monoclonal Antibodies (MAbs)

In one embodiment, therapeutic MAbs to STEAP-1 variants comprise those that react with epitopes specific for each variant protein or specific to sequences in common between the variants that would bind, internalize, disrupt or modulate the biological function of the STEAP-1 variants, for example those that would disrupt the interaction with ligands and binding partners. Immunogens for generation of such MAbs include those designed to encode or contain the extracellular domain or the entire STEAP-1 protein variant sequence, regions predicted to contain functional motifs, and regions of the STEAP-1 protein variants predicted to be antigenic from computer analysis of the amino acid sequence (see, e.g., FIG. 5(a)-(b), FIG. 6(a)-(b), FIG. 7(a)-(b), FIG. 8(a)-(b), or FIG. 9(a)-(b), and the Example entitled "Antigenicity Profiles and Secondary Structure"). Immunogens include peptides, recombinant bacterial proteins, and mammalian expressed Tag 5 proteins and human and murine IgG FC fusion proteins. In addition, pTAG5 protein, DNA vectors encoding the pTAG5 cells engineered to express high levels of a respective STEAP-1 variant, such as 293T-STEAP-1 variant 1 or 3T3, RAT, or 300.19-STEAP-1 variant Imurine Pre-B cells, are used to immunize mice.

To generate MAbs to STEAP-1 variants, mice are first immunized intraperitoneally (IP) or in the foot pad with, typically, 10-50 µg of protein immunogen or 107 STEAP-1-expressing cells mixed in complete Freund's adjuvant. Examples of other adjuvants used are Titermax (Sigma) and Immuneasy (Qiagen). Mice are then subsequently immunized IP every 2-4 weeks with, typically, 10-50 µg of protein immunogen or $10^7$ cells mixed in incomplete Freund's adjuvant. Alternatively, MPL-TDM adjuvant is used in immunizations. In addition to the above protein and cell-based immunization strategies, a DNA-based immunization protocol is employed in which a mammalian expression vector encoding a STEAP-1 variant sequence is used to immunize mice by direct injection of the plasmid DNA. For example, amino acids 185-218 of STEAP-1 of variant 1 was cloned into the Tag5 mammalian secretion vector and the recombinant vector was used as immunogen. In another example, the same amino acids were cloned into an Fc-fusion secretion vector in which the STEAP-1 variant 1 sequence is fused at the amino-terminus to an IgK leader sequence and at the carboxyl-terminus to the coding sequence of the human or murine IgG Fc region. This recombinant vector was then used as immunogen. The plasmid immunization protocols were used in combination with purified proteins expressed from the same vector and with cells expressing the respective STEAP-1 variant. In another example, a monoclonal antibody to STEAP-1 variant 3 is generated by using a peptide encoding amino acids 250-282. The peptide is conjugated to KLH and used as immunogen. ELISA on free peptide is used to identify immunoreactive clones. Reactivity and specificity of the monoclonal antibodies to full length STEAP-1 variant 1 protein is monitored by Western blotting, immunoprecipitation, and flow cytometry using both recombinant and endogenous-expressing STEAP-1 variant 1 cells.

During the immunization protocol, test bleeds are taken 7-10 days following an injection to monitor titer and specificity of the immune response. Once appropriate reactivity and specificity is obtained as determined by ELISA, Western blotting, immunoprecipitation, fluorescence microscopy, and flow cytometric analyses, fusion and hybridoma generation is then carried out with established procedures well known in the art (see, e.g., Harlow and Lane, 1988).

The binding affinity of STEAP-1 variant 1 specific monoclonal antibodies was determined using standard technologies. Affinity measurements quantify the strength of antibody to epitope binding and are used to help define which STEAP-1 variant monoclonal antibodies preferred for diagnostic or therapeutic use, as appreciated by one of skill in the art. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

To generate monoclonal antibodies specific for other STEAP-1 variants, immunogens are designed to encode amino acid sequences unique to the variants. In one embodiment, a peptide encoding amino acids unique to STEAP-1 variants are synthesized, coupled to KLH, and used as immunogen. In another embodiment, peptides or bacterial fusion proteins are made that encompass the unique sequence generated by alternative splicing in the variants. Hybridomas are then selected that recognize the respective variant specific antigen and also recognize the full length variant protein expressed in cells. Such selection utilizes immunoassays described above such as Western blotting, immunoprecipitation, and flow cytometry.

In one embodiment, the invention provides for monoclonal antibodies designated X92.1.30.1.1(1) (a.k.a. M2/92.30) and X120.545.1.1 (a.k.a. M2.120.545). M2/92.30 and M2/120.545 were identified and are shown to react and bind with cell surface STEAP-1 (See, FIGS. 15 and 18). FIG. 16 shows that the anti-STEAP-1 MAb M2/92.30 binds endogenous cell surface STEAP-1 expressed in bladder and prostate cancer xenograft cells. Additionally, M2/92.30 reacts and binds with murine STEAP-1 as shown in FIG. 17.

The antibodies designated X92.1.30.1.1(1) (a.k.a. M2/92.30) and X120.545.1.1 (a.k.a. M2.120.545) were sent (via Federal Express) to the American Type Culture Collection (ATCC), P.O. Box 1549, Manassas, Va. 20108 on 06 Feb. 2004 and assigned Accession numbers PTA-5802 and PTA-5803 respectively.

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit and for at least five (5) years after the most recent request for the fUrnishing of a sample of the deposit received by the depository. The deposits will be made available by ATCC under the terms of the Budapest Treaty, and subject to an agreement between Genentech, Inc. and ATCC, which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

To clone the M2/X92.30 and M2/X120.545 antibodies the following protocols were used. Hybridoma cells were lysed with Trizol reagent (Life Technologies, Gibco BRL). Total RNA was purified and quantified. First strand cDNAs was generated from total RNA with oligo (dT)12-18 priming using the Gibco-BRL Superscript Preamplification system. PCR products were cloned into the pCRScript vector (Stratagene, La Jolla). Several clones were sequenced and the variable heavy ("VH") and variable light ("VL") chain regions determined. The nucleic acid and amino acid sequences of M2/X92.30 and M2/X120.545 variable heavy and light chain regions are listed in FIGS. 19(a)-19(d) and FIG. 20(a)-(e).

Example 12

Characterization of STEAP-1 Antibodies

A. Cell Surface Binding

Reactivity of STEAP-1 antibodies with a STEAP-1-related protein can be established by a number of well known means, including Western blot, immunoprecipitation, ELISA, and FACS analyses using, as appropriate, STEAP-1-related proteins, STEAP-1-expressing cells or extracts thereof. As shown in FIG. 15 FACS analysis of recombinant 3T3 and Rat-1 cells stably expressing either STEAP-1 or a control stained with anti-STEAP MAb M2/92.30 (10 ug/ml) and cell surface bound MAb was detected with a goat anti-mouse IgG-PE conjugate secondary reagent. The stained cells were then subjected to FACS analysis. As indicated by the fluorescent shift of the Rat1-STEAP1 and 3T3-STEAP1 cells compared to the respective control cells, M2/92.30 specifically binds to cell surface STEAP1.

In addition, when UGB1 bladder cancer cells and LAPC-9 prostate cancer cells were stained with 10 ug/ml of either MAb M2/92.30 or with a control anti-KLH MAb. Surface bound MAb 92.30 was detected with goat-anti-mouse IgG-PE conjugated secondary Ab. Stained cells were then subjected to FACS analysis. These results demonstrate that the anti-STEAP1 MAb M2/92.30 specifically binds endogenous cell surface STEAP1 expressed in bladder and prostate cancer xenograft cells (FIG. 21).

STEAP-1 M2/92.30 is also shown to bind to murine STEAP-1 protein (See FIG. 17). In this experiment 293T cells were transiently transfected with either pCDNA3.1 encoding the murine STEAP1 cDNA or with an empty vector. 48 hours later, the cells were harvested and stained with anti-STEAP1 MAb M2/92.30 (10 ug/ml) and cell surface bound MAb 92.30 was detected with a goat anti-mouse IgG-PE conjugate secondary reagent. Cells were then subjected to FACS analysis. STEAP-1 M2/92.30 was shown to bind specifically to STEAP-1-expressed 293T cells.

STEAP-1 M2/120.545 is also shown to specifically bind to STEAP-1 (See FIG. 18). 3T3-neo (Panel A, filled histograms) and 3T3-STEAP1 cells (Panel A, no fill histograms) and Rat1-neo (Panel B, filled histograms) and Rat1-STEAP cells (Panel B, no fill histograms) were stained with MAb M2/120.545 (10 ug/ml) and surface bound MAb was detected with goat anti-mouse IgG-PE conjugated secondary Ab. Cells were then subjected to FACS analysis. As indicated by the fluorescence shift of the 3T3-STEAP1 and Rat1-STEAP1 cells compared to their respective neo controls, MAb M2/120.545 specifically binds cell surface STEAP1. In Panel C, LNCaP cells were stained with either MAb M2/120.545 or a control anti-KLH MAb and subjected to FACS analysis as above. In Panel D, Fluorescence microscopy of the M2/120.545 stained LNCaP cells showing bright cell surface fluorescence.

Reactivity and specificity of M2/92.30 and M2/120.545 were also determined by immunoprecipitation. FIG. 25 shows 3T3-STEAP1 and 3T3-neo cells were lysed in RIPA buffer (25 mM Tris-Cl pH7.4; 150 mM NaCl, 0.5 mM EDTA, 1% Triton X-100, 0.5% deoxycholic acid, 0.1% SDS, and protease inhibitor cocktail). The cell lysates were precleared with protein G sepharose beads and then incubated with 5 ug of either MAb M2/92.30 or M2/120.545 for 2 hours at room temperature. Protein G beads were added and the mixture was further incubated for 1 hour. The immune complexes were washed and solubilized in SDS-PAGE sample buffer. The solubilized samples were then subjected to SDS-PAGE and Western blot analysis using a rabbit anti-STEAP pAb. Whole cell lysates of 293T cells transfected with STEAP1 was also run as a positive control. An immunoreactive band of ~37 kD was seen only in samples derived from 3T3-STEAP1 cells indicative of specific immunoprecipitation of STEAP1 by both M2/92.30 and M2/120.545 MAbs.

B. STEAP-1 Antibody Internalization

Immunotherapy based on the delivery of toxins towards specific cell targets using monoclonal antibodies is considered a modality in the therapy of malignancies. The general principle is the delivery of toxins or antineoplastic drugs to cancer cells with molecules that bind to antigens or receptors that are either uniquely expressed or overexpressed on the target cells relative to normal tissues.

Immunotoxins consist of cell selective ligands (usually monoclonal antibodies or cytokines) linked covalently to toxins. The interaction of antibody or ligand with cell surface receptors triggers internalization. In defined intracellular vesicle compartments, the toxin moiety escapes to the cytosol, where it catalytically alters critical cell functions leading to cell death. See, Frankel A E., Increased Sophistication of Immunotoxins, *Clinical cancer research* 8: 942-944, (2002) and Allen T M, Ligand-Targeted Therapeutics in Anti-cancer Therapy. *Nature Reviews*. 2:750-760, (2002).

Saporin is a ribosome-inactivating protein (RIP) that catalyzes the in vitro depurination of a specific adenine residue in large ribosomal RNAs. EndoY, et. al., Mechanism of Action of the Toxin Lectin Ricin on Eukaryotic Cells; The Site and Characteristics of the Modification in 28S RNA Caused by the Toxin, *J. Biol. Chem.* 262,5908-5912, (1987). It usually cannot enter cells unless complexed to an appropriate carrier molecule. Covalent conjugation of saporin to monoclonal antibodies that recognize tumor antigens produces immunotoxins that possess both cancer cell selectivity and are internalized. See, Flavell, D J, Sapoin Immunotoxins, *Curr. Top. Microbiol. Immunol.* 234: 51-61, (1998) and Flavell D J, et. al., Therapy of Human T-cell Acute Lymphoblastic Leukemia with a Combination of Anti-CD7 and Anti-CD38-Saporin Immunotoxins is Significantly Better than Therapy with Each Individual Immunotoxins. *Br. J. Cancer* 84: 571-578, (2001). These molecules have recently entered phase I clinical trails for leukemia and multiple myeloma. Foon K A. Monoclonal Antibody Therapies for Lymohomas. *Cancer J.* 6: 273-278, (2000).

The internalization of STEAP-1 M2/92.30 is shown in FIG. 22. In this experiment, PC3-STEAP1 cells were stained at 4 degrees C. with M2/120.545 MAb (10 ug/ml), washed, then incubated with goat anti-mouse IgG-PE conjugate secondary Ab. One-half of the cells were moved to 37 degrees C. for 30 minutes and the other half remained at 4 degrees C. Cells from each treatment were then subjected to fluorescent microscopy. Cells that remained at 4 degrees C. showed bright staining on the circumference of the cell surface. Cells that were moved to 37 degrees C. showed loss of the staining on the cell circumference and the appearance of punctate and aggregated fluorescence indicative of capping and internalization.

STEAP-1 internalization by STEAP1 M2/120.545 MAb is shown in FIG. 23. PC3-STEAP1 cells were stained at 4C with M2/120.545 MAb (10 ug/ml), washed, then incubated with goat anti-mouse IgG-PE conjugate secondary Ab. One-half of the cells were moved to 37C for 30 minutes and the other half remained at 4C. Cells from each treatment were then subjected to fluorescent microscopy. Cells that remained at 4C showed bright "ring-like" cell surface fluorescence. Cells that were moved to 37C showed loss of the "ring-like" cell surface fluorescence and the appearance of punctate and aggregated fluorescence indicative of capping and internalization.

One approach for selecting appropriate antibody candidates for immunotoxin delivery employs killing with a secondary antibody conjugated with a drug or toxin molecule. The secondary conjugated antibody piggybacks onto the primary antibody allowing the evaluation of the primary antibody to internalize and traffic to appropriate intracellular compartments. Once the conjugate is internalized, saporin breaks away from the targeting agent and inactivates the ribosomes to eliminate target cells. Kohls M D and Lappi D A. MAb-ZAP: A Tool for Evaluating Antibody Efficacy for Use in an Immunotoxin. *Bio Techniques*. 28(1): 162-165 (2000).

To select the appropriate antibody candidate using the above approach, a secondary immunotoxin, anti-mouse IgG—saporin conjugates (Advanced Targeting Systems, San Diego, Calif.) was used to demonstrate that murine Steap-1 M2/120.545 enters target cells via expression of Steap-1 on the cell surface of LNCaP cell. The following protocols were used. LNCap cells were plated at 5000 cells/90 μl/well in 96-well plate and incubated overnight. Second immunotoxin conjugates (anti-mouse IgG-saporine and anti-goat IgG-saporin) and anti-mouse IgG were made in cell medium containing the final concentration at 100 ng/ml. 10 μl were added to each well. The primary antibody is added at the concentration from 1-1000 ng/ml. The plates were incubated 72 hours and the viability was determined by MTT assay. The results in FIG. 24 show that LNCaP cells were killed in the presence of anti-mouse IgG-saporin. No effects were detected with either the secondary antibody alone (anti-mouse IgG) or nonspecific secondary antibody conjugates (anti-goat IgG saporin). No toxicity was observed with the primary antibody (M2/120.545) alone tested up to 1 μg/ml.

Example 13

HLA Class I and Class II Binding Assays

HLA class I and class II binding assays using purified HLA molecules are performed in accordance with disclosed protocols (e.g., PCT publications WO 94/20127 and WO 94/03205; Sidney et al., *Current Protocols in Immunology* 18.3.1 (1998); Sidney, et al., *J. Immunol*. 154:247 (1995); Sette, et al., *Mol. Immunol*. 31:813 (1994)). Briefly, purified MHC molecules (5 to 500 nM) are incubated with various unlabeled peptide inhibitors and 1-10 nM $^{125}$I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10-20% of the total radioactivity. All subsequent inhibition and direct binding assays are performed using these HLA concentrations.

Since under these conditions [label]<[HLA] and $IC_{50} \geqq$ [HLA], the measured $IC_{50}$ values are reasonable approximations of the true $K_D$ values. Peptide inhibitors are typically tested at concentrations ranging from 120 μg/ml to 1.2 ng/ml, and are tested in two to four completely independent experiments. To allow comparison of the data obtained in different experiments, a relative binding figure is calculated for each peptide by dividing the $IC_{50}$ of a positive control for inhibition by the ICso for each tested peptide (typically unlabeled versions of the radiolabeled probe peptide). For database purposes, and inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermofif and/or HLA motif-bearing peptides (see Table IV).

Example 14

Construction of "Minigene" Multi-Epitope DNA Plasmids

This example discusses the construction of a minigene expression plasmid. Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived STEAP-1, are selected such that multiple supermotifs/motifs are represented to ensure broad population coverage. Similarly, HLA class II epitopes are selected from STEAP-1 to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the li protein may be fused to one or more HTL epitopes as described in the art, wherein the CLIP sequence of the li protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (50° below the lowest calculated ™ of each primer pair) for 30 sec, and 72° C. for 1 min.

For example, a minigene is prepared as follows. For a first PCR reaction, 5 µg of each of two oligonucleotides are annealed and extended: In an example using eight oligonucleotides, i.e., four pairs of primers, oligonucleotides 1+2, 3+4, 5+6, and 7+8 are combined in 100 µl reactions containing Pfu polymerase buffer (1×=10 mM KCL, 10 mM $(NH4)_2SO_4$, 20 mM Tris-chloride, pH 8.75, 2 mM $MgSO_4$, 0.1% Triton X-100, 100 µg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 15

The Plasmid Construct and the Degree to Which It Induces Immunogenicity.

The degree to which a plasmid construct, for example a plasmid constructed in accordance with the previous Example, is able to induce immunogenicity is confirmed in vftro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683-692, 1996; Demotz et al., *Nature* 342:682-684, 1989); or the number of peptide-HLA class I complexes can be estimated by measuring the amount of lysis or lymphokine release induced by diseased or transfected target cells, and then determining the concentration of peptide necessary to obtain equivalent levels of lysis or lymphokine release (see, e.g., Kageyama et al., *J. Immunol.* 154:567-576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander et al., *Immunity* 1:751-761, 1994.

For example, to confirm the capacity of a DNA minigene construct containing at least one HLA-A2 supermotif peptide to induce CTLs in vivo, HLA-A2.1/Kb transgenic mice, for example, are immunized intramuscularly with 100 µg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}Cr$ release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, l-Ab-restricted mice, for example, are immunized intramuscularly with 100 µg of plasmid DNA. As a means of comparing the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^3H$-thymidine incorporation proliferation assay, (see, e.g., Alexander et al. Immunity 1:751-761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Barnett et al., *Aids Res. and Human Retrovinuses* 14, Supplement 3:S299-S309, 1998) or recombinant vaccinia, for example, expressing a minigene or DNA encoding the complete protein of interest (see, e.g., Hanke et al., *Vaccine* 16:439-445, 1998; Sedegah et al., *Proc. Natl. Acad. Sci USA* 95:7648-53, 1998; Hanke and McMichael, *Immunol. Letters* 66:177-181, 1999; and Robinson et al., *Nature Med.* 5:526-34, 1999).

For example, the efficacy of the DNA minigene used in a prime boost protocol is initially evaluated in transgenic mice. In this example, A2.1/$K^b$ transgenic mice are immunized IM with 100 µg of a DNA minigene encoding the immunogenic peptides including at least one HLA-A2 supermotif-bearing peptide. After an incubation period (ranging from 3-9 weeks), the mice are boosted IP with $10^7$ pfulmouse of a recombinant vaccinia virus expressing the same sequence encoded by the DNA minigene. Control mice are immunized with 100 μg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol."

Example 16

Polyepitopic Vaccine Compositions from Multiple Antigens

The STEAP-1 peptide epitopes of the present invention are used in conjunction with epitopes from other target tumor-associated antigens, to create a vaccine composition that is useful for the prevention or treatment of cancer that expresses STEAP-1 and such other antigens. For example, a vaccine composition can be provided as a single polypeptide that incorporates multiple epitopes from STEAP-1 as well as tumor-associated antigens that are often expressed with a target cancer associated with STEAP-1 expression, or can be administered as a composition comprising a cocktail of one or more discrete epitopes. Alternatively, the vaccine can be administered as a minigene construct or as dendritic cells which have been loaded with the peptide epitopes in vitro.

Example 17

Use of Peptides to Evaluate an Immune Response

Peptides of the invention may be used to analyze an immune response for the presence of specific antibodies, CTL or HTL directed to STEAP-1. Such an analysis can be performed in a manner described by Ogg et al., Science 279: 2103-2106, 1998. In this Example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, STEAP-1 HLA-A*0201-specific CTL frequencies from HLA A*0201-positive individuals at different stages of disease or following immunization comprising a STEAP-1 peptide containing an A*0201 motif. Tetrameric complexes are synthesized as described (Musey et al., N. Engl. J. Med. 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 μl of cold phosphate-buffered saline. Tricolor analysis is performed with the tetramer-phycoerythrin, along with anti-CD8-Tricolor, and anti-CD38. The PBMCs are incubated with tetramer and antibodies on ice for 30 to 60 m and then washed twice before formaldehyde fixation. Gates are applied to contain >99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the STEAP-1 epitope, and thus the status of exposure to STEAP-1, or exposure to a vaccine that elicits a protective or therapeutic response.

Example 18

Induction of Immune Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of "Minigene" Multi-Epitope DNA Plasmids" in the form of naked nucleic acid administered IM (or SC or ID) in the amounts of 0.5-5 mg at multiple sites. The nucleic acid (0.1 to 1000 μg) can also be administered using a gene gun. Following an incubation period of 3-4 weeks, a booster dose is then administered. The booster can be recombinant fowlpox virus administered at a dose of $5$-$10^7$ to $5 \times 10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve a therapeutic or protective immunity against STEAP-1 is generated.

Example 19

Complementary Polynucleotides

Sequences complementary to the STEAP-1-encoding sequences, or any parts thereof, are used to detect, decrease, or inhibit expression of naturally occurring STEAP-1. Although use of oligonucleotides comprising from about 15 to 30 base pairs is described, essentially the same procedure is used with smaller or with larger sequence fragments. Appropriate oligonucleotides are designed using, e.g., OLIGO 4.06 software (National Biosciences) and the coding sequence of STEAP-1. To inhibit transcription, a complementary oligonucleotide is designed from the most unique 5' sequence and used to prevent promoter binding to the coding sequence. To inhibit translation, a complementary oligonucleotide is designed to prevent ribosomal binding to a STEAP-1-encoding transcript.

Example 20

Purification of Naturally-occurring or Recombinant STEAP-1 Using STEAP-1-Specific Antibodies Naturally occurring or recombinant STEAP-1 is substantially purified by immunoaffinity chromatography using antibodies specific for STEAP-1. An immunoaffinity column is constructed by covalenUy coupling anti-STEAP-1 antibody to an activated chromatographic resin, such as CNBr-activated SEPHAROSE (Amersham Pharmacia Biotech). After the coupling, the resin is blocked and washed according to the manufacturer's instructions.

Media containing STEAP-1 are passed over the immunoaffinity column, and the column is washed under conditions that allow the preferential absorbance of STEAP-1 (e.g., high ionic strength buffers in the presence of detergent). The column is eluted under conditions that disrupt antibody/STEAP-1 binding (e.g., a buffer of pH 2 to pH 3, or a high concentration of a chaotrope, such as urea or thiocyanate ion), and GCR.P is collected.

Example 21

Identification of Molecules Which Interact with STEAP-1

STEAP-1, or biologically active fragments thereof, are labeled with 121 1 Bolton-Hunter reagent. (See, e.g., Bolton et al. (1973) Biochem. J. 133:529.) Candidate molecules previously arrayed in the wells of a multi-well plate are incubated with the labeled STEAP-1, washed, and any wells with labeled STEAP-1 complex are assayed. Data obtained using different concentrations of STEAP-1 are used to calculate values for the number, affinity, and association of STEAP-1 with the candidate molecules.

Example 22

In Vivo Assay for STEAP-1 Tumor Growth Promotion

The effect of the STEAP-1 protein on tumor cell growth is evaluated in vivo by evaluating tumor development and growth of cells expressing or lacking STEAP-1. For example, SCID mice are injected subcutaneously on each flank with $1 \times 10^6$ of either 3T3, or prostate cancer cell lines (e.g. PC3 cells) containing tkNeo empty vector or STEAP-1. At least two strategies may be used: (1) Constitutive STEAP-1 expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as ecdysone, tetracycline, etc., provided such promoters are compatible with the host cell systems. Tumor volume is then monitored by caliper measurement at the appearance of palpable tumors and followed over time to determine if STEAP-1-expressing cells grow at a faster rate and whether tumors produced by STEAP-1-expressing cells demonstrate characteristics of altered aggressiveness (e.g. enhanced metastasis, vascularization, reduced responsiveness to chemotherapeutic drugs).

Additionally, mice can be implanted with $1 \times 10^5$ of the same cells orthotopically to determine if STEAP-1 has an effect on local growth in the prostate, and whether STEAP-1 affects the ability of the cells to metastasize, specifically to lymph nodes, and bone (Miki T et al, Oncol Res. 2001; 12:209; Fu X et al, Int J Cancer. 1991, 49:938). The effect of STEAP on bone tumor formation and growth may be assessed by injecting prostate tumor cells intratibially.

The assay is also useful to determine the STEAP-1 inhibitory effect of candidate therapeutic compositions, such as for example, STEAP-1 intrabodies, STEAP-1 antisense molecules and ribozymes.

Example 23

STEAP-1 Monoclonal Antibody-mediated Inhibition of Tumors In Vivo

The significant expression of STEAP-1 in cancer tissues and surface localization, together with its restrictive expression in normal tissues makes STEAP-1 a good target for antibody therapy. Similarly, STEAP-1 is a target for T cell-based immunotherapy. Thus, the therapeutic efficacy of anti-STEAP-1 MAbs in human prostate cancer xenograft mouse models is evaluated by using recombinant cell lines such as PC3-STEAP-1, and 3T3-STEAP-1 (see, e.g., Kaighn, M. E. et al., Invest Urol, 1979. 17(1): 16-23), as well as human prostate xenograft models such as LAPC 9AD (Saffran et al PNAS 1999, 10:1073-1078).

Antibody efficacy on tumor growth and metastasis formation is studied, e.g., in a mouse orthotopic prostate cancer xenograft models. The antibodies can be unconjugated, as discussed in this Example, or can be conjugated to a therapeutic modality, as appreciated in the art. Anti-STEAP-1 MAbs inhibit formation of both lung and prostate xenografts. Anti-STEAP-1 MAbs also retard the growth of established orthotopic tumors and prolonged survival of tumor-bearing mice. These results indicate the utility of anti-STEAP-1 MAbs in the treatment of local and advanced stages prostate cancer. (See, e.g., Saffran, D., et al., PNAS 10:1073-1078 or world wide web URL pnas.org/cgi/doi/10.1073/pnas.051624698).

Administration of the anti-STEAP-1 MAbs led to retardation of established orthotopic tumor growth and inhibition of metastasis to distant sites, resulting in a significant prolongation in the survival of tumor-bearing mice. These studies indicate that STEAP-1 as an attractive target for immunotherapy and demonstrate the therapeutic potential of anti-STEAP-1 MAbs for the treatment of local and metastatic prostate cancer. This example demonstrates that unconjugated STEAP-1 monoclonal antibodies are effective to inhibit the growth of human prostate tumor xenografts grown in SCID mice; accordingly a combination of such efficacious monoclonal antibodies is also effective.

Tumor Inhibition using Multiple Unconjugated STEAP-1 MAbs

Materials and Methods

STEAP-1 Monoclonal Antibodies:

Monoclonal antibodies are raised against STEAP-1 as described in the Example entitled "Generation of STEAP-1 Monoclonal Antibodies (MAbs)." The antibodies are characterized by ELISA, Western blot, FACS, and immunoprecipitation for their capacity to bind STEAP-1. Epitope mapping data for the anti-STEAP-1 MAbs, as determined by ELISA and Western analysis, recognize epitopes on the STEAP-1 protein. Immunohistochemical analysis of prostate cancer tissues and cells with these antibodies is performed.

The monoclonal antibodies are purified from ascites or hybridoma tissue culture supernatants by Protein-G Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of UM-UC3 and CaLu1 tumor xenografts.

Cell Lines and Xenografts

The prostate cancer cell lines, PC3 and LNCaP cell line as well as the fibroblast line NIH 3T3 (American Type Culture Collection) are maintained in RPMI and DMEM respectively, supplemented with L-glutamine and 10% FBS.

PC3-STEAP-1 and 3T3-STEAP-1 cell populations are generated by retroviral gene transfer as described in Hubert, R. S., et al., Proc Natl Acad Sci U S A, 1999. 96(25): 14523.

The LAPC-9 xenograft, which expresses a wild-type androgen receptor and produces prostate-specific antigen (PSA), is passaged in 6- to 8-week-old male ICR-severe combined immunodeficient (SCID) mice (Taconic Farms) by s.c. trocar implant (Craft, N., et al., Nat Med. 1999, 5:280). Single-cell suspensions of LAPC-9 tumor cells are prepared as described in Craft, et al.

Xenograft Mouse Models.

Subcutaneous (s.c.) tumors are generated by injection of $1\times10^6$ cancer cells mixed at a 1:1 dilution with Matrigel (Collaborative Research) in the right flank of male SCID mice. To test antibody efficacy on tumor formation, i.e. antibody injections are started on the same day as tumor-cell injections. As a control, mice are injected with either purified mouse IgG (ICN) or PBS; or a purified monoclonal antibody that recognizes an irrelevant antigen not expressed in human cells. In preliminary studies, no difference is found between mouse IgG or PBS on tumor growth. Tumor sizes are determined by caliper measurements, and the tumor volume is calculated as length×width×height. Mice with Subcutaneous tumors greater than 1.5 cm in diameter are sacrificed.

Orthotopic injections are performed under anesthesia by using ketamine/xylazine. For prostate orthotopic studies, an incision is made through the abdomen to expose the prostate and LAPC or PC3 tumor cells ($5\times10^5$) mixed with Matrigel are injected into the prostate capsule in a 10-µl volume. To monitor tumor growth, mice are palpated and blood is collected on a weekly basis to measure PSA levels. The mice are segregated into groups for the appropriate treatments, with anti-STEAP-1 or control MAbs being injected i.p.

Anti-STEAP-1 MAbs Inhibit Growth of STEAP-1-Expressing Xenograft-Cancer Tumors

The effect of anti-STEAP-1 MAbs on tumor formation is tested by using LNCaP and LAPC-9 orthotopic models. As compared with the s.c. tumor model, the orthotopic model, which requires injection of tumor cells directly in the mouse prostate, respectively, results in a local tumor growth, development of metastasis in distal sites, deterioration of mouse health, and subsequent death (Saffran, D., et al., PNAS supra). The features make the orthotopic model more representative of human disease progression and allowed us to follow the therapeutic effect of MAbs on clinically relevant end points.

Accordingly, tumor cells are injected into the mouse prostate, and 2 days later, the mice are segregated into two groups and treated with either: a) 200-500 µg, of anti-STEAP-1 Ab, or b) PBS three times per week for two to five weeks.

A major advantage of the orthotopic cancer models is the ability to study the development of metastases. Formation of metastasis in mice bearing established orthotopic tumors is studies by IHC analysis on lung sections using an antibody against a tumor-specific cell-surface protein such as anti-CK20 for prostate cancer (Lin S et at, Cancer Detect Prev. 2001;25:202).

Another advantage of xenograft cancer models is the ability to study neovascularization and angiogenesis. Tumor growth is partly dependent on new blood vessel development. Although the capillary system and developing blood network is of host origin, the initiation and architecture of the neovasculature is regulated by the xenograft tumor (Davidoff A M et at, Clin Cancer Res. 2001;7:2870; Solesvik O et al., Eur J Cancer Clin Oncol. 1984, 20:1295). The effect of antibody and small molecule on neovascularization is studied in accordance with procedures known in the art, such as by IHC analysis of tumor tissues and their surrounding microenvironment.

Mice bearing established orthotopic tumors are administered 1OOOpg injections of either anti-STEAP-1 MAb or PBS over a 4-week period. Mice in both groups are allowed to establish a high tumor burden, to ensure a high frequency of metastasis formation in mouse lungs. Mice then are killed and their bladders, livers, bone and lungs are analyzed for the presence of tumor cells by IHC analysis. These studies demonstrate a broad anti-tumor efficacy of anti-STEAP-1 antibodies on initiation and progression of prostate cancer in xenograft mouse models. Anti-STEAP-1 antibodies inhibit tumor formation of tumors as well as retarding the growth of already established tumors and prolong the survival of treated mice. Moreover, anti-STEAP-1 MAbs demonstrate a dramatic inhibitory effect on the spread of local prostate tumor to distal sites, even in the presence of a large tumor burden. Thus, anti-STEAP-1 MAbs are efficacious on major clinically relevant end points (tumor growth), prolongation of survival, and health.

Effect of STEAP-1 MAbs on the Growth of Human Prostate Cancer Xenografts in Mice Male ICR-SCID mice, 5-6 weeks old (Charles River Laboratory, Wilmington, Mass. were used. The mice were maintained in a controlled environment using the protocols set forth in the *NIH Guide for the Care and Use of Laboratory Animals*. A LAPC-9 AD androgen-dependent human prostate cancer tumor was used to establish xenograft models. Stock tumors regularly maintained in SCID mice were sterilely dissected, minced, and digested using Pronase (Calbiochem, San Diego, Calif.). Cell suspensions generated were incubated overnight at 37 degrees C. to obtain a homogeneous single-cell suspension.

STEAP-1 M2/92.30 and M2/120.545 were tested at two different doses of 100 µg and 500 µg. PBS and anti-KLH MAb were used as controls. The study cohort consisted of 6 groups with 10 mice in each group. MAbs were dosed IP twice a week for a total of 12 doses, starting the same day as tumor cell injection.

Tumor size was monitored through caliper measurements twice a week. The longest dimension (L) and the dimension perpendicular to it (W) were taken to calculate tumor volume using the formula: $W^2 \times L/2$. Serum PSA concentration at treatment day 40 for each animal was measured using commercial ELISA kit. The Kruskal-Wallis test and the Mann-Whitney U test were used to evaluate differences of tumor growth and PSA level among groups. All tests were two-sided with á=0.05.

The results of the experiment set forth in FIG. 26 and FIG. 27 show that STEAP-1 M2/92.30 and M2/120.545 significantly retard the growth of human prostate xenograft in a dose-dependent manner.

Example 24

Therapeutic and Diagnostic use of Anti-STEAP-1 Antibodies in Humans

Anti-STEAP-1 monoclonal antibodies are safely and effectively used for diagnostic, prophylactic, prognostic and/or therapeutic purposes in humans. Western blot and immunohistochemical analysis of cancer tissues and cancer xenografts with anti-STEAP-1 MAb show strong extensive staining in carcinoma but significantly lower or undetectable levels in normal tissues. Detection of STEAP-1 in carcinoma and in metastatic disease demonstrates the usefulness of the MAb as a diagnostic and/or prognostic indicator. Anti-STEAP-1 antibodies are therefore used in diagnostic applications such as immunohistochemistry of kidney biopsy specimens to detect cancer from suspect patients.

As determined by flow cytometry, anti-STEAP-1 MAb specifically binds to carcinoma cells. Thus, anti-STEAP-1 antibodies are used in diagnostic whole body imaging applications, such as radioimmunoscintigraphy and radioimmunotherapy, (see, e.g., Potamianos S., et. al. Anticancer Res 20(2A):925-948 (2000)) for the detection of localized and metastatic cancers that exhibit expression of STEAP-1. Shedding or release of an extracellular domain of STEAP-1 into the extracellular milieu, such as that seen for alkaline phosphodiesterase B10 (Meerson, N. R., Hepatology 27:563-568 (1998)), allows diagnostic detection of STEAP-1 by anti-STEAP-1 antibodies in serum and/or urine samples from suspect patients.

Anti-STEAP-1 antibodies that specifically bind STEAP-1 are used in therapeutic applications for the treatment of cancers that express STEAP-1. Anti-STEAP-1 antibodies are used as an unconjugated modality and as conjugated form in which the antibodies are attached to one of various therapeutic or imaging modalities well known in the art, such as a prodrugs, enzymes or radioisotopes. In preclinical studies, unconjugated and conjugated anti-STEAP-1 antibodies are tested for efficacy of tumor prevention and growth inhibition in the SCID mouse cancer xenograft models, e.g., kidney cancer models AGS-K3 and AGS-K6, (see, e.g., the Example entitled "STEAP-1 Monoclonal Antibody-mediated Inhibition of Bladder and Lung Tumors In Vivo"). Either conjugated and unconjugated anti-STEAP-1 antibodies are used as a therapeutic modality in human clinical trials either alone or in combination with other treatments as described in following Examples.

Example 25

Human Clinical Trials for the Treatment and Diagnosis of Human Carcinomas through use of Human Anti-STEAP-1 Antibodies In vivo Antibodies are used in accordance with the present invention which recognize an epitope on STEAP-1, and are used in the treatment of certain tumors such as those listed in Table I. Based upon a number of factors, including STEAP-1 expression levels, tumors such as those listed in Table I are presently preferred indications. In connection with each of these indications, three clinical approaches are successfully pursued.

I.) Adjunctive therapy: In adjunctive therapy, patients are treated with anti-STEAP-1 antibodies in combination with a chemotherapeutic or antineoplastic agent and/or radiation therapy. Primary cancer targets, such as those listed in Table I, are treated under standard protocols by the addition anti-STEAP-1 antibodies to standard first and second line therapy. Protocol designs address effectiveness as assessed by reduction in tumor mass as well as the ability to reduce usual doses of standard chemotherapy. These dosage reductions allow additional and/or prolonged therapy by reducing dose-related toxicity of the chemotherapeutic agent. Anti-STEAP-1 antibodies are utilized in several adjunctive clinical trials in combination with the chemotherapeutic or antineoplastic agents adriamycin (advanced prostate carcinoma), cisplatin (advanced head and neck and lung carcinomas), taxol (breast cancer), and doxorubicin (preclinical).

II.) Monotherapy: In connection with the use of the anti-STEAP-1 antibodies in monotherapy of tumors, the antibodies are administered to patients without a chemotherapeutic or antineoplastic agent. In one embodiment, monotherapy is conducted clinically in end stage cancer patients with extensive metastatic disease. Patients show some disease stabilization. Trials demonstrate an effect in refractory patients with cancerous tumors.

III.) Imaging Agent: Through binding a radionuclide (e.g., iodine or yttrium ($I^{131}$, $Y^{90}$) to anti-STEAP-1 antibodies, the radiolabeled antibodies are utilized as a diagnostic and/or imaging agent. In such a role, the labeled antibodies localize to both solid tumors, as well as, metastatic lesions of cells expressing STEAP-1. In connection with the use of the anti-STEAP-1 antibodies as imaging agents, the antibodies are used as an adjunct to surgical treatment of solid tumors, as both a pre-surgical screen as well as a post-operative follow-up to determine what tumor remains and/or returns. In one embodiment, a ($^{111}$In)-STEAP-1 antibody is used as an imaging agent in a Phase I human clinical trial in patients having a carcinoma that expresses STEAP-1 (by analogy see, e.g., Divgi et al. *J. Natl. Cancer Inst.* 83:97-104 (1991)). Patients are followed with standard anterior and posterior gamma camera. The results indicate that primary lesions and metastatic lesions are identified.

Dose and Route of Administration

As appreciated by those of ordinary skill in the art, dosing considerations can be determined through comparison with the analogous products that are in the clinic. Thus, anti-STEAP-1 antibodies can be administered with doses in the range of 5 to 400 mg/m$^2$, with the lower doses used, e.g., in connection with safety studies. The affinity of anti-STEAP-1 antibodies relative to the affinity of a known antibody for its target is one parameter used by those of skill in the art for determining analogous dose regimens. Further, anti-STEAP-1 antibodies that are fully human antibodies, as compared to the chimeric antibody, have slower clearance; accordingly, dosing in patients with such fully human anti-STEAP-1 antibodies can be lower, perhaps in the range of 50 to 300 mg/M², and still remain efficacious. Dosing in mg/m², as opposed to t conventional measurement of dose in mg/kg, is a measurement based on surface area and is a convenient dosing measurement that is designed to include patients of all sizes from infants to adults.

Three distinct delivery approaches are useful for delivery of anti-STEAP-1 antibodies. Conventional intravenous delivery is one standard delivery technique for many tumors. However, in connection with tumors in the peritoneal cavity, such as tumors of the ovaries, biliary duct, other ducts, and the like, intraperitoneal administration may prove favorable for obtaining high dose of antibody at the tumor and to also minimize antibody clearance. In a similar manner, certain solid tumors possess vasculature that is appropriate for regional perfusion. Regional perfusion allows for a high dose of antibody at the site of a tumor and minimizes short term clearance of the antibody.

Clinical Development Plan (CDP)

Overview: The CDP follows and develops treatments of anti-STEAP-1 antibodies in connection with adjunctive therapy, monotherapy, and as an imaging agent. Trials initially demonstrate safety and thereafter confirm efficacy in repeat doses. Trails are open label comparing standard chemotherapy with standard therapy plus anti-STEAP-1 antibodies. As will be appreciated, one criteria that can be utilized in connection with enrollment of patients is STEAP-1 expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express STEAP-1. Standard tests and follow-up are utilized to monitor each of these safety concerns. Anti-STEAP-1 antibodies are found to be safe upon human administration.

Example 26

Human Clinical Trial: Monotherapy with Human Anti-STEAP-1 Antibody

Anti-STEAP-1 antibodies are safe in connection with the above-discussed adjunctive trial, a Phase II human clinical trial confirms the efficacy and optimum dosing for monotherapy. Such trial is accomplished, and entails the same safety and outcome analyses, to the above-described adjunctive trial with the exception being that patients do not receive chemotherapy concurrently with the receipt of doses of anti-STEAP-1 antibodies.

Example 27

Human Clinical Trial: Diagnostic Imaging with Anti-STEAP-1 Antibody

Once again, as the adjunctive therapy discussed above is safe within the safety criteria discussed above, a human clinical trial is conducted concerning the use of anti-STEAP-1 antibodies as a diagnostic imaging agent. The protocol is designed in a substantially similar manner to those described in the art, such as in Divgi et al. *J. Natl. Cancer Inst.* 83:97-104 (1991). The antibodies are found to be both safe and efficacious when used as a diagnostic modality.

Example 28

Human Clinical Trial Adjunctive Therapy with Human Anti-STEAP-1 Antibody and Chemotherapeutic, Radiation, and/or Hormone Ablation Therapy A phase I human clinical trial is initiated to assess the safety of six intravenous doses of a human anti-STEAP-1 antibody in connection with the treatment of a solid tumor, e.g., a cancer of a tissue listed in Table I. In the study, the safety of single doses of anti-STEAP-1 antibodies when utilized as an adjunctive therapy to an antineoplastic or chemotherapeutic or hormone ablation agent as defined herein, such as, without limitation: cisplatin, topotecan, doxorubicin, adriamycin, taxol, Lupron, Zoladex, Eulexin, Casodex, Anandron or the like, is assessed. The trial design includes delivery of six single doses of an anti-STEAP-1 antibody with dosage of antibody escalating from approximately about 25 mg/M² to about 275 mg/m² over the course of the treatment in accordance with the following schedule:

|  | Day 0 | Day 7 | Day 14 | Day 21 | Day 28 | Day 35 |
| --- | --- | --- | --- | --- | --- | --- |
| MAb Dose | 25 mg/m² | 75 mg/m² | 125 mg/m² | 175 mg/m² | 225 mg/m² | 275 mg/m² |
| Chemotherapy (standard dose) | + | + | + | + | + | + |

Patients are closely followed for one-week following each administration of antibody and chemotherapy. In particular, patients are assessed for the safety concerns mentioned above: (i) cytokine release syndrome, i.e., hypotension, fever, shaking, chills; (ii) the development of an immunogenic response to the material (i.e., development of human antibodies by the patient to the human antibody therapeutic, or HAHA response); and, (iii) toxicity to normal cells that express STEAP-1. Standard tests and follow-up are utilized to monitor each of these safety concerns. Patients are also assessed for clinical outcome, and particularly reduction in tumor mass as evidenced by MRI or other imaging.

The anti-STEAP-1 antibodies are demonstrated to be safe and efficacious, Phase II trials confirm the efficacy and refine optimum dosing.

Example 29

Identification and Confirmation of Potential Signal Transduction Pathways

Many mammalian proteins have been reported to interact with signaling molecules and to participate in regulating signaling pathways. (J Neurochem. 2001; 76:217-223). Fibronecion in particular has been associated with the MAPK signaling cascade that control cell mitogenesis (Jiang F, Jia Y, Cohen I. Blood. 2002, 99:3579). In addition, the STEAP-1 protein contains several phosphorylation sites (see Table XXI) indicating an association with specific signaling cascades. Using immunoprecipitation and Western blotting techniques, proteins are identified that associate with STEAP-1 and mediate signaling events. Several pathways known to play a role in cancer biology can be regulated by STEAP-1, including phospholipid pathways such as PI3K, AKT, etc, adhesion and migration pathways, including FAK, Rho, Rac-1, ☐catenin, etc, as well as mitogenic/survival cascades such as ERK, p38, etc (Cell Growth Differ. 2000,11:279; J Biol Chem. 1999, 274:801; Oncogene. 2000, 19:3003, J. Cell Biol. 1997, 138:913.).). In order to determine whether expression of STEAP-1 is sufficient to regulate specific signaling pathways not otherwise active in resting PC3 cells, the effect of these genes on the activation of the p38 MAPK cascade was investigated in the prostate cancer cell line PC3. Activation of the p38 kinase is dependent on its phosphorylation on tyrosine and serine residues. Phosphorylated p38 can be distinguished from the non-phosphorylated state by a Phospho-p38 MAb. This phospho-specific Ab was used to study the phosphorylation state of p38 in engineered PC3 cell lines.

PC3 cells were transfected with neomycin resistance gene alone or with STEAP-1 in pSRa vector. Cells were grown overnight in 0.5% FBS, then stimulated with 10% FBS for 5 minutes with or without 10 µg/ml MEK inhibitor PD98058. Cell lysates were resolved by 12.5% SDS-PAGE and Western blotted with anti-phospho-ERK (Cell Signaling) and anti-ERK(Zymed). NIH-3T3 cells were transfected with neomycin resistance gene alone or with STEAP-1 in pSRa vector. Cells were treated as above but without the MEK inhibitor. In addition, NIH-3T3-Neo cells were treated with 10 mg/ml Na salycilate. Expression of STEAP-1 induces the phosphorylation of ERK-1 and ERK-2 in serum and was inhibited by the upstream MEK kinase inhibitor PD98058.

In another set of experiments, the sufficiency of expression of STEAP-1 in the prostate cancer cell line PC3 to activate the mitogenic MAPK pathway, namely the ERK cascade, was examined. Activation of ERK is dependent on its phosphorylation on tyrosine and serine residues. Phosphorylated ERK can be distinguished from the non-phosphorylated state by a Phospho-ERK MAb. This phospho-specific Ab was used to study the phosphorylation state of ERK in engineered PC3 cell lines. PC3 cells, expressing an activated form of Ras, were used as a positive control.

The results show that while expression of the control neo gene has no effect on ERK phosphorylation, expression of STEAP-1 in PC3 cells is sufficient to induce an increase in ERK phosphorylation (FIG. 28). These results were verified using anti-ERK western blotting and confirm the activation of the ERK pathway by STEAP-1.

Since FBS contains several components that may contribute to receptor-mediated ERK activation, we examined the effect of STEAP-1 in low and optimal levels of FBS. PC3 cells expressing neo or STEAP-1 were grown in either 0.1% or 10% FBS overnight. The cells were analyzed by anti-Phospho-ERK western blotting. This experiment shows that STEAP-1 induces the phosphorylation of ERK in 0.1% FBS, and confirms that expression of STEAP-1 is sufficient to induce activation of the ERK signaling cascade in the absence of additional stimuli.

To confirm that STEAP-1 directly or indirectly activates known signal transduction pathways in cells, luciferase (luc) based transcriptional reporter assays are carried out in cells expressing individual genes. These transcriptional reporters contain consensus-binding sites for known transcription factors that lie downstream of well-characterized signal transduction pathways. The reporters and examples of these associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress
7. TCF-luc, TCF/Lef; ☐-catenin, Adhesion/invasion Gene-mediated effects can be assayed in cells showing mRNA expression. Luciferase reporter plasmids can be introduced by lipid-mediated transfection (TFX-50, Promega). Luciferase activity, an indicator of relative transcriptional activity, is measured by incubation of cell extracts with luciferin substrate and luminescence of the reaction is monitored in a luminometer.

Signaling pathways activated by STEAP-1 are mapped and used for the identification and validation of therapeutic targets. When STEAP-1 is involved in cell signaling, it is used as target for diagnostic, prognostic, preventative and/or therapeutic purposes.

Example 30

Involvement of STEAP-1 in Small Molecule Transport and Cell-cell Communication Cell-cell communication is essential in maintaining organ integrity and homeostasis, both of which become deregulated during tumor formation and progression. Intercellular communications can be measured using two types of assays (J. Biol. Chem. 2000, 275:25207). In the first assay, cells loaded with a fluorescent dye are incubated in the presence of unlabeled recipient cells and the cell populations are examined under fluorescent microscopy. This qualitative assay measures the exchange of dye between adjacent cells. In the second assay system, donor and recipient cell populations are treated as above and quantitative measurements of the recipient cell population are performed by FACS analysis. Using these two assay systems, cells expressing STEAP-1 are compared to controls that do not express STEAP-1, and it is found that STEAP-1 enhances cell communications. FIG. 29 demonstrate that STEAP-1 mediates the transfer of the small molecule calcein between adjacent cells, and thereby regulates cell-cell communication in prostate cancer cells. In this experiment, recipient PC3 cells were labeled with dextran- Texas Red and donor PC3 cells were labeled with calcein AM (green). The donor (green) and recipient (red) cells were co-cultured at 37° C. and analyzed by microscopy for the co-localization of Texas red and calcein. The results demonstrated that while PC3 control cells (no detectable STEAP-1 protein expression) exhibit little calcein transfer, the expression of STEAP-1 allows the transfer of small molecules between cells, whereby the initially red recipient cells take on a brownish color, and co-localize the red and green molecules. Small molecules and/or antibodies that modulate cell-cell communication mediated by STEAP-1 are used as therapeutics for cancers that express STEAP-1. FIG. 30 demonstrates that expression of STEAP-1 is necessary on both donor and recipient populations for the transfer of small molecules to take place. In this experiment, PC3 cells were transfected with neomycin resistance gene alone or with STEAP-1 in pSRa vector. Recipient cells were labeled with 1 mg/ml dextran-Texas Red and donor cells were tabled with 2.5 μg/ml calcein AM. The donor (green) and recipient (red) cells were co-cultured at 37° C. for 18-24 hours and analyzed by microscopy for the co-localization of fluorescent dyes. Upper panels: light microscopy; lower panels: UV fluorescence. Left panels: PC3-Neo cells were both donor and recipient. Center panels: PC3-Neo were donor cells and PC3-STEAP-1 were recipient. Right panels: PC3-STEAP-1 cells were both donor and recipient. Only when STEAP-1 was expressed on both donor and recipient was cell-cell communication detected.

The results show that co-culturing of control PC3 and PC3 cells fail to mediate calcein transfer. Similarly, co-incubation of control PC3 and PC3-STEAP-1 does not allow the transfer of calcein. However, co-culturing PC3-STEAP-1 donor and PC3-STEAP-1 recipient cells mediates small molecule transfer as depicted by co-localization of green and red pigments in the same cells. Taken together, the data shown in FIGS. 29 and 30 demonstrate that STEAP-1 mediates small molecule transfer and regulates cell-cell communication by forming intercellular communication channels that are similar in function to gap junctions.

Additionally, STEAP-1 M2/120.545 effect on Gap junction was confirmed (See, FIG. 31). In this experiment, PC3 cells were transfected with neomycin resistance gene alone or with STEAP-1 in pSRα vector. Recipient cells were labeled with 1 mg/ml dextran-Texas Red and donor cells were labeled with 2.5 μg/ml calcein AM. The donor (green) and recipient (red) cells were co-cultured at 37° C. for 18-24 hours and analyzed by microscopy for the co-localization of fluorescent dyes. In all experiments, the same cells were used as donor and acceptor. Cells were incubated with the indicated amounts of STEAP-1/120.545 MAb for 10 minutes prior to plating and MAb was maintained in the culture for 24 hours prior to analysis. STEAP1/120.545 reduces STEAP-1 mediated gap junction in a dose-dependent manner. The results show that STEAP-1/120.545 reduces STEAP-1 mediated gap junction in a dose-dependent manner.

Thus, because STEAP-1 functions in cell-cell communication and small molecule transport, it is used as a target or marker for diagnostic, prognostic, preventative and/or therapeutic purposes.

Example 31

RNA Interference (RNAi)

RNA interference (RNAi) technology is implemented to a variety of cell assays relevant to oncology. RNAi is a post-transcriptional gene silencing mechanism activated by double-stranded RNA (dsRNA). RNAi induces specific mRNA degradation leading to changes in protein expression and subsequently in gene function. In mammalian cells, these dsRNAs called short interfering RNA (siRNA) have the correct composition to activate the RNAi pathway targeting for degradation, specifically some mRNAs. See, Elbashir S. M., et. al., *Duplexes of* 21-*nucleotide RNAs Mediate RNA interference in Cultured Mammalian Cells*, Nature 411(6836): 494-8 (2001). Thus, RNAi technology is used successfully in mammalian cells to silence targeted genes.

Loss of cell proliferation control is a hallmark of cancerous cells; thus, assessing the role of STEAP-1 in cell survival/proliferation assays is relevant. Accordingly, RNAi was used to investigate the function of the STEAP-1 antigen. To generate siRNA for STEAP-1, algorithms were used that predict oligonucleotides that exhibit the critical molecular parameters (G:C content, melting temperature, etc.) and have the ability to significantly reduce the expression levels of the STEAP-1 protein when introduced into cells. Accordingly, one targeted sequence for the STEAP-1 siRNA is: 5' AAGCT-CATTCTAGCGGGAAAT 3' (SEQ ID NO: 81). In accordance with this Example, STEAP-1 siRNA compositions are used that comprise siRNA (double stranded, short interfering RNA) that correspond to the nucleic acid ORF sequence of the STEAP-1 protein or subsequences thereof. Thus, siRNA subsequences are used in this manner are generally 5, 6, 7, 8, 9, 10, 11, 12, 13, 14, 15, 16, 17, 18, 19, 20, 21, 22, 23, 24, 25, 26, 27, 28, 29, 30,31, 32, 33, 34, 35 or more than 35 contiguous RNA nucleotides in length. These siRNA sequences are complementary and non-complementary to at least a portion of the mRNA coding sequence. In a preferred embodiment, the subsequences are 19-25 nucleotides in length, most preferably 21-23 nucleotides in length. In preferred embodiments, these siRNA achieve knockdown of STEAP-1 antigen in cells expressing the protein and have functional effects as described below.

The selected siRNA (STEAP-1.b oligo) was tested in numerous cell lines in the survival/proliferation MTS assay (measures cellular metabolic activity). Tetrazolium-based colorimetric assays (i.e., MTS) detect viable cells exclusively, since living cells are metabolically active and therefore can reduce tetrazolium salts to colored formazan compounds; dead cells, however do not. Moreover, this STEAP-1.b oligo achieved knockdown of STEAP-1 antigen in cells expressing the protein and had functional effects as described below using the following protocols.

Mammalian siRNA transfections: The day before siRNA transfection, the different cell lines were plated in media (RPMI 1640 with 10% FBS w/o antibiotics) at $2\times10^3$ cells/well in 80 μl (96 well plate format) for the survival/MTS assay. In parallel with the STEAP-1 specific siRNA oligo, the following sequences were included in every experiment as controls: a) Mock transfected cells with Lipofectamine 2000 (Invitrogen, Carlsbad, Calif.) and annealing buffer (no siRNA); b) Luciferase-4 specific siRNA (targeted sequence: 5'-MGGGACGAAGACGAACACUUCTT-3') (SEQ ID NO: 82); and, c) Eg5 specific siRNA (targeted sequence: 5'-MCT-GAAGACCTGMGACMTAA-3') (SEQ ID NO: 83). SiRNAs were used at 10 nM and 1 μg/ml Lipofectamine 2000 final concentration.

The procedure was as follows: The siRNAs were first diluted in OPTIMEM (serum-free transfection media, Invitrogen) at 0.1 μM IM (10-fold concentrated) and incubated 5-10 min RT. Lipofectamine 2000 was diluted at 10 μg/ml (10-fold concentrated) for the total number transfections and incubated 5-10 minutes at room temperature (RT). Appropriate amounts of diluted 10-fold concentrated Lipofectamine 2000 were mixed 1:1 with diluted 10-fold concentrated siRNA and incubated at RT for 20-30" (5-fold concentrated transfection solution). 20 µls of the 5-fold concentrated transfection solutions were added to the respective samples and incubated at 37° C. for 96 hours before analysis.

MTS assay: The MTS assay is a colorimetric method for determining the number of viable cells in proliferation, cytotoxicity or chemosensitivity assays based on a tetrazolium compound [3-(4,5-dimethylthiazol-2-yl)-5-(3-carboxymethoxyphenyl)-2-(4-sulfophenyl)-2H-tetrazolium, inner salt; MTS(b)] and an electron coupling reagent (phenazine ethosulfate; PES). Assays were performed by adding a small amount of the Solution Reagent directly to culture wells, incubating for 1-4 hours and then recording absorbance at 490 nm with a 96-well plate reader. The quantity of colored formazan product as measured by the amount of 490 nm absorbance is directly proportional to the mitochondrial activity and/or the number of living cells in culture.

In order to address the function of STEAP-1 in cells, STEAP-1 was silenced by transfecting the endogenously expressing STEAP-1 cell lines. As shown in FIG. 32, ERK-1 and ERK-2 phosphorylation were both induced by 10% serum, and were inhibitedby M2/92.30 MAb and siRNA to STEAP-1. In this experiment, PC3 cells were transfected with neomycin resistance gene alone or with STEAP-1 and MAb in pSHa vector. For RNAi knockdown, PCE-STEAP-1 cells were stably transfected with a pPUR-U6-27-STEAP-1 vector containing siRNA to STEAP-1. Cells were starved in 0.1% FBS for 18 hours at 37° C., placed on ice for 10 minutes without or with 10 µg/ml M2/92.30 MAb, brought to RT for 3 minutes stimulated with 10% FBS for 5 minutes. Cells were lysed in RIPA buffer, whole cell lysates resolved by 12.5% SDS-PAGE and proteins detected by Western blotting. Phospho-ERK was detected with rabbit antiserum (Cell Signaling) and ERK was detected with rabbit anti-ERK (Zymed). STEAP-1 was detected with sheep anti-STEAP-1 and actin was detected with anti-actin MAb (Santa Cruz).

Additionally, As shown in FIG. 33, Specific STEAP-1 RNAi stably expressed in PC3-STEAP-1 cells reduces the STEAP-1 induced cell-cell communication. In this experiment, PC3 cells were transfected with neomycin resistance gene alone or with STEAP-1 in pSRα vector. For RNAi knockdown, PCE-STEAP-1 cells were stably transfected with a pPUR-U6-27-STEAP-1 vector containing siRNA to STEAP-1 or an empty vector. Recipient cells were labeled with 1 mg/ml dextran-Texas Red and donor cells were labeled with 2.5 µg/ml calcein AM. The donor (green) and recipient (red) cells were co-cultured at 37° C. for 18-24 hours and analyzed by microscopy for the co-localization of fluorescent dyes. In all experiments, the same cells were used as donor and acceptor.

Another embodiment of the invention is a method to analyze STEAP-1 related cell proliferation is the measurement of DNA synthesis as a marker for proliferation. Labeled DNA precursors (i.e. $^3$H-Thymidine) are used and their incorporation to DNA is quantified. Incorporation of the labeled precursor into DNA is directly proportional to the amount of cell division occurring in the culture. Another method used to measure cell proliferation is performing clonogenic assays. In these assays, a defined number of cells are plated onto the appropriate matrix and the number of colonies formed after a period of growth following siRNA treatment is counted.

In STEAP-1 cancer target validation, complementing the cell survival/proliferation analysis with apoptosis and cell cycle profiling studies are considered. The biochemical hallmark of the apoptotic process is genomic DNA fragmentation, an irreversible event that commits the cell to die. A method to observe fragmented DNA in cells is the immunological detection of histone-complexed DNA fragments by an immunoassay (i.e. cell death detection ELISA) which measures the enrichment of histone-complexed DNA fragments (mono- and oligo-nucleosomes) in the cytoplasm of apoptotic cells. This assay does not require pre-labeling of the cells and can detect DNA degradation in cells that do not proliferate in vitro (i.e. freshly isolated tumor cells).

The most important effector molecules for triggering apoptotic cell death are caspases. Caspases are proteases that when activated cleave numerous substrates at the carboxy-terminal site of an aspartate residue mediating very early stages of apoptosis upon activation. All caspases are synthesized as pro-enzymes and activation involves cleavage at aspartate residues. In particular, caspase 3 seems to play a central role in the initiation of cellular events of apoptosis. Assays for determination of caspase 3 activation detect early events of apoptosis. Following RNAi treatments, Western blot detection of active caspase 3 presence or proteolytic cleavage of products (i.e. PARP) found in apoptotic cells further support an active induction of apoptosis. Because the cellular mechanisms that result in apoptosis are complex, each has its advantages and limitations. Consideration of other criteria/endpoints such as cellular morphology, chromatin condensation, membrane blebbing, apoptotic bodies help to further support cell death as apoptotic. Since not all the gene targets that regulate cell growth are anti-apoptotic, the DNA content of permeabilized cells is measured to obtain the profile of DNA content or cell cycle profile. Nuclei of apoptotic cells contain less DNA due to the leaking out to the cytoplasm (sub-G1 population). In addition, the use of DNA stains (i.e., propidium iodide) also differentiate between the different phases of the cell cycle in the cell population due to the presence of different quantities of DNA in G0/G1, S and G2/M. In these studies the subpopulations can be quantified.

For the STEAP-1 gene, RNAi studies facilitate the understanding of the contribution of the gene product in cancer pathways. Such active RNAi molecules have use in identifying assays to screen for MAbs that are active anti-tumor therapeutics. Further, siRNA are administered as therapeutics to cancer patients for reducing the malignant growth of several cancer types, including those listed in Table 1. When STEAP-1 plays a role in cell survival, cell proliferation, tumorigenesis, or apoptosis, it is used as a target for diagnostic, prognostic, preventative and/or therapeutic purposes.

Example 32

Modulation of STEAP-1 Function

Ion transport plays an important role regulating cell growth intracellular permeability, molecular trafficking and signal transduction (Minke B. Cell Mol Neurobiol. 2001, 21:629; Golovina et al, Am J Physiol Heart Circ Physiol. 2001, 280: H746) these are functions that are especially relevant to the neoplastic condition. Cell-cell communication regulates homeostasis, cell proliferation and cell death (Evans W H, Martin P E. Mol Membr Biol. 2002 19:121; Carruba G, et al, Ann N Y Acad Sci. 2002, 963:156) these functions too are especially relevant to the neoplastic condition.

Using control cell lines and cell lines expressing STEAP-1, inhibitors of STEAP-1 function are identified. For example, PC3 and PC3-STEAP-1 cells can be incubated in the presence and absence of MAb or small molecule inhibitors. The effect of these MAb or small molecule inhibitors are investigated using the ion flux, cell communication, proliferation and signaling assays described above.

Signal transduction and biological output mediated by transporters can be modulated through various mechanisms, including inhibition of receptor and ligand binding, ion antagonists, protein interactions, regulation of ion and small molecule transport, etc (Tang W et al, Front Biosci 2002, 7:1583). Using control cell lines and cell lines expressing STEAP-1, modulators (inhibitors or enhancers) of STEAP-1 function are identified. For example, PC3 and PC3-STEAP-1 cells are incubated in the presence and absence of MAb or small molecule modulators. In view of the functions of STEAP-1 disclosed herein, modulators that are ion channel blockers used in the context of the present invention include such compounds as amlodipine, azulene, dihydropyridines, thianines, nifedine, verapamil and their derivatives (Tanaka Y, Shigenobu K. Cardiovasc Drug Rev. 2001, 19:297; Djuric D, Mitrovic V, Jakovljevic V. Arzneimittelforschung. 2002, 52:365; Kourie J I, Wood H B. Prog Biophys Mol Biol. 2000;73:91); and, modulators that are inhibitors of cell communication used in the context of the present invention include such compounds as beta-glycyrrhetinic acid, retinoids, TPA (Krutovskikh V A et al, Oncogene. 2002, 21:1989; Rudkin et al, J Surg Res. 2002, 103:183; Ruch J et al, J Cell Biochem. 2001, 83:163). Accordingly, the effect(s) of MAb or small molecule inhibitors are investigated using the ion flux, cell communication, proliferation and signaling assays described Examples above.

When MAb and small molecules modulate, e.g., inhibit, the transport and tumorigenic function of STEAP-1, they are used for preventative, prognostic, diagnostic and/or therapeutic purposes.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

Tissues that Express STEAP-1 when malignant:

Prostate
Bladder
Kidney
Colon
Lung
Pancreas
Ovary
Breast
Stomach
Rectum
Lymphoma

TABLE II

Amino Acid Abbreviations

| SINGLE LETTER | THREE LETTER | FULL NAME |
| --- | --- | --- |
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III(a)

Amino Acid Substitution Matrix
Adapted from the GCG Software 9.0 BLOSUM62 amino acid substitution matrix
(block substitution matrix). The higher the value, the more likely a substitution is found
in related, natural proteins. (See world wide web URL ikp.unibe.ch/manual/blosum62.html)

| A | C | D | E | F | G | H | I | K | L | M | N | P | Q | R | S | T | V | W | Y | . |
| --- | --- | --- | --- | --- | --- | --- | --- | --- | --- | --- | --- | --- | --- | --- | --- | --- | --- | --- | --- | --- |
| 4 | 0 | −2 | −1 | −2 | 0 | −2 | −1 | −1 | −1 | −1 | −2 | −1 | −1 | −1 | 1 | 0 | 0 | −3 | −2 | A |
| | 9 | −3 | −4 | −2 | −3 | −3 | −1 | −3 | −1 | −1 | −3 | −3 | −3 | −3 | −1 | −1 | −1 | −2 | −2 | C |
| | | 6 | 2 | −3 | −1 | −1 | −3 | −1 | −4 | −3 | 1 | −1 | 0 | −2 | 0 | −1 | −3 | −4 | −3 | D |
| | | | 5 | −3 | −2 | 0 | −3 | 1 | −3 | −2 | 0 | −1 | 2 | 0 | 0 | −1 | −2 | −3 | −2 | E |
| | | | | 6 | −3 | −1 | 0 | −3 | 0 | 0 | −3 | −4 | −3 | −3 | −2 | −2 | −1 | 1 | 3 | F |
| | | | | | 6 | −2 | −4 | −2 | −4 | −3 | 0 | −2 | −2 | −2 | 0 | −2 | −3 | −2 | −3 | G |
| | | | | | | 8 | −3 | −1 | −3 | −2 | 1 | −2 | 0 | 0 | −1 | −2 | −3 | −2 | 2 | H |
| | | | | | | | 4 | −3 | 2 | 1 | −3 | −3 | −3 | −3 | −2 | −1 | 3 | −3 | −1 | I |
| | | | | | | | | 5 | −2 | −1 | 0 | −1 | 1 | 2 | 0 | −1 | −2 | −3 | −2 | K |
| | | | | | | | | | 4 | 2 | −3 | −3 | −2 | −2 | −2 | −1 | 1 | −2 | −1 | L |
| | | | | | | | | | | 5 | −2 | −2 | 0 | −1 | −1 | −1 | 1 | −1 | −1 | M |
| | | | | | | | | | | | 6 | −2 | 0 | 0 | 1 | 0 | −3 | −4 | −2 | N |
| | | | | | | | | | | | | 7 | −1 | −2 | −1 | −1 | −2 | −4 | −3 | P |
| | | | | | | | | | | | | | 5 | 1 | 0 | −1 | −2 | −2 | −1 | Q |
| | | | | | | | | | | | | | | 5 | −1 | −1 | −3 | −3 | −2 | R |
| | | | | | | | | | | | | | | | 4 | 1 | −2 | −3 | −2 | S |
| | | | | | | | | | | | | | | | | 5 | 0 | −2 | −2 | T |

TABLE III(a)-continued

Amino Acid Substitution Matrix
Adapted from the GCG Software 9.0 BLOSUM62 amino acid substitution matrix
(block substitution matrix). The higher the value, the more likely a substitution is found
in related, natural proteins. (See world wide web URL ikp.unibe.ch/manual/blosum62.html)

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
|   |   |   |   |   |   |   |   |   |   |   |   |   |   |   |   |   | 4 | -3 | -1 | V |
|   |   |   |   |   |   |   |   |   |   |   |   |   |   |   |   |   |   | 11 | 2 | W |
|   |   |   |   |   |   |   |   |   |   |   |   |   |   |   |   |   |   |   | 7 | Y |

TABLE III(b)

| Original residue | Conservative substitution |
|---|---|
| Ala (A) | Gly; Ser; Val |
| Arg (R) | Lys |
| Asn (N) | Gln; His |
| Asp (D) | Glu |
| Cys (C) | Ser |
| Gln (Q) | Asn, His |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile; Val |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu; Ala |

TABLE IV

HLA Class I/II Motifs/Supermotifs

TABLE IV (A)

| | HLA Class I Supermotifs/Motifs | | |
|---|---|---|---|
| | POSITION 2 (Primary Anchor) | POSITION 3 (Primary Anchor) | POSITION C Terminus (Primary Anchor) |
| SUPERMOTIF | | | |
| A1 | TILVMS | | FWY |
| A2 | LIVMATQ | | IVMATL |
| A3 | VSMATLI | | RK |
| A24 | YFWIVLMT | | FIYWLM |
| B7 | P | | VILFMWYA |
| B27 | RHK | | FYLWMIVA |
| B44 | ED | | FWYLIMVA |
| B58 | ATS | | FWYLIVMA |
| B62 | QLIVMP | | FWYMIVLA |
| MOTIFS | | | |
| A1 | TSM | | Y |
| A1 | | DEAS | Y |
| A2.1 | LMVQIAT | | VLIMAT |
| A3 | LMVISATFCGD | | KYRHFA |
| A11 | VTMLISAGNCDF | | KRYH |
| A24 | YFWM | | FLIW |
| A*3101 | MVTALIS | | RK |
| A*3301 | MVALFIST | | RK |
| A*6801 | AVTMSLI | | RK |
| B*0702 | P | | LMFWYAIV |
| B*3501 | P | | LMFWYIVA |
| B51 | P | | LIVFWYAM |
| B*5301 | P | | IMFWYALV |
| B*5401 | P | | ATIVLMFWY |

Bolded residues are preferred, italicized residues are less preferred: A peptide is considered motif-bearing if it has primary anchors at each primary anchor position for a motif or supermotif as specified in the above table.

Bolded residues are preferred, italicized residues are less preferred: A peptide is considered motif-bearing if it has primary anchors at each primary anchor position for a motif or supermotif as specified in the above table.

TABLE IV (B)

| HLA Class II Supermotif | | |
|---|---|---|
| 1 | 6 | 9 |
| W, F, Y, V, .I, L | A, V, I, L, P, C, S, T | A, V, I, L, C, S, T, M, Y |

TABLE IV (C)

| | | HLA Class II Motifs | | | | | | | |
|---|---|---|---|---|---|---|---|---|---|
| MOTIFS | | 1° anchor 1 | 2 | 3 | 4 | 5 | 1° anchor 6 | 7 | 8 | 9 |
| DR4 | preferred | FMYLIVW | M | T | | I | VSTCPALIM | MH | | MH |
|  | deleterious | | | | W | | | R | | WDE |
| DR1 | preferred | MFLIVWY | | | PAMQ | | VMATSPLIC | M | | AVM |
|  | deleterious | | C | CH | FD | CWD | | GDE | D | |
| DR7 | preferred | MFLIVWY | M | W | A | | IVMSACTPL | M | | IV |
|  | deleterious | | C | | G | | | GRD | N | G |

TABLE IV (C)-continued

HLA Class II Motifs

| MOTIFS | | 1° anchor 1 | 2 | 3 | 4 | 5 | 1° anchor 6 | 7 | 8 | 9 |
|---|---|---|---|---|---|---|---|---|---|---|
| DR3 | MOTIFS | 1° anchor 1 | 2 | 3 | 1° anchor 4 | 5 | 1° anchor 6 | | | |
| Motif a preferred | | LIVMFY | | | D | | | | | |
| Motif b preferred | | LIVMFAY | | | DNQEST | | KRH | | | |
| DR Supermotif | | MF*LIVWY* | | | | | VMSTA*CPLI* | | | |

Italicized residues indicate less preferred or "tolerated" residues

TABLE IV (D)

HLA Class I Supermotifs

| SUPERMOTIFS | | 1 | 2 | 3 | 4 | 5 | 6 | 7 | 8 | C-terminus |
|---|---|---|---|---|---|---|---|---|---|---|
| A1 | | | 1° Anchor TI*LVMS* | | | | | | | 1° Anchor FWY |
| A2 | | | 1° Anchor LIVM*ATQ* | | | | | | | 1° Anchor LIVMAT |
| A3 | Preferred deleterious | DE (3/5); P (5/5) | 1° Anchor VSMA*TLI* | YFW (4/5) DE (4/5) | | | YFW (3/5) | YFW (4/5) | P (4/5) | 1° Anchor RK |
| A24 | | | 1° Anchor YF*WIVLMT* | | | | | | | 1° Anchor FIY*WLM* |
| B7 | Preferred deleterious | FWY (5/5) LIVM (3/5) DE (3/5); P (5/5); G (4/5); A (3/5); QN (3/5) | 1° Anchor P | FWY (4/5) | | DE (3/5) | G (4/5) | QN (4/5) | FWY (3/5) DE (4/5) | 1° Anchor VILF*MWYA* |
| B27 | | | 1° Anchor RHK | | | | | | | 1° Anchor FYL*WMIVA* |
| B44 | | | 1° Anchor E*D* | | | | | | | 1° Anchor FWYLIMVA |
| B58 | | | 1° Anchor ATS | | | | | | | 1° Anchor FWY*LIVMA* |
| B62 | | | 1° Anchor Q*LIVMP* | | | | | | | 1° Anchor FWY*MIVLA* |

Italicized residues indicates less preferred or "tolerated" residues

TABLE IV (E)

HLA Class I Motifs

| | | 1 | 2 | 3 | 4 | 5 | 6 | 7 | 8 | 9 or C-terminus | C-terminus |
|---|---|---|---|---|---|---|---|---|---|---|---|
| A1 9-mer | preferred | GFYW | 1° Anchor STM | DEA | YFW | | P | DEQN | YFW | 1° Anchor Y | |
| | deleterious | DE | | RHKLIVMP | A | G | A | | | | |
| A1 9-mer | preferred | GRHK | ASTCLIVM | 1° Anchor DE*AS* | GSTC | | ASTC | LIVM | DE | 1° Anchor Y | |
| | deleterious | A | RHKDEPYFW | | DE | PQN | RHK | PG | GP | | |
| A1 10-mer | preferred | YFW | 1° Anchor STM | DEAQN | A | YFWQN | | PASTC | GDE | P | 1° Anchor Y |
| | deleterious | GP | | RHKGLIVM | DE | RHK | QNA | RHKYFW | RHK | A | |
| A1 10-mer | preferred | YFW | STCLIVM | 1° Anchor DE*AS* | A | YFW | | PG | G | YFW | 1° Anchor Y |
| | deleterious | RHK | RHKDEPYFW | | | P | G | | PRHK | QN | |
| A2.1 9-mer | preferred | YFW | 1° Anchor LM*IVQAT* | YFW | STC | YFW | | A | P | 1° Anchor V*LIMAT* | |
| | deleterious | DEP | | DERKH | | | | RKH | DERKH | | |

TABLE IV (E)-continued

HLA Class I Motifs

| | | POSITION: | | | | | | | | | C-Terminus |
|---|---|---|---|---|---|---|---|---|---|---|---|
| | | 1 | 2 | 3 | 4 | 5 | 6 | 7 | 8 | 9 | |
| A2.1 10-mer | preferred | AYFW | 1° Anchor LM*IVQAT* | LVIM | G | | G | | FYWLVIM | | 1° Anchor V*LIMAT* |
| | deleterious | DEP | | DE | RKHA | P | | RKH | DERKH RKH | | |
| A3 | preferred | RHK | 1° Anchor LMVISATFCGD | YFW | PRHKYFW | A | YFW | | P | 1° Anchor KYR*HFA* | |
| | deleterious | DEP | | DE | | | | | | | |
| A11 | preferred | A | 1° Anchor VTLMISAGN*CDF* | YFW | YFW | A | YFW | YFW | P | 1° Anchor K*RYH* | |
| | deleterious | DEP | | | | | | A | G | | |
| A24 9-mer | preferred | YFWRHK | 1° Anchor YFW*M* | | STC | | | YFW | YFW | 1° Anchor FLIW | |
| | deleterious | DEG | | DE | G | QNP | DERHK | G | AQN | | |
| A24 10-mer | Preferred | | 1° Anchor YFW*M* | | P | YFWP | | P | | | 1° Anchor FLIW |
| | Deleterious | | | GDE | QN | RHK | DE | A | QN | DEA | |
| A3101 | Preferred | RHK | 1° Anchor MVT*ALIS* | YFW | P | | YFW | YFW | AP | 1° Anchor R*K* | |
| | Deleterious | DEP | | DE | | ADE | DE | DE | DE | | |
| A3301 | Preferred | | 1° Anchor MVALF*IST* | YFW | | | | AYFW | | 1° Anchor RK | |
| | Deleterious | GP | | DE | | | | | | | |
| A6801 | Preferred | YFWSTC | 1° Anchor AVT*MSLI* | | | YFW LIVM | | YFW | P | 1° Anchor RK | |
| | deleterious | GP | | DEG | | RHK | | | A | | |
| B0702 | Preferred | RHKFWY | 1° Anchor P | RHK | | RHK | RHK | RHK | PA | 1° Anchor LMF*WYAIV* | |
| | deleterious | DEQNP | | DEP | DE | DE | GDE | QN | DE | | |
| B3501 | Preferred | FWYLIVM | 1° Anchor P | FWY | | | | FWY | | 1° Anchor LMFWY*IVA* | |
| | deleterious | AGP | | | | G | G | | | | |

| | | POSITION | | | | | | | | | C-terminus |
|---|---|---|---|---|---|---|---|---|---|---|---|
| | | 1 | 2 | 3 | 4 | 5 | 6 | 7 | 8 | 9 or C-terminus | |
| A1 9-mer | preferred | GFYW | 1° Anchor STM | DEA | YFW | | P | DEQN | YFW | 1° Anchor Y | |
| | deleterious | DE | | RHKLIVMP | A | G | A | | | | |
| A1 9-mer | preferred | GRHK | ASTCLIVM | 1° Anchor DE*AS* | GSTC | | A STC | LIVM | DE | 1° Anchor Y | |
| | deleterious | A | RHKDEP YFW | | DE | PQN | RHK | PG | GP | | |
| | deleterious | AGP | | | | G | G | | | | |

TABLE IV (E)-continued

HLA Class I Motifs

| | | | | | | | | | | | |
|---|---|---|---|---|---|---|---|---|---|---|---|
| B51 | Preferred | LIVMFWY | 1° Anchor P | FWY | STC | FWY | | G | | FWY | 1° Anchor LIVF*WYAM* |
| | deleterious | AGPDERHKSTC | | | | DE | G | | DEQN | GDE | |
| B5301 | preferred | LIVMFWY | 1° Anchor P | FWY | STC | FWY | | LIVM FWY | | FWY | 1° Anchor IMFWY*ALV* |
| | deleterious | AGPQN | | | | | G | | RHKQN | DE | |
| B5401 | preferred | FWY | 1° Anchor P | FWYLIVM | | LIVM | | ALIVM | | FWYAP | 1° Anchor ATIV*LMFWY* |
| | deleterious | GPQNDE | | GDESTC | | RHKDE | DE | QNDGE | | DE | |

TABLE IV (F)

Summary of HLA-supertypes
Overall phenotypic frequencies of HLA-supertypes in different ethnic populations

| | Specificity | | Phenotypic frequency | | | | | |
|---|---|---|---|---|---|---|---|---|
| Supertype | Position 2 | C-Terminus | Caucasian | N.A. Black | Japanese | Chinese | Hispanic | Average |
| B7 | P | AILMVFWY | 43.2 | 55.1 | 57.1 | 43.0 | 49.3 | 49.5 |
| A3 | AILMVST | RK | 37.5 | 42.1 | 45.8 | 52.7 | 43.1 | 44.2 |
| A2 | AILMVT | AILMVT | 45.8 | 39.0 | 42.4 | 45.9 | 43.0 | 42.2 |
| A24 | YF (WIVLMT) | FI (YWLM) | 23.9 | 38.9 | 58.6 | 40.1 | 38.3 | 40.0 |
| B44 | E (D) | FWYLIMVA | 43.0 | 21.2 | 42.9 | 39.1 | 39.0 | 37.0 |
| A1 | TI (LVMS) | FWY | 47.1 | 16.1 | 21.8 | 14.7 | 26.3 | 25.2 |
| B27 | RHK | FYL (WMI) | 28.4 | 26.1 | 13.3 | 13.9 | 35.3 | 23.4 |
| B62 | QL (IVMP) | FWY (MIV) | 12.6 | 4.8 | 36.5 | 25.4 | 11.1 | 18.1 |
| B58 | ATS | FWY (LIV) | 10.0 | 25.1 | 1.6 | 9.0 | 5.9 | 10.3 |

TABLE IV (G)

Calculated population coverage afforded by different HLA-supertype combinations

| | Phenotypic frequency | | | | | |
|---|---|---|---|---|---|---|
| HLA-supertypes | Caucasian | N.A Blacks | Japanese | Chinese | Hispanic | Average |
| A2, A3 and B7 | 83.0 | 86.1 | 87.5 | 88.4 | 86.3 | 86.2 |
| A2, A3, B7, A24, B44 and A1 | 99.5 | 98.1 | 100.0 | 99.5 | 99.4 | 99.3 |
| A2, A3, B7, A24, B44, A1, B27, B62, and B58 | 99.9 | 99.6 | 100.0 | 99.8 | 99.9 | 99.8 |

Motifs indicate the residues defining supertype specificites. The motifs incorporate residues determined on the basis of published data to be recognized by multiple alleles within the supertype. Residues within brackets are additional residues also predicted to be tolerated by multiple alleles within the supertype.

TABLE IV(h)

Frequently Occurring Motifs

| Name | avrg. % identity | Description | Potential Function |
|---|---|---|---|
| zf-C2H2 | 34% | Zic finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| Ig | 19% | Immunoglobulin domain | domains are one hundred amino acids long and include a conserved intradomain disulfide bond. |

TABLE IV(h)-continued

Frequently Occurring Motifs

| Name | avrg. % identity | Description | Potential Function |
|---|---|---|---|
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| Pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| Rvt | 49% | Reverse transcriptase (RNA-dependent DNA polymerase) | |
| Ank | 25% | Ank repeat | Cytoplasmic protein, associates integral membrane proteins to the cytoskeleton |
| Oxidored_q1 | 32% | NADH-Ubiquinone/plastoquinone (complex I), various chains | membrane associated. Involved in proton translocation across the membrane |
| Efhand | 24% | EF hand | calcium-binding domain, consists of a 12 residue loop flanked on both sides by a 12 residue alpha-helical domain |
| Rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| Fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE IV(I)

Examples of Medical Isotopes:

| Isotope | Description of use |
|---|---|
| Actinium-225 (AC-225) | See Thorium-229 (Th-229) |
| Actinium-227 (AC-227) | Parent of Radium-223 (Ra-223) which is an alpha emitter used to treat metastases in the skeleton resulting from cancer (i.e., breast and prostate cancers), and cancer radioimmunotherapy |
| Bismuth-212 (Bi-212) | See Thorium-228 (Th-228) |
| Bismuth-213 (Bi-213) | See Thorium-229 (Th-229) |
| Cadmium-109 (Cd-109) | Cancer detection |
| Cobalt-60 (Co-60) | Radiation source for radiotherapy of cancer, for food irradiators, and for sterilization of medical supplies |
| Copper-64 (Cu-64) | A positron emitter used for cancer therapy and SPECT imaging |
| Copper-67 (Cu-67) | Beta/gamma emitter used in cancer radioimmunotherapy and diagnostic studies (i.e., breast and colon cancers, and lymphoma) |
| Dysprosium-166 (Dy-166) | Cancer radioimmunotherapy |

TABLE IV(I)-continued

Examples of Medical Isotopes:

| Isotope | Description of use |
| --- | --- |
| Erbium-169 (Er-169) | Rheumatoid arthritis treatment, particularly for the small joints associated with fingers and toes |
| Europium-152 (Eu-152) | Radiation source for food irradiation and for sterilization of medical supplies |
| Europium-154 (Eu-154) | Radiation source for food irradiation and for sterilization of medical supplies |
| Gadolinium-153 (Gd-153) | Osteoporosis detection and nuclear medical quality assurance devices |
| Gold-198 (Au-198) | Implant and intracavity therapy of ovarian, prostate, and brain cancers |
| Holmium-166 (Ho-166) | Multiple myeloma treatment in targeted skeletal therapy, cancer radioimmunotherapy, bone marrow ablation, and rheumatoid arthritis treatment |
| Iodine-125 (I-125) | Osteoporosis detection, diagnostic imaging, tracer drugs, brain cancer treatment, radiolabeling, tumor imaging, mapping of receptors in the brain, interstitial radiation therapy, brachytherapy for treatment of prostate cancer, determination of glomerular filtration rate (GFR), determination of plasma volume, detection of deep vein thrombosis of the legs |
| Iodine-131 (I-131) | Thyroid function evaluation, thyroid disease detection, treatment of thyroid cancer as well as other non-malignant thyroid diseases (i.e., Graves disease, goiters, and hyperthyroidism), treatment of leukemia, lymphoma, and other forms of cancer (e.g., breast cancer) using radioimmunotherapy |
| Iridium-192 (Ir-192) | Brachytherapy, brain and spinal cord tumor treatment, treatment of blocked arteries (i.e., arteriosclerosis and restenosis), and implants for breast and prostate tumors |
| Lutetium-177 (Lu-177) | Cancer radioimmunotherapy and treatment of blocked arteries (i.e., arteriosclerosis and restenosis) |
| Molybdenum-99 (Mo-99) | Parent of Technetium-99m (Tc-99m) which is used for imaging the brain, liver, lungs, heart, and other organs. Currently, Tc-99m is the most widely used radioisotope used for diagnostic imaging of various cancers and diseases involving the brain, heart, liver, lungs; also used in detection of deep vein thrombosis of the legs |
| Osmium-194 (Os-194) | Cancer radioimmunotherapy |
| Palladium-103 (Pd-103) | Prostate cancer treatment |
| Platinum-195m (Pt-195m) | Studies on biodistribution and metabolism of cisplatin, a chemotherapeutic drug |
| Phosphorus-32 (P-32) | Polycythemia rubra vera (blood cell disease) and leukemia treatment, bone cancer diagnosis/treatment; colon, pancreatic, and liver cancer treatment; radiolabeling nucleic acids for in vitro research, diagnosis of superficial tumors, treatment of blocked arteries (i.e., arteriosclerosis and restenosis), and intracavity therapy |
| Phosphorus-33 (P-33) | Leukemia treatment, bone disease diagnosis/treatment, radiolabeling, and treatment of blocked arteries (i.e., arteriosclerosis and restenosis) |
| Radium-223 (Ra-223) | See Actinium-227 (Ac-227) |
| Rhenium-186 (Re-186) | Bone cancer pain relief, rheumatoid arthritis treatment, and diagnosis and treatment of lymphoma and bone, breast, colon, and liver cancers using radioimmunotherapy |
| Rhenium-188 (Re-188) | Cancer diagnosis and treatment using radioimmunotherapy, bone cancer pain relief, treatment of rheumatoid arthritis, and treatment of prostate cancer |
| Rhodium-105 (Rh-105) | Cancer radioimmunotherapy |
| Samarium-145 (Sm-145) | Ocular cancer treatment |
| Samarium-153 (Sm-153) | Cancer radioimmunotherapy and bone cancer pain relief |
| Scandium-47 (Sc-47) | Cancer radioimmunotherapy and bone cancer pain relief |
| Selenium-75 (Se-75) | Radiotracer used in brain studies, imaging of adrenal cortex by gamma-scintigraphy, lateral locations of steroid secreting tumors, pancreatic scanning, detection of hyperactive parathyroid glands, measure rate of bile acid loss from the endogenous pool |
| Strontium-85 (Sr-85) | Bone cancer detection and brain scans |
| Strontium-89 (Sr-89) | Bone cancer pain relief, multiple myeloma treatment, and osteoblastic therapy |
| Technetium-99m (Tc-99m) | See Molybdenum-99 (Mo-99) |
| Thorium-228 (Th-228) | Parent of Bismuth-212 (Bi-212) which is an alpha emitter used in cancer radioimmunotherapy |
| Thorium-229 (Th-229) | Parent of Actinium-225 (Ac-225) and grandparent of Bismuth-213 (Bi-213) which are alpha emitters used in cancer radioimmunotherapy |
| Thulium-170 (Tm-170) | Gamma source for blood irradiators, energy source for implanted medical devices |
| Tin-117m (Sn-117m) | Cancer immunotherapy and bone cancer pain relief |
| Tungsten-188 (W-188) | Parent for Rhenium-188 (Re-188) which is used for cancer diagnostics/treatment, bone cancer pain relief, rheumatoid arthritis treatment, and treatment of blocked arteries (i.e., arteriosclerosis and restenosis) |

TABLE IV(I)-continued

Examples of Medical Isotopes:

| Isotope | Description of use |
|---|---|
| Xenon-127 (Xe-127) | Neuroimaging of brain disorders, high resolution SPECT studies, pulmonary function tests, and cerebral blood flow studies |
| Ytterbium-175 (Yb-175) | Cancer radioimmunotherapy |
| Yttrium-90 (Y-90) | Microseeds obtained from irradiating Yttrium-89 (Y-89) for liver cancer treatment |
| Yttrium-91 (Y-91) | A gamma-emitting label for Yttrium-90 (Y-90) which is used for cancer radioimmunotherapy (i.e., lymphoma, breast, colon, kidney, lung, ovarian, prostate, pancreatic, and inoperable liver cancers) |

Tables V-XVIII: Set forth in U.S. patent application Ser. No. 10/236,878; filed 06 Sep. 2002, the specific contents are fully incorporated by reference herein.

TABLE XIX

Frequently Occurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| Ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| Pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| Rvt | 49% | Reverse transcriptase (RNA-dependent DNA polymerase) | |
| Ank | 25% | Ank repeat | Cytoplasmic protein, associates integral membrane proteins to the cytoskeleton |
| Oxidored_q1 | 32% | NADH-Ubiquinone/plastoquinone (complex I), various chains | membrane associated. Involved in proton translocation across the membrane |
| Efhand | 24% | EF hand | calcium-binding domain, consists of a 12 residue loop flanked on both sides by a 12 residue alpha-helical domain |
| Rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE XX

Motifs and Post-translational Modifications of STEAP-1:

N-glycosylation site 143-146 NGTK (SEQ ID NO: 84)
331-334 NKTE (SEQ ID NO: 85)
Protein kinase C phosphorylation site 3-5 SrK
160-162 TrK
187-189 SyR
246-248 TwR
Casein kinase II phosphorylation site 3-6 SrkD (SEQ ID NO: 86)
8-11 TnqE (SEQ ID NO: 87)

TABLE XX-continued

Motifs and Post-translational Modifications of STEAP-1:

240-243 SvsD (SEQ ID NO: 88)
246-249 TwrE (SEQ ID NO: 89)
Tyrosine kinase phosphorylation site 19-27 RRNLEEDDY (SEQ ID NO: 90)
N-myristoylation site 133-138 GVIAAI (SEQ ID NO: 91)
265-270 GTIHAL (SEQ ID NO: 92)
Bipartite nuclear targeting sequence 4-20 RKDITNQEELWKMKPRR (SEQ ID NO: 93)

TABLE XXI

Protein Characteristics of STEAP-1

| | Bioinformatic Program | URL (Located on the World Wide Web at) | Outcome |
|---|---|---|---|
| ORF | ORF finder | | 1193 bp |
| Protein length | | | 339 aa |
| Transmembrane region | TM Pred | (.ch.embnet.org/) | 6 TM at aa 73–91, 120–141, 163–181, 218–236, 253–274, 286–304 |
| | HMMTop | (.enzim.hu/hmmtop/) | 6 TM at aa 73–90, 117–139, 164–182, 220–238, 257–274, 291–309 |
| | Sosui | (.genome.ad.jp/SOSui/) | 6 TM at aa 70–92, 114–136, 163–184, 219–241, 255–273, 292–313 |
| | TMHMM | (.cbs.dtu.dk/services/TMHMM) | 6 TM at aa 73–95, 117–139, 164–182, 218–240, 252–274, 289–311 |
| Signal Peptide | Signal P | (.cbs.dtu.dk/services/SignalP/) | potential cleavage between aa 136 and 137 |
| pI | pI/MW tool | (.expasy.ch/tools/) | 9.2 pI |
| Molecular weight | pI/MW tool | (.expasy.ch/tools/) | 39.8 kD |
| Localization | PSORT | http://psort.nibb.ac.jp/ | 60% plama membrane, 40% golgi, 30% endoplasmic reticulum |
| | PSORT II | http://psort.nibb.ac.jp/ | 66% endoplasmic reticulum, 11% mitochondria, 11% plasma membrane |
| Motifs | Pfam | (.sanger.ac.uk/Pfam/) | none |
| | Prints | (.biochem.ucl.ac.uk/) | Transforming protein P21 ras signature, Fibronectin type III repeat signature |
| | Blocks | (.blocks.fhcrc.org/) | Half-A-TPR repeat, Arsenical pump membrane protein signature, M protein repeat |

Tables V-XVIII: Set forth in U.S. patent application Ser. No. 10/236,878; filed 06 Sep. 2002, the specific contents are fully incorporated by reference herein.

TABLE LII

Search Peptides

```
STEAP 1 Variant 1:
nonamers, decamers and 15-mers: aa 1-339 (SEQ ID NO: 94)
MESRKDITNQ EELWKMKPRR NLEEDDYLHK DTGETSMLKR PVLLHLHQTA HADEFDCPSE    60
LQHTQELFPQ WHLPIKIAAI IASLTFLYTL LREVIHPLAT SHQQYFYKIP ILVINKVLPM   120
VSITLLALVY LPGVIAAIVQ LHNGTKYKKF PHWLDKWMLT RKQFGLLSFF FAVLHAIYSL   180
SYPMRRSYRY KLLNWAYQQV QQNKEDAWIE HDVWRMEIYV SLGIVGLAIL ALLAVTSIPS   240
VSDSLTWREF HYIQSKLGIV SLLLGTIHAL IFAWNKWIDI KQFVWYTPPT FMIAVFLPIV   300
VLIFKSILFL PCLRKKILKI RHGWEDVTKI NKTEICSQL                         339
Variant 2:
9-mers aa 247-258 (SEQ ID NO: 95)
WREFHYIQVNNI
10-mers aa 246-258 (SEQ ID NO: 96)
TWREFHYIQVNNI
15-mers aa 241-258 (SEQ ID NO: 97)
VSDSLTWREFHYIQVNNI
Variant 3:
9-mers aa 247- (SEQ ID NO: 98)
WREFHYIQIIHKKSDVPESLWDPCLTRFKGLNLIQS
10-mers aa 246- (SEQ ID NO: 99)
TWREFHYIQIIHKKSDVPESLWDPCLTRFKGLNLIQS
15-mers aa 241- (SEQ ID NO: 100)
VSDSLTWREFHYIQIIHKKSDVPESLWDPCLTRFKGLNLIQS
Variant 4:
9-mers aa 160-176 (SEQ ID NO: 101)
RKQFGLLSLFFAVLHAI
10-mers aa 159-177 (SEQ ID NO: 102)
TRKQFGLLSLFFAVLHAIY
15-mers aa 154-182 (SEQ ID NO: 103)
DKWMLTRKQFGLLSLFFAVLHAIYSLSYP
```

TABLE LIII

Exon Compostion of STEAP-1 (8P1D4) variant 1.

| Exon number | Start | End |
|---|---|---|
| 1 | 1 | 34 |
| 2 | 35 | 149 |
| 3 | 150 | 662 |
| 4 | 663 | 827 |
| 5 | 828 | 1176 |

The invention claimed is:

1. A method of delivering a cytotoxic agent or a diagnostic agent to a cell that expresses a STEAP-1 protein (SEQ ID NO:2), comprising providing a cytotoxic agent, a therapeutic agent or a diagnostic agent conjugated to:

(a) an antibody or antibody fragment, comprising all heavy and light chain complementarity determining regions (CDRs) from an antibody designated X92.1.30.1.1(1) (ATCC Accession number PTA-5802) or X120.545.1.1 (ATCC Accession number PTA-5803), or (b) an antibody or antibody fragment, comprising the heavy chain variable region sequence of SEQ ID NO:50 and a light chain variable region sequence selected from the group consisting of SEQ ID NO:52, SEQ ID NO:54 and SEQ ID NO:56, wherein the antibody or antibody fragment of (a) and (b) binds to the STEAP-1 protein (SEQ ID NO: 2), to form an antibody-agent or antibody fragment-agent conjugate; and exposing the cell to the antibody-agent or antibody fragment-agent conjugate.

2. The method of claim 1, wherein the cytotoxic agent or the diagnostic agent comprises a detectable marker or a toxin.

3. The method of claim 2, wherein the detectable marker is a radioisotope, a metal chelator, an enzyme, a substrate, a cofactor, an inhibitor, a fluorescent compound, a bioluminescent compound, a magnetic particle or a chemiluminescent compound.

4. The method of claim 3, wherein the radioisotope comprises $^{212}$Bi, $^{131}$I, $^{131}$In, $^{90}$Y, $^{186}$RE, $^{211}$At, $^{125}$I, $^{188}$Re, $^{153}$Sm, $^{213}$Bi, $^{32}$P, or Lu.

5. The method of claim 2, wherein the toxin comprises ricin, ricin A-chain, doxorubicin, daunorubicin, a maytansinoid, taxol, ethidium bromide, mitomycin, etoposide, tenoposide, vincristine, vinbiastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *sapaonaria officinalis* inhibitor, glucocorticoid, auristatin, auromycin, yttrium, bismuth, combrestatin, duocarmycins, dolostatin, cc1065, or a cisplatin.

6. The method of claim 5 wherein the toxin comprises auristatin.

7. The method of claim 1, wherein the antibody is a monoclonal antibody.

8. The method of claim 1, wherein the antibody is designated X92.1.30.1.1(1) and assigned A.T.C.C. Accession No.: PTA-5802.

9. The method of claim 1, wherein the antibody is designated X120.545.1.1 and assigned A.T.C.C. Accession No.: PTA-5803.

10. The method of claim 7, wherein the monoclonal antibody is a humanized antibody.

11. The method of claim 1, wherein the antibody fragment is an Fab, F(ab')$_2$, Fv or Sfv fragment.

12. The method of claim 1, wherein the antibody or antibody fragment are chimeric.

13. The method of claim 1, wherein the antibody or antibody fragment thereof is recombinantly produced.

14. The method of claim 13, wherein the recombinant protein comprises the antigen binding region.

15. The method of claim 1, wherein the therapeutic agent comprises paclitaxel, an androgen blocker, or an immune modulator.

16. The method of claim 1, further comprising the administration of radiation, chemotherapy, or hormone ablation.

17. The method of claim 1 wherein the antibody or antibody fragment is administered to a human patient who has received one or more rounds of chemotherapy prior to the administration of said antibody or antibody fragment.

18. The method of claim 1 wherein the antibody comprises the six complementary determining regions (CDRs) from an antibody designated X92. 1.30.1.1(1) (ATCC Accession number PTA-5802) or X120.545.1.1 (ATCC Accession number PTA-5803).

19. The method of claim 1 wherein the antibody comprises the amino acid sequence of SEQ ID NO:52.

20. The method of claim 1 wherein the antibody comprises the amino acid sequence of SEQ ID NO:54.

21. The method of claim 1 wherein the antibody comprises the amino acid sequence of SEQ ID NO:56.

* * * * *

UNITED STATES PATENT AND TRADEMARK OFFICE
CERTIFICATE OF CORRECTION

PATENT NO.         : 7,494,646 B2  
APPLICATION NO. : 10/830899  
DATED                  : February 24, 2009  
INVENTOR(S)        : Aya Jakobovits et al.

It is certified that error appears in the above-identified patent and that said Letters Patent is hereby corrected as shown below:

In claim 17, lines 1-2 and 4, replace "antibody or antibody fragment" with --antibody-agent or antibody fragment-agent conjugate--.

Signed and Sealed this

Eighteenth Day of August, 2009

David J. Kappos  
*Director of the United States Patent and Trademark Office*

UNITED STATES PATENT AND TRADEMARK OFFICE
CERTIFICATE OF CORRECTION

PATENT NO. : 7,494,646 B2
APPLICATION NO. : 10/830899
DATED : February 24, 2009
INVENTOR(S) : Aya Jakobovits et al.

It is certified that error appears in the above-identified patent and that said Letters Patent is hereby corrected as shown below:

Column 310, in claim 17, lines 16-17 and 19, replace "antibody or antibody fragment" with --antibody-agent or antibody fragment-agent conjugate--.

This certificate supersedes the Certificate of Correction issued August 18, 2009.

Signed and Sealed this

Eighth Day of September, 2009

David J. Kappos
*Director of the United States Patent and Trademark Office*

SEQUENCE LISTING

```
<160> NUMBER OF SEQ ID NOS: 103

<210> SEQ ID NO 1
<211> LENGTH: 436
<212> TYPE: DNA
<213> ORGANISM: Homo sapiens

<400> SEQUENCE: 1
gtacagcaaa aagaaactg agaagcccaa actgctttct tgttaacatc cacttatcca     60
accaatgtgg aaacttctta tacttggttc cattatgaag ttggacaatt gctgctatca   120
cacctggcag gtaaaccaat gccaagagag tgatggaaac cattggcaag actttgttga   180
tgaccaggat tggaattta taaaaatatt gttgatggga agttgctaaa gggtgaatta    240
cttccctcag aagagtgtaa agaaaagtca gagatgctat aatagcagct attttaattg    300
gcaagtgcca ctgtggaaag agttcctgtg tgtgctgaag ttctgaaggg cagtcaaatt    360
```

-continued

```
catcagcatg ggctatttgg tgcaaatgca aaagcacagg tctttttagc atgctggtct       420
ctcccgtgtc cttatg                                                       436

<210> SEQ ID NO 2
<211> LENGTH: 1193
<212> TYPE: DNA
<213> ORGANISM: Homo sapiens
<220> FEATURE:
<221> NAME/KEY: CDS
<222> LOCATION: (66)...(1085)

<400> SEQUENCE: 2
ccgagactca cggtcaagct aaggcgaaga gtgggtggct gaagccatac tattttatag       60 aatta atg gaa agc aga aaa gac atc aca aac caa gaa gaa ctt tgg aaa      110
      Met Glu Ser Arg Lys Asp Ile Thr Asn Gln Glu Glu Leu Trp Lys
       1               5                  10                  15 atg aag cct agg aga aat tta gaa gaa gac gat tat ttg cat aag gac        158
Met Lys Pro Arg Arg Asn Leu Glu Glu Asp Asp Tyr Leu His Lys Asp
             20                  25                  30 acg gga gag acc agc atg cta aaa aga cct gtg ctt ttg cat ttg cac        206
Thr Gly Glu Thr Ser Met Leu Lys Arg Pro Val Leu Leu His Leu His
         35                  40                  45 caa aca gcc cat gct gat gaa ttt gac tgc cct tca gaa ctt cag cac        254
Gln Thr Ala His Ala Asp Glu Phe Asp Cys Pro Ser Glu Leu Gln His
     50                  55                  60 aca cag gaa ctc ttt cca cag tgg cac ttg cca att aaa ata gct gct        302
Thr Gln Glu Leu Phe Pro Gln Trp His Leu Pro Ile Lys Ile Ala Ala
 65                  70                  75 att ata gca tct ctg act ttt ctt tac act ctt ctg agg gaa gta att        350
Ile Ile Ala Ser Leu Thr Phe Leu Tyr Thr Leu Leu Arg Glu Val Ile
 80                  85                  90                  95 cac cct tta gca act tcc cat caa caa tat ttt tat aaa att cca atc        398
His Pro Leu Ala Thr Ser His Gln Gln Tyr Phe Tyr Lys Ile Pro Ile
                100                 105                 110 ctg gtc atc aac aaa gtc ttg cca atg gtt tcc atc act ctc ttg gca        446
Leu Val Ile Asn Lys Val Leu Pro Met Val Ser Ile Thr Leu Leu Ala
            115                 120                 125 ttg gtt tac ctg cca ggt gtg ata gca gca att gtc caa ctt cat aat        494
Leu Val Tyr Leu Pro Gly Val Ile Ala Ala Ile Val Gln Leu His Asn
        130                 135                 140 gga acc aag tat aag aag ttt cca cat tgg ttg gat aag tgg atg tta        542
Gly Thr Lys Tyr Lys Lys Phe Pro His Trp Leu Asp Lys Trp Met Leu
    145                 150                 155 aca aga aag cag ttt ggg ctt ctc agt ttc ttt ttt gct gta ctg cat        590
Thr Arg Lys Gln Phe Gly Leu Leu Ser Phe Phe Phe Ala Val Leu His
160                 165                 170                 175 gca att tat agt ctg tct tac cca atg agg cga tcc tac aga tac aag        638
Ala Ile Tyr Ser Leu Ser Tyr Pro Met Arg Arg Ser Tyr Arg Tyr Lys
                180                 185                 190 ttg cta aac tgg gca tat caa cag gtc caa caa aat aaa gaa gat gcc        686
Leu Leu Asn Trp Ala Tyr Gln Gln Val Gln Gln Asn Lys Glu Asp Ala
            195                 200                 205 tgg att gag cat gat gtt tgg aga atg gag att tat gtg tct ctg gga        734
Trp Ile Glu His Asp Val Trp Arg Met Glu Ile Tyr Val Ser Leu Gly
        210                 215                 220 att gtg gga ttg gca ata ctg gct ctg ttg gct gtg aca tct att cca        782
Ile Val Gly Leu Ala Ile Leu Ala Leu Leu Ala Val Thr Ser Ile Pro
    225                 230                 235 tct gtg agt gac tct ttg aca tgg aga gaa ttt cac tat att cag agc        830
Ser Val Ser Asp Ser Leu Thr Trp Arg Glu Phe His Tyr Ile Gln Ser
```

```
                240                 245                 250                 255
aag cta gga att gtt tcc ctt cta ctg ggc aca ata cac gca ttg att       878
Lys Leu Gly Ile Val Ser Leu Leu Leu Gly Thr Ile His Ala Leu Ile
                    260                 265                 270 ttt gcc tgg aat aag tgg ata gat ata aaa caa ttt gta tgg tat aca       926
Phe Ala Trp Asn Lys Trp Ile Asp Ile Lys Gln Phe Val Trp Tyr Thr
                    275                 280                 285 cct cca act ttt atg ata gct gtt ttc ctt cca att gtt gtc ctg ata       974
Pro Pro Thr Phe Met Ile Ala Val Phe Leu Pro Ile Val Val Leu Ile
                    290                 295                 300 ttt aaa agc ata cta ttc ctg cca tgc ttg agg aag aag ata ctg aag      1022
Phe Lys Ser Ile Leu Phe Leu Pro Cys Leu Arg Lys Lys Ile Leu Lys
                    305                 310                 315 att aga cat ggt tgg gaa gac gtc acc aaa att aac aaa act gag ata      1070
Ile Arg His Gly Trp Glu Asp Val Thr Lys Ile Asn Lys Thr Glu Ile
320                 325                 330                 335 tgt tcc cag ttg tag aattactgtt tacacacatt tttgttcaat attgatatat      1125
Cys Ser Gln Leu * tttatcacca acatttcaag tttgtatttg ttaataaaat gattacaagg aaaaaaaaaa      1185
aaaaaaaa                                                                1193

<210> SEQ ID NO 3
<211> LENGTH: 339
<212> TYPE: PRT
<213> ORGANISM: Homo sapiens

<400> SEQUENCE: 3

Met Glu Ser Arg Lys Asp Ile Thr Asn Gln Glu Leu Trp Lys Met
  1               5                  10                  15

Lys Pro Arg Arg Asn Leu Glu Glu Asp Asp Tyr Leu His Lys Asp Thr
                 20                  25                  30

Gly Glu Thr Ser Met Leu Lys Arg Pro Val Leu Leu His Leu His Gln
             35                  40                  45

Thr Ala His Ala Asp Glu Phe Asp Cys Pro Ser Glu Leu Gln His Thr
         50                  55                  60

Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Leu Arg Glu Val Ile His
                 85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Leu His Asn Gly
        130                 135                 140

Thr Lys Tyr Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220
```

```
Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
            245                 250                 255

Leu Gly Ile Val Ser Leu Leu Gly Thr Ile His Ala Leu Ile Phe
        260                 265                 270

Ala Trp Asn Lys Trp Ile Asp Ile Lys Gln Phe Val Trp Tyr Thr Pro
            275                 280                 285

Pro Thr Phe Met Ile Ala Val Phe Leu Pro Ile Val Val Leu Ile Phe
        290                 295                 300

Lys Ser Ile Leu Phe Leu Pro Cys Leu Arg Lys Ile Leu Lys Ile
305                 310                 315                 320

Arg His Gly Trp Glu Asp Val Thr Lys Ile Asn Lys Thr Glu Ile Cys
            325                 330                 335

Ser Gln Leu

<210> SEQ ID NO 4
<211> LENGTH: 3627
<212> TYPE: DNA
<213> ORGANISM: Homo sapiens
<220> FEATURE:
<221> NAME/KEY: CDS
<222> LOCATION: (96)...(872)

<400> SEQUENCE: 4
ggggcccgca cctctgggca gcagcggcag ccgagactca cggtcaagct aaggcgaaga      60
gtgggtggct gaagccatac tattttatag aatta atg gaa agc aga aaa gac       113
                                      Met Glu Ser Arg Lys Asp
                                        1               5 atc aca aac caa gaa gaa ctt tgg aaa atg aag cct agg aga aat tta      161
Ile Thr Asn Gln Glu Glu Leu Trp Lys Met Lys Pro Arg Arg Asn Leu
        10                  15                  20 gaa gaa gac gat tat ttg cat aag gac acg gga gag acc agc atg cta      209
Glu Glu Asp Asp Tyr Leu His Lys Asp Thr Gly Glu Thr Ser Met Leu
    25                  30                  35 aaa aga cct gtg ctt ttg cat ttg cac caa aca gcc cat gct gat gaa      257
Lys Arg Pro Val Leu Leu His Leu His Gln Thr Ala His Ala Asp Glu
40                  45                  50 ttt gac tgc cct tca gaa ctt cag cac aca cag gaa ctc ttt cca cag      305
Phe Asp Cys Pro Ser Glu Leu Gln His Thr Gln Glu Leu Phe Pro Gln
55                  60                  65                  70 tgg cac ttg cca att aaa ata gct gct att ata gca tct ctg act ttt      353
Trp His Leu Pro Ile Lys Ile Ala Ala Ile Ile Ala Ser Leu Thr Phe
            75                  80                  85 ctt tac act ctt ctg agg gaa gta att cac ccc tta gca act tcc cat      401
Leu Tyr Thr Leu Leu Arg Glu Val Ile His Pro Leu Ala Thr Ser His
        90                  95                  100 caa caa tat ttt tat aaa att cca atc ctg gtc atc aac aaa gtc ttg      449
Gln Gln Tyr Phe Tyr Lys Ile Pro Ile Leu Val Ile Asn Lys Val Leu
    105                 110                 115 cca atg gtt tcc atc act ctc ttg gca ttg gtt tac ctg cca ggt gtg      497
Pro Met Val Ser Ile Thr Leu Leu Ala Leu Val Tyr Leu Pro Gly Val
120                 125                 130 ata gca gca att gtc caa ctt cat aat gga acc aag tat aag aag ttt      545
Ile Ala Ala Ile Val Gln Leu His Asn Gly Thr Lys Tyr Lys Lys Phe
135                 140                 145                 150 cca cat tgg ttg gat aag tgg atg tta aca aga aag cag ttt ggg ctt      593
Pro His Trp Leu Asp Lys Trp Met Leu Thr Arg Lys Gln Phe Gly Leu
            155                 160                 165
```

```
ctc agt ttc ttt ttt gct gta ctg cat gca att tat agt ctg tct tac    641
Leu Ser Phe Phe Phe Ala Val Leu His Ala Ile Tyr Ser Leu Ser Tyr
        170                 175                 180 cca atg agg cga tcc tac aga tac aag ttg cta aac tgg gca tat caa    689
Pro Met Arg Arg Ser Tyr Arg Tyr Lys Leu Leu Asn Trp Ala Tyr Gln
            185                 190                 195 cag gtc caa caa aat aaa gaa gat gcc tgg att gag cat gat gtt tgg    737
Gln Val Gln Gln Asn Lys Glu Asp Ala Trp Ile Glu His Asp Val Trp
    200                 205                 210 aga atg gag att tat gtg tct ctg gga att gtg gga ttg gca ata ctg    785
Arg Met Glu Ile Tyr Val Ser Leu Gly Ile Val Gly Leu Ala Ile Leu
215                 220                 225                 230 gct ctg ttg gct gtg aca tct att cca tct gtg agt gac tct ttg aca    833
Ala Leu Leu Ala Val Thr Ser Ile Pro Ser Val Ser Asp Ser Leu Thr
                235                 240                 245 tgg aga gaa ttt cac tat att cag gta aat aat ata taa aataaccta      882
Trp Arg Glu Phe His Tyr Ile Gln Val Asn Asn Ile *
                250                 255 agaggtaaat cttctttttg tgtttatgat atagaatatg ttgactttac cccataaaaa   942
ataacaaatg ttttttcaaca gcaaagatct tatacttgtt ccaattaata atgtgctctc  1002
ctgttgtttt ccctattgct tctaattagg acaagtgttt cctagacata aataaaaggc  1062
attaaaatat tctttgtttt ttttttttttg tttgtttgtt tttgtttgt ttgtttgttt  1122
ttttgagatg aagtctcgct ctgttgccca tgctggagta cagtggcacg atctcggctc  1182
actgcaacct gcgcctcctg ggttcaggcg attctcttgc ctcagcctcc tgagtagctg  1242
ggattacagg cacccatcac catgtccagc taattttgt attttagta gagacagggt    1302
tttcccatgt tggccaggct ggtctcgatc tcctgacctc aaatgatccg cccacctcgg  1362
cctcccaaag tgctgggatg acagttgtga gccaccacac tcagcctgct ctttctaata  1422
tttgaaactt gttagacaat ttgctaccca tctaatgtga tattttagga atccaatatg  1482
catggtttat tatttcttaa aaaaaatatt cttttacctg tcacctgaat ttagtaatgc  1542
cttttatgtt acacaactta gcactttcca gaaacaaaaa ctctctcctt gaaataatag  1602
agttttatc taccaaagat atgctagtgt ctcatttcaa aggctgcttt ttccagctta   1662
cattttatat acttactcac ttgaagtttc taaatattct tgtaattta aaactatctc   1722
agatttactg aggttatct tctggtggta gattatccat aagaagagtg atgtgccaga   1782
atcactctgg gatccttgtc tgacaagatt caaaggacta aatttaattc agtcatgaac  1842
actgccaatt accgtttatg ggtagacatc tttggaaatt tccacaaggt cagacattcg  1902
caactatccc ttctacatgt ccacacgtat actccaacac tttattaggc atctgattag  1962
tttggaaagt atgcctccat ctgaattagt ccagtgtggc ttagagttgg tacaacattc  2022
tcacagaatt tcctaatttt gtaggttcag cctgataacc actggagttc tttggtcctc  2082
attaaatagc tttcttcaca cattgctctg cctgttacac atatgatgaa cactgctttt  2142
tagacttcat taggaattta ggactgcatc ttgacaactg agcctattct actatatgta  2202
caatacctag cccataatag gtatacaata cacatttggt aaaactaatt ttcaaccaat  2262
gacatgtatt tttcaactag taacctagaa atgtttcact taaatctga gaactggtta   2322
cactacaagt taccttggag attcatatat gaaaacgcaa acttagctat ttgattgtat  2382
tcactgggac ttaagaatgc gcctgaataa ttgtgagttc gatttgttct ggcaggctaa  2442
tgaccatttc cagtaaagtg aatagaggtc agaagtcgta taaagaggt gttgtcagaa   2502
```

-continued

```
caccgttgag attacatagg tgaacaacta ttttttaagca actttatttg tgtagtgaca    2562
aagcatccca atgcaggctg aaatgtttca tcacatctct ggatctctct attttgtgca    2622
gacattgaaa aaattgttca tattatttcc atgttatcag aatatttgat tttttaaaaa    2682
cataggccaa gttcattcac ttcattattc atttatcaaa atcagagtga atcacattag    2742
tcgccttcac aactgataaa gatcactgaa gtcaaattga ttttttgctat aatcttcaat    2802
ctacctatat ttaattgaga atctaaaatg tacaaatcat tgtgttgatt ctgcagtgat    2862
cctgctataa gtaagactca gtccctgatt ttaggtatcc tgtgaaaagc agaattaaga    2922
caaatacaca agagacaaag cacaaaaaat aaatatcata aggggatgaa caaaatggtg    2982
gagaaagagt agacaaagtt tttgatcacc tgccttcaaa gaaaggctgt gaattttgtt    3042
cacttagaca gcttggagac aagaaattac ccaaaagtaa ggtgaggagg ataggcaaaa    3102
agagcagaaa gatgtgaatg gacattgttg agaaatgtga taggaaaaca atcatagata    3162
aaggatttcc aagcaacaga gcatatccag atgaggtagg atgggataaa ctcttattga    3222
accaatcttc accaattttg ttttttctttt gcagagcaag ctaggaattg tttcccttct    3282
actgggcaca atacacgcat tgattttttgc ctggaataag tggatagata taaaacaatt    3342
tgtatggtat acacctccaa ctttttatgat agctgttttc cttccaattg ttgtcctgat    3402
atttaaaagc atactattcc tgccatgctt gaggaagaag atactgaaga ttagacatgg    3462
ttgggaagac gtcaccaaaa ttaacaaaac tgagatatgt tcccagttgt agaattactg    3522
tttacacaca tttttgttca atattgatat atttttatcac caacatttca gtttgtatt    3582
tgttaataaa atgattattc aaggaaaaaa aaaaaaaaaa aaaaa    3627
```

<210> SEQ ID NO 5
<211> LENGTH: 258
<212> TYPE: PRT
<213> ORGANISM: Homo sapiens

<400> SEQUENCE: 5

```
Met Glu Ser Arg Lys Asp Ile Thr Asn Gln Glu Glu Leu Trp Lys Met
 1               5                  10                  15

Lys Pro Arg Arg Asn Leu Glu Glu Asp Asp Tyr Leu His Lys Asp Thr
                20                  25                  30

Gly Glu Thr Ser Met Leu Lys Arg Pro Val Leu Leu His Leu His Gln
            35                  40                  45

Thr Ala His Ala Asp Glu Phe Asp Cys Pro Ser Glu Leu Gln His Thr
        50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Arg Glu Val Ile His
                85                  90                  95

Pro Leu Ala Thr Ser His Gln Gln Tyr Phe Tyr Lys Ile Pro Ile Leu
                100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Leu His Asn Gly
        130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175
```

```
Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

<210> SEQ ID NO 6
<211> LENGTH: 1365
<212> TYPE: DNA
<213> ORGANISM: Homo sapiens
<220> FEATURE:
<221> NAME/KEY: CDS
<222> LOCATION: (96)...(944)

<400> SEQUENCE: 6
ggggcccgca cctctgggca gcagcggcag ccgagactca cggtcaagct aaggcgaaga       60
gtgggtggct gaagccatac tattttatag aatta atg gaa agc aga aaa gac       113
                                      Met Glu Ser Arg Lys Asp
                                        1               5 atc aca aac caa gaa gaa ctt tgg aaa atg aag cct agg aga aat tta       161
Ile Thr Asn Gln Glu Glu Leu Trp Lys Met Lys Pro Arg Arg Asn Leu
         10                  15                  20 gaa gaa gac gat tat ttg cat aag gac acg gga gag acc agc atg cta       209
Glu Glu Asp Asp Tyr Leu His Lys Asp Thr Gly Glu Thr Ser Met Leu
     25                  30                  35 aaa aga cct gtg ctt ttg cat ttg cac caa aca gcc cat gct gat gaa       257
Lys Arg Pro Val Leu Leu His Leu His Gln Thr Ala His Ala Asp Glu
 40                  45                  50 ttt gac tgc cct tca gaa ctt cag cac aca cag gaa ctc ttt cca cag       305
Phe Asp Cys Pro Ser Glu Leu Gln His Thr Gln Glu Leu Phe Pro Gln
 55                  60                  65                  70 tgg cac ttg cca att aaa ata gct gct att ata gca tct ctg act ttt       353
Trp His Leu Pro Ile Lys Ile Ala Ala Ile Ile Ala Ser Leu Thr Phe
                 75                  80                  85 ctt tac act ctt ctg agg gaa gta att cac cct tta gca act tcc cat       401
Leu Tyr Thr Leu Leu Arg Glu Val Ile His Pro Leu Ala Thr Ser His
             90                  95                 100 caa caa tat ttt tat aaa att cca atc ctg gtc atc aac aaa gtc ttg       449
Gln Gln Tyr Phe Tyr Lys Ile Pro Ile Leu Val Ile Asn Lys Val Leu
        105                 110                 115 cca atg gtt tcc atc act ctc ttg gca ttg gtt tac ctg cca ggt gtg       497
Pro Met Val Ser Ile Thr Leu Leu Ala Leu Val Tyr Leu Pro Gly Val
    120                 125                 130 ata gca gca att gtc caa ctt cat aat gga acc aag tat aag aag ttt       545
Ile Ala Ala Ile Val Gln Leu His Asn Gly Thr Lys Tyr Lys Lys Phe
135                 140                 145                 150 cca cat tgg ttg gat aag tgg atg tta aca aga aag cag ttt ggg ctt       593
Pro His Trp Leu Asp Lys Trp Met Leu Thr Arg Lys Gln Phe Gly Leu
                155                 160                 165 ctc agt ttc ttt ttt gct gta ctg cat gca att tat agt ctg tct tac       641
Leu Ser Phe Phe Phe Ala Val Leu His Ala Ile Tyr Ser Leu Ser Tyr
            170                 175                 180 cca atg agg cga tcc tac aga tac aag ttg cta aac tgg gca tat caa       689
```

```

Pro Met Arg Arg Ser Tyr Arg Tyr Lys Leu Leu Asn Trp Ala Tyr Gln
        185                 190                 195 cag gtc caa caa aat aaa gaa gat gcc tgg att gag cat gat gtt tgg      737
Gln Val Gln Gln Asn Lys Glu Asp Ala Trp Ile Glu His Asp Val Trp
    200                 205                 210 aga atg gag att tat gtg tct ctg gga att gtg gga ttg gca ata ctg      785
Arg Met Glu Ile Tyr Val Ser Leu Gly Ile Val Gly Leu Ala Ile Leu
215                 220                 225                 230 gct ctg ttg gct gtg aca tct att cca tct gtg agt gac tct ttg aca      833
Ala Leu Leu Ala Val Thr Ser Ile Pro Ser Val Ser Asp Ser Leu Thr
                235                 240                 245 tgg aga gaa ttt cac tat att cag att atc cat aag aag agt gat gtg      881
Trp Arg Glu Phe His Tyr Ile Gln Ile Ile His Lys Lys Ser Asp Val
            250                 255                 260 cca gaa tca ctc tgg gat cct tgt ctg aca aga ttc aaa gga cta aat      929
Pro Glu Ser Leu Trp Asp Pro Cys Leu Thr Arg Phe Lys Gly Leu Asn
        265                 270                 275 tta att cag tca tga acactgccaa ttaccgttta tgggtagaca tctttggaaa      984
Leu Ile Gln Ser  *
    280 tttccacaag agcaagctag gaattgtttc ccttctactg ggcacaatac acgcattgat    1044 ttttgcctgg aataagtgga tagatataaa acaatttgta tggtatacac ctccaacttt    1104 tatgatagct gttttccttc caattgttgt cctgatattt aaaagcatac tattcctgcc    1164 atgcttgagg aagaagatac tgaagattag acatggttgg gaagacgtca ccaaaattaa    1224 caaaactgag atatgttccc agttgtgaaa ttactgttta cacacatttt tgttcaatat    1284 tgatatattt tatcaccaac atttcaagtt tgtatttgtt aataaaatga ttattcaagg    1344 aaaaaaaaaa aaaaaaaaa a                                               1365

<210> SEQ ID NO 7
<211> LENGTH: 282
<212> TYPE: PRT
<213> ORGANISM: Homo sapiens

<400> SEQUENCE: 7

Met Glu Ser Arg Lys Asp Ile Thr Asn Gln Glu Leu Trp Lys Met
1               5                   10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160
```

```
          Arg Lys Gln Phe Gly Leu Leu Ser Phe Phe Ala Val Leu His Ala
                          165                 170                 175

Ile Tyr Ser Leu Ser Tyr Pro Met Arg Arg Ser Tyr Arg Tyr Lys Leu
                      180                 185                 190

Leu Asn Trp Ala Tyr Gln Gln Val Gln Gln Asn Lys Glu Asp Ala Trp
                  195                 200                 205

Ile Glu His Asp Val Trp Arg Met Glu Ile Tyr Val Ser Leu Gly Ile
          210                 215                 220

Val Gly Leu Ala Ile Leu Ala Leu Leu Ala Val Thr Ser Ile Pro Ser
          225                 230                 235                 240

Val Ser Asp Ser Leu Thr Trp Arg Glu Phe His Tyr Ile Gln Ile Ile
                          245                 250                 255

His Lys Lys Ser Asp Val Pro Glu Ser Leu Trp Asp Pro Cys Leu Thr
                      260                 265                 270

Arg Phe Lys Gly Leu Asn Leu Ile Gln Ser
                  275                 280

<210> SEQ ID NO 8
          <211> LENGTH: 3627
          <212> TYPE: DNA
          <213> ORGANISM: Homo sapiens
          <220> FEATURE:
          <221> NAME/KEY: CDS
          <222> LOCATION: (96)...(872)

<400> SEQUENCE: 8
ggggcccgca cctctgggca gcagcggcag ccgagactca cggtcaagct aaggcgaaga      60
gtgggtggct gaagccatac tattttatag aatta atg gaa agc aga aaa gac        113
                                                 Met Glu Ser Arg Lys Asp
                                                   1               5 atc aca aac caa gaa gaa ctt tgg aaa atg aag cct agg aga aat tta      161
          Ile Thr Asn Gln Glu Glu Leu Trp Lys Met Lys Pro Arg Arg Asn Leu
                       10                  15                  20 gaa gaa gac gat tat ttg cat aag gac acg gga gag acc agc atg cta      209
          Glu Glu Asp Asp Tyr Leu His Lys Asp Thr Gly Glu Thr Ser Met Leu
                   25                  30                  35 aaa aga cct gtg ctt ttg cat ttg cac caa aca gcc cat gct gat gaa      257
          Lys Arg Pro Val Leu Leu His Leu His Gln Thr Ala His Ala Asp Glu
           40                  45                  50 ttt gac tgc cct tca gaa ctt cag cac aca cag gaa ctc ttt cca cag      305
          Phe Asp Cys Pro Ser Glu Leu Gln His Thr Gln Glu Leu Phe Pro Gln
           55                  60                  65                  70 tgg cac ttg cca att aaa ata gct gct att ata gca tct ctg act ttt      353
          Trp His Leu Pro Ile Lys Ile Ala Ala Ile Ile Ala Ser Leu Thr Phe
                           75                  80                  85 ctt tac act ctt ctg agg gaa gta att cac ccc tta gca act tcc cat      401
          Leu Tyr Thr Leu Leu Arg Glu Val Ile His Pro Leu Ala Thr Ser His
                       90                  95                 100 caa caa tat ttt tat aaa att cca atc ctg gtc atc aac aaa gtc ttg      449
          Gln Gln Tyr Phe Tyr Lys Ile Pro Ile Leu Val Ile Asn Lys Val Leu
                  105                 110                 115 cca atg gtt tcc atc act ctc ttg gca ttg gtt tac ctg cca ggt gtg      497
          Pro Met Val Ser Ile Thr Leu Leu Ala Leu Val Tyr Leu Pro Gly Val
           120                 125                 130 ata gca gca att gtc caa ctt cat aat gga acc aag tat aag aag ttt      545
          Ile Ala Ala Ile Val Gln Leu His Asn Gly Thr Lys Tyr Lys Lys Phe
          135                 140                 145                 150 cca cat tgg ttg gat aag tgg atg tta aca aga aag cag ttt ggg ctt      593
          Pro His Trp Leu Asp Lys Trp Met Leu Thr Arg Lys Gln Phe Gly Leu
```

-continued

|  | 155 |  |  |  | 160 |  |  |  | 165 |  |  |  |  |
|---|---|---|---|---|---|---|---|---|---|---|---|---|---|
| ctc | agt | ttg | ttt | ttt | gct | gta | ctg | cat | gca | att | tat | agt | ctg tct tac | 641 |
| Leu | Ser | Leu | Phe | Phe | Ala | Val | Leu | His | Ala | Ile | Tyr | Ser | Leu Ser Tyr |  |
|  |  | 170 |  |  |  |  | 175 |  |  |  |  | 180 |  |  |

| cca | atg | agg | cga | tcc | tac | aga | tac | aag | ttg | cta | aac | tgg | gca tat caa | 689 |
|---|---|---|---|---|---|---|---|---|---|---|---|---|---|---|
| Pro | Met | Arg | Arg | Ser | Tyr | Arg | Tyr | Lys | Leu | Leu | Asn | Trp | Ala Tyr Gln |  |
|  | 185 |  |  |  |  | 190 |  |  |  |  | 195 |  |  |  |

| cag | gtc | caa | caa | aat | aaa | gaa | gat | gcc | tgg | att | gag | cat | gat gtt tgg | 737 |
|---|---|---|---|---|---|---|---|---|---|---|---|---|---|---|
| Gln | Val | Gln | Gln | Asn | Lys | Glu | Asp | Ala | Trp | Ile | Glu | His | Asp Val Trp |  |
| 200 |  |  |  |  | 205 |  |  |  |  | 210 |  |  |  |  |

| aga | atg | gag | att | tat | gtg | tct | ctg | gga | att | gtg | gga | ttg | gca ata ctg | 785 |
|---|---|---|---|---|---|---|---|---|---|---|---|---|---|---|
| Arg | Met | Glu | Ile | Tyr | Val | Ser | Leu | Gly | Ile | Val | Gly | Leu | Ala Ile Leu |  |
| 215 |  |  |  | 220 |  |  |  | 225 |  |  |  |  | 230 |  |

| gct | ctg | ttg | gct | gtg | aca | tct | att | cca | tct | gtg | agt | gac | tct ttg aca | 833 |
|---|---|---|---|---|---|---|---|---|---|---|---|---|---|---|
| Ala | Leu | Leu | Ala | Val | Thr | Ser | Ile | Pro | Ser | Val | Ser | Asp | Ser Leu Thr |  |
|  |  |  |  | 235 |  |  |  |  | 240 |  |  |  | 245 |  |

| tgg | aga | gaa | ttt | cac | tat | att | cag | gta | aat | aat | ata | taa | aataaccccta | 882 |
|---|---|---|---|---|---|---|---|---|---|---|---|---|---|---|
| Trp | Arg | Glu | Phe | His | Tyr | Ile | Gln | Val | Asn | Asn | Ile | * |  |  |
|  |  | 250 |  |  |  |  | 255 |  |  |  |  |  |  |  |

| agaggtaaat cttcttttg tgtttatgat atagaatatg ttgactttac cccataaaaa | 942 |
|---|---|
| ataacaaatg tttttcaaca gcaaagatct tatacttgtt ccaattaata atgtgctctc | 1002 |
| ctgttgtttt ccctattgct tctaattagg acaagtgttt cctagacata aataaaaggc | 1062 |
| attaaaatat tctttgtttt ttttttttg tttgtttgtt ttttgtttgt tgtttgttt | 1122 |
| ttttgagatg aagtctcgct ctgttgccca tgctggagta cagtggcacg atctcggctc | 1182 |
| actgcaacct gcgcctcctg ggttcaggcg attctcttgc ctcagcctcc tgagtagctg | 1242 |
| ggattacagg cacccatcac catgtccagc taattttgt attttagta gagacagggt | 1302 |
| tttcccatgt tggccaggct ggtctcgatc tcctgacctc aaatgatccg cccacctcgg | 1362 |
| cctcccaaag tgctgggatg acagttgtga gccaccacac tcagcctgct ctttctaata | 1422 |
| tttgaaactt gttagacaat ttgctaccca tctaatgtga tatttagga atccaatatg | 1482 |
| catggtttat tatttcttaa aaaaaatatt cttttacctg tcacctgaat ttagtaatgc | 1542 |
| cttttatgtt acacaactta gcactttcca gaaacaaaaa ctctctcctt gaaataatag | 1602 |
| agttttatc taccaaagat atgctagtgt ctcatttcaa aggctgcttt ttccagctta | 1662 |
| cattttatat acttactcac ttgaagtttc taaatattct tgtaatttta aaactatctc | 1722 |
| agatttactg aggtttatct tctggtggta gattatccat aagaagagtg atgtgccaga | 1782 |
| atcactctgg gatccttgtc tgacaagatt caaaggacta aatttaattc agtcatgaac | 1842 |
| actgccaatt accgtttatg ggtagacatc tttggaaatt ccacaaggt cagacattcg | 1902 |
| caactatccc ttctacatgt ccacacgtat actccaacac tttattaggc atctgattag | 1962 |
| tttggaaagt atgcctccat ctgaattagt ccagtgtggc ttagagttgg tacaacattc | 2022 |
| tcacagaatt tcctaatttt gtaggttcag cctgataacc actggagttc tttggtcctc | 2082 |
| attaaatagc tttcttcaca cattgctctg cctgttacac atatgatgaa cactgcttt | 2142 |
| tagacttcat taggaattta ggactgcatc ttgacaactg agcctattct actatatgta | 2202 |
| caatacctag cccataatag gtatacaata cacatttggt aaaactaatt ttcaaccaat | 2262 |
| gacatgtatt tttcaactag taacctagaa atgtttcact taaaatctga gaactggtta | 2322 |
| cactacaagt taccttggag attcatatat gaaaacgcaa acttagctat ttgattgtat | 2382 |
| tcactgggac ttaagaatgc gcctgaataa ttgtgagttc gatttgttct ggcaggctaa | 2442 |
| tgaccatttc cagtaaagtg aatagaggtc agaagtcgta taaaagaggt gttgtcagaa | 2502 |

```
caccgttgag attacatagg tgaacaacta tttttaagca actttatttg tgtagtgaca    2562
aagcatccca atgcaggctg aaatgtttca tcacatctct ggatctctct attttgtgca    2622
gacattgaaa aaattgttca tattatttcc atgttatcag aatatttgat ttttaaaaa     2682 cataggccaa gttcattcac ttcattattc atttatcaaa atcagagtga atcacattag    2742
tcgccttcac aactgataaa gatcactgaa gtcaaattga ttttgctat aatcttcaat     2802 ctacctatat ttaattgaga atctaaaatg tacaaatcat tgtgttgatt ctgcagtgat    2862
cctgctataa gtaagactca gtccctgatt ttaggtatcc tgtgaaaagc agaattaaga   2922
caaatacaca agagacaaag cacaaaaaat aaatatcata aggggatgaa caaaatggtg    2982
gagaaagagt agacaaagtt tttgatcacc tgccttcaaa gaaaggctgt gaattttgtt   3042
cacttagaca gcttggagac aagaaattac ccaaaagtaa ggtgaggagg ataggcaaaa    3102
agagcagaaa gatgtgaatg gacattgttg agaaatgtga taggaaaaca atcatagata   3162
aaggatttcc aagcaacaga gcatatccag atgaggtagg atgggataaa ctcttattga    3222
accaatcttc accaattttg ttttctttt gcagagcaag ctaggaattg tttcccttct     3282
actgggcaca atacacgcat tgattttgc ctggaataag tggatagata taaaacaatt     3342
tgtatggtat acacctccaa cttttatgat agctgttttc cttccaattg ttgtcctgat    3402
atttaaaagc atactattcc tgccatgctt gaggaagaag atactgaaga ttagacatgg    3462
ttgggaagac gtcaccaaaa ttaacaaaac tgagatatgt tcccagttgt agaattactg   3522
tttacacaca ttttgttca atattgatat atttttatcac caacatttca agtttgtatt   3582
tgttaataaa atgattattc aaggaaaaaa aaaaaaaaaa aaaaa                    3627
```

<210> SEQ ID NO 9
<211> LENGTH: 258
<212> TYPE: PRT
<213> ORGANISM: Homo sapiens

<400> SEQUENCE: 9

```
Met Glu Ser Arg Lys Asp Ile Thr Asn Gln Glu Glu Leu Trp Lys Met
  1               5                  10                  15

Lys Pro Arg Arg Asn Leu Glu Glu Asp Asp Tyr Leu His Lys Asp Thr
             20                  25                  30

Gly Glu Thr Ser Met Leu Lys Arg Pro Val Leu Leu His Leu His Gln
         35                  40                  45

Thr Ala His Ala Asp Glu Phe Asp Cys Pro Ser Glu Leu Gln His Thr
     50                  55                  60

Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Leu Arg Glu Val Ile His
                 85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Leu Phe Phe Ala Val Leu His Ala
                165                 170                 175
```

```
Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

<210> SEQ ID NO 10
<211> LENGTH: 3627
<212> TYPE: DNA
<213> ORGANISM: Homo sapiens
<220> FEATURE:
<221> NAME/KEY: CDS
<222> LOCATION: (96)...(872)

<400> SEQUENCE: 10
ggggcccgca cctctgggca gcagcggcag ccgagactca cggtcaagct aaggcgaaga     60
gtgggtggct gaagccatac tattttatag aatta atg gaa agc aga aaa gac       113
                                       Met Glu Ser Arg Lys Asp
                                         1               5 atc aca aac caa gaa gaa ctt tgg aaa atg aag cct agg aga aat tta     161
Ile Thr Asn Gln Glu Glu Leu Trp Lys Met Lys Pro Arg Arg Asn Leu
        10                  15                  20 gaa gaa gac gat tat ttg cat aag gac acg gga gag acc agc atg cta     209
Glu Glu Asp Asp Tyr Leu His Lys Asp Thr Gly Glu Thr Ser Met Leu
    25                  30                  35 aaa aga cct gtg ctt ttg cat ttg cac caa aca gcc cat gct gat gaa     257
Lys Arg Pro Val Leu Leu His Leu His Gln Thr Ala His Ala Asp Glu
 40                  45                  50 ttt gac tgc cct tca gaa ctt cag cac aca cag gaa ctc ttt cca cag     305
Phe Asp Cys Pro Ser Glu Leu Gln His Thr Gln Glu Leu Phe Pro Gln
 55                  60                  65                  70 tgg cac ttg cca att aaa ata gct gct att ata gca tct ctg act ttt     353
Trp His Leu Pro Ile Lys Ile Ala Ala Ile Ile Ala Ser Leu Thr Phe
                 75                  80                  85 ctt tac act ctt ctg agg gaa gta att cac cct tta gca act tcc cat     401
Leu Tyr Thr Leu Leu Arg Glu Val Ile His Pro Leu Ala Thr Ser His
             90                  95                 100 caa caa tat ttt tat aaa att cca atc ctg gtc atc aac aaa gtc ttg     449
Gln Gln Tyr Phe Tyr Lys Ile Pro Ile Leu Val Ile Asn Lys Val Leu
        105                 110                 115 cca atg gtt tcc atc act ctc ttg gca ttg gtt tac ctg cca ggt gtg     497
Pro Met Val Ser Ile Thr Leu Leu Ala Leu Val Tyr Leu Pro Gly Val
    120                 125                 130 ata gca gca att gtc caa ctt cat aat gga acc aag tat aag aag ttt     545
Ile Ala Ala Ile Val Gln Leu His Asn Gly Thr Lys Tyr Lys Lys Phe
135                 140                 145                 150 cca cat tgg ttg gat aag tgg atg tta aca aga aag cag ttt ggg ctt     593
Pro His Trp Leu Asp Lys Trp Met Leu Thr Arg Lys Gln Phe Gly Leu
                155                 160                 165 ctc agt ttc ttt ttt gct gta ctg cat gca att tat agt ctg tct tac     641
Leu Ser Phe Phe Phe Ala Val Leu His Ala Ile Tyr Ser Leu Ser Tyr
            170                 175                 180
```

| | | |
|---|---|---|
| cca atg agg cga tcc tac aga tac aag ttg cta aac tgg gca tat caa<br>Pro Met Arg Arg Ser Tyr Arg Tyr Lys Leu Leu Asn Trp Ala Tyr Gln<br>     185                     190                  195 | | 689 |
| cag gtc caa caa aat aaa gaa gat gcc tgg att gag cat gat gtt tgg<br>Gln Val Gln Gln Asn Lys Glu Asp Ala Trp Ile Glu His Asp Val Trp<br>    200                     205                  210 | | 737 |
| aga atg gag att tat gtg tct ctg gga att gtg gga ttg gca ata ctg<br>Arg Met Glu Ile Tyr Val Ser Leu Gly Ile Val Gly Leu Ala Ile Leu<br>215                    220                  225                 230 | | 785 |
| gct ctg ttg gct gtg aca tct att cca tct gtg agt gac tct ttg aca<br>Ala Leu Leu Ala Val Thr Ser Ile Pro Ser Val Ser Asp Ser Leu Thr<br>                 235                  240                 245 | | 833 |
| tgg aga gaa ttt cac tat att cag gta aat aat ata taa aataaccta<br>Trp Arg Glu Phe His Tyr Ile Gln Val Asn Asn Ile *<br>           250                  255 | | 882 |
| agaggtaaat cttcttttg tgtttatgat atagaatatg ttgactttac cccataaaaa | | 942 |
| ataacaaatg ttttcaaca gcaaagatct tatacttgtt ccaattaata atgtgctctc | | 1002 |
| ctgttgtttt ccctattgct tctaattagg acaagtgttt cctagacata aataaaaggc | | 1062 |
| attaaaatat tctttgtttt ttttttttg tttgtttgtt ttttgtttgt tgtttgttt | | 1122 |
| ttttgagatg aagtctcgct ctgttgccca tgctggagta cagtggcacg atctcggctc | | 1182 |
| actgcaacct gcgcctcctg ggttcaggcg attctcttgc ctcagcctcc tgagtagctg | | 1242 |
| ggattacagg cacccatcac catgtccagc taatttttgt attttagta gagacagggt | | 1302 |
| tttcccatgt tggccaggct ggtctcgatc tcctgacctc aaatgatccg cccacctcgg | | 1362 |
| cctcccaaag tgctgggatg acagttgtga gccaccacac tcagcctgct ctttctaata | | 1422 |
| tttgaaactt gttagacaat ttgctaccca tctaatgtga tattttagga atccaatatg | | 1482 |
| catggtttat tatttcttaa aaaaatatt cttttacctg tcacctgaat ttagtaatgc | | 1542 |
| cttttatgtt acacaactta gcactttcca gaaacaaaaa ctctctcctt gaaataatag | | 1602 |
| agttttatc taccaaagat atgctagtgt ctcatttcaa aggctgcttt ttccagctta | | 1662 |
| cattttatat acttactcac ttgaagtttc taaatattct tgtaatttta aaactatctc | | 1722 |
| agatttactg aggtttatct tctggtggta gattatccat aagaagagtg atgtgccaga | | 1782 |
| atcactctgg gatccttgtc tgacaagatt caaaggacta aatttaattc agtcatgaac | | 1842 |
| actgccaatt accgtttatg ggtagacatc tttggaaatt tccacaaggt cagacattcg | | 1902 |
| caactatccc ttctcatgt ccacacgtat actccaacac tttattaggc atctgattag | | 1962 |
| tttgaaagt atgcctccat ctgaattagt ccagtgtggc ttagagttgg tacaacattc | | 2022 |
| tcacagaatt tcctaatttt gtaggttcag cctgataacc actggagttc tttggtcctc | | 2082 |
| attaaatagc tttcttcaca cattgctctg cctgttacac atatgatgaa cactgctttt | | 2142 |
| tagacttcat taggaattta ggactgcatc ttgacaactg agcctattct actatatgta | | 2202 |
| caatacctag cccataatag gtatacaata cacatttggt aaaactaatt ttcaaccaat | | 2262 |
| gacatgtatt tttcaactag taacctagaa atgtttcact taaaatctga gaactggtta | | 2322 |
| cactacaagt taccttggag attcatatat gaaaacgcaa acttagctat ttgattgtat | | 2382 |
| tcactgggac ttaagaatgc gcctgaataa ttgtgagttc gatttgttct ggcaggctaa | | 2442 |
| tgaccatttc cagtaaagtg aatagaggtc agaagtcgta taaagaggt gttgtcagaa | | 2502 |
| caccgttgag attacatagg tgaacaacta ttttaagca actttatttg tgtagtgaca | | 2562 |
| aagcatccca atgcaggctg aaatgtttca tcacatctct ggatctctct attttgtgca | | 2622 |
| gacattgaaa aaattgttca tattatttcc atgttatcag aatatttgat ttttaaaaa | | 2682 |

-continued

| | |
|---|---|
| cataggccaa gttcattcac ttcattattc atttatcaaa atcagagtga atcacattag | 2742 |
| tcgccttcac aactgataaa gatcactgaa gtcaaattga ttttgctat aatcttcaat | 2802 |
| ctacctatat ttaattgaga atctaaaatg tacaaatcat tgtgttgatt ctgcagtgat | 2862 |
| cctgctataa gtaagactca gtccctgatt ttaggtatcc tgtgaaaagc agaattaaga | 2922 |
| caaatacaca agagacaaag cacaaaaaat aaatatcata aggggatgaa caaaatggtg | 2982 |
| gagaaagagt agacaaagtt tttgatcacc tgccttcaaa gaaggctgt gaattttgtt | 3042 |
| cacttagaca gcttggagac aagaaattac ccaaaagtaa ggtgaggagg ataggcaaaa | 3102 |
| agagcagaaa gatgtgaatg gacattgttg agaaatgtga taggaaaaca atcatagata | 3162 |
| aaggatttcc aagcaacaga gcatatccag atgaggtagg atgggataaa ctcttattga | 3222 |
| accaatcttc accaattttg ttttctttt gcagagcaag ctaggaattg tttcccttct | 3282 |
| actgggcaca atacacgcat tgatttttgc ctggaataag tggatagata taaaacaatt | 3342 |
| tgtatggtat acacctccaa cttttatgat agctgttttc cttccaattg ttgtcctgat | 3402 |
| atttaaaagc atactattcc tgccatgctt gaggaagaag atactgaaga ttagacatgg | 3462 |
| ttgggaagac gtcaccaaaa ttaacaaaac tgagatatgt tcccagttgt agaattactg | 3522 |
| tttacacaca tttttgttca atattgatat atttttatcac caacatttca agtttgtatt | 3582 |
| tgttaataaa atgattattc aaggaaaaaa aaaaaaaaa aaaaa | 3627 |

<210> SEQ ID NO 11
<211> LENGTH: 258
<212> TYPE: PRT
<213> ORGANISM: Homo sapiens

<400> SEQUENCE: 11

Met Glu Ser Arg Lys Asp Ile Thr Asn Gln Glu Leu Trp Lys Met
 1               5                  10                  15

Lys Pro Arg Arg Asn Leu Glu Glu Asp Asp Tyr Leu His Lys Asp Thr
                 20                  25                  30

Gly Glu Thr Ser Met Leu Lys Arg Pro Val Leu Leu His Leu His Gln
             35                  40                  45

Thr Ala His Ala Asp Glu Phe Asp Cys Pro Ser Glu Leu Gln His Thr
         50                  55                  60

Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Arg Glu Val Ile His
                 85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Leu His Asn Gly
        130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

```
Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

<210> SEQ ID NO 12
<211> LENGTH: 3627
<212> TYPE: DNA
<213> ORGANISM: Homo sapiens
<220> FEATURE:
<221> NAME/KEY: CDS
<222> LOCATION: (96)...(872)

<400> SEQUENCE: 12
ggggcccgca cctctgggca gcagcggcag ccgagactca cggtcaagct aaggcgaaga      60
gtgggtggct gaagccatac tattttatag aatta atg gaa agc aga aaa gac        113
                                      Met Glu Ser Arg Lys Asp
                                        1               5 atc aca aac caa gaa gaa ctt tgg aaa atg aag cct agg aga aat tta       161
Ile Thr Asn Gln Glu Glu Leu Trp Lys Met Lys Pro Arg Arg Asn Leu
         10                  15                  20 gaa gaa gac gat tat ttg cat aag gac acg gga gag acc agc atg cta       209
Glu Glu Asp Asp Tyr Leu His Lys Asp Thr Gly Glu Thr Ser Met Leu
             25                  30                  35 aaa aga cct gtg ctt ttg cat ttg cac caa aca gcc cat gct gat gaa       257
Lys Arg Pro Val Leu Leu His Leu His Gln Thr Ala His Ala Asp Glu
     40                  45                  50 ttt gac tgc cct tca gaa ctt cag cac aca cag gaa ctc ttt cca cag       305
Phe Asp Cys Pro Ser Glu Leu Gln His Thr Gln Glu Leu Phe Pro Gln
 55                  60                  65                  70 tgg cac ttg cca att aaa ata gct gct att ata gca tct ctg act ttt       353
Trp His Leu Pro Ile Lys Ile Ala Ala Ile Ile Ala Ser Leu Thr Phe
                 75                  80                  85 ctt tac act ctt ctg agg gaa gta att cac ccc tta gca act tcc cat       401
Leu Tyr Thr Leu Leu Arg Glu Val Ile His Pro Leu Ala Thr Ser His
             90                  95                 100 caa caa tat ttt tat aaa att cca atc ctg gtc atc aac aaa gtc ttg       449
Gln Gln Tyr Phe Tyr Lys Ile Pro Ile Leu Val Ile Asn Lys Val Leu
        105                 110                 115 cca atg gtt tcc atc act ctc ttg gca ttg gtt tac ctg cca ggt gtg       497
Pro Met Val Ser Ile Thr Leu Leu Ala Leu Val Tyr Leu Pro Gly Val
    120                 125                 130 ata gca gca att gtc caa ctt cat aat gga acc aag tat aag aag ttt       545
Ile Ala Ala Ile Val Gln Leu His Asn Gly Thr Lys Tyr Lys Lys Phe
135                 140                 145                 150 cca cat tgg ttg gat aag tgg atg tta aca aga aag cag ttt ggg ctt       593
Pro His Trp Leu Asp Lys Trp Met Leu Thr Arg Lys Gln Phe Gly Leu
                155                 160                 165 ctc agt ttc ttt ttt gct gta ctg cat gca att tat agt ctg tct tac       641
Leu Ser Phe Phe Phe Ala Val Leu His Ala Ile Tyr Ser Leu Ser Tyr
            170                 175                 180 cca atg agg cga tcc tac aga tac aag ttg cta aac tgg gca tat caa       689
Pro Met Arg Arg Ser Tyr Arg Tyr Lys Leu Leu Asn Trp Ala Tyr Gln
        185                 190                 195 cag gtc caa caa aat aaa gaa gat gcc tgg att gag cat gat gtt tgg       737
Gln Val Gln Gln Asn Lys Glu Asp Ala Trp Ile Glu His Asp Val Trp
    200                 205                 210
```

-continued

```
            200             205             210
aga atg gag att tat gtg tct ctg gga att gtg gga ttg gca ata ctg      785
Arg Met Glu Ile Tyr Val Ser Leu Gly Ile Val Gly Leu Ala Ile Leu
215                 220                 225                 230 gct ctg ttg gct gtg aca tct att cca tct gtg agt gac tct ttg aca      833
Ala Leu Leu Ala Val Thr Ser Ile Pro Ser Val Ser Asp Ser Leu Thr
                235                 240                 245 tgg aga gaa ttt cac tat att cag gta aat aat ata taa aataaccta        882
Trp Arg Glu Phe His Tyr Ile Gln Val Asn Asn Ile *
            250                 255 agaggtaaat cttcttttg tgtttatgat atagaatatg ttgactttac cccataaaaa     942
ataacaaatg tttttcaaca gcaaagatct tatacttgtt ccaattaata atgtgctctc   1002
ctgttgtttt ccctattgct tctaattagg acaagtgttt cctagacata aataaaaggc   1062
attaaaatat tctttgtttt ttttgttttg tttgttgtt ttttgtttgt tgtttgttt    1122
ttttgagatg aagtctcgct ctgttgccca tgctggagta cagtggcacg atctcggctc   1182
actgcaacct gcgcctcctg ggttcaggcg attctcttgc ctcagcctcc tgagtagctg   1242
ggattacagg cacccatcac catgtccagc taatttttgt attttttagta gagacagggt   1302
tttcccatgt tggccaggct ggtctcgatc tcctgacctc aaatgatccg cccacctcgg   1362
cctcccaaag tgctgggatg acagttgtga gccaccacac tcagcctgct ctttctaata   1422
tttgaaactt gttagacaat tgctaccca tctaatgtga tattttagga atccaatatg    1482
catggtttat tatttcttaa aaaaaatatt ctttttacctg tcacctgaat ttagtaatgc   1542
cttttatgtt acacaactta gcactttcca gaaacaaaaa ctctctcctt gaaataatag   1602
agttttatc taccaaagat atgctagtgt ctcatttcaa aggctgcttt ttccagctta    1662
cattttatat acttactcac ttgaagtttc taaatattct tgtaattttta aaactatctc   1722
agatttactg aggtttatct tctggtggta gattatccat aagaagagtg atgtgccaga   1782
atcactctgg gatccttgtc tgacaagatt caaaggacta aatttaattc agtcatgaac   1842
actgccaatt accgtttatg ggtagacatc tttggaaatt tccacaaggt cagacattcg   1902
caactatccc ttctacatgt ccacacgtat actccaacac tttattaggc atctgattag   1962
tttggaaagt atgcctccat ctgaattagt ccagtgtggc ttagagttgg tacaacattc   2022
tcacagaatt tcctaatttt gtaggttcag cctgataacc actggagttc tttggtcctc   2082
attaaatagc tttcttcaca cattgctctg cctgttacac atatgatgaa cactgctttt   2142
tagacttcat taggaattta ggactgcatc ttgacaactg agcctattct actatatgta   2202
caatacctag cccataatag gtatacaata cacatttggt aaaactaatt ttcaaccaat   2262
gacatgtatt tttcaactag taacctagaa atgtttcact taaaatctga gaactggtta   2322
cactacaagt taccttggag attcatatat gaaaacgcaa acttagctat ttgattgtat   2382
tcactgggac ttaagaatgc gcctgaataa ttgtgagttc gatttgttct ggcaggctaa   2442
tgaccatttc cagtaaagtg aatagaggtc agaagtcgta taaagaggt gttgtcagaa    2502
caccgttgag attacatagg tgaacaacta ttttaagca actttatttg tgtagtgaca   2562
aagcatccca atgcaggctg aaatgtttca tcacatctct ggatctctct attttgtgca   2622
gacattgaaa aaattgttca tattatttcc atgttatcag aatatttgat ttttttaaaa   2682
cataggccaa gttcattcac ttcattattc atttatcaaa atcagagtga atcacattag   2742
tcgccttcac aactgataaa gatcactgaa gtcaaattga ttttgctat aatcttcaat    2802
ctacctatat ttaattgaga atctaaaatg tacaaatcat tgtgttgatt ctgcagtgat   2862
```

```
cctgctataa gtaagactca gtccctgatt ttaggtatcc tgtgaaaagc agaattaaga    2922
caaatacaca agagacaaag cacaaaaaat aaatatcata agggatgaa caaaatggtg     2982 gagaaagagt agacaaagtt tttgatcacc tgccttcaaa gaaaggctgt gaattttgtt   3042
cacttagaca gcttggagac aagaaattac ccaaaagtaa ggtgaggagg ataggcaaaa    3102
agagcagaaa gatgtgaatg gacattgttg agaaatgtga taggaaaaca atcatagata   3162
aaggatttcc aagcaacaga gcatatccag atgaggtagg atgggataaa ctcttattga   3222
accaatcttc accaattttg ttttctttt gcagagcaag ctaggaattg tttcccttct    3282
actgggcaca atacacgcat tgattttgc ctggaataag tggatagata taaaacaatt    3342
tgtatggtat acacctccaa cttttatgat agctgttttc cttccaattg ttgtcctgat   3402
atttaaaagc atactattcc tgccatgctt gaggaagaag atactgaaga ttagacatgg   3462
ttgggaagac gtcaccaaaa ttaacaaaac tgagatatgt tcccagttgt agaattactg   3522
tttacacaca ttttgttca atattgatat attttatcac caacatttca agtttgtatt    3582
tgttaataaa atgattattc aaggaaaaaa aaaaaaaaaa aaaaa                    3627

<210> SEQ ID NO 13
<211> LENGTH: 258
<212> TYPE: PRT
<213> ORGANISM: Homo sapiens

<400> SEQUENCE: 13

Met Glu Ser Arg Lys Asp Ile Thr Asn Gln Glu Glu Leu Trp Lys Met
1               5                   10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
            115                 120                 125

Val Tyr Leu Pro Gly Val Ile Ala Ala Val Gln Leu His Asn Gly
        130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
            165                 170                 175

Ile Tyr Ser Leu Ser Tyr Pro Met Arg Arg Ser Tyr Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240
```

```
Val Ser Asp Ser Leu Thr Trp Arg Glu Phe His Tyr Ile Gln Val Asn
            245                 250                 255

Asn Ile

<210> SEQ ID NO 14
<211> LENGTH: 3627
<212> TYPE: DNA
<213> ORGANISM: Homo sapiens
<220> FEATURE:
<221> NAME/KEY: CDS
<222> LOCATION: (96)...(872)

<400> SEQUENCE: 14
ggggcccgca cctctgggca gcagcggcag ccgagactca cggtcaagct aaggcgaaga       60
gtgggtggct gaagccatac tattttatag aatta atg gaa agc aga aaa gac        113
                                      Met Glu Ser Arg Lys Asp
                                        1               5 atc aca aac caa gaa gaa ctt tgg aaa atg aag cct agg aga aat tta       161
Ile Thr Asn Gln Glu Glu Leu Trp Lys Met Lys Pro Arg Arg Asn Leu
            10                  15                  20 gaa gaa gac gat tat ttg cat aag gac acg gga gag acc agc atg cta       209
Glu Glu Asp Asp Tyr Leu His Lys Asp Thr Gly Glu Thr Ser Met Leu
        25                  30                  35 aaa aga cct gtg ctt ttg cat ttg cac caa aca gcc cat gct gat gaa       257
Lys Arg Pro Val Leu Leu His Leu His Gln Thr Ala His Ala Asp Glu
    40                  45                  50 ttt gac tgc cct tca gaa ctt cag cac aca cag gaa ctc ttt cca cag       305
Phe Asp Cys Pro Ser Glu Leu Gln His Thr Gln Glu Leu Phe Pro Gln
55                  60                  65                  70 tgg cac ttg cca att aaa ata gct gct att ata gca tct ctg act ttt       353
Trp His Leu Pro Ile Lys Ile Ala Ala Ile Ile Ala Ser Leu Thr Phe
                75                  80                  85 ctt tac act ctt ctg agg gaa gta att cac ccc tta gca act tcc cat       401
Leu Tyr Thr Leu Leu Arg Glu Val Ile His Pro Leu Ala Thr Ser His
            90                  95                 100 caa caa tat ttt tat aaa att cca atc ctg gtc atc aac aaa gtc ttg       449
Gln Gln Tyr Phe Tyr Lys Ile Pro Ile Leu Val Ile Asn Lys Val Leu
        105                 110                 115 cca atg gtt tcc atc act ctc ttg gca ttg gtt tac ctg cca ggt gtg       497
Pro Met Val Ser Ile Thr Leu Leu Ala Leu Val Tyr Leu Pro Gly Val
    120                 125                 130 ata gca gca att gtc caa ctt cat aat gga acc aag tat aag aag ttt       545
Ile Ala Ala Ile Val Gln Leu His Asn Gly Thr Lys Tyr Lys Lys Phe
135                 140                 145                 150 cca cat tgg ttg gat aag tgg atg tta aca aga aag cag ttt ggg ctt       593
Pro His Trp Leu Asp Lys Trp Met Leu Thr Arg Lys Gln Phe Gly Leu
                155                 160                 165 ctc agt ttc ttt ttt gct gta ctg cat gca att tat agt ctg tct tac       641
Leu Ser Phe Phe Phe Ala Val Leu His Ala Ile Tyr Ser Leu Ser Tyr
            170                 175                 180 cca atg agg cga tcc tac aga tac aag ttg cta aac tgg gca tat caa       689
Pro Met Arg Arg Ser Tyr Arg Tyr Lys Leu Leu Asn Trp Ala Tyr Gln
        185                 190                 195 cag gtc caa caa aat aaa gaa gat gcc tgg att gag cat gat gtt tgg       737
Gln Val Gln Gln Asn Lys Glu Asp Ala Trp Ile Glu His Asp Val Trp
    200                 205                 210 aga atg gag att tat gtg tct ctg gga att gtg gga ttg gca ata ctg       785
Arg Met Glu Ile Tyr Val Ser Leu Gly Ile Val Gly Leu Ala Ile Leu
215                 220                 225                 230
```

-continued

| | | |
|---|---|---|
| gct ctg ttg gct gtg aca tct att cca tct gtg agt gac tct ttg aca<br>Ala Leu Leu Ala Val Thr Ser Ile Pro Ser Val Ser Asp Ser Leu Thr<br>                            235                        240                        245 | | 833 |
| tgg aga gaa ttt cac tat att cag gta aat aat ata taa aataaccctc<br>Trp Arg Glu Phe His Tyr Ile Gln Val Asn Asn Ile  *<br>                    250                        255 | | 882 |
| agaggtaaat cttcttttg tgtttatgat atagaatatg ttgactttac cccataaaaa | | 942 |
| ataacaaatg tttttcaaca gcaaagatct tatacttgtt ccaattaata atgtgctctc | | 1002 |
| ctgttgtttt ccctattgct tctaattagg acaagtgttt cctagacata aataaaaggc | | 1062 |
| attaaaatat tctttgtttt ttttttttg tttgtttgtt ttttgtttgt ttgtttgttt | | 1122 |
| ttttgagatg aagtctcgct ctgttgccca tgctggagta cagtggcacg atctcggctc | | 1182 |
| actgcaacct gcgcctcctg ggttcaggcg attctcttgc ctcagcctcc tgagtagctg | | 1242 |
| ggattacagg cacccatcac catgtccagc taattttgt attttagta gagacagggt | | 1302 |
| tttccatgt tggccaggct ggtctcgatc tcctgacctc aaatgatccg cccacctcgg | | 1362 |
| cctcccaaag tgctgggatg acagttgtga gccaccacac tcagcctgct ctttctaata | | 1422 |
| tttgaaactt gttagacaat ttgccaccca tctaatgtga tattttagga atccaatatg | | 1482 |
| catggtttat tatttcttaa aaaaaatatt cttttacctg tcacctgaat ttagtaatgc | | 1542 |
| cttttatgtt acacaactta gcactttcca gaaacaaaaa ctctctcctt gaaataatag | | 1602 |
| agtttttatc taccaaagat atgctagtgt ctcatttcaa aggctgcttt tccagctta | | 1662 |
| cattttatat acttactcac ttgaagtttc taaatattct tgtaatttta aaactatctc | | 1722 |
| agatttactg aggtttatct tctggtggta gattatccat aagaagagtg atgtgccaga | | 1782 |
| atcactctgg gatccttgtc tgacaagatt caaaggacta aatttaattc agtcatgaac | | 1842 |
| actgccaatt accgtttatg ggtagacatc tttggaaatt tccacaaggt cagacattcg | | 1902 |
| caactatccc ttctacatgt ccacacgtat actccaacac tttattaggc atctgattag | | 1962 |
| tttggaaagt atgcctccat ctgaattagt ccagtgtggc ttagagttgg tacaacattc | | 2022 |
| tcacagaatt tcctaatttt gtaggttcag cctgataacc actggagttc tttggtcctc | | 2082 |
| attaaatagc tttcttcaca cattgctctg cctgttacac atatgatgaa cactgctttt | | 2142 |
| tagacttcat taggaattta ggactgcatc ttgacaactg agcctattct actatatgta | | 2202 |
| caatacctag cccataatag gtatacaata cacatttggt aaaactaatt ttcaaccaat | | 2262 |
| gacatgtatt tttcaactag taacctagaa atgtttcact taaatctga gaactggtta | | 2322 |
| cactacaagt taccttggag attcatatat gaaaacgcaa acttagctat ttgattgtat | | 2382 |
| tcactgggac ttaagaatgc gcctgaataa ttgtgagttc gatttgttct ggcaggctaa | | 2442 |
| tgaccatttc cagtaaagtg aatagaggtc agaagtcgta taaagaggt gttgtcagaa | | 2502 |
| caccgttgag attacatagg tgaacaacta tttttaagca actttatttg tgtagtgaca | | 2562 |
| aagcatccca atgcaggctg aaatgtttca tcacatctct ggatctctct attttgtgca | | 2622 |
| gacattgaaa aaattgttca tattatttcc atgttatcag aatatttgat ttttaaaaa | | 2682 |
| cataggccaa gttcattcac ttcattattc atttatcaaa atcagagtga atcacattag | | 2742 |
| tcgccttcac aactgataaa gatcactgaa gtcaaattga ttttgctat aatcttcaat | | 2802 |
| ctacctatat ttaattgaga atctaaaatg tacaaatcat tgtgttgatt ctgcagtgat | | 2862 |
| cctgctataa gtaagactca gtccctgatt ttaggtatcc tgtgaaaagc agaattaaga | | 2922 |
| caaatacaca agagacaaag cacaaaaaat aaatatcata aggggatgaa caaaatggtg | | 2982 |
| gagaaagagt agacaaagtt tttgatcacc tgccttcaaa gaaaggctgt gaattttgtt | | 3042 |

-continued

| | |
|---|---|
| cacttagaca gcttggagac aagaaattac ccaaaagtaa ggtgaggagg ataggcaaaa | 3102 |
| agagcagaaa gatgtgaatg gacattgttg agaaatgtga taggaaaaca atcatagata | 3162 |
| aaggatttcc aagcaacaga gcatatccag atgaggtagg atgggataaa ctcttattga | 3222 |
| accaatcttc accaattttg ttttctttt gcagagcaag ctaggaattg tttcccttct | 3282 |
| actgggcaca atacacgcat tgattttgc ctggaataag tggatagata taaaacaatt | 3342 |
| tgtatggtat acacctccaa cttttatgat agctgttttc cttccaattg ttgtcctgat | 3402 |
| atttaaaagc atactattcc tgccatgctt gaggaagaag atactgaaga ttagacatgg | 3462 |
| ttgggaagac gtcaccaaaa ttaacaaaac tgagatatgt tcccagttgt agaattactg | 3522 |
| tttacacaca tttttgttca atattgatat attttatcac caacatttca agtttgtatt | 3582 |
| tgttaataaa atgattattc aaggaaaaaa aaaaaaaaaa aaaaa | 3627 |

<210> SEQ ID NO 15
<211> LENGTH: 258
<212> TYPE: PRT
<213> ORGANISM: Homo sapiens

<400> SEQUENCE: 15

Met Glu Ser Arg Lys Asp Ile Thr Asn Gln Glu Glu Leu Trp Lys Met
1               5                   10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Arg Glu Val Ile His
                85                  90                  95

Pro Leu Ala Thr Ser His Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

```
<210> SEQ ID NO 16
<211> LENGTH: 3627
<212> TYPE: DNA
<213> ORGANISM: Homo sapiens
<220> FEATURE:
<221> NAME/KEY: CDS
<222> LOCATION: (96)...(872)

<400> SEQUENCE: 16
ggggcccgca cctctgggca gcagcggcag ccgagactca cggtcaagct aaggcgaaga        60
gtgggtggct gaagccatac tattttatag aatta atg gaa agc aga aaa gac          113
                                       Met Glu Ser Arg Lys Asp
                                         1               5 atc aca aac caa gaa gaa ctt tgg aaa atg aag cct agg aga aat tta         161
Ile Thr Asn Gln Glu Glu Leu Trp Lys Met Lys Pro Arg Arg Asn Leu
             10                  15                  20 gaa gaa gac gat tat ttg cat aag gac acg gga gag acc agc atg cta         209
Glu Glu Asp Asp Tyr Leu His Lys Asp Thr Gly Glu Thr Ser Met Leu
         25                  30                  35 aaa aga cct gtg ctt ttg cat ttg cac caa aca gcc cat gct gat gaa         257
Lys Arg Pro Val Leu Leu His Leu His Gln Thr Ala His Ala Asp Glu
 40                  45                  50 ttt gac tgc cct tca gaa ctt cag cac aca cag gaa ctc ttt cca cag         305
Phe Asp Cys Pro Ser Glu Leu Gln His Thr Gln Glu Leu Phe Pro Gln
 55                  60                  65                  70 tgg cac ttg cca att aaa ata gct gct att ata gca tct ctg act ttt         353
Trp His Leu Pro Ile Lys Ile Ala Ala Ile Ile Ala Ser Leu Thr Phe
                 75                  80                  85 ctt tac act ctt ctg agg gaa gta att cac ccc tta gca act tcc cat         401
Leu Tyr Thr Leu Leu Arg Glu Val Ile His Pro Leu Ala Thr Ser His
             90                  95                 100 caa caa tat ttt tat aaa att cca atc ctg gtc atc aac aaa gtc ttg         449
Gln Gln Tyr Phe Tyr Lys Ile Pro Ile Leu Val Ile Asn Lys Val Leu
        105                 110                 115 cca atg gtt tcc atc act ctc ttg gca ttg gtt tac ctg cca ggt gtg         497
Pro Met Val Ser Ile Thr Leu Leu Ala Leu Val Tyr Leu Pro Gly Val
120                 125                 130 ata gca gca att gtc caa ctt cat aat gga acc aag tat aag aag ttt         545
Ile Ala Ala Ile Val Gln Leu His Asn Gly Thr Lys Tyr Lys Lys Phe
135                 140                 145                 150 cca cat tgg ttg gat aag tgg atg tta aca aga aag cag ttt ggg ctt         593
Pro His Trp Leu Asp Lys Trp Met Leu Thr Arg Lys Gln Phe Gly Leu
                155                 160                 165 ctc agt ttc ttt ttt gct gta ctg cat gca att tat agt ctg tct tac         641
Leu Ser Phe Phe Phe Ala Val Leu His Ala Ile Tyr Ser Leu Ser Tyr
            170                 175                 180 cca atg agg cga tcc tac aga tac aag ttg cta aac tgg gca tat caa         689
Pro Met Arg Arg Ser Tyr Arg Tyr Lys Leu Leu Asn Trp Ala Tyr Gln
        185                 190                 195 cag gtc caa caa aat aaa gaa gat gcc tgg att gag cat gat gtt tgg         737
Gln Val Gln Gln Asn Lys Glu Asp Ala Trp Ile Glu His Asp Val Trp
    200                 205                 210 aga atg gag att tat gtg tct ctg gga att gtg gga ttg gca ata ctg         785
Arg Met Glu Ile Tyr Val Ser Leu Gly Ile Val Gly Leu Ala Ile Leu
215                 220                 225                 230 gct ctg ttg gct gtg aca tct att cca tct gtg agt gac tct ttg aca         833
Ala Leu Leu Ala Val Thr Ser Ile Pro Ser Val Ser Asp Ser Leu Thr
                235                 240                 245 tgg aga gaa ttt cac tat att cag gta aat aat ata taa aataaccta          882
Trp Arg Glu Phe His Tyr Ile Gln Val Asn Asn Ile
```

```
Trp Arg Glu Phe His Tyr Ile Gln Val Asn Asn Ile  *
            250                 255
```

| | |
|---|---|
| agaggtaaat cttcttttg tgtttatgat atagaatatg ttgactttac cccataaaaa | 942 |
| ataacaaatg ttttcaaca gcaaagatct tatacttgtt ccaattaata atgtgctctc | 1002 |
| ctgttgtttt ccctattgct tctaattagg acaagtgttt cctagacata aataaaaggc | 1062 |
| attaaaatat tctttgtttt ttttttttg tttgtttgtt tttgtttgt ttgtttgttt | 1122 |
| ttttgagatg aagtctcgct ctgttgccca tgctggagta cagtggcacg atctcggctc | 1182 |
| actgcaacct gcgcctcctg ggttcaggcg attctcttgc ctcagcctcc tgagtagctg | 1242 |
| ggattacagg cacccatcac catgtccagc taatttttgt attttagta gagacagggt | 1302 |
| tttcccatgt tggccaggct ggtctcgatc tcctgacctc aaatgatccg cccacctcgg | 1362 |
| cctcccaaag tgctgggatg acagttgtga gccaccacac tcagcctgct ctttctaata | 1422 |
| tttgaaactt gttagacaat ttgctaccca tctaatgtga tattttagga atccaatatg | 1482 |
| catggtttat tatttcttaa aaaaatatt cttttacctg tcacctgaat ttagtaatgc | 1542 |
| cttttatgtt acacaactta gcactttcca gaaacaaaaa ctctctcctt gaaataatag | 1602 |
| agttttatc taccaaagtt atgctagtgt ctcatttcaa aggctgcttt ttccagctta | 1662 |
| cattttatat acttactcac ttgaagtttc taaatattct tgtaatttta aaactatctc | 1722 |
| agatttactg aggtttatct tctggtggta gattatccat aagaagagtg atgtgccaga | 1782 |
| atcactctgg gatccttgtc tgacaagatt caaaggacta aatttaattc agtcatgaac | 1842 |
| actgccaatt accgtttatg ggtagacatc tttggaaatt tccacaaggt cagacattcg | 1902 |
| caactatccc ttctacatgt ccacacgtat actccaacac tttattaggc atctgattag | 1962 |
| tttgaaagt atgcctccat ctgaattagt ccagtgtggc ttagagttgg tacaacattc | 2022 |
| tcacagaatt tcctaatttt gtaggttcag cctgataacc actggagttc tttggtcctc | 2082 |
| attaaatagc tttcttcaca cattgctctg cctgttacac atatgatgaa cactgctttt | 2142 |
| tagacttcat taggaattta ggactgcatc ttgacaactg agcctattct actatatgta | 2202 |
| caatacctag cccataatag gtatacaata cacatttggt aaaactaatt ttcaaccaat | 2262 |
| gacatgtatt tttcaactag taacctagaa atgtttcact taaaatctga gaactggtta | 2322 |
| cactacaagt taccttggag attcatatat gaaaacgcaa acttagctat ttgattgtat | 2382 |
| tcactgggac ttaagaatgc gcctgaataa ttgtgagttc gatttgttct ggcaggctaa | 2442 |
| tgaccatttc cagtaaagtg aatagaggtc agaagtcgta taaagaggt gttgtcagaa | 2502 |
| caccgttgag attacatagg tgaacaacta ttttaagca actttatttg tgtagtgaca | 2562 |
| aagcatccca atgcaggctg aaatgtttca tcacatctct ggatctctct attttgtgca | 2622 |
| gacattgaaa aaattgttca tattattcc atgttatcag aatatttgat tttttaaaaa | 2682 |
| cataggccaa gttcattcac ttcattattc atttatcaaa atcagagtga atcacattag | 2742 |
| tcgccttcac aactgataaa gatcactgaa gtcaaattga ttttgctat aatcttcaat | 2802 |
| ctacctatat ttaattgaga atctaaaatg tacaaatcat tgtgttgatt ctgcagtgat | 2862 |
| cctgctataa gtaagactca gtccctgatt ttaggtatcc tgtgaaaagc agaattaaga | 2922 |
| caaatacaca agagacaaag cacaaaaaat aaatatcata aggggatgaa caaaatggtg | 2982 |
| gagaaagagt agacaaagtt tttgatcacc tgccttcaaa gaaaggctgt gaattttgtt | 3042 |
| cacttagaca gcttggagac aagaaattac ccaaaagtaa ggtgaggagg ataggcaaaa | 3102 |
| agagcagaaa gatgtgaatg gacattgttg agaaatgtga taggaaaaca atcatagata | 3162 |

-continued

```
aaggatttcc aagcaacaga gcatatccag atgaggtagg atgggataaa ctcttattga    3222
accaatcttc accaattttg tttttctttt gcagagcaag ctaggaattg tttcccttct    3282
actgggcaca atacacgcat tgattttgc ctggaataag tggatagata taaaacaatt    3342
tgtatggtat acacctccaa cttttatgat agctgttttc cttccaattg ttgtcctgat    3402
atttaaaagc atactattcc tgccatgctt gaggaagaag atactgaaga ttagacatgg    3462
ttgggaagac gtcaccaaaa ttaacaaaac tgagatatgt tcccagttgt agaattactg    3522
tttacacaca ttttgttca atattgatat attttatcac caacatttca gtttgtatt     3582 tgttaataaa atgattattc aaggaaaaaa aaaaaaaaa aaaaa                     3627
```

<210> SEQ ID NO 17
<211> LENGTH: 258
<212> TYPE: PRT
<213> ORGANISM: Homo sapiens

<400> SEQUENCE: 17

```
Met Glu Ser Arg Lys Asp Ile Thr Asn Gln Glu Leu Trp Lys Met
 1               5                  10                  15

Lys Pro Arg Arg Asn Leu Glu Glu Asp Asp Tyr Leu His Lys Asp Thr
                20                  25                  30

Gly Glu Thr Ser Met Leu Lys Arg Pro Val Leu Leu His Leu His Gln
            35                  40                  45

Thr Ala His Ala Asp Glu Phe Asp Cys Pro Ser Glu Leu Gln His Thr
        50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile
```

<210> SEQ ID NO 18
<211> LENGTH: 3627
<212> TYPE: DNA
<213> ORGANISM: Homo sapiens

```
<220> FEATURE:
<221> NAME/KEY: CDS
<222> LOCATION: (96)...(872)

<400> SEQUENCE: 18
ggggcccgca cctctgggca gcagcggcag ccgagactca cggtcaagct aaggcgaaga      60
gtgggtggct gaagccatac tattttatag aatta atg gaa agc aga aaa gac         113
                                       Met Glu Ser Arg Lys Asp
                                        1               5 atc aca aac caa gaa gaa ctt tgg aaa atg aag cct agg aga aat tta        161
Ile Thr Asn Gln Glu Glu Leu Trp Lys Met Lys Pro Arg Arg Asn Leu
             10                  15                  20 gaa gaa gac gat tat ttg cat aag gac acg gga gag acc agc atg cta        209
Glu Glu Asp Asp Tyr Leu His Lys Asp Thr Gly Glu Thr Ser Met Leu
         25                  30                  35 aaa aga cct gtg ctt ttg cat ttg cac caa aca gcc cat gct gat gaa        257
Lys Arg Pro Val Leu Leu His Leu His Gln Thr Ala His Ala Asp Glu
     40                  45                  50 ttt gac tgc cct tca gaa ctt cag cac aca cag gaa ctc ttt cca cag        305
Phe Asp Cys Pro Ser Glu Leu Gln His Thr Gln Glu Leu Phe Pro Gln
 55                  60                  65                  70 tgg cac ttg cca att aaa ata gct gct att ata gca tct ctg act ttt        353
Trp His Leu Pro Ile Lys Ile Ala Ala Ile Ile Ala Ser Leu Thr Phe
                 75                  80                  85 ctt tac act ctt ctg agg gaa gta att cac ccc tta gca act tcc cat        401
Leu Tyr Thr Leu Leu Arg Glu Val Ile His Pro Leu Ala Thr Ser His
             90                  95                 100 caa caa tat ttt tat aaa att cca atc ctg gtc atc aac aaa gtc ttg        449
Gln Gln Tyr Phe Tyr Lys Ile Pro Ile Leu Val Ile Asn Lys Val Leu
        105                 110                 115 cca atg gtt tcc atc act ctc ttg gca ttg gtt tac ctg cca ggt gtg        497
Pro Met Val Ser Ile Thr Leu Leu Ala Leu Val Tyr Leu Pro Gly Val
    120                 125                 130 ata gca gca att gtc caa ctt cat aat gga acc aag tat aag aag ttt        545
Ile Ala Ala Ile Val Gln Leu His Asn Gly Thr Lys Tyr Lys Lys Phe
135                 140                 145                 150 cca cat tgg ttg gat aag tgg atg tta aca aga aag cag ttt ggg ctt        593
Pro His Trp Leu Asp Lys Trp Met Leu Thr Arg Lys Gln Phe Gly Leu
                155                 160                 165 ctc agt ttc ttt ttt gct gta ctg cat gca att tat agt ctg tct tac        641
Leu Ser Phe Phe Phe Ala Val Leu His Ala Ile Tyr Ser Leu Ser Tyr
            170                 175                 180 cca atg agg cga tcc tac aga tac aag ttg cta aac tgg gca tat caa        689
Pro Met Arg Arg Ser Tyr Arg Tyr Lys Leu Leu Asn Trp Ala Tyr Gln
        185                 190                 195 cag gtc caa caa aat aaa gaa gat gcc tgg att gag cat gat gtt tgg        737
Gln Val Gln Gln Asn Lys Glu Asp Ala Trp Ile Glu His Asp Val Trp
    200                 205                 210 aga atg gag att tat gtg tct ctg gga att gtg gga ttg gca ata ctg        785
Arg Met Glu Ile Tyr Val Ser Leu Gly Ile Val Gly Leu Ala Ile Leu
215                 220                 225                 230 gct ctg ttg gct gtg aca tct att cca tct gtg agt gac tct ttg aca        833
Ala Leu Leu Ala Val Thr Ser Ile Pro Ser Val Ser Asp Ser Leu Thr
                235                 240                 245 tgg aga gaa ttt cac tat att cag gta aat aat ata taa aataaccta         882
Trp Arg Glu Phe His Tyr Ile Gln Val Asn Asn Ile *
            250                 255 agaggtaaat cttctttttg tgtttatgat atagaatatg ttgactttac cccataaaaa      942
ataacaaatg tttttcaaca gcaaagatct tatacttgtt ccaattaata atgtgctctc     1002
```

```
ctgttgtttt ccctattgct tctaattagg acaagtgttt cctagacata aataaaaggc    1062
attaaaatat tctttgtttt ttttttttg tttgtttgtt ttttgtttgt ttgtttgttt    1122
ttttgagatg aagtctcgct ctgttgccca tgctggagta cagtggcacg atctcggctc    1182
actgcaacct gcgcctcctg ggttcaggcg attctcttgc ctcagcctcc tgagtagctg    1242
ggattacagg cacccatcac catgtccagc taatttttgt attttagta gagacagggt     1302 tttcccatgt tggccaggct ggtctcgatc tcctgacctc aaatgatccg cccacctcgg    1362
cctcccaaag tgctgggatg acagttgtga gccaccacac tcagcctgct ctttctaata    1422
tttgaaactt gttagacaat tgctaccca tctaatgtga tattttagga atccaatatg     1482
catggtttat tatttcttaa aaaaatatt cttttacctg tcacctgaat ttagtaatgc     1542
cttttatgtt acacaactta gcactttcca gaaacaaaaa ctctctcctt gaaataatag    1602 agttttttatc taccaaagat attctagtgt ctcatttcaa aggctgcttt ttccagctta   1662
cattttatat acttactcac ttgaagtttc taaatattct tgtaatttta aaactatctc    1722
agatttactg aggtttatct tctggtggta gattatccat aagaagagtg atgtgccaga    1782
atcactctgg gatccttgtc tgacaagatt caaaggacta aatttaattc agtcatgaac    1842
actgccaatt accgtttatg ggtagacatc tttggaaatt tccacaaggt cagacattcg    1902
caactatccc ttctacatgt ccacacgtat actccaacac tttattaggc atctgattag    1962
tttggaaagt atgcctccat ctgaattagt ccagtgtggc ttagagttgg tacaacattc    2022
tcacagaatt tcctaatttt gtaggttcag cctgataacc actggagttc tttggtcctc    2082
attaaatagc tttcttcaca cattgctctg cctgttacac atatgatgaa cactgctttt    2142
tagacttcat taggaattta ggactgcatc ttgacaactg agcctattct actatatgta    2202
caatacctag cccataatag gtatacaata cacatttggt aaaactaatt ttcaaccaat    2262
gacatgtatt tttcaactag taacctagaa atgtttcact taaaatctga gaactggtta    2322
cactacaagt taccttggag attcatatat gaaaacgcaa acttagctat ttgattgtat    2382
tcactgggac ttaagaatgc gcctgaataa ttgtgagttc gatttgttct ggcaggctaa    2442
tgaccatttc cagtaaagtg aatagaggtc agaagtcgta taaagaggt gttgtcagaa     2502 caccgttgag attacatagg tgaacaacta ttttaagca actttatttg tgtagtgaca     2562
aagcatccca atgcaggctg aaatgtttca tcacatctct ggatctctct attttgtgca    2622
gacattgaaa aaattgttca tattatttcc atgttatcag aatatttgat ttttaaaaa    2682 cataggccaa gttcattcac ttcattattc atttatcaaa atcagagtga atcacattag    2742
tcgccttcac aactgataaa gatcactgaa gtcaaattga tttttgctat aatcttcaat    2802
ctacctatat ttaattgaga atctaaaatg tacaaatcat tgtgttgatt ctgcagtgat    2862
cctgctataa gtaagactca gtccctgatt ttaggtatcc tgtgaaaagc agaattaaga    2922
caaatacaca agagacaaag cacaaaaaat aaatatcata aggggatgaa caaaatggtg    2982
gagaaagagt agacaaagtt tttgatcacc tgccttcaaa gaaaggctgt gaattttgtt    3042
cacttagaca gcttggagac aagaaattac ccaaaagtaa ggtgaggagg ataggcaaaa    3102
agagcagaaa gatgtgaatg gacattgttg agaaatgtga taggaaaaca atcatagata    3162
aaggatttcc aagcaacaga gcatatccag atgaggtagg atgggataaa ctcttattga    3222
accaatcttc accaattttg ttttctttt gcagagcaag ctaggaattg tttcccttct     3282
actgggcaca atacacgcat tgattttgc ctggaataag tggatagata taaacaatt     3342
```

```
tgtatggtat acacctccaa cttttatgat agctgttttc cttccaattg ttgtcctgat    3402
atttaaaagc atactattcc tgccatgctt gaggaagaag atactgaaga ttagacatgg    3462
ttgggaagac gtcaccaaaa ttaacaaaac tgagatatgt tcccagttgt agaattactg    3522
tttacacaca ttttgttca atattgatat attttatcac caacatttca agtttgtatt    3582
tgttaataaa atgattattc aaggaaaaaa aaaaaaaaaa aaaaa                   3627
```

```
<210> SEQ ID NO 19
<211> LENGTH: 258
<212> TYPE: PRT
<213> ORGANISM: Homo sapiens

<400> SEQUENCE: 19
```

Met Glu Ser Arg Lys Asp Ile Thr Asn Gln Glu Glu Leu Trp Lys Met
1               5                   10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

```
<210> SEQ ID NO 20
<211> LENGTH: 3627
<212> TYPE: DNA
<213> ORGANISM: Homo sapiens
<220> FEATURE:
<221> NAME/KEY: CDS
<222> LOCATION: (96)...(872)

<400> SEQUENCE: 20
```

-continued

```
ggggcccgca cctctgggca gcagcggcag ccgagactca cggtcaagct aaggcgaaga      60
gtgggtggct gaagccatac tattttatag aatta atg gaa agc aga aaa gac       113
                                        Met Glu Ser Arg Lys Asp
                                          1               5 atc aca aac caa gaa gaa ctt tgg aaa atg aag cct agg aga aat tta       161
Ile Thr Asn Gln Glu Glu Leu Trp Lys Met Lys Pro Arg Arg Asn Leu
             10                  15                  20 gaa gaa gac gat tat ttg cat aag gac acg gga gag acc agc atg cta       209
Glu Glu Asp Asp Tyr Leu His Lys Asp Thr Gly Glu Thr Ser Met Leu
             25                  30                  35 aaa aga cct gtg ctt ttg cat ttg cac caa aca gcc cat gct gat gaa       257
Lys Arg Pro Val Leu Leu His Leu His Gln Thr Ala His Ala Asp Glu
         40                  45                  50 ttt gac tgc cct tca gaa ctt cag cac aca cag gaa ctc ttt cca cag       305
Phe Asp Cys Pro Ser Glu Leu Gln His Thr Gln Glu Leu Phe Pro Gln
 55                  60                  65                  70 tgg cac ttg cca att aaa ata gct gct att ata gca tct ctg act ttt       353
Trp His Leu Pro Ile Lys Ile Ala Ala Ile Ile Ala Ser Leu Thr Phe
                 75                  80                  85 ctt tac act ctt ctg agg gaa gta att cac ccc tta gca act tcc cat       401
Leu Tyr Thr Leu Leu Arg Glu Val Ile His Pro Leu Ala Thr Ser His
             90                  95                 100 caa caa tat ttt tat aaa att cca atc ctg gtc atc aac aaa gtc ttg       449
Gln Gln Tyr Phe Tyr Lys Ile Pro Ile Leu Val Ile Asn Lys Val Leu
        105                 110                 115 cca atg gtt tcc atc act ctc ttg gca ttg gtt tac ctg cca ggt gtg       497
Pro Met Val Ser Ile Thr Leu Leu Ala Leu Val Tyr Leu Pro Gly Val
120                 125                 130 ata gca gca att gtc caa ctt cat aat gga acc aag tat aag aag ttt       545
Ile Ala Ala Ile Val Gln Leu His Asn Gly Thr Lys Tyr Lys Lys Phe
135                 140                 145                 150 cca cat tgg ttg gat aag tgg atg tta aca aga aag cag ttt ggg ctt       593
Pro His Trp Leu Asp Lys Trp Met Leu Thr Arg Lys Gln Phe Gly Leu
                155                 160                 165 ctc agt ttc ttt ttt gct gta ctg cat gca att tat agt ctg tct tac       641
Leu Ser Phe Phe Phe Ala Val Leu His Ala Ile Tyr Ser Leu Ser Tyr
            170                 175                 180 cca atg agg cga tcc tac aga tac aag ttg cta aac tgg gca tat caa       689
Pro Met Arg Arg Ser Tyr Arg Tyr Lys Leu Leu Asn Trp Ala Tyr Gln
        185                 190                 195 cag gtc caa caa aat aaa gaa gat gcc tgg att gag cat gat gtt tgg       737
Gln Val Gln Gln Asn Lys Glu Asp Ala Trp Ile Glu His Asp Val Trp
    200                 205                 210 aga atg gag att tat gtg tct ctg gga att gtg gga ttg gca ata ctg       785
Arg Met Glu Ile Tyr Val Ser Leu Gly Ile Val Gly Leu Ala Ile Leu
215                 220                 225                 230 gct ctg ttg gct gtg aca tct att cca tct gtg agt gac tct ttg aca       833
Ala Leu Leu Ala Val Thr Ser Ile Pro Ser Val Ser Asp Ser Leu Thr
                235                 240                 245 tgg aga gaa ttt cac tat att cag gta aat aat ata taa aataaccta        882
Trp Arg Glu Phe His Tyr Ile Gln Val Asn Asn Ile *
            250                 255 agaggtaaat cttcttttg tgtttatgat atagaatatg ttgactttac cccataaaaa      942
ataacaaatg tttttcaaca gcaaagatct tatacttgtt ccaattaata atgtgctctc    1002
ctgttgtttt ccctattgct tctaattagg acaagtgttt cctagacata aataaaaggc    1062
attaaaatat tctttgtttt ttttttttg tttgttgtt ttttgtttgt tgtttgttt       1122 ttttgagatg aagtctcgct ctgttgccca tgctggagta cagtggcacg atctcggctc    1182
```

```
actgcaacct gcgcctcctg ggttcaggcg attctcttgc ctcagcctcc tgagtagctg   1242
ggattacagg cacccatcac catgtccagc taattttgt attttagta gagacagggt    1302
tttcccatgt tggccaggct ggtctcgatc tcctgacctc aaatgatccg cccacctcgg   1362
cctcccaaag tgctgggatg acagttgtga gccaccacac tcagcctgct ctttctaata   1422
tttgaaactt gttagacaat tgctaccca tctaatgtga tattttagga atccaatatg    1482
catggtttat tatttcttaa aaaaaatatt cttttacctg tcacctgaat ttagtaatgc   1542
cttttatgtt acacaactta gcactttcca gaaacaaaaa ctctctcctt gaaataatag   1602
agtttttatc taccaaagat atgctagtgt ctcatttcaa aggctgcttt ttccagctta   1662
cattttatat acttactcac ttgaagtttc taaatattct tgtaatttta aaaatatctc   1722
agatttactg aggtttatct tctggtggta gattatccat aagaagagtg atgtgccaga   1782
atcactctgg gatccttgtc tgacaagatt caaaggacta aatttaattc agtcatgaac   1842
actgccaatt accgtttatg ggtagacatc tttggaaatt tccacaaggt cagacattcg   1902
caactatccc ttctacatgt ccacacgtat actccaacac tttattaggc atctgattag   1962
tttggaaagt atgcctccat ctgaattagt ccagtgtggc ttagagttgg tacaacattc   2022
tcacagaatt tcctaatttt gtaggttcag cctgataacc actggagttc tttggtcctc   2082
attaaatagc tttcttcaca cattgctctg cctgttacac atatgatgaa cactgctttt   2142
tagacttcat taggaattta ggactgcatc ttgacaactg agcctattct actatatgta   2202
caatacctag cccataatag gtatacaata cacatttggt aaaactaatt ttcaaccaat   2262
gacatgtatt tttcaactag taacctagaa atgtttcact taaaatctga gaactggtta   2322
cactacaagt taccttggag attcatatat gaaaacgcaa acttagctat ttgattgtat   2382
tcactgggac ttaagaatgc gcctgaataa ttgtgagttc gatttgttct ggcaggctaa   2442
tgaccatttc cagtaaagtg aatagaggtc agaagtcgta taaaagaggt gttgtcagaa   2502
caccgttgag attacatagg tgaacaacta ttttaagca actttatttg tgtagtgaca    2562
aagcatccca atgcaggctg aaatgtttca tcacatctct ggatctctct attttgtgca   2622
gacattgaaa aaattgttca tattatttcc atgttatcag aatatttgat ttttaaaaa    2682
cataggccaa gttcattcac ttcattattc atttatcaaa atcagagtga atcacattag   2742
tcgccttcac aactgataaa gatcactgaa gtcaaattga ttttgctat aatcttcaat    2802
ctacctatat ttaattgaga atctaaaatg tacaaatcat tgtgttgatt ctgcagtgat   2862
cctgctataa gtaagactca gtccctgatt ttaggtatcc tgtgaaaagc agaattaaga   2922
caaatacaca agagacaaag cacaaaaaat aaatatcata aggggatgaa caaaatggtg   2982
gagaaagagt agacaaagtt tttgatcacc tgccttcaaa gaaaggctgt gaattttgtt   3042
cacttagaca gcttggagac aagaaattac ccaaaagtaa ggtgaggagg ataggcaaaa   3102
agagcagaaa gatgtgaatg acattgttg agaaatgtga taggaaaaca atcatagata    3162
aaggatttcc aagcaacaga gcatatccag atgaggtagg atgggataaa ctcttattga   3222
accaatcttc accaattttg ttttttcttt gcagagcaag ctaggaattg tttcccttct   3282
actgggcaca atacacgcat tgattttgc ctggaataag tggatagata taaacaatt    3342
tgtatggtat acacctccaa ctttatgat agctgttttc cttccaattg ttgtcctgat    3402
atttaaaagc atactattcc tgccatgctt gaggaagaag atactgaaga ttagacatgg   3462
ttgggaagac gtcaccaaaa ttaacaaaac tgagatatgt tcccagttgt agaattactg   3522
```

-continued

```
tttacacaca tttttgttca atattgatat attttatcac caacatttca agtttgtatt    3582
tgttaataaa atgattattc aaggaaaaaa aaaaaaaaaa aaaaa                    3627
```

<210> SEQ ID NO 21
<211> LENGTH: 258
<212> TYPE: PRT
<213> ORGANISM: Homo sapiens

<400> SEQUENCE: 21

```
Met Glu Ser Arg Lys Asp Ile Thr Asn Gln Glu Leu Trp Lys Met
 1               5                  10                  15

Lys Pro Arg Arg Asn Leu Glu Glu Asp Tyr Leu His Lys Asp Thr
                20                  25                  30

Gly Glu Thr Ser Met Leu Lys Arg Pro Val Leu Leu His Leu His Gln
                35                  40                  45

Thr Ala His Ala Asp Glu Phe Asp Cys Pro Ser Glu Leu Gln His Thr
 50                  55                  60

Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Arg Glu Val Ile His
                 85                  90                  95

Pro Leu Ala Thr Ser His Gln Gln Tyr Phe Tyr Lys Ile Pro Ile Leu
                100                 105                 110

Val Ile Asn Lys Val Leu Pro Met Val Ser Ile Thr Leu Leu Ala Leu
                115                 120                 125

Val Tyr Leu Pro Gly Val Ile Ala Ala Ile Val Gln Leu His Asn Gly
            130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
                180                 185                 190

Leu Asn Trp Ala Tyr Gln Gln Val Gln Gln Asn Lys Glu Asp Ala Trp
                195                 200                 205

Ile Glu His Asp Val Trp Arg Met Glu Ile Tyr Val Ser Leu Gly Ile
            210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile
```

<210> SEQ ID NO 22
<211> LENGTH: 3627
<212> TYPE: DNA
<213> ORGANISM: Homo sapiens
<220> FEATURE:
<221> NAME/KEY: CDS
<222> LOCATION: (96)...(872)

<400> SEQUENCE: 22

```
ggggcccgca cctctgggca gcagcggcag ccgagactca cggtcaagct aaggcgaaga     60
gtgggtggct gaagccatac tattttatag aatta atg gaa agc aga aaa gac       113
                                     Met Glu Ser Arg Lys Asp
                                      1               5
```

```
atc aca aac caa gaa gaa ctt tgg aaa atg aag cct agg aga aat tta       161
Ile Thr Asn Gln Glu Glu Leu Trp Lys Met Lys Pro Arg Arg Asn Leu
         10                  15                  20 gaa gaa gac gat tat ttg cat aag gac acg gga gag acc agc atg cta       209
Glu Glu Asp Asp Tyr Leu His Lys Asp Thr Gly Glu Thr Ser Met Leu
             25                  30                  35 aaa aga cct gtg ctt ttg cat ttg cac caa aca gcc cat gct gat gaa       257
Lys Arg Pro Val Leu Leu His Leu His Gln Thr Ala His Ala Asp Glu
 40                  45                  50 ttt gac tgc cct tca gaa ctt cag cac aca cag gaa ctc ttt cca cag       305
Phe Asp Cys Pro Ser Glu Leu Gln His Thr Gln Glu Leu Phe Pro Gln
 55                  60                  65                  70 tgg cac ttg cca att aaa ata gct gct att ata gca tct ctg act ttt       353
Trp His Leu Pro Ile Lys Ile Ala Ala Ile Ile Ala Ser Leu Thr Phe
                 75                  80                  85 ctt tac act ctt ctg agg gaa gta att cac ccc tta gca act tcc cat       401
Leu Tyr Thr Leu Leu Arg Glu Val Ile His Pro Leu Ala Thr Ser His
             90                  95                 100 caa caa tat ttt tat aaa att cca atc ctg gtc atc aac aaa gtc ttg       449
Gln Gln Tyr Phe Tyr Lys Ile Pro Ile Leu Val Ile Asn Lys Val Leu
         105                 110                 115 cca atg gtt tcc atc act ctc ttg gca ttg gtt tac ctg cca ggt gtg       497
Pro Met Val Ser Ile Thr Leu Leu Ala Leu Val Tyr Leu Pro Gly Val
120                 125                 130 ata gca gca att gtc caa ctt cat aat gga acc aag tat aag aag ttt       545
Ile Ala Ala Ile Val Gln Leu His Asn Gly Thr Lys Tyr Lys Lys Phe
135                 140                 145                 150 cca cat tgg ttg gat aag tgg atg tta aca aga aag cag ttt ggg ctt       593
Pro His Trp Leu Asp Lys Trp Met Leu Thr Arg Lys Gln Phe Gly Leu
                155                 160                 165 ctc agt ttc ttt ttt gct gta ctg cat gca att tat agt ctg tct tac       641
Leu Ser Phe Phe Phe Ala Val Leu His Ala Ile Tyr Ser Leu Ser Tyr
            170                 175                 180 cca atg agg cga tcc tac aga tac aag ttg cta aac tgg gca tat caa       689
Pro Met Arg Arg Ser Tyr Arg Tyr Lys Leu Leu Asn Trp Ala Tyr Gln
        185                 190                 195 cag gtc caa caa aat aaa gaa gat gcc tgg att gag cat gat gtt tgg       737
Gln Val Gln Gln Asn Lys Glu Asp Ala Trp Ile Glu His Asp Val Trp
200                 205                 210 aga atg gag att tat gtg tct ctg gga att gtg gga ttg gca ata ctg       785
Arg Met Glu Ile Tyr Val Ser Leu Gly Ile Val Gly Leu Ala Ile Leu
215                 220                 225                 230 gct ctg ttg gct gtg aca tct att cca tct gtg agt gac tct ttg aca       833
Ala Leu Leu Ala Val Thr Ser Ile Pro Ser Val Ser Asp Ser Leu Thr
                235                 240                 245 tgg aga gaa ttt cac tat att cag gta aat aat ata taa aataaccta        882
Trp Arg Glu Phe His Tyr Ile Gln Val Asn Asn Ile *
            250                 255 agaggtaaat cttcttttg tgtttatgat atagaatatg ttgactttac cccataaaaa       942
ataacaaatg ttttcaaca gcaaagatct tatacttgtt ccaattaata atgtgctctc      1002
ctgttgtttt ccctattgct tctaattagg acaagtgttt cctagacata aataaaaggc     1062
attaaaatat tctttgtttt tttttttttg tttgtttgtt ttttgtttgt tgtttgttt      1122 ttttgagatg aagtctcgct ctgttgccca tgctggagta cagtggcacg atctcggctc     1182
actgcaacct gcgcctcctg ggttcaggcg attctcttgc ctcagcctcc tgagtagctg     1242
ggattacagg cacccatcac catgtccagc taatttttgt attttttagta gagacagggt    1302 tttcccatgt tggccaggct ggtctcgatc tcctgacctc aaatgatccg cccacctcgg     1362
```

```
cctcccaaag tgctgggatg acagttgtga gccaccacac tcagcctgct ctttctaata    1422
tttgaaactt gttagacaat ttgctaccca tctaatgtga tattttagga atccaatatg    1482
catggtttat tatttcttaa aaaaaatatt cttttacctg tcacctgaat ttagtaatgc    1542
cttttatgtt acacaactta gcactttcca gaaacaaaaa ctctctcctt gaaataatag    1602 agttttatc taccaaagat atgctagtgt ctcatttcaa aggctgcttt ttccagctta     1662
cattttatat acttactcac ttgaagtttc taaatattct tgtaatttta aaactatctc    1722
agatttactg aggtttatct tctggtggta gattatccat aagaagagtg atgtgccaga    1782
atcactctgg gatccttgtc tgacaagatt caaaggacta aatttaattc agtcatgaac    1842
actgccaatt accgttttatg ggtagacatc tttggaaatt ccacaaggt cagacattcg    1902 caactatccc ttctacatgt ccacacgtat actccaacac tttattaggc atctgattag    1962
tttggaaagt atgcctccat ctgaattagt ccagtgtggc ttagagttgg tacaacattc    2022
tcacagaatt tcctaatttt gtaggttcag cctgataacc actggagttc tttggtcctc    2082
attaaatagc tttcttcaca cattgctctg cctgttacac atatgatgaa cactgctttt    2142
tagacttcat taggaattta ggactgcatc ttgacaactg agcctattct actatatgta    2202
caatacctag cccataatag gtatacaata cacatttggt aaaactaatt ttcaaccaat    2262
gacatgtatt tttcaactag taacctagaa atgtttcact taaaatctga gaactggtta    2322
cactacaagt taccttggag attcatatat gaaaatgcaa acttagctat ttgattgtat    2382
tcactgggac ttaagaatgc gcctgaataa ttgtgagttc gatttgttct ggcaggctaa    2442
tgaccatttc cagtaaagtg aatagaggtc agaagtcgta taaaagaggt gttgtcagaa    2502
caccgttgag attacatagg tgaacaacta tttttaagca actttatttg tgtagtgaca    2562
aagcatccca atgcaggctg aaatgtttca tcacatctct ggatctctct attttgtgca    2622
gacattgaaa aaattgttca tattatttcc atgttatcag aatatttgat tttttaaaaa    2682
cataggccaa gttcattcac ttcattattc atttatcaaa atcagagtga atcacattag    2742
tcgccttcac aactgataaa gatcactgaa gtcaaattga ttttgtctat aatcttcaat    2802
ctacctatat ttaattgaga atctaaaatg tacaaatcat tgtgttgatt ctgcagtgat    2862
cctgctataa gtaagactca gtccctgatt ttaggtatcc tgtgaaaagc agaattaaga    2922
caaatacaca agagacaaag cacaaaaaat aaatatcata aggggatgaa caaaatggtg    2982
gagaaagagt agacaaagtt tttgatcacc tgccttcaaa gaaaggctgt gaattttgtt    3042
cacttagaca gcttggagac aagaaattac ccaaaagtaa ggtgaggagg ataggcaaaa    3102
agagcagaaa gatgtgaatg gacattgttg agaaatgtga taggaaaaca atcatagata    3162
aaggatttcc aagcaacaga gcatatccag atgaggtagg atgggataaa ctcttattga    3222
accaatcttc accaatttg ttttttctttt gcagagcaag ctaggaattg tttcccttct    3282
actgggcaca atacacgcat tgattttgc ctggaataag tggatagata taaaacaatt    3342
tgtatggtat acacctccaa cttttatgat agctgttttc cttccaattg ttgtcctgat    3402
atttaaaagc atactattcc tgccatgctt gaggaagaag atactgaaga ttagacatgg    3462
ttgggaagac gtcaccaaaa ttaacaaaac tgagatatgt tcccagttgt agaattactg    3522
tttacacaca ttttttgttca atattgatat attttatcac caacatttca agtttgtatt    3582
tgttaataaa atgattattc aaggaaaaaa aaaaaaaaaa aaaaa                    3627

<210> SEQ ID NO 23
```

<211> LENGTH: 258
<212> TYPE: PRT
<213> ORGANISM: Homo sapiens

<400> SEQUENCE: 23

Met Glu Ser Arg Lys Asp Ile Thr Asn Gln Glu Glu Leu Trp Lys Met
1               5                   10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

<210> SEQ ID NO 24
<211> LENGTH: 3627
<212> TYPE: DNA
<213> ORGANISM: Homo sapiens
<220> FEATURE:
<221> NAME/KEY: CDS
<222> LOCATION: (96)...(872)

<400> SEQUENCE: 24
ggggcccgca cctctgggca gcagcggcag ccgagactca cggtcaagct aaggcgaaga      60
gtgggtggct gaagccatac tattttatag aatta atg gaa agc aga aaa gac       113
                                      Met Glu Ser Arg Lys Asp
                                      1               5 atc aca aac caa gaa gaa ctt tgg aaa atg aag cct agg aga aat tta       161
Ile Thr Asn Gln Glu Glu Leu Trp Lys Met Lys Pro Arg Arg Asn Leu
            10                  15                  20 gaa gaa gac gat tat ttg cat aag gac acg gga gag acc agc atg cta       209
Glu Glu Asp Asp Tyr Leu His Lys Asp Thr Gly Glu Thr Ser Met Leu

```
                    25                  30                  35
aaa aga cct gtg ctt ttg cat ttg cac caa aca gcc cat gct gat gaa      257
Lys Arg Pro Val Leu Leu His Leu His Gln Thr Ala His Ala Asp Glu
         40                  45                  50 ttt gac tgc cct tca gaa ctt cag cac aca cag gaa ctc ttt cca cag      305
Phe Asp Cys Pro Ser Glu Leu Gln His Thr Gln Glu Leu Phe Pro Gln
 55                  60                  65                  70 tgg cac ttg cca att aaa ata gct gct att ata gca tct ctg act ttt      353
Trp His Leu Pro Ile Lys Ile Ala Ala Ile Ile Ala Ser Leu Thr Phe
                 75                  80                  85 ctt tac act ctt ctg agg gaa gta att cac ccc tta gca act tcc cat      401
Leu Tyr Thr Leu Leu Arg Glu Val Ile His Pro Leu Ala Thr Ser His
             90                  95                 100 caa caa tat ttt tat aaa att cca atc ctg gtc atc aac aaa gtc ttg      449
Gln Gln Tyr Phe Tyr Lys Ile Pro Ile Leu Val Ile Asn Lys Val Leu
        105                 110                 115 cca atg gtt tcc atc act ctc ttg gca ttg gtt tac ctg cca ggt gtg      497
Pro Met Val Ser Ile Thr Leu Leu Ala Leu Val Tyr Leu Pro Gly Val
    120                 125                 130 ata gca gca att gtc caa ctt cat aat gga acc aag tat aag aag ttt      545
Ile Ala Ala Ile Val Gln Leu His Asn Gly Thr Lys Tyr Lys Lys Phe
135                 140                 145                 150 cca cat tgg ttg gat aag tgg atg tta aca aga aag cag ttt ggg ctt      593
Pro His Trp Leu Asp Lys Trp Met Leu Thr Arg Lys Gln Phe Gly Leu
                155                 160                 165 ctc agt ttc ttt ttt gct gta ctg cat gca att tat agt ctg tct tac      641
Leu Ser Phe Phe Phe Ala Val Leu His Ala Ile Tyr Ser Leu Ser Tyr
            170                 175                 180 cca atg agg cga tcc tac aga tac aag ttg cta aac tgg gca tat caa      689
Pro Met Arg Arg Ser Tyr Arg Tyr Lys Leu Leu Asn Trp Ala Tyr Gln
        185                 190                 195 cag gtc caa caa aat aaa gaa gat gcc tgg att gag cat gat gtt tgg      737
Gln Val Gln Gln Asn Lys Glu Asp Ala Trp Ile Glu His Asp Val Trp
    200                 205                 210 aga atg gag att tat gtg tct ctg gga att gtg gga ttg gca ata ctg      785
Arg Met Glu Ile Tyr Val Ser Leu Gly Ile Val Gly Leu Ala Ile Leu
215                 220                 225                 230 gct ctg ttg gct gtg aca tct att cca tct gtg agt gac tct ttg aca      833
Ala Leu Leu Ala Val Thr Ser Ile Pro Ser Val Ser Asp Ser Leu Thr
                235                 240                 245 tgg aga gaa ttt cac tat att cag gta aat aat ata taa aataaccta       882
Trp Arg Glu Phe His Tyr Ile Gln Val Asn Asn Ile *
            250                 255 agaggtaaat cttcttttg tgtttatgat atagaatatg ttgactttac cccataaaaa     942
ataacaaatg tttttcaaca gcaaagatct tatacttgtt ccaattaata atgtgctctc    1002
ctgttgtttt ccctattgct tctaattagg acaagtgttt cctagacata aataaaaggc    1062
attaaaatat tctttgtttt ttttttttg tttgtttgtt tttgtttgt ttgtttgttt     1122
ttttgagatg aagtctcgct ctgttgccca tgctggagta cagtggcacg atctcggctc    1182
actgcaacct gcgcctcctg ggttcaggcg attctcttgc ctcagcctcc tgagtagctg    1242
ggattacagg cacccatcac catgtccagc taattttgt attttagta gagacagggt      1302
tttcccatgt tggccaggct ggtctcgatc tcctgacctc aaatgatccg cccacctcgg    1362
cctcccaaag tgctgggatg acagttgtga gccaccacac tcagcctgct ctttctaata    1422
tttgaaactt gttagacaat ttgctaccca tctaatgtga tatttagga atccaatatg    1482
catggtttat tatttcttaa aaaaaatatt cttttacctg tcacctgaat ttagtaatgc    1542
```

```
cttttatgtt acacaactta gcactttcca gaaacaaaaa ctctctcctt gaaataatag    1602
agtttttatc taccaaagat atgctagtgt ctcatttcaa aggctgcttt ttccagctta    1662
cattttatat acttactcac ttgaagtttc taaatattct tgtaatttta aaactatctc    1722
agatttactg aggtttatct tctggtggta gattatccat aagaagagtg atgtgccaga    1782
atcactctgg gatccttgtc tgacaagatt caaaggacta aatttaattc agtcatgaac    1842
actgccaatt accgtttatg ggtagacatc tttggaaatt ccacaaggt cagacattcg     1902
caactatccc ttctacatgt ccacacgtat actccaacac tttattaggc atctgattag    1962
tttgaaagt atgcctccat ctgaattagt ccagtgtggc ttagagttgg tacaacattc     2022
tcacagaatt tcctaatttt gtaggttcag cctgataacc actggagttc tttggtcctc    2082
attaaatagc tttcttcaca cattgctctg cctgttacac atatgatgaa cactgctttt    2142
tagacttcat taggaattta ggactgcatc ttgacaactg agcctattct actatatgta    2202
caatacctag cccataatag gtatacaata cacatttggt aaaactaatt ttcaaccaat    2262
gacatgtatt tttcaactag taacctagaa atgtttcact taaatctga gaactggtta     2322
cactacaagt taccttggag attcatatat gaaaacgcaa acttagctat ttgattgtat    2382
tcactgggac ttaagaatgc gcctgaataa ttgtgagttc gatttgttct ggcaggctaa    2442
tgaccatttc cagtaaagtg aatagaggtc agaagtcgta taaagaggt gttgtcagaa     2502
caccgttgag attacatagg tgaacaacta ttttaagca actttatttg tgtagtgaca     2562
aagcatccca atgcaggctg aaatgtttca tcacatctct ggatctctct attttgtgca    2622
gacattgaaa aaattgttca tatgatttcc atgttatcag aatatttgat tttttaaaaa    2682
cataggccaa gttcattcac ttcattattc atttatcaaa atcagagtga atcacattag    2742
tcgccttcac aactgataaa gatcactgaa gtcaaattga ttttgctat aatcttcaat     2802
ctacctatat ttaattgaga atctaaaatg tacaaatcat tgtgttgatt ctgcagtgat    2862
cctgctataa gtaagactca gtccctgatt ttaggtatcc tgtgaaaagc agaattaaga    2922
caaatacaca agagacaaag cacaaaaaat aaatatcata aggggatgaa caaaatggtg    2982
gagaaagagt agacaaagtt tttgatcacc tgccttcaaa gaaaggctgt gaattttgtt    3042
cacttagaca gcttggagac aagaaattac ccaaaagtaa ggtgaggagg ataggcaaaa    3102
agagcagaaa gatgtgaatg acattgttg agaaatgtga taggaaaaca atcatagata     3162
aaggatttcc aagcaacaga gcatatccag atgaggtagg atgggataaa ctcttattga    3222
accaatcttc accaattttg ttttcttt gcagagcaag ctaggaattg tttcccttct      3282
actgggcaca atacacgcat tgattttgc ctggaataag tggatagata taaaacaatt     3342
tgtatggtat acacctccaa ctttatgat agctgttttc cttccaattg ttgtcctgat     3402
atttaaaagc atactattcc tgccatgctt gaggaagaag atactgaaga ttagacatgg    3462
ttgggaagac gtcaccaaaa ttaacaaaac tgagatatgt tcccagttgt agaattactg    3522
tttacacaca tttttgttca atattgatat attttatcac caacatttca agtttgtatt    3582
tgttaataaa atgattattc aaggaaaaaa aaaaaaaaa aaaaa                     3627
```

<210> SEQ ID NO 25
<211> LENGTH: 258
<212> TYPE: PRT
<213> ORGANISM: Homo sapiens

<400> SEQUENCE: 25

```
Met Glu Ser Arg Lys Asp Ile Thr Asn Gln Glu Leu Trp Lys Met
 1               5                  10                  15

Lys Pro Arg Arg Asn Leu Glu Glu Asp Asp Tyr Leu His Lys Asp Thr
             20                  25                  30

Gly Glu Thr Ser Met Leu Lys Arg Pro Val Leu Leu His Leu His Gln
         35                  40                  45

Thr Ala His Ala Asp Glu Phe Asp Cys Pro Ser Glu Leu Gln His Thr
     50                  55                  60

Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Arg Glu Val Ile His
                 85                  90                  95

Pro Leu Ala Thr Ser His Gln Gln Tyr Phe Tyr Lys Ile Pro Ile Leu
             100                 105                 110

Val Ile Asn Lys Val Leu Pro Met Val Ser Ile Thr Leu Leu Ala Leu
         115                 120                 125

Val Tyr Leu Pro Gly Val Ile Ala Ala Ile Val Gln Leu His Asn Gly
     130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                 165                 170                 175

Ile Tyr Ser Leu Ser Tyr Pro Met Arg Arg Ser Tyr Arg Tyr Lys Leu
                 180                 185                 190

Leu Asn Trp Ala Tyr Gln Gln Val Gln Gln Asn Lys Glu Asp Ala Trp
             195                 200                 205

Ile Glu His Asp Val Trp Arg Met Glu Ile Tyr Val Ser Leu Gly Ile
         210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                 245                 250                 255

Asn Ile

<210> SEQ ID NO 26
<211> LENGTH: 3627
<212> TYPE: DNA
<213> ORGANISM: Homo sapiens
<220> FEATURE:
<221> NAME/KEY: CDS
<222> LOCATION: (96)...(872)

<400> SEQUENCE: 26
gggccccgca cctctgggca gcagcggcag ccgagactca cggtcaagct aaggcgaaga      60
gtgggtggct gaagccatac tattttatag aatta atg gaa agc aga aaa gac       113
                                      Met Glu Ser Arg Lys Asp
                                       1               5 atc aca aac caa gaa gaa ctt tgg aaa atg aag cct agg aga aat tta       161
Ile Thr Asn Gln Glu Glu Leu Trp Lys Met Lys Pro Arg Arg Asn Leu
            10                  15                  20 gaa gaa gac gat tat ttg cat aag gac acg gga gag acc agc atg cta       209
Glu Glu Asp Asp Tyr Leu His Lys Asp Thr Gly Glu Thr Ser Met Leu
        25                  30                  35 aaa aga cct gtg ctt ttg cat ttg cac caa aca gcc cat gct gat gaa       257
Lys Arg Pro Val Leu Leu His Leu His Gln Thr Ala His Ala Asp Glu
    40                  45                  50
```

```
ttt gac tgc cct tca gaa ctt cag cac aca cag gaa ctc ttt cca cag      305
Phe Asp Cys Pro Ser Glu Leu Gln His Thr Gln Glu Leu Phe Pro Gln
 55              60                  65                  70 tgg cac ttg cca att aaa ata gct gct att ata gca tct ctg act ttt      353
Trp His Leu Pro Ile Lys Ile Ala Ala Ile Ile Ala Ser Leu Thr Phe
                 75                  80                  85 ctt tac act ctt ctg agg gaa gta att cac ccc tta gca act tcc cat      401
Leu Tyr Thr Leu Leu Arg Glu Val Ile His Pro Leu Ala Thr Ser His
                         90                  95                 100 caa caa tat ttt tat aaa att cca atc ctg gtc atc aac aaa gtc ttg      449
Gln Gln Tyr Phe Tyr Lys Ile Pro Ile Leu Val Ile Asn Lys Val Leu
                    105                 110                 115 cca atg gtt tcc atc act ctc ttg gca ttg gtt tac ctg cca ggt gtg      497
Pro Met Val Ser Ile Thr Leu Leu Ala Leu Val Tyr Leu Pro Gly Val
    120                 125                 130 ata gca gca att gtc caa ctt cat aat gga acc aag tat aag aag ttt      545
Ile Ala Ala Ile Val Gln Leu His Asn Gly Thr Lys Tyr Lys Lys Phe
135                 140                 145                 150 cca cat tgg ttg gat aag tgg atg tta aca aga aag cag ttt ggg ctt      593
Pro His Trp Leu Asp Lys Trp Met Leu Thr Arg Lys Gln Phe Gly Leu
                155                 160                 165 ctc agt ttc ttt ttt gct gta ctg cat gca att tat agt ctg tct tac      641
Leu Ser Phe Phe Phe Ala Val Leu His Ala Ile Tyr Ser Leu Ser Tyr
            170                 175                 180 cca atg agg cga tcc tac aga tac aag ttg cta aac tgg gca tat caa      689
Pro Met Arg Arg Ser Tyr Arg Tyr Lys Leu Leu Asn Trp Ala Tyr Gln
        185                 190                 195 cag gtc caa caa aat aaa gaa gat gcc tgg att gag cat gat gtt tgg      737
Gln Val Gln Gln Asn Lys Glu Asp Ala Trp Ile Glu His Asp Val Trp
    200                 205                 210 aga atg gag att tat gtg tct ctg gga att gtg gga ttg gca ata ctg      785
Arg Met Glu Ile Tyr Val Ser Leu Gly Ile Val Gly Leu Ala Ile Leu
215                 220                 225                 230 gct ctg ttg gct gtg aca tct att cca tct gtg agt gac tct ttg aca      833
Ala Leu Leu Ala Val Thr Ser Ile Pro Ser Val Ser Asp Ser Leu Thr
                235                 240                 245 tgg aga gaa ttt cac tat att cag gta aat aat ata taa aataaccta       882
Trp Arg Glu Phe His Tyr Ile Gln Val Asn Asn Ile *
            250                 255 agaggtaaat cttctttttg tgtttatgat atagaatatg ttgactttac cccataaaaa    942
ataacaaatg ttttcaaca  gcaaagatct tatacttgtt ccaattaata atgtgctctc   1002
ctgttgtttt ccctattgct tctaattagg acaagtgttt cctagacata aataaaaggc   1062
attaaaatat tctttgtttt tttttttttg tttgttgtt ttttgtttgt tgtttgttt    1122 ttttgagatg aagtctcgct ctgttgccca tgctggagta cagtggcacg atctcggctc   1182
actgcaacct gcgcctcctg ggttcaggcg attctcttgc ctcagcctcc tgagtagctg   1242
ggattacagg cacccatcac catgtccagc taatttttgt attttagta gagacagggt    1302 tttcccatgt tggccaggct ggtctcgatc tcctgacctc aaatgatccg cccacctcgg   1362
cctcccaaag tgctgggatg acagttgtga gccaccacac tcagcctgct ctttctaata   1422
tttgaaactt gttagacaat ttgctaccca tctaatgtga tattttagga atccaatatg   1482 catggttat  tatttcttaa aaaaatatt  cttttacctg tcacctgaat ttagtaatgc   1542
cttttatgtt acacaactta gcactttcca gaaacaaaaa ctctctcctt gaaataatag   1602 agttttatc  taccaaagat atgctagtgt ctcatttcaa aggctgcttt ttccagctta   1662
cattttatat acttactcac ttgaagtttc taaatattct tgtaattta  aaactatctc   1722
```

-continued

```
agatttactg aggtttatct tctggtggta gattatccat aagaagagtg atgtgccaga    1782
atcactctgg gatccttgtc tgacaagatt caaaggacta aatttaattc agtcatgaac    1842
actgccaatt accgtttatg ggtagacatc tttggaaatt tccacaaggt cagacattcg    1902
caactatccc ttctacatgt ccacacgtat actccaacac tttattaggc atctgattag    1962
tttggaaagt atgcctccat ctgaattagt ccagtgtggc ttagagttgg tacaacattc    2022
tcacagaatt tcctaatttt gtaggttcag cctgataacc actggagttc tttggtcctc    2082
attaaatagc tttcttcaca cattgctctg cctgttacac atatgatgaa cactgctttt    2142
tagacttcat taggaattta ggactgcatc ttgacaactg agcctattct actatatgta    2202
caatacctag cccataatag gtatacaata cacatttggt aaaactaatt ttcaaccaat    2262
gacatgtatt tttcaactag taacctagaa atgtttcact taaaatctga aactggtta     2322
cactacaagt taccttggag attcatatat gaaaacgcaa acttagctat ttgattgtat    2382
tcactgggac ttaagaatgc gcctgaataa ttgtgagttc gatttgttct ggcaggctaa    2442
tgaccatttc cagtaaagtg aatagagggtc agaagtcgta taaaagaggt gttgtcagaa   2502
caccgttgag attacatagg tgaacaacta ttttttaagca acttttatttg tgtagtgaca  2562
aagcatccca atgcaggctg aaatgtttca tcacatctct ggatctctct attttgtgca   2622
gacattgaaa aaattgttca tattatttcc atgttatcag aatatttgat ttttaaaaa    2682
cataggccaa gttcattcac ttcattattc atttatcaaa atcagagtga atcacattag   2742
tcgccttcac aactgataaa gatcactgaa gtcaaattga tttttgctat aatcttcaat   2802
ctacctatat ttaattgaga atctaaaatg tacaaatcat tgtgttgatt ctgcagggat   2862
cctgctataa gtaagactca gtccctgatt ttaggtatcc tgtgaaaagc agaattaaga   2922
caaatacaca agagacaaag cacaaaaaat aaatatcata aggggatgaa caaaatggtg   2982
gagaaagagt agacaaagtt tttgatcacc tgccttcaaa gaaaggctgt gaattttgtt   3042
cacttagaca gcttggagac aagaaattac ccaaaagtaa ggtgaggagg ataggcaaaa    3102
agagcagaaa gatgtgaatg acattgttg  agaaatgtga taggaaaaca atcatagata   3162
aaggatttcc aagcaacaga gcatatccag atgaggtagg atgggataaa ctcttattga   3222
accaatcttc accaattttg ttttttcttttt gcagagcaag ctaggaattg tttcccttct   3282
actgggcaca atacacgcat tgattttttgc ctggaataag tggatagata taaaacaatt   3342
tgtatggtat acacctccaa cttttatgat agctgttttc cttccaattg ttgtcctgat    3402
atttaaaagc atactattcc tgccatgctt gaggaagaag atactgaaga ttagacatgg   3462
ttgggaagac gtcaccaaaa ttaacaaaac tgagatatgt tcccagttgt agaattactg   3522
tttacacaca tttttgttca atattgatat attttatcac caacatttca gtttgtatt    3582
tgttaataaa atgattattc aaggaaaaaa aaaaaaaaa aaaaa                      3627
```

<210> SEQ ID NO 27
<211> LENGTH: 258
<212> TYPE: PRT
<213> ORGANISM: Homo sapiens

<400> SEQUENCE: 27

```
Met Glu Ser Arg Lys Asp Ile Thr Asn Gln Glu Glu Leu Trp Lys Met
 1               5                  10                  15

Lys Pro Arg Arg Asn Leu Glu Glu Asp Asp Tyr Leu His Lys Asp Thr
            20                  25                  30
```

```
Gly Glu Thr Ser Met Leu Lys Arg Pro Val Leu Leu His Leu His Gln
         35                  40                  45

Thr Ala His Ala Asp Glu Phe Asp Cys Pro Ser Glu Leu Gln His Thr
 50                  55                  60

Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Arg Glu Val Ile His
                 85                  90                  95

Pro Leu Ala Thr Ser His Gln Gln Tyr Phe Tyr Lys Ile Pro Ile Leu
                100                 105                 110

Val Ile Asn Lys Val Leu Pro Met Val Ser Ile Thr Leu Leu Ala Leu
                115                 120                 125

Val Tyr Leu Pro Gly Val Ile Ala Ala Ile Val Gln Leu His Asn Gly
                130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
                180                 185                 190

Leu Asn Trp Ala Tyr Gln Gln Val Gln Gln Asn Lys Glu Asp Ala Trp
                195                 200                 205

Ile Glu His Asp Val Trp Arg Met Glu Ile Tyr Val Ser Leu Gly Ile
                210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

<210> SEQ ID NO 28
<211> LENGTH: 3627
<212> TYPE: DNA
<213> ORGANISM: Homo sapiens
<220> FEATURE:
<221> NAME/KEY: CDS
<222> LOCATION: (96)...(872)

<400> SEQUENCE: 28
ggggcccgca cctctgggca gcagcggcag ccgagactca cggtcaagct aaggcgaaga    60
gtgggtggct gaagccatac tattttatag aatta atg gaa agc aga aaa gac      113
                                       Met Glu Ser Arg Lys Asp
                                         1               5 atc aca aac caa gaa gaa ctt tgg aaa atg aag cct agg aga aat tta    161
Ile Thr Asn Gln Glu Glu Leu Trp Lys Met Lys Pro Arg Arg Asn Leu
         10                  15                  20 gaa gaa gac gat tat ttg cat aag gac acg gga gag acc agc atg cta    209
Glu Glu Asp Asp Tyr Leu His Lys Asp Thr Gly Glu Thr Ser Met Leu
             25                  30                  35 aaa aga cct gtg ctt ttg cat ttg cac caa aca gcc cat gct gat gaa    257
Lys Arg Pro Val Leu Leu His Leu His Gln Thr Ala His Ala Asp Glu
         40                  45                  50 ttt gac tgc cct tca gaa ctt cag cac aca cag gaa ctc ttt cca cag    305
Phe Asp Cys Pro Ser Glu Leu Gln His Thr Gln Glu Leu Phe Pro Gln
 55                  60                  65                  70 tgg cac ttg cca att aaa ata gct gct att ata gca tct ctg act ttt    353
Trp His Leu Pro Ile Lys Ile Ala Ala Ile Ile Ala Ser Leu Thr Phe
```

|  |  |
|---|---|
| ```
                   75                  80                  85
ctt tac act ctt ctg agg gaa gta att cac ccc tta gca act tcc cat
Leu Tyr Thr Leu Leu Arg Glu Val Ile His Pro Leu Ala Thr Ser His
                90                  95                 100
``` | 401 |
| ```
caa caa tat ttt tat aaa att cca atc ctg gtc atc aac aaa gtc ttg
Gln Gln Tyr Phe Tyr Lys Ile Pro Ile Leu Val Ile Asn Lys Val Leu
            105                 110                 115
``` | 449 |
| ```
cca atg gtt tcc atc act ctc ttg gca ttg gtt tac ctg cca ggt gtg
Pro Met Val Ser Ile Thr Leu Leu Ala Leu Val Tyr Leu Pro Gly Val
        120                 125                 130
``` | 497 |
| ```
ata gca gca att gtc caa ctt cat aat gga acc aag tat aag aag ttt
Ile Ala Ala Ile Val Gln Leu His Asn Gly Thr Lys Tyr Lys Lys Phe
    135                 140                 145                 150
``` | 545 |
| ```
cca cat tgg ttg gat aag tgg atg tta aca aga aag cag ttt ggg ctt
Pro His Trp Leu Asp Lys Trp Met Leu Thr Arg Lys Gln Phe Gly Leu
                155                 160                 165
``` | 593 |
| ```
ctc agt ttc ttt ttt gct gta ctg cat gca att tat agt ctg tct tac
Leu Ser Phe Phe Phe Ala Val Leu His Ala Ile Tyr Ser Leu Ser Tyr
            170                 175                 180
``` | 641 |
| ```
cca atg agg cga tcc tac aga tac aag ttg cta aac tgg gca tat caa
Pro Met Arg Arg Ser Tyr Arg Tyr Lys Leu Leu Asn Trp Ala Tyr Gln
        185                 190                 195
``` | 689 |
| ```
cag gtc caa caa aat aaa gaa gat gcc tgg att gag cat gat gtt tgg
Gln Val Gln Gln Asn Lys Glu Asp Ala Trp Ile Glu His Asp Val Trp
    200                 205                 210
``` | 737 |
| ```
aga atg gag att tat gtg tct ctg gga att gtg gga ttg gca ata ctg
Arg Met Glu Ile Tyr Val Ser Leu Gly Ile Val Gly Leu Ala Ile Leu
215                 220                 225                 230
``` | 785 |
| ```
gct ctg ttg gct gtg aca tct att cca tct gtg agt gac tct ttg aca
Ala Leu Leu Ala Val Thr Ser Ile Pro Ser Val Ser Asp Ser Leu Thr
                235                 240                 245
``` | 833 |
| ```
tgg aga gaa ttt cac tat att cag gta aat aat ata taa aataaccta
Trp Arg Glu Phe His Tyr Ile Gln Val Asn Asn Ile *
            250                 255
``` | 882 |
| agaggtaaat cttcttttg tgtttatgat atagaatatg ttgactttac cccataaaaa | 942 |
| ataacaaatg ttttcaaca gcaaagatct tatacttgtt ccaattaata atgtgctctc | 1002 |
| ctgttgtttt ccctattgct tctaattagg acaagtgttt cctagacata aataaaaggc | 1062 |
| attaaaatat tctttgtttt ttttttttg tttgtttgtt ttttgtttgt ttgtttgttt | 1122 |
| ttttgagatg aagtctcgct ctgttgccca tgctggagta cagtggcacg atctcggctc | 1182 |
| actgcaacct gcgcctcctg ggttcaggcg attctcttgc ctcagcctcc tgagtagctg | 1242 |
| ggattacagg cacccatcac catgtccagc taattttgt attttagta gagacagggt | 1302 |
| tttcccatgt tggccaggct ggtctcgatc tcctgacctc aaatgatccg cccacctcgg | 1362 |
| cctcccaaag tgctgggatg acagttgtga gccaccacac tcagcctgct ctttctaata | 1422 |
| tttgaaactt gttagacaat ttgctaccca tctaatgtga tattttagga atccaatatg | 1482 |
| catggtttat tatttcttaa aaaaatatt cttttacctg tcacctgaat ttagtaatgc | 1542 |
| cttttatgtt acacaactta gcactttcca gaaacaaaaa ctctctcctt gaaataatag | 1602 |
| agttttatc taccaaagat atgctagtgt ctcatttcaa aggctgcttt tccagctta | 1662 |
| cattttatat acttactcac ttgaagtttc taaatattct tgtaattta aaactatctc | 1722 |
| agatttactg aggtttatct tctggtggta gattatccat aagaagagtg atgtgccaga | 1782 |
| atcactctgg gatccttgtc tgacaagatt caaaggacta aatttaattc agtcatgaac | 1842 |
| actgccaatt accgtttatg ggtagacatc tttggaaatt tccacaaggt cagacattcg | 1902 |

-continued

```
caactatccc ttctacatgt ccacacgtat actccaacac tttattaggc atctgattag      1962
tttggaaagt atgcctccat ctgaattagt ccagtgtggc ttagagttgg tacaacattc      2022
tcacagaatt tcctaatttt gtaggttcag cctgataacc actggagttc tttggtcctc      2082
attaaatagc tttcttcaca cattgctctg cctgttacac atatgatgaa cactgctttt      2142
tagacttcat taggaattta ggactgcatc ttgacaactg agcctattct actatatgta      2202
caatacctag cccataatag gtatacaata cacatttggt aaaactaatt ttcaaccaat      2262
gacatgtatt tttcaactag taacctagaa atgtttcact taaaatctga aactggtta      2322 cactacaagt taccttggag attcatatat gaaaacgcaa acttagctat ttgattgtat      2382
tcactgggac ttaagaatgc gcctgaataa ttgtgagttc gatttgttct ggcaggctaa      2442
tgaccatttc cagtaaagtg aatagaggtc agaagtcgta taaagaggt gttgtcagaa       2502 caccgttgag attacatagg tgaacaacta tttttaagca actttatttg tgtagtgaca      2562
aagcatccca atgcaggctg aaatgtttca tcacatctct ggatctctct attttgtgca     2622
gacattgaaa aaattgttca tattatttcc atgttatcag aatatttgat ttttttaaaa    2682
cataggccaa gttcattcac ttcattattc atttatcaaa atcagagtga atcacattag      2742
tcgccttcac aactgataaa gatcactgaa gtcaaattga tttttgctat aatcttcaat      2802
ctacctatat ttaattgaga atctaaaatg tacaaatcat tgtgttgatt ctgcagtgat      2862
cctgctataa gtaagactca gtccctgatt ttaggtatcc tgtgataagc agaattaaga     2922
caaatacaca agagacaaag cacaaaaaat aaatatcata aggggatgaa caaaatggtg      2982
gagaaagagt agacaaagtt tttgatcacc tgccttcaaa gaaaggctgt gaattttgtt      3042
cacttagaca gcttggagac aagaaaattac ccaaaagtaa ggtgaggagg ataggcaaaa    3102
agagcagaaa gatgtgaatg acattgttg agaaatgtga taggaaaaca atcatagata      3162
aaggatttcc aagcaacaga gcatatccag atgaggtagg atgggataaa ctcttattga     3222
accaatcttc accaattttg ttttctttt gcagagcaag ctaggaattg tttcccttct      3282
actgggcaca atacacgcat tgattttgc ctggaataag tggatagata taaaacaatt      3342
tgtatggtat acacctccaa cttttatgat agctgttttc cttccaattg ttgtcctgat      3402
atttaaaagc atactattcc tgccatgctt gaggaagaag atactgaaga ttagacatgg     3462
ttgggaagac gtcaccaaaa ttaacaaaac tgagatatgt tcccagttgt agaattactg      3522
tttacacaca tttttgttca atattgatat attttatcac caacatttca agtttgtatt     3582
tgttaataaa atgattattc aaggaaaaaa aaaaaaaaa aaaaa                       3627
```

<210> SEQ ID NO 29
<211> LENGTH: 258
<212> TYPE: PRT
<213> ORGANISM: Homo sapiens

<400> SEQUENCE: 29

```
Met Glu Ser Arg Lys Asp Ile Thr Asn Gln Glu Glu Leu Trp Lys Met
 1               5                   10                  15

Lys Pro Arg Arg Asn Leu Glu Glu Asp Asp Tyr Leu His Lys Asp Thr
                20                  25                  30

Gly Glu Thr Ser Met Leu Lys Arg Pro Val Leu Leu His Leu His Gln
            35                  40                  45

Thr Ala His Ala Asp Glu Phe Asp Cys Pro Ser Glu Leu Gln His Thr
        50                  55                  60
```

```
Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Leu Arg Glu Val Ile His
             85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Leu His Asn Gly
        130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala Ile
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

<210> SEQ ID NO 30
<211> LENGTH: 3627
<212> TYPE: DNA
<213> ORGANISM: Homo sapiens
<220> FEATURE:
<221> NAME/KEY: CDS
<222> LOCATION: (96)...(872)

<400> SEQUENCE: 30
ggggcccgca cctctgggca gcagcggcag ccgagactca cggtcaagct aaggcgaaga      60
gtgggtggct gaagccatac tattttatag aatta atg gaa agc aga aaa gac       113
                                      Met Glu Ser Arg Lys Asp
                                        1               5 atc aca aac caa gaa gaa ctt tgg aaa atg aag cct agg aga aat tta      161
Ile Thr Asn Gln Glu Glu Leu Trp Lys Met Lys Pro Arg Arg Asn Leu
         10                  15                  20 gaa gaa gac gat tat ttg cat aag gac acg gga gag acc agc atg cta      209
Glu Glu Asp Asp Tyr Leu His Lys Asp Thr Gly Glu Thr Ser Met Leu
         25                  30                  35 aaa aga cct gtg ctt ttg cat ttg cac caa aca gcc cat gct gat gaa      257
Lys Arg Pro Val Leu Leu His Leu His Gln Thr Ala His Ala Asp Glu
     40                  45                  50 ttt gac tgc cct tca gaa ctt cag cac aca cag gaa ctc ttt cca cag      305
Phe Asp Cys Pro Ser Glu Leu Gln His Thr Gln Glu Leu Phe Pro Gln
 55                  60                  65                  70 tgg cac ttg cca att aaa ata gct gct att ata gca tct ctg act ttt      353
Trp His Leu Pro Ile Lys Ile Ala Ala Ile Ile Ala Ser Leu Thr Phe
                 75                  80                  85 ctt tac act ctt ctg agg gaa gta att cac ccc tta gca act tcc cat      401
Leu Tyr Thr Leu Leu Arg Glu Val Ile His Pro Leu Ala Thr Ser His
             90                  95                 100
```

| | | |
|---|---|---|
| caa caa tat ttt tat aaa att cca atc ctg gtc atc aac aaa gtc ttg<br>Gln Gln Tyr Phe Tyr Lys Ile Pro Ile Leu Val Ile Asn Lys Val Leu<br>     105                      110                    115 | | 449 |
| cca atg gtt tcc atc act ctc ttg gca ttg gtt tac ctg cca ggt gtg<br>Pro Met Val Ser Ile Thr Leu Leu Ala Leu Val Tyr Leu Pro Gly Val<br>120                      125                    130 | | 497 |
| ata gca gca att gtc caa ctt cat aat gga acc aag tat aag aag ttt<br>Ile Ala Ala Ile Val Gln Leu His Asn Gly Thr Lys Tyr Lys Lys Phe<br>135                      140                    145                    150 | | 545 |
| cca cat tgg ttg gat aag tgg atg tta aca aga aag cag ttt ggg ctt<br>Pro His Trp Leu Asp Lys Trp Met Leu Thr Arg Lys Gln Phe Gly Leu<br>                   155                    160                    165 | | 593 |
| ctc agt ttc ttt ttt gct gta ctg cat gca att tat agt ctg tct tac<br>Leu Ser Phe Phe Phe Ala Val Leu His Ala Ile Tyr Ser Leu Ser Tyr<br>          170                      175                    180 | | 641 |
| cca atg agg cga tcc tac aga tac aag ttg cta aac tgg gca tat caa<br>Pro Met Arg Arg Ser Tyr Arg Tyr Lys Leu Leu Asn Trp Ala Tyr Gln<br>     185                      190                    195 | | 689 |
| cag gtc caa caa aat aaa gaa gat gcc tgg att gag cat gat gtt tgg<br>Gln Val Gln Gln Asn Lys Glu Asp Ala Trp Ile Glu His Asp Val Trp<br>200                      205                    210 | | 737 |
| aga atg gag att tat gtg tct ctg gga att gtg gga ttg gca ata ctg<br>Arg Met Glu Ile Tyr Val Ser Leu Gly Ile Val Gly Leu Ala Ile Leu<br>215                      220                    225                    230 | | 785 |
| gct ctg ttg gct gtg aca tct att cca tct gtg agt gac tct ttg aca<br>Ala Leu Leu Ala Val Thr Ser Ile Pro Ser Val Ser Asp Ser Leu Thr<br>                   235                    240                    245 | | 833 |
| tgg aga gaa ttt cac tat att cag gta aat aat ata taa aataaccta<br>Trp Arg Glu Phe His Tyr Ile Gln Val Asn Asn Ile  *<br>                   250                    255 | | 882 |
| agaggtaaat cttcttttg tgtttatgat atagaatatg ttgactttac cccataaaaa | | 942 |
| ataacaaatg tttttcaaca gcaaagatct tatacttgtt ccaattaata atgtgctctc | | 1002 |
| ctgttgtttt ccctattgct tctaattagg acaagtgttt cctagacata aataaaaggc | | 1062 |
| attaaaatat tctttgtttt ttttttttg tttgttgtt ttttgtttgt tgtttgttt | | 1122 |
| ttttgagatg aagtctcgct ctgttgccca tgctggagta cagtggcacg atctcggctc | | 1182 |
| actgcaacct gcgcctcctg ggttcaggcg attctcttgc ctcagcctcc tgagtagctg | | 1242 |
| ggattacagg cacccatcac catgtccagc taatttttgt atttttagta gagacagggt | | 1302 |
| tttcccatgt tggccaggct ggtctcgatc tcctgacctc aaatgatccg cccacctcgg | | 1362 |
| cctcccaaag tgctgggatg acagttgtga gccaccacac tcagcctgct ctttctaata | | 1422 |
| tttgaaactt gttagacaat ttgctaccca tctaatgtga tattttagga atccaatatg | | 1482 |
| catggtttat tatttcttaa aaaaatatt cttttacctg tcacctgaat ttagtaatgc | | 1542 |
| cttttatgtt acacaactta gcactttcca gaaacaaaaa ctctctcctt gaaataatag | | 1602 |
| agttttatc taccaaagat atgctagtgt ctcatttcaa aggctgcttt ttccagctta | | 1662 |
| cattttatat acttactcac ttgaagtttc taaatattct tgtaatttta aaactatctc | | 1722 |
| agatttactg aggtttatct tctggtggta gattatccat aagaagagtg atgtgccaga | | 1782 |
| atcactctgg gatccttgtc tgacaagatt caaaggacta aatttaattc agtcatgaac | | 1842 |
| actgccaatt accgtttatg ggtagacatc tttggaaatt tccacaaggt cagacattcg | | 1902 |
| caactatccc ttctacatgt ccacacgtat actccaacac tttattaggc atctgattag | | 1962 |
| tttggaaagt atgcctccat ctgaattagt ccagtgtggc ttagagttgg tacaacattc | | 2022 |
| tcacagaatt tcctaatttt gtaggttcag cctgataacc actggagttc tttggtcctc | | 2082 |

-continued

```
attaaatagc tttcttcaca cattgctctg cctgttacac atatgatgaa cactgctttt     2142
tagacttcat taggaattta ggactgcatc ttgacaactg agcctattct actatatgta     2202
caatacctag cccataatag gtatacaata cacatttggt aaaactaatt ttcaaccaat     2262
gacatgtatt tttcaactag taacctagaa atgtttcact taaaatctga gaactggtta     2322
cactacaagt taccttggag attcatatat gaaaacgcaa acttagctat ttgattgtat     2382
tcactgggac ttaagaatgc gcctgaataa ttgtgagttc gatttgttct ggcaggctaa     2442
tgaccatttc cagtaaagtg aatagaggtc agaagtcgta taaaagaggt gttgtcagaa     2502
caccgttgag attacatagg tgaacaacta ttttaagca actttatttg tgtagtgaca     2562
aagcatccca atgcaggctg aaatgtttca tcacatctct ggatctctct attttgtgca     2622
gacattgaaa aaattgttca tattatttcc atgttatcag aatatttgat ttttaaaaa     2682 cataggccaa gttcattcac ttcattattc atttatcaaa atcagagtga atcacattag     2742
tcgccttcac aactgataaa gatcactgaa gtcaaattga ttttgctat aatcttcaat     2802 ctacctatat ttaattgaga atctaaaatg tacaaatcat tgtgttgatt ctgcagtgat     2862
cctgctataa gtaagactca gtccctgatt ttaggtatcc tgtgaaaagc agaattaaga     2922
caaatacaca agagacaaag cacaaaaaat aaatatcata aggggatgaa caaaatggtg     2982
gagaaagagt agacaaagtt tttcatcacc tgccttcaaa gaaaggctgt gaattttgtt     3042
cacttagaca gcttggagac aagaaattac ccaaaagtaa ggtgaggagg ataggcaaaa     3102
agagcagaaa gatgtgaatg gacattgttg agaaatgtga taggaaaaca atcatagata     3162
aaggatttcc aagcaacaga gcatatccag atgaggtagg atgggataaa ctcttattga     3222
accaatcttc accaattttg ttttttcttt gcagagcaag ctaggaattg tttcccttct     3282
actgggcaca atacacgcat tgattttgc ctggaataag tggatagata taaaacaatt     3342
tgtatggtat acacctccaa cttttatgat agctgttttc cttccaattg ttgtcctgat     3402
atttaaaagc atactattcc tgccatgctt gaggaagaag atactgaaga ttagacatgg     3462
ttgggaagac gtcaccaaaa ttaacaaaac tgagatatgt tcccagttgt agaattactg     3522
tttacacaca tttttgttca atattgatat attttatcac caacatttca agtttgtatt     3582
tgttaataaa atgattattc aaggaaaaaa aaaaaaaaa aaaaa                     3627
```

<210> SEQ ID NO 31
<211> LENGTH: 258
<212> TYPE: PRT
<213> ORGANISM: Homo sapiens

<400> SEQUENCE: 31

```
Met Glu Ser Arg Lys Asp Ile Thr Asn Gln Glu Leu Trp Lys Met
 1               5                  10                  15

Lys Pro Arg Arg Asn Leu Glu Glu Asp Asp Tyr Leu His Lys Asp Thr
                 20                  25                  30

Gly Glu Thr Ser Met Leu Lys Arg Pro Val Leu Leu His Leu His Gln
             35                  40                  45

Thr Ala His Ala Asp Glu Phe Asp Cys Pro Ser Glu Leu Gln His Thr
         50                  55                  60

Gln Glu Leu Phe Pro Gln Trp His Leu Pro Ile Lys Ile Ala Ala Ile
     65                  70                  75                  80

Ile Ala Ser Leu Thr Phe Leu Tyr Thr Leu Leu Arg Glu Val Ile His
                 85                  90                  95
```

```
Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ile Val Gln Leu His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

<210> SEQ ID NO 32
<211> LENGTH: 3627
<212> TYPE: DNA
<213> ORGANISM: Homo sapiens
<220> FEATURE:
<221> NAME/KEY: CDS
<222> LOCATION: (96)...(872)

<400> SEQUENCE: 32
ggggcccgca cctctgggca gcagcggcag ccgagactca cggtcaagct aaggcgaaga    60
gtgggtggct gaagccatac tattttatag aatta atg gaa agc aga aaa gac        113
                                      Met Glu Ser Arg Lys Asp
                                        1               5 atc aca aac caa gaa gaa ctt tgg aaa atg aag cct agg aga aat tta     161
Ile Thr Asn Gln Glu Glu Leu Trp Lys Met Lys Pro Arg Arg Asn Leu
            10                  15                  20 gaa gaa gac gat tat ttg cat aag gac acg gga gag acc agc atg cta     209
Glu Glu Asp Asp Tyr Leu His Lys Asp Thr Gly Glu Thr Ser Met Leu
        25                  30                  35 aaa aga cct gtg ctt ttg cat ttg cac caa aca gcc cat gct gat gaa     257
Lys Arg Pro Val Leu Leu His Leu His Gln Thr Ala His Ala Asp Glu
    40                  45                  50 ttt gac tgc cct tca gaa ctt cag cac aca cag gaa ctc ttt cca cag     305
Phe Asp Cys Pro Ser Glu Leu Gln His Thr Gln Glu Leu Phe Pro Gln
55                  60                  65                  70 tgg cac ttg cca att aaa ata gct gct att ata gca tct ctg act ttt     353
Trp His Leu Pro Ile Lys Ile Ala Ala Ile Ile Ala Ser Leu Thr Phe
                75                  80                  85 ctt tac act ctt ctg agg gaa gta att cac ccc tta gca act tcc cat     401
Leu Tyr Thr Leu Leu Arg Glu Val Ile His Pro Leu Ala Thr Ser His
            90                  95                  100 caa caa tat ttt tat aaa att cca atc ctg gtc atc aac aaa gtc ttg     449
Gln Gln Tyr Phe Tyr Lys Ile Pro Ile Leu Val Ile Asn Lys Val Leu
        105                 110                 115 cca atg gtt tcc atc act ctc ttg gca ttg gtt tac ctg cca ggt gtg    497
Pro Met Val Ser Ile Thr Leu Leu Ala Leu Val Tyr Leu Pro Gly Val
```

```
                   120                 125                 130
ata gca gca att gtc caa ctt cat aat gga acc aag tat aag aag ttt       545
Ile Ala Ala Ile Val Gln Leu His Asn Gly Thr Lys Tyr Lys Lys Phe
135             140                 145                 150 cca cat tgg ttg gat aag tgg atg tta aca aga aag cag ttt ggg ctt      593
Pro His Trp Leu Asp Lys Trp Met Leu Thr Arg Lys Gln Phe Gly Leu
                155                 160                 165 ctc agt ttc ttt ttt gct gta ctg cat gca att tat agt ctg tct tac      641
Leu Ser Phe Phe Phe Ala Val Leu His Ala Ile Tyr Ser Leu Ser Tyr
        170                 175                 180 cca atg agg cga tcc tac aga tac aag ttg cta aac tgg gca tat caa      689
Pro Met Arg Arg Ser Tyr Arg Tyr Lys Leu Leu Asn Trp Ala Tyr Gln
            185                 190                 195 cag gtc caa caa aat aaa gaa gat gcc tgg att gag cat gat gtt tgg      737
Gln Val Gln Gln Asn Lys Glu Asp Ala Trp Ile Glu His Asp Val Trp
        200                 205                 210 aga atg gag att tat gtg tct ctg gga att gtg gga ttg gca ata ctg      785
Arg Met Glu Ile Tyr Val Ser Leu Gly Ile Val Gly Leu Ala Ile Leu
215                 220                 225                 230 gct ctg ttg gct gtg aca tct att cca tct gtg agt gac tct ttg aca      833
Ala Leu Leu Ala Val Thr Ser Ile Pro Ser Val Ser Asp Ser Leu Thr
            235                 240                 245 tgg aga gaa ttt cac tat att cag gta aat aat ata taa aataaccta        882
Trp Arg Glu Phe His Tyr Ile Gln Val Asn Asn Ile *
                250                 255 agaggtaaat cttcttttg tgtttatgat atagaatatg ttgactttac cccataaaaa     942
ataacaaatg ttttcaaca gcaaagatct tatacttgtt ccaattaata atgtgctctc    1002
ctgttgtttt ccctattgct tctaattagg acaagtgttt cctagacata aataaaaggc   1062
attaaaatat tctttgtttt ttttttttg tttgtttgtt tttgtttgt ttgtttgttt    1122
ttttgagatg aagtctcgct ctgttgccca tgctggagta cagtggcacg atctcggctc   1182
actgcaacct gcgcctcctg ggttcaggcg attctcttgc ctcagcctcc tgagtagctg   1242
ggattacagg cacccatcac catgtccagc taatttttgt attttagta gagacagggt    1302
tttcccatgt tggccaggct ggtctcgatc tcctgacctc aaatgatccg cccacctcgg   1362
cctcccaaag tgctgggatg acagttgtga gccaccacac tcagcctgct ctttctaata   1422
tttgaaactt gttagacaat ttgctaccca tctaatgtga tatttagga atccaatatg    1482
catggtttat tatttcttaa aaaaatatt cttttacctg tcacctgaat ttagtaatgc    1542
cttttatgtt acacaactta gcactttcca gaaacaaaaa ctctctcctt gaataatag    1602
agttttatc taccaaagat atgctagtgt ctcatttcaa aggctgcttt ttccagctta   1662
catttatat acttactcac ttgaagtttc taaatattct tgtaatttta aaactatctc   1722
agatttactg aggtttatct tctggtggta gattatccat aagaagagtg atgtgccaga   1782
atcactctgg gatccttgtc tgacaagatt caaaggacta aatttaattc agtcatgaac   1842
actgccaatt accgtttatg ggtagacatc tttggaaatt ccacaaggt cagacattcg    1902
caactatccc ttctacatgt ccacacgtat actccaacac tttattaggc atctgattag   1962
tttggaaagt atgcctccat ctgaattagt ccagtgtggc ttagagttgg tacaacattc   2022
tcacagaatt tcctaatttt gtaggttcag cctgataacc actggagttc tttggtcctc   2082
attaaatagc tttcttcaca cattgctctg cctgttacac atatgatgaa cactgctttt   2142
tagacttcat taggaattta ggactgcatc ttgacaactg agcctattct actatatgta   2202
caatacctag cccataatag gtatacaata cacatttggt aaaactaatt ttcaaccaat   2262
```

-continued

```
gacatgtatt tttcaactag taacctagaa atgtttcact taaaatctga gaactggtta    2322
cactacaagt taccttggag attcatatat gaaaacgcaa acttagctat ttgattgtat    2382
tcactgggac ttaagaatgc gcctgaataa ttgtgagttc gatttgttct ggcaggctaa    2442
tgaccatttc cagtaaagtg aatagaggtc agaagtcgta taaaagaggt gttgtcagaa    2502
caccgttgag attacatagg tgaacaacta tttttaagca actttatttg tgtagtgaca    2562
aagcatccca atgcaggctg aaatgtttca tcacatctct ggatctctct attttgtgca    2622
gacattgaaa aaattgttca tattatttcc atgttatcag aatatttgat tttttaaaaa    2682
cataggccaa gttcattcac ttcattattc atttatcaaa atcagagtga atcacattag    2742
tcgccttcac aactgataaa gatcactgaa gtcaaattga tttttgctat aatcttcaat    2802
ctacctatat ttaattgaga atctaaaatg tacaaatcat tgtgttgatt ctgcagtgat    2862
cctgctataa gtaagactca gtccctgatt ttaggtatcc tgtgaaaagc agaattaaga    2922
caaatacaca agagacaaag cacaaaaaat aaatatcata aggggatgaa caaaatggtg    2982
gagaaagagt agacaaagtt tttgatcacc tgccttcaaa gaaaggctgt gaattttgtt    3042
cacttagaca gcttggagac aagaaattac ccaaaagtaa ggtgaggagg ataggcaaaa    3102
agagtagaaa gatgtgaatg gacattgttg agaaatgtga taggaaaaca atcatagata    3162
aaggatttcc aagcaacaga gcatatccag atgaggtagg atgggataaa ctcttattga    3222
accaatcttc accaattttg ttttctttt gcagagcaag ctaggaattg tttcccttct    3282
actgggcaca atacacgcat tgattttgc ctggaataag tggatagata taaacaatt    3342 tgtatggtat acacctccaa cttttatgat agctgttttc cttccaattg ttgtcctgat    3402
atttaaaagc atactattcc tgccatgctt gaggaagaag atactgaaga ttagacatgg    3462
ttgggaagac gtcaccaaaa ttaacaaaac tgagatatgt tcccagttgt agaattactg    3522
tttacacaca ttttgttca atattgatat attttatcac caacatttca agtttgtatt    3582
tgttaataaa atgattattc aaggaaaaaa aaaaaaaaaa aaaaa                   3627
```

```
<210> SEQ ID NO 33
<211> LENGTH: 258
<212> TYPE: PRT
<213> ORGANISM: Homo sapiens

<400> SEQUENCE: 33

Met Glu Ser Arg Lys Asp Ile Thr Asn Gln Glu Glu Leu Trp Lys Met
  1               5                  10                  15

Lys Pro Arg Arg Asn Leu Glu Glu Asp Asp Tyr Leu His Lys Asp Thr
              20                  25                  30

Gly Glu Thr Ser Met Leu Lys Arg Pro Val Leu Leu His Leu His Gln
          35                  40                  45

Thr Ala His Ala Asp Glu Phe Asp Cys Pro Ser Glu Leu Gln His Thr
     50                   55                  60

Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Leu Arg Glu Val Ile His
                 85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125
```

```
Val Tyr Leu Pro Gly Val Ile Ala Ala Ile Val Gln Leu His Asn Gly
        130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
                180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
        210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

<210> SEQ ID NO 34
<211> LENGTH: 3627
<212> TYPE: DNA
<213> ORGANISM: Homo sapiens
<220> FEATURE:
<221> NAME/KEY: CDS
<222> LOCATION: (96)...(872)

<400> SEQUENCE: 34
ggggcccgca cctctgggca gcagcggcag ccgagactca cggtcaagct aaggcgaaga      60
gtgggtggct gaagccatac tattttatag aatta atg gaa agc aga aaa gac         113
                                      Met Glu Ser Arg Lys Asp
                                        1               5 atc aca aac caa gaa gaa ctt tgg aaa atg aag cct agg aga aat tta        161
Ile Thr Asn Gln Glu Glu Leu Trp Lys Met Lys Pro Arg Arg Asn Leu
                10                  15                  20 gaa gaa gac gat tat ttg cat aag gac acg gga gag acc agc atg cta        209
Glu Glu Asp Asp Tyr Leu His Lys Asp Thr Gly Glu Thr Ser Met Leu
            25                  30                  35 aaa aga cct gtg ctt ttg cat ttg cac caa aca gcc cat gct gat gaa        257
Lys Arg Pro Val Leu Leu His Leu His Gln Thr Ala His Ala Asp Glu
        40                  45                  50 ttt gac tgc cct tca gaa ctt cag cac aca cag gaa ctc ttt cca cag        305
Phe Asp Cys Pro Ser Glu Leu Gln His Thr Gln Glu Leu Phe Pro Gln
55                  60                  65                  70 tgg cac ttg cca att aaa ata gct gct att ata gca tct ctg act ttt        353
Trp His Leu Pro Ile Lys Ile Ala Ala Ile Ile Ala Ser Leu Thr Phe
                75                  80                  85 ctt tac act ctt ctg agg gaa gta att cac ccc tta gca act tcc cat        401
Leu Tyr Thr Leu Leu Arg Glu Val Ile His Pro Leu Ala Thr Ser His
            90                  95                  100 caa caa tat ttt tat aaa att cca atc ctg gtc atc aac aaa gtc ttg        449
Gln Gln Tyr Phe Tyr Lys Ile Pro Ile Leu Val Ile Asn Lys Val Leu
        105                 110                 115 cca atg gtt tcc atc act ctc ttg gca ttg gtt tac ctg cca ggt gtg        497
Pro Met Val Ser Ile Thr Leu Leu Ala Leu Val Tyr Leu Pro Gly Val
    120                 125                 130 ata gca gca att gtc caa ctt cat aat gga acc aag tat aag aag ttt        545
Ile Ala Ala Ile Val Gln Leu His Asn Gly Thr Lys Tyr Lys Lys Phe
135                 140                 145                 150
```

```
cca cat tgg ttg gat aag tgg atg tta aca aga aag cag ttt ggg ctt      593
Pro His Trp Leu Asp Lys Trp Met Leu Thr Arg Lys Gln Phe Gly Leu
            155                 160                 165 ctc agt ttc ttt ttt gct gta ctg cat gca att tat agt ctg tct tac      641
Leu Ser Phe Phe Phe Ala Val Leu His Ala Ile Tyr Ser Leu Ser Tyr
        170                 175                 180 cca atg agg cga tcc tac aga tac aag ttg cta aac tgg gca tat caa      689
Pro Met Arg Arg Ser Tyr Arg Tyr Lys Leu Leu Asn Trp Ala Tyr Gln
                185                 190                 195 cag gtc caa caa aat aaa gaa gat gcc tgg att gag cat gat gtt tgg      737
Gln Val Gln Gln Asn Lys Glu Asp Ala Trp Ile Glu His Asp Val Trp
    200                 205                 210 aga atg gag att tat gtg tct ctg gga att gtg gga ttg gca ata ctg      785
Arg Met Glu Ile Tyr Val Ser Leu Gly Ile Val Gly Leu Ala Ile Leu
215                 220                 225                 230 gct ctg ttg gct gtg aca tct att cca tct gtg agt gac tct ttg aca      833
Ala Leu Leu Ala Val Thr Ser Ile Pro Ser Val Ser Asp Ser Leu Thr
                235                 240                 245 tgg aga gaa ttt cac tat att cag gta aat aat ata taa aataacccta      882
Trp Arg Glu Phe His Tyr Ile Gln Val Asn Asn Ile  *
            250                 255 agaggtaaat cttctttttg tgtttatgat atagaatatg ttgactttac cccataaaaa    942
ataacaaatg ttttttcaaca gcaaagatct tatacttgtt ccaattaata atgtgctctc   1002
ctgttgtttt ccctattgct tctaattagg acaagtgttt cctagacata aataaaaggc    1062
attaaaatat tctttgtttt tttttttttg tttgtttgtt ttttgtttgt tgtttgttt     1122
ttttgagatg aagtctcgct ctgttgccca tgctggagta cagtggcacg atctcggctc    1182
actgcaacct gcgcctcctg ggttcaggcg attctcttgc ctcagcctcc tgagtagctg    1242
ggattacagg cacccatcac catgtccagc taattttttgt attttagta gagacagggt    1302
tttcccatgt tggccaggct ggtctcgatc tcctgacctc aaatgatccg cccacctcgg    1362
cctcccaaag tgctgggatg acagttgtga gccaccacac tcagcctgct ctttctaata    1422
tttgaaactt gttagacaat ttgctaccca tctaatgtga tatttagga atccaatatg     1482
catggtttat tatttcttaa aaaaatatt cttttacctg tcacctgaat ttagtaatgc     1542
cttttatgtt acacaactta gcactttcca gaaacaaaaa ctctctcctt gaaataatag    1602
agttttatc taccaaagat atgctagtgt ctcatttcaa aggctgcttt ttccagctta     1662
cattttatat acttactcac ttgaagtttc taaatattct tgtaattta aaactatctc     1722
agatttactg aggtttatct tctggtggta gattatccat aagaagagtg atgtgccaga    1782
atcactctgg gatccttgtc tgacaagatt caaaggacta aatttaattc agtcatgaac    1842
actgccaatt accgttatg ggtagacatc tttggaaatt tccacaaggt cagacattcg     1902
caactatccc ttctacatgt ccacacgtat actccaacac tttattaggc atctgattag    1962
tttgaaaagt atgcctccat ctgaattagt ccagtgtggc ttagagttgg tacaacattc    2022
tcacagaatt tcctaatttt gtaggttcag cctgataacc actggagttc tttggtcctc    2082
attaaatagc tttcttcaca cattgctctg cctgttacac atatgatgaa cactgctttt    2142
tagacttcat taggaattta ggactgcatc ttgacaactg agcctattct actatatgta    2202
caatacctag cccataatag gtatacaata cacatttggt aaaactaatt ttcaaccaat    2262
gacatgtatt tttcaactag taacctagaa atgtttcact taaaatctga gaactggtta   2322
cactacaagt taccttggag attcatatat gaaaacgcaa acttagctat ttgattgtat    2382
tcactgggac ttaagaatgc gcctgaataa ttgtgagttc gatttgttct ggcaggctaa    2442
```

-continued

```
tgaccatttc cagtaaagtg aatagaggtc agaagtcgta taaaagaggt gttgtcagaa    2502
caccgttgag attacatagg tgaacaacta tttttaagca actttatttg tgtagtgaca    2562
aagcatccca atgcaggctg aaatgtttca tcacatctct ggatctctct attttgtgca    2622
gacattgaaa aaattgttca tattatttcc atgttatcag aatatttgat ttttttaaaaa   2682
cataggccaa gttcattcac ttcattattc atttatcaaa atcagagtga atcacattag    2742
tcgccttcac aactgataaa gatcactgaa gtcaaattga tttttgctat aatcttcaat    2802
ctacctatat ttaattgaga atctaaaatg tacaaatcat tgtgttgatt ctgcagtgat    2862
cctgctataa gtaagactca gtccctgatt ttaggtatcc tgtgaaaagc agaattaaga    2922
caaatacaca agagacaaag cacaaaaaat aaatatcata aggggatgaa caaaatggtg    2982
gagaaagagt agacaaagtt tttgatcacc tgccttcaaa gaaaggctgt gaattttgtt    3042
cacttagaca gcttggagac aagaaattac ccaaaagtaa ggtgaggagg ataggcaaaa    3102
agagcagaaa gatgtgaatg gacattgttg agaaatgtga taggaaaaca atcatagata    3162
aaggatttcc aagcaactga gcatatccag atgaggtagg atgggataaa ctcttattga    3222
accaatcttc accaattttg tttttctttt gcagagcaag ctaggaattg tttcccttct    3282
actgggcaca atacacgcat tgattttttgc ctggaataag tggatagata taaaacaatt   3342
tgtatggtat acacctccaa ctttatgat agctgttttc cttccaattg ttgtcctgat     3402
atttaaaagc atactattcc tgccatgctt gaggaagaag atactgaaga ttagacatgg    3462
ttgggaagac gtcaccaaaa ttaacaaaac tgagatatgt tcccagttgt agaattactg    3522
tttacacaca ttttttgttca atattgatat attttatcac caacatttca agtttgtatt   3582
tgttaataaa atgattattc aaggaaaaaa aaaaaaaaa aaaaa                      3627
```

<210> SEQ ID NO 35
<211> LENGTH: 258
<212> TYPE: PRT
<213> ORGANISM: Homo sapiens

<400> SEQUENCE: 35

```
Met Glu Ser Arg Lys Asp Ile Thr Asn Gln Glu Leu Trp Lys Met
 1               5                  10                  15

Lys Pro Arg Arg Asn Leu Glu Glu Asp Asp Tyr Leu His Lys Asp Thr
                20                  25                  30

Gly Glu Thr Ser Met Leu Lys Arg Pro Val Leu Leu His Leu His Gln
            35                  40                  45

Thr Ala His Ala Asp Glu Phe Asp Cys Pro Ser Glu Leu Gln His Thr
        50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160
```

```
Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
            210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

<210> SEQ ID NO 36
<211> LENGTH: 339
<212> TYPE: PRT
<213> ORGANISM: Homo sapiens

<400> SEQUENCE: 36

Met Glu Ser Arg Lys Asp Ile Thr Asn Gln Glu Leu Trp Lys Met
 1               5                  10                  15

Lys Pro Arg Arg Asn Leu Glu Glu Asp Asp Tyr Leu His Lys Asp Thr
                20                  25                  30

Gly Glu Thr Ser Met Leu Lys Arg Pro Val Leu Leu His Leu His Gln
            35                  40                  45

Thr Ala His Ala Asp Glu Phe Asp Cys Pro Ser Glu Leu Gln His Thr
 50                  55                  60

Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
            210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                245                 250                 255

Leu Gly Ile Val Ser Leu Leu Leu Gly Thr Ile His Ala Leu Ile Phe
            260                 265                 270
```

```
Ala Trp Asn Lys Trp Ile Asp Ile Lys Gln Phe Val Trp Tyr Thr Pro
        275                 280                 285

Pro Thr Phe Met Ile Ala Val Phe Leu Pro Ile Val Val Leu Ile Phe
        290                 295                 300

Lys Ser Ile Leu Phe Leu Pro Cys Leu Arg Lys Lys Ile Leu Lys Ile
305                 310                 315                 320

Arg His Gly Trp Glu Asp Val Thr Lys Ile Asn Lys Thr Glu Ile Cys
                325                 330                 335

Ser Gln Leu

<210> SEQ ID NO 37
<211> LENGTH: 258
<212> TYPE: PRT
<213> ORGANISM: Homo sapiens

<400> SEQUENCE: 37

Met Glu Ser Arg Lys Asp Ile Thr Asn Gln Glu Glu Leu Trp Lys Met
  1               5                  10                  15

Lys Pro Arg Arg Asn Leu Glu Glu Asp Asp Tyr Leu His Lys Asp Thr
                 20                  25                  30

Gly Glu Thr Ser Met Leu Lys Arg Pro Val Leu Leu His Leu His Gln
             35                  40                  45

Thr Ala His Ala Asp Glu Phe Asp Cys Pro Ser Glu Leu Gln His Thr
         50                  55                  60

Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Leu Arg Glu Val Ile His
                 85                  90                  95

Pro Leu Ala Thr Ser His Gln Gln Tyr Phe Tyr Lys Ile Pro Ile Leu
                100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Leu His Asn Gly
130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
                180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
        210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

<210> SEQ ID NO 38
<211> LENGTH: 282
<212> TYPE: PRT
<213> ORGANISM: Homo sapiens

<400> SEQUENCE: 38
```

```
Met Glu Ser Arg Lys Asp Ile Thr Asn Gln Glu Glu Leu Trp Lys Met
 1               5                  10                  15

Lys Pro Arg Arg Asn Leu Glu Glu Asp Asp Tyr Leu His Lys Asp Thr
             20                  25                  30

Gly Glu Thr Ser Met Leu Lys Arg Pro Val Leu Leu His Leu His Gln
         35                  40                  45

Thr Ala His Ala Asp Glu Phe Asp Cys Pro Ser Glu Leu Gln His Thr
 50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Leu Arg Glu Val Ile His
                 85                  90                  95

Pro Leu Ala Thr Ser His Gln Gln Tyr Phe Tyr Lys Ile Pro Ile Leu
                100                 105                 110

Val Ile Asn Lys Val Leu Pro Met Val Ser Ile Thr Leu Leu Ala Leu
                115                 120                 125

Val Tyr Leu Pro Gly Val Ile Ala Ala Ile Val Gln Leu His Asn Gly
        130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
                180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
        210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ile Ile
                245                 250                 255

His Lys Lys Ser Asp Val Pro Glu Ser Leu Trp Asp Pro Cys Leu Thr
                260                 265                 270

Arg Phe Lys Gly Leu Asn Leu Ile Gln Ser
                275                 280

<210> SEQ ID NO 39
<211> LENGTH: 258
<212> TYPE: PRT
<213> ORGANISM: Homo sapiens

<400> SEQUENCE: 39

Met Glu Ser Arg Lys Asp Ile Thr Asn Gln Glu Glu Leu Trp Lys Met
 1               5                  10                  15

Lys Pro Arg Arg Asn Leu Glu Glu Asp Asp Tyr Leu His Lys Asp Thr
             20                  25                  30

Gly Glu Thr Ser Met Leu Lys Arg Pro Val Leu Leu His Leu His Gln
         35                  40                  45

Thr Ala His Ala Asp Glu Phe Asp Cys Pro Ser Glu Leu Gln His Thr
 50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Leu Arg Glu Val Ile His
```

-continued

```
                    85                  90                  95
Pro Leu Ala Thr Ser His Gln Gln Tyr Phe Tyr Lys Ile Pro Ile Leu
                100                 105                 110
Val Ile Asn Lys Val Leu Pro Met Val Ser Ile Thr Leu Leu Ala Leu
                115                 120                 125
Val Tyr Leu Pro Gly Val Ile Ala Ala Ile Val Gln Leu His Asn Gly
            130                 135                 140
Thr Lys Tyr Lys Lys Phe Pro His Trp Leu Asp Lys Trp Met Leu Thr
145                 150                 155                 160
Arg Lys Gln Phe Gly Leu Leu Ser Leu Phe Phe Ala Val Leu His Ala
                165                 170                 175
Ile Tyr Ser Leu Ser Tyr Pro Met Arg Arg Ser Tyr Arg Tyr Lys Leu
                180                 185                 190
Leu Asn Trp Ala Tyr Gln Gln Val Gln Gln Asn Lys Glu Asp Ala Trp
            195                 200                 205
Ile Glu His Asp Val Trp Arg Met Glu Ile Tyr Val Ser Leu Gly Ile
            210                 215                 220
Val Gly Leu Ala Ile Leu Ala Leu Leu Ala Val Thr Ser Ile Pro Ser
225                 230                 235                 240
Val Ser Asp Ser Leu Thr Trp Arg Glu Phe His Tyr Ile Gln Val Asn
                245                 250                 255
Asn Ile

<210> SEQ ID NO 40
<211> LENGTH: 270
<212> TYPE: PRT
<213> ORGANISM: Homo sapiens

<400> SEQUENCE: 40

Glu Leu Phe Pro Gln Trp His Leu Pro Ile Lys Ile Ala Ala Ile Ile
1               5                   10                  15
Ala Ser Leu Thr Phe Leu Tyr Thr Leu Leu Arg Glu Val Ile His Pro
                20                  25                  30
Leu Ala Thr Ser His Gln Gln Tyr Phe Tyr Lys Ile Pro Ile Leu Val
            35                  40                  45
Ile Asn Lys Val Leu Pro Met Val Ser Ile Thr Leu Leu Ala Leu Val
        50                  55                  60
Tyr Leu Pro Gly Val Ile Ala Ala Ile Val Gln Leu His Asn Gly Thr
65                  70                  75                  80
Lys Tyr Lys Lys Phe Pro His Trp Leu Asp Lys Trp Met Leu Thr Arg
                85                  90                  95
Lys Gln Phe Gly Leu Leu Ser Leu Phe Phe Ala Val Leu His Ala Ile
                100                 105                 110
Tyr Ser Leu Ser Tyr Pro Met Arg Arg Ser Tyr Arg Tyr Lys Leu Leu
            115                 120                 125
Asn Trp Ala Tyr Gln Gln Val Gln Gln Asn Lys Glu Asp Ala Trp Ile
        130                 135                 140
Glu His Asp Val Trp Arg Met Glu Ile Tyr Val Ser Leu Gly Ile Val
145                 150                 155                 160
Gly Leu Ala Ile Leu Ala Leu Leu Ala Val Thr Ser Ile Pro Ser Val
                165                 170                 175
Ser Asp Ser Leu Thr Trp Arg Glu Phe His Tyr Ile Gln Ser Lys Leu
                180                 185                 190
Gly Ile Val Ser Leu Leu Leu Gly Thr Ile His Ala Leu Ile Phe Ala
```

```
                195                 200                 205
Trp Asn Lys Trp Ile Asp Ile Lys Gln Phe Val Trp Tyr Thr Pro Pro
    210                 215                 220

Thr Phe Met Ile Ala Val Phe Leu Pro Ile Val Val Leu Ile Phe Lys
225                 230                 235                 240

Ser Ile Leu Phe Leu Pro Cys Leu Arg Lys Lys Ile Leu Lys Ile Arg
                245                 250                 255

His Gly Trp Glu Asp Val Thr Lys Ile Asn Lys Thr Glu Ile
            260                 265                 270

<210> SEQ ID NO 41
<211> LENGTH: 270
<212> TYPE: PRT
<213> ORGANISM: Homo sapiens

<400> SEQUENCE: 41

Gln Leu Phe Pro Met Trp Arg Phe Pro Phe Tyr Leu Ser Ser Val Leu
1               5                   10                  15

Cys Ile Phe Phe Phe Val Tyr Cys Ala Ile Arg Glu Val Ile Tyr Pro
                20                  25                  30

Tyr Val Asn Gly Lys Thr Asp Ala Thr Tyr Arg Leu Ala Ile Ser Ile
            35                  40                  45

Pro Asn Arg Val Phe Pro Ile Thr Ala Leu Ile Leu Ala Leu Val
50                  55                  60

Tyr Leu Pro Gly Ile Leu Ala Ala Ile Leu Gln Leu Tyr Arg Gly Thr
65                  70                  75                  80

Lys Tyr Arg Arg Phe Pro Asn Trp Leu Asp His Trp Met Leu Cys Arg
                85                  90                  95

Lys Gln Leu Gly Leu Val Ala Leu Gly Phe Ala Phe Leu His Val Ile
                100                 105                 110

Tyr Thr Leu Val Ile Pro Ile Arg Tyr Tyr Val Arg Trp Arg Leu Arg
            115                 120                 125

Asn Ala Thr Ile Thr Gln Ala Leu Thr Asn Lys Asp Ser Pro Phe Ile
130                 135                 140

Thr Ser Tyr Ala Trp Ile Asn Asp Ser Tyr Leu Ala Leu Gly Ile Leu
145                 150                 155                 160

Gly Phe Phe Leu Phe Leu Leu Leu Gly Ile Thr Ser Leu Pro Ser Val
                165                 170                 175

Ser Asn Met Val Asn Trp Arg Glu Phe Arg Phe Val Gln Ser Lys Leu
            180                 185                 190

Gly Tyr Leu Thr Leu Val Leu Cys Thr Ala His Thr Leu Val Tyr Gly
        195                 200                 205

Gly Lys Arg Phe Leu Ser Pro Ser Ile Leu Arg Trp Ser Leu Pro Ser
    210                 215                 220

Ala Tyr Ile Leu Ala Leu Ile Ile Pro Cys Ala Val Leu Val Leu Lys
225                 230                 235                 240

Cys Ile Leu Ile Met Pro Cys Ile Asp Lys Thr Leu Thr Arg Ile Arg
                245                 250                 255

Gln Gly Trp Glu Arg Asn Ser Lys Tyr Thr Gln Ser Ala Leu
            260                 265                 270

<210> SEQ ID NO 42
<211> LENGTH: 259
<212> TYPE: PRT
<213> ORGANISM: Homo sapiens
```

```
<400> SEQUENCE: 42

Leu Phe Pro Gln Trp His Leu Pro Ile Lys Ile Ala Ala Ile Ile Ala
 1               5                  10                  15

Ser Leu Thr Phe Leu Tyr Thr Leu Leu Arg Glu Val Ile His Pro Leu
            20                  25                  30

Ala Thr Ser His Gln Gln Tyr Phe Tyr Lys Ile Pro Ile Leu Val Ile
        35                  40                  45

Asn Lys Val Leu Pro Met Val Ser Ile Thr Leu Leu Ala Leu Val Tyr
 50                  55                  60

Leu Pro Gly Val Ile Ala Ala Ile Val Gln Leu His Asn Gly Thr Lys
 65                  70                  75                  80

Tyr Lys Lys Phe Pro His Trp Leu Asp Lys Trp Met Leu Thr Arg Lys
                85                  90                  95

Gln Phe Gly Leu Leu Ser Phe Phe Ala Val Leu His Ala Ile Tyr
            100                 105                 110

Ser Leu Ser Tyr Pro Met Arg Arg Ser Tyr Arg Tyr Lys Leu Leu Asn
            115                 120                 125

Trp Ala Tyr Gln Gln Val Gln Gln Asn Lys Glu Asp Ala Trp Ile Glu
130                 135                 140

His Asp Val Trp Arg Met Glu Ile Tyr Val Ser Leu Gly Ile Val Gly
145                 150                 155                 160

Leu Ala Ile Leu Ala Leu Leu Ala Val Thr Ser Ile Pro Ser Val Ser
                165                 170                 175

Asp Ser Leu Thr Trp Arg Glu Phe His Tyr Ile Gln Ser Lys Leu Gly
            180                 185                 190

Ile Val Ser Leu Leu Leu Gly Thr Ile His Ala Leu Ile Phe Ala Trp
            195                 200                 205

Asn Lys Trp Ile Asp Ile Lys Gln Phe Val Trp Tyr Thr Pro Pro Thr
210                 215                 220

Phe Met Ile Ala Val Phe Leu Pro Ile Val Val Leu Ile Phe Lys Ser
225                 230                 235                 240

Ile Leu Phe Leu Pro Cys Leu Arg Lys Lys Ile Leu Lys Ile Arg His
                245                 250                 255

Gly Trp Glu

<210> SEQ ID NO 43
<211> LENGTH: 259
<212> TYPE: PRT
<213> ORGANISM: Homo sapiens

<400> SEQUENCE: 43

Leu Leu Pro Ser Trp Lys Val Pro Thr Leu Leu Ala Leu Gly Leu Ser
 1               5                  10                  15

Thr Gln Ser Tyr Ala Tyr Asn Phe Ile Arg Asp Val Leu Gln Pro Tyr
            20                  25                  30

Ile Arg Lys Asp Glu Asn Lys Phe Tyr Lys Met Pro Leu Ser Val Val
        35                  40                  45

Asn Thr Thr Ile Pro Cys Val Ala Tyr Val Leu Leu Ser Leu Val Tyr
 50                  55                  60

Leu Pro Gly Val Leu Ala Ala Leu Gln Leu Arg Arg Gly Thr Lys
 65                  70                  75                  80

Tyr Gln Arg Phe Pro Asp Trp Leu Asp His Trp Leu Gln His Arg Lys
                85                  90                  95

Gln Ile Gly Leu Leu Ser Phe Phe Ala Met Leu His Ala Leu Tyr
```

```
                100                 105                 110
Ser Phe Cys Leu Pro Leu Arg Arg Ser His Arg Tyr Asp Leu Val Asn
            115                 120                 125

Leu Ala Val Lys Gln Val Leu Ala Asn Lys Ser Arg Leu Trp Val Glu
130                 135                 140

Glu Glu Val Trp Arg Met Glu Ile Tyr Leu Ser Leu Gly Val Leu Ala
145                 150                 155                 160

Leu Gly Met Leu Ser Leu Leu Ala Val Thr Ser Ile Pro Ser Ile Ala
                165                 170                 175

Asn Ser Leu Asn Trp Lys Glu Phe Ser Phe Val Gln Ser Thr Leu Gly
            180                 185                 190

Phe Val Ala Leu Met Leu Ser Thr Met His Thr Leu Thr Tyr Gly Trp
195                 200                 205

Thr Arg Ala Phe Glu Glu Asn His Tyr Lys Phe Tyr Leu Pro Pro Thr
210                 215                 220

Phe Thr Leu Thr Leu Leu Pro Cys Val Ile Ile Leu Ala Lys Gly
225                 230                 235                 240

Leu Phe Leu Leu Pro Cys Leu Ser His Arg Leu Thr Lys Ile Arg Arg
                245                 250                 255

Gly Trp Glu

<210> SEQ ID NO 44
<211> LENGTH: 303
<212> TYPE: PRT
<213> ORGANISM: Homo sapiens

<400> SEQUENCE: 44

Met Leu Lys Arg Pro Val Leu Leu His Leu His Gln Thr Ala His Ala
1               5                   10                  15

Asp Glu Phe Asp Cys Pro Ser Glu Leu Gln His Thr Gln Glu Leu Phe
            20                  25                  30

Pro Gln Trp His Leu Pro Ile Lys Ile Ala Ala Ile Ala Ser Leu
            35                  40                  45

Thr Phe Leu Tyr Thr Leu Leu Arg Glu Val Ile His Pro Leu Ala Thr
50                  55                  60

Ser His Gln Gln Tyr Phe Tyr Lys Ile Pro Ile Leu Val Ile Asn Lys
65                  70                  75                  80

Val Leu Pro Met Val Ser Ile Thr Leu Leu Ala Leu Val Tyr Leu Pro
                85                  90                  95

Gly Val Ile Ala Ala Ile Val Gln Leu His Asn Gly Thr Lys Tyr Lys
            100                 105                 110

Lys Phe Pro His Trp Leu Asp Lys Trp Met Leu Thr Arg Lys Gln Phe
            115                 120                 125

Gly Leu Leu Ser Phe Phe Phe Ala Val Leu His Ala Ile Tyr Ser Leu
130                 135                 140

Ser Tyr Pro Met Arg Arg Ser Tyr Arg Tyr Lys Leu Leu Asn Trp Ala
145                 150                 155                 160

Tyr Gln Gln Val Gln Gln Asn Lys Glu Asp Ala Trp Ile Glu His Asp
                165                 170                 175

Val Trp Arg Met Glu Ile Tyr Val Ser Leu Gly Ile Val Gly Leu Ala
            180                 185                 190

Ile Leu Ala Leu Leu Ala Val Thr Ser Ile Pro Ser Val Ser Asp Ser
            195                 200                 205

Leu Thr Trp Arg Glu Phe His Tyr Ile Gln Ser Lys Leu Gly Ile Val
```

-continued

```
            210                 215                 220
Ser Leu Leu Gly Thr Ile His Ala Leu Ile Phe Ala Trp Asn Lys
225                 230                 235                 240

Trp Ile Asp Ile Lys Gln Phe Val Trp Tyr Thr Pro Thr Phe Met
                245                 250                 255

Ile Ala Val Phe Leu Pro Ile Val Leu Ile Phe Lys Ser Ile Leu
                260                 265                 270

Phe Leu Pro Cys Leu Arg Lys Lys Ile Leu Lys Ile Arg His Gly Trp
                275                 280                 285

Glu Asp Val Thr Lys Ile Asn Lys Thr Glu Ile Cys Ser Gln Leu
290                 295                 300
```

<210> SEQ ID NO 45
<211> LENGTH: 303
<212> TYPE: PRT
<213> ORGANISM: Homo sapiens

<400> SEQUENCE: 45

```
Met Leu Lys Arg Pro Gly Leu Ser His Leu Gln His Ala Val His Val
1               5                   10                  15

Asp Ala Phe Asp Cys Pro Ser Glu Leu Gln His Thr Gln Glu Phe Phe
                20                  25                  30

Pro Asn Trp Arg Leu Pro Val Lys Val Ala Ala Ile Ile Ser Ser Leu
            35                  40                  45

Thr Phe Leu Tyr Thr Leu Leu Arg Glu Ile Ile Tyr Pro Leu Val Thr
        50                  55                  60

Ser Arg Glu Gln Tyr Phe Tyr Lys Ile Pro Ile Leu Val Ile Asn Lys
65                  70                  75                  80

Val Leu Pro Met Val Ala Ile Thr Leu Leu Ala Leu Val Tyr Leu Pro
                85                  90                  95

Gly Glu Leu Ala Ala Val Val Gln Leu Arg Asn Gly Thr Lys Tyr Lys
            100                 105                 110

Lys Phe Pro Pro Trp Leu Asp Arg Trp Met Leu Ala Arg Lys Gln Phe
        115                 120                 125

Gly Leu Leu Ser Phe Phe Ala Val Leu His Ala Val Tyr Ser Leu
            130                 135                 140

Ser Tyr Pro Met Arg Arg Ser Tyr Arg Tyr Lys Leu Leu Asn Trp Ala
145                 150                 155                 160

Tyr Lys Gln Val Gln Gln Asn Lys Glu Asp Ala Trp Val Glu His Asp
                165                 170                 175

Val Trp Arg Met Glu Ile Tyr Val Ser Leu Gly Ile Val Gly Leu Ala
                180                 185                 190

Ile Leu Ala Leu Leu Ala Val Thr Ser Ile Pro Ser Val Ser Asp Ser
            195                 200                 205

Leu Thr Trp Arg Glu Phe His Tyr Ile Gln Ser Lys Leu Gly Ile Val
        210                 215                 220

Ser Leu Leu Gly Thr Val His Ala Leu Val Phe Ala Trp Asn Lys
225                 230                 235                 240

Trp Val Asp Val Ser Gln Phe Val Trp Tyr Met Pro Pro Thr Phe Met
                245                 250                 255

Ile Ala Val Phe Leu Pro Thr Leu Leu Ile Cys Lys Ile Ala Leu
                260                 265                 270

Cys Leu Pro Cys Leu Arg Lys Lys Ile Leu Lys Ile Arg Cys Gly Trp
                275                 280                 285
```

Glu Asp Val Ser Lys Ile Asn Arg Thr Glu Met Ala Ser Arg Leu
    290                 295                 300

<210> SEQ ID NO 46
<211> LENGTH: 339
<212> TYPE: PRT
<213> ORGANISM: Homo sapiens

<400> SEQUENCE: 46

Met Glu Ser Arg Lys Asp Ile Thr Asn Gln Glu Leu Trp Lys Met
 1               5                  10                  15

Lys Pro Arg Arg Asn Leu Glu Glu Asp Asp Tyr Leu His Lys Asp Thr
                20                  25                  30

Gly Glu Thr Ser Met Leu Lys Arg Pro Val Leu Leu His Leu His Gln
            35                  40                  45

Thr Ala His Ala Asp Glu Phe Asp Cys Pro Ser Glu Leu Gln His Thr
 50                  55                  60

Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Leu His Asn Gly
130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                245                 250                 255

Leu Gly Ile Val Ser Leu Leu Leu Gly Thr Ile His Ala Leu Ile Phe
            260                 265                 270

Ala Trp Asn Lys Trp Ile Asp Ile Lys Gln Phe Val Trp Tyr Thr Pro
            275                 280                 285

Pro Thr Phe Met Ile Ala Val Phe Leu Pro Ile Val Val Leu Ile Phe
            290                 295                 300

Lys Ser Ile Leu Phe Leu Pro Cys Leu Arg Lys Lys Ile Leu Lys Ile
305                 310                 315                 320

Arg His Gly Trp Glu Asp Val Thr Lys Ile Asn Lys Thr Glu Ile Cys
                325                 330                 335

Ser Gln Leu

<210> SEQ ID NO 47
<211> LENGTH: 258

```
<212> TYPE: PRT
<213> ORGANISM: Homo sapiens

<400> SEQUENCE: 47

Met Glu Ser Arg Lys Asp Ile Thr Asn Gln Glu Glu Leu Trp Lys Met
 1               5                  10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
 50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Leu His Asn Gly
        130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
            165                 170                 175

Ile Tyr Ser Leu Ser Tyr Pro Met Arg Arg Ser Tyr Arg Tyr Lys Leu
                180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
        210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

<210> SEQ ID NO 48
<211> LENGTH: 282
<212> TYPE: PRT
<213> ORGANISM: Homo sapiens

<400> SEQUENCE: 48

Met Glu Ser Arg Lys Asp Ile Thr Asn Gln Glu Glu Leu Trp Lys Met
 1               5                  10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
 50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Leu Arg Glu Val Ile His
```

```
                    85                  90                  95
Pro Leu Ala Thr Ser His Gln Gln Tyr Phe Tyr Lys Ile Pro Ile Leu
               100                 105                 110
Val Ile Asn Lys Val Leu Pro Met Val Ser Ile Thr Leu Leu Ala Leu
               115                 120                 125
Val Tyr Leu Pro Gly Val Ile Ala Ala Ile Val Gln Leu His Asn Gly
               130                 135                 140
Thr Lys Tyr Lys Lys Phe Pro His Trp Leu Asp Lys Trp Met Leu Thr
145                 150                 155                 160
Arg Lys Gln Phe Gly Leu Leu Ser Phe Phe Ala Val Leu His Ala
                   165                 170                 175
Ile Tyr Ser Leu Ser Tyr Pro Met Arg Arg Ser Tyr Arg Tyr Lys Leu
               180                 185                 190
Leu Asn Trp Ala Tyr Gln Gln Val Gln Gln Asn Lys Glu Asp Ala Trp
               195                 200                 205
Ile Glu His Asp Val Trp Arg Met Glu Ile Tyr Val Ser Leu Gly Ile
               210                 215                 220
Val Gly Leu Ala Ile Leu Ala Leu Leu Ala Val Thr Ser Ile Pro Ser
225                 230                 235                 240
Val Ser Asp Ser Leu Thr Trp Arg Glu Phe His Tyr Ile Gln Ile Ile
                   245                 250                 255
His Lys Lys Ser Asp Val Pro Glu Ser Leu Trp Asp Pro Cys Leu Thr
               260                 265                 270
Arg Phe Lys Gly Leu Asn Leu Ile Gln Ser
               275                 280

<210> SEQ ID NO 49
<211> LENGTH: 339
<212> TYPE: DNA
<213> ORGANISM: Homo sapiens
<220> FEATURE:
<221> NAME/KEY: CDS
<222> LOCATION: (1)...(339)

<400> SEQUENCE: 49 gtc aag ctg cag gag tct gga cct gag ctg aag aag cct gga gag aca      48
Val Lys Leu Gln Glu Ser Gly Pro Glu Leu Lys Lys Pro Gly Glu Thr
1               5                  10                  15 gtc aag atc tcc tgc aag gct tct ggg tat acc ttc aca aac tat gga      96
Val Lys Ile Ser Cys Lys Ala Ser Gly Tyr Thr Phe Thr Asn Tyr Gly
            20                  25                  30 atg aac tgg gtg aag cag gct cca gga aag ggt tta aag tgg atg ggc     144
Met Asn Trp Val Lys Gln Ala Pro Gly Lys Gly Leu Lys Trp Met Gly
        35                  40                  45 tgg ata aac acc tac act gga gag cca aca tat gct gat gac ttc aag     192
Trp Ile Asn Thr Tyr Thr Gly Glu Pro Thr Tyr Ala Asp Asp Phe Lys
    50                  55                  60 gga cgg ttt gcc ttc tct ttg gaa acc tct gcc agc act gcc tat ttg     240
Gly Arg Phe Ala Phe Ser Leu Glu Thr Ser Ala Ser Thr Ala Tyr Leu
65                  70                  75                  80 cag atc aac aac ctc aaa aat gag gac acg gct aca tat ttc tgt gca     288
Gln Ile Asn Asn Leu Lys Asn Glu Asp Thr Ala Thr Tyr Phe Cys Ala
            85                  90                  95 aga ccc tgg ttt gct tac tgg ggc caa ggg acc acg gtc acc gtc tcc     336
Arg Pro Trp Phe Ala Tyr Trp Gly Gln Gly Thr Thr Val Thr Val Ser
        100                 105                 110 tca                                                                339
Ser
```

<210> SEQ ID NO 50
<211> LENGTH: 113
<212> TYPE: PRT
<213> ORGANISM: Homo sapiens

<400> SEQUENCE: 50

Val Lys Leu Gln Glu Ser Gly Pro Glu Leu Lys Lys Pro Gly Glu Thr
1               5                   10                  15

Val Lys Ile Ser Cys Lys Ala Ser Gly Tyr Thr Phe Thr Asn Tyr Gly
            20                  25                  30

Met Asn Trp Val Lys Gln Ala Pro Gly Lys Gly Leu Lys Trp Met Gly
        35                  40                  45

Trp Ile Asn Thr Tyr Thr Gly Glu Pro Thr Tyr Ala Asp Asp Phe Lys
50                  55                  60

Gly Arg Phe Ala Phe Ser Leu Glu Thr Ser Ala Ser Thr Ala Tyr Leu
65                  70                  75                  80

Gln Ile Asn Asn Leu Lys Asn Glu Asp Thr Ala Thr Tyr Phe Cys Ala
                85                  90                  95

Arg Pro Trp Phe Ala Tyr Trp Gly Gln Gly Thr Thr Val Thr Val Ser
            100                 105                 110

Ser

<210> SEQ ID NO 51
<211> LENGTH: 435
<212> TYPE: DNA
<213> ORGANISM: Homo sapiens
<220> FEATURE:
<221> NAME/KEY: CDS
<222> LOCATION: (1)...(435)

<400> SEQUENCE: 51

```
gga ctg ttc gaa gcc gcc acc atg aag ttg cct gtt agg ctg ttg gtg        48
Gly Leu Phe Glu Ala Ala Thr Met Lys Leu Pro Val Arg Leu Leu Val
  1               5                  10                  15 ctc tgg att cgg gaa acc aac ggt gat gtt gtg atg acc cag act cca        96
Leu Trp Ile Arg Glu Thr Asn Gly Asp Val Val Met Thr Gln Thr Pro
              20                  25                  30 ctc act ttg tcg gtt acc att gga caa cca gcc tcc atc tct tgc aag       144
Leu Thr Leu Ser Val Thr Ile Gly Gln Pro Ala Ser Ile Ser Cys Lys
          35                  40                  45 tca agt cag agc ctc tta gat agt gat gga aag aca tat ttg aat tgg       192
Ser Ser Gln Ser Leu Leu Asp Ser Asp Gly Lys Thr Tyr Leu Asn Trp
     50                  55                  60 ttg tta cag agg cca ggc cag tct cca aag cgc cta atc tat ctg gtg       240
Leu Leu Gln Arg Pro Gly Gln Ser Pro Lys Arg Leu Ile Tyr Leu Val
 65                  70                  75                  80 tct aaa ctg gac tct gga gtc cct gac agg ttc act ggc agt gga tca       288
Ser Lys Leu Asp Ser Gly Val Pro Asp Arg Phe Thr Gly Ser Gly Ser
                 85                  90                  95 ggg aca gat ttc aca ctg aaa atc agc aga gtg gag gct gag gat ttg       336
Gly Thr Asp Phe Thr Leu Lys Ile Ser Arg Val Glu Ala Glu Asp Leu
            100                 105                 110 gga gtt tat tat tgc tgg caa ggt aca cat ttt cca ttc acg ttc ggc       384
Gly Val Tyr Tyr Cys Trp Gln Gly Thr His Phe Pro Phe Thr Phe Gly
        115                 120                 125 tcg ggg aca aag ttg gaa ata aaa cgt acg gat gct gca cca act gta       432
Ser Gly Thr Lys Leu Glu Ile Lys Arg Thr Asp Ala Ala Pro Thr Val
    130                 135                 140
```

```
tcc                                                                          435
Ser
145

<210> SEQ ID NO 52
<211> LENGTH: 145
<212> TYPE: PRT
<213> ORGANISM: Homo sapiens

<400> SEQUENCE: 52

Gly Leu Phe Glu Ala Ala Thr Met Lys Leu Pro Val Arg Leu Leu Val
 1               5                  10                  15

Leu Trp Ile Arg Glu Thr Asn Gly Asp Val Val Met Thr Gln Thr Pro
            20                  25                  30

Leu Thr Leu Ser Val Thr Ile Gly Gln Pro Ala Ser Ile Ser Cys Lys
        35                  40                  45

Ser Ser Gln Ser Leu Leu Asp Ser Asp Gly Lys Thr Tyr Leu Asn Trp
    50                  55                  60

Leu Leu Gln Arg Pro Gly Gln Ser Pro Lys Arg Leu Ile Tyr Leu Val
65                  70                  75                  80

Ser Lys Leu Asp Ser Gly Val Pro Asp Arg Phe Thr Gly Ser Gly Ser
                85                  90                  95

Gly Thr Asp Phe Thr Leu Lys Ile Ser Arg Val Glu Ala Glu Asp Leu
            100                 105                 110

Gly Val Tyr Tyr Cys Trp Gln Gly Thr His Phe Pro Phe Thr Phe Gly
        115                 120                 125

Ser Gly Thr Lys Leu Glu Ile Lys Arg Thr Asp Ala Ala Pro Thr Val
    130                 135                 140

Ser
145

<210> SEQ ID NO 53
<211> LENGTH: 378
<212> TYPE: DNA
<213> ORGANISM: Homo sapiens
<220> FEATURE:
<221> NAME/KEY: CDS
<222> LOCATION: (1)...(378)

<400> SEQUENCE: 53 gga ctg ttc gaa gcc gcc acc atg gaa gcc cca gct cag ctc act ttg        48
Gly Leu Phe Glu Ala Ala Thr Met Glu Ala Pro Ala Gln Leu Thr Leu
 1               5                  10                  15 tcg gtt acc att gga caa cca gcc tcc atc tct tgc aag tca agt cag        96
Ser Val Thr Ile Gly Gln Pro Ala Ser Ile Ser Cys Lys Ser Ser Gln
            20                  25                  30 agc ctc tta gat agt gat gga aag aca tat ttg aat tgg ttg tta cag       144
Ser Leu Leu Asp Ser Asp Gly Lys Thr Tyr Leu Asn Trp Leu Leu Gln
        35                  40                  45 agg cca ggc cag tct cca aag cgc cta atc tat ctg gtg tct aaa ctg       192
Arg Pro Gly Gln Ser Pro Lys Arg Leu Ile Tyr Leu Val Ser Lys Leu
    50                  55                  60 gac tct gga gtc cct gac agg ttc act ggc agt gga tca ggg aca gat       240
Asp Ser Gly Val Pro Asp Arg Phe Thr Gly Ser Gly Ser Gly Thr Asp
65                  70                  75                  80 ttc aca ctg aaa atc agc aga gtg gag gct gag gat ttg gga gtt tat       288
Phe Thr Leu Lys Ile Ser Arg Val Glu Ala Glu Asp Leu Gly Val Tyr
                85                  90                  95 tat tgc tgg caa ggt aca cat ttt cca ttc acg ttc ggc tcg ggg aca       336
Tyr Cys Trp Gln Gly Thr His Phe Pro Phe Thr Phe Gly Ser Gly Thr
```

```
                   100                 105                 110
aag ttg gaa ata aaa cgt acg gat gct gca cca act gta tcc         378
Lys Leu Glu Ile Lys Arg Thr Asp Ala Ala Pro Thr Val Ser
            115                 120                 125

<210> SEQ ID NO 54
<211> LENGTH: 126
<212> TYPE: PRT
<213> ORGANISM: Homo sapiens

<400> SEQUENCE: 54

Gly Leu Phe Glu Ala Ala Thr Met Glu Ala Pro Ala Gln Leu Thr Leu
 1               5                  10                  15

Ser Val Thr Ile Gly Gln Pro Ala Ser Ile Ser Cys Lys Ser Ser Gln
            20                  25                  30

Ser Leu Leu Asp Ser Asp Gly Lys Thr Tyr Leu Asn Trp Leu Leu Gln
        35                  40                  45

Arg Pro Gly Gln Ser Pro Lys Arg Leu Ile Tyr Leu Val Ser Lys Leu
    50                  55                  60

Asp Ser Gly Val Pro Asp Arg Phe Thr Gly Ser Gly Ser Gly Thr Asp
65                  70                  75                  80

Phe Thr Leu Lys Ile Ser Arg Val Glu Ala Glu Asp Leu Gly Val Tyr
                85                  90                  95

Tyr Cys Trp Gln Gly Thr His Phe Pro Phe Thr Phe Gly Ser Gly Thr
            100                 105                 110

Lys Leu Glu Ile Lys Arg Thr Asp Ala Ala Pro Thr Val Ser
        115                 120                 125

<210> SEQ ID NO 55
<211> LENGTH: 438
<212> TYPE: DNA
<213> ORGANISM: Homo sapiens
<220> FEATURE:
<221> NAME/KEY: CDS
<222> LOCATION: (1)...(438)

<400> SEQUENCE: 55 atg ggc ttc aag atg gag tca cag gcc cag gtt ctt atg tta ctg ctg          48
Met Gly Phe Lys Met Glu Ser Gln Ala Gln Val Leu Met Leu Leu Leu
 1               5                  10                  15 cta tgg gta tct ggt acc tgt ggg gac att gtg atg tca cag tct cca          96
Leu Trp Val Ser Gly Thr Cys Gly Asp Ile Val Met Ser Gln Ser Pro
            20                  25                  30 tcc tcc cta gct gtg tca gtt gga gag aag gtt acc atg agc tgc aag         144
Ser Ser Leu Ala Val Ser Val Gly Glu Lys Val Thr Met Ser Cys Lys
        35                  40                  45 tcc agt cag agc ctt tta tat agg agc aat caa aag aac tac ttg gcc         192
Ser Ser Gln Ser Leu Leu Tyr Arg Ser Asn Gln Lys Asn Tyr Leu Ala
    50                  55                  60 tgg tac cag cag aaa cca ggg cag tct cct aaa ctg ctg att tat tgg         240
Trp Tyr Gln Gln Lys Pro Gly Gln Ser Pro Lys Leu Leu Ile Tyr Trp
65                  70                  75                  80 gcc tcc act agg gaa tct ggg gtc cct gat cgc ttc aca ggc agt gga         288
Ala Ser Thr Arg Glu Ser Gly Val Pro Asp Arg Phe Thr Gly Ser Gly
                85                  90                  95 tct ggg aca gat ttc act ctc acc atc agc agt gtg aag gct gaa gac         336
Ser Gly Thr Asp Phe Thr Leu Thr Ile Ser Ser Val Lys Ala Glu Asp
            100                 105                 110 ctg gca gtt tat tac tgt cag caa tat tat aac tat cct cgg acg ttc         384
Leu Ala Val Tyr Tyr Cys Gln Gln Tyr Tyr Asn Tyr Pro Arg Thr Phe
```

```
                 115                 120                 125
ggt gga ggc acc aag ctg gaa atc aaa cgt acg gat gct gca cca act    432
Gly Gly Gly Thr Lys Leu Glu Ile Lys Arg Thr Asp Ala Ala Pro Thr
130                 135                 140 gta tcc                                                            438
Val Ser
145
```

<210> SEQ ID NO 56
<211> LENGTH: 146
<212> TYPE: PRT
<213> ORGANISM: Homo sapiens

<400> SEQUENCE: 56

```
Met Gly Phe Lys Met Glu Ser Gln Ala Gln Val Leu Met Leu Leu Leu
1               5                   10                  15

Leu Trp Val Ser Gly Thr Cys Gly Asp Ile Val Met Ser Gln Ser Pro
            20                  25                  30

Ser Ser Leu Ala Val Ser Val Gly Glu Lys Val Thr Met Ser Cys Lys
        35                  40                  45

Ser Ser Gln Ser Leu Leu Tyr Arg Ser Asn Gln Lys Asn Tyr Leu Ala
    50                  55                  60

Trp Tyr Gln Gln Lys Pro Gly Gln Ser Pro Lys Leu Leu Ile Tyr Trp
65                  70                  75                  80

Ala Ser Thr Arg Glu Ser Gly Val Pro Asp Arg Phe Thr Gly Ser Gly
                85                  90                  95

Ser Gly Thr Asp Phe Thr Leu Thr Ile Ser Ser Val Lys Ala Glu Asp
            100                 105                 110

Leu Ala Val Tyr Tyr Cys Gln Gln Tyr Tyr Asn Tyr Pro Arg Thr Phe
        115                 120                 125

Gly Gly Gly Thr Lys Leu Glu Ile Lys Arg Thr Asp Ala Ala Pro Thr
    130                 135                 140

Val Ser
145
```

<210> SEQ ID NO 57
<211> LENGTH: 113
<212> TYPE: PRT
<213> ORGANISM: Homo sapiens

<400> SEQUENCE: 57

```
Val Lys Leu Gln Glu Ser Gly Pro Glu Leu Lys Lys Pro Gly Glu Thr
1               5                   10                  15

Val Lys Ile Ser Cys Lys Ala Ser Gly Tyr Thr Phe Thr Asn Tyr Gly
            20                  25                  30

Met Asn Trp Val Lys Gln Ala Pro Gly Lys Gly Leu Lys Trp Met Gly
        35                  40                  45

Trp Ile Asn Thr Tyr Thr Gly Glu Pro Thr Tyr Ala Asp Asp Phe Lys
    50                  55                  60

Gly Arg Phe Ala Phe Ser Leu Glu Thr Ser Ala Ser Thr Ala Tyr Leu
65                  70                  75                  80

Gln Ile Asn Asn Leu Lys Asn Glu Asp Thr Ala Thr Tyr Phe Cys Ala
                85                  90                  95

Arg Pro Trp Phe Ala Tyr Trp Gly Gln Gly Thr Thr Val Thr Val Ser
            100                 105                 110

Ser
```

<210> SEQ ID NO 58
<211> LENGTH: 145
<212> TYPE: PRT
<213> ORGANISM: Homo sapiens

<400> SEQUENCE: 58

```
Gly Leu Phe Glu Ala Ala Thr Met Lys Leu Pro Val Arg Leu Leu Val
1               5                   10                  15

Leu Trp Ile Arg Glu Thr Asn Gly Asp Val Val Met Thr Gln Thr Pro
            20                  25                  30

Leu Thr Leu Ser Val Thr Ile Gly Gln Pro Ala Ser Ile Ser Cys Lys
        35                  40                  45

Ser Ser Gln Ser Leu Leu Asp Ser Asp Gly Lys Thr Tyr Leu Asn Trp
    50                  55                  60

Leu Leu Gln Arg Pro Gly Gln Ser Pro Lys Arg Leu Ile Tyr Leu Val
65                  70                  75                  80

Ser Lys Leu Asp Ser Gly Val Pro Asp Arg Phe Thr Gly Ser Gly Ser
                85                  90                  95

Gly Thr Asp Phe Thr Leu Lys Ile Ser Arg Val Glu Ala Glu Asp Leu
            100                 105                 110

Gly Val Tyr Tyr Cys Trp Gln Gly Thr His Phe Pro Phe Thr Phe Gly
        115                 120                 125

Ser Gly Thr Lys Leu Glu Ile Lys Arg Thr Asp Ala Ala Pro Thr Val
    130                 135                 140

Ser
145
```

<210> SEQ ID NO 59
<211> LENGTH: 378
<212> TYPE: DNA
<213> ORGANISM: Homo sapiens
<220> FEATURE:
<221> NAME/KEY: CDS
<222> LOCATION: (1)...(378)

<400> SEQUENCE: 59

```
gga ctg ttc gaa gcc gcc acc atg gaa gcc cca gct cag ctc act ttg      48
Gly Leu Phe Glu Ala Ala Thr Met Glu Ala Pro Ala Gln Leu Thr Leu
1               5                   10                  15 tcg gtt acc att gga caa cca gcc tcc atc tct tgc aag tca agt cag      96
Ser Val Thr Ile Gly Gln Pro Ala Ser Ile Ser Cys Lys Ser Ser Gln
            20                  25                  30 agc ctc tta gat agt gat gga aag aca tat ttg aat tgg ttg tta cag     144
Ser Leu Leu Asp Ser Asp Gly Lys Thr Tyr Leu Asn Trp Leu Leu Gln
        35                  40                  45 agg cca ggc cag tct cca aag cgc cta atc tat ctg gtg tct aaa ctg     192
Arg Pro Gly Gln Ser Pro Lys Arg Leu Ile Tyr Leu Val Ser Lys Leu
    50                  55                  60 gac tct gga gtc cct gac agg ttc act ggc agt gga tca ggg aca gat     240
Asp Ser Gly Val Pro Asp Arg Phe Thr Gly Ser Gly Ser Gly Thr Asp
65                  70                  75                  80 ttc aca ctg aaa atc agc aga gtg gag gct gag gat ttg gga gtt tat     288
Phe Thr Leu Lys Ile Ser Arg Val Glu Ala Glu Asp Leu Gly Val Tyr
                85                  90                  95 tat tgc tgg caa ggt aca cat ttt cca ttc acg ttc ggc tcg ggg aca     336
Tyr Cys Trp Gln Gly Thr His Phe Pro Phe Thr Phe Gly Ser Gly Thr
            100                 105                 110 aag ttg gaa ata aaa cgt acg gat gct gca cca act gta tcc             378
Lys Leu Glu Ile Lys Arg Thr Asp Ala Ala Pro Thr Val Ser
```

<210> SEQ ID NO 60
<211> LENGTH: 126
<212> TYPE: PRT
<213> ORGANISM: Homo sapiens

<400> SEQUENCE: 60

Gly Leu Phe Glu Ala Ala Thr Met Glu Ala Pro Ala Gln Leu Thr Leu
1               5                   10                  15

Ser Val Thr Ile Gly Gln Pro Ala Ser Ile Ser Cys Lys Ser Ser Gln
            20                  25                  30

Ser Leu Leu Asp Ser Asp Gly Lys Thr Tyr Leu Asn Trp Leu Leu Gln
        35                  40                  45

Arg Pro Gly Gln Ser Pro Lys Arg Leu Ile Tyr Leu Val Ser Lys Leu
    50                  55                  60

Asp Ser Gly Val Pro Asp Arg Phe Thr Gly Ser Gly Ser Gly Thr Asp
65                  70                  75                  80

Phe Thr Leu Lys Ile Ser Arg Val Glu Ala Glu Asp Leu Gly Val Tyr
                85                  90                  95

Tyr Cys Trp Gln Gly Thr His Phe Pro Phe Thr Phe Gly Ser Gly Thr
            100                 105                 110

Lys Leu Glu Ile Lys Arg Thr Asp Ala Ala Pro Thr Val Ser
        115                 120                 125

<210> SEQ ID NO 61
<211> LENGTH: 145
<212> TYPE: PRT
<213> ORGANISM: Homo sapiens

<400> SEQUENCE: 61

Gly Leu Phe Glu Ala Ala Thr Met Lys Leu Pro Val Arg Leu Leu Val
1               5                   10                  15

Leu Trp Ile Arg Glu Thr Asn Gly Asp Val Val Met Thr Gln Thr Pro
            20                  25                  30

Leu Thr Leu Ser Val Thr Ile Gly Gln Pro Ala Ser Ile Ser Cys Lys
        35                  40                  45

Ser Ser Gln Ser Leu Leu Asp Ser Asp Gly Lys Thr Tyr Leu Asn Trp
    50                  55                  60

Leu Leu Gln Arg Pro Gly Gln Ser Pro Lys Arg Leu Ile Tyr Leu Val
65                  70                  75                  80

Ser Lys Leu Asp Ser Gly Val Pro Asp Arg Phe Thr Gly Ser Gly Ser
                85                  90                  95

Gly Thr Asp Phe Thr Leu Lys Ile Ser Arg Val Glu Ala Glu Asp Leu
            100                 105                 110

Gly Val Tyr Tyr Cys Trp Gln Gly Thr His Phe Pro Phe Thr Phe Gly
        115                 120                 125

Ser Gly Thr Lys Leu Glu Ile Lys Arg Thr Asp Ala Ala Pro Thr Val
    130                 135                 140

Ser
145

<210> SEQ ID NO 62
<211> LENGTH: 126
<212> TYPE: PRT
<213> ORGANISM: Homo sapiens

<400> SEQUENCE: 62

```
Gly Leu Phe Glu Ala Ala Thr Met Glu Ala Pro Ala Gln Leu Thr Leu
  1               5                  10                  15

Ser Val Thr Ile Gly Gln Pro Ala Ser Ile Ser Cys Lys Ser Ser Gln
             20                  25                  30

Ser Leu Leu Asp Ser Asp Gly Lys Thr Tyr Leu Asn Trp Leu Leu Gln
         35                  40                  45

Arg Pro Gly Gln Ser Pro Lys Arg Leu Ile Tyr Leu Val Ser Lys Leu
     50                  55                  60

Asp Ser Gly Val Pro Asp Arg Phe Thr Gly Ser Gly Ser Gly Thr Asp
 65                  70                  75                  80

Phe Thr Leu Lys Ile Ser Arg Val Glu Ala Glu Asp Leu Gly Val Tyr
                 85                  90                  95

Tyr Cys Trp Gln Gly Thr His Phe Pro Phe Thr Phe Gly Ser Gly Thr
            100                 105                 110

Lys Leu Glu Ile Lys Arg Thr Asp Ala Ala Pro Thr Val Ser
        115                 120                 125
```

<210> SEQ ID NO 63
<211> LENGTH: 146
<212> TYPE: PRT
<213> ORGANISM: Homo sapiens

<400> SEQUENCE: 63

```
Met Gly Phe Lys Met Glu Ser Gln Ala Gln Val Leu Met Leu Leu Leu
  1               5                  10                  15

Leu Trp Val Ser Gly Thr Cys Gly Asp Ile Val Met Ser Gln Ser Pro
             20                  25                  30

Ser Ser Leu Ala Val Ser Val Gly Glu Lys Val Thr Met Ser Cys Lys
         35                  40                  45

Ser Ser Gln Ser Leu Leu Tyr Arg Ser Asn Gln Lys Asn Tyr Leu Ala
     50                  55                  60

Trp Tyr Gln Gln Lys Pro Gly Gln Ser Pro Lys Leu Leu Ile Tyr Trp
 65                  70                  75                  80

Ala Ser Thr Arg Glu Ser Gly Val Pro Asp Arg Phe Thr Gly Ser Gly
                 85                  90                  95

Ser Gly Thr Asp Phe Thr Leu Thr Ile Ser Ser Val Lys Ala Glu Asp
            100                 105                 110

Leu Ala Val Tyr Tyr Cys Gln Gln Tyr Tyr Asn Tyr Pro Arg Thr Phe
        115                 120                 125

Gly Gly Gly Thr Lys Leu Glu Ile Lys Arg Thr Asp Ala Ala Pro Thr
    130                 135                 140

Val Ser
145
```

<210> SEQ ID NO 64
<211> LENGTH: 14
<212> TYPE: PRT
<213> ORGANISM: Tetanus toxoid

<400> SEQUENCE: 64

```
Gln Tyr Ile Lys Ala Asn Ser Lys Phe Ile Gly Ile Thr Glu
  1               5                  10
```

<210> SEQ ID NO 65
<211> LENGTH: 21
<212> TYPE: PRT
<213> ORGANISM: plasmodium falciparum

```
<400> SEQUENCE: 65

Asp Ile Glu Lys Lys Ile Ala Lys Met Glu Lys Ala Ser Ser Val Phe
 1               5                  10                  15

Asn Val Val Asn Ser
            20

<210> SEQ ID NO 66
<211> LENGTH: 16
<212> TYPE: PRT
<213> ORGANISM: Streptococcus

<400> SEQUENCE: 66

Gly Ala Val Asp Ser Ile Leu Gly Gly Val Ala Thr Tyr Gly Ala Ala
 1               5                  10                  15

<210> SEQ ID NO 67
<211> LENGTH: 13
<212> TYPE: PRT
<213> ORGANISM: Artificial Sequence
<220> FEATURE:
<221> NAME/KEY: VARIANT
<222> LOCATION: 3
<223> OTHER INFORMATION: Xaa = cyclohexyalanine, phenylalanine, or
      tyrosine
<221> NAME/KEY: VARIANT
<222> LOCATION: 1, 13
<223> OTHER INFORMATION: Xaa = D-alanine or L-alanine
<220> FEATURE:
<223> OTHER INFORMATION: pan-DR-binding epitope

<400> SEQUENCE: 67

Xaa Lys Xaa Val Ala Ala Trp Thr Leu Lys Ala Ala Xaa
 1               5                  10

<210> SEQ ID NO 68
<211> LENGTH: 14
<212> TYPE: DNA
<213> ORGANISM: Artificial Sequence
<220> FEATURE:
<223> OTHER INFORMATION: Primer

<400> SEQUENCE: 68
ttttgatcaa gctt                                                           14

<210> SEQ ID NO 69
<211> LENGTH: 42
<212> TYPE: DNA
<213> ORGANISM: Artificial Sequence
<220> FEATURE:
<223> OTHER INFORMATION: Primer

<400> SEQUENCE: 69
ctaatacgac tcactatagg gctcgagcgg ccgcccgggc ag                            42

<210> SEQ ID NO 70
<211> LENGTH: 12
<212> TYPE: DNA
<213> ORGANISM: Artificial Sequence
<220> FEATURE:
<223> OTHER INFORMATION: Primer

<400> SEQUENCE: 70
gatcctgccc gg                                                             12

<210> SEQ ID NO 71
```

```
<211> LENGTH: 40
<212> TYPE: DNA
<213> ORGANISM: Artificial Sequence
<220> FEATURE:
<223> OTHER INFORMATION: Primer

<400> SEQUENCE: 71
gtaatacgac tcactatagg gcagcgtggt cgcggccgag                              40

<210> SEQ ID NO 72
<211> LENGTH: 10
<212> TYPE: DNA
<213> ORGANISM: Artificial Sequence
<220> FEATURE:
<223> OTHER INFORMATION: Primer

<400> SEQUENCE: 72
gatcctcggc                                                              10

<210> SEQ ID NO 73
<211> LENGTH: 22
<212> TYPE: DNA
<213> ORGANISM: Artificial Sequence
<220> FEATURE:
<223> OTHER INFORMATION: Primer

<400> SEQUENCE: 73
ctaatacgac tcactatagg gc                                                22

<210> SEQ ID NO 74
<211> LENGTH: 22
<212> TYPE: DNA
<213> ORGANISM: Artificial Sequence
<220> FEATURE:
<223> OTHER INFORMATION: Primer

<400> SEQUENCE: 74
tcgagcggcc gcccgggcag ga                                                22

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
agcgtggtcg cggccgagga                                                   20

<210> SEQ ID NO 76
<211> LENGTH: 25
<212> TYPE: DNA
<213> ORGANISM: Artificial Sequence
<220> FEATURE:
<223> OTHER INFORMATION: Primer

<400> SEQUENCE: 76
atatcgccgc gctcgtcgtc gacaa                                             25

<210> SEQ ID NO 77
<211> LENGTH: 26
<212> TYPE: DNA
<213> ORGANISM: Artificial Sequence
<220> FEATURE:
<223> OTHER INFORMATION: Primer

<400> SEQUENCE: 77
```

```
agccacacgc agctcattgt agaagg                                          26

<210> SEQ ID NO 78
<211> LENGTH: 24
<212> TYPE: DNA
<213> ORGANISM: Artificial Sequence
<220> FEATURE:
<223> OTHER INFORMATION: Primer

<400> SEQUENCE: 78
actttgttga tgaccaggat tgga                                            24

<210> SEQ ID NO 79
<211> LENGTH: 24
<212> TYPE: DNA
<213> ORGANISM: Artificial Sequence
<220> FEATURE:
<223> OTHER INFORMATION: Primer

<400> SEQUENCE: 79
cagaacttca gcacacacag gaac                                            24

<210> SEQ ID NO 80
<211> LENGTH: 24
<212> TYPE: DNA
<213> ORGANISM: Artificial Sequence
<220> FEATURE:
<223> OTHER INFORMATION: FLAG tag

<400> SEQUENCE: 80
gattacaagg atgacgacga taag                                            24

<210> SEQ ID NO 81
<211> LENGTH: 21
<212> TYPE: DNA
<213> ORGANISM: Homo sapiens

<400> SEQUENCE: 81
aagctcattc tagcgggaaa t                                               21

<210> SEQ ID NO 82
<211> LENGTH: 24
<212> TYPE: DNA
<213> ORGANISM: Homo sapiens

<400> SEQUENCE: 82
aagggacgaa gacgaacacu uctt                                            24

<210> SEQ ID NO 83
<211> LENGTH: 23
<212> TYPE: DNA
<213> ORGANISM: Homo sapiens

<400> SEQUENCE: 83
aactgaagac ctgaagacaa taa                                             23

<210> SEQ ID NO 84
<211> LENGTH: 4
<212> TYPE: PRT
<213> ORGANISM: Homo sapiens

<400> SEQUENCE: 84

Asn Gly Thr Lys
 1
```

```
<210> SEQ ID NO 85
<211> LENGTH: 4
<212> TYPE: PRT
<213> ORGANISM: Homo sapiens

<400> SEQUENCE: 85

Asn Lys Thr Glu
  1

<210> SEQ ID NO 86
<211> LENGTH: 4
<212> TYPE: PRT
<213> ORGANISM: Homo sapiens

<400> SEQUENCE: 86

Ser Arg Lys Asp
  1

<210> SEQ ID NO 87
<211> LENGTH: 4
<212> TYPE: PRT
<213> ORGANISM: Homo sapiens

<400> SEQUENCE: 87

Thr Asn Gln Glu
  1

<210> SEQ ID NO 88
<211> LENGTH: 4
<212> TYPE: PRT
<213> ORGANISM: Homo sapiens

<400> SEQUENCE: 88

Ser Val Ser Asp
  1

<210> SEQ ID NO 89
<211> LENGTH: 4
<212> TYPE: PRT
<213> ORGANISM: Homo sapiens

<400> SEQUENCE: 89

Thr Trp Arg Glu
  1

<210> SEQ ID NO 90
<211> LENGTH: 9
<212> TYPE: PRT
<213> ORGANISM: Homo sapiens

<400> SEQUENCE: 90

Arg Arg Asn Leu Glu Glu Asp Asp Tyr
  1               5

<210> SEQ ID NO 91
<211> LENGTH: 6
<212> TYPE: PRT
<213> ORGANISM: Homo sapiens

<400> SEQUENCE: 91

Gly Val Ile Ala Ala Ile
  1               5
```

-continued

<210> SEQ ID NO 92
<211> LENGTH: 6
<212> TYPE: PRT
<213> ORGANISM: Homo sapiens

<400> SEQUENCE: 92

Gly Thr Ile His Ala Leu
1               5

<210> SEQ ID NO 93
<211> LENGTH: 17
<212> TYPE: PRT
<213> ORGANISM: Homo sapiens

<400> SEQUENCE: 93

Arg Lys Asp Ile Thr Asn Gln Glu Glu Leu Trp Lys Met Lys Pro Arg
1               5                   10                  15

Arg

<210> SEQ ID NO 94
<211> LENGTH: 339
<212> TYPE: PRT
<213> ORGANISM: Homo sapiens

<400> SEQUENCE: 94

Met Glu Ser Arg Lys Asp Ile Thr Asn Gln Glu Glu Leu Trp Lys Met
1               5                   10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                245                 250                 255

```
Leu Gly Ile Val Ser Leu Leu Leu Gly Thr Ile His Ala Leu Ile Phe
                260                 265                 270

Ala Trp Asn Lys Trp Ile Asp Ile Lys Gln Phe Val Trp Tyr Thr Pro
            275                 280                 285

Pro Thr Phe Met Ile Ala Val Phe Leu Pro Ile Val Leu Ile Phe
        290                 295                 300

Lys Ser Ile Leu Phe Leu Pro Cys Leu Arg Lys Ile Leu Lys Ile
305                 310                 315                 320

Arg His Gly Trp Glu Asp Val Thr Lys Ile Asn Lys Thr Glu Ile Cys
                325                 330                 335

Ser Gln Leu
```

<210> SEQ ID NO 95
<211> LENGTH: 12
<212> TYPE: PRT
<213> ORGANISM: Homo sapiens

<400> SEQUENCE: 95

```
Trp Arg Glu Phe His Tyr Ile Gln Val Asn Asn Ile
1               5                   10
```

<210> SEQ ID NO 96
<211> LENGTH: 13
<212> TYPE: PRT
<213> ORGANISM: Homo sapiens

<400> SEQUENCE: 96

```
Thr Trp Arg Glu Phe His Tyr Ile Gln Val Asn Asn Ile
1               5                   10
```

<210> SEQ ID NO 97
<211> LENGTH: 18
<212> TYPE: PRT
<213> ORGANISM: Homo sapiens

<400> SEQUENCE: 97

```
Val Ser Asp Ser Leu Thr Trp Arg Glu Phe His Tyr Ile Gln Val Asn
1               5                   10                  15

Asn Ile
```

<210> SEQ ID NO 98
<211> LENGTH: 36
<212> TYPE: PRT
<213> ORGANISM: Homo sapiens

<400> SEQUENCE: 98

```
Trp Arg Glu Phe His Tyr Ile Gln Ile Ile His Lys Lys Ser Asp Val
1               5                   10                  15

Pro Glu Ser Leu Trp Asp Pro Cys Leu Thr Arg Phe Lys Gly Leu Asn
            20                  25                  30

Leu Ile Gln Ser
        35
```

<210> SEQ ID NO 99
<211> LENGTH: 37
<212> TYPE: PRT
<213> ORGANISM: Homo sapiens

<400> SEQUENCE: 99

```
Thr Trp Arg Glu Phe His Tyr Ile Gln Ile Ile His Lys Lys Ser Asp
1               5                   10                  15
```

```
Val Pro Glu Ser Leu Trp Asp Pro Cys Leu Thr Arg Phe Lys Gly Leu
            20                  25                  30

Asn Leu Ile Gln Ser
        35

<210> SEQ ID NO 100
<211> LENGTH: 42
<212> TYPE: PRT
<213> ORGANISM: Homo sapiens

<400> SEQUENCE: 100

Val Ser Asp Ser Leu Thr Trp Arg Glu Phe His Tyr Ile Gln Ile Ile
 1               5                  10                  15

His Lys Lys Ser Asp Val Pro Glu Ser Leu Trp Asp Pro Cys Leu Thr
            20                  25                  30

Arg Phe Lys Gly Leu Asn Leu Ile Gln Ser
        35                  40

<210> SEQ ID NO 101
<211> LENGTH: 17
<212> TYPE: PRT
<213> ORGANISM: Homo sapiens

<400> SEQUENCE: 101

Arg Lys Gln Phe Gly Leu Leu Ser Leu Phe Phe Ala Val Leu His Ala
 1               5                  10                  15

Ile

<210> SEQ ID NO 102
<211> LENGTH: 19
<212> TYPE: PRT
<213> ORGANISM: Homo sapiens

<400> SEQUENCE: 102

Thr Arg Lys Gln Phe Gly Leu Leu Ser Leu Phe Phe Ala Val Leu His
 1               5                  10                  15

Ala Ile Tyr

<210> SEQ ID NO 103
<211> LENGTH: 29
<212> TYPE: PRT
<213> ORGANISM: Homo sapiens

<400> SEQUENCE: 103

Asp Lys Trp Met Leu Thr Arg Lys Gln Phe Gly Leu Leu Ser Leu Phe
 1               5                  10                  15

Phe Ala Val Leu His Ala Ile Tyr Ser Leu Ser Tyr Pro
            20                  25
```